US010202603B2

(12) United States Patent
Hung et al.

(10) Patent No.: US 10,202,603 B2
(45) Date of Patent: Feb. 12, 2019

(54) MODULATION OF HUNTINGTIN EXPRESSION

(71) Applicant: Ionis Pharmaceuticals, Inc., Carlsbad, CA (US)

(72) Inventors: Gene Hung, Carlsbad, CA (US); C. Frank Bennett, Carlsbad, CA (US); Susan M. Freier, San Diego, CA (US); Holly Kordasiewicz, San Diego, CA (US); Lisa Stanek, Cambridge, MA (US); Don W. Cleveland, Del Mar, CA (US); Seng H. Cheng, Natick, MA (US); Lamya Shihabuddin, Brighton, MA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/596,249

(22) Filed: May 16, 2017

(65) Prior Publication Data

US 2018/0087052 A1 Mar. 29, 2018

Related U.S. Application Data

(63) Continuation of application No. 15/005,712, filed on Jan. 25, 2016, now Pat. No. 9,683,236, which is a continuation of application No. 14/528,656, filed on Oct. 30, 2014, now Pat. No. 9,273,315, which is a continuation of application No. 13/395,188, filed as application No. PCT/US2010/048532 on Sep. 10, 2010, now Pat. No. 8,906,873.

(60) Provisional application No. 61/241,853, filed on Sep. 11, 2009.

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/113* (2013.01); *C12N 2310/315* (2013.01); *C12N 2310/321* (2013.01); *C12N 2310/3341* (2013.01); *C12N 2310/341* (2013.01); *C12N 2310/345* (2013.01); *C12N 2310/346* (2013.01)

(58) Field of Classification Search
None
See application file for complete search history.

(56) References Cited

U.S. PATENT DOCUMENTS 5,595,756 A 1/1997 Bally et al.
5,686,288 A 11/1997 MacDonald et al.
5,700,922 A 12/1997 Cook
5,801,154 A 9/1998 Baracchini et al.
5,998,148 A 12/1999 Bennett et al.
6,043,060 A 3/2000 Imanishi
6,147,200 A 11/2000 Manoharan et al.
6,582,908 B2 6/2003 Fodor et al.
6,670,461 B1 12/2003 Wengel et al.
7,320,965 B2 1/2008 Sah et al.
7,374,927 B2 5/2008 Palma et al.
2001/0053519 A1 12/2001 Fodor et al.
2003/0109476 A1 6/2003 Kmiec
2003/0144242 A1 7/2003 Ward et al.
2003/0228597 A1 12/2003 Cowsert et al.
2004/0092465 A1 5/2004 Dobie
2004/0096880 A1 5/2004 Kmiec
2004/0137471 A1 7/2004 Vickers et al.
2004/0146902 A1 7/2004 Ecker et al.
2005/0042646 A1 2/2005 Davidson
2005/0096284 A1 5/2005 McSwiggen
2005/0191638 A1 9/2005 McSwiggen
2005/0245475 A1 11/2005 Khvorova et al.
2005/0255086 A1 11/2005 Davidson
2005/0255487 A1 11/2005 Khvorova et al.
2006/0051769 A1 3/2006 Barts
2007/0031844 A1 2/2007 Khvorova et al.
2007/0099860 A1 5/2007 Sah
2007/0299027 A1 12/2007 Hung et al.
2008/0015158 A1 1/2008 Ichiro
2008/0039415 A1 2/2008 Stewart et al.
2008/0039418 A1* 2/2008 Freier .................. C12N 15/113 514/44 A
2008/0274989 A1 11/2008 Davidson et al.
2009/0092981 A1 4/2009 Swayze et al.

FOREIGN PATENT DOCUMENTS

CA 2526893 11/2004
JP 2009-513144 4/2009
JP 2009-524431 7/2009
WO WO 1994/026764 11/1994
WO WO 1999/050409 10/1999
(Continued)

OTHER PUBLICATIONS

Anderson, "An Overview of Psychiatric Symptoms in Huntington's Disease" Current Psychiatry Reports (2001) 3:379-388.
Bennett et al., "Antisense oligonucleoties as a tool for gene functionalization and target validation" Biochimica Biophysica Acta (1999) 1489:19-30.
Boado et al., "Antisense-mediated down-regulation of the human huntington gene" Journal of Pharmacology and Experimental Therapeutics (2000) 295:239-243.
Boffa et al., "Isolation of active genes containing CAG repeats by DNA strands invasion by a peptide nucleic acid" PNAS (1995) 92:1901-5.
(Continued)

*Primary Examiner* — Kimberly Chong
(74) *Attorney, Agent, or Firm* — McDonnell Boehnen Hulbert & Berghoff LLP

(57) ABSTRACT

Provided herein are methods, compounds, and compositions for reducing expression of huntingtin mRNA and protein in an animal. Such methods, compounds, and compositions are useful to treat, prevent, delay, or ameliorate Huntington's disease, or a symptom thereof.

16 Claims, 10 Drawing Sheets

Specification includes a Sequence Listing.

(56) References Cited

FOREIGN PATENT DOCUMENTS

| | | |
|---|---|---|
| WO | WO 2000/003720 | 1/2000 |
| WO | WO 2001/079283 | 10/2001 |
| WO | WO 2003/013437 | 2/2003 |
| WO | WO 2003/064625 | 8/2003 |
| WO | WO 2004/044123 | 5/2004 |
| WO | WO 2004/048601 | 6/2004 |
| WO | WO 2004/101787 | 11/2004 |
| WO | WO 2004/013280 | 12/2004 |
| WO | WO 2005/027980 | 3/2005 |
| WO | WO 2005/045032 | 5/2005 |
| WO | WO 2005/083436 | 9/2005 |
| WO | WO 2005/105995 | 11/2005 |
| WO | WO 2005/116204 | 12/2005 |
| WO | WO 2007/022470 | 2/2007 |
| WO | WO 2007/051045 | 5/2007 |
| WO | WO 2007/089584 | 8/2007 |
| WO | WO 2007089584 | 11/2007 |
| WO | WO 2008/005562 | 1/2008 |
| WO | WO 2008/018795 | 2/2008 |
| WO | WO 2011/097388 | 8/2011 |

OTHER PUBLICATIONS

Borovecki et al., "Genome-wide expression profiling of human blood reveals biomarkers for Huntington's disease" Proc. Natl. Acad. Sci. USA (2005) 102:11023-11028.

Branch et al., "A good antisense molecule is hard to find," TIBS (1998) 23:45-50.

Caplen et al., "Rescue ofpolyglutamine-mediated cytotoxicity by double-stranded RNA-mediated RNA interference" Human Molecular Genetics (2002) II (2): 175-184.

Chang et al., "Structural Analysis of Complementary DNA and Amino Acid Sequences of Human and Rat Androgen Receptors" PNAS (1988) 85:7211-7215.

Chin "On the Preparation and Utilization oflsolated and Purififed Oligonucleotides." Document purportedly located on a CD-ROM and contributed to the public collection of the Katherine R. Everett Law Library of the University ofNorth Carolina on Mar. 14, 2002.

Brooke et al., "Basic Principles of Antisense Therapeutics" Antisense Research and Application (1998) Chapter 1:1-50.

Davidson et al., "Molecular medicine for the brain: silencing of disease genes with RNA interference" Lancet Neural. (2004) 3:145-149.

Diaz-Hernandez et al., "Full Motor Recovery Despite Striatal Neuron Loss and Formation of Irreversible Amyloid-Like Inclusions in a Conditional Mouse Model of Huntington's Disease" J Neurosci(2005) 25:9773-9781.

Drouet et al., "Sustained effects of nonallele-specific Huntingtin silencing" Ann Neural. (2009) 65(3): 276-285.

Eder et al., "Inhibition of LNCaP Prostate Cancer Cells by Means of Androgen Receptor Antisense Oligonucleotides" Cancer Gene Therapy (2000) 7(7):997-1007.

Gagnon et al., "HD Therapeutics—CHDI Fifth Annual Conference" IDrugs 13( 4): 219-223 (2010).

Gonzalez-Alegre et al., "Technology Insight: therapeutic RNA interference—how far from the neurology clinic?" Nature Clinical Practice 3:394-404, 2007.

Gryaznov et al., "Oligodeoxyribonucleotide N3'->P5' Phosphoramidates Synthesis and Hybridization Properties" JAm. Chern. Soc. (1994) 116:3143-3144.

Haque et al., "Antisense gene therapy for neurodegenerative disease" Experimental Neurology (1997) 144:139-146.

Harper et al., "Ten years ofpresymptomatic testing for Huntington's disease: the experience of the UK Huntington's Disease Prediction Consortium" J. Med. Genet. 37:567-571, 2000.

Harper et al., "RNA interference improves motor and neuropathological abnormalities in a Huntington'sdisease mouse model" PNAS (2005) I 02:5820-5825.

Hasholt et al., "Antisense downregulation of mutant huntingtin in a cell model" Journal of Gene Medicine (2003) 5:528-538.

Hersch et al., "Translating Therapies for Huntington's Disease from Genetic Animal Models to Clinical Trials" NeuroRX (2004) 1:298-306.

Hersch et al., "Neuroprotection for Huntington's disease: Ready, set, slow" Neurotherapeutics (2008) 5(2):226-236.

Liu et al., "Specific inhibition of Huntington's disease gene expression by siRNAs in cultures cells" Proceedings of the Japan Academy. Series B, Physical and Biological Sciences (2003) 79B:293-298.

MacDonald et al., "A novel gene containing a trinucleotide repeat that is expanded and unstable on Huntington's disease chromosomes" Cell (1993) 72(6):971-983.

Machida et al., "rAAV-mediated shRNA ameliorated neuropathology in Huntington disease model mouse" Biochem. Biophys. Res. Commun. (2006) 343:190-197.

MacMillan et al., "Molecular analysis and clinical correlations oftheHuntington's disease mutation" Lancet (1993) 342:954-958.

Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.

Martin et al., "38. Ein neuer Zugang zu 2'-0-Alkylribonucleosiden und Eigenschaften deren Oligonucleotide" Helv. Chim. Acta (1995) 78:486-504.

Nellemann et al., "Inhibition of Huntington synthesis by antisense oligonucleotides" Molecular and Cellular Neurosciences (2000) 16:313-323.

New England BioLabs, Inc. Catalogue (1998): 121, 284.

Nguyen et al., "Clioquinol down-regulates mutant huntingtin expression in vitro and mitigates pathology in a Huntington's disease mouse model" PNAS (2005) 102:11840-11845.

Nikiforov et al., "The Use ofPhosphorothioate Primers and Exonuclease Hydrolysis for the Preparation of Single-stranded PCR Products and their Detection by Solid-phase Hybridization" PCR Methods and Applications (1994) 3:285-291.

Pakula et al., "Genetic analysis of protein stability and function" Annual review of genetics 23: 289-310 (1989).

Reynolds et al., "Rational siRNA design for RNA interference" Nature Biotechnology (2004) 22:326-330.

Sanghvi et al., "Heterocyclic Base Modifications in Nucleic Acids and Their Applications in Antisense Oligonucleotides" Antisense Research and Applications (1993) pp. 273-288.

Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.

Sheehan et al., "Biochemical properties ofphosphonoacetate and thiophosphonoacetate oligodeoxyribonucleotides" Nucleic Acids Research (2003) 31 :4109-4118.

Uhlmann et al., "Antisense oligonucleotides: a new therapeutic principle" Chemical Reviews (1990) 90:543-584.

Vickers et al., "Efficient Reduction of Target RNAs by Small Interfering RNA and Rnase H-dependent Antisense Agents. A comparative analysis." J Bioi. Chem. (2003) 278:7108-7118.

Wang et al., "Clinico-pathological rescue of a model mouse of Huntington's disease by siRNA" Neurosci. Res. (2005) 53:241-249.

Woolf et al., "Specificity of antisense oligonucleotides in vivo" Proc. Natl. Acad. Sci. USA (1992) 89:7305-7309.

Yen et al., "Sequence-specific cleavage ofHuntingtin mRNA by catalytic DNA" Annals ofNeurology (1999) 46 (3)366-373.

International Search Report for Application No. PCT/US2007/002215 dated Nov. 16, 2007 (RTS-0838WO).

International Search Report for Application No. PCT/US2007/002171 dated Sep. 26, 2007 (RTS-0838W02).

International Search Report for Application # PCT /US2010/048532 dated Jan. 26, 2011.

* cited by examiner

SEQUENCE LISTING

```
<160> NUMBER OF SEQ ID NOS: 56

<210> SEQ ID NO 1
<211> LENGTH: 13481
<212> TYPE: DNA
<213> ORGANISM: Homo sapiens

<400> SEQUENCE: 1

gctgccggga cgggtccaag atggacggcc gctcaggttc tgcttttacc tgcggcccag     60

agccccattc attgccccgg tgctgagcgg cgccgcgagt cggcccgagg cctccgggga    120

ctgccgtgcc gggcgggaga ccgccatggc gaccctggaa aagctgatga aggccttcga    180

gtccctcaag tccttccagc agcagcagca gcagcagcag cagcagcagc agcagcagca    240

gcagcagcag cagcagcagc aacagccgcc accgccgccg ccgccgccgc cgcctcctca    300

gcttcctcag ccgccgccgc aggcacagcc gctgctgcct cagccgcagc cgcccccgcc    360

gccgcccccg ccgccacccg gcccggctgt ggctgaggag ccgctgcacc gaccaaagaa    420

agaactttca gctaccaaga aagaccgtgt gaatcattgt ctgacaatat gtgaaaacat    480

agtggcacag tctgtcagaa attctccaga atttcagaaa cttctgggca tcgctatgga    540

actttttctg ctgtgcagtg atgacgcaga gtcagatgtc aggatggtgg ctgacgaatg    600

cctcaacaaa gttatcaaag ctttgatgga ttctaatctt ccaaggttac agctcgagct    660

ctataaggaa attaaaaaga atggtgcccc tcggagtttg cgtgctgccc tgtggaggtt    720

tgctgagctg gctcacctgg ttcggcctca gaaatgcagg ccttacctgg tgaaccttct    780

gccgtgcctg actcgaacaa gcaagagacc cgaagaatca gtccaggaga ccttggctgc    840

agctgttccc aaaattatgg cttcttttgg caattttgca aatgacaatg aaattaaggt    900

tttgttaaag gccttcatag cgaacctgaa gtcaagctcc cccaccattc ggcggacagc    960

ggctggatca gcagtgagca tctgccagca ctcaagaagg acacaatatt tctatagttg   1020

gctactaaat gtgctcttag gcttactcgt tcctgtcgag gatgaacact ccactctgct   1080

gattcttggc gtgctgctca ccctgaggta tttggtgccc ttgctgcagc agcaggtcaa   1140
```

```
ggacacaagc ctgaaaggca gcttcggagt gacaaggaaa gaaatggaag tctctccttc   1200
tgcagagcag cttgtccagg tttatgaact gacgttacat catacacagc accaagacca   1260
caatgttgtg accggagccc tggagctgtt gcagcagctc ttcagaacgc ctccacccga   1320
gcttctgcaa accctgaccg cagtcggggg cattgggcag ctcaccgctg ctaaggagga   1380
gtctggtggc cgaagccgta gtgggagtat tgtggaactt atagctggag ggggttcctc   1440
atgcagccct gtcctttcaa gaaaacaaaa aggcaaagtg ctcttaggag aagaagaagc   1500
cttggaggat gactctgaat cgagatcgga tgtcagcagc tctgccttaa cagcctcagt   1560
gaaggatgag atcagtggag agctggctgc ttcttcaggg gtttccactc cagggtcagc   1620
aggtcatgac atcatcacag aacagccacg gtcacagcac acactgcagg cggactcagt   1680
ggatctggcc agctgtgact tgacaagctc tgccactgat ggggatgagg aggatatctt   1740
gagccacagc tccagccagg tcagcgccgt cccatctgac cctgccatgg acctgaatga   1800
tgggacccag gcctcgtcgc ccatcagcga cagctcccag accaccaccg aagggcctga   1860
ttcagctgtt accccttcag acagttctga aattgtgtta gacggtaccg acaaccagta   1920
tttgggcctg cagattggac agccccagga tgaagatgag gaagccacag gtattcttcc   1980
tgatgaagcc tcggaggcct tcaggaactc ttccatggcc cttcaacagg cacatttatt   2040
gaaaaacatg agtcactgca ggcagccttc tgacagcagt gttgataaat ttgtgttgag   2100
agatgaagct actgaaccgg gtgatcaaga aaacaagcct tgccgcatca aaggtgacat   2160
tggacagtcc actgatgatg actctgcacc tcttgtccat tgtgtccgcc ttttatctgc   2220
ttcgtttttg ctaacagggg gaaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa taccctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacatttttct ttggcggatt gcattccttt   2580
gctgcggaaa acactgaagg atgagtcttc tgttacttgc aagttagctt gtacagctgt   2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aacccttgca gagattgact tcaggctggt gagctttttg gaggcaaaag cagaaaactt   2820
acacagaggg gctcatcatt atacagggct tttaaaactg caagaacgag tgctcaataa   2880
tgttgtcatc catttgcttg gagatgaaga ccccagggtg cgacatgttg ccgcagcatc   2940
actaattagg cttgtcccaa agctgtttta taaatgtgac caaggacaag ctgatccagt   3000
agtggccgtg gcaagagatc aaagcagtgt ttacctgaaa cttctcatgc atgagacgca   3060
gcctccatct catttctccg tcagcacaat aaccagaata tatagaggct ataacctact   3120
accaagcata acagacgtca ctatggaaaa taacctttca agagttattg cagcagtttc   3180
tcatgaacta atcacatcaa ccaccagagc actcacattt ggatgctgtg aagctttgtg   3240
tcttctttcc actgccttcc cagtttgcat ttggagttta ggttggcact gtggagtgcc   3300
tccactgagt gcctcagatg agtctaggaa gagctgtacc gttgggatgg ccacaatgat   3360
tctgaccctg ctctcgtcag cttggttccc attggatctc tcagcccatc aagatgcttt   3420
gattttggcc ggaaacttgc ttgcagccag tgctcccaaa tctctgagaa gttcatgggc   3480
```

ctctgaagaa gaagccaacc cagcagccac caagcaagag gaggtctggc cagccctggg 3540
ggaccgggcc ctggtgccca tggtggagca gctcttctct cacctgctga aggtgattaa 3600
catttgtgcc cacgtcctgg atgacgtggc tcctggaccc gcaataaagg cagccttgcc 3660
ttctctaaca aaccccctt ctctaagtcc catccgacga aaggggaagg agaaagaacc 3720
aggagaacaa gcatctgtac cgttgagtcc caagaaaggc agtgaggcca gtgcagcttc 3780
tagacaatct gatacctcag gtcctgttac aacaagtaaa tcctcatcac tggggagttt 3840
ctatcatctt ccttcatacc tcaaactgca tgatgtcctg aaagctacac acgctaacta 3900
caaggtcacg ctggatcttc agaacagcac ggaaaagttt ggagggtttc tccgctcagc 3960
cttggatgtt ctttctcaga tactagagct ggccacactg caggacattg ggaagtgtgt 4020
tgaagagatc ctaggatacc tgaaatcctg ctttagtcga gaaccaatga tggcaactgt 4080
ttgtgttcaa caattgttga agactctctt tggcacaaac ttggcctccc agtttgatgg 4140
cttatcttcc aaccccagca agtcacaagg ccgagcacag cgccttggct cctccagtgt 4200
gaggccaggc ttgtaccact actgcttcat ggccccgtac acccacttca cccaggccct 4260
cgctgacgcc agcctgagga acatggtgca ggcggagcag gagaacgaca cctcgggatg 4320
gtttgatgtc ctccagaaag tgtctaccca gttgaagaca aacctcacga gtgtcacaaa 4380
gaaccgtgca gataagaatg ctattcataa tcacattcgt ttgtttgaac ctcttgttat 4440
aaaagcttta aaacagtaca cgactacaac atgtgtgcag ttacagaagc aggttttaga 4500
tttgctggcg cagctggttc agttacgggt taattactgt cttctggatt cagatcaggt 4560
gtttattggc tttgtattga aacagtttga atacattgaa gtgggccagt tcagggaatc 4620
agaggcaatc attccaaaca tctttttctt cttggtatta ctatcttatg aacgctatca 4680
ttcaaaacag atcattggaa ttcctaaaat cattcagctc tgtgatggca tcatggccag 4740
tggaaggaag gctgtgacac atgccatacc ggctctgcag cccatagtcc acgacctctt 4800
tgtattaaga ggaacaaata aagctgatgc aggaaaagag cttgaaaccc aaaaagaggt 4860
ggtggtgtca atgttactga gactcatcca gtaccatcag gtgttggaga tgttcattct 4920
tgtcctgcag cagtgccaca aggagaatga agacaagtgg aagcgactgt ctcgacagat 4980
agctgacatc atcctcccaa tgttagccaa acagcagatg cacattgact ctcatgaagc 5040
ccttggagtg ttaaatacat tatttgagat tttggcccct tcctccctcc gtccggtaga 5100
catgctttta cggagtatgt tcgtcactcc aaacacaatg gcgtccgtga gcactgttca 5160
actgtggata tcgggaattc tggccatttt gagggttctg atttcccagt caactgaaga 5220
tattgttctt tctcgtattc aggagctctc cttctctccg tatttaatct cctgtacagt 5280
aattaatagg ttaagagatg gggacagtac ttcaacgcta gaagaacaca gtgaagggaa 5340
acaaataaag aatttgccag aagaaacatt ttcaaggttt ctattacaac tggttggtat 5400
tcttttagaa gacattgtta caaaacagct gaaggtggaa atgagtgagc agcaacatac 5460
tttctattgc caggaactag gcacactgct aatgtgtctg atccacatct tcaagtctgg 5520
aatgttccgg agaatcacag cagctgccac taggctgttc cgcagtgatg gctgtggcgg 5580
cagtttctac accctggaca gcttgaactt gcgggctcgt tccatgatca ccacccaccc 5640
ggccctggtg ctgctctggt gtcagatact gctgcttgtc aaccacaccg actaccgctg 5700
gtgggcagaa gtgcagcaga ccccgaaaag acacagtctg tccagcacaa agttacttag 5760
tccccagatg tctggagaag aggaggattc tgacttggca gccaaacttg gaatgtgcaa 5820
tagagaaata gtacgaagag ggctctcat tctcttctgt gattatgtct gtcagaacct 5880

-continued

```
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac ctttcaactc caaccatgct   6060
gaagaaaact cttcagtgct tggaggggat ccatctcagc cagtcgggag ctgtgctcac   6120
gctgtatgtg gacaggcttc tgtgcacccc tttccgtgtg ctggctcgca tggtcgacat   6180
ccttgcttgt cgccgggtag aaatgcttct ggctgcaaat ttacagagca gcatggccca   6240
gttgccaatg gaagaactca acagaatcca ggaatacctt cagagcagcg ggctcgctca   6300
gagacaccaa aggctctatt ccctgctgga caggtttcgt ctctccacca tgcaagactc   6360
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca gaagagtgcc ctttttgaag cagcccgtga   6660
ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg gccctggcac agtacctggt   6840
ggtggtctcc aaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gagcagcttc ttagtccaga   7140
aagaaggaca aatacccca aagccatcag cgaggaggag gaggaagtag atccaaacac   7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgcccca ctggtgtgga agcttggatg gtcacccaaa ccgggagggg attttggcac   7440
agcattccct gagatccccg tggagttcct ccaggaaaag gaagtcttta aggagttcat   7500
ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct tggagcagca   7740
gccccggaac aagcctctga aagctctcga caccaggttt gggaggaagc tgagcattat   7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag tttttgcttg agttgtacag ccgctggatc ctgccgtcca gctcagccag   8220
```

```
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccacctgc ccagcagggt tggagccctg cacggcgtcc tctatgtgct   8520
ggagtgcgac ctgctggacg acactgccaa gcagctcatc ccggtcatca gcgactatct   8580
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
cccctccatc atttaccact gtgccctcag aggcctggag cgcctcctgc tctctgagca   8820
gctctcccgc ctggatgcag aatcgctggt caagctgagt gtggacagag tgaacgtgca   8880
cagcccgcac cgggccatgg cggctctggg cctgatgctc acctgcatgt acacaggaaa   8940
ggagaaagtc agtccgggta gaacttcaga ccctaatcct gcagcccccg acagcgagtc   9000
agtgattgtt gctatggagc gggtatctgt tctttttgat aggatcagga aaggctttcc   9060
ttgtgaagcc agagtggtgg ccaggatcct gccccagttt ctagacgact tcttcccacc   9120
ccaggacatc atgaacaaag tcatcggaga gtttctgtcc aaccagcagc cataccccca   9180
gttcatggcc accgtggtgt ataaggtgtt tcagactctg cacagcaccg ggcagtcgtc   9240
catggtccgg gactgggtca tgctgtccct ctccaacttc acgcagaggg ccccggtcgc   9300
catggccacg tggagcctct cctgcttctt tgtcagcgcg tccaccagcc cgtgggtcgc   9360
ggcgatcctc ccacatgtca tcagcaggat gggcaagctg gagcaggtgg acgtgaacct   9420
tttctgcctg gtcgccacag acttctacag acaccagata gaggaggagc tcgaccgcag   9480
ggccttccag tctgtgcttg aggtggttgc agccccagga agcccatatc accggctgct   9540
gacttgttta cgaaatgtcc acaaggtcac cacctgctga gcgccatggt gggagagact   9600
gtgaggcggc agctggggcc ggagcctttg gaagtctgcg cccttgtgcc ctgcctccac   9660
cgagccagct tggtccctat gggcttccgc acatgccgcg ggcggccagg caacgtgcgt   9720
gtctctgcca tgtggcagaa gtgctctttg tggcagtggc caggcaggga gtgtctgcag   9780
tcctggtggg gctgagcctg aggccttcca gaaagcagga gcagctgtgc tgcaccccat   9840
gtgggtgacc aggtcctttc tcctgatagt cacctgctgg ttgttgccag gttgcagctg   9900
ctcttgcatc tgggccagaa gtcctccctc ctgcaggctg gctgttggcc cctctgctgt   9960
cctgcagtag aaggtgccgt gagcaggctt tgggaacact ggcctgggtc tccctggtgg  10020
ggtgtgcatg ccacgccccg tgtctggatg cacagatgcc atggcctgtg ctgggccagt  10080
ggctgggggt gctagacacc cggcaccatt ctcccttctc tcttttcttc tcaggattta  10140
aaatttaatt atatcagtaa agagattaat tttaacgtaa ctctttctat gcccgtgtaa  10200
agtatgtgaa tcgcaaggcc tgtgctgcat gcgacagcgt ccggggtggt ggacagggcc  10260
cccggccacg ctccctctcc tgtagccact ggcatagccc tcctgagcac ccgctgacat  10320
ttccgttgta catgttcctg tttatgcatt cacaaggtga ctgggatgta gagaggcgtt  10380
agtgggcagg tggccacagc aggactgagg acaggccccc attatcctag gggtgcgctc  10440
acctgcagcc cctcctcctc gggcacagac gactgtcgtt ctccacccac cagtcaggga  10500
cagcagcctc cctgtcactc agctgagaag gccagccctc cctggctgtg agcagcctcc  10560
actgtgtcca gagacatggg cctcccactc ctgttccttg ctagccctgg ggtggcgtct  10620
```

gcctaggagc tggctggcag gtgttgggac ctgctgctcc atggatgcat gccctaagag 10680
tgtcactgag ctgtgttttg tctgagcctc tctcggtcaa cagcaaagct tggtgtcttg 10740
gcactgttag tgacagagcc cagcatccct tctgcccccg ttccagctga catcttgcac 10800
ggtgacccct tttagtcagg agagtgcaga tctgtgctca tcggagactg ccccacggcc 10860
ctgtcagagc cgccactcct atccccaggc caggtccctg gaccagcctc ctgtttgcag 10920
gcccagagga gccaagtcat taaaatggaa gtggattctg gatggccggg ctgctgctga 10980
tgtaggagct ggatttggga gctctgcttg ccgactggct gtgagacgag gcaggggctc 11040
tgcttcctca gccctagagg cgagccaggc aaggttggcg actgtcatgt ggcttggttt 11100
ggtcatgccc gtcgatgttt tgggtattga atgtggtaag tggaggaaat gttggaactc 11160
tgtgcaggtg ctgccttgag acccccaagc ttccacctgt ccctctccta tgtggcagct 11220
ggggagcagc tgagatgtgg acttgtatgc tgcccacata cgtgaggggg agctgaaagg 11280
gagcccctcc tctgagcagc ctctgccagg cctgtatgag gcttttccca ccagctccca 11340
acagaggcct cccccagcca ggaccacctc gtcctcgtgg cggggcagca ggagcggtag 11400
aaaggggtcc gatgtttgag gaggccctta agggaagcta ctgaattata acacgtaaga 11460
aaatcaccat tccgtattgg ttgggggctc ctgtttctca tcctagcttt ttcctggaaa 11520
gcccgctaga aggtttggga acgaggggaa agttctcaga actgttggct gctccccacc 11580
cgcctcccgc ctcccccgca ggttatgtca gcagctctga gacagcagta tcacaggcca 11640
gatgttgttc ctggctagat gtttacattt gtaagaaata acactgtgaa tgtaaaacag 11700
agccattccc ttggaatgca tatcgctggg ctcaacatag agtttgtctt cctcttgttt 11760
acgacgtgat ctaaaccagt ccttagcaag gggctcagaa caccccgctc tggcagtagg 11820
tgtcccccac ccccaaagac ctgcctgtgt gctccggaga tgaatatgag ctcattagta 11880
aaaatgactt cacccacgca tatacataaa gtatccatgc atgtgcatat agacacatct 11940
ataattttac acacacacct ctcaagacgg agatgcatgg cctctaagag tgcccgtgtc 12000
ggttcttcct ggaagttgac tttccttaga cccgccaggt caagttagcc gcgtgacgga 12060
catccaggcg tgggacgtgg tcagggcagg gctcattcat tgcccactag gatcccactg 12120
gcgaagatgg tctccatatc agctctctgc agaagggagg aagactttat catgttccta 12180
aaaatctgtg gcaagcaccc atcgtattat ccaaatttg ttgcaaatgt gattaatttg 12240
gttgtcaagt tttgggggtg ggctgtgggg agattgcttt tgttttcctg ctggtaatat 12300
cgggaaagat tttaatgaaa ccagggtaga attgtttggc aatgcactga agcgtgtttc 12360
tttcccaaaa tgtgcctccc ttccgctgcg ggcccagctg agtctatgta ggtgatgttt 12420
ccagctgcca agtgctcttt gttactgtcc accctcattt ctgccagcgc atgtgtcctt 12480
tcaaggggaa aatgtgaagc tgaacccccct ccagacaccc agaatgtagc atctgagaag 12540
gccctgtgcc ctaaaggaca cccctcgccc ccatcttcat ggagggggtc atttcagagc 12600
cctcggagcc aatgaacagc tcctcctctt ggagctgaga tgagccccac gtggagctcg 12660
ggacggatag tagacagcaa taactcggtg tgtggccgcc tggcaggtgg aacttcctcc 12720
cgttgcgggg tggagtgagg ttagttctgt gtgtctggtg ggtggagtca ggcttctctt 12780
gctacctgtg agcatccttc ccagcagaca tcctcatcgg gctttgtccc tcccccgctt 12840
cctccctctg cggggaggac ccgggaccac agctgctggc cagggtagac ttggagctgt 12900
cctccagagg ggtcacgtgt aggagtgaga agaaggaaga tcttgagagc tgctgaggga 12960
ccttggagag ctcaggatgg ctcagacgag gacactcgct tgccgggcct gggcctcctg 13020
ggaaggaggg agctgctcag aatgccgcat gacaactgaa ggcaacctgg aaggttcagg 13080
ggccgctctt cccccatgtg cctgtcacgc tctggtgcag tcaaaggaac gccttcccct 13140
cagttgtttc taagagcaga gtctcccgct gcaatctggg tggtaactgc cagccttgga 13200
ggatcgtggc caacgtggac ctgcctacgg agggtgggct ctgacccaag tggggcctcc 13260
ttgtccaggt ctcactgctt tgcaccgtgg tcagagggac tgtcagctga gcttgagctc 13320
ccctggagcc agcagggctg tgatgggcga gtcccggagc cccacccaga cctgaatgct 13380
tctgagagca aagggaagga ctgacgagag atgtatattt aattttttaa ctgctgcaaa 13440
cattgtacat ccaaattaaa ggaaaaaaat ggaaaccatc a 13481

<210> SEQ ID NO 2
<211> LENGTH: 172001
<212> TYPE: DNA
<213> ORGANISM: Homo sapiens

<400> SEQUENCE: 2
cctgcagggg cctctccagc tcactggggg tggggtgggg gtcacacttg ggtcctcag 60 gtcgtgccga ccacgcgcat tctctgcgct ctgcgcagga gctcgcccac cctctccccg 120
tgcagagagc cccgcagctg gctccccgca gggctgtccg ggtgagtatg gctctggcca 180
cgggccagtg tggcgggagg gcaaacccca aggccacctc ggctcagagt ccacggccgg 240
ctgtcgcccc gctccaggcg tcggcggggg atcctttccg catgggcctg cgcccgcgct 300
cggcgccccc tccacggccc cgccccgtcc atggccccgt ccttcatggg cgagcccctc 360
catggccctg cccctccgcg ccccaccct ccctcgcccc acctctcacc ttcctgcccc 420
gcccccagcc tccccaaccc tcaccggcca gtcccctccc ctatcccgtc cgcccctcag 480
ccgccccgcc cctcagccgg cctgcctaat gtccccgtcc ccagcatcgc cccgccccgc 540
ccccgtctcg ccccgcccct caggcggcct ccctgctgtg ccccgccccg gcctcgccac 600
gcccctacct caccacgccc cccgcatcgc cacgcccccc gcatcgccac gcctccctta 660
ccatgcagtc ccgccccgtc ccttcctcgt cccgcctcgc cgcgacactt cacacacagc 720
ttcgcctcac cccattacag tctcaccacg ccccgtcccc tctccgttga gccccgcgcc 780
ttcgcccggg tggggcgctg cgctgtcagc ggccttgctg tgtgaggcag aacctgcggg 840
ggcaggggcg ggctggttcc ctggccagcc attggcagag tccgcaggct agggctgtca 900
atcatgctgg ccggcgtggc cccgcctccg ccggcgcggc cccgcctccg ccggcgcagc 960
gtctgggacg caaggcgccg tgggggctgc cgggacgggt ccaagatgga cggccgctca 1020
ggttctgctt ttacctgcgg cccagagccc cattcattgc cccggtgctg agcggcgccg 1080
cgagtcggcc cgaggcctcc ggggactgcc gtgccgggcg ggagaccgcc atggcgaccc 1140
tggaaaagct gatgaaggcc ttcgagtccc tcaagtcctt ccagcagcag cagcagcagc 1200
agcagcagca gcagcagcag cagcagcagc agcagcagca acagccgcca ccgccgccgc 1260
cgccgccgcc gcctcctcag cttcctcagc cgccgccgca ggcacagccg ctgctgcctc 1320
agccgcagcc gcccccgccg ccgcccccgc cgccacccgg cccggctgtg gctgaggagc 1380
cgctgcaccg accgtgagtt tgggcccgct gcagctccct gtcccggcgg gtcccaggct 1440
acggcgggga tggcggtaac cctgcagcct gcgggccggc gacacgaacc cccggccccg 1500
cagagacaga gtgacccagc aacccagagc ccatgaggga cacccgcccc ctcctggggc 1560
gaggccttcc cccacttcag ccccgctccc tcacttgggt cttcccttgt cctctcgcga 1620

```
ggggaggcag agccttgttg gggcctgtcc tgaattcacc gaggggagtc acggcctcag   1680
ccctctcgcc cttcgcagga tgcgaagagt tggggcgaga acttgtttct ttttatttgc   1740
gagaaaccag ggcgggggtt cttttaactg cgttgtgaag agaacttgga ggagccgaga   1800
tttgctcagt gccacttccc tcttctagtc tgagagggaa gagggctggg ggcgcgggac   1860
acttcgagag gaggcggggt ttggagctgg agagatgtgg gggcagtgga tgacataatg   1920
cttttaggac gcctcggcgg gagtggcggg gcaggggggg ggcggggagt gagggcgcgt   1980
ccaatgggag atttcttttc ctagtggcac ttaaaacagc ctgagatttg aggctcttcc   2040
tacattgtca ggacatttca tttagttcat gatcacggtg gtagtaacac gattttaagc   2100
accacctaag agatctgctc atctaagcct aagttggtct gcaggcgttt gaatgagttg   2160
tggttgccaa gtaaagtggt gaacttacgt ggtgattaat gaaattatct taaatattag   2220
gaagagttga ttgaagtttt ttgcctatgt gtgttgggaa taaaaccaac acgttgctga   2280
tggggaggtt aattgccgag ggatgaatga ggtgtacatt ttaccagtat tccagtcagg   2340
cttgccagaa tacggggggt ccgcagactc cgtgggcatc tcagatgtgc cagtgaaagg   2400
gtttctgttt gcttcattgc tgacagcttg ttactttttg gaagctaggg gtttctgttg   2460
cttgttcttg ggagaaattt ttgaaacagg aaaagagaga ccattaaaac atctagcgga   2520
accccaggac tttccctgga agtctgtgtg tcgagtgtac agtaggagtt aggaagtact   2580
ctggtgcagt tcaggccttt ctcttacctc tcagtattct atttccgatc tggatgtgtc   2640
ccagatggca tttggtaaga atatctctgt taagactgat taatttttag taatatttct   2700
tgttctttgt ttctgttatg atccttgtct cgtcttcaaa gtttaattag aaaatgattc   2760
ggagagcagt gttagcttat ttgttggaat aaaatttagg aataaattat tctaaaggat   2820
ggaaaaactt tttggatatt tggagaaatt ttaaaacaat ttggcttatc tcttcagtaa   2880
gtaatttctc atccagaaat ttactgtagt gcttttctag gaggtaggtg tcataaaagt   2940
tcacacattg catgtatctt gtgtaaacac taaacagggc tcctgatggg aaggaagacc   3000
tttctgctgg gctgcttcag acacttgatc attctaaaaa tatgccttct ctttcttatg   3060
ctgatttgac agaacctgca tttgcttatc ttcaaaatat gggtatcaag aaatttcctt   3120
tgctgccttg acaaaggaga tagattttgt ttcattactt taaggtaata tatgattacc   3180
ttatttaaaa aatttaatca ggactggcaa ggtggcttac acctttaatc cgagcacttt   3240
gggaggccta ggtggacgaa tcacctgagg tcaggagttt gagaccagcc tggctaacat   3300
ggtgaaaccc tgtctctact aaaaatacaa aaattagctg gtcatggtgg cacgtgcctg   3360
taatccaagc tacctgggag gctgaggcag gaaaatcgct tgaacccggg aggcagagtc   3420
tgcagtgagt tgagatcacg ccactgcact ccagcctggg tgacagagcg agactctatc   3480
tcaaaaaaaa tttttttaa tgtattattt ttgcataagt aatacattga catgatacaa   3540
attctgtaat tacaaaaggg caataattaa aatatcttcc ttccacccct ttcctctgag   3600
tacctaactt tgtccccaag aacaagcact atttcagttc ctcatgtatc ctgccagata   3660
taacctgttc atattgtaag atagatttaa aatgctctaa aaacaaaagt agtttagaat   3720
aatatatatc tatatatttt ttgagatgta gtctcacatt gtcacccagg ctggagtgca   3780
gtgatacaat ctcggctcac tgcagtctct gcctcccagg ttcaaatgct tctcctgcct   3840
cagccttctg agtagctggg attacaggcg cccaccacca tgtccagcta atttttgtat   3900
ttttagtaga gatggggttt caccatgttg gccaggctgg tcttgaactc ctgaccttgt   3960
```

-continued

```
gatctgtcca cctcggcctc ccaaagtgct gggattacag gtgtgagcca ccatgcctgg   4020
ctagaataat aacttttaaa ggttcttagc atgctctgaa atcaactgca ttaggtttat   4080
ttatagtttt atagttattt taaataaaat gcatatttgt catatttctc tgtattttgc   4140
tgttgagaaa ggaggtattc actaattttg agtaacaaac actgctcaca aagtttggat   4200
tttggcagtt ctgttcacgt gcttcagcca aaaaatcctc ttctcaaagt aagattgatg   4260
aaagcaattt agaaagtatc tgttctgttt ttatggctct tgctctttgg tgtggaactg   4320
tggtgtcacg ccatgcatgg gcctcagttt atgagtgttt gtgctctgct cagcatacag   4380
gatgcaggag ttccttatgg ggctggctgc aggctcagca aatctagcat gcttgggagg   4440
gtcctcacag taattaggag gcaattaata cttgcttctg gcagtttctt attctccttc   4500
agattcctat ctggtgtttc cctgacttta ttcattcatc agtaaatatt tactaaacat   4560
gtactatgtg cctggcactg ttataggtgc agggctcagc agtgagcaga caaagctctg   4620
ccctcgtgaa gctttcattc taatgaagga catagacagt aagcaagata gataagtaaa   4680
atatacagta cgttaatacg tggaggaact tcaaagcagg gaaggggata gggaaatgtc   4740
agggttaatc gagtgttaac ttatttttat ttttaaaaaa attgttaagg gctttccagc   4800
aaaacccaga aagcctgcta gacaaattcc aaaagagctg tagcactaag tgttgacatt   4860
tttattttat tttgttttgt tttgtttttt ttgagacagt tcttgctcta tcagccaggc   4920
tggagtgcac tagtgtgatc ttggctcact gcaacctctg cctcttgggt tcaagtgatt   4980
ctcatgcctc agcctcctgt ttagctggga ttatagacat gcactgccat gcctgggtaa   5040
tttttttttt ttcccccgag acggagtctt gctctgtcgc ccaggctgga gtgcagtggc   5100
gcgatctcag ctcactgcaa gctccgcttc ccgagttcac gccattctcc tgcctcagtc   5160
tcccaagtag ctgggactac aggcgcctgc caccacgtcc agctaatttt tttgtatttt   5220
taatagagac ggggtttcac cgtgttagcc aggatgatct tgatctcctg acctcgtcat   5280
ccgccgacct tgtgatccgc ccacctcggc ctcccaaagt gctgggatta caggcatgag   5340
ccactgtgcc cggccacgcc tgggtaattt ttgtattttt agtagagatg gggttttgcc   5400
atgatgagca ggctggtctc gaactcccgg cctcatgtga tctgcctgcc ttggcctccc   5460
aaagtgctag gattacaggc atgagccacc atacctggcc agtgttgata ttttaaatac   5520
ggtgttcagg gaaggtccac tgagaagaca gctttttttt tttttttttt tggggttggg   5580
gggcaaggtc ttgctcttta acccaggctg gaatgcagta tcactatcgt agctcacttc   5640
agccttgaac tcctgggctc aagtgatcct cccacctcaa cctcacaatg tgttgggact   5700
ataggtgtga gccatcacac ctggccagat gatggctttt gagtaaagac ctcaagcgag   5760
ttaagagtct agtgtaaggg tgtatgaagt agtggtattc cagatggggg gaacaggtcc   5820
aaaatcttcc tgtttcagga atagcaagga tgtcatttta gttgggtgaa ttgagtgagg   5880
gggacatttg tagtaagaag taaggtccaa gaggtcaagg gagtgccata tcagaccaat   5940
actacttgcc ttgtagatgg aataaagata ttggcattta tgtgagtgag atgggatgtc   6000
actggaggat tagagcagag gagtagcatg atctgaattt caatcttaag tgaactctgg   6060
ctgacaacag agtgaagggg aacaccggca aaagcagaaa ccagttagga agccactgca   6120
gtgctcagat aagcatggtg ggttctgtca gggtaccggc tgtcggctgt gggcagtgtg   6180
aggaatgact gactggattt tgaatgcgga accaactgca cttgttgaac tctgctaagt   6240
ataacaattt agcagtagct tgcgttatca ggtttgtatt cagctgcaag taacagaaaa   6300
tcctgctgca atagcttaaa ctggtaacaa gcaagagctt atcagaagac aaaaataagt   6360
```

```
ctggggaaat tcaacaataa gttaaggaac ccaggctctt tctttttttt tttttgaaa   6420
cggagtttcg ctcttgtcac ccgggctgga gtgcaatgat gtgatctcag ctcactaaaa   6480
cctctacctc ctgggttcaa gtgattcttc tgcctcagcc tcccaagtaa ctgggattac   6540
aggcgtatac caccatgccc agctaatttt tgtgttttta gtagagatgg ggtttcacca   6600
tgttggccag gctggtctcg aacttctgac ctcaggtgat ccactcgcct cagcctgcca   6660
aagtgctggg attacaggtt tgggccactg cacccggtca gaacccaggc tctttcttat   6720
acttaccttg caaacccttg ttctcatttt ttccctttgt atttttattg ttgaattgta   6780
atagttcttt atatattctg gatactggat tcttatcaga tagatgattt gtaaaaactc   6840
tcccttcctt tggattgtct ttttactttc ttgatagtgt cttttgaagt gtaaaagttt   6900
ttaattttga tgaagtcgag tttatctatt ttgtctttgg ttgctgtgct tcaagtgtca   6960
tatctaagaa atcattgtct aatccaaagt caaaaaggtt tactcctatg ttttcttcta   7020
agaattttag agttttacat ttaagtctga tccattttga gttaattttt atatatggtt   7080
caggtagaag tccaacttta ttcttttcca tgtggttatt cagttgtccc agcactgttt   7140
gttgaagaga ctattctttc cccatggaat tatcttagta cccttgttga aaattaatcg   7200
tccttaattg tataaattta tttctagact gtcagttcta cctgttggtc tttatgtcga   7260
tcctgtgcca gtaccataca gtcttgatta ctgaagtttg tgtcacagtt taaattcatg   7320
aaatgtgagt tctccaactt tgttcctttt caagattgat ttggccatgc tgggtccctt   7380
gcatttccgt acgaattgta ggatcagctt gtcagtttca acaaagaagc caagtaggat   7440
tctgagaggg attgtgttga atctgtagat caacttgggg agtattcgca tcttaacaat   7500
attgtcttcc acctatgaac atgggcaaac tttgtgtaaa tggtcagatt gtaagtattt   7560
cgggctgtgt gggcacagtg tctctgtcac agctacgcgg ctctgccatt gtagcatgaa   7620
agtagccata agcaatatgt atgagtgtct gtgttccaat agaattttat taatgacaag   7680
gaagtttgaa tttcatataa ttttcacctg tcatgagata gtatttgatt attttggtca   7740
accatttaaa aatgtaaaaa catttcttag cttgtgaact agccaaaaat atgcaggtta   7800
tagttttccc actcctaggt taaaatatga taggaccaca tttggaaagc atttcttttt   7860
tttttttttt tttttttttt gagacggagt ttcactcttg ttgcccaggc tggagtgcag   7920
tggcgcgatc tcggctcact gcaacctctg cctcccaggt tcaagacatt ctcctgcacg   7980
gcctccctag tagctgggat tacaggcatg cgccaccaca cccagctaat tttgtatttt   8040
tagtagagac ggggtttctc catgttggtc aggctggtct tgaactcctg acctcaggtg   8100
atccacccgc ctcagcctcc caaagtgctg ggattacagg gtgtgagcca ccacaccctg   8160
ctggaaagca tttctttttt ggctgttttt gttttttttt taaactagtt ttgaaaatta   8220
taaaagttac acatatacat tataaaaata tcttcaagca gcacagatga aaaacaaagc   8280
ccttcttgca agtctgtcat ctttgtctaa cttcctaaga acaaaagtgt ttcttgtgtc   8340
ttcttcccag attttaatat gcatatacaa gcatttaaat gtgtcatttt ttgtttgctt   8400
gactgagatc acattacata tgtatttttt tacttaacaa tgtgtcatag atattgttcc   8460
atagcagtac ctgtaattct tattaattgc tatgtaatat tttagaattt ctttttaaaa   8520
gaggactttt ggagatgtaa aggcaaaggt ctcacatttt tgtggctgta gaatgtgctg   8580
gtgacatatt ctctctacct tgagaagtcc ccatccccat cacctccatt tcctgtaaat   8640
aagtcaacca cttgataaac tacctttgaa tggatccaca ctcaaaacat ttagtcttat   8700
```

-continued

```
tcagacaaca aggaggaaaa ataaaatacc ttataaagca ctgtttaata ttgtattaaa   8760
ttggatcaat ttgggggcta gaatgtatgt tagagacatg atatgtccat aggtccttgc   8820
tatcacagtg aggtctcagg gacagtcgtt tggtatcatt tgggatctca taagcagact   8880
ctctctgctt gacctgacaa atcagagtct gtgttttaac aggttcagtg agtgacttac   8940
atgcacattg gagtttggga agctccactg taggtgctta gaccttacct ttgttgttgc   9000
taataacaat gcaagcattt gggaggaaga cctgtgttgc tcatatgtgt ccaggtgtag   9060
ctgaggtggc cttgcttatc tgctgtaggg ccgttgagca tttctgtagc tgtgatgagt   9120
gagctgaggt gagcctgcgg agagctccca gccattggta gtgggactcg cttagatgaa   9180
ctggaaggac cctttcatct gagcagccac tatggagaaa aacaaccgaa tgaggggaga   9240
gacaatgtgc aattttattt agggcacaaa ggagagctgt ggttagaagg tgacatttga   9300
gtggaaaggg ggcaagccat gtgtatagcg ggagaagaga ggtccaggca gagttaacag   9360
aaggcagaaa tgctttccat gtttgagaac cagtaaggag gccagtggct gaagtaaggt   9420
gaagggcaga aataaggatg aggctgcgag agatgagagg ttagagacga gcgtcttgtg   9480
caccaagata agcttgtgtg gtcaaaacaa gtagtttaat ttatgttttt aaaagatcat   9540
tttggctggg cacaatggtt catgcctgta ataccagtag tttgagacgg tgtggtggga   9600
ggattgcctg aggccagacg accagcatag ccaacatagc agcacctata aggtctctac   9660
aaaaaacttt aaaaaattag ctgggcatag tggtgtgtgc ctgtagtccc agctactcag   9720
gaggctgagg aggctggagg attgcttgag tccaggagtt tgaggctgca gtgagctatg   9780
attatgccac tacactacaa cctgggcaag agagtgagac cctgtctcta aatatacaca   9840
cacacacaca cacacacaca cacacacaca cacacacaca cacacacaca catatatatg   9900
tatatatatg catttagatg aaaagatcac tttgacaata ccacatgctg gtgaggattt   9960
agaaaaacta ggtcacttat tgctggtggg aatataatat agtacggcca ctctggaaaa  10020
cagtttggca gtttgtcata aaactgaaca taccgttagt atacagccca gcagcaacta  10080
caatcctggg cattaatcct agagaaatga aaccttaatg ttcacataaa aacctatact  10140
caagtatgca tagcagcttt acccataata tctaagaact ggaatcagct cagatgtcct  10200
tcaacaggtg aatggttaaa ctactcagta ataaaaagga atgagctact gatagcatgc  10260
aacagtttag gtgaagttat gctaatgaaa aaagccaatc ccaaaaggtt atacatactg  10320
tatgattcta tgtttttttg caatggcaca gttttaggga tggagaatag attagtggtt  10380
gcctggggtt agagatgggg tagtagagta ggttagtggt ggcagaggag agaaaagaga  10440
gggaggtgaa tgtggttata aaaggacaac acaggggaat acttgtaatg gaaatgcttt  10500
gtcttttttt tttttttttt ttttttggcg acagagtctt gctctgttgc ccaggctgga  10560
gtgcagtggc atgatctttt ctcactgcaa cctctgcctc ctgggttcaa gtgatacttg  10620
tgtctcagtc tcccatgttc agagtgaaac aaaccagagg taatgttcat ccaaataatc  10680
caacacacat gacattaaaa catcaagatc aggtcggacg tggtggctca tgcctgtaat  10740
cccagcactt ttgggaggcc aaggtgggca gatcacttga ggtcaggagt tcgagaccag  10800
ccgggccaac atgatgaaac cccatcttga ctaaaaatac aaaaattagc cgggcatggt  10860
ggtgtgcacc tgtagtccca gctacttggg aggctgaggc aagagaactg cttgaacccg  10920
aggggcagag gttgcagtga gctgagagtg cgccattgca cttcagcctg tgtgacagag  10980
taagactcca tctccaaaaa aaaaaaacca agatcaatta aaatacagca ttactgggcc  11040
gggtgtggtg gctcacacct gtaatcccag cactttggga ggccgagatg ggcagatcac  11100
```

```
gaggtcagga gatccagacc atcccggcta acacggtgaa accccgtctc tactaaaaaa  11160
tacaaaaaat tagccgggta tagtggtggg tgcctgtagt cccagctact tgggaggctg  11220
aagcaggaga atggtgtgaa cccgggaggc agagctggca gtgagctgag atcgcgccac  11280
tgcactccag cctgggcgac agagcaagac tccgtctcgg gggaaaaaaa aaaataaata  11340
aatagaatgc tgtagtgtcc ttgagtttac atgcccctcc ttacgcttgt gtgcccgtgc  11400
agattgcttg attacacaat tagaggaggc tggcggagga ttgttttaat ttttttttt  11460
ttgagacagt ctggctctgt tccccaggct agagtgcaat ggcgcaatct tggtgcactg  11520
caacctctgc ctcctgggtt caagcagttc ttctgccgca gcctcccgag tagctgggat  11580
tataggcgcc cgccaccacg cccaactatt ttttgtattt ttagtagagc agcgtttcac  11640
catgctggcc aggctggtct cgaactcctg acctcagatg atctgctgcc ccagcctccc  11700
aaagtgctgg gattacaggc gtgagccaca cctggccgtt tgttttaatt ttgaaggtga  11760
agtgaaagtg actacattta ccaaaagtga ttgaaaagcc aggactgttc ttaccctgtt  11820
tttccagttc ttgctcagag caaggtggtt tctttttcac ttaatcacca tacttacttt  11880
tcatgtagaa caagtcagtt tgagttatca gttcatcatc ttaactaaat tccatggggg  11940
aaggaattag ttttagtttc ttaaacttcc aggtttgctt attggacaaa atgagatagc  12000
aaggcagtgt ttttaagtta gattttttat ttctttggta atacaatttt ctcagaaact  12060
tagtagtctt ttagtttagt tgtttttagt tggtcctatg ttttggatca cccctctcta  12120
ctttattttg atagtgccaa ctgtgaagac atctgaagcc ataggtttgg atgggaagga  12180
ggcatcttta gcctgatcat cttcgccagg ctgtttatct ccttttgctt ggctgagaag  12240
tcttaatagg aggcttattc ccagctattt ggggacatag aagcagttag ccattgctta  12300
tattttactg aggtctgtgt ggtatgttga ttgtagtcag ttaacgattt tgagaactga  12360
aggcagcctg gtatatatag agtaggtatt agactgtgtt tcttctaatt gaatttccca  12420
tctcttgtaa tctatgccat catcttctgt actgctgaga aagaaagaaa gtttctaatc  12480
aaactatacc actggttgta agatgcagtt tggctttagt gatgttaaca catgattcaa  12540
acgtgaaatt gattgagtat tggtgaaata cagaggagat ttaaagccag aagacctggg  12600
tttaaatgct ggctgtatga cttcatatct gtgtgatctt gggcatgtca tggttggcac  12660
ttcaatttct tctctctata atgggggaag tgaggccagt catggtggct catacctata  12720
atcccagtgc tttgggaggc caagatggga agatcgcttg aggccaggag tttgagcaat  12780
tgggcaacat cgtgaggccc cgtctctaca aaatattttg aaaaaattag ccaggcccag  12840
tggtgcgtgc ctgtggtccg cgccactcag gaggctgaga cgggaggatc ctttcagcct  12900
aggagtttaa ggctaaagtg agccatgatt gtgctatcgt actccagcct gggcagcaga  12960
gcaagatcct gactctaaaa aaaagtaaaa taaagtaaaa tgggggaaat gaactgcttt  13020
agtaacatca tctgtttttt ctgtgagcag cgtagcttga cagccattgg tgaactcgtg  13080
ccctgtgctt ccctgtccag atccccattc tgcccgcaac atggagtata acggtttatt  13140
catagtagtc gagaaacact cactgaatga atgaatgagg tgtagaacta agtggagtgg  13200
gtaattcaac acatattaat ttccttcttt tttttatttt tagaaagaaa gaactttcag  13260
ctaccaagaa agaccgtgtg aatcattgtc tgacaatatg tgaaaacata gtggcacagt  13320
ctgtcaggta attgcacttt gaactgtcta gagaaaataa gaactttgta tattttcagt  13380
cttaatgggc tagaatattc tttgtgtccc agctatttta aatggattca gaaatccatt  13440
```

taagatgaag aaggaccctt ttcccatatt tctggctata tacaaggata tccagacact 13500
gaaatgaata atgttccctt tttgtaatct tttatgcaaa aattaaaacc attatggtaa 13560
ttgaacaaca tgtttatgtt tagttaacac ccttagcaac tatagttatt ttaaaaccat 13620
ctatggtttg atatttttgc atttgttgca atagtaggaa cagcacaaga cagttcagtt 13680
tgtctctctt atttgctttt tcttggcagt ttgctgtcct attgtacctc tgctcctagc 13740
agtggctgga gcccactcct ctgtgcttcg ggattagtgg ggatcgtggg gcattgactg 13800
taggtcagct ttccttgctt gatctttctc actgggatga actagcagca ccttcttttg 13860
tagctgcttt gcttttgact atctttctga ccgttgttcc tagtagctgt agatggtaaa 13920
tatatttagg cctgtttcca atggctcagt aggagacata ttcacctatg atatctgaat 13980
tctgttaccc acatgggcat gcgtgaaata gttgccttgc cttactttcc cttggaataa 14040
ataattcatg ttattctcct ggtagaagct agaaaaagcc tttatagtca gtcagaaaaa 14100
aatttttaga caaataatct tgattttagt actgacaaaa acgtgtggtg attctttttt 14160
taattttttt ttgagacgga gtttcactct tgttgcccag gctggagtgc aatggcgtga 14220
tctcggctca ctgcaacctc tgcctcctgg gttcaagtga ttctcctgcc tcagcctccc 14280
aagtagctgg agttacaggc atgtgctact gtgcccagct aattttgtat ttttagtaga 14340
gatgttggtc aggctgatct cgaactccca accttaggtg atctgcccgc ctcagcctcc 14400
caaagtgctg ggattacagg cgtgagccag ggcgcccggt gattcatttg tttttttcaaa 14460
aaatttcctc ttggccattg cttttcactt ttgttttttt ttttttttttg agacggagtc 14520
acgatctgtc acccaggctg gagtgcagtg gcatgatctt ggcttactgc aagctctgcc 14580
tcccaggttc acgccattct cctgcttcag cctggcgagt agctgggact acaggtgctc 14640
gccaccacac ccggctaatt ttttgtattt ttagtagaga tggggtttca ccgtggtctt 14700
gatctcctga cctcatgacc cgctcaactc agcctcccaa agtgctggga ttacaggcgt 14760
gagccaccgc gcccggccct ctcttgtctt tttattgtgg taaaatgcac ataaaattga 14820
ctgtcttaac catttttagg ggtacagttc agtatatata ttcgtaatgt tgtacagcca 14880
tcactgccat ctacttcata agtttttctt ctgtcaaaac tgaacatctg tcttcattaa 14940
actccctatc atccattctt tcctgtagtc cctttctact ttctgtctgt atgagtgtaa 15000
ctgctctgga gacctcatgt aagtggattc ctacaggatt tgtgtttttt ttttggtgat 15060
ctgcttattt ttaatgcctc tgtgcatttg tattatatac tttcaaagtg atttcacaaa 15120
accgtttcat tttaggttaa ctcatttctg ttgtttgtga aatactgtgt atgattctgt 15180
tctgtttctg tctaatttgt ggaaatgttg tgggaagaaa atgaaataac aaatgagcat 15240
atgtcctgaa aataaaaata taaaaattct aagttagcat gctattgtag aatacaacgc 15300
tatgataaaa gtaggaaaaa aaaaggtttg aattctatct ctgctacctg tgtaagctgg 15360
gtgactttag ataagctgta acgtgtttga gccttactgg ctcatttttg aaatgtaatc 15420
cctagttaca cagttcttgt gggatcagat ggtacatgtg aaacactgtg aaaaagcaac 15480
tgcatagata tgttcattag ccacctgagc gggaagcgta tcccattgcg atgcccatca 15540
tccaaagcta tatgttatct ttactttttt ttttttgaga cagagtcttg ctctgttgcc 15600
caggctagag tgcagtggtg caatctcagc tcactgcaag ctccacctcc cgggttcacg 15660
ctattctcct gccccagcct cccaagtagc tgggactaca ggcacccgcc accatgcctg 15720
gctaaatttt tgtattttta gtagagatgg ggtttcaccg tgttagccag gatggtcttg 15780
atctcctgac ctcgtgatcc gcccgcctcg gcctcccaaa gtgctgggat tacaggcgtg 15840

-continued

```
agccactgcc cctggccatc tttacttttt ttgtgaaatg actttaaata cttggcaaac  15900
atttggtcat tgttcatctg atctccacca tccaggtctc agagaacata atttctctct  15960
gaaagcttat tgacccagga aataagatct ctttcaatct gagtgcgtca ggctttattc  16020
ttgtcatttt gtcttttgat aattttcaaa tggaattcat ggaatgttgg cttatattca  16080
tatattagta aagtatgttg agacatctta agattgattt gtggttctat atgccatatt  16140
aaatcaaaat aatagctgtt aatggttttc acattagtct gtctcttgtt tttatggagt  16200
aatgctgaga gttcattatg cttgttctac agaagagcat gttaaaagga gtttttggag  16260
tcagagaggt tattcttggt ttcataggat acactctata ctttttaggg atttcagagt  16320
atatagctga aggtgatatt ttatgtaaat atgttttatg gaaacttatt gctcatcgct  16380
gtttcctgtt aactctccta aaatataatt aaacttttgg aacttttttta tagcttttgt  16440
gctagactaa tttttgtctc taatgaggtt atataaatgg cagcttctga cgttttcaat  16500
gtaggaagtc atttaaaact tcatgtatat tgtgaaaatg tagtctgctt taagctctct  16560
aaagtggtct aagttactgg ttcctaagta tggatgagca tcaaaatcat ctggaaaatt  16620
tgttaaaaat acagtaatga aggcacctca ctgtcctttt tcccaaacat acttctgcat  16680
tctgtttgag taggtaggga ctacacattt ttcacaagta tcctcttggg aatacccagg  16740
aatgcttact tgagcaacct cttactaata tgtaccttga taaggtggct aggtaaacat  16800
aaatatacaa aaatccatag atctcccata tattagcata aatcagctag aaaatataac  16860
gtttaaagat ctagttcaca gtagcaccaa tatatcgaac tctaaggaat cgataaatat  16920
gcaaaaactt tataaaaact tctgttaatg tttctgaaag atataggtga ccactttcta  16980
gataggaaga ttttatatta ctaagttgaa ttttctctaa attaacacag aaatttaaaa  17040
taatcttgat caaaattcta gtagaggtat ttttgaactt gttcactgca agaataaata  17100
cataattgca aagaatatct caaaatcatc accaggcctg gtgtggtggc ccatgcctgt  17160
aatcccagca ctttgggagg ctgaggcagg cagatcacct gaggtcaaga gtttgagacc  17220
agctggacca gtgcggtgaa acactgcctc tactaaaaat acaaaaatta gctgggtgtg  17280
gtggtgcatg cctgtagtcc cagctacttg ggaggctgag gcaggagaat tgcttgaacc  17340
caggaggtac aggttgcggt gagcctagat cgcaccactg cattccagcc tgggcgacaa  17400
gagcaaaatt ctgtctcaag aaaaaagaga aaaaagaaaa agaaatcaac actaatatgg  17460
tgagacttaa tgtatgtgac attaaaatag tgattggatg ttaaaacagg tatagaacag  17520
aaagaagagt gtatgtgtgt atctgtatga atttatgatg ggtgtaacat atatgtatta  17580
gggaaatgag ggaaatgata catttctctg actttgggag aacattatat ctctacctca  17640
tattgcaaac aaacataaag ttcagattaa ttacctaaat gtgaaaaaat gaaataattt  17700
ctttaaaaaa tgtaatctta gtttgaggaa ggttaacatt ataaaggaaa aaactgtttt  17760
gagtggaata tagttcaata tgtcaaaatc caccttcaac aaaattgaaa gtaaattgaa  17820
cttggggaaa gtattgacag catatagatc aaaggttact agcctgtgta aagagcagtt  17880
ataaatatcg ttaagaaaaa cactgtcgac ctgtcggcac cttgttctcc gactcccagc  17940
ctccagaact gtgacgagta agtgcttatt gtttaaacca cccagtctgt atgtggtatt  18000
ttgttataga aactcaagct gattaggaca ctagtaatca gtagactgaa actgaaacaa  18060
aaataagaac ctttttttacc tgtcaaattg gcaaacatta agaatattca gatttttgtc  18120
agaggtgata caaccttcta agaaggcaat ttgggaaaat ataaagcttt agattattat  18180
```

-continued atgtctgacc tagcagtttt acctctaggg tgcttacccc taggaaagtg tgtaatgata 18240
ttggtgcagt gcccttcatc ccattagaaa attaaaaata accttaatgg cctaccacta 18300
aaaggggatt gaaaatttaa gatatattta tttatgtgtt tattgagatg gagtcttgca 18360
ctgtccgcct gggccagagt gcaatggtgc gatctcggct cactgcaacc tctgcttccc 18420
gggttcatgt gattctcctg cctcagcctc ctgagtagct gggattacag gctcacacca 18480
ccgcacccgg ctaatttttt gtatttttag tagagatggg gtttcactgt gttggccaga 18540
ctggtctcga actcctgacc tcatgatccg cgcccctcgg cctcccagtg ttgggattac 18600
aggtgtgagc cactgcgcct ggccagatac atttatacaa gagaatgtta gttaacattc 18660
atagatattt atattttgtt tactttttat taaaaaaatt ttttttagag acaggatctt 18720
actctgtcac ccaggcagga tgcagttgca caatcatagc ccactgcagc ctgaactcct 18780
gggcttaagt gatccttctg cctcagcctt ttgagtacct gggggacttt aggcagtgct 18840
actatacctg gctaattttt aaatgtttta tagatgagat cttgctgtat tgcccaggct 18900
ggtctagaat tcctgggccc aagtgatcct cccaccttgg cctcccaaag cgctgagatt 18960
acaggcatga gccaccactt ctgaccaata gatatttata tttgtgactg gaaaatatat 19020
taacaatgtg ttaaaaaatt cagttaaaaa ataatgaaag atttttgctt ctggctaaga 19080
tagaataaca aggacagcat ttatcttctt gccttgaaat agttgaaaac ggaagaaata 19140
tatgtaacag tggttttcaa gttattgggc atcaggcaaa gaagaatagt tatcccagga 19200
aaatgaatgt ggagagccct acaatttcct tacattactg cctggtcatg gcaagaggaa 19260
aaactgagag gagactgagg ctgagccagt ggtttgctgg gttgaggagg cagagctggg 19320
agtgcagaga tgcaaggtgg tgagagccca tatggaagaa taccagggaa gagagctgca 19380
gagggagctc cggagacctg caccctgccc tctcagtacc ctgtcatgtg tgtagctgag 19440
tactgacgag cacttgcttg tgcggaaatg acccagggct ggaggtagag ccacctgaaa 19500
ggattagaag gaacagttgc tgaaagtcac acagggccag gaagaatttc taatcacacc 19560
agttggagtg gaaaacctca gctctcatag agcaggtagg gtactcagaa gggtttgccc 19620
acctagcccc agactaagtt tcgttactct gaccctacct aatattaaaa agagattaat 19680
taaattgttc gcaacaaaaa taatatattt cagtgtttgt aacacgtaga agtgaattgt 19740
atgacaatag cataaaggct ggaagagcag aaattgacat gtatttgcgc tgggcagaat 19800
aatgctcccc tctttcccca aaagatatca agtcctaatc cctggagcct gtaaatatta 19860
ctttatatgg aaaattgttt tatgatgtga ttaaattcag gatcttgaga tgagggggct 19920
atcttggatg atctgggtag gcactaaatg caatcacata tatataaaaa ggaggcagag 19980
ggagatttta cacacagaga gaaggccctg tgaagatgga acagaaagat ttgaaggtgc 20040
tggccttgaa aattggagtg atgaagctat aagccaagga atgcagcagc caccaaagct 20100
ggaagaggca cggagcagtt ctcatttaga gcctactcca gagggaatgt ggtgctgcca 20160
attccttttt tttttttttt tttaagatat catttacccc tttaagttgg tttttttttt 20220
tttttttttt ttttagtatt tattgatcat tcttgggtgt ttcttggaga gggggatttg 20280
gcagggtcat aggacaatag tggagggaag gtcagcagat aaacatgtaa acaaaggtct 20340
ctggttttcc taggcagagg gccctgccac gttctgcagt gtttgtgtcc ctgggtactt 20400
gagattaggg agtggtgatg actcttaacg agtatgctgc cttcaagcat ctgtttaaca 20460
aagcacatct tgcaccgccc ttaatccatt taacccttag tggacacagc acatgtttca 20520
gagagcacgg ggttgggggt aaggttatag attaacagca tcccaaggca gaagaatttt 20580

-continued

```
tcttagtaca gaacaaaatg gagtgtccta tgtctacttc tttctacgca gacacagtaa  20640
caatctgatc tctctttctt ttcccacatt tcctcctttt ctattcgaca aaactgccac  20700
cgtcatcatg gactgttctc aatgagctat tgggtacacc tcccagatgg ggtggcggcc  20760
gggcagaggg gctcctcact tcccagatgg ggcggccggg cagaggcgcc ccccaacctc  20820
ccagacgggg cggcggctgg gcgggggctg ccccccacct cccggacggg gcgggtggcc  20880
gggcgggggc tgcccaccac ctcccggacg gggcggctgg ccgggcgggg gctgcccccc  20940
acctcccgga cggggcgggt ggccgggcgg gggctgcccc ccacctcccg gacggggcgg  21000
ctggccgggc gggggctgcc ccccacctcc cggacggagc ggctgccggg cggaggggct  21060
cctcacttcc cggacggggc ggctgctggg cggaggggct cctcacttct cagacggggc  21120
ggctggtcag agacgctcct cacctcccag acggggtggc agtggggcag agacattctt  21180
aagttcccag acggagtcac ggccgggcag aggtgctctt cacatctcag acggggcggc  21240
ggggcagagg tgctccccac ttcccagacg atgggcggcc gggcagagat gctcctcact  21300
tcctagatgg gatgacagcc gggaagaggc gctcctcact tcccagactg ggcagccagg  21360
cagaggggct cctcacatcc cagacgatgg gcggccaggc agaaacgctc ctcacttcct  21420
agacggggtg gcggctgggc agaggccgca atcttggcac tttgggaggc caaggcaggc  21480
ggctgggagg tgaaggttgt agtgacccga gatcacgcca ctgcactcca gcctgggcaa  21540
cactgagcac tgagtgagcg agactccgtc tgcaatcccg gcacctcggg aggccgaggc  21600
tggcagatca cttgcagtca ggagctggag accagcccgg ccaacacggc gaaaccccgt  21660
ctccaccaaa aaacacgaaa accagtcaga catggcggtg cgtgcctgca atcccaggca  21720
cttggcaggc tgaggcagga gaatcaggta gggaggttgc agtgagtaga gatggtggca  21780
gtacagtcca gccttggctc ggcatcagag ggagactgtg cgagggcgag ggcgagggcg  21840
agggaattcc ttaatttcag tttagtgata ctaattttgg actctggcct ctaaaactgt  21900
gaaagaaaaa attttttgtt tgtttgtttc ttttaagcca catagtttgt ggtaatttgt  21960
tacagcagct gcaggaaact aatttatgct gcatgtgaaa tggtgtaata aggtagattg  22020
tgatgaagat acatagtata aacaattaag caacaactaa aagcacaaca aggaattata  22080
gctaatgaac caaaaaagga gattagaata ataaaaatgg tgaatcccaa agaagccaga  22140
aataggggaa gaggcaaata aaggaaagaa agagcttgat ggtagatttc aacctaacta  22200
tgtcaaaaag gacattacat gtaaaaggca gcgatttttc agattgaatg gaaaagtaag  22260
actcggtata tgctgctgcc tgcaagaaac acattctaaa tataaaggca aaaataacct  22320
acaggtaaca gaacggaaag aagttcactg tgcttacaag aattagatgc aagctagact  22380
ggttctgtta atatcagaca aagtggattt caaagcaaag gctcttgccc aggatgagat  22440
ggtcatttca taatgatgaa ggggattcgt tcatcagcct ggcatagcaa gctgaaatgt  22500
ttatgcaccg gactacagag ctaaaataca tgaagcaaag cctgacagaa ctacaagtag  22560
aaacagacaa atccacagtg atagagattt cagtagccgc tctcaatgat ttgtagaaca  22620
cgtagccata atatctggat ctagaacact tgaccaacac tgtcccctgt gcaacctcat  22680
tggcatttac aggacactcc acccagcacc agcagaagag acactctctc aagtgctcac  22740
agaatgtttg ccaagataga gcagatgctg ggccataaaa caagtctcta aattaaaagc  22800
attcaaatta ttcagagtat gttttctgac ctcagtatca ttaagttgga atatattata  22860
ggaagataac ctggaaaagc ctcagatatg tggaaaaacc catttccaca tggcccatgg  22920
```

-continued

```
gtcagaagtg aagtcaaaag ggaaatttga aagtcttttg gattgactga tataaaaaca  22980
atagatttct aaacttgtgg ggtgctgtta cagcatagta aatggaaatt tctagcatta  23040
aatgcctgtt ttaggaaaga aagatttcaa atcaatgacc tcagcttcta cctttggaaa  23100
cttgaaaatg acaagcaaat ggaatccaga gttaccagaa gggccaggta cggtggctta  23160
tgcctgcagt tctgccactt tgggaggccg aggcaggtgg attgtttgag actggcagtt  23220
gaagaccagc ctgggcagcc tagggagacc ccatatctac aaaaaacaaa aaaattagcc  23280
aggtgtggtg gcatgtgcct gtagtcccag ctaaccagga gtctaaggtg ggaggattgc  23340
ttgagtctgg gaggttgagg ctgcagtgaa ctgtgattgt gccactgtgt tccatcctgg  23400
gcaacagaat gagaccctgt ctcaaaaaca aaaacagtta ctagaagaat ggacatcata  23460
aagataggag cagaagtcag taaaatagaa aacaaaaata cataggaaat caataaaacc  23520
aaaagctggt tcatcaagaa catcaataaa ttggtaaagc tgataggaaa aacagtgaag  23580
tcacaaatta gcaatatcag gaatgaggga gatgacagta gtatagatta tatagatatt  23640
aaaaggactg tatgaggcag gtgtggtggt tcacgcctgt aatcccagca ccttgggagg  23700
ccgaggtgga cagatcacct gaggtcagga gtttgggacc agcctggcca acatggtgaa  23760
actctgtctc tactaaaaat acaaaaatta gttggtcgtg gtgctgtgtg cctgtaatcc  23820
cagctacttg ggaggctgag gcaggagaat tgcttgaacc tgggaggcgg aggttgcagt  23880
gagctgagat tgtgccgttg cactccagcc tgggtgacag agcaagactc catctcaaaa  23940
caaataaata aataaaaagg actatatggt aatattatga acaactttat gccaataaat  24000
ttgacaactt atagatgaaa tggatgagtt ccttgaaaga cacagaaact attaaagctc  24060
tctcaagaag atatagataa gctgattagc cctatatcta ttttattgaa tttaaatgta  24120
aaaatcaata tttagttact ggaaaacttt taagtgtggt tggaaatggt atacgaactt  24180
tttcaactga attttatgaa gtctaatcac aggtaaaggt tttctgatga aaatttagtg  24240
tctgaattga gatatactgt aaaaaatgtt atatatctta attatttctt cacattaatt  24300
acatgttgaa ataatacttt gggtgtattg ggttaaatta aatattatga aaatcttgcc  24360
tgttttcttt ttacttttga tgcgtcagct aggaaatata aaagtgtagc tcacattctg  24420
tttctgttga cagtactgct ttggagcaca gtgtttgaat gatctatcat ttcaaagacc  24480
tttcctcagt tcgttattca tggctgtctg tattccacat agataaggtc tgaaatactg  24540
ctaagtggca tgttttgttt tatgctttta taagtttgtt gatcattact gatgtggact  24600
tttggtgcct cttaggctca ttgctatctt ccaaccattg tttgcaattt ttacctagag  24660
ataaagagaa agagacattt ggtttcagag tagttagatt gggatcatga aagagcaacc  24720
tcattttgat gcttcaaaaa tagcacatcc cccgtattac tgggatttgc tattcttggg  24780
attacttcaa gaacatcctt gtgttactgg tttggatgct tctgaatgct gtgaagtcag  24840
tttcatgtac atggctcatc agtttagctc tctcttggct ttgtttagac agttggagca  24900
tgatggccta aacagcttct ttcaattaaa cattttaaaa tagtttacaa atagtaaaca  24960
aactccagtt tttgtgactc tttgtctcgc acaacaaaaa cacaatctga ccatgatcat  25020
ctggcatctt agggtgaaat atggttatac tttggcccat accgaaagca agattaaaaa  25080
ggggcaggag agatagactg ctgaactgat tttcaaggtt ccaagaatat tgtaggttaa  25140
gagtaaaagt aaacttttgg tagaaagcag tgggttgtct aggattgaag tatctgaagt  25200
ttttaaacga aaatttaaaa agaaaaatga gaattgcctt acaagtacaa tctcttcttt  25260
tttaaaaaat aaactttatt ttgaaatagt tttagattta tagaaaaaaa ttagataggg  25320
```

-continued

```
taggaagttt tcatataccc tacatccagt taccccagtt attatcatcc taatttagtg  25380
tgagacattt tcatgtttaa tgaatcaata ttgatatgct attaacttaa gtccagactt  25440
tattcagatt ttcttaattt ctatgtaatg tccttttttct gttccagaat tccatgcagg  25500
acaccggata cctcattaca tttcattgtc atgtcacctt aggctcctct tgacagtttc  25560
tcttcttttt ttgcttagaa attctccaga atttcagaaa cttctgggca tcgctatgga  25620
actttttctg ctgtgcagtg atgacgcaga gtcagatgtc aggatggtgg ctgacgaatg  25680
cctcaacaaa gttatcaaag taagaaccgt gtggatgatg ttctcctcag agctatcatt  25740
gttgtaggct gagagaagaa gcgatcattg agtgttcttc tgttttgagt ccctgaggat  25800
gtctgcactt ttttcctttc tgatgtatgg tttggaggtg ctctgttgta tggtttggag  25860
gtgctctgtt gtatggtttg gaggtgctct attgtatggt ttggaggtgc tctgttgtat  25920
ggtttggagg tgctcttgta tggtttggag gtgctcttgt atggtttgga ggtgctctgt  25980
tgtatggttt ggaggtggtc ttgtatggtt tgcaggtgct ctattgcatg gtttgcaggt  26040
gctctattgt atggtttgga agtgctcttg tatggtttgg aggtgctctt gtatggtttg  26100
gagatgctct attgtatggt ttgcaggtgc tctattgtat ggtttggaag tgctcttgta  26160
tggtttggag gtgctcttgt atggtttgga ggtgctctgt tgtatggttt ggaggtgctc  26220
tgttgtatgg tttggaggtg ctcttgtatg gtttggaggt gctctattgt atggtttgga  26280
gatgctctgg tatctgcctg cattgcttgc cacacctgcc cggtcagaag gcgctatgtt  26340
gacaattgtg cctgcacggt gcctaggtca atgaagggaa ccgatggtag ccactggatg  26400
ctcctgggaa aatgtcacta caggcaccag agaagccaga gctatgccca aatttctatg  26460
agtctcagtt ttcttaacca taaaatggga tcaatgtttt tgtggcatgt gtatgagtgt  26520
gtgtctgtgt atgtgtgagg attaaattgt gtatgtgtga ggactaattg ccactactgg  26580
atcctcaaag tggtaagaag tgttcttatt aataatgaca tccttacact cttacccagc  26640
aagattgatg ggtgtggcac tgcttctctt tttccatcac atggtttcca tggtatcctt  26700
ttgcccaggg aatctttgct ttgtggctag cactttgttg tttggctaat cacgctttct  26760
gtggtcagga cgctggcttc tctggagcca tgggattcta gctccctgtc ttgtccctag  26820
agtggtcact gtcttctctc tccgcttgca attcctgctt tgctcgcatc tcacttatgc  26880
agtgacgtat atcagtttca ccttgttctc cgtgcctgct gatcattggc accacttgca  26940
tggtgccatt tagggcctgc ttccagttaa gcttgcttct ccacaggcct aaatatcctt  27000
gcttgcttct tttattctca ctggcaggac cagggcggtc tgtctttgca tgagacaggg  27060
tctcgctcag tcacccaggc tggagtgcag tggctgatca cggctcattg cagccttgag  27120
ctaccgggct caagctatcc tcctggcttg gccccttgag tagctgggac tacaggcgtg  27180
caccaccatg cccagctaat ttttaaaatt atttgtagag atgggatctc gccaggttgc  27240
ccaggctggt cttgaacgcc tgggctcaag tgatcctccc tccttggttt cccaaagtgc  27300
tgggatcaca ggtgtgagcc actgtgcctg gcccttgatg tttcagttct tgatatttga  27360
tcctcagagt cagaaaatct aaaaagaggg ctatcccagg ttgccttggt tcatggcaaa  27420
tgggacgtta agagggcaga gagaatatga acagaaactg ttctaatatt ggtcatttaa  27480
tgtgtaagta ttgttctttt ttaaacctcc ttcatttttt ttccaggaat tgctggacac  27540
agtggcttgg tgtgtgtctg aggactgtag gccatggccc taggttgtgg ttttaggtct  27600
caggtgctct tcctggctgt ctccttgctt ctttcccatg tcctcttctt tgtttccagc  27660
```

-continued

```
catttctccc ttatgcttaa gtttggtgca gcagggtttg gctgctctca gattcctgct  27720
tcctcagatg ctgtagttgt caggcccagc gggctggcag cgggatcagg atctggctag  27780
gtttgctctc actgtggcag agtaggggga ggcgtgggag agcacgtgtg accccaggcc  27840
agctgtaggg agcataggca tggtcacgta gccttcaggt cctagacttt gtcttctcat  27900
gagtatggct gtgtgtgtat ggtgaaaact aggttctact tagcccaaga aaatgggcac  27960
attttgcatg tggtttctgt agagaaatgc actgggtatc tgacatagcc tggcagcatg  28020
cctccctcag gtaggttagt ctcaggcggt gaagcacgtg tgtccagcaa gaacttcata  28080
tgtggcataa agtctccgtt ctgtgaggtg ctggcaaatc accaccaccg tcaagaggct  28140
gaagtgattt ttgtctaggg aggcaggaaa ggcttcctgg agtcagcagc cagtaggtga  28200
aagagtagat tggagacctt cttaatcatc accgcctctt gtctcaaggg gtgccaggaa  28260
gctgtggagg ctgaacccat cttatgctgc cagagagtgg gacaccatga gggtcaggtc  28320
aaggggttgt accttgtttg gtagagaatt aggggctctt gaagactttg gatgtggtca  28380
ggggagtgta tcatttagga agagtgaccc ggtgaggacg tggggtagag gaggacaggt  28440
gggagggagt ccaggtggga gtgagtagac ccagcaggag tgcagggcct cgagccagga  28500
tggtggcagg gctgtgagga gaggcagcca cctgtgtgtc tgcggaagca ggggcaagag  28560
ggaagaggcc agcagcgtgc tgccatcacc cagcgactgg cgtagattgt gagagaccat  28620
tccctgctct taggaggggc tgagttttag ttttctcttg ttatacaata agcttggtat  28680
ttgtttacaa aacatttgta aagctaaatc aaggtttgat aaggcttcta gttttattta  28740
agaagtaatg ttgaaataaa tgtttgtcca attcgctttg ctcatttaag gactttcagt  28800
acaaactgca acaacaggat taggatttaa acgtttctga gatgttttta ctcctcagaa  28860
tttcccagaa tgtgatctgg ttttgatttt caagcttgct gacccaatag gttaacccac  28920
aagttttacg aagaccatct cagtccactt acatcaactg cccatgccac ggttaaagag  28980
atcatcgact gatgtttggc acagcttcct ccctcttggg tgggcaagca tttggaagag  29040
aaggctccta tgggtgagag tggggcacca aagtcttccc tgtcccatcc cctagcttga  29100
gaagcccttc tctaatgtgg actttgtgcc gttagcatcg ttactagctt gaagttgacc  29160
atctggacgt actttctggt ttagcctcac aagtgagcaa ggagggttga gagatgtgct  29220
gtgaggaatg tggggcccca gctggcagca ggctctgggt caggggggca gggaccacgg  29280
gcatacctga cagtgaggag gggccacacc tgcagaaaag gatgcaggac tccgccttgg  29340
gaagtgttct aggccagagc gagggtctgt ggtttataag tacacccaca gtgctcggga  29400
ccctgcagat gtccagggtg ccgtctgagc ccgtatcatc caacagaatg ttctgctagt  29460
gaagattaaa gatttactcc aggggcttta ggatttatta tatatatata aatcctatat  29520
atataatttt tttttttttt ttttttgaga tggagtttcg ctcttgttgc ccaggctgga  29580
gtgcaatggc gtgatcttgg ctcactgcaa cctccgcctc ccgggttcaa actattctcc  29640
tgcctcagcc tctcgagtag ctgggattac aggcgcccac caccacaccc ggctaatttt  29700
tgtatttttt agtagagacg gagtttctcc atgttggtca ggctggtctt gaactcctga  29760
cctcaggtga tctgcccgcc ttggcctccc aaagtgctgg gattacaggc atgagccacc  29820
ccacctggcc aggatttatt gtatttgaac catctaccat tttaattttg atgttatgta  29880
gtatttgatg ataatgaaag ttaaattgtt tttctttcca tttttctgtt taagtgaatg  29940
acctgtatct agtttattca gtaacttcct gcatatattt gtttctttca ttcttaatga  30000
atatattctt aatttagttg ctattatgtt ttgctttgcc ccaaaattga aatcttagtt  30060
```

-continued

```
tccttttagc tcgttttaga actagtgatg ggatgtgtct tccataaatc tcttgtgatt  30120
tgttgtaggc tttgatggat tctaatcttc caaggttaca gctcgagctc tataaggaaa  30180
ttaaaaaggt gggccttgct tttctttttt aaaaatgttt taaattttaa atttttatag  30240
gtacacgtat tttgtaggta catgtaaatg tatatattta tggggtacat gagatatttt  30300
gatacaggta tacaatacat aataatcaca ccatggaaag ttggatatcc atgccctcaa  30360
gcatttatcc tttgtgttac aaacaatcca gttacatgct ttacttattt tattttattt  30420
ttgagacaga gtcttgcttt cacccatgct agagtacagt ggcatgacct tggctcactg  30480
caacctccgc ctcccgggtt caaccgaact ttgggctggt ctcgaactcc tgacctcagg  30540
tgatccgccc gcctcggcct cccaaagtgt tgggattaca ggcgtgagcc actgtgccgg  30600
gcctgattgt acattttaaa ataactaaaa cagtcagggc acagtggctc atgcctgtaa  30660
tcccagcatt ttgggaggct gaggcaggtg atcacctgag atcaggagtt cgagaccagc  30720
ctggccaaca tggagaaacc ctgtctctac taaaaataca aaaattagcc aagtgtggtg  30780
gcgggcgcct gtaatcctgg ctactcggga ggctgaggta ggggaatcgc ttgaacctgg  30840
gggtggaggt tgcagtgagc cgagatcacg ccactgcatt ccagcctgag cgacagagtg  30900
agactttgtc tcaaaaaata aaaatgaaat aaaattgggc cgggtgtggt ggctcacacc  30960
ttagtcccag cactttggga acctgaggca ggtggatgct tgagaccagg agtttgagac  31020
cagcatgggc aacatggcaa aacgctgtct gtacagaaat tagctgggtg tggtggtgca  31080
caactatagt ctcagctact tgggagattg aggtgggagg attaattgag cctggaaggt  31140
tgaatctata ggtagctgag attgtgccac tgcccttcag cctgggcgac caagtgagac  31200
cctgtctcaa aagaaaaaca aaaaaacaaa aaacaaacca ctattatcga ctatatatta  31260
ttgtctatga tccctctgct gtgctgtcga ataccaggtc ttgggccctt atttccatca  31320
ctgagcaaac ttcactctgt taagcagcag gtgtgggatt tcatcgttat tcagtaattc  31380
acaatgttag aaggaaatgc tgtttggtag acgattgctt tacttttctt caaaaggtta  31440
ctctttatta gatgagatga gaattaaaaa tggtaactta ctttatatct ttataattga  31500
agcccactag accttaaagt agttaccaga tgttttatgc atttaaatgg ccttttctct  31560
aaaattagaa agtaacaagg aaagaaaatg cttcgtttct atgcaaccct cttggtgact  31620
agtatgtgac tcttaatgca accctcattg caccccctca gaatggtgcc cctcggagtt  31680
tgcgtgctgc cctgtggagg tttgctgagc tggctcacct ggttcggcct cagaaatgca  31740
ggtaagttgt acactctgga tgttggtttt tgtcgggggc cagctgctac tgatccttta  31800
tgtctcagct cagatgtcat ttcaaaagtc tgctctgccc tctccaaatt gcagtcgacc  31860
ttgccctgtt tatgtttccc tcatagcact aatccatgtc agaaattgtc acgtacagtc  31920
tatctgtgtg cttgtttatt ttctatccca cccttccgca agagacttat gggatgtgtg  31980
ccccaggaca gcaggggtct tactgtctta tgctctgttg cagcccagca gcgataacag  32040
tgtctgcaca tagtacttgc ttaaaagata cttgccaaat tgttgaaggt tgaggtacca  32100
atttcattat tgctgactat aggagttata gcaaaatatc catttgtctg ttacatgagt  32160
taaaaatatg gttgttgcac tgtgaatagt ttggtttagt caaaacagtt gtatcttaac  32220
ggattgagaa acaaaagcag gaccactttt catcagctcc ctccttctcc ttaaccagca  32280
atacatgctg atgctgatat cccatagacc ctcagctcca tcctgagtca ctgggaatgt  32340
ggtctaaacc ctcactatta atatgaactg agtttcaata agaatcttat atgggtcggg  32400
```

-continued

```
catagtggct catacctttg atcccagcac ttcaggaggc caaggcaggt ggattgcttg  32460
acccagacta ggcaacatgg tgaaacgccg cctctacaaa aaatacaaaa cttagccagg  32520
catggtggtg cgtgcctgtg gtcacagcca ctcgagaggc tgaggtggga ggatcacttg  32580
agcctgggag gtggaggtcg tgttgagcca agatcgcacc actgcactcc agcctgggca  32640
acagagtgag acctgtctca aaaaaaccaa aatccagaaa agaacttata tggctgcaga  32700
ggtataatca ctaaggaaat ttccttttgt ataatctttt ttcttttact atcatttaaa  32760
aaaatgtgtt atatttctga agcaacacat ccaggttctg cacatagcag ccaaagtgac  32820
cttaaagaat ataactgggt cttgtcattc ccttatttaa actcttgtac ccatttccca  32880
gtgccgttta gatagagatt ccagactcgt caatggctct gtcacctcag acaccctgca  32940
ttgactcatt agtctgatta gagtcaggtt tttcttcctc ctgatggttt tttttcccc  33000
cttagttctc agcggaacag tcacttcctt agggaggttt ccccagccac cctctgaggc  33060
cgtgcttgtt gccagactct gccactagag ggcagggctg caccactcct ggcacctcgc  33120
acccggcctg ccctgtcact ctgtgtgttg ggtgaattcc tgtgatctgt gactcactgc  33180
tctgtgtcct acacattcgg cttttcttct ctccccacaa ccccatttta taattctcct  33240
ttttcaggaa agctttattc ccatttaaaa atttttgttt ttaaaatggt attttcttac  33300
acttattttc taattaaaaa tgagtgtttt aagaagtatt atgatttact gcaaataatt  33360
tttaaaccca gccttttaga tcctctgtga tcataagaga aatgaaggat gtctcccaac  33420
acttgagctt catccacatt tcatcctcct gttctttcag ctgagttttc cccatcccat  33480
tagggactgt tggaatataa aactggcttt tccctaacag ggaatgaatt gcttctgttt  33540
ctcctgaagg agagctggaa gaatgacttg cgttcttttg catacacagg ccttacctgg  33600
tgaaccttct gccgtgcctg actcgaacaa gcaagagacc cgaagaatca gtccaggaga  33660
ccttggctgc agctgttccc aaaattatgg cttcttttgg caattttgca aatgacaatg  33720
aaattaaggt atgattgttg cctcaggtca caaacatgcg agtgatgctg tgagtgagtc  33780
tgtggagggt gagggcttct gaacagggag tcctgtggga gtgcttcttg ggtatgttg  33840
tatgtcgtaa tttagactac catcatttgt gttattttg aggcacctaa ggacttcttt  33900
ccacttctca tttcttactg tggggtgaag agttgaattg ggagatggtt tctagatgca  33960
aattgaaaag gcatttttcc agagcagatt tgttttcggc gtactagagt gactctttaa  34020
cctagctgcg ggaagatgac tgtgccaaga ctgcaggtag gagaaagctc actgacgagg  34080
ccttgtgggt ctgaacgtcc tgcagctatc agagcctgtt ggcttcctgt tgtgcattcc  34140
aacaaatcat cttcaaaccc actttagtgt tttgtttata atgtccagaa atagtgaccc  34200
tgtcacatgc tctacagatt acaggattct tagcctcttc ctttttggta ggtcagtcct  34260
gggtttgagc ccaagtgacc ctcctgggag gtgatgatac acactgggta gagtggaatc  34320
agatggactt ggattagaat tctgtcctct ttactagtta ttttcctcta ggcaaactgc  34380
ccaacagctc taagctattt ccttcgtatt ctgaaaaata agccttaatg ggacccatat  34440
agggcaactc tgagagtaaa ataaaggaat atgtgttaga gtgtagcata gtcacccacg  34500
ggaagggctt agatgttagc tgctactgct cttattagct gaatgatttg gaataaactg  34560
ttagcctctc tcatgttttt tctcttgagc ttcgaagttt tcttgttaat actaaggaga  34620
tattcaaact agtcatgggg ttttggaatg acgaagggag atgatgaatc taaagaattt  34680
agtgtaatat ttcttcatgc tcagtaaatg gtagtttctg ctgctgttat ttttattacc  34740
atctctttgg aatgggagta ggtgctcctt tgtggtcaga ggctgtgaga gctccacagc  34800
```

gccagtttgc ccatctgtac actggggtct gttgaaggca gtcccctctg tgatatctct 34860
ggctgtcaga gctcagatga tagatggtat ttttgtactc ttagttctca tcattttcat 34920
gatttcgatc accatttgag tatgatgatg ctaacacttt gttgaacgta gaatccgtta 34980
attacttcct tcctgaacct ttggcattaa aaaaaatcta ttctgctacc tctctgctca 35040
tttatggtta ttcaaattta ttatcaagag cctggtacag tggcttgtgc ctataattgt 35100
agctacttgg gaggctgagg taggaggatt gcttgaggcc aggagtttga gaccagcctg 35160
ggcaagatag tgagacccta tctctaaaaa aactgaaaaa aaattagctg gacatgatgg 35220
catgtgcctg tggtcctagc tactcaggag gctgagacag gaggctcggt tgagcccagg 35280
agttggagtt cgaggctaca ctgagctgtg attgtgccac cacactccag catgggtggt 35340
aaaacaagat gccatttctt aaaaaaaaaa aatatatata tatatattat caatgaaatt 35400
cagtagtacc aacaggatta taaacaaaga tagtagttcc cttcctactt tttctcttaa 35460
tccttgtgtc tcacaggcaa acataactct tagtatttct tccaatattt actttcatgt 35520
ttctttcttt ctttcttttt ttttctttga gatggagttt tgctcttgtt gccaaggctg 35580
gagtgcaatg acgcaatctt ggctcaccac aacctctgtc tcccgggttc aagcgattct 35640
cctgcctcag cctcctagta gctgggatta caggcatgca tcaccacgct cggctaattt 35700
tgtactttta gtagagatgg ggtttctccg ggttggtcag gctggtctcg aactcctgac 35760
ctcaggtgat cctcccacct cagcctccca aagtgctggg attacaggcg tgagccactg 35820
cgcccagcaa cttccacatt tctaaataac atgcttctac tgctattttt tttttcaatt 35880
ttagacattt ttttactttc actatagttc tatcagaatt cagtgtgtac gttattatgc 35940
ctaagtaaat agtcatggtt gcttacgtat tatatttctt tgattgtgtt tcttatttga 36000
tgagaaagct gtgtttttg ctctgggttg aaactggaga gaggacctgg ggaggaggag 36060
gaggacagat gaagttggtg actgtacctt catggccata gctgggttct cagcacccgg 36120
ggatctgctg atcacctact cataggccag gcccctatcg aagttctagg tgacccagtg 36180
ctggggacgg gggggccacc tgcaaggtct aatcatggag gtgggggcta cagtgttggc 36240
ttgtgctggg gccagcatcc ttaggaaggc atcttggagg tggaggagac agccgcccac 36300
ttcttgattg gggccttcag cagcaccagc ttcttgggca ggctggtgct ggctttcatc 36360
accatgtcgt gttcaatctt cttccagatc ctgacttcta ggttcagctt tcctcagacc 36420
ctggttcctt tcagaggcca ttgctgctgc cttgctcttt gctggcttgt gccttgatta 36480
tatgtctttg tacaactttt tgttttcctg gagttaatct tcacatctgt tttcttggag 36540
ttaatcgtta cctctatatc gcttgcttat tattctttgg ccttttgtc ttctcacacc 36600
ttccaacttc tttgtaatat gtgtttagta caatttttca tgacaggtag tttactgaat 36660
cagtttttcc ccagtgtggt catccaactt gagttatcca gctctctgcc ccagtctggg 36720
caggttgatc ttcaggtctg tagtacactt gtatcctagg acttctcttt gccattagcc 36780
tggaatttcc tttgcagttc tcccgttgga tgcccagttc ctagatgcca tatgtttttc 36840
tatcgtctag tagcttcctg agagaagatg aatgggaggg aaattgtatg aggttttgca 36900
ttcataaaaa tgccattttt tttcctgtac acttggctgg gtatggtgtt ctggggtaga 36960
aatcattttc cctcagaaat gcaaagtctt tgccctgttg tcttaaaatc tccaacgtga 37020
cccgattcct taacctatga atgtactttt ctttggaagc tttccatttt tggggaggtg 37080
aagtgctagg tacttagtag gccttttaat ttggaaactt acatcccttc agttctggga 37140

-continued

```
aaattttctt aacatttctc tgagaagttc ttgcctttta ttttctgtgt tctctcctga  37200
aattggttag ttggatgttg gtcctcctag attgactcac atcttacctt tttcttttct  37260
ttttctggta ctttttagat atccatctca aactcttcta ttcattgtta tgtttttaac  37320
ttctttcttt tctttgtctc ttgatggggt cttgccctgt tgcccaggtt gtggtgcagt  37380
ggtgcgatca tagctcactg cagcctcaaa ttcctgggct caagcagctg ttctgcctca  37440
ccctcccaag tagttgggac tacaggtatg caccaccacg tccagctatt ttctttactt  37500
tttttttttt ttttttgaga tggagtccta ctctgtcgcc caggctagag tgcggtggtg  37560
ggattttggc tcacttaagc ctctgcctcc caggttcaag cagttctcct gcctcagcct  37620
ctcaagtagc tgggattaca ggtgtgcacc accatgcccg gctaattttt gtatttttag  37680
tagagccaga gtttcaccat gttggccagg ctggtctcga acgcctgacc tcaggtgatc  37740
cgcctgcctt ggcctccgaa agtgccggga ttacaggcgt gagcccatca ttagatcttt  37800
aaataccagt atctataagt cttttcctct tgagtcagct agtatccctg gaaggaaatt  37860
actcattttc ctgcttggag gctataagct tggctatgtt tatcctgcaa ccggggactg  37920
gaagggaggg gactgacagt gttgctggtc agggtgccct cttacttttt gttttctgtg  37980
tgcatctcac gtctgtcctc agcctatgta aacacctctt gagattatcc ctctcaatct  38040
ttgccggagg tgggggaggg gctgcttcct gggctgcctt ggattggagg gaagacctca  38100
ggtgagtggg tgggaatttg cccaaggagc catgagacca gccactattt caccctctcc  38160
atccctccac tttcagatgt atgtggcgcc tccaaagccc gagctcttct tggcgtctgt  38220
ggcttcaata agcttgcttt ttgctggtat ccctcctacc ctcccctgtc cccagcaaag  38280
cttgcatttg aacttcttcc tacgggctaa caaatcagtc agttatgtag ctcttgttac  38340
tttttagctt ccgaagtttt gttgacaccc gtagtctgct aatgtccctg ttctgttctt  38400
tctgttcgtg taaatatatg ctttatacaa cttctttaca tgatttttgt ggggtttctg  38460
ggtagcagag cttcacaagt tcaatccagc gtgttggatt agaaatctcc caccctctgg  38520
tttattctta ttctcaaaat tacctgccaa acactgatac tcccttgttt ttccttttcc  38580
tgacaggaaa tgtacatacc atacaggaca gaaatcatta gtgtatccct tggtgaataa  38640
ccacaaagtg aacttaaccc ttgtaaccgc cacccaggtc aagacagaat attaccaagc  38700
actcagaagc ctctccccta ttcccccgtc actgctcctg ccttcctccc caaggtcatg  38760
actgctggct tctaattcca gagtctgttt ttaaattctg tgtacataga ccatggatta  38820
agtgttcttt ttgtctggtt tattttggtc gacattaagt tcatgagagt cttctatatt  38880
atcgtgtgta ttagtattcc tgtagtttta ggagcttcat agcattccat tgtagggata  38940
taccacagtt tattcattgt attatcactg ggttgtttct agttcttggc tattgcgagc  39000
agtgctactg tgaccactct taggtgtgtc ttttggagta catgtgcagg tttccatctt  39060
gcacagctag aggtggagtt gttgggtgat agggtgtgtg catctcagct gcagtagaaa  39120
ctgccaaata gctttccttg agtgcttgta ccagctcacc cttttgccac tgtgtatggg  39180
gattccagga gctctggtcc tcgctagcac ttggaattgc tgatgctttt actcttagcc  39240
ttcctgatgg gtgttttctg gaatcacatt atgattttaa tttccattcc ttaaagtacc  39300
cttggctctg aagtttaatg attcatgcat ctcttccctt ttgaagtact cttacaggta  39360
tgttgtgcat gtgttgaaaa gtggcactat ctattctaaa atacagtatg cctcctctgt  39420
gtttgaacag ttgtagcgtg gccttggggc ctcctgttag ctggcttgga gaagggattc  39480
ttgggattgt agagattaga cctgaggagg ccccttggag ctctctgact aaattttatt  39540
```

```
ctttattatt ccaaactatt taagctcacc gtgtgctgac tcatcataat aatgagtagc  39600
tctcattgtg cttgtctatt tggactcata caatgatttt tttttttct ttgagacaga  39660
gtcttgctct gttgcctagg ctggagtgca gtggcacaat ctcggctcac tgcagcctcc  39720
acctcccagg ttcaagtgat tcttgtgcct cagcttctca agtagctgag actgcaggtg  39780
cgtaccacca tgcctggcta atgtttgtat ttttagtaga gacggggttt caccatgttg  39840
gccaggttgg tctcaaactc ctgacctcaa gtgatctgcc ttcttcagcc tcccaaagtg  39900
ctgggattac aggtgtgagc cactgagctt ggccaaagta gttttttaag atgttagtat  39960
cttttcttgc agctaaaaaa gtttgtcaga gatgattcta ctttgttctc caggtgtttt  40020
ctcagggaga aattggaggc agtaagccac tgggggagtc ctgtggctgg ggggtggggt  40080
agtcctgtgg ctccttgtca gggagtcctg tggctggcaa ggagagaagt cctgtggctg  40140
ggttgggagg gagtcctgtg gctggggtct catcctgtgc ctaacagtgt ccagaggtgc  40200
cgagaccagc tcagtcgggg agaccctaac ccagcagcgc tagaggaatt aaagacacac  40260
acacagaaat atagaggtgt gaagtgggaa atcaggggtc tcacagcctt tagagctgag  40320
agccctgaac agagatttac ccacatattt attaatagca aaccagtcat tagcattgtt  40380
tctatagatg ttaaattaac taaaagtatc ccttatggga aacgagggga tgggccgaat  40440
taaaagaaga ggttgggcta gttaaccgca gcaggagcat gtccttaagg cacagatcgc  40500
tcatgctatt gtttgtggct taagaatgcc tttaagcggt tttccaccct gggtgggcca  40560
ggtgttcctt gccctcattc ctgtcaaccc acaaccttcc agtgtgggca ttagggccat  40620
tatgaacatg ttacagtgct tcagagattt tgtttatggc cagttttggg gccagtttat  40680
ggccagattt tggggggcct gctcccaata cagaggtctc gtgtaaattc cctgggaggc  40740
gataagcctc tgagaaacag actatgctaa ccacgccatg aaagagaaac ttatttataa  40800
atcagatgcc agttactagt ttactgctta tttgcccagg cgtagctctg acagagtccc  40860
cgactcatag tgcttgctca gtgcatgctg aacaatgatt ggaatcaagt catggctcag  40920
agcatagttt tgaataatgg gaaatggatg ttcttaagta acatagtcac caagataatg  40980
cgactagctg ggtcacccct tttcaatttt aggatatttt tatcaagatt taaatggcca  41040
tcattagagt tatagcactt tctcctttgg attgtcctag aggcccatga gaaagtattc  41100
cctaatttct taggagaaca gtttgtgggt agtatgcggt catgtccagt taaattgcag  41160
atatttccga tcgaagatgt tccagtcctg agaacttcgt gacattagca ggacttctac  41220
aagccatctc ttagggtggg gcatttactg cagttggcta gtactctttt ctccttaact  41280
ttgtcatttg ttgatttttt tttaactgtc cccaaatact gtgggcagag tgtatctaga  41340
attgaggcct ccaccattgc ggagaggaca tggatgctga gcagtcccct gagtgaaggt  41400
tataaagaag caaatagact acacatgtct gtaaactgct cttgagtgtc ccaaatttgg  41460
ggtacttcag ttcagctgta ggaaaagcct caaactgttt atactttgca agaattggaa  41520
acttctaatt cacgttaagt tttatgtaat acatgataag cttcatagga gcttcatctt  41580
ttatctactt ggacttttgc ttccgtaggt tttgttaaag gccttcatag cgaacctgaa  41640
gtcaagctcc cccaccattc ggcggacagc ggctggatca gcagtgagca tctgccagca  41700
ctcaagaagg acacaatatt tctatagttg gctactaaat gtgctcttag gtaaggtgga  41760
ggcatatgag tggaagagtc tccagcatgt actcaagata gacctttgaa ataaataaaa  41820
ccagatgatc cctcagcttc tagaccaggc tatttggcac tggttgattg aatgtgaact  41880
```

-continued

```
gcactggggc tgctgtgagc ccgcatgggt ctctgtgacc ctgcagatgc agccgtgccc  41940
agggactggg cagtgggtgt gggctggtgt gagccctgtc tgccacccag ggcctggccc  42000
tctgtctgtg tcggccatga ctatggtgag tcttgtaggc ttgagactgt gcctcgggtt  42060
cctgcgggtt ctctgtaggt cagttgacag tttctcctgt tgtttgggta actgtggaaa  42120
cgaacactgg caagtgctga agcgagcatg tggacgtgcg atatgaaata acgacctggc  42180
tttcaaaggc agtgaggctc tctggaaagg accttgctga gctagggatg tgggtgtgta  42240
gccattccca gtgggcctca tggcgtactc gttcatgatc atgtttgtgc catcttgatc  42300
tctcaggatc tcttcttttt taacagatta agccgggaat ctccaaacag tgagtcagat  42360
gttaagatgt cttgcttcca cccccacagg cttactcgtt cctgtcgagg atgaacactc  42420
cactctgctg attcttggcg tgctgctcac cctgaggtat ttggtgccct tgctgcagca  42480
gcaggtcaag gacacaagcc tgaaaggcag cttcggagtg acaaggaaag aaatggaagt  42540
ctctccttct gcagagcagc ttgtccaggt aggagcacag ggtttactct aggccctgca  42600
tgtgaatgac tgacattcaa agaaccgatt aatttggaag agaagcggca gaaccgagag  42660
ttagaggtgt ggactctgga gctgcgctgc tcgtttccaa ccctaggtgc tgacctctag  42720
ctgtcttccc tctgtatgtc cctgtcaccg tgagtcaaat gcgggtgatg cctcctcagg  42780
tgccgtgtta cctaagcctc tcagagacca ctgctaccct gtttctaaaa ccagaggtca  42840
cgatatgtgt tcatccaccc agtaaatact gattgagcac ccactgtgtg ctaggctctg  42900
ggataggggc tgggtataca atggtgagta tttcagctgc agcttctgcc ccgtggaggc  42960
tgtggcctag cacactggtc taggcacggt ggtatatgct cactcaagga gatagggacg  43020
tggtcgtttg ggtgtcgga acaaaatgtc ggaacttctc tttccaatgc agagaaacct  43080
tgcagtaatt ctaatgtact gtgattggca gttgacttca gttctttgta gcacgcttac  43140
tcaggttatt tcactaacta tgtaaccatg cagcctcatt ttaagcaatt ggattttttg  43200
aactttactt aaaatgttat gtcagggttt ttattgtgct taatgtgtgc catttagcta  43260
agttttgtag gatacgaaat tgtaagtggc ttaaaatgat tcttaataga atcatgaatt  43320
gaagataatg ctaataattt aagcactgag ttaggtagtg tttgtaaaat gcttagaatg  43380
cttcctggca catgttaagg ccatgtaagt gctgcgtgtt gataaacagc tgagcaaaag  43440
tggactctta agaaagtatt ggggctgaga gttctgttcc aaccagctgc cctttggtta  43500
tttttcagaa taaaagcaga gtctcatggg atatgacatt tatatttcct tcacaaaaaa  43560
cactgctgag tgttttgttg agtaaaaagg gtgtagccat ggtaataata catttaaaat  43620
atagtttatt tcatctttac cttgccttgt ttttttttta agctagcttt ttattgagaa  43680
ttccacacat acaaaagtat caactcatga ccagttatat ttcatttata atcctacttc  43740
tcccttttttt tattatttga aagcaaaccc caattatcct cttatttcat ctataagtat  43800
ttcagtatct ctatagatga ggactcttct ttatttttaa aactttattt ttaaaatgat  43860
ggtcagatgc agtgttcatg cctgtaatcc cagaactttg ggaggccaag ctgggcggat  43920
cacttgaacc tgggagtttg agaccagccc gggaaacatg gcgaaacccc atgtcttaaa  43980
gaaaaaaatc agccaagtgt ggtgatgcat gcctgtagtc ccagctactt gggaggctga  44040
gatgggaggg tcacatgagc ctggaagatc aaggctgcag tgatccatga ttgtaccact  44100
gcactccatc ctgggtgatg gagcaagatt ctgtctcaaa aaaacaaaac tgcaaaacaa  44160
cgtcacaaaa cagtgccatt gttagacctg aaaatattaa acatttccta catcaaatac  44220
ccaccaactc attatcaatt tttctctcta ctcttttgga atcagcatct aaataaaatt  44280
```

ggtcgataag gattgtaaat ctctttgatg aactggttcc cctccatccc agttttttc 44340
ccttagagtt catttattga gaaaccagat tgtttgtctt ctaagttttc ctgtggtctg 44400
atatactgct tccatctcca ctgtgtaaat taacaccttt ttctcttctc tgtatttcct 44460
gtaaatcaat aattggagga aaagccttgt cagatttagt gtatatttta tatctgagtc 44520
cagtatttct tatataatat tttaagataa gtgtactctt ttaaaaagta ttgaaactat 44580
atgctcaatt ttttttaact gatgctttta agaaggctgc ttgatcataa aagtttagag 44640
atcattggtc tgatgggaaa agcaaataat tactaaaccg tttagcaagg ttgaggtgca 44700
catggtgggg cctggagaag ttcagtcatg agccgtcact tatgggcacg tggaatctga 44760
cccggcacag agttgggaga agacaggagc tttatagaca gaaaatgtgg tctttgctaa 44820
gtcccaggag tgaaagggtg agacagtgct cacagcacac gagtgtgggt gcgtagacag 44880
agcaagggtg ggtcctgaaa aggcctgcag gctttctcat agattagcaa gagtgctggt 44940
tacggaggtt tctaacattt gtgaacagat cgaaactgtg ttaaattggg attgcagtaa 45000
tcctggaagg acagggatag agggtgaagg ggaaaaaagg gtatggatgt gagacttaat 45060
tgctgatttt cttaagacct ttctccaaag taaataaatg atgtggcaca tttttgaact 45120
ggcaaattct aaactctaga tatgattatc tctataacat atcttactcc atcttctttt 45180
gactaaaaac tgttcttaat taaattacca tgagacgttc aattcagcaa atgtagtttg 45240
gctaaccata tttaattaga atttaatata atcctaggcc tggccaaact attaagcaag 45300
tgtgggcaaa atattgataa ttttagatat gcaggaactt agtttgcttt ccatgtgtgc 45360
ttttcgaaaa aggaataaat tgaaaaatag aggaagccct gaaatccaag aagcaaactc 45420
tctcacctag gcatgcagta aaagcaattc taggatgatt gctgtttggc gcgtagttcg 45480
tattagaaac cattcttctt gaataaatag tatgtttaag aagctgggca gagggaaggc 45540
atatgcatat attatcaaca aggagggaga aaaaggcaat tagtaaccat ccataggagg 45600
gtcagcaaga tttataaagg aaatttgtga tccaagtatg aagcaaaata aggtgcagaa 45660
taaattttaa gcaagtaata gattagagta agagaaccca tttgaccatt aaccttggga 45720
cattctcttt caaatgacat ggagtagtac tgaaatcttt ctttctttct gagtctaggt 45780
tattgtgact ggactcagaa agaaatattt cattattgca gtgaataaca tttgtgaaca 45840
ttattgttca taaattatgc agtgaataac atttatgaac acgtgatgtg taagatacat 45900
actgtttatt tttagttaag ttttttggct caacttctag gcagagaaca ttaaatgtaa 45960
atagtgttac ctaggagcat gtaaatggaa atctccatag tatgaaagca gtgctgttgc 46020
taacagaatt taggaggggg cagatgaggt gaaggaaatg tgggtgctga tttccttatt 46080
acattgagag gagccaggag attctttgtt caaaatggat ggcttaagaa gtcaaagtat 46140
aagctgatta cgtagagcag gtacccaaaa atgttttgtg taaggggcca gatagtaaat 46200
attttcagtc ttgcaggcca tcccaagtct gtggcagcta ctcaacacta cctttgtagc 46260
atgaaagcag ccacaggcag cccataaatg tggctctgtt ccggtgaaac tttaggtaca 46320
aaagcaggtg caggccagac ctgacctgtg cactgtggtt tgctgacctg ggattcaggg 46380
gtatagaagt taccatcaga agagctaaaa gtgagacttt ttactttata ctcttctaca 46440
ctgtctgatt ttgaaaaaaa gaaacatgta ttttataata ttaaagatag ggttggcaaa 46500
tagcaaataa aaatacagaa taccagtgaa atttgaactt cagatacatt atgagtaatt 46560
ttatggtgta agtatattcc aaatcatgtg ggacatactt acactacaaa attatttgtt 46620

-continued

```
gtttgtttac agtttaaatt tgagtgcctt gtattttatc tggcaactgt aattaaaggg  46680
aaaaagaata aattcattat gttcatataa tgtgatatag caggggtccc caaccccccag  46740
gctgcagagt ggtactggtc catgggtccc caaccccccag gctgcagagc ggtattggtc  46800
catggcctgt taggaaccag gctgcccagc aggaagtgag cagcaggtga gctggcattc  46860
ccacctgagc accgcctcct gtcagatcag tggcagcatt agattcccat aggagtgcaa  46920
accctattgt gaactgcaca tgtgaggggt ctaggttgtg cgctccttat gagaatctaa  46980
tgcctgatga tctgaggtgg aacagtctcg tcttgaaacc atcccctggc cctgtggaaa  47040
aattgtctcc catgaaacca gtctctggtg ccagaaaggt tgggtagcac tgtgatatag  47100
tattaaaagt gctaataaat atggcatact gcctttaaaa tgtctggtag ctctttctca  47160
gtggcactca taatagtgtt ttttgatttt taaatgtgtg tcaagctgac tctcccctcc  47220
gtgtatgctg ggctttattt tccctttcct agtcaccagt tttgggaaat agagatcttc  47280
attctcatgc tgctcctcta gtgcaagtgc tccatttatt tttaaggaat taatataaca  47340
aaaaatcatg ggaatttaga aaacaacatg gaagctaatg atcacattgg tggaagtgat  47400
agggaaatat ttagggggag aagttaaggt ataaactttg tcaatgaagt cctattaaaa  47460
acaacaaaaa agtgaagctt aggatgcatt ttataaactc tgaccagaac acctgtgttt  47520
ctctgtttct aggtttatga actgacgtta catcatacac agcaccaaga ccacaatgtt  47580
gtgaccggag ccctggagct gttgcagcag ctcttcagaa cgcctccacc cgagcttctg  47640
caaaccctga ccgcagtcgg gggcattggg cagctcaccg ctgctaagga ggagtctggt  47700
ggccgaagcc gtagtgggag tattgtggaa cttataggca agttattagc aaggtctact  47760
cttacaatta actttgcagt aatactagtt acactctatt gattatgggc ctgccctgtg  47820
ctaagcagtc tgcattccat cttccttgcc aaaacttata atacaaattt catctttatt  47880
ttataaatag gggagttggg ctgggtgtgg tggctcacgc ctgtaatttc agcactttgg  47940
aaggatcgct tcagcccagg agtttgagac aacctggcca agtgagaccc tgtctctaca  48000
aaaaaaaaaa aaaaaaaaaa attagctggg catggtggca catgcctgta gtcccagctg  48060
ctttggaggc tgaggtggta ggattgctta agcccaagag gttgaggctg cagtgaatct  48120
tgatggcagc tgcactgagc ctggtgacag agcaagatgc tgtctcaaaa taaatttaaa  48180
aataaaataa gagaattaaa gtttagcagg ttgggtggca aaatgaggcc acacatttaa  48240
agcccctcct cctgattctt ttctctgcct tggctgcctc ctgtggcatt ttaggtgctg  48300
agaaatgaaa acagtaggga aaatagttcc aggatcctca tgttaatttg ccagaaatgg  48360
catcttcaag tcgtcagagg gatctgagag ttccttcctg gcctgacttg agaaaatccg  48420
tctgtcccca gctctgcgtc tgcctccact gcccagtcac ctcctctcca tgctcttggg  48480
gctgggccct accccaccat gcagtgctgc cctggagcag tgagcttggt gggtcctgtc  48540
tggcatgaga gctgcctttg ggagctggat cccagcctct accactgggt ctggtgccta  48600
gcaggctatg gataaacttc tgctgactcc ggcctctcct aagccactgc aacgtggtcg  48660
gtgtagtgca cagtgtgtgt gcagcgtggc cttactcaca gcctccacat tagagagaat  48720
ctgactgaag tcttactgct gcctcgtgtg aacataaatg tttgccagaa ccatgagcag  48780
gaaatgttaa tctgccttgt ttcctgtcct ttacacggaa gaattttttt ctgtatggaa  48840
tgcgtgcctt acaaataatg agtggaaata cccatcgcta atgaaaagtt atacttgact  48900
gttagtcagc taaataatct gagatttcta atacttttaa tttggctttt acaatgcaat  48960
ttatcttagc tttttgatt tcttaggtca tatctttaga actatatatt tgaatgttaa  49020
```

tgtaatttc atattgaaat taaaatgttg aactgcgatg ttaagtgttt cctgtggaaa 49080
aacgttcaca ttttctctag ttttaaagtt gaatcaagct gtttgaagat tttcacattt 49140
cttctagatt ttatcagctt gttactttat ctgtcacttt ctgtgatttg cagctggagg 49200
gggttcctca tgcagccctg tcctttcaag aaaacaaaaa ggtgattatt tcagaaatca 49260
gagtcttgtg ttgaatctta ctgattttct tgtatttctg taatgtaatg tatcttgtat 49320
ttcttgtaat actgtattgg actctgtgta tatctcttct cagatgagtg attatatgtg 49380
tgaatgttgc tggaatctga taaccaggcc tgaatagttt tgtagggtgg cttttaaaaa 49440
ttactttcat atcagaattg ctttgtcata aattttgaac gcatcataaa tttctaatgt 49500
tcggggtcag cagacttttt ttgtaaaggg acagagtgta aacatcttag ctttatgggc 49560
catatggtct cttttgcaac attcagctct gccctgtgac aggaatgcag ttgtaaagac 49620
atgagctact ggccagctat gttccagtag aactttactt acagaaacag acaggctgta 49680
gtttgccaat acctgcctta gggaatgtgt tgttatattt tgtgagttac cttctcagta 49740
aattttattt agtattagtc aggaatatta ttaagtagct tcttttccag cctggtcaac 49800
atagtgagac ccggtctcta ccaaaacaaa acaaaacaaa aaaacagcca cgcatgtggc 49860
atgtgcctgt agcctcagct gctgctcagg gggctgaggc aagaggattg tttgagccca 49920
ggagtttgag gtcacagtga gctgtagtca tgccactgca ctccagccta ggcaacagaa 49980
tgagaccttg tgtcttaaaa aaaaaaagtt tcctttgttg ggttatttta atttggacct 50040
ggttatcatt tttcagccat atttaacttt gtacatatca gaatgttctg ataaaactta 50100
acttttatta aagtgtttgt gatataatct gctagttttg gtacacatta tcttttgcaa 50160
tgccagttat tttcttttcc agtgtgggtt tgcataggaa aagaattgct gtcactttct 50220
attttgaaat cttaaaagac tgatcctttt ttgtgtcatg atttgagtat ttaattgaga 50280
gcctaatgcc taatattatt tgcagtatta aatgggatct taacaggaat agcattctag 50340
ccttcattga attaagtaaa catttcttaa gagaacttgg aatctataat atttgcgtca 50400
tcatagtatg agatacttaa tcaagtttga gattttagtg aaacattgtt tagaagccaa 50460
aaggattcta ggaaaaatta atgtctatat tcttgaatta ggagagattt tgggacgtgt 50520
gactaagtta cgctgacact tgtttgtttc ttagtcgctt tttccagtgg cggtgagaac 50580
gaagatgact gattcacatt gctcagatga gtttatcctc ttctggctgg gacatgggat 50640
atatcctgtc tcttttaagc ctttttggta tttttccccc attgagagct gtgtcttcaa 50700
actcttctgt tatagctgga aaatcctttt taagtgaaat ctgcccaaat tataagacag 50760
atgaaggtag agttgtgttg gatataggat tagggtgaaa gtagtggggg tgtcctggag 50820
cctctcttct ggtggcagcc tagctcttgt gcctttgagg aaattaccct ggggacggct 50880
ctgtggaaca tatttgcaaa ccactgattt ggaagataga gatggctttt gttaagatct 50940
gaattcacct ttttggcatt ttatttgatt tctcaaggta aagaacttat tttgtaataa 51000
agtttcctat tatttagtag ataggccaag ttgctgtgtt aattccatgt agattttggg 51060
tttcctttgc tcatttttttc actcttaatc tcacatcatt gtaagtttat ggaagttatc 51120
atacttctga ctttttcttt gaagagcaga aattagaaat tcccaataat tattttgata 51180
gtgtcattta atgacactca catgtgatgt agccacaaag atttaatgag ttcagtttta 51240
aatcatatta agactgttgg tttcatttgt tctcattaat gtaattctga agatgaacaa 51300
taaaatgtat ttttagaact ttcaaatgaa atattatttc atccttccag atcatataat 51360

```
gcttaagttc tgattgttaa tcataaagtc tagaaaatta aaagataata aaatgaaagt  51420
gacttttagg tattagagtt ttattataaa ttctggtgtg tcattggagc tatgacatga  51480
atatttcaaa ggccaatagc attggatctt tacagttata acttaccatt tttaagttta  51540
agtagtaata tagattattt aataatcaaa atcaataaat attaattatt aaaatgtttt  51600
gtggtatagt ttgagaatca ttgcttttaa ctttttccat ataggtttat tgactttaat  51660
agcattctaa acataacatc tctacattct ttgtgtttaa tactgtggag gtataaaaat  51720
acttatatat gatgataaac tatattagag taaattaaat attcttatga gtttcatttt  51780
agagtgcatt tacttaattt tgaagtcctt atttttagca aactaaaagg aatgttggta  51840
cattatttac taggcaaagt gctcttagga gaagaagaag ccttggagga tgactctgaa  51900
tcgagatcgg atgtcagcag ctctgcctta acaggtagtt ctcactagtt agccgctggt  51960
gtggaccttc actgtctgcc ttccacccct tgcccttcct gctcgtcccc ctgcacctgg  52020
tggacagcac gactgggggc agcagtggag ccaggttgct taaatggggc atattcgggc  52080
ttcttttata atacttactc tgaagcttgt gtgtctgtgg tgtttgcatc atatatttgt  52140
tgttttccat ggtttaggct gttttaaaat taggtttatg gcttgagcat agggctttgt  52200
gagtagggga tggcaggtcg aaacatctca tgagttggat gggttatgct gggggttggg  52260
aaatgggatg aaaaattatg ggatgaaaaa ttgcctatgg atagtttaac ttgaaagaat  52320
ctgcctttgt ttacagatag ttatcttttt tcttttttga gatagagtct cacactgtca  52380
cccagtgcag atacccagtg tcactggagt gcagtggtgt gctcttggtg cactgcagcc  52440
tccgccttct gggttccagc gattctcctg cctcagcctc ccaagtagct gggactacag  52500
gtgcccgcca ccacgcttgg ctaatttttg tatttttttg tggagacggg tttttgccat  52560
gttggtcagg ctggtcttga actcctgacc tcaagtgatc tgcctgcctc agcctcccac  52620
agtgccggga ttacaggagt gagccactgt gcccggccag ttacagatac ttatctaatg  52680
aaattctctg tgtactttat aaaagatgag gattaactga aggtactaat aactggatta  52740
tatgagggtg gttttggttg tataatccta tctaaaagaa tattttagct ataactgaaa  52800
gtaagactta aatatttaga gaggaaaatc tgaataattc tagtagtaat tatttattta  52860
caaaataaaa atagattttt ttttgattac acaaattaaa caacaataaa acatcacagc  52920
aatccggata ctataaagct cacatgctta ccgacccaac tgccccagga gtgaccactg  52980
ccaacagctt catgtcgacc tttttgccat aatttttata tagccttttt tgtttttaaa  53040
tggtaattta gaaagtcaac taggaaaatg tgttacaggt ttatcttcca ggagaatagg  53100
actggagtcg agatcttgaa tgtggcttgg aagaaggcaa gcccacccca gagagatgag  53160
ttgacagttg tttctgacca ctgcttgctt agagggcctg cgtgtctgtg accgcctagc  53220
tttgcgcccc tgactaggct gccccttaat tacaaatgtc tttatatatt gctccagcta  53280
aggcttggag tagtcggtta agaacttgaa cttcggtttt tgcagtgaaa cagcatttga  53340
gaatatcacc ttctgataag ccttatttta taaggtgggt actgtagtgg gaggcagtgt  53400
gagagatgct tgaaggatgc actgctgtcc tgcatttcag catcttcagg atgctgtgca  53460
gctgaaacat ttgataacgg tggaactgtt cgttattttg caagcctgtg attccctatt  53520
gaatgttttc tctcgccatt tgacaaatga gtgtttctct gtcttcagcc tcagtgaagg  53580
atgagatcag tggagagctg gctgcttctt caggggtttc cactccaggg tcagcaggtc  53640
atgacatcat cacagaacag ccacggtcac agcacacact gcaggcggac tcagtggatc  53700
tggccagctg tgacttgaca agctctgcca ctgatgggga tgaggaggat atcttgagcc  53760
```

acagctccag ccaggtcagc gccgtcccat ctgaccctgc catggacctg aatgatggga 53820
cccaggcctc gtcgcccatc agcgacagct cccagaccac caccgaaggg cctgattcag 53880
ctgttacccc ttcagacagt tctgaaattg taagtgggca gaggggcctg acatcttttt 53940
ttttattttt tatttgagac agagtctcac tccatagtgc agtggaggcc gggcacaggg 54000
gctcatgcct gtaatcccag cactttggga gactgaggca ggcggatcac ttgaggtcag 54060
gagttcgaga ccagcctggc caacatggtg aaaccctgtc tctactaaaa atacaaaaat 54120
tagttgggcg tggtggcaca tgtctgtagt cccagctgtt agggaggctg aggcaggaga 54180
attgcttgag cctgggaggc agaggttgca atgagccgag atcgtgacac tgcactccag 54240
cccgggcaac agagcaagac tccatttcaa aaaaaataaa aaaataaagt gcagtggctc 54300
gttctcagcc cactgcaact tctgcctccc aggctcgagc gattctcccg cctcagcctc 54360
ctgagtaggt gggattacag gtgggcacca ccacactcag ctaatgtttg tattttcagt 54420
agagacaggg tttcaccatg ttggccaggc tggtctcaaa ctcctgacct tagatgatcc 54480
acccaccttg gcctcctaaa gtattgggat tatagttgtg agccaccatg cccggccctg 54540
ccacctgcca tcttttgagt tcttccctgg agacctagac ctgaaccctc ctgcttgttc 54600
tcttgttatc taatacccct attgacagcg cagcttagat cattaatgga gagcttgacc 54660
tcatctgata ccttcactga aggaaacaac ttagtgtctt ttgtgttgaa cactgaggta 54720
aaaaattgga atagttgatt atatgaactc tgctaaaatt gagtgcattt tacatttttt 54780
aaggccttgt tgggccctgg ttaaataatt atttttaaaa atccttaagg agcctattat 54840
aaacagatct gtggtcttaa tgaaatgtga ttaatactgt gcattatttt aagaactttt 54900
gacttttcaa aaaactttta caacatttcc catttgatag cggcataggt ttaagcactt 54960
ctcatctcta agttagtgga caaaaaaccc tcatggatag tctaataatg tttgctacaa 55020
gtccatgttg agttttatac tccattttat tttcagtttt aaaaactgtg gttaaatatg 55080
tgtaacataa aatttatgtt cttaaccatt ttttgcgtat acagttcgct ggtattaaat 55140
acatttaaat aatgtcatgg aatcattgct accacccatc tctgtaacct tttgatcatg 55200
taacactgaa gctctgttcc cattgaactc tattcctcct ttcccgccaa gtccctggca 55260
accacgattc ttctttctgt cttctgaatt tgactacttt gggttctcat atactttagg 55320
agtcacacag tatttgtttt acttagcata atgtccccaa agctcatgca tgttgtagcc 55380
tatgttagaa cttcctaatg tttcaggcca aatactattc cattgtatgg ataggccaca 55440
ttttgctttt ccattcctct gtccatggac acttgtattg cttcatgttt tagccattgt 55500
gaatcatgct gttatgaacg tgggtgtaca gatagctcct ggagactctg ctttccattt 55560
ttttggctaa atacccagaa atggagttgc ttttacattc caattttaat ttaaaacatt 55620
catatcattg agtgttttac ttaatagtat agtagttaac aaacttaata aaatagtatt 55680
ttggtaataa tttgctggta gtccattgtt cagttttttt aggtaaatta cacaggacat 55740
ttcaagtgga catgaaacat cttgtgatgt ggaatcatgc cccaagctga tggctaaaca 55800
tatgaaatac catacctaa atttagtaga tttagtcttt gcaatttagg agataacctg 55860
ttatattgtt aggtttttgt cgaaaagctt tgtcctcata tttccaactt gctgtaaaat 55920
ttgtttgtga agacaaatat ttttgtatgg gttttttctt tttcatatta aaaagaaatg 55980
tccacattgg aattttttg gagtttttag agctaataga gcttttcata atgtagtggg 56040
aatgagtgat cagtaagctc ttagcagttt ccatgcgtgc atttctgtgc cttgaaataa 56100
atgacagatg agtacatttg tgttctgtgt gtaaaatgtg ctctttcctc attgcacttc 56160
catgttggag ggcttgtctc ttggtgatca cacttcaaaa ttctcacagc ccccttgaa 56220 ccgtttaggt gttagacggt accgacaacc agtatttggg cctgcagatt ggacagcccc 56280
aggatgaaga tgaggaagcc acaggtattc ttcctgatga agcctcggag gccttcagga 56340
actcttccat gggtatgtgg actacaggtg atgcgctaca aagtggtttg tattcagacc 56400
tggacatctt aattatatct ttgcttccaa gaagaagtcc tttgatactg ttttctgagt 56460
tctgaatagc tgatgaaaat gaccaattga ggaataatca tactttttct tgatctaaat 56520
cttatacttt tgagttatct tagcataaat gtataattgt attttaagtg gaaatttgtc 56580
acttaatctt gatttctctg tttttaaagc ccttcaacag gcacatttat tgaaaaacat 56640
gagtcactgc aggcagcctt ctgacagcag tgttgataaa tttgtgttga gagatgaagc 56700
tactgaaccg ggtgatcaag aaaacaaggt gagggacata ggcttgagac gacttggtgt 56760
ttctgagctt gtgtgaggat ttaaaatcgc cctggctact gtctacttta ttgctttccc 56820
atccctgggc ctttaaattt cccctttaaa taccagctct tcccaggcct gttgttttct 56880
gcctttccag gtactaccca cagccttgag aattgcctga gttctgcctc ctttgagagt 56940
gtgccccaga caaatctatt ctgtactgaa tgtttccttg tctgatttct tggatcattc 57000
atttgatggt tgcgtatggc ctgcaacgtt tcttgttttg gttctactga actgttctaa 57060
aagtctctct tcatattatc tttttacatg taaatgtaac tgtcttcact tttaattcct 57120
caaggacaag gaatagcgtt tcacagttcg tcccatcaat cagaattata gcctttggca 57180
tctccctatc taccaggccc acttcctctt agatttgggc ttccccaggc tgttgccttt 57240
ccccaagtag cttctgcttg tcctgtagaa gacctttcat gctttgcttc tgcagcagcc 57300
gttcctgaat gcctagtgtc aactgccttc ttaccacgcc caccctccct gcatgctgca 57360
tttatcccct gccacagccc tgtgaccctg tgtcctgctg cctctgactt gtctgtttct 57420
gcttggccat ggtctctgtg aggtcaggtg tgcatatggg cacaaaccag ggcatctctt 57480
tatccccagc acctggctta agtgctgctc tggaactatc tgttgaatga actaatgcat 57540
gaatgtattg ttgagtatga gacaaacaag tgtcattgtc tcctttctag ccttgccgca 57600
tcaaaggtga cattggacag tccactgatg atgactctgc acctcttgtc cattgtgtcc 57660
gccttttatc tgcttcgttt ttgctaacag ggggaaaaaa tggtgagtac aaaaggggat 57720
gtgcacagtt gaaggaaata actaggtttc agaggtcagc ttggtggcct gtttttgcct 57780
tgcgtgcagc agaggaagta gaatctgagg atgagtttgg ttttcactag ccgaggggag 57840
ggaggaaatg atgggagcag gtaggttatt gggtctggtt ttgttcattt gaaaacaatc 57900
tgttgtttga ggctgaaggt ggcttgggtg atttcttggc agtgctggtt ccggacaggg 57960
atgtgagggt cagcgtgaag gccctggccc tcagctgtgt gggagcagct gtggccctcc 58020
acccggaatc tttcttcagc aaactctata aagttcctct tgacaccacg gaataccctg 58080
gtatgttaaa agttcacatc ttattttctc agatttaatc attattgtaa aaactatttc 58140
agtattgact attttagttt tagagcagta agtgttttga gttcatttgg gatatttgac 58200
ctgcgttgta gctcttcaga aaacacatga atagtgaagt tctttgtttc atgggttccc 58260
tttagatgaa acccatagag gagaaaagta gaaacctcag cacgtaagag ccaacatata 58320
tacacatcgg atttaaacct aaagcacaaa ttgtgcctgg tcgcagtggc gctgagtcgc 58380
actcagccag gccaggcatt cacactcagg gtgagtggga accaggactg gctgaggcag 58440
cagtggaccc aagtctccat cgcgcccatg cttactatgg agccttctcg ttctctcttt 58500
ttctttgggt gagagggtac acttgtgttt ttgaatttat atgaggtaag tgtgtaatag 58560
ggttttttct aatctttttt aagtggaatc tggaatttta atcagattta ttatctgaca 58620
acctagaatt ataatccaga aagtctgtgg tattgaggac atattggcaa tatgatgaat 58680
ctctaattct taaatcctga aacttttttt tttttaatca cttagggtta ttatagtgaa 58740
gtcatttctg aatttggatc ttctcttcac acctcttttt ctctttcctg agaattaagc 58800
ttttgtttcg agttagaaag ttgatagtag ggaattgttc catggctgag caatttatct 58860
ccacagagga acagtatgtc tcagacatct tgaactacat cgatcatgga gacccacagg 58920
ttcgaggagc cactgccatt ctctgtggga ccctcatctg ctccatcctc agcaggtccc 58980
gcttccacgt gggagattgg atgggcacca ttagaaccct cacaggtaac ggccagtttt 59040
tcagctgtgt tttttctagt tatgcttact aaggtttaag tttagatgat gatgtttgtt 59100
gcttgttctt ctggttagga aatacatttt ctttggcgga ttgcattcct ttgctgcgga 59160
aaacactgaa ggatgagtct tctgttactt gcaagttagc ttgtacagct gtgagggtga 59220
gcataatctt ctgtggaacc atttcttcac ttagtggaca ttttatcatt gctacaatta 59280
aaattggagc ttaataggaa atatttccat gcactctaaa gctgtaacca gtaataccca 59340
ccatgtatcc atctctcagc tttagaaaga aaacgttgcc agtaaagtta atgcttcata 59400
aacttcagtt taagttctaa ttctcagaat atttgtttga aatagacctc ttcctaaagg 59460
atatatttag aaataaccta tcattaagtg taaagtctgt tgaatatgct gggcacggtg 59520
actcacacct gtaatctgac cactttggga ggccaaggtg gaaggattgc ttgagcccag 59580
gagttcaaga ctatgggcaa catagttgac cctgtcccta cagaaaatta aaaaaaaaaa 59640
aaaaaaaagt agctgggtat ggtggtgcat acctgtagtc tcagctactc gggaagctga 59700
ggtggagggg ggattgcttg agccccagag atcaaggctg cagtaaggcg tggttacacc 59760
actgccctct agcctgggca acagagtgag actgtctcaa aaataatagt aataataatc 59820
agttgaatta aaaaaaaaaa aaaaaaaacc actgtgctag gcccatagta tggtaagagt 59880
taaagtgagc cttagggatt atttactcaa cctctgtttc tgtataaagt ggaataggct 59940
caattcttta agtgatagca tgttgaacct ttccatacca actggctcat aagtcacaac 60000
tggccagtca acaagagtaa aaattaactg gtaaaaatca aagcaaaaaa cctacaattg 60060
tcaaatttgt gggataactc cccttttaa aatgtcatgc ctgacagtaa tttctctcta 60120
gtttccaggt tttcagtcag ttgtgtcttt tttgagcaga aggaagcatg ctaagagctc 60180
aatcttgtgg ctagctgggg gtctttgtgt cagccatgca tgtgatggtg cccctgggtg 60240
cttggggctg caggggaggg gtacagcagt aggggcctgt tctgttctct cgtgctgtgg 60300
agtacatagt gacatagtgg ggtggtcctt ggtgtaggtc ccttgttcct acccctgggt 60360
ctgagattta tttagaagtg gtgttggggc tgtgcggcag gcccctctgt aactgatcaa 60420
tgtttgtgaa gttgctgttt gagagttgaa accatgacat aagcagaaat ggaaggaaga 60480
aagaaccagt tatgtgaaag ggacacattt acttttaagc ttgtatttac tgagataaag 60540
tattcttaat caatgttctt gagaggtgtg ggaaaaatgc aacatcctgg ttgcagttaa 60600
acccagaaca ttgtgtgttg aagagtgacg gttctcaaac cgtcaagacg cgggtactga 60660
gtgggactaa cctgctgtcc tcttgccttg gaccttgtgt tccagaactg tgtcatgagt 60720
ctctgcagca gcagctacag tgagttagga ctgcagctga tcatcgatgt gctgactctg 60780
aggaacagtt cctattggct ggtgaggaca gagcttctgg aaacccttgc agagattgac 60840

-continued

```
ttcaggtaag tgagtcacat ccattagatt tcatgaacta agctcaattg aaagttctgg  60900
gatcacttga tgcaaggaat gatgttatca agtaccctgt ccatcagaaa tccgagtggt  60960
ttaggtagat gacagtgatt ttctcctccc agtggctttt tgctgaactt tgccctatgc  61020
ttggaatttt attttatttt attatttatt tagagacaag atcttgctct gtcgcccagg  61080
cttgaatgca gtagcacaat catagctcac tgaagctttg aactctagga ctcaagtggt  61140
cctcctgcct cagcctcccg attagctagg agaataggtg tgtgccgtca cactggctaa  61200
tattttttgt agaaatgggg tcttgctatg ttgcccaggc tggtctcaaa ctcctgggct  61260
tgattgatcc tccatcttgg cctcccaaag tgctgggatt acaggcatga gccactgtgc  61320
ctggcctaga attttaaaat ataagtagaa gagtagattt tttttttgg tagtcctcgt  61380
catttaagta ttctggatag tgggaataaa agagcttaga atttttcatc tttgtcttaa  61440
acttttaaaa aaatgtagct tatattaatt ctgcttgttt aaaaagaata tactcttcat  61500
tatactgaac ctaggtaaga cagctggttt atattttgtt gcaattaaaa aacgtgagct  61560
gtggttgcag tgagccaaga ttgtggccat tgcacttcag cctggcaaca gagtgagact  61620
tggcctcaaa aaaaaaaaaa taacatgagc tgtgttggca ctttcatttt ctaagagtag  61680
ttttggctgg agaagttttc tttcagtact ttcttttaga agggaaattt tcctttataa  61740
tttagggttt gttttttttt tttccaagcc accttttata gagcccttgt gggttatttc  61800
atttaatcct tagaatgttt ataaatctgg gcttgttctc ggctccaccc acagataggg  61860
acgctgagcg tgcatgagtg ggcagcaaga tagcaggtta tggagggccc agctcacccc  61920
ttctgtggct tgagccaatt ttatagggca cttacagagt cttttgaaat agtatttatt  61980
ttgaagaaaa agaaaaacag tttactgagt actgtcttat tgagtctgga attgtgagag  62040
gaatgccacc tctatttatt taaagccatt ggcctttttt gttgttttga gtaagtgctg  62100
cccaaggtcc ttccagggca cctggatgag cctgctctgg agcaagctgg cggtaagtgt  62160
ttactgagta actaaatgat ttcattgtta aatgtgctct tttgttaggc tggtgagctt  62220
tttggaggca aaagcagaaa acttacacag aggggctcat cattatacag ggtaagcgg  62280
tttatttttg tgagatgctg ttttaccttc aagaaggtga aagtgaggct ttccttgtgg  62340
aatttctcta aatgcattcg tcatgtttta gatgtttatt tcacagttta tatcatgaaa  62400
gttataatct tgtcatatgg atttaagtct agtaatgttg agttctttct cactagcttt  62460
ccaaaatatc ttacctaaaa tttagtcaaa tacaagatta tgtttatttt tattatcctt  62520
ctctctaaag cttttaaaac tgcaagaacg agtgctcaat aatgttgtca tccatttgct  62580
tggagatgaa gaccccaggg tgcgacatgt tgccgcagca tcactaatta ggtatttacc  62640
aatattttat ctcttttcct tttttggttg aagtactaaa agatacgaga atggaaagag  62700
agggaagaat tcaaaggatg tagagcagta ttcctgaatc tgagctcatt tcagccattc  62760
tattcttaaa ctataatgaa aaaaaaatcc aaaaaagtct aaaattataa ttaaaaaaac  62820
aacaaaatac taactgtcca ttgtaaaaag taatgcactt tcattgtaaa aattttggac  62880
tatagagaat agtactaaga agaaaaaaaa aatcaccttc aattctgctg ccacctggag  62940
gtaatcactg ttaatatttt gctatatact ctatgagttt cttgttcaaa atcaggtcaa  63000
aattacatgc aattttgtaa tctgacaatt tccacttaat attttattag cattttcctg  63060
ttatgaaaca gtaattttag ttatgggtcg ttgttttgct atgcggttgg gataaaattt  63120
tatatacttt ttttggcaat tacttattat acataaatgt ttgtgtatag ttttcttttt  63180
ctgagaattc ctggaagttg agttaccagg cccggctttg aatttttttt tttattttt  63240
```

-continued

```
ttttgagaca gagtcctgct ctattgtcca ggtgctatct cggctcactg caacctctgt  63300
ctccctggtt caagcgattc tcctgcctca gcctcccgag tagctgggat tacaggggca  63360
caccaccacg cccaattaat ttttgtattt ttagtagaga cagggtttca cgatattggc  63420
caggctggtc tcgaacttct gaccccgtga tccacctgca ttggcctccc aaagtgctgg  63480
gattacaggc gtgagccatg gcgcctggcc aggctttaaa tttaaaacaa atcttctaat  63540
agctttatgg aggttataat ttacatttct tgaaatgtac tcactttgag tgtatagtaa  63600
actccaattt tatcacattt ctgtcacccc aaatgtatcc ttgtgcccat ttgctgtaac  63660
ctccggttcc tgccccaact cctaggcagc cactcatcta ttttctgtcc cttaagattt  63720
gtgttttcgc caggcgctca tgcctgtaat cccagcactt tgggaggccg aggttggtgg  63780
atcacttgag gtcaggagtt cgagaccagc ctggccaaca tggtgaaacc ttgtctctac  63840
taaaaataca aaaattagtc ggatgtggtg gcacacgcct gtaatcccag ctactcggga  63900
ggctgaggca ggagaatcac ttgaacctgg gaggcggagg ttgcagtgag cagagatcgc  63960
gccactgcct tccaacctgg gcaacagaga gagactgtct caaaacaaac aaagatttgt  64020
attttctgga cattttatag tactggggtc atagtataga tggacttttg catttggctt  64080
cttttactta attgtgagat tggttcttgt tgtagcatgt atcagtagtt tgttcatttt  64140
tattggcgaa agtattctat tatatgaata ataccatatt ttatctatcc atcagatgga  64200
tattatagag ttcatgtttt ggctaattta tgaattatgg tactgtgaac atttgcctgc  64260
aagattttgt gtagacatgt cttcatttct cttgagtaga tcacctagaa gtggattttt  64320
aaataatttt ggtacttact gtgaaactgc tcttcaaaaa cataccattg ttccttcctt  64380
ccttccttcc ttccttcctt ccttctttcc ttcctccctt cctccctccc ttccctactt  64440
ccctctccct ttccctttcc cttccccttt tcccttcccc ttcccgcctg cctgcctgcc  64500
tgccttcctt ccttccttcc ttcgtttctt tctacatata cacatttttt taaatttcaa  64560
tggtttttgg ggtacaagtg gtttttggtt acatggctga attttggtta catggtgaag  64620
tctgagattt tagtacacct gtcacccgag tagtgtacct tgtacccaat atgtagtttt  64680
ttgtccctca ccttccagcc ttccgccttg tgagtctcca atgtccatta taccacactg  64740
tatgcccttg cgtacccaca gctcagctcc cacttctgag aacatatagc agaaacatgc  64800
caaagtatac tcccactacc agaatgtgat tgtgcctgat tcttctcacc agtacaaata  64860
tttcaaaaaa agttaaatat gtatcagttt tttgggcaga agttgatact tctctttatt  64920
tatttatttt ttttgagata gggtctcatt ctatgatgcc caggctggag tgtggtggtg  64980
cgatctcggc tcactgcagt ctctgcctcc caggttcaag tgattcccac gtcagcctcc  65040
caggaagctg gaattacagg cgagggccac cactgccagc taatttttgt atttttttggt  65100
agagatgggg tttcaccatg ttggccagac tggtctcaag ctcctgacct caagtgatcc  65160
acctgccttg gccttccaaa gtgctgggat tacaggcgtg agctaccaca cccggctgat  65220
atttcttttt aaaataactt accttctttt gaaagtaata catgtttaat gaacagaatt  65280
taaggaaaat ataaaaaaac gaaataatct ttgtaatcaa actactgaaa agaaaaccaa  65340
agttacattt tggtgcatat tctttttcat tttcatcatt gtaatttgca tttctttgat  65400
tacttgtgag acactccttt catttactta ataggtttat atgacttgcc tattcagaga  65460
ttttgcagct ttaccatttt ctgcaaatga tagcaacttc tttttgtttg tttgtttgtg  65520
gagacagagt ctcgctctgt cactcaggca ggaatgcagt ggtggaatct tggctcattg  65580
```

-continued

```
caactattgc ctcctgggtt caagcgattt tcctgcctca gcctcccaag tagctgggat  65640
tacaggagtg tgccaccatg cccggctaat ttttgtatct ttagtagaga tggggttttg  65700
ccatgttggc cgggctgatc ttgaactcct ggcctcaagc ggtccccctg tctcggcctc  65760
ccaaagtgct gggattacag gcgtgagcac cgtacccagc cagtagttac ttcttatatt  65820
ctagaaaaaa ttctactcat gatcaagtct ccatgaggaa agagacttta attgaagatc  65880
atggggcttg cagaccaata tgataaaata gttcattgtt tctaaaagta ttactgagtg  65940
ttgatggcag atatgaaccc ttttgttttt gtaggaaaat gttacccgta ttctccattt  66000
gaattcagtt tagatttgtt aggaatcgca gcttaagctt tgccatctgg gagtgtttgg  66060
gacagttttg cagacaaaat tgcaaaagtg cctaaggaat gcagctggca ttcagacctg  66120
ctctgtgctc agtactctgt ggacagacac tgttcagcac ttgttgatca gaaggtttag  66180
aaagagaact ttcaaagttg gtttttaatt aaagcattta atagtgtaaa tagaaaggga  66240
ttaaatttta tgacagacaa aagaaagtac agcacccagc tgggcgtggg ggctcacgcc  66300
tgtaatccag cactatgggg ggctgaggtg ggtggatcac gaggtcagga gttcaagagt  66360
tcaagaacag cctggccaag gtgatgaaac cctgtctcta ctaaaactac aaaaattagc  66420
cgggcgcggt ggcaggcgcc tgtaatccca gctactcagg aggctgaggc aggagaatca  66480
cttgaacctg gacggcagag gttgcagtga gccaagattg caccattgta ctccggcctg  66540
ggccacagag tgacattctg tctcaaaaaa aaaaaaaaaa gaaaaaaaga aagtacagca  66600
cccagttatg tccgagtggg tgcatgagag tgaccctgag attggagaca acgctgtcac  66660
gtgcttgaag aacgccacct gagaaagggg gcgagaagtg gtgtccgctg gtaaccagag  66720
gtgttggctt agccatctgc agggaggagg gtggtctatc acaggtgagt ttcatctact  66780
ttcttaagca aattaacctt acttttgtgt taggcttgtc ccaaagctgt tttataaatg  66840
tgaccaagga caagctgatc cagtagtggc cgtggcaaga gatcaaagca gtgtttacct  66900
gaaacttctc atgcatgaga cgcagcctcc atctcatttc tccgtcagca caataaccag  66960
gtatgctgac ccagtggcat cttcacattg tcgggaaaat gccctttcct gatgcctttc  67020
tttaggcttt aattgaaaac attttatttt ctagaaaaaa gcttcagctc aggatgtttg  67080
agtgtaggtc agtcctttga taggatatta tcattttgag gattgaccac accacctctg  67140
tatttaagct ctgccacaat cactcagctg tgacactgta aatctcttaa tagtttatta  67200
cattccatgt gctgacagtt gtatttttgt ttgtgacact tacgtattat ctgttaaaac  67260
attttcactt tagttgtgtt acctttaaag aggattgtat tctatcatgc ctgttgattt  67320
tttggtgagc gggctattaa agtcagtgtt atttagggtt atccactagt tcagtgattt  67380
gcgagattat cattcacatt tattgtggag cttttgaata tcgtgtcaaa tggccacata  67440
tatcccattc ttatctgctt cttaggtgag tgggacacag tgctttaatg aagctataat  67500
cttcagaatt ctagcttgca gagaagattg cagaagtgat aagacttgtg ctttttaatt  67560
ttgtctttta aatgttattt taaaaattgg ctttatatga tactcttttt ttctgctgag  67620
taacagtgtt ttacaaaact tggactaaat gacttctaag cttaaatgat cacttgatgc  67680
tttttttctg aattaggaac tcagcttatc aaatatcaaa gtcataattc ctgaataaat  67740
aacgtctttt ttcatgtaaa gactgcttta aaaaacacat ggaaggctgg gtgcggtggc  67800
tcacgcctgt aatcctaaca ctttgggagg cccaggtggg caggtcgctt gagctcaggg  67860
gttcaagacc acccagggca acatggcaaa acccacctct actcaaatac aaaaaattag  67920
ccaggcgtgg tggcgggccc ctgtaatccc agctactcgg gaggctgagg gatgagaatc  67980
```

acttgagccc cggaggcaga ggttgcagtg agccaagatt gtgccattgc actcccagct 68040
tgggctacag agtgagactc tgtctcaaaa aaagacacac acacaaacaa aaaaaacatg 68100
gagacatttt tttggccacc ttaatatttc ccctcagata atttcctttg tttaaactca 68160
gaactggcat tttctctctt ggagaagatt caggacaaat actcctttaa gataagtaga 68220
agcagtgaaa gaggatttga ttatcaggaa tttgataagc ttagaataaa ttgttgcttc 68280
ttaatgtcat ttcagaagat gaatatttat taatagatgc caactgagat atcattaaaa 68340
ttgattacta actactactt ggaaaagtct cccagttcca aacttcagca ggcctcttga 68400
caattcagct gtggtcaatt gggtcttgcg tgatagatac aatgaccaat tgtgcagcag 68460
agtgtgctgc ttagctgcct attctgttag cattcatgtg ttaacttaaa atcataatct 68520
ccttagtttt gttgagtgtc tccgtggaca agacactgtg agggatacaa aatcagattg 68580
gctttattca aaccactggg gtattataat tcatttataa tttattttat tttttgcctt 68640
ttttccatgt gttctaaagg aattagagtt tgtatataac tataatgggg gatagaaatt 68700
gacatgtgcc atgaagggaa tgcaaaaaag tgccgtggga gatgagaagt ggagaaagga 68760
atttcttttt tcttggaagc aggaataact tcatgaagca tgtatttcaa cttaaacaga 68820
tagtaggcaa cgctgtaagg ggagtatggc tgcagcaaaa gtgttcgggg cagactggga 68880
ggaagggagg gaataaattc agccattgtt atggaataat gatcaaaatt tattttcagc 68940
ccgtttcact taaaagttga gactgcttaa cttttttaa tctttaatct taaactttta 69000
aatgccattt gatctttaaa aatatatgtt ttaatagtgt attttaagtc tctatatttt 69060
tgttattaga atatatagag gctataacct actaccaagc ataacagacg tcactatgga 69120
aaataacctt tcaagagtta ttgcagcagt ttctcatgaa ctaatcacat caaccaccag 69180
agcactcaca gtaagtctct ttcttgatcg gtcttactga cattgtaata gtttttggta 69240
gcttgtatgg ccagttagtt gtatggtcat cttacggtga ggtgcttgtc ttacagctct 69300
tacttatcca tgaggcttgc taagaaattg tgcttctgtg aaaagaatct cagcttactc 69360
caggaatgta aatgactatg ttttttctga ttattaaagt aatacacgcc caaaataaaa 69420
aaattcagcc aatttaggaa gacacaacaa ttaaaataag ccaggcatgg tggctcatgc 69480
ctgtaatccc agcactttgg gaggccaagg ttgggggctc acttgaggtc aggagtcgga 69540
taccagcctg gccaacgtgg tgaaacccca tctctactaa aaatacaaaa attagctggg 69600
cgtggtggcg ggcgcctgta atcccagcta ctcaggaggc tgaggcagga gaatcgcttg 69660
aacctgggag gtagaggttg cagtgagctg aggtcaagcc actgcactcc agcctgtgca 69720
atagagcgag actctgtctc aaaaaaaaaa aaaaaaaaag aaaagaaaaa agtaaactac 69780
tgtcacctgc attggtaatg tatcagaagt ttaaaatgtc tagattataa ttaactcagt 69840
gacctggtaa tatatactaa gggaaaaata tttataattt acatttttac atttttattt 69900
ttttaatttt attatttttt ttttgagaca gagttttgct cttgttgccc aggctggagt 69960
gcaatggcat gatctcagct caccacaacc tccacctccc gggttcaagc aattctcctg 70020
cctcagcctc ctgagtagct gggattacag gcatgcacca ccatgcccgg ctaattttgt 70080
atttttagta gagacagggt ttctccatgt tggtcaggct ggtctcaaac tcccaacctc 70140
aggtgatccg ccctcctcga ccccccaaag tgctgggatt acaggtgtga gccaccatgc 70200
ctggccttac atttttataa taagaattta tgttgctgac attagaaaag aaccataata 70260
tccaagaatc caagaataat taaattatgt acatatgcta gtatatagtg tgatgctttg 70320

-continued

```
gagaatttttt aacaatatgg agatgtataa tctggattgt aatattgagt gaaaaaaggc  70380
agaatacaaa cctggtgggg gtatagtcgg atttcagtta agaaaaataa tatttacata  70440
tatacatttc tcacactggc agataatcac caagataaat tttgggattg tggatgattt  70500
ttttcttctt tatatttttc agatattctc aaattttcta aaatgagcaa gtataacttt  70560
tgttatcaga aaaaaataat atacaaaagt aatgttaatt tgctggtgac caggttaaac  70620
ctttttattt ttattttttg agatggaatc tcactctgtt gcccaggcta gagcacagtg  70680
gcatgatctt ggctcactgc agcctccgct tcctgggttc aaatgattct ctggccccag  70740
cctcctgagt ggctggaatt acaggcgtgt ggcaccacac ctggctaatt tttgtatttt  70800
tagtagaggt agggtttcac caggttggtc aggctggtct cgaactcctg acctcgtgat  70860
ccacccacct cggcctccca aagtgctggg attacaggcg tgagctactg cgcccagcca  70920
gacctttttta ttttatttga caaaagaaat acttccatgt tatagaagac taaatattgt  70980
ttgggctgtc tgcagtatgg tcttcccttg atttgttcaa aatatcgtaa actttgctta  71040
tttattttta ttgtggccga ctgtgtcggg cactgttgta ggcttgggat ggaaaaacag  71100
gattcctgcc cttagggttt ctgcaggctg gtcagggaga cgatgtggta agctggagct  71160
cagctcctaa ggatgtgcag gggcagttga gaggcggaag ggtgggagat cattccaggg  71220
tgtgggcagc acaggaacct ctcttcattg ggatataatt gccattctga taacacgtgt  71280
ttgaggtgtc taaagtagga agttgtacca tggtgggaca gatatcctgt ggttatcata  71340
cacagatctc agttttcttc tcattgtttg tactttttat aaagggtaac aggagatata  71400
attcaataaa cctttgtggt gtttgggtgt gattttattg tttctttctt ctcagtttgg  71460
atgctgtgaa gctttgtgtc ttctttccac tgccttccca gtttgcattt ggagtttagg  71520
ttggcactgt gggtatgtat tttcctcagt atatattaat agttgtctac aacagtatga  71580
cataaacata gttattagga tgcccttttt ctttcttttt aagtctttta tcaatttggc  71640
tttttggaaa aatatctgat ggaatacttg tttctgctat attagctgtg tgagactagt  71700
gacaggagct gtgggaaatg aatgccaaat gttcttaggc attgatggga atttcagggt  71760
gtggtcttca agttcattta agggaatttt catatgctgg caaaaggctt ttctcattag  71820
cttgactctt tccaaaatta tttgctgtga attagaagtt taggaacctt ttttcactta  71880
attgtgacct agcatacgaa atggtgatga tttaggaact actgttcttg tattaacagc  71940
ttttatttaa aaatgatttt cctccagtag atggccctac tagcatctgg gaaataattt  72000
caagtcttct ccagcattca ggaataggct ttcattttgt gtatcaatta ctgagaatga  72060
ttttggtgac tcacatcaca tttgagaagt aaacctgcag atttcttgtg tgtgtcagca  72120
aatgaccaac tgatatttgc ttgaagtgga ttacattatc tgctctagaa tgattgcttt  72180
cccaccttcc tcacatacag actgagcagc tacggtttct aatcataggt ctggcactag  72240
acttcacttc tgggcaactt tggcattgga gtaaaatgta ttaatttaaa gaaagttaaa  72300
aatccgttca agtaaacata cagttctaat actttttaca atttaaaata tagatttaaa  72360
tgataaaata aaaaagaaaa tatgggtaga caccataatc ctcgtttctg catctgttca  72420
caaggggttg atatttatga gttctattct ccatatccat tctatgttct cttaatgctc  72480
agtcagcacc tcaggtggtt ggagttcaat gcttggtagt ttgacttaca ctgtcttttc  72540
taggggattg agccctgggt agtcctgctt atttgaggtt gcaatttgtc tttcaataac  72600
ttttactaca agatatggcg tgttaaagga taccattggg gaaccaacat aataatatca  72660
ggaaaactaa ccacgtcaga cctgccccat tgtgtatcaa gtacactatt tttccatagt  72720
```

```
aataaagagt tcaccccagc caattctctt ttattttgtg cctgtttact caatggcatt  72780
aacatgccca aatgtctggg tagctgtctc atctccagtt cagcagaacc attgtcatat  72840
gccctagtaa aagcattcct tcattggaca cttaggcccc aatactttca ttcagatcta  72900
ctacctgatt tcatttctca aatgattttt atggagctct gatttatagg aaagatgtta  72960
gttgattaaa aataaaacaa tttctgagct ggtataaaat gtattgtgac atgccttcct  73020
cttggaattg caagagaaag gaagactgtt gtttgcttaa aaattgtcta taatttgact  73080
ttgcaaatgt ctgcttccag agtgcctcca ctgagtgcct cagatgagtc taggaagagc  73140
tgtaccgttg ggatggccac aatgattctg accctgctct cgtcagcttg gttcccattg  73200
gatctctcag cccatcaaga tgctttgatt ttggccggaa acttgcttgc aggtactggt  73260
actgagttga aacagggact ccaggacttg gattttgatt tccttagggg gaatgggggt  73320
ggtgagcata tgaggggaaa atactataag gtcattgcca gtgatggctt gtccctttag  73380
tcaaatttca gatgttacct atatgcataa acacatgcag ttggcagctg ttctgtgctg  73440
agtattttaa agtagcctct tcccaatata gcccctcagt taactacaag taaactcatt  73500
ttgaatttca ttttaatggg caccatatgc cagtactccc tcgggcactg ggatgttaag  73560
aaagtataat gtatggactt cattctcaag ttagttttag attagagggg gatacacgta  73620
aacaaaagtg cagtggtcac acagagtggc cctaatcact ctccttgggc agatttatgg  73680
gctggtagga aagagcacaa cacggagagg gtgtagcacc ttggcgatga taatggagga  73740
tgtggccagc aaggaagacg gagtccattg aaattgattt tgggagaagt tgccaatctc  73800
catgaaagaa ttggggcctg tgctatttgc ttcagggggc tataggagag tttcgtgaaa  73860
gggactaaaa gatgagtatt ttaataagat cattcatcca acttgaacat gggctggagg  73920
agaaggtagg gagactcagg agattaatgt tgatgctaag gcaagataat ggctttggga  73980
ctgtagggaa gacactgatt gtaagagaat gaaggaggca gaattgccag gcctggttca  74040
ccaactgaac ttcggttgtg aagacaaaga aacctgggat gacttcacat cctgggcagg  74100
tgtgtggtgg tgacagtcat ggaaattggg aacacagatt tgtgcgggaa acatcagttt  74160
cagtttgagt ttggcttatc agttgaatat caggcacaga tgtctggcca actctcaaca  74220
tagggtctta aatgacttca gttcccccaag caatttgtcc ttcccatgct attggggtgg  74280
agaggtaatg tctgtgccca tatcacagcc agtgctccca aatctctgag aagttcatgg  74340
gcctctgaag aagaagccaa cccagcagcc accaagcaag aggaggtctg gccagccctg  74400
ggggaccggg ccctggtgcc catggtggag cagctcttct ctcacctgct gaaggtgatt  74460
aacatttgtg cccacgtcct ggatgacgtg gctcctggac ccgcaataaa ggtaatgtcc  74520
cacttgggtg ctggattcat acagccttaa tgactatggg tttccagact acctttgttt  74580
agtaatctgt cccttcttta ttctcttttt gctttaaatg aacaaaattg ctcagattgt  74640
gacactaaat ttaacatcaa aatgtgacca tgtggatggg tgcagtggct cgtgcctgtt  74700
attccagcac tttgggagac tgaggcaagt ggatcacttg aggccaagag ttcgagacca  74760
gcctgggcaa catcacgaaa ccccctctct actaaaaata caaaaaatta gatgggttgg  74820
gccgggcgtg gtggctcaag cctgtaatcc cagcactttg ggaggccgag gtgggcggat  74880
cacgaggtca agagatcaag accatcctgg ctaacacagt gaaaccccgt ctctactaaa  74940
aatacaaaaa aattatctga gcatggtggc gggcgcctgt agtcccagct gctcgggagg  75000
ctgaggcagg agaatggcgt gaatccggga ggcggagctt gcagtgagcc gagatcgtgc  75060
```

```
cactgcactc cagcctgggt gacagagcga gactccgtct caaaaaaaaa attagatggg  75120
catggtggtg cgtgcctgta atcccagcta cttgggaggc tgaggcaaga gagttgcttg  75180
aacctgggag gcggagtttg cagtaagcct tgattgtgcc gctgcactcc agcctgggtg  75240
acagagtcag actctttcca aaagaagaaa aaaatgtgac catgtgtttt atagctcttt  75300
tagtatcatc agtcactgtt atccctaaga gggaaatacc tagctttagt tttaggtttc  75360
cagcattagc caagaaagct cagaattgat gttcctggcc aagtacctca ttgctgtctc  75420
cttaaatctt ggttaatggc tactgtcctg gctagcatag ttatggagca tttccatggt  75480
tgtagaatgt tctgccaatc tcagggacag ttttgctttt ctgtgaagca ataaaatcaa  75540
cttcaaaaca aatgttaact atttgtacaa tggatttaag atagaccagt tcacatactt  75600
tttttttttt ttttttttga gatggagttt cattcttgtt gcctgggctg gagtgcaatg  75660
gtgtgatctc agctcactgc aacttctgcc tcctgggttc aaacgattct tctgcctcag  75720
cctctcgagg cagattacag ctgggattac aggcatgcac caccacaccc agctaatttt  75780
tttgtagttt tagtagagac ggggtttcac catgttggtc aggttggtct caaactcctg  75840
acctgaagtg atctatccgc ttcggcctcc caaagtgttg ggattacggg catgagccac  75900
cacgcccagc ctaagataga ccagttcact tactgtttat atctgattac tctctctttg  75960
ccttgtcttc tacctttaaa aatctcccta ctaacttccc attctccttt agctgccatc  76020
agtcttctcc cttctctgca aacatctctg gagagtccca gcctcagccc acagagcttc  76080
ccactgctct gaggtggacc ttgtttgcaa ggcttctttg gctctcttgg cctggaccct  76140
gtctactact tcagccatcc ttccttaacc cctgctggtg gtttctgttg ccacactcca  76200
tagcagcgtt tcccgcccag atcatgtctt tacatctctg ggcactgctc tggtcctgcc  76260
tgcctttccc tctttgtatc ctgcaggctg ctaccccccat cttgagtgtc ctcttcagtt  76320
ggctttcaga gggcctcctg ggtgttccct tacccacttg ccactcccca gtcactgggt  76380
tcagtccttc ctgcccacca gcacatgctt tctaggctct gtcctaggcc gtcttctctc  76440
tttgtagtct ctgggccagt gctgttctag agagtggcag aattttctat aaccatggca  76500
gtgctccata gctatgccag gcaagacagt agccactaaa cacatatagc tgttgagccc  76560
ttgaaatgca gctagtgtga ctgaagaact gaaccccgat tcggtttaat tttcattaaa  76620
tttaaattta aataacctta tgtgggtagt ggctccagta ttgggcaggg cagcctgaga  76680
gtcggggctg ttctcctgtc ttcagtgtct agatgaggga cctcagagga cctgtctctg  76740
gagctgcagt tcaatgtagc cagctgcccc gtgacactta catatagctg atttgtggat  76800
atgtcagaca cggtgtgatg agctcagctt tctgtcctcc tccccacatc tgcccctgcc  76860
ccatttaccc cactttgtgt cttatcaagc tagaaacagg tcaccacaag tcttcatttc  76920
cactcaccaa gtcttttgtt tcccctacta aatattttgc gagaagaaag tgtgtacctt  76980
tgtattcaca tacatgtaca tgcacatata catgcacata tgcaggggtc cccaacctct  77040
gttaaaaacc ggactgcagg ccgtgcgtgg tggctcacgc ctgtaattcc agaactttgg  77100
gaggccgaga ccagtgcatc acaaggtcag gagatcgaga ccattccggc tcacacggtg  77160
aaaccccgtc tctactaaaa atacaaaaaa aaattagccg ggtgtggtgg cgggcgccca  77220
tagtcccagc tacctgggag gctgatgcag gagaacggcg tgaacctggg aggcggagct  77280
tgcagtgagc cgagattgtg ccattgcact ccagcctggg cgacagagcg agactctgtc  77340
tcaaaaacaa aacaaaacaa aaaaaaaaaa aaccaggctg cacaggaaga agtgagcaag  77400
cattaccatc tgagctctat ctcctctcag gccagtggtg gcattagatt ctcataggag  77460
```

```
cgtgtatgag ttcgttctca cacttctgta aagacatacc tgagacatat aaagaaaaga  77520
ggtttaattg gctcacagtt ctgcaggctg tacaggcttc tgtttctggg aaggcctcag  77580
gaaacttgca gtcatggcag aaggtgaagg ggaagtaggc acatcttcac atggcccaca  77640
ggaaaaagag agaaggagag agagagagag acagagagag agagagaaaa agaaagattg  77700
agagggagag aggagggaga aaggagagtg cctgtagggg gagttgctac acaaaggagc  77760
accaggggga tggtgctcaa ccattagaaa ctacccccat gatccaatca cctcccacca  77820
ggccccacct ccgacactgg agattacaat tcagcatgag atttgggtgg ggacacagag  77880
ccaaaccata tcagagcatg aaccctattg tgaactgcac atttgaggga tctaggttgc  77940
atgctcctta tgagaatcta atgcctgatg atgatttgag gtggaacagt ttcatcccga  78000
aaccatcccc cgccaaccct ggtttgtgga aaaattgtct tccacagaac cggtccctgg  78060
tgccaaaaag tttggggacc tctgcacata tgcatgcacc tgtacatgga cacataatac  78120
atgtacatat gcatacttta tattctctgc cacttctggt ccagactgat atactatctc  78180
atttggatta ctgcactagc cttttgtttt ggaaacagca ttttttaaaa aatttaattt  78240
aatttttttg agatagggtg tcattctgtt gcccagcttg gagtgcagtg tcatgatcat  78300
agctcactgc ggcctcgatc tcccaggctc aagtgatcct tctgcctcag ccttctcagt  78360
agttgggact acaggcatac ccaccatgcc cagctaattt tttgattttt tttttttttt  78420
gagacagagt ctcagcctgt cgcccaggct ggagtgggtt ggcgcgatct cagctcactg  78480
caacttctgc ctcccaggtt caagtgattc tcctgcctca gcctcccgag tagttgggat  78540
tacaggcgcc tgccaccaca cccagctaac tttttgtatt tttagtagag acggggtttc  78600
accatgttgg ccaggctggt ctcgaacttg tgacctcgtg attagcccgc ctcggcctcc  78660
caaagtgctg ggattacagg cgtgagctac cgctcccagc caggaaacag cattcttgag  78720
ataattcata taattcaccc atttaaagta tataattcat tctctttagt atgcccacag  78780
agttgtacag ccatcaccag aatcagtttt agaacccata aaggaactct gtactcttta  78840
cccaaaacct ccatgcctcc agctgcaggc agccactaac ctgccttctg tctctgtgac  78900
tctacgtctt ctggacatta ctgtggatgg gctcatacag tcagtgagct tgtgactggt  78960
gccttctacc aagcagggtt ttcagtgtag cagcctctct gtttttcttt tttttttaaa  79020
ttgtgacgga acttctgcct cccgggttca agcgattctc ctgcctcagc ctcccgagtg  79080
gctgggacta caggcccatg tcaccatgcc tggctaattt tttttttttt tttttttagt  79140
agagatgggt ttcaacatgt tagccagggt ggtctcgatc tcctgacttc atgatccgcc  79200
tgcctcggcc tcccaaagtg ctgggattac aggcgtgagc caccatgccc ggctaacctt  79260
tcatttactg tctgcatttc ttccctgatg ccttccagtc catgcacccg attgtagcca  79320
ttcatcctat tatggtttaa ggtgactgtc ttagtcagca tgggttgcca taacaaaata  79380
ccatagcctg ggtggcttca acaacagaat ttacttctca cacttctgga ggttgggaag  79440
tccaagatcc aggactttcg ccttgccctc atgtggtgag ggggtgagga agctctgtgg  79500
ggcctcttat atatggatgc taatctcatt catgaggggt ctgccctcat gacccagtca  79560
cctcccaaag gccccacctc ctaataccat caccctggta attaagtttc agtgtataaa  79620
tttgggggac tatagacatt gaaaccataa caagcacttt tctaagatca gggagtgagt  79680
aagtagcaga gctaggacct caattccaca tgtcagtcat cttgccttca ctctgctcca  79740
tgatggctgc ctcctagagc attgggagtc tcgatgttct atatgctctc atgtgttgtg  79800
```

-continued

```
tattggagat agttgaggct ttatgaatac atctggattt gttgacttct agctttgctg  79860
gtaaccagct gtgaccttga ataagttact tcatctctga gcctgtttcc tcttttagaa  79920
acaggagttt aaaatgctgc tttgggttgg gcacggtggc tcatgcctgt aattccagca  79980
ctttgggagg ctgagatggg aggatcactg gagcttggag ttcgagacca gcctgggcat  80040
catagtgtga gatcctgtct cctcaagaaa ttaaaaaatt agctgggtga tgtggcgtgt  80100
gcctgtggtc ccatctactc tggaggctga ggtgggagga ttgcttgagc ccaggaggtt  80160
gaggctacaa tgaaatatga ttgcacccca tcctgggtga cgagtgagac cctgtctcaa  80220
aaaagaaaaa aaaaatgctg ctttgtaccc ctttcatgtc atggcgtcat ggccaacata  80280
gaatgccctg gttgtttgct gttggagggc atgggcctgg gggctccctg agggctcctt  80340
ccatcttcaa ctcattctct gtgcacctgt taggaagttg tgggccagtc cctaccatgt  80400
atcattgtgt gggtaaaagt aaataaaatg tgtacagtgt ctgaactgta catatcaggg  80460
tccaagaaca aaatgagtga catgggttag ctctttttaa taaatggtaa aaccaaatat  80520
tctaatttc agtttgtta tacttccatc acatgttttt gtttttttgt tttttgtttt  80580
tgtttttcta ttttaggcag ccttgccttc tctaacaaac ccccccttctc taagtcccat  80640
ccgacgaaag gggaaggaga aagaaccagg agaacaagca tctgtaccgt tgagtcccaa  80700
gaaaggcagt gaggccagtg caggtaggaa acagcgtggg gaagggaggg acatgagtgc  80760
agcatctgtc atgtagaaac ataggattta agtaacttgg tgttttagag aaataaatat  80820
aatacacatc agtaaagtga gagaaagttt ctccaggtgc ggttcaagat attagaaact  80880
aatgactgat gtacacagac cacctttttgg tctgaagcat ttctaagtgc cactggctga  80940
catgcagccc ctacagcctc caggcttcca gccctagcat ggagcatcac tctcctatgc  81000
ttccctggtt gcaggtgatg gctggagagg cctcctgatt ttcagtaagg gaagtggtgt  81060
agatgcttag gaatagatgt agtgagtgaa aaaactgatt ctgatatgtc aaaaattctg  81120
attggaaatg gaatatttac atttggaaga gctaaaggcg agagaaagtg gggataaagt  81180
catctgagtt ggaggagctt aaaccattca caagtttgga ggaccttttt ttacccatga  81240
aaaggtcaga acagaagggg ctaggattta ggtgtgactg cagtttattg aattcccatc  81300
catactgctc tcggtgggca gtggcagggg caggagagga gcctggcaaa gcatgaagtg  81360
actgctgctg cctctgctat ctgggacgcc tggccacctg tctgtacagt ctccctccag  81420
acccattctc acgctgtctc ttggcaccca ggggccagtg atggttctcc catttgtttt  81480
gtgtatatag catttatatc aaggctattt atttatttat ttatttttatt tatttatttt  81540
tttgagacag agtctcactc tgtcacccag gctggagtgc agtggtgcaa tctcggctca  81600
gtgcaagctc tgcctcctgg gttcaagcaa ttctcctgcc tcagcctcct gagtagctgg  81660
gactacaggt gtgcaccacc acacctggct aattttttgt atttttttatt agtggagacg  81720
gggtttcacc ttgttggcca ggatggtctt gatctcctga cctcgtgatc cgtccacctc  81780
agcctctcaa agtgctggga ttacaggcat gagtcactgt acccggccta tttatttatt  81840
tttaattgac aaaattgtat atatctgtaa tatacaacat gatgtttgaa atatgtgtac  81900
attggccagg cgtggtggct cacacctttt atcccagcac tttgggaggc tgaggtgggc  81960
ggattacgag gtcgggggtt taaggccaaa ctggccagca tggtgaagag gtgcccctac  82020
taaaaatacc ccaaaaaaaa aaaaaaaaaa aaaaagccgg gcatggtggc tcgcgccagt  82080
cgtcccagct acttgggagg ctgaggcagg agaattgctt gaatctggca ggtggaggtt  82140
gcagtgagct gagttcatgc cactgcactc tagcctgggc gatagagcga gactccgtct  82200
```

caaaaaaaaa aaaaaaagaa gaaatacata tgcattgtgg aatggctaat taacctgtgc 82260
atcacctcac gtatcattgt tttgtggtga gaacacttaa aatctactct ttcagtgatt 82320
ttcttgcata tggtacattg ctattaactg cagtcaccat gctatacagt agatctcttg 82380
aactcattcc tcctgtctat aaatgaaatt ttgtatcctt gaccaacaca ttcaaggttt 82440
tttttgagat ggagtcttct tcacccaggc tggagtacca tggcacgatc tcatctcact 82500
gcaacctccg cctcccaggt tcaagcaatt ctcctgcctc agcctcctga gtagctggga 82560
ttacaggcac atgctactgc acctggctaa tttttgtatt tttagtagaa gtggagtttc 82620
accatgttgg ccaggctggt ctcgaactcc tgacctcaag tgatccgcct gccttggcct 82680
gccaaagtgc tgggattaca ggtgtgagcc actgcacccg gcctcaagcg ttttaaaaga 82740
tgctcttttc taaggattga ctgtagtaca ggaggaagat tgacctgttg aaaagcctca 82800
gcctttacaa gtgtaaaatt atcagtatat tactatcatc tttctgatga attaaataaa 82860
ctaaggactc caagtcaaaa gtcttcaaac tgaagtagaa tagttgtata tagtgcttgg 82920
cactttaata tttagtatcg gtttaatgat aatgtttgtg cctttgccgt ctttaaaaca 82980
tttttacatc atccctgttt gattacttgg tgtgctcatg aagttgttgg ccactaagga 83040
atcttaggct cagagaggtt ctggaattgg ccagtggtcc ttgaatcagc tgctcctatg 83100
attctctaac tgatttctca caaagcaaac aagcaatcat aacaaaacaa ctgtgcacac 83160
tgctcttctt attttgttat ttaaaaagta cttaggctct acttatgttt gttagtcaat 83220
ttctcattac ttctagttaa tcaaaaggtc agaggaaata cttgaatatt ttcatactag 83280
aatactttaa aaaatcatga tttccagtaa tctctttaaa acttggcaag ttattttgat 83340
ctaaaagttt atcttttgtg tgcatatttt taaagcttct agacaatctg atacctcagg 83400
tcctgttaca acaagtaaat cctcatcact ggggagtttc tatcatcttc cttcatacct 83460
caaactgcat gatgtcctga aagctacaca cgctaactac aaggtatggg cctctgcatc 83520
ttttaaaaat atatatgcac acatacttac gtctaatgga tagttgatgt ttttcttatg 83580
atttgtagga tgtataagcc ctttgagata tgagttacat ttagtttttt caagtttgtt 83640
tgtctttcag ctttgtttat gatagcttct atcatacagg tgttttggat tttcatattg 83700
tttgtactca cagctaagat tgattacagt gacagagcta ggatgtgcag ccaggttata 83760
gggggaagtg gccctggtgg agtctggagg gatccgtgta caggcttcct tccctcccgt 83820
gaggctcaca caaaaataca gcaacatgct ggtcctgcag gtaccctctg cctaacatga 83880
gccacaattc cagactcaca gaagaaaagc aggtgttcgg cataaaccat gtgtttcaaa 83940
tagtctgggc atggtgagcc acttgttatc agctagggaa agtttatgtc agcgtaagaa 84000
actgttcacc agataccccc aagagccagc ctttctgtct agggatgttt tagtttttta 84060
gttcattttt ttttttaact ttaaaatttt ctgttcatct gcaatttgtt agatatgaag 84120
tatgtgtcta atttaatttt tgtttttggt tgtccccaat aatgtttaca gaagaatttt 84180
tctgcactaa ttggcttgag ttacttacat tctcatagtt ctctagtttc agtagtttca 84240
tttattattt tgttatatca atctatctgt ctgctcatct attagaagca tccttgtttt 84300
tttttttct tttttagaca gagtcttgct ctgtccccag gttggagtgc agtggtgcaa 84360
ccatgcctcc ctgcagtctc agggctcaag tgatcctccc acctcagctc ctgagtacct 84420
gggactaccg gcatgtgcca ccacacccag ctaattttta catttttttgt agagacaggg 84480
tctccctaag ttgcctgggc tggtctcaag ctcctggctt aagtaatcct ccctccttgg 84540

```
cctcccaaag tgctgggatt acaggtgtga gcaactgcac ccggctacaa gtatacttct  84600
taattattgt agcttaatgg tatttatgag gggatcagtt cccctgttgt tctttagaat  84660
tttctggata ttcttcttta ttgattttgg gatgtgaaca atagaatcaa cttctacttg  84720
tagattgatt tagggagaac ttatacctca gatgttaagt caccctgtcc agaatgtggg  84780
atgctttcct atttgttcag aactttttaa attacctcag aagcacatga aatttaaagg  84840
attttaaaaa aaacttaaag attatttcac atagctcttg cacatttctt gataaatgaa  84900
tcctcaggta ttcctctgtt tttgttacta atagttactt cttatgggtt tttttcccc  84960
tgaaaatcat ttatcaaacg tatgtggctt attttctgaa ggatgtttga taattttgga  85020
agatatgaaa gtcttcatat tttacaaggt ttgaggtctc tttaagctgc atggttctca  85080
tgtcagctcc caaagcagaa gacggcatgt tgaaaaatgc cgtagagaag atacttcttt  85140
tccacctgtt ttcaactcat atcatcttga atttcagggc acctttccat gctcctagtg  85200
cttgctatct gtttattatt ttccttcctg aataccctga actccagcat gttctgctgt  85260
aattctggcc tccctggcat cttggactcc tgtttccttt gctctgtcat ccccgcggtc  85320
agctcctgct gcgcagcttc tcagctgaag tgcgtttgga gtgcctggcg tgtcttgctg  85380
gatctttgag tattgcctct ggtttccttg gttccttctg ctgagttgct cagcgtctcc  85440
actccccatt tcttgtgtgg cccttcctgc actcctctga ttccttttgt cttccctggt  85500
ttcttgcttt ggtttcgagt ctccacagaa cttttgcagc tcttctgaag acctggaagc  85560
tttttcatct taattctcat ctcatgacct cttttccctt ctttgagagc tagaacttcc  85620
catggtgaac ttctctttcc agaattccat gccttctttt ccctcccact tacctgttgt  85680
ccaggagagg tcagattgct gtgcatattg gaggagaacc ctttcttccc tgggctcttc  85740
atctcacatg acatcaccac atcacctcgt tccttggacc ctcagtggtg tcactgctgg  85800
atttttcttt cctttggctg gccttagggc acacccaggt tgactagcgt agtcatggta  85860
tttagatcca ctcacatttt cagtttctgt gtctgtctct tgcctgcttc tgacttcgcc  85920
cagagaaagc ttctctttca caagggttct tagatttatg ttcactgagc accttctttt  85980
ctgaggcagt gttttaccaa tatttatttt cctagtcagt ctcgccttac ctttcttgtt  86040
atgcatgtct ttggtcctga cccattctct gagtctgtaa aatagaattg ctgtataatt  86100
taattacatg aaatccttta gaatcttaac acatcttaca cctgatttaa tattttattg  86160
tatccaaatt gaaccaaccc tatgtgaatt tgacagtgat ttctcccagg gatcctagtg  86220
tataaggaat aggacttagt attttctatt ttttgatata ccacatacca gatactgatt  86280
atgatggaca tttaaccctt ttttctcatt atgaaagaaa gttaggaatt atttcttcca  86340
gtagcgccag tgtaacctga aagcctttga aagagtagtt tttgtatagc tatctgaaag  86400
gaatttcttt ccaaaatatt tttccagtgc tgacaacaaa cacgcagaca caccctgcaa  86460
ggtgagtgta cggcgccgca cagtggaggc atctgctgca gccgtcgatg tttgtgtctt  86520
tggttgtaca ttatgagatc gtgacagggc cagtaaccgt gtgttctctc cttcaccttc  86580
ccaaggtcac gctggatctt cagaacagca cggaaaagtt tggagggttt ctccgctcag  86640
ccttggatgt tctttctcag atactagagc tggccacact gcaggacatt gggaaggttt  86700
gtgtcttgtt ttttctcctt gggttgtggc tggcacactt gatgtgcgtc ttctgggctg  86760
agttcatcta ggatggagcc tggttctcca gggtgcctcc gggagactcc tccctgcccc  86820
acgtgcttgc gtcacaggac ccaagtctga ctctgcctta gccatgaagt ttagggggaa  86880
gtttctattt gtattctatt tttgtctgtt atcatgtatt agcttagacc cagtttagtt  86940
```

```
tggaaaatca gtgggtttca aaatgtgttt gtagagtcct ttatttctta acttgacctt  87000
ttcaagtgga aaggggcaaa acagacgggt aagggggcgg ggcgggaggt gtgacttgct  87060
cttttgtgcc tgaggaagta acagagctgg ggttgacagt catattctct gacacagata  87120
gtctctgact tatctcacag aaagtcagcg gcagagcctg agttaaaagt ctcgtagatt  87180
ttctttttct ttttttggt ggctaatttc agttttattt atatttgttt atttatttat  87240
tatactttaa gttctgggtt acatgtgcag aatgtgcagt tttgttacat aggtatacac  87300
gtgccatgat ggtttgctgc acccatcaac ccatcaccta cattaggtat ttctcctaat  87360
gttatccctc ccccagtccc ctcactcccc atgggccccg gtgtgtgatg ttctcctccc  87420
tgtgcccatg tgttctcatt gttcaatttc cacttgtgag tgagaacatg cggtgtttgg  87480
ttttctgatc ttgtgatagt ttgctgagaa tgatggtttc cagcatcatc catgtgcctg  87540
caaaggacat gaactcatcc ttttttatgg ctgtatagta ttccatggtg tatatgtgcc  87600
acattttctt aatccagtct atcattgatg gacattcggg ttggttccaa gtctttgcta  87660
ttgtgactag tgccacaata aacatacatg tgcatgtgtc tttatcgtag aatgatttat  87720
aatcctttgg gtatatgccc agtaatggga ttgctgggtc aaatggtatt tctagttcta  87780
gacctttgag gaatcgccag actgtcttcc acaatagttg aactaattta cactcccacc  87840
aacagtgtaa aagtgttcct atttttccac aacctctcca gcatctgttg tttcgtgact  87900
ttttaacgat cgccatccta actggcgtga gatggtatct cattgtgatt ttgatctgca  87960
tttctctaat gaccagtggt gatgagcatt ttttcgtatg tctgttggct gcataaatgt  88020
cttcttttgc gaagtgtctg ttcatatcct ttgtccattt tttgatgggg ttgtttgctt  88080
ttttttcgta aatttgttta agttctttgt agattctgga tgttaatctt ttgtcagatg  88140
ggtagattgc aaaaatttta tcccattctg taggttgcct gttcactctg atgatagttt  88200
cttttgctat gcagaagctc tttagtttaa ttagatcccg tttgtcaatt ttggcttttg  88260
ttgccattgc ttttggtgtt ttagacatga agtctttgcc tatgcctatg tcctgaatgt  88320
tatggcccag gttttcttct aggattttta tggtcctagg tcttatgttt aagtctttga  88380
tccatcttga gttgattttt gtgtaaggta taaggaaggg gtccagtttc agttttctgc  88440
atgtggctag ccagttttcc caacaccatt tattaaatag ggaatctttt ccccattgct  88500
tatgtgtgtc aggtttgtca aagatcagat gattgtagat gtgtggtggt atttctgagg  88560
cctctgttct gttccattgg tctatatatc tgttttggta ccagtaccat gcagttttgg  88620
ttactgtagt gttgtagtat agtttgaagt caggtagtgt gatgcctcca gctttgttct  88680
tctagcccag gattgtcttg gctatgcagg ctcttttttg gttccatatg aagtttaaaa  88740
tagtttttc caattctgtg aagaaagtca gtgatagctt gatgggggga tagcattgaa  88800
tctataaatt actttgggca gcaaggccat tttcacgata ttgattcgtc ctatccatga  88860
acatggaatg tttttctatt tgtttgtgtc ctctcttatt tccttgagca gtggtttgta  88920
gttctccttg aagaggtcct tcacatccct tgtaagttgt cttcctaggt gtttcattcc  88980
cttagtagca tttgtgaatg ggagttcact catgatttgg ctctctgttt gtctgttatt  89040
ggtgtatagg aatgcttgtg atttttgcac attgattttg tatcctgaga ctttgctgaa  89100
gttgctaatc agcttaagga gattttgagc tgaaccaata gggttttcta aatatacaat  89160
catgtcatct gcaaacaggg acagttttac ttcctctctt cctatttgaa taccctttat  89220
tgctttctct tgcctgattg cgctggccag aacttccaat actatgttga ataggagtgg  89280
```

tgagagaggg catccttgtc ttgtgccggt tttcgaaggg aatgcttcca gtttttgccc 89340
attcagtatg atattagctg tgggtttgtc ataaatagct cttactatgt tgagatacgt 89400
tccatcgata cctagtttat tgagagtttt tagcatgaaa ggctgttgaa ttttgtcaaa 89460
ggccttttct gcatctgttg agataatcat atggtttttg ttgttggttc tgtttatgtg 89520
atggattacg tttattgatt tgcgtatgtt gaaccagcct tgcattccag ggatgaagct 89580
gacttgattg tggtggataa gctttttgat gtgctgctgg attcagtttg ccagtatttt 89640
attgaggatt ttcacatcga tgttcatcag ggatattggc ctaaaattct cttttttgt 89700
tgtgtctctg ccaggctttg gtatcaggat gatgctggcc tcataaaatg agttagggag 89760
gattctctct ttttctattg attggaatag tttcagaagg aatggtacca tctcctcttt 89820
gtacctctgg tagaattcgg ctgtgaatcc atcctggact tttttggtt agtaggctat 89880
taactattgc ctcaagttta gaacctgtta tcagtctatt cagagattca gctttttct 89940
ggtttagtct tgggagggtg tatgtgtcca ggaatttatc catttcttct agatttcta 90000
gtttatttgg gtagagatgt ttatagtatt ctctgatggt agtttgtatt tctgtgggat 90060
cggtggtgat atccccttta tcgtttttat tgagtctatt tgattcttct ctcttttctt 90120
ctttattagt cttgctagcg gtctacctat tttattgatc ttttcaaaaa accagcacct 90180
ggattcattg atttttttg gagggttttt tttcgtgtct ctatctcctt cagttctgct 90240
ctgatcttag ttatttttg tcttctgcta gcttttgaat ttgtttgctc ttgcttttct 90300
agttctttta attgtgatgt tagggtgtta attttagatc ttttctgctt tctcttgtgg 90360
gcatttagtg ctataaattt ccctctacac actgctttaa atgtgtccca gagattctgg 90420
tatgttgtgt cttcgttctc attggtttcc aagaaaattt ttatttctgc cttcatttcg 90480
ttatttaccc agtagtcatt caagagcagg ttgttcagtt tccatgtagt tgtgtggttt 90540
tgagtgagat tctcaatcct gagttctaat ttgattgcac tgtggtctga cagacagttt 90600
gttgtgattt ctgttctttt acatttgctg aggagtgttt tacttccaac tatgtggtca 90660
gttttagaat aagtgcaatg tggtgctgag aagaatgtat gttctgttga tttggggtgc 90720
agagttctgt agatgtctat taggtccgct tggtccagtg ctgagttcaa gtcctggata 90780
tccttgttaa ttttctggct cattgatctg cctaatattg acagtggggt gttaaagtct 90840
cccactatta ccgggtggga gtctctttgt aggtctctaa gaacttgctt catgaatctg 90900
ggtgctcctg tattgggggc gtgtatattt aggatagtta gctcttcttg ttgaattgat 90960
ccctttacca ttatgtaatg gccttctttg tctcctttga actttgttga tttaaagtct 91020
gttttatcag agactaggat tgcaatccct gcttttttt tgctttccat ttgcttgtta 91080
gatcttcctc catcccttta ttttgagcca atgagtgtct ttgcatgtga gatgggtctc 91140
ctgaatacag cacaccaatg ggtcttgact ctttatccaa tttgccagtc tgtgtctttt 91200
aattggggca tttagcccat ttacatttaa ggttaatatt gctatgtgtg aatttgatcc 91260
tgtcattatg atcctagttg gttattttgc ccgttaactg atgcagtttc ttcatagcgt 91320
cagtagtctt tacaatttgg catgtttttg cagtggctgg tactggttgt tcctttccat 91380
gtttagtgct tccttcagga gctcttgtaa ggcaggcctg gtggtgacaa aatctctgca 91440
tttgcttgtc tgtaaaggat tttatttctc gttcacttat gaagcttagt ttggctggat 91500
atgaaattct gggttgaaaa tactttttt aaagaatgtt gaatattggc tcccactctt 91560
ttctggcttg taggatttct gcagagagat ctgctgttag tctgatgggc ttccctttgt 91620
gggtaacccg acctttctct ctggctgccc tttccttcat ttcaatcttg gtggatctga 91680
tgattatgtg tcttggggtt gctcttctcg aggagtatct ttgtggtgtt ctctgtattt 91740
cctgaatttg aatgttggtc tgccttgcta ggttggggaa gttctcctgg ataatatcct 91800
gaagagtgtt ttctaacttg gttctattct ccccatcact ttcaggtaca ccaatcaaac 91860
gtagatttgg tcttttcaca tagtcccata tttcttggag gcttggttca tttcttttca 91920
ctctttttc tctaatcttg tcttctcgct ttatttcatt aatttgatct tcaatcactg 91980
atatcctttc ttctgcttga ttgaatcggc tgtcgaagct tgtgtatact tcacaaaatt 92040
ctcgttctgt ggtttttagc tccatcaggt catttaagct cttctctaca ctggttattc 92100
tagccattag tctaacattt ttttcaaggt ttttagcttc cttgtgatgg gttagaacat 92160
gctcctttag ctcggagaag tttgttatta ccgaccttct gaagcctact tctgtcaatt 92220
catcaaactc attctccatc cagttttgtt cccttgctgg tgaggagttg tgatcctttg 92280
gaggagaaga ggtgttctgg tttttggaat tttcagcctt tctgctatgg tttctcccca 92340
tcattgtggt tttatctacc tttggtcttt gatgttggtg acctacggat ggggttttgg 92400
tgtgggtgtc ctttttgttg atgttgatgc tattcctttc tgtttgttag ttttccttct 92460
aacagacagg cccctcagct gcaggtctgt tggagtttgc tggaggtcca ctccaggccc 92520
tgtttgcctg ggcatcacca gcagaggctg cagaacagca aatattgctg cctgatcctt 92580
cctctggaaa catcgtccca gagcacgaag gtgtctgcct gtatgaggtg tttgttggcc 92640
cctactggga ggtgtctccc agtcaggcta catgggggtc agggacccac ttgaggcagt 92700
ctgttcatta tcggagcttg aatgccgtac cgggagaacc actgctctct tcagagctgt 92760
caggcacgta tgtttaaatc tggagaagct gtctgctgcc ttttgttcag atgtgccctt 92820
cccccagagg tggaatctag agaggcagta ggccttgctg agctgcagtg ggctctgccc 92880
agttcgagct tccctgctgc tttgtttaca ctgtgagcat agaaccacct actctagcct 92940
cagcagtggt ggacacccct cccccagcca agctcctgca tcccaggtcg atttcagagt 93000
gctgcgctag cagtgagcaa ggccccatgg gcgtgggacc cgctgagcca ggcacaggag 93060
agaatctcct ggtctgctgg ttgtgaagac tgtgggaaaa gtgcagtatt tgggcaggag 93120
tgtactgctc cttcaggtac agtcactcat ggcttccttt ggcttggaaa gggaagtccc 93180
ccgacccctt gtgcttccca ggtgaggcaa caccccgccc tgcttcggct tgccctccgt 93240
gggctgcacc cactgtccag caagtcccag tgagatgaac taggtacctc agttggaaat 93300
gcagaaatca cctgtcttct gtgtcgatct cactgggagc tgtagactgg agctgttcct 93360
attcggccat tttggaagca tcccttgttt tttgaggtgg agtcttgctc tgtcgcccag 93420
gctgacgtgc atcggcacaa tctcggccca ctgcaacctt tgcctcctgg tttcaagcga 93480
ttctcctacc tcagcctccg gagtagctgg gattacaggc acctgccacc atgcctggct 93540
aattttttgt atttttagtg gagatggggt ttcaccacat tggccaggct agtctcgaac 93600
tcctgacctt gtgatccacc cacctcagcc tcctagagtg ctgggatcac aggtgtcagc 93660
caccacgccc agccatattt tcagatctcc ctctctttgc cctaaaccac tgtgcttaat 93720
aagtagtttt tagtggccag cagtctccat gtataacaca ttttagcaaa atggaaaata 93780
ctatatgttt taaatttgaa cgtgagatta tactgaaata aaaatcatct aactgggatt 93840
ctttaaatag taagattttc ttttttgtat gtgggttttt ttttaacctt attattatga 93900
ctgtcatata tagaaatggc tgtttttcag ttacagtcag tgaatgtatc aaatgctgcc 93960
ttatccaaat aataaaagta aattattaat aagtcacaat ttaatgaaga ttgatgttag 94020

-continued ttgatcttta tattcttgaa atcagccata tggttgtgtg tgtatgtata tatttttaaa 94080
ggtacataaa gataataagc tcatctctga aaatttttac atttggcata agaataactg 94140
gataattaag catcttattc tctggcctgt gtctttacag ttaaaggtag atttactcac 94200
ctctcctttt ttgtttttct aagttcatct tttttgctgt ttcaagacag aggcccattt 94260
tagctttctc gcatatcctt ttgtttgtac tttggaagcc tcacctgctt aattgttgag 94320
tttttatccg tggtctttta gagggggata tgtagggtag aagctttcac aggttcttgt 94380
ttgcacttgg cccctgactg ttttgaggaa tctccctcac tgactcacag catggcaagg 94440
tttcagatct ctttctgcca cacagcagtt ctgaggcagc tggaaagata tccagatgct 94500
tagattgtca ggccaggctt gagatataca aactattgag ccttatctgt gaccttgctt 94560
aggtgaaggc atcagagccc ctgcaccaac atgcataggc ctctgcatgt gtgcggggct 94620
gggtgttgag gtctgagcac aagtgtagct ggagaggtga gcttgatgtg gcgacgggta 94680
tgagcaggtt ttcttcagac ttctgtgagt ttacctagtt ccaggattta aaggcacaga 94740
gactttagaa ttaaaataga atcattttct ttttctaaat agcaacacta ggaataaaaa 94800
ataataattc cacattcttg acaggtaatg ttttttcttg tcttctaatc cttatttatt 94860
ccatactcat ttttatacat aattgaaatg tattatgcat tggatttttc ttttgcatta 94920
tattatagac gatttttcat gtaactcctt actgttccat tttatatgtt ttgtctggtt 94980
taagacttta tctgcaaacc gggaaactgt ctctacaaaa agaaaaaacaa aaatagttgg 95040
ccgcagtggc atgcgtctgt ggtcccagct actcggggct gaggtgggag gattgcttga 95100
gccttgggag gttgaggctg caaagagcca tgatcatgcc attgcactcc agcatgggtg 95160
acagacttta tactgtctgt tttgggtgat ttgataatga tatgccctga tgtagttttt 95220
ttatatcttg tgtttcttgt gcctgggttt attgaggttg ggtctgtggc ttcatagtat 95280
ttttaaagtt tggaaaattt taggccattc tttctttctt tctttctttt tttttttttt 95340
gagacagtgt ctcgctctgt cgcctgcgtt ggagtgcagt gacactatct tggctcactg 95400
caagctctgc ctcctgggtt cacgccattc tcctgcctca gcctcctgag tagctgggac 95460
tacaggcgcc tgccaccacg cctggctaat tttttgtatt tttagtagag acgaggtttc 95520
actgtgttag ccaggatggt ctcaatctcc tgacctcgtg atctgcccgc ctgggcctcc 95580
caaagtgctg ggattacagg cgtgagccac tgcacccagc taggccatta tttcttcaaa 95640
gatttttttt ctgccctgcc tccctccttt tttccctctc ttaaaggggc tgtgatttcc 95700
tgaatgattg cttagtgttg tcccatagct tactgatgct cttttcagtg tttgattgtt 95760
ttatgtgttt tctgttttgt atagtttcta ttattgtgtt ttcaagttct ctgatctttt 95820
cttctacagt gtctactctg ttgttaatct gttaatctgt tgttaatcct gtccagcgta 95880
tttttttttt tgtttttgaa acagtctcac tctgttgccc aggctggagt ttagtggtgc 95940
gatatcagct cactgcaacc tccacctccc aggctcaagc aattcttctg cctcagcctc 96000
ccgagtagct gggactatag gcacgtgcca ccacacctgg ctaatttgtg tatttttatt 96060
agagatgggg tttcaccatg ttggccaaac tggccttgaa ctcctgacct caggtgattc 96120
atccgcctcg gtctcccaaa gtgttgggat tataggcatg agccaccgtg tctggcccct 96180
gttcagtgta tatcactaat tttgttttta tctctagaag tttgatttag gtcttttaaa 96240
aatgtctccc tgtgtttctg tttagctttg tgaacacaat tgtaataact gttttaatat 96300
ccttctctgc tagttctaag atcttctaat aacttcccag ttcttggtgt ttctcattgg 96360
ttgattgata ctcctcgttt tgggttgtat tttcctgcct ctttgtatgg ctgccaattt 96420
tttattggat gcccaacctt gtgaatttta ctttgttgga tgctatatat ttttgtgttc 96480
ccatagatct tcttgagctt tgttctgagg ttagttgagt tacatataga tggtttactc 96540
ttttgggtct tgctttataa tttgtcagat gggttggagc agtgcttagt ttaggactaa 96600
ttttttttt ggactaatta ttcctcttta ggaataatta ggtaccatgc ttaggaggca 96660
agaccatcct gagtactcta cctaatgaac cagaaagttt gggttttcca gtccgcctgc 96720
tgagaacagt gactttctag ccctgtgtga gcgctgagct ctgctccttc taatcctttc 96780
caatgcttct ttccctggcc tcagggagtt ttctcacaca catatctctg ctgagtactc 96840
gagagggacc ttccccagat ctccagagct ctctctgtct tgttttctct tctctggtgc 96900
tctgtcttat gaactgtggc tgtcttggtc tccttagatt ctcagcacct cttcaattca 96960
gagggttgcc tgtccctcct ccttgtgcca cagcctagga actctctcaa agcagcgagt 97020
tggggcagcc atagggctga cttagtctct cgtctcccag ggatcactgt ccttcattgc 97080
tcatgtccag tgtcttgagg actctgggtt ttgtctgttt tgttttttgg tttgctttgg 97140
ttgtctcagg caggagggta aacccagtcc ctcaccctca ttgtgctcag tagtggaagt 97200
ctcactctat tacattagat attagtattt gtagcagagc cctggttccc tggtacttgg 97260
ggagctcttg aaaggccaga aacagcatgc tttctcacct tttccagggc ttcagtttct 97320
ggtgcacatc aagcattcca tacacatttg ttaaagtcct ttgttagaca agtagtgatt 97380
cacaggttct atttgtaatt ttttcagtta acatgtattg ggtatctgct gggagctagt 97440
aaaaacaaaa agtggtgtgt gacaaattca attctgacaa gaacaacctt aaacacttag 97500
aatatacttt gagcatatca gaattttaaa aatgtgtggc ccttgagtat ttgaaaccaa 97560
caagaatcta ttgcttatta gtagaggata ttttgttaaa caagtggaga gagaggcatt 97620
ttcagtctaa ttggtgttgg cttttagcag ctgatggaaa ccagttcgtg attagccagg 97680
cagtggtgaa acaggctgtg cattctgaat gcctaggtat ctaggcattc agaatggtgg 97740
cgctctttga gttagcatct tcttctttct tgattctttt tttttttttt ttgagatgga 97800
ctttcgctct tgttgcccag gtaacaactc cagtgcaatg gcgccatctc ggctcactgt 97860
aacctctgcc tccctggttc aagcgattct cctgcctcag cctctcaagt agctgggatt 97920
acaggtgtgc gccaccacgc ctggctaatt ttgtattttt ggtagagatg gggtttcact 97980
atattggtca ggctggtctt gaactcctga cctcaagtga tgcacctgcc tcgatctccc 98040
aaaatgctgg gattacaggc gtgagccacc actcccagcc ccttcttgat tcttgaaaag 98100
gacattgggt gctgtacatc tcgttataga tgttgataaa aatgcttgtg agaagagtaa 98160
cattaaggta gttatttggt catttttgca gattatttta agacaattct aggactgatt 98220
tgtggtaaat cacacattgc tgtatcatag ttgtgttcac tgaacatatt caggggctct 98280
acagatgcag ggctcttagc tgctttgcac acttctgaat tcctgccctg cgaacaggac 98340
tggataccta atagacaaca ggtacttgat aacagtttat tgaattaatg agtgaatgaa 98400
cagatacata aatgcatgaa agaatggttg taatgtatat aacttggatt tcaagacttt 98460
ttactgactg ttcaaaataa gaaattgaaa actttcctct gattttcctc tactatttac 98520
acaatttaaa tggaagttat cttgtacctt caatttctgt ctaggattcg tacaataacg 98580
ggtcatctct gagtcgctta atgtctcact tgtctttcta cagtgtgttg aagagatcct 98640
aggatacctg aaatcctgct ttagtcgaga accaatgatg gcaactgttt gtgttcaaca 98700
agtaagagct tcattctttt cctcttctgt taagacgttc gggtatgaca gcaaaacgct 98760
gctactcctt aagaggcagg cgctgttggc ataatcagct gggaggattg tggggtccag 98820
cgcagcactt tttggctcag tccatgattg agccaagagg ccatccttcc cttcactccc 98880
caggaggacg aggtctgtca ctgtggaggg cagaggacac cagaagctcc tctgcaacct 98940
cgctagttaa cttccagtcc ctcggagttt ctgtttagaa tgctcaatct catttagaat 99000
tgcaaggaaa cccaaaacgc ctatttaagg tacaaacagc acttcataca atatctcatg 99060
aggtattaat agtgattcac aggaagaatt tcacgctgtg agtctttgct aacatatcca 99120
gttatttaca gatggatttg atatttgtgt gggagattct taaaagtgtt gttcacgcca 99180
cattgttgat gcctcatttt tttcactgta gttgttgaag actctctttg gcacaaactt 99240
ggcctcccag tttgatggct tatcttccaa ccccagcaag tcacaaggcc gagcacagcg 99300
ccttggctcc tccagtgtga ggccaggctt gtaccactac tgcttcatgg ccccgtacac 99360
ccacttcacc caggccctcg ctgacgccag cctgaggaac atggtgcagg cggagcagga 99420
gaacgacacc tcggggtaac agttgtggca agaatgctgt cgttggtgga agcacgaaag 99480
agcaagcagg aaatactttg taaaagaata aaaacgaaaa atgttagcga acatcttcta 99540
atagtctgct gtattcagag aactctagga gatatatatg gttgatgcaa agatgattta 99600
aggcatagcc cggccttcca agaagtgtgt ggccagtgag tgagatgggc ttgggactta 99660
cacatctcag aggtgggggt agaggaggag gaacactgag tgggctgaga agcagccagc 99720
tctcattgcc aaagtgtgtc agcaaaccag aatgcagttc ataatgtccc cacccattca 99780
aagcacagga cctgtagagt ggtgtggcat gtgttggtgg cacttttcag gcctgtaaca 99840
aggatgaaag aacagcttca tagcagcaca gtagtgctgg tgttcagagg tgtgtgaagg 99900
ccatagaagc atcttggata tattaccttg tgttttgtca gctttatgac tagaagtctc 99960
ttttcactta aatttgtttt tttttttttt gagacggagt cttgctctgt cgcccaggct 100020
ggagtgcagt ggtgcaatct cagctcactg caagctctgc atcctgggtt catgccattc 100080
tcctgcctca gcctcccgag tagctgggac tacaggcgcc tgccatcacg cctggctaac 100140
ttttttttgt atttttagta gagacggggt ttcaccatgt tagccaggat ggtctcgatc 100200
tcctgacctc gtgatctgcc cgtcccggcc tcccaaagtg ctgggattac aggcgtgagc 100260
caccgcgccc ggcctctttt cacttaaatt tatgtttgtg tttttaatgc ctagtataca 100320
ggacttctta aattgcctta agtatgaaca ggtatttgag ttgctaatct gtatagtagc 100380
aataatagaa tcccttgttt ttccttttat aaatttagcg attaaatagc tacaattaaa 100440
acactagagt caggagtcaa ggaaaatacc catgttccag gctgtatgtt agtgatgtac 100500
ttactatata ttggagtttc aggagtaagt ctgtttcaat gctttctgta accatttggg 100560
gtattaataa gcatgtgagt gtgtgcatgt ttgggttaat ttcatatatg tttcttagaa 100620
gggatatcat tgatgtaaat attttaaagg cttgtcctcc aaaaaaatca tgtaatttct 100680
tctaaattac tgatctttta aatgaccttc acctttctct caaatctcac ttaagactgg 100740
gctgagtagt cagtttcctg tagcagaaaa aagctcagac ttgagtagcc ttctgcgagt 100800
gaggagactt gatggctgtc aggcagctgt aaactctaaa tagagtgtca ttatctgaag 100860
agggcgatgc tgccacactg agtggccttt caagttgttt ctcaatctga cacgttctga 100920
tcgtgtgaat gtgaaattgg tttgagcagg agtatatctg agtgcagagg agattattta 100980
aagatattct cattctctgc ttccctttta ttcccatttg gcagatggtt tgatgtcctc 101040
cagaaagtgt ctacccagtt gaagacaaac ctcacgagtg tcacaaagaa ccgtgcagat 101100
aaggtaaatg gtgccgtttg tggcatgtga actcaggcgt gtcagtgcta gagaggaaac 101160
tggagctgag actttccagg tattttgctt gaagctttta gttgaaggct tacttatgga 101220
ttctttcttt cttttttttct tttttataga atgctattca taatcacatt cgtttgtttg 101280
aacctcttgt tataaaagct ttaaaacagt acacgactac aacatgtgtg cagttacaga 101340
agcaggtttt agatttgctg gcgcagctgg ttcagttacg ggttaattac tgtcttctgg 101400
attcagatca ggtttgtcac ttttatcttt catccatcat acctgttcct aatttagtac 101460
aaattaccct aaaagacact gaaatctact ttaaagaaat gtggtctgca tgtttccctc 101520
atcagttgct gctgcttatc tttttcatgc acctagctgg tgcagaaggc ctggggcata 101580
gccagcctca gcaagtcagc atccttgccc cagctccctg gactcaaggc taacctgggg 101640
ttggctgtta gggatttcca aaggtttgtc ccatccactt gcctcccctc caaaataagt 101700
ttgaatttaa attgtgagat acaattaaga tttattgttt ggggaacatt tttgcaaaat 101760
ctagagttag tttaaacaga ttatcaatta ttaccataat tgatcatctg cagtttcaag 101820
ctatctaaca ggttcactta cctctttaaa aaggaatgga atttagcagg acagtaactg 101880
agacccgtgc tcctggagtc catgtgggag ctgtgtggct ctgcacaagc atttgcacgc 101940
ttcccctctt gactgcatta ccttcctcct atagttgctg tgggcaccag attctggcta 102000
gtcctgtccc ttcatgatgc acattttcct caagattcgt cccagttaaa tcactgcaga 102060
tgaaactgcc ttttcatcgt caaaatttaa ctgtcatttt tgagccgtga tcttgggcta 102120
ctttcttatg tggggtagga atatttgtga gttagaaata ttacacttct ctatttcctt 102180
ctagacgtaa atctgttaat cctgtcagca ctgttactca cctgaaaggg tctgtttccc 102240
taggagaact gagggcactc ggtcaacact gattttccac agtgggtatt ggggtggtat 102300
ctgcttgttt tttttgttgt tgttgtttgt tttttttttgt tttttttttg agatggagtc 102360
tcgctctgtc acccaggctg gagtgcaggg gtgcgatctc ggctcactgc cagctccgcc 102420
tcagaggttc acgccattct cctgcctcag cctcccgagt agctgggact acaggcaccc 102480
accactacgc caggctaatt ttttgtattt ttagtagaga cgaggtttca ctgtgttagc 102540
caggatggtc tccatctcct gacctcgtga tctgcccgcc tcggcctccc aaagtgctgg 102600
gatgacaggc gtgagccacc gcgcccggcc tggggtctgc ttttaatgaa ggaggcatca 102660
aggggtgggc tttgcgttgg cctgatgctt tcatctttct ttcacaaaac ctgtccgaag 102720
aaaatccgtc taaatgggcc attgctctcc tcaggaaata gtcattggga acttcttttc 102780
ctttcctttg acactaggag gctgactggg gagaagccct ggtctatggc tgtgggcagc 102840
aggggctgag aggagcaggc tctcaggggg gcacgggtac cccaagggaa gccagagccc 102900
tgatttgttc cattctagta agaacaaaga ctgctctggt ttcatgtttg ttctgattgc 102960
ctttcatcaa ccggtcccct ttctcccagt tcttaagatt cagtacagtg acagttttat 103020
gaacaagaat agaacactag aacagacaaa ccattgaact ctatgctgat aaagatttat 103080
tgagctcctg ctgtatgttt gcattctgcc cagaggctct gagaaaacca ggccatatgc 103140
tccatgcttt atccatggaa gctccccgtc aggttgggaa agctgacagc tgcagggaat 103200
acagtgtgac acaaaaactgg ctcccatgca gcccttacgt gtcgcctctc agatggttgg 103260
gggacgaagg tcgactcctt tgggtatctt attactaaac cagtttcagg gaatctgtgc 103320
caccctatct gccattaacg tgaacagatg agtccccaag gtgtaatttt gggtattgtc 103380
tgatgtctct tggaatttat tatttgtttt tccaatgaga tttcacctca gggtatagta 103440
aagttgttga ggggattcct ggatgtgttc tgcaattatc taggctgatt tcagaataga 103500
gttatgctta tagtcaaatt tatcagctgt caagaatttt atttaaaatt tatgcagata 103560
agcaggagga aaagaagcct ggtttttaca ttttaatcct attattgatg tgaaatttta 103620
ttttccttcc tgtaggtgtt tattggcttt gtattgaaac agtttgaata cattgaagtg 103680
ggccagttca ggtaatagca ttttattatt ttagattttt ttcttcttct tgtgtactta 103740
catgtaattt aggttattaa gtgaatgttt aaactactgt taggcatttt tgctgttttc 103800
tttaaatgga aatctgacta acatactgtg catttttgct tctcttaaaa attaatgtat 103860
atctcaagac ttgtttggaa gtagttatgt atctgaaaat tccatatgtt gtcagtattc 103920
attgcacatt tcaaagcatt taattgtgtt gacagatggt ggaatgaaat cttgtggtgg 103980
agcactagtt tttaaatctt cttagagaaa gcagttttat ataatgttgt ctttagtaat 104040
tattatgcat ttgtattctc tgcagctttt tcttgctaga tgttgaggtt ttaatacttc 104100
ttgctagtcc attacaggtt tataattatt aaaagttaaa attcttttag tacctaaaat 104160
gcttaataaa cattgtaatt aggaaaattt agtgcagaag gaaagtgttc ccagattccc 104220
tggggtctgg aaacatagtg tttattctaa ttacatgaca cctccactgt gttttggggc 104280
aagttactgt ttctcttttg agtttcaatt tcttcaagag caaagaggca gaggagagct 104340
aggaagatcg tagctgctgt gcccctgtgc cgtcgggtgc cttctacctg ctgcctccga 104400
acctttacac atgtccctgc tctgcgcgag ggcacagatg ggatgcactg tggcaggggt 104460
ggggttagag tagatcacgg acacctgtta gcttgatgtg tgcttgctgt caaggttgaa 104520
tcatgaatta ttttatgttg cttatattga tatgtatctt aattttaaaa gaaaggtcta 104580
aatggatgtt tttgttttta gggaatcaga ggcaatcatt ccaaacatct ttttcttctt 104640
ggtattacta tcttatgaac gctatcattc aaaacagatc attggaattc ctaaaatcat 104700
tcagctctgt gatggcatca tggccagtgg aaggaaggct gtgacacatg gtaacgggac 104760
acacctttca ctgtcgtctt cggtgtcgtg atgtgcttgg cagtgttcgt tttcatatac 104820
ccactttgaa cgttgtcagt ggcagccatg tgcttctcag gctctgcatg tgtgtctgtg 104880
tatgtgaagg tactggttag agacgtttca aaagagaaga gagcatattc tttactctca 104940
gcaatttgta atcttctcag ggaaaaaaat tcaagaaaca gtaagataac ctaaggtaca 105000
gatagattct gaatataaag ttcctgttca ttcacatgaa acgctaaaag ttcttcactt 105060
gatcttagcc aaaaggccaa gaagcgatgc aacactaaaa attcttaaat cgaacttgcc 105120
gtgaattaaa ttttgatctc tcatccagtg gtattggaga tatagtttga cttgggttca 105180
gggctttctg ttttgcctga tgattttgct ggagcttaaa taaggaaccc aggagatggc 105240
cagctgtgca agcccccagc ctgtggaagg agctagtgtg gttttatgaa tgagttgcaa 105300
atctttcttt gagcttttttg aactgatctt ccagcattgc cctattgacc cctccctgac 105360
tcctttgctg gaatctgtag gcttttgaac tttgacaggg acacatccta agacccttgc 105420
aaactcccag atgtgagaat ggcactacta cttagagtct tttcgactca gcgtgtgtgc 105480
agaagagcat caaccgggct gtgttgcgag gcagggcctt ggctgacctc tcagtgttta 105540
catagctaag ccagttagtg tttgccacgg cctcacaagg gcttcagatt cacacagcca 105600
aagtatagat tattaaaggc ataggtgttt ggtttcctgg acttggaggg tctttggaca 105660
gaaaatcagt aggcaaccac acccagtact ttgtgctggg aagcttggtc atctgtgaga 105720
gggtcagaga gtatacccat gcgtgcatgc caccgaaggg tcagtgagta ttcctgtgtg 105780
tgcatgtctc agggccggag agagtatgtg tcactgagag gtcagagtgt ttgtgtgtgt 105840
gtcaaagagg gttgcattgt gcccttcact gaggggtcag agggtgcctc gcgtgtgtgt 105900
gtgtgtacgt gtgtgtgtgt cactgagggg tcagagtgtg cctgtgtgtg tgcttgtgtg 105960
tgcgtacatg tcactgaggg gtcagagtgt gcctctgtgt gtgtgctcat gtgtgtgcat 106020
acgtgtcact gaggggtcag agtgtgcctc tgtgtgtgct catttgtgag cgtatgtgtc 106080
actgaggggg tcagagtgtg cctctgtgtg tgtgctcatg tgtgagcgta tgtgtcactg 106140
agggggtcag agtgtgcctc tgtgtgtgtg ctcatgtgtg agcgtatgtg tcactgaggg 106200
gtcagtgttc ctatgtgctc atgacattga gggtcagagt gtgcctgtgt gccaatgaaa 106260
ggcatttctt atattttttt atatgtggtc atagtagacc agttaattta ttttgactcc 106320
tgtgttagac caaaataaga cttgggggaa agtcccttat ctatctaatg acagagtgag 106380
tttacttaaa aaagcataat aatccagtgg ctttgactaa atgtattatg tggaagtctt 106440
tattgtcttt tcagatgaat caagtagatt attcttgaga ccaggaatgt tgctgttttg 106500
gttatttgga aagttttatc attttcaaat tgacttttga atttgagtca cctttttttca 106560 gaagtggtgt taaattatag gagccctagg tttttttttct ttttttagaa gtcatcacaa 106620
aatgatcagt gttcagagga agagctttga ccttccacat ggtataatga ttgataacct 106680
taattcatct cttaccataa accaagtatg tgtaagggtt ttctttattt cttgaaagca 106740
ttttgtagat gttgagagca gttttccaaa tgtaatttcc atgaaatgcc tgataagggt 106800
acccttttgt ccccacagcc ataccggctc tgcagcccat agtccacgac ctctttgtat 106860
taagaggaac aaataaagct gatgcaggaa aagagcttga aacccaaaaa gaggtggtgg 106920
tgtcaatgtt actgagactc atccagtacc atcaggtaag aggaatgtat gttggaactg 106980
tcgtggatac tttattgacc cgtgcagatg gaaggaagtg ccatgtggta acgctcactg 107040
ttaactgtgt tactttgaac caggtttggg ctttctgggg cctgggtaga tgccggtgca 107100
gggggatggg gagggaggcg gggggtgggg gggtgtggtg gagttgggga ggtgcagtgg 107160
caggaggtgt tgttggtgtg tatccttttt tttttttttga gatggagtct ctctccgtcg 107220
cccaggctgg agtgtggtgg cacgatcttg gctcattgca agctccacct cccgggttta 107280
agcaattctc ctgcctccac ctcccgagta gctgggatta caggcatgca ccaccatgcc 107340
cagcaaattt tttttttgt atttttagta gagatggggt ttcaccatga tggccaagct 107400
gtttcgaact cctgacctca agtgatcctc ctgccttggc ctcccaaagt gctaggatta 107460
caggcgtgag ccaccatgcc cagcctggtg tttatcttta aagtgggcac agccacagga 107520
gttcacctga ctcctggtct gagagtcacg agatcgttca agatagtgag gccctctttt 107580
ccaaaacgag gaccaaaaat caattgacag tgttggtcaa gatggtagaa accttaaaat 107640
gatagaaatc tcaactctga aataaaaact ttatttgtat atttatttac cactattttg 107700
acatagggct aaggtctttt tctttgagct gatttctggt tttgttttct taaagtggca 107760
taagaattca aagacatttt gaggaaggct gagtgcagaa atctctcttt ttaaatgact 107820
tctcctttct tttaacttgc actgttgtct agccctcact tattttgtca attcttttta 107880
gctgtttgtc tttgaatctt cataaagcca tagcttttct cataagaagc agcactttct 107940
ttgttcattc atattttaat gaacccctgt agtatttaat taaatactta atgcctaatt 108000
aaatcacata attgcaatgc aaaagtacat gtatcataaa gaggtctgaa aatgagcaac 108060
tggcaagcag gtggtggcag gcagagctgc ttgggtgggt gggtgtcatg gagaggagtt 108120
catcagccac atgttcagtg agctctggat atgtctgttt agaaatgatc actaataaac 108180
ttgtgctcaa ccatgtatac ctctgggaag caggtgctct tcagtagatt gcctctgcag 108240
agaacacaga attgaagtga atgtccacaa aggcaatgag ccacctgcag aatagtttag 108300
tcaaggctgt gtttgaagtt tgccaaagat taatatacat ttgattttca tgttgtgcct 108360
tttctctgat tgtgaaatat tacaaattct atacaaataa caatgatggc aaatcctcct 108420
gagcaaagtg tgcaccttgt atgtgcccta gaggaacttg tgtttcgttc tgattcccct 108480
acatttctca tgtcatagag tgggggttgc attagtgtcc ccctgtcctc gctgggatca 108540
catctgtttg gatcctagag tcttccagct gaactgggac aagtataaca gacggacacg 108600
taggggtgga aaggcgtctc ttggcagcag actttctaat tgtgcacgct cttataggtg 108660
ttggagatgt tcattcttgt cctgcagcag tgccacaagg agaatgaaga caagtggaag 108720
cgactgtctc gacagatagc tgacatcatc ctcccaatgt tagccaaaca gcaggtttgt 108780
ccccgcagcc ttggcttgtt gttgcatagt gatggtagct taaggtcctt gtgaaaggtg 108840
ggtggctgga atcagctctt ccttcagtcc taatctgtgc cttgatagca gttctccgtg 108900
ctagtcatgg gacagctgac ttcatttctt ctcacaatgc catctcaggt tggtattgcc 108960
cacctacttt acagggggga tcccacagct ccgagaggtt atggaggtga tcaggcagca 109020
cacagcttta gagtgctggg gtgagggcgg gccaaggcta actctaaagc ccgaaccctt 109080
acctcctaca ctgcctcctg cattctggtc aacccagtgt tttatttggt ggttagattt 109140
ttgtttttgt taccttactg cttgtaattt agcagttttc ctttcctttc ccttcctttc 109200
ctttccgaca gggtctcact ctgtcaccca ggctagagtg cagtcgtgta atctcactgc 109260
aacaacctct gcctcccagg ttcaaccaat tctcccacct cagcctcctg agtagcaagg 109320
accacaggtg tgcaccacta cgcctggcta gttttttgta tttttagtag agatgaggtc 109380
tcgctgtgtt gcccaggctg gttttaaact cctgggcgca agtgatccac caaccttggc 109440
ctgccaaagt gctggcatta caggtgtgag ccacctcgcc tggcctattc atcactaatc 109500
agaatttcta tgatcaaatg acatgaatca ttgtttccac aactgcagtg gaaggaaatg 109560
gcctggcagt gccagtttca gaagcagcct gcccccagtc aggcacaggc cactgtgccc 109620
ccagtgtagc agcacctctg tagctcacag agaagggtgg tggggacctc cttgaggcag 109680
ctctgccaga aaatctcatg agctgcctgg cacagcttga ggttgccttt taagtggact 109740
cagcaaatac atgtttgttc atcttgatta tacacaataa acaactactc tgtatagtac 109800
gagtagtccg tggtttttgg catttgattt aaacttagag gcatgtgata ttgatgttac 109860
tgccttcatg actgcacccc cattctgatt tcataatgga atgttatctt gagaccagtt 109920
agacaacagg acagggatct tggcttctgg tgagattgac agcagtttta gtgtggtcag 109980
ggtctccctg cctacagatg gttttagaat ggtgccctgg aagctttatc ccattctttt 110040
ctgtgcgtaa tctgagtaga gtggagatcg aaggcctgaa tacatagtaa atacctgact 110100
taatatctgc cgcaatggaa attgtgtgat acaacattta tgaaacgctt agtgcagcac 110160
ctgccaggta gctcaccaca ggtgcatgtt gcattcagaa gtagtgctag atactatcct 110220
gttactggca gtgcatacat cagtgatcaa agcagattaa agaaagaccc cctgccttct 110280
tggagtgaag attttgttgg gatgcgggta aggggacaga caatagaaaa gcaagtgagt 110340
gaagtctata ccatggcggc tgatcaggaa caccgtacag aagaatccag gagggaagag 110400
agttaggtgg tgtctgcggt gggagtggca ttgttcagct ggtgatgaga agaagctttg 110460
gtgatctggt gacatttgag tgaatttgca gaaaggaaag atacaagcct aggagatacc 110520
tggggaagga acattccagg cagagcaaat agcagtgcaa aggccctggc ggggggcgga 110580
catgctgtta gggtacaagc aatgagggtg gaggagtggg gcagccatgg ggagggaagg 110640

-continued gagtgaggcc tggtggggtg aggccagtgt ggaggagcct tgagagggtt tgcgctgatg 110700
tggtgtaggt tttagcagga tcattcttat tcctgagttg agaatagcct tgagggggag 110760
gtgagggcag agcagggcca cccatgtgag acccggcact ggagtggaat ggcccaagtc 110820
agcatccctt ggcagcatga aagcaaaacc agcaaggttt gctggtggct tagatgtggc 110880
atgtgagaga gagcagggct ttgggggtga tttcagggtg aggacagggt ggctgtggac 110940
aaggtagggc agacattggg ggcagcagga ggtcagagcc tgtctggatg tagcagttga 111000
gaccccatag gtgcctaatg aggtgaggcc agcatcaggt gtatgagcct ggagttgtcg 111060
agagactgtg gggcaggggg tcagcatctg agatgtccac tcacagtgga cccagactgg 111120
ctggagagga ggaggagctt gaataccgag cctgctgagt cccagctcca aggtcaggta 111180
ggtgagggga gccagtgctg gggcaggggg agtaggcagg tgtggggttc ctaaagccaa 111240
gattttttt aaggcatttt gtgcaggagg gcgacatctg ctgtcagcac cttgggaact 111300
tggcccaggt ttggcagcac cgagggcact gatgagtgct tttggaggag caaagggagc 111360
caaaccctaa tgggaatgtg ttcctgaaag gacaggagag agacttggga aaaggtttta 111420
cttgaagagg gaacggagaa atagggcagt agccagagga ggagaggagt cggcaatggg 111480
ttaagttggc agaaatgaag gcctgtttac gcactgaggg cagaagcaac agggaggatc 111540
agttcatgac acaggagaca caaatcgccg ttgtggtgtt cacagacatg ggttaggatt 111600
ggctgcatgg atgacagagc actgtgggtt ctcccagagt tgctggggag gaggcagagt 111660
tggtgagcac aggcgagggt ccaggatgca ggaatcctgg agctcaagtc agttgttccc 111720
ttgttgtaag atgtggccag tgttgtgagc ttcacatctg tgccttgaaa aacaccacat 111780
ctgtttgcag agttgtttac tatgtataca cactcagtag aaacaaaaat tggaaacagt 111840
cagtgcccac catcaataag taatggttga acacactgtg gtataagctt agactatttt 111900
agcttgggct attttgcatg attaaaaatg ttctggccag gtgtggtggc tcatgcctgt 111960
aatcccagca ctttgggagg ccaaggcagg cagattgctt gagctcagga gtttgagacc 112020
agcctgggca acatggtgaa accctgtctc tactagaaat acaaaaagta gctgggtgtg 112080
gtggtgtgcg cctgtagtcc tggctaactc aggaggctga ggtgggagga tcacttgagc 112140
ccattcgtgc gccactgcac tcctggggca cagagtgaga ctctgttaga aagagagaga 112200
gagaaagaag agagagggag ggaggaagga aggaaggaaa taaatggaag aaatggaagg 112260
gaggaagggg agggaggaag gaagaaagga agttcagcca gttgccttgg gagttctcca 112320
ttgcactggg ttaagtgaga agagcagaga cgtttatgat ttttcaaaac aactaaaaca 112380
aaacctctgt gggtgagggg gcaaggatat ggctatagga acatggggca gattaagaaa 112440
gggatataca cacaccactt agcatttgtt acaactgttg tgggagggat ggagtgcaga 112500
aaaagaaaaa aaaaagtgca caccatccca tgtatgtgta tacaaaggga cgcttggaag 112560
actggtcccc aaaatgttgg taatgattgt gtcagggtgc tgcagtgcta gttgattttt 112620
tttcacactt ttgtatattt gagtctttta cagaaagcat ttattattta tgtaataaaa 112680
atctaaatga caagatttct gttatgggaa aaatgtagct atacagtgtt gttgtaaaaa 112740
tgtttgcttg gttcaccact gaacttaaaa tgcttttaaa tgagggaagg tgacgatgag 112800
atgattatga tgatttgccc ttgagttaca tagctggtgt acaggaagct gtcgtttctt 112860
ttggcttacg tagaaatgtt tgtggtgtct aattccacag atgcacattg actctcatga 112920
agcccttgga gtgttaaata cattatttga gattttggcc ccttcctccc tccgtccggt 112980

-continued agacatgctt ttacggagta tgttcgtcac tccaaacaca atggtgagtc tctcgcctgg 113040
ctcagcagat gaatctggac ggcttgttca ggctctgatt actgggacca cccccagaat 113100
gtctgagtca gtcagtttgg gtagggcttc ttgagagttt gctttttttt tttttttttt 113160
ttttggtgtg ggggtggtgc ggaacagagt ctcactctgt cgcccaggct ggagtacagt 113220
gtcatgatct cggctcactg caagctctgc cttccagctt cacaccattc tcctgcctca 113280
gcctcccgag ttgctgggac tacaagcgcc caccaccacg cccggctaat ttttttgtat 113340
ttttagtaga gatggggttt caccgtgtta gccaggatgg tcttgatctc ctgacctcgt 113400
gacccgccca tctcagcctc ccaaagtgct gggattacag gcgtgagcca ccgcacccgg 113460
ccttttttatt tttttggag atggagcctt gctctgtcac ccaggctgga gtacagtggc 113520
gctacctcga ctcactgcaa cctccgcctc ccgggttcaa gcaattttcc tgcctcagcc 113580
tcccgagtag ctgggactac aggtgcgtgc cactgtgccc ggctaatttt ttgtattttt 113640
agtagagacg gggtttcact gtgttagcca ggatggtcgc gatctcctga ccttgtgatc 113700
cgcccgcctc ggcctcccaa agtgttggga ttacaggtgg ctctcgcacc aagccaagag 113760
tttgcatttt tagcaaattc ccaggtgaaa ctaatgcctg cttttctggg agcacacttt 113820
gggactcagt gatagagagg tttattggta ggatagtaaa ataggagtta ttttctttca 113880
caaaattggc aattgggggga aatttaatct tcctttttttc ttcagctgtg acttatgtat 113940
tatgtttatt ttaggcgtcc gtgagcactg ttcaactgtg gatatcggga attctggcca 114000
ttttgagggt tctgatttcc cagtcaactg aagatattgt tctttctcgt attcaggagc 114060
tctccttctc tccgtattta atctcctgta cagtaattaa taggttaaga gatggggaca 114120
gtacttcaac gctagaagaa cacagtgaag ggaaacaaat aaagaatttg ccagaagaaa 114180
cattttcaag gtatgctttc tatctgagcc tataactaac ccatgccttt tgggaagtca 114240
cgtgatgttt cacagtcagt aagtctggaa taatacctgg tcttgcttca cttctgagtt 114300
gggtaaagaa gtctgtatca gtgtaatttt ctaatccgtc ctgcattatc tatggctctt 114360
ggttcatacc tgtcttgaag ttctgtcatg ttctgtctct tgtcctcagt agagatgcta 114420
cagcagtggc tcgcctcagg cagggcaggg cagtggggtg gctgtcctgg gggcaggcag 114480
taggggcacg ctgacgtcag ggaagttgaa acccaagaga agccagtaaa agtgagtctc 114540
agattgtcac catgtgctgg cagttttaca cgctgtcagt aataaaagtc ttctccctgc 114600
agggcagcct gcctccaata aatacgtgta gtatcaaatc ctgtcttccc tcataaattg 114660
tttggaagct ccccaaggac agtgatgagg cactcgtaag tgcttgctgc ctagatgggt 114720
ccctctccac ctttgctaga ttctgagcat tcactgagtt agagctgctt ctgcaaatgt 114780
gctgcttctg ctaagtggct gtgacttcat gcagccttca cttggtttgt catcagtgga 114840
gatgccctgt gttgtcgaag gagataagcc cagtaagcct gctgggcacc ttttggtttg 114900
caggttcagc aggcagccca tggctttccc tgtgtcgcat tgaagcagct ggctaaaatt 114960
gatgatacat taaattcctg tgacagatga tcagcttgta tttgtgtaat ggtgtacagt 115020
tcacaaagct taaaaaaatg ctacctgcca tttcatcctc agtgaggaag gtgatacaca 115080
gagagaccaa gtgactgtgt ccacggcgac ggcgctctgc atttcacttt agcggttaat 115140
gtactctacc tatattttta ctttatattt accatatatc ttttcatgta tacttggcgt 115200
aagtgcttta tagtagtcac ctaattcact gtcatctttt ttgtttcttg gaaggtttct 115260
attacaactg gttggtattc ttttagaaga cattgttaca aaacagctga aggtggaaat 115320
gagtgagcag caacatactt tctattgcca ggaactaggc acactgctaa tgtgtctgat 115380

-continued ccacatcttc aagtctggta ggtgaatcac attagtcttc ctggagtgtc tcgttcccca 115440
ttctgcacta tacactctca gagtgtagga gctgtgctgc ccggtagaaa ctctgccttg 115500
cccagtgtgc cagttgaaaa tatttgttgc tgtaagagta cacctgatac catgtgaccc 115560
agcagttcca ctcttgggta tatacccaaa agaatggaaa gcagggtggt gaaaagatat 115620
ttgcatgcca gcattcatag cagcattatt cacgatagct aaaatgtgga accaactgaa 115680
gtgtccctcg atggatgaat ggataagcaa aatctggtgt atatttacag tggaatatta 115740
ttcagcctta aaaaaaggac attctgacac atgctacaac atgggtgacc cttaaggaca 115800
ttatgctaaa tgaaataagc cagtcacaaa aggacaaata ctatgtgatt ccacttacat 115860
gagggacctg gagtagttaa ttcatagata tagaaagtag aatggtggtt gccaggggct 115920
gcaggggagg ggagttattt ttacaagatg aagagagtta ttctagaaat gaatggtggt 115980
gatggttgta taacattatg aatgtactta atgctactga actgtacagt taaaaatagt 116040
taagaggacc aggtgtcatg gctcatgcct gaaatccaag cactttgaga ggccaaggca 116100
ggaggattgc ttgagccaag gagtttgaga ccagcctcag caacatggta ggaccccatc 116160
tgtacaaaca aactagccgg ggatagtggt gtgcatgtgg tcccagctac tcaggagact 116220
gaggctggag gatcgcttga gcccaggagg ttaagtctct agtgagatgt gttcatgcca 116280
ctgcactcca gcctcggcta tagagtaaga ccctgcctca aaaaaacaaa acaaaacaag 116340
acaagagcca aaaatggtta agatgggcca atcacagtgg cttatgcctg taatcccaac 116400
actttgggag gtcaaggtaa aaggatcact tgaagccagg agcttgggac cagcctgagc 116460
aacatatcga gacccctatc tctacaaaga aaatcaaaaa ctagctagat atggtgggca 116520
catgcctgta gtcccagcta cttgggaggc tgaggtggga ggatctcttg agctcaggag 116580
ttcgaggctg cagggagcta ttattgcact ccagcctggg ctacagaatg ataccctgcc 116640
tcttattaaa aaaaaatcca aaaaaaaaaa aaagtaaacc tgagagcttc ctcctcctgt 116700
gttaaatttg gaggccaaga tgtttttgtt acttttacaa atgatcaagg acggtgaagg 116760
ttgggcatgg tagctcacac ctgaaatccc agcactttgg gaggctgagg cggggtgatc 116820
gcttgagctt gagaccagcc tggacaacat agcaagagac cccatctcca caaaaataaa 116880
aaaataaaaa aaaatagcca ggagtagtgg catgagcctg agcccaggag gtcaagctgt 116940
agtgagccat gatcatgcca ctgcactcca gcctgggcga gatcgagacc atgtctctag 117000
agaaagaaaa tgacaaggac agtgaaccca agaaagtcat aagatgccag ctgtgcagca 117060
agcatggaaa gcagccagtc caaattagga cagtgtgttt tccaagaaga acgatcgttt 117120
gtaatgagaa tgctttgctt taaataaatg actaaatagc tagaagccta gttctagggg 117180
ataggcacgt ctttcttctc tcaagaaaat agaaaggcaa ttctaatttc tagtaacagc 117240
aaacagcatt aagtcatggt ccaaatatga ggcaaaccaa aatgtggctt gattgttcag 117300
cagttgatct gttggaagcc cttgatatta aaaaggttct cctttaagcg gcttaggagt 117360
cacgatcaaa gacctataga aagagatgcc atccttctag gatccttggc tctcttggga 117420
actagattca gatagtcata atgtaaatac tgcttgagct ttctttcttt ctttctttct 117480
ttcttttttt ttttgagaca gagtttcact cttgttgccc atcctggagt gcaatggtgc 117540
catctcggct caccgcaacc tctgcctccc aggttcaagc aattctcctg cctcagcctc 117600
ccgagtagct gggattacgg gcatgcacca ccacgcctgg ctaatttttt gtatttttag 117660
tagagacagg gtttctccat gttgaggctg gtctcgaact cctgacctca ggtgatccac 117720
ccgcctcggc ctcccaaagt gctgggatta caggtgtgag ccaccgcacc cggcccgagc 117780
tttcattttt gaaatcaatg tatgactgaa acactgaaga cttactgact taattatggt 117840
ttcagaacag aatgaaaatg tcttcggttc tgatgaatat aaaaggaaaa ctaaccaagt 117900
taatttggca agtagatggt agagatagag gtggggagtg gaaggggaac taaaatcttc 117960
acctagcatt gttgggatta tatggttaca tcatctgaag ttgacagacc aaaatataga 118020
ggcttcagag gtctccaaat agaactaaac atgtaattca gattgttagg aggtagtata 118080
aatgagctaa atctcatctt tattacggta gagttaatgg gtgatgtcta aagttgtctg 118140
aagtctataa atcatgacaa attatgatgt ggtgattgta ttcaacagtc tttcagttgc 118200
agggataaaa ccccagttta aactagagta agagaaagaa tgtgttggtt taagctcctg 118260
gaaagtgcag gcaagggtag ttggtaggac tgcatctagt gttgtaattc tgtggtctgc 118320
attgtatatt tatgcatctc agctctgctt tcttcttttc atttatataa tttttaaatt 118380
ttattttaaa gatagggtct cactttgtcg cctaggctga agtgcagtgg catgaagtgc 118440
agtgcgaggc tcactctagc ctcgaactcc tgggctctag agttcttcct gcctcagcct 118500
tctaagtagc tgagacaata ggcatgtacc aacatgcctg gataggtttt aaaatttttt 118560
tgtagaaatg gaagtcttgc tgtgttgccc aggcgggtct ttaactctta gcttcaggcg 118620
atcctcctgc ctctgcctcc caaaatgctg aggttatagg tgtcacccac cacgcccagt 118680
ctcatctctg cttcctgtgt tagttttgtt ctctggtggg ctgttttcac atgaccgaag 118740
atgacctcta gcaggctgtg ttctcagccc ctcaagtagg cctatgtgat tggccttgca 118800
tgagtaatat gggtgaccat aaacccctga atgctctggt ccacatgggc caaatgggag 118860
actggacagc attccattga tgaggaggtg gggctggtct ccgggagtaa gggagaggag 118920
cacatgcagt aactgatggt ctgctgcaag ggatagcagc acagcagtta gaattttgga 118980
ggtaactacc agaactgaaa acagaaatga taacaagtag ttgccttaaa aagggatggg 119040
agcagggtgc ttttgtgatc aaagctcctt tctcttactg gatttttgta cacattttgc 119100
atacatatct tagagtaaaa gatagcattt tcagccttgg tccatttgag gatactcttg 119160
gcgtggcccg cctccatgct agcaggctct ggttgtgcca agttcagttg agcatcctgg 119220
ctcttgcctg cacggaactt ccagtcagtg cgtcagtatc acaagtcttg atatttccta 119280
tgaagaagaa cagtagtgca gtgacagacg aaatgggtgg gcaggcagag gcaggatttc 119340
tgagggagag aagtagctag ctttttgcag agaagagttc cggcacccaa gagagcagct 119400
gagagtacag gcaggcaggc aggatgccgg tagggcccgg ccgcacggcg ccacagaatc 119460
ctggagaaag gggcctcttc atggcctctg cattcagctg ctgtcaccct ccgcacaggc 119520
catggccaaa atttaatttt catagtggac tctagttttt gagccttact tgctattatt 119580
gaaataattt tcttgtttct ttttaaagat cttcggatta tgcttcactg accactgtaa 119640
taagtttaaa gttgagaaaa tatggcttgt taatgaatga taggtcaatt ttagtatgtt 119700
ggtcatttta atattttgcc accagttggt ttggatttga tgccaggagg agacagcctc 119760
atttctaagg actagtcttg cctttgtggg ataagggtgg tgtgttctgt gtccttctac 119820
atgtccgagc gatctctgtg cagctcaaat gtggtcactg tcttattgcg ctgatttcct 119880
ctccttccat ctcacaattg aggcaaaata ttgttactgt tgaagtgttg tccaatagga 119940
cttccagcag agacaggatg tctgcactgt ctaatttagt tgcctttagc cacatgtggt 120000
gttctgtacc tgaaatgtgg ctggtctgat tggatagctt aatttataat tttatttaat 120060
tttaattaac ttaaatttaa acagctctgt gtggatagtg gctcctgtat gagacagtgc 120120
aggtctgttg agaagcagct ttactggtgg gagtggaggg cttggagagg gcacgtgggt 120180
ttcctgctgg tatcttttga ccttatttaa tctgcccaac atttgcaagt aagttgtgtg 120240
tgtgtgtata tataaatgtg tgtttctgtc ttcttgtttc ctttgactgc atttatttga 120300
aagacactag gtggcagaat tactgtattt gattggtttc aagataagag ttgaaataat 120360
tcatctcgtg tttttatata agtaaggtgt gtttagcatg taaaattggt aatatgtatt 120420
cacgtactgc ttaaacaaag gctatgaatt ccacccataa accgaaaatg aagaccttta 120480
aatttgtcca tttcaggcgt gggtacttct taaataatac ctggttcagg aactagtcag 120540
aatggcaccc ttgacttttt gtttcctgct tttcctcttg ttgggagagg agggtattca 120600
tcccaaagtg gtttgcctat ttcacattcc atctaggata agcagaatag ccaagaaaga 120660
tagctgtcct cctgtttaca acatttgggg taaccagcat ccctctcttt tggtccaaga 120720
tagactggtt tagaaacaga tgatggcacc agaggcccag gaggtggaaa catcagcttt 120780
gtttgttgtc catgtggctg aattagagct gtctggcctt gtagcctcaa cacggccttc 120840
cagctttgct caccgtgatt ttcaaggaca catcttgtgc tcttccctgc ctgccatcca 120900
gactataccc agtcagggtg gcaggagctg ctgccccttc ctccctgagt cctggtcgtg 120960
ggtggtggag atgtgccatg acgctcacgg aggcatgctc acccccttcct ctgtggcaga 121020
ggggatggct gcacgacagc tcttccctgt cctttccaaa gcgtctgtgg ttccactttt 121080
tggggcaaag caggaatact ggaagagaga gaaagtggtc ctttctatag taataaagtt 121140
gacattgatt caagttcatg cttggggaaa ggacagggct actaacaatt ataatgctgg 121200
gagcaatgga attttctcat gggtatgtgg taggtttaat tttaattatc ccagttaatt 121260
cttagaactg ctctgtgaag tatttcccgc tttgtgctta agttctaaaa gatcctgtgc 121320
caaaaccaag aatgaaaacc caagcattct ttcttgccca tcgatctttc tctcatcagg 121380
ccacttcttg ggttgatagt ggtgagtgta gccgctgcca ctttcagaat acccaccatg 121440
ggccccagtc actgtgtggc gtggagaaga gatggttctc tctgtgtcat agctgaacaa 121500
gcccagccca gagaggtttc tgccctagga gctctcgatg gtggaattgg gatgcgatcc 121560
cacatcctgc ctgttttgaa aacagcattc tttatttcca attcctgctt ccattgttcc 121620
ttttaatatt tctttgttta gctcacaaaa acacggcttg cggagctgct gcgtgcagct 121680
gtagctgttt ctctgggtgc agcctgcatc cgccttcctg cccgcctcct ttcctgcact 121740
gccatcgtgg tctccgggca cttggtccct ttctcttccc ctgagtccct ttggctcccc 121800
tgtgccaccc ttgtgatcca caggctctgc cttctttctg tctcagactg ctgctcatca 121860
ctactcggga ccctaggaag ggaggttcca ccgagaagca tcttctcatc tcagccacgt 121920
tctcagtgcc actgttgtct ttgttaggta atggtagcta ctgtaacaaa taaaccaaca 121980
tttccatggc ttcacaccag agaaggttgt ttcttggttt tatgacaatg tattgagggt 122040
gttcttggtt cacggatggt tttcctccat gtgggaattc ggggacccag gctcctttcc 122100
ttcttttggt tctgttctcc aggccttcac atcctctgtg tctggttggg gacaaggaga 122160
gggaaggtaa agaaggcttt gtggccttgg ataagtgaca ggcatgcctt tgctggtgtt 122220
ctctcgtggt gacaggtcac agccccaccc tgtaaaaggg gactgagaga cgtcgtcctg 122280
ctgcttccca gcagcagcac tgtggtctct gatgtgtttt ctgtgaggat aaaaacaggt 122340
gattccagga tgaggaaagt cagggaaacc cttggaagga ggggaccagg cgggtgtcac 122400
catgggatta gtggtggctt cagaatgagc tgcagcgagt gccatgcctt ctaaagcttt 122460
tgctattctg atatgcccac accatgccca gcaggtgtct gccttgctct ccgcagagag 122520
agtgatgaat ccttctcatg agcctctgtc cagttgttcc tccctccacc tggaagggac 122580
cctgggttcc tcataacatc ccagcggaac aggggacctt ctatcctgtc cccaagttca 122640
tcctcatcct cctgccggct tcctggcccc tcttatgtct gcttcctgac gccacatcct 122700
tctggattct ctggaattga attttgcctt tgatgcttat ttaaaaatat ccattgcagg 122760
ccaggtgtgg tggctcacac ctgtaatcct gtgcactttg ggaagccaag gtgggcagat 122820
tgcttgagcc caggagtttg agattagcct gagcaacatg ttgaaatcct gtttctatag 122880
aaaatacaaa aattagctgg gcatggtggc gcacacctat actcccagct actcaggaac 122940
ctgagacagg aggatcaatt gagccccgga ggccaaagct acagtgggct gtgatcgtgc 123000
cactgtactc cagtctggtc aaacagagtg agaccctgtc tgaaaaaaaa aaaaaaatcc 123060
attgcatact tcaccgtagc gaaacatgta tgtcttacct ttcctttcct gcctgtagct 123120
gctcttttac acttaacagc cacactaagc cagccttaaa tgaaaaacaa accagcactt 123180
cctgtgccct cctgcttcct tcatgagggg tccctccctc tgtgtacact ccattctcat 123240
tgcccatggt ggtttgtttc cctcttgttt ctcaagccat ggcagcctgc ctcttgccct 123300
ctttactaaa aaggcctttg cagaggctgc ctgtgttctt tctttctagg tctctctcat 123360
cctaggccct ccagcttgat tctgtggagc tgccctcttg tcactcagta gcttgtgggg 123420
tcttctctgt ctagccactt aattgattgt gttcctcgag ttgctgtcca tggtctctcg 123480
ttactgtttt ctctgtgttt ctgcctctct ccttggcctt ggtaggtcca tccccttttgt 123540 gaccttggct gttgctctca tggacaactt tctcttgctg gtccttgtag tcctggcatc 123600
cagcttctcg acacgggact tgtcctgcca gtacctcaga cttgcactta aaattgaact 123660
agcaccactg tcactctcca gggcctcttc ttgttaatta gatcattagg gatgttcaga 123720
atcccagcat catagtatgt tcctcctccc gctaccccag gaaccctaac cttacctcct 123780
cctctctatc tactaggagg tggccctcag agtccgtctc atcttccacc tgaacttccc 123840
taataggctc cagcagctgc caccccgggg gctgagtact tcctccatgc cttgtgcagt 123900
gctgagccct ttacctgggt tctcctgttt gctccttatt acagccctgc gaacagatac 123960
tgctcttaat tccatcttac acctaaggaa gctgaggccc caggtaaggt gcatccaagg 124020
tcacccaggt agtagacagt agagccacga tctgaaccag gcagtctgat tcagagcctg 124080
tgttgacact cagccaccta gaacacagct tggattgtgg gtttctatta cctgttcaaa 124140
acccctacat cccgggtctg tccctgcacg tgctctgtgg cctggctgca tcttccttga 124200
aggcagtgca tgcctcttca ctcagggggc ccatgcagga acagagggcc ccacagaagg 124260
atgaggccag tgcagaatgg gctggagggg acaatgctga ccaggaagca agtgtagaga 124320
aatcccagga aacctggagg agccagagac aaggcattag aactcctcgt cgtgacctgg 124380
tctgcattct ctgagtgtgc tgcttctgtt agctcgcttc cttggtctca ggttatagtt 124440
taaggcattg tggagcccta aaaagcctgt actctgtttt tacctgtttt aggacccttt 124500
cactttgggg atgtgttgat ttttttttt ttttttttt tttttttgag atagagtctc 124560
gctccattgc ccaggctaga gtgcagtggc acgatcttgg ccactgctgc ccctgcctcc 124620
tgggttcaag caattcttgt gctcccgcct cccaaatacc tgggattaca ggcacccgcc 124680
accacactcg gccaattttt gtatttttag tggagacagg gttttaccat gttggtcagg 124740
ctggtctcga actcctgacc tcaagtgatc tgcccacctt ggcctcccaa agtgctgtga 124800
ttataggcgt gagccaccac acccggcctg aaatttaaat cagaaataaa attttgatcc 124860
caacagtgat gccaggcagc ccagatctgg gggagagggt ggccttggcc agctgggcct 124920
ttctctgttt cccaagtctt gctgcctctc cctgctgggc tttgcagcct gtgcatgtct 124980
ctgtgccttt gaccttgttt atccaaagga gaggatagaa tgaagtcatg attcctggag 125040
ccctgagaag gatgctgtgg agaaatttgc cggtagaatc tagctgagtg tgttgctgag 125100
gtgccagcat tgtgtgtggg gaggctgacc gcttggcctg cctaggccca ggatgctcca 125160
tggccgggca cagaggccac ttggctgtca ggtgtcagga gcctgcagag ggcacacaga 125220
gcctggaccg caggggggtc ctgctttctc acctggcctc cttcagcatt tctgtccctc 125280
agtccttagc aagcccagga gctgttgagt ttggcaggtg ccgagtgctg ttcctgcctg 125340
tgtagctgtg gctcagtcct gtgggggccc cgctgtggcc cgagtgcagt gattcgaggc 125400
gctgagtgtt ccctgactcc ttctccagga gctgtgttca gactttcgca gctcttggct 125460
tggagctcct ggagggcttg gcattgccga ccaatgtgga ggtcgacagt gagagaggag 125520
gaatgctagc tttcttgacc agtccattaa ataagtggga tattggccag gcacggcggc 125580
tcacgcctta atcccagcac tttgggaggc tgaggcgggt ggatcacgag ctcaggagtt 125640
caagaccagc ctggccaaca tggtgaaacc ccctctatac taaaaataca aatattagct 125700
gggcgtggtg gcaggcgcct gtaatcctag ctacttggga ggctgaggca ggagaacagc 125760
ttgaaaccgg aaggtggagt ttgcagtgag ccaagattgc gccactgcac tccaacctgg 125820
gcaacaagag caaaactcta tctcaaaaaa aaaaaaaaaa gtaggatatc tgtttctgct 125880
tagaaaaatc agaattttct aaatgccagg tgttctgaat acgtaagtat gggagacgac 125940
tcagcctgtt tcatttttat gtaaaatctt cgcgtagcca tgtggcactg gaccgagatg 126000
aaagcaaaga catttctcct taactttgtt tctaggaatg ttccggagaa tcacagcagc 126060
tgccactagg ctgttccgca gtgatggctg tggcggcagt ttctacaccc tggacagctt 126120
gaacttgcgg gctcgttcca tgatcaccac ccacccggcc ctggtgctgc tctggtgtca 126180
gatactgctg cttgtcaacc acaccgacta ccgctggtgg gcagaagtgc agcagacccc 126240
gaagtaggtt cataatgccc cacagcccag ggcgccagcc cagcaccctg tcctgagact 126300
cccagtaacc tgagctttgg ccaccgttaa agcattttca ttttccattt tttgtgaggg 126360
cttgtgaaat ttctgctgca tattaatatt cctttcatgg acagcatatt attgggacaa 126420
acatgcggtc cagctaaagg cattcaaaat agcagttgct ttctaaatgc gattttcttt 126480
ggcaggttct ttgacaccat tgcatcttgt gggatatgct tgtcatgctc tgtggctcct 126540
actaagttct agtccttaaa ttggttccat agccagacat gttgcaatgt cttaacctca 126600
ttataaagta aatgtggttc tggttatcct tagataatga agtaacagtg tagcaaattt 126660
caaaacctct tggaaatgtt attttaccat tcaaaaaggc ttactaaggt tctcgttatg 126720
ggtggccctc tttttgcaaa aggttttcag gcttaagctc catttctagg tgctccaaca 126780
ctccattatt tgtatatgta tggaaataaa agctgtgacc acccccaacc ctggcccccg 126840
cccagctgaa tcctcagcac agtatttctg gaaggctcaa gatcccacgc tggggaaaag 126900
aagttctgga gacaaaagag ggcaggtgct gccgtgcctc tctgctcagt atggatactg 126960
gaccttgtgc tgccagggct cccagtaggg ccagttcatg gcactcagct ggaaagtcca 127020
ctgttgggag gcattcttaa ccatccactc tgtgccgtat gtagtggggt ctggtcattc 127080
tgttggagga gacagaccag tgacgacatt tgaaatgctt ggtggatgtc ttaggcctgt 127140
tacgatgact gagcactgtg gggcaggag acagaaagtc agtgtctcct agttctgtgc 127200

-continued tgctttaacg tgcatagaaa tcagctgcgg attcagcaga tcactccttt tctgacagat 127260
gggcctgctt actctgatgt tatatcagaa agctctgaat ctgggaattg tgtcccctga 127320
attggagtaa cagaaatgct tagatgatga gtgtttaaaa gaaataaacc aaaggtaaat 127380
ttagtttgga attcagcaag cgtcttcatt cagccctctg agggcaaact acagcttttt 127440
gtaaatgtag gtaaattctg tgactgtttc gtgacccct ctgatccagt tttcctttat 127500
aaccttctgt attgttcctt ctattatcct gaaataacat taatagatta ggctgggcgt 127560
ggtggctcat gcctataatc ccagcacctt gggaagccaa ggcgggcaga tcacctgagg 127620
ccaggacttc gagaccagcc tggccaacat gatgaaatgc tgtctctact gaaaataaca 127680
aaaattagcc gagcatggtg acaggtgcct gtagtccctg ctactcagaa ggctgaggcg 127740
ggagaatcgc ttgaacctag gaggaaaagg ttgcagtgag ctgagatcgc gccactgcac 127800
tctagcctgg gtgacagagt gagactccat ctcaaaaaaa aaaaaaaaaa aaaaaaatta 127860
atggatcaat ggatttttaa cctaataatt aaatttcaaa aatatcgtt ctttaatggt 127920
aatgtaaagg taaaattaag ataatatgta acaagcatgt gagtgtctaa ggtgtccccg 127980
tggtggaagg aaaaaataaa tccccataag tgtccaagat gcccatagag agcagagctg 128040
ttctggttta aacccctgct cttagcactg tgtttttcca gctgtgggtg gtgggggatg 128100
agtatctttt tatttccatg agatgagaaa aatgaattac tagaagtgtg aaatacaaaa 128160
cacagctgct cttttttag ccatagactc agcagccata aaattgctgt atccagttgc 128220
agaaattcct gctgcttact cttgaccctc tctcggtttg tgtgcatctc ctctcaggct 128280
ggctcccaga tgggagctgg ctccaggcga cactgggtgc tctgctccag gaggtcctta 128340
tgtgggtcct gccctagcct agcccctctc ttatggactc tgtcactgtg ggtttatgat 128400
tcactctcaa tctgtcttac ctcttggtga actgttagag tcctgcctat actttggcgc 128460
ttgtgggtgt gttgtggtac acatgatgtg ttggtcactt cccagctcat cttgttctga 128520
gtcaccctag atttgggaca ttcattcgcc accagtaccg ggcggtgtat ggcctgagat 128580
ttgggggggc ttgtgctgct acaaattggg gctgaatttg agttgacagt ggaccttctt 128640
tatgtctact gctcatattt gaattgcaaa tactgcctct tctctttcag aggctcatta 128700
ccctatagct gtattattgc aaagtgcaca attacagctt gagtgtaagt cacactgcgc 128760
tggcaggacg gcccactgag aaagggcacg tttcctgttc gttagttttc acattgacac 128820
ataatttaca atacagtaaa atgtactttt ctatcaactg tagtcagtaa cagcccccct 128880
cccccaacca catcaagata tagaggagtg ctgtcacttc aaacagttcc ctcttcctct 128940
gccacatcct gcccctcccc aggtctaacc accaatccgt gctctgtccc tctgttcagc 129000
ccattgcaga aggccataga aatagaatct ataggctagg tgtggtggct catgcctgta 129060
atcccagtat tttgagaggc tgaagtggga ggatgacttg aggctgggag ttcaagacta 129120
gcctgggctg cctagcaaga ccccatctcc agaaaaaaaa aatttaaaaa ttacaatcac 129180
gtccctgtag ttcagctgct tgggaggctg aggcaggagg atcacttgag ctcaggagtt 129240
agaggttaca gtgagctatg atcgtgccac tgtgctccag cctaggtgac acagcaagac 129300
gttgtctctg gggaaaaaag aaagaaacgg aaccacgcgg tgtgcagcct tctgagtctg 129360
gcccctttcg gtgagcagtg tctaaagttc tgtcgcgtgt tgcccacgcg tcggtggctc 129420
gctccttgca actgctgagc attgtatggc taggctgtag tttgttttca cttcaccagt 129480
tgggaaacag agaaaaggca ctttttaaaa agtttaaatc tgtagaattt tggtttttac 129540
cagttctctt ctaaatcctg agggattaca ggaaaagttg ttgtatttca gaatattctt 129600
agcttgatgt gacctctgtc cccgttaagg ccctttgccg caatgggaag gacgtcgctc 129660
ggtcagaccc tgaaggtcag aggggcagtt tgggagtgtg tcaacatttt aactgtatgg 129720
actagagcca agagtctcaa ggtttataat tcccacgtat tcaaaaagaa aaaaacaata 129780
aagtgagaag tcagtgtaga gtgaaataac ctgtgttagt ggggaagaag tgtttttaaa 129840
caggatttcc ataacgtata acatcaacat gtttagagtg gtgatgtttc attgggaaac 129900
gaacagtaaa acatgaaagc agggaggttt tcattctggc agttggcaac tttcacggca 129960
gatggagaat ttcaaaagca attgctcaat tatcaaacat agccagtgtg agttctgaaa 130020
taaaggtgct gattgaatgt gcagctttat ggtggatttt gctattcagg caagcatttt 130080
aattttctgc ctgttaaatt ctgttttctt tagtttttca tatgtggttt attgtagctt 130140
aggaatagat aactgagagt atatattaca catacaacat tctgatatgg caatatttaa 130200
aacaacttgt ctgttttaga actagaatta aacataatca tcttcagtat tttgcaaata 130260
agctcactgc catccagaaa cattgtcaat gcatctgttg ctccttctag aagacacagt 130320
ctgtccagca caaagttact tagtccccag atgtctggag aagaggagga ttctgacttg 130380
gcagccaaac ttggaatgtg caatagagaa atagtacgaa gaggggctct cattctcttc 130440
tgtgattatg tcgtaagttt gaaatgcctg taaacggggt tgagggaggt ggggaccagg 130500
agaacatcct gtgtagatga cacttgcatg gaccctctgg aacccagacc gcccggtgtc 130560
ctgccaagct ccatcgaaac taaatctaga atgaatgttt acttctgctg tgacatataa 130620
ttggagacca ggcctggcct tccagtcact ggattctaag ttggactgtg agagtttttg 130680
cagctgactc atttatcaaa tgcccggcta ttggctcacg cctacatgat gctgggtatg 130740
tttgttaatt tgagggaagc aatggaataa taataactaa tgatttaaaa aacaaagtaa 130800
gtgcattgac tgtagtgggg ttctgatttt aaattttttt aaaaattaat accaggagca 130860
gtggcttatg cctaaattcc agcaactcga gaggctgagg taggaagatc acttgagccc 130920
aggagtttga gacaagcctg ggctatggtg tgagacaccc atctctaaaa aaataaaaaa 130980
taaaaaatta tccaagtgtg gtggctcgtg cctgtaatca cagctctttg agaagctgag 131040
ggcggaggat ggcttgagcc tgggagttcg agaccagcct ggcaacacag agaaaccctg 131100
cctctaccaa aaaaagaaag agaggaagaa agaaaaatta gcctggcgtg gtggtgcatg 131160
cctgtggtcc cagccacctg agagactgag aagggaggat tgcttgagcc cagaagtttg 131220
aggctgcagt gagctgtgac tgtgtcactg cactccggcc tgggtgacaa ggcgagaccc 131280
ctgctctaaa ataatttttt taagttaatt tgtagaaaag gtgttagatg ttctttgtca 131340
cattttatga tggattcctg tttaaatgcc gttctcttta aagaaaaaaa aataacttgt 131400
gggagttttt aaccataaaa ctagcatcac atatttacca tggagaattt acaaaaaaac 131460
aaataaacgg aggaaaataa aacctcctgt aatcatacta ctcagagata acttgctgtt 131520
agattttggt ctagatttaa tactttttct atatttatat taaaaatatt taaaacatat 131580
gcatttcttt gtcacaaaca tggtatctta tagatactac tgtcacatag caaaacagtg 131640
ttaaatattc tgaatcagaa aaggaagccg actctccaac tgaaagaggt gttatcctag 131700
agactttttc tggtgatgac aatttattaa tagtcacttt ttgctttact ttctctattg 131760
aagtagtttt tctattttgt tctactttta aggataatat aatttataat gctgtttttc 131820
acagaaatat aagaaaaaag atactaattt tataagttaa taaagtttga tcatcccaaa 131880
tccaaaaatc tgaaatccaa aatgctccaa attctgaagc tttttgagtg ctgacattat 131940

-continued gttcaaagga aatgttcatt ggaaggtttc agattttcgg atttagggag ctcaacaaat 132000
aagtataatg cacatatttc aaaacctgaa aaaaatccta aattcagaat acttctgatc 132060
ccaaacattt cagataaggg ttattcaacc tgtactgtca gatgatccca aatgaaaaat 132120
attaatcgtt aaccaaatat caaggaattg atcacatttt acagtttctg cctaggatta 132180
tgaatcaaga tgaaaaggct ctgcatgttt aaaaatatat atttttattt tcttataaat 132240
cttaaatatc tacacttaag atttatttga tatgtgggat ccattcatat tttggattca 132300
acagttctgt caaaactgtg gcagtgatag gggattcttt ttttcccact gaactatcac 132360
aaaattggaa aaagagtaat tggagaaccc cactggctta gccggcccga agcccgggag 132420
agggcaggca gtgctgtgga tggggtcatc ccagcgcaac gctgcccctg ctacctgcgg 132480
atctcgctga ggcctgcctt tgtcctttga cccttggcca tttgttagtg tctctgagag 132540
ctggactgct gtaccctact tccccagggg gcctaacttc acacagcctc tgccgcagtg 132600
cgtggttgga ggtgacggcc ttggtaaatc gagtttccta cctcctcaat tatttgtgct 132660
catacactgt atatttttag tgaggtttat atttgggatg tgttttctcc ttcttaccct 132720
ttctggcctt tctatggcat taatacctgg tctcttcttg tgtacttgaa aatgaatctc 132780
tcatcatatt tttccttagt gtcagaacct ccatgactcc gagcacttaa cgtggctcat 132840
tgtaaatcac attcaagatc tgatcagcct ttcccacgag cctccagtac aggacttcat 132900
cagtgccgtt catcggaact ctgctgccag cggcctgttc atccaggcaa ttcagtctcg 132960
ttgtgaaaac ctttcaactg tacgtcttca tcctgccgac tattgccagt tgcagttttc 133020
cctgccttaa aaatggagta ttgaaatttt taactttaat ttctgatttg caaaatagtc 133080
atcttttgtt cttttccttc ttgctgttag ccaaccatgc tgaagaaaac tcttcagtgc 133140
ttggagggga tccatctcag ccagtcggga gctgtgctca cgctgtatgt ggacaggctt 133200
ctgtgcaccc ctttccgtgt gctggctcgc atggtcgaca tccttgcttg tcgccgggta 133260
gaaatgcttc tggctgcaaa tttacaggta ttgggaagag aaaccctgat attgatttat 133320
attgaaaatt tagcaggcca agcaaaacag gtggctggct ttttcctccg taagtatggt 133380
cttgacatgg tcaccgatag aaacatggaa acatctgcaa acttgccgtt actcgtgtgt 133440
ccgatctgac tgtttcttgt atttttttct agtctgccct tactaggatg aactgtacac 133500
atcagttcat cctttttaaa tgagcatgag gttattttgg gttgttaggt gttacaaaca 133560
cactaatgtg tttttgtcta ttagagcagc atggcccagt tgccaatgga agaactcaac 133620
agaatccagg aataccttca gagcagcggg ctcgctcaga ggtaatgctg gaaacacagg 133680
tcgtccttgt gttaggacaa cccaggatat aaaggatata gatttgtacg ggaataaatt 133740
cacaggacaa gaaatcgatg tgccttatag gtgggtttac tgcagaagtg ccataataga 133800
accttcctac ttttaaaaca accagatctc actttctaaa gagtaaagga tgaccggcag 133860
gatcacgtct gtgacgtgag tggaggcagt ttgcactcct ggtggctgtt tgagaggtag 133920
catttagaat gcctgtattc actgtcctgt gatgagtggg aaaataggtt atcaggttta 133980
tcttagcaaa atcaaagcat gtcatctaat tgctaaacaa gagttggcaa atctgagaga 134040
cattactcaa tccttggcat gcaggactta catctgcatc ctgttgccat tttatgtctt 134100
caaagcattt aatcatttag ttgtgtttgc aaagtctttg agaagccttt gtcagaaatc 134160
cctacatctc ctatgtgagt gtatttccat gactgcagaa taagttaaac ttttaccttt 134220
ttccttccct tgcggggcgg ggtgggggc agggattgtg tgtgtgagag ggagagagag 134280
acagcagaga aggagaatat aattatcatg ctgtgtactt tgagctgaaa ctgcaaaaaa 134340
ggaaaaacac acaaaaatta ttatgctttt cagtctttag agtaccttgt ctattatgct 134400
tttcagtctt tagagtacct tgttgatggt gtttttaaat gggattgggc acaattaggt 134460
ggacagtttg ggatgatttt tcagtctgta gggccaagct cttttgtaat ttgcattatg 134520
aagttgtcac tctcatagca gatggcggga gataaactat tattactttt tgaccctaga 134580
cttagtcttc agtccagatg agggagatta aaagattata aatatcttgt gccagatgag 134640
gtgattttat tttgaaatga ccatgaattc ctatcagttg tcttactggg atatttgata 134700
gtggaatttg tgcatttgag tcttagatga tctgttttac atttattaag aaagccttta 134760
ttagctttta tactgtgtat tgcctgttgc agtgtttgag tataaatgaa atttctggaa 134820
aatattaatg gagtacaaac tgtgatactt aaaagtaaac tagggcctgc atttgtatca 134880
tgacctgttt gagtattgat gagaagatag ctgtgaagaa aaaggtttaa acaagtgtat 134940
tttcctttaa gaagccacta atagtgcatc tccttagagt gtatatttct agaatcctag 135000
tgtgcagagt ttagactaag actaaaaaaa aaaaaaaaca aattatactg taatttcatt 135060
tttatttgta ttttagacac caaaggctct attccctgct ggacaggttt cgtctctcca 135120
ccatgcaaga ctcacttagt ccctctcctc cagtctcttc ccacccgctg gacggggatg 135180
ggcacgtgtc actggaaaca gtgagtccgg acaaagtaag tgtccagcgt gtctgcatgg 135240
gaggcacagg gcgctgagtg cctctgtcac ctgtggcaga tacagagagt gcagaggagg 135300
tgccgtggac ccaaggagtt ctggcgctcg gctcggctca gtgaagctgt ggttagagac 135360
gtgggggcc atcaaggtct gagggagcca agcagtgctg atgtgggacc cttttggtag 135420
gagtgtgggg tgagtagtta gtgggtgaat caaggaatag tcggccgtgg cctgcaggcc 135480
cctgactgca caggccttca agcacatgtc aatgccgtta gcctccctcc atctcctcat 135540
accttctggc cacctgtgag ttgcactgcc actgccagcc attctggtat gttgtcagca 135600
cctccactgc tcatacctca tggttaggga ccacctggag ccttggtaga gccttggtag 135660
agccttggta ctctactttc ctggacaaag ttcagcttat gaatatgaat ttagatttca 135720
aaaaccagca gcccaagtat aagaaagcga aggttcagtc ctgccttctt aggctctatt 135780
cgctaagcac ctgccctgcc ctggttgctg gggagagatg agtaaagcag acaacccagg 135840
agaggatggc aaaggggccg ctaaccctta gtggtttagc tatatttgga aggcctattg 135900
gaagttcacc aggtgaaggg ggaggctgtg agggtgccca ggcaggtaac agaagtccaa 135960
aggggaaaac ctgtggtgtg gtgagccgta tagccacagc ctgccggccg gcagccctct 136020
cagcctagtg cggtgttccc aagcactggc ctaggcctgt agctccaggg atgtgaagtc 136080
cccttgaacg ccgcccatca tgttcccctt atccattttt ttcttcccag gactggtacg 136140
ttcatcttgt caaatcccag tgttggacca ggtcagattc tgcactgctg gaaggtgcag 136200
agctggtgaa tcggattcct gctgaagata tgaatgcctt catgatgaac tcggtacggg 136260
gggagcagtg gaggcaagga atcctcagct tttcttgtga cttccaagtg ggatttgtct 136320
catcatcatg tgacccactt gttgacaaca catgttgggg actccagtct gggcagggac 136380
gggatgtcgg agagactcca ctctgaatgg ggccgggaag tggggaggac tccatttcag 136440
atggggtcgg gacatggggg ttatgctgat cgagacagaa aagcacattg tttcagccac 136500
attagaatcc acggaggtgt tgttttgaaa tccagctggc cccaaggctg ggtgtatggt 136560
ttgggatgag aactatctgg cctccactgg aggaacaaac acaggatgtt atcatctaag 136620
ctccatggcc aagacagaat ggaagtcaag gttgcgtatt tgccgtagac ttcaacacag 136680

-continued

```
tgtcgtaatg cgtgacgtca ataacttgtt tctagtgtct tggaagttga tctttagtcg 136740
taaaagagac ccttggatgc agcgagattt cctctactca cacctctgtt agatgtagtg 136800
aggttcttca ccccccaacc ccagatgtca gagggcaccc tgcgcagagc taggaggcca 136860
tgcaaagcct tggtgtccct gtccctcacc cgtgggcagg tcctgtgagc agtggggggg 136920
ccacctcttg ggtatggtgc agccatggcc caagcagggc ttcttctcag acctactagg 136980
acgggagaaa cctcctggtg ctttagccct gcgttgatat gcagcaaatg ggagggaagt 137040
gggcacctgg gaggacaaat gcctgtagag gccgggagtg acggcaggtg ttcatgaaaa 137100
gagaccttgt ggggagggca acacaacagt gtgttctgat gtactgaaga gctcaactga 137160
aaacaacagg agaattagcc caaaatccat ttactaaaat tgtttatctt tttttttttt 137220
tttgagacaa agtctcgctg ttgtccccca ggctggagtg caatggcgct atcttggctc 137280
actgcaacct ccgcctcctg ggttcatacg attctcctgc ctcagcctcc caaatagctg 137340
gtattaacag gcatgcacca ccacgcccgg ctaatttttg tatttttagt agagacggga 137400
tttcaccatg ttggccaggc tggtctcaaa ctcctgacct caggtgatcc gcccacctcg 137460
gcctcccaaa gtgctgggat tataggcctg agccaccacg cccggcctaa aattgtttat 137520
cttaagattc atgcagtgaa agctaactta ctgagtgata aatttgctta gtgatctgtt 137580
tattaggttt tccaaatttg ctaattgggc tttgaacagc tgtaaaagtt ctgactgtaa 137640
aagaaagctt caacttttgg cattcatgat gcttttctga gtattaaact aagatagatg 137700
ttttacctga aggatcggcc accaatcttt aaatggctaa acaaaagggt tgctaaaaca 137760
taatccaaat tgacataaga aataccattt ttccaaccaa aattttggca ttcatatggc 137820
tacttttacg tatttcagct gcatttgaac atctttttca aactttaggg tggttggtgt 137880
atcactgagg tcttggatga cactttagct ttgattttgt ttttatgaat taaaattgtc 137940
ataccaaaat ttttatttca agcaaatcca agagcataaa aaattaaaat attacttaaa 138000
atactaagag agaacagata tatattttac taagcatatg ttgaatgaaa ttgttcaaat 138060
atttataaca ggcatagagt agaattttct taaaaatatt tttgatggta taccaatttg 138120
tattttctca gaaacatttg ccttattctt ttttctgttg tgtttttctt acctgattga 138180
aagctcataa tctgttgtta ttgtttgtta acctttaatg ctctgatttc aggagttcaa 138240
cctaagcctg ctagctccat gcttaagcct agggatgagt gaaatttctg gtggccagaa 138300
gagtgccctt tttgaagcag cccgtgaggt gactctggcc cgtgtgagcg gcaccgtgca 138360
gcagctccct gctgtccatc atgtcttcca gcccgagctg cctgcagagc cggcggccta 138420
ctggagcaag ttgaatgatc tgtttggtaa ttaaaattaa aatttatctt atttttaaaa 138480
agcattccag ggccagtata gtactttgca ccaagtaaat gtacaataaa ggcagtggat 138540
ctaatacatt gaaagcgttt acagaggtag ctaaagagca gcacgggtgt cctcggctca 138600
gaatttcttc ctgtgtgttt gccactttgc cattcattga catggtcatg gacatagggc 138660
tctaagccct tgaggaaggc tgggccagac ctcaggggag atgcagcccc aaaccacgtg 138720
cagtcctgtg gacggatgtg tagatgtgcc actgaggaac aatgtcttga gctttcatca 138780
gattctcaga gaattgcttg actgcctttc gaagttgatg catctgtgct cacgtttgca 138840
cccacccacg aggtccttct gtttcagggg atgctgcact gtatcagtcc ctgcccactc 138900
tggcccgggc cctggcacag tacctggtgg tggtctccaa actgcccagt catttgcacc 138960
ttcctcctga gaaagagaag gacattgtga aattcgtggt ggcaaccctt gaggtaagag 139020
gcagctcggg agctcagtgt tgctgtgggg agggggcatg gggctgacac tgaagagggt 139080
```

-continued aaagcagttt tatttgaaaa gcaagatctc tgaccagtcc agtcactttt ccatctcagc 139140
ctggcagtaa gtcttgtcac cgtcaagtta ttgtagccat ccttcaccct cacctcgcca 139200
ctcctcatgg tggcctgtga ggtcagccag gtccccttct catctgcacc taccatgtta 139260
ggtggatcct aattttagag acatgaaaaa taatcatctg gaagtacttt atgtcttaag 139320
ttggcctgga catgtcagcc aaggaatact tacttggttt gtgttagtgc ttgtaattcg 139380
cccccagaat gtgtacacgt tctggatgca ttaaagtctg gcctgtatcc ttaaagggcc 139440
atcgctgtgc tgcctgccct cagcaaggac acactttgca gacccacaga ggctccgcct 139500
ccacctcaca ccaaagaaag ggaggagtcc aaagggcatc agtgccatta ctcacaaaat 139560
gataaataca cccttattct gaaccacgtg gagtcatatg gtttgtgatc cctgtccttc 139620
aggtttcagc ttagtgggga agtgggaaag tcagcgtgtg atcacagcac agggtgattg 139680
ctgctgatta tattatgtgc ctgctgtatg caggatgaaa tactttatat gcgtcatctt 139740
atttgactct cacaaccccc tgtgagatag gctctgttac tcccatttga caggtgagga 139800
aagcaaggct tagagaattt cagtgacttg cccaggtcct ctgagctagg aagtagccat 139860
tctggcattt gaacccaagg cctgctatcc ctagaaccca cgctctcaaa ttcaacctat 139920
gacagaggca agccctggtg ctgtgggagc cccaaggaag agcctctggc ctggtggcca 139980
cgtagcccag gagagatttc tacaggagcc cacagcgctg aaggagagag aggcagcaga 140040
gtaagggggc tttgtggcag agaggggact ggcactttgg ggaataggtg ggtcaggact 140100
gaatgtaatg gagccatgtc agagctgtcc ttctggaagg gcaagggcac ctggacgcgc 140160
tgcccctcag tgctttggac ggttccacaa ctgtgattca cacggcttcc ccaaacgaag 140220
gtacacgagt gggcattctg tgactcggta cttcccttta ggccctgtcc tggcatttga 140280
tccatgagca gatcccgctg agtctggatc tccaggcagg gctggactgc tgctgcctgg 140340
ccctgcagct gcctggcctc tggagcgtgg tctcctccac agagtttgtg acccacgcct 140400
gctccctcat ctactgtgtg cacttcatcc tggaggccgg tgagtccccg tccatgaacg 140460
gtgggttcct atcatagttc ctgtctgctt caccatgttt ttattttgtg ctgcctgttt 140520
gccaggtact aagctaggaa ttggggatgg agaggtagat aaaatatgca tcaggaaggg 140580
ctgggcccca tctcttactc tccaatatat tggagtctac actggaattt aactggaatt 140640
tgctttttta gtcattttat ttagattttg aagtttcagc tttcatcaaa aatacctcta 140700
aactttatgt ctctgtgatc tttggtctta gctgttttat gtatttagtc ttatatgatc 140760
ataagattaa taacattaca ttcagaagat tatttgtttt ctgtcagagt taaaatgttt 140820
gtttttatac tgcattgtaa tattaacgta ctgtaaaata aaagtggctt gttcttttca 140880
aggaacagta tcctcaacaa gggtcattag ccacaatttt taaaaaattg gacgtcatag 140940
tttacatgtt agagggcgtt ttgaagcttt gtatttttaa attaaatgtt atagagtgat 141000
gttttcatgt ttcataattg ttttcatctg tgcatttgta gccaacttga aaacaaagat 141060
ccagggatta ctacttaaaa gccagacttc ttggaggtta tagtgatgat tttgatagta 141120
tcttgagccg tctcataata acctcagggt gagagatggc caacaggaga cagtcgaggg 141180
acttagaaat ctgaatgaaa tctgaagttc aaatcttcag acatatacca ctaaccaaga 141240
gattggtacc tcagtctagt attgtctgtt tgtctaaaat tggttctaag gaatctaggc 141300
tagtctgtct atccctttca acttttgtga ggctgcacaa atgtaaaatg ttgaataaaa 141360
agcactgatg gaagtgtgta gaaattcttc tctttgttct gttgtaattt tagttgcagt 141420

-continued gcagcctgga gagcagcttc ttagtccaga aagaaggaca aataccccaa aagccatcag 141480
cgaggaggag gaggaagtag atccaaacac acagagtaag tctcaggacc cattttttc 141540
ttacatgttg ttcctccagg acttaaaaat cattcacaga gacgtgcacc gcggtgagtg 141600
tggactcctg gaagcgcacc gtagctccgc tgtgtcctgc tgctcctccc tagctgtcag 141660
ggaggctgta gtccattgct ttgccagctc ttttgtttcc gagtgaacac cttatccgta 141720
cacatgcggc tgtctctgac cctacagacc agctgggatg ccactggggg agcgctccct 141780
tccccccgca cttcccacac tctgcagtta ttctgagatc cttgagggca gggaacaggt 141840
ttgtcttctt tgtgttctca gaaattaatg ctcggcctct ggtcagcaag caacaacctt 141900
ttgttgagtg ataatgaata aataaatgtt tcccacatga gtattcagta acctcagtgt 141960
caggttcagc catctgtttt ggtggatatt taaaagaaaa ttccgctttt cctacagaaa 142020
aaaaaaaaaa tccaaatccc agtgatttaa gccagttata gacttagaca tatactacgg 142080
cttttcatgc actttcctcc caattctaga gtaggtattt tactaggaaa atggtggcag 142140
tgcctgttgg gaggaagatt ctttggccaa gtgtcttttg ttcttgccag ggcccctagg 142200
ctgctggggt gcttcagctt ctttagccca gtgtctggtg gggaatggcc cctgttgcct 142260
gtcccacaga ggtgggggtg cctcacctgg agcctgtcca cacattttac acagcacgct 142320
tacctggagc atcaggcatc ttttccatgc tctgtggctc aggaaacacg ccttttcaat 142380
catgagtgca ccagtgcttt tgggcttttt ctccccgctt ttgtgcaatc ctggttgtgg 142440
atggagtttt cctgtcttta gtcttctgca tagtactttt ctcttctggt tcccggttca 142500
aggttttgta attagagaat gacccagaag caatggcatt ttaatgcaca gccaaggact 142560
tctctgaatt tgtatctcaa acctctgtgg gtccttcagg cttcagtttg tgatttcatg 142620
atttcttgtt gctacctaag gaatatgaaa acacccacct ccctactctg catcttccag 142680
ccgagtggca cctcaggctg tggatcctgt gcttctgtgg tgaggataag aatagtgcca 142740
accgtgtgga ttgaaatcaa tcagttaatc cctccatgta aagcacctgg aacggatgac 142800
agtcttgtta tgaatactca acaaatgcta tcatgatttt tagttagatt tccattgctt 142860
taaaacagtt gagacatctt ggcggtttga gttagagcaa cgggccctga agtgggttct 142920
gtttgggtga agatgattat gcttattccc catggccctc tttaggcaag agtgggaagc 142980
tttctttgtt tttttaatca cctcgatagg acgttacttc ttaaaggtca tccaataaat 143040
attaataggc cgggcgcggt ggctcacgcc tgtaatccca gcactttggg aggccgaggc 143100
gggcggatca cgaggtcagg agatcgagac catcccagct aaaacggtga aaccccgtct 143160
ctactaaaaa tacaaaaaat tagccgggcg tagtggcggg cgcctgtagt cccagctact 143220
tgggaggctg aggcaggaga atggcgtgaa cccgggaggc ggagcttgca gtgagccgag 143280
atcccgccac tgcactccag cctgggcgac agagcaagac tccgtctcaa aaaaaaaaaa 143340
aaatattaat aaagccaact cgttagcgtg gggcttaatt gcttaagtcc aatgagaagt 143400
ccttctctat cctaggaagt tgcccaaact gtagaatctc gtggcctgtg ggtaatagcc 143460
acgtaataca cactcactgc ctcaacaaat catattttag taggtatgat attctagact 143520
caagacacca ttctgtggat cttcccaagg gtgtgaagtg tccacagcgt ctgccttggg 143580
agtttccatg cccaccagaa ccatgcccca agcccctcaa gcactctgac ctaggaaagc 143640
cagtgaagca aggatgacaa catggccctt tgatactagc tgagggacag acacaggtcc 143700
tgggagacca gagaaagacg aggggcagag gaggtgtcct aaaggaagtc tgaggctgag 143760
gagccacagg atggcttcca gctgtcacag gctgctgctg gccttatcac agagagtggg 143820
ccagagggct gggaaccaag gccagagctc aggttcagga ccattccagc aatcccagca 143880
gaaaatgggg agaattgtat ggtataggcg gatatgaagg tagaatctgc aggccttcag 143940
tggccaactc agagtctaag tggattccac agttacagct tgagcagctg gttgtaggtc 144000
atgctttcta cactgggcat ataggatgtg ttttttaaaa agtcctctct taaccgttgc 144060
ttgtttagat cctaagtata tcactgcagc ctgtgagatg gtggcagaaa tggtggagtc 144120
tctgcagtcg gtgttggcct tgggtcataa aaggaatagc ggcgtgccgg cgtttctcac 144180
gccattgcta aggaacatca tcatcagcct ggcccgcctg ccccttgtca acagctacac 144240
acgtgtgccc ccactggtga gtctgctcgt tccttgcaga agaccaagta cggtgaaagg 144300
caccggtagg ccctgggctg ggcacacgtg agagggcggg acagaatccc cgcagcccag 144360
aggctgcctg ctgtggttct ggtgcccact gtggttctgg tgccaggctg ctttcctcag 144420
gcaccacgtg tggaggtcgc tagtagaaat actgggtttt ctaaaatgaa ctgaggccct 144480
acatccctaa gagattagtg ttagacctga ttctagagca actagaccac tttgcttaat 144540
agcagaccag aaaccacacc ccctcgagtg agtgagattt tcctttggag ataattcatg 144600
tttttctaca cagttttgca gttgtcttca gaattggttt aaagtaggtg ttattgccag 144660
gcgcagtagc tcatgcctgt aatcccagca ctttgggaag ccaaggtggg cggatcactt 144720
gaggtcagga tttcgagacc agcctggcca acatggtgaa accccatctc tactaaaaat 144780
ataaaaatta gccaggtgtg gtggtgtacg cctgtaatcc cagctactca ggagactgag 144840
acaggagaat cgcttgaacc caggaggcga aggttgcagt aagccgagat cgcgccactg 144900
cactctagcc tgggcaacag agcaagactc cgtctcaaaa aaaaaaaagg taggtgttat 144960
tgatcagaac ccttgtttca gataacatga ggagcttagc ttgaggagag tgagggttga 145020
tggaggggga ctgacttctg cccagtgaaa tggcatcatc tcccaccagc ccgctgaaat 145080
aagatgatgg ggcctgttcc ttagggcctg cagcatcctc aggcaggaaa gaaaggccga 145140
cctggcaggg tgtgagccag caggtgtagg tcagggagaa tggagccagg tcccagggaa 145200
gaggcttgtg gctgcctgag aagggtgcgt gcctgcctgt gtgtgtgtgt gcacgtgtgt 145260
gtatgtatgc tggagagtct agggaggctt gctccaagga cgcagtattg tttgatcctg 145320
agagataagg attctgccgc agggaatgaa ggtattccag atggcgggct tattccgaag 145380
aagaggccag tgcctggcgg tgctggaagc agttgcagaa cagggagttg taggctttcc 145440
tgggaagaga gcagcagggg tgctggagaa gcaggccaca cttgctgcat ggggttgctc 145500
tcggccccac tcttggtgca cagcgagtca ctgtgggttc attagcatct ggttatgaga 145560
cagtaactgc tcctttggag gggctcgtgg agaccatgca ggagggcacg gtcttgaggt 145620
catgccgtcc agagcacacc tgaggatagg ccaggacggg ctgcacgctg taggtaaaat 145680
tcctccagca agctcttcac tggcattgag gagttccctg agtgcggtca tctggaaggc 145740
agctgtaaca ggcactgcag tctctccctg ggtgggtacc agagaggagc ataggggagc 145800
ataaccgatt taaagagagg gctttcctgt ggtgaggtaa gagattagct ggtcattatc 145860
atagagcccc ctctgccttt gtgcagatgg gctgtgggaa tcctggggtt ccgttgggtc 145920
ctttgtcacc tcactgaagg catgtaagct gagctggcca gaccgtgagc tgatcctgcc 145980
acttgaacag catcaagcct gcctctggat tcttctgtgc atggcacttg tctgagcacc 146040
tcacgcacag agaactggac ttcagagttt acagaaataa gctgtatggt tcattttcat 146100
gcctgcttgc caataaacat atctgagctg aacctcattg aacgcctgcc tttattctag 146160

-continued cacagcacct gctgtttgtg ggcgaggggt gctgtctcta actcctgcct gcttctccca 146220
gcactccctg agtggggtgt gccagcagcc tcaggatgag gacaggaagt gggagggcag 146280
agcagatttg ggagggccac ttgatgggga aggaagtccc aggaagcagt tggagctgtt 146340
ttctggggga gaaggtgcca gctctgggac agtgttgggg tagtgaggag ggagcccagt 146400
ggagagaagt cgggcttcct gcttcctcac agtatgtctg tcctgactca actcggatga 146460
tgtcacttcc ttttcatctt ctcaggtgtg gaagcttgga tggtcaccca aaccgggagg 146520
ggattttggc acagcattcc ctgagatccc cgtggagttc ctccaggaaa aggaagtctt 146580
taaggagttc atctaccgca tcaacacact aggtactctt ggggcctctc cttcaggtca 146640
ccattgtcgg acatctaccg ggaggaaatc cagagccccc agtactggga tcttctcatt 146700
tgactccaga aaagatttaa gcatgataat aatacaaacc tatgtgaata cattttgcag 146760
tgttggcaaa actcctttta tactgagaaa atagatccca gttcctgtgt tttgtggctt 146820
gaatcccagc tttgtgtatt ccgggcttgt ttgaagtcag gaaaggttca tgtgtagtgg 146880
acaacgtgag accaaattct gccttagatt ttgcatttag gctaaacagt ggcagcactt 146940
gtctcagaat gttttcttgt gttcaccagt ctgatcctgt tgtgtctcag tggtccattt 147000
tctcatatgg gaacaagcag acgggagcag atggagtcag gtttcttggc actcgccttc 147060
cccagagcct agaggcagca tggggagaaa gcaggcttgg ggctcagaca gtcctggtct 147120
gcttccagcc ctcctacctg agcagcgcag ggcaagtccg tctaacctct agagaccctc 147180
agttttgtca tatgtaaaat gggggtcgtg tctatttcat agaattgttg cagatttaga 147240
aattacattt ctaaacaaat gttacccctt atttctaaat aagtgtctaa atgaataagt 147300
caccactttt gcccctattt gatggcaaga ggtgtgatct tgtggtggga ctgtaatcag 147360
tcagttctca gtgactgtgc cctgctgtgg tgtttcctgg aatgttcctg tcttgtccta 147420
gaaagtctgg caggggcacc ctgactccac tgtccagtcc tctccccagt ccctcgggct 147480
tctgcagatt tgaggcttgt ttggatccca gaaggttgtg gcaggagaca ccttgcctct 147540
actttcccct ttataattca atgtccaaag agagccctga gcaggtacct cacgccagct 147600
gcctcacgga gctcctcctc ttcctggctg tgaggatcgg tatcagtggc ctcctgctct 147660
ctcccccttg cctaacacga gcacctttgc ttacttgggt gcccttgctc ttgaactgcc 147720
catcggacgt gcgtgaccca agactgtgcc gcagtccttg ccttgtctgt gctcattttc 147780
tttgttcatt tttttccctg taacgtaaat tgttatattt gtctgtatct gtgtctgaat 147840
cagtcctgca cgctctcctt ctctctgtct cttgttcttt ctttaccccg tttatcacgg 147900
ggaccccgat gtccattgct ctagttctcc tgtcctaagc accccatccc gtctctctgg 147960
ccttaccaca agtggcgtgg ctgcctcaga catcatgatg gggacatgaa gcacagctgt 148020
cagaaacaac tgttcgttag atacactcga atgcagctca tcaataggga tggagggtct 148080
gtcggatgta ttttcactga atccccgttc ctaccttgat acactctttt taatctattc 148140
ttctagacag gtcagaggaa ccattacttt gacttttaaa tttttagcag ctttattgag 148200
gtagaattca catactacag atttcaccca ctctaagcgg acagcttggt ggccattagt 148260
tttatccaca gagttgtgca gccagctgca cagtctcagg gctggactcc agggaagatt 148320
ttagcccatt tagtgagtgg ggcagaagtg gccctggccc tgcacgaggt tgcctgcatg 148380
ggcgtccctg ccctgtccct gtgtctgctc cactgggggt tgaccaggct gccagggccg 148440
acttgggcct gtgccacctg cctctcatgt gtctcggaca gtgcagccga tgtctatact 148500
tcggtttcct caatgatgaa atggagggga tagtgttccc cgcatcatag aactgtgtga 148560
ggtttaaggg actcactgcc cttggcgtgg agccttctcc aggggccgtg ctgtgtcggc 148620
gtagctgtca gctctccgtt acaggcttga gaagggttga cactctctca tgtaacattt 148680
atatttctag gctggaccag tcgtactcag tttgaagaaa cttgggccac cctccttggt 148740
gtcctggtga cgcagcccct cgtgatggag caggaggaga gcccaccaga agtaaggcca 148800
caccctgtgc tggttggcac atgggcagtt atggccgctt gcaggccttt ggtggggaat 148860
aaaataaggc agcaagctgg tgttcttttt ttctcttacc ttatttttga aagagtagct 148920
gaatggtgtc ttgactgata ttccagagca gggacaaagc ctgctgaggt ctgggggctg 148980
cgattaccaa tggctggaat gcattttatt acggtgcatt ccatgttaag gatcaatacg 149040
attgtgccct ttctggaaaa tatcttttag tttatcaata ttcagaggag tgtaggttga 149100
attaaaatga aaaggcactt tataaaggcc atgagtagta cctggtttca tttttctaat 149160
gtcttgcaga gattttatca ggcttcttga agtgttcacg tacattacgc taacacgata 149220
ttaataataa ctgtgctctg gtacagcgga gccagcagaa tgggaagttg tggaatgcag 149280
gcccttgatt ctgatagaag gtgtggtttg aactcacaga aatgacagtt tggagggtag 149340
acatatgtca caagtcatca agattgtctt taaattcatg catagaagct aacagggtgt 149400
cataagcaag gcctgtaaaa tgtatgaggg aattcaaaga taatttatta aaaagtaatt 149460
catgtttgga gttttgtgcc caaaggagtc cttgatttga aaaatgggct tttgcccatc 149520
agattgtttc agggcccgtg tgtgcggagg ccctgccttg tgccccgtga gctcagcctg 149580
acagaaatcc tttggtagca cttaaggctc ctcttcctcc cattgaggca gggaagactc 149640
tgggttctgc aggcagaggt ggttgtgggt gtcttgctgc tcttgttgac atgtgggctc 149700
tccttccagg aagacacaga gaggacccag atcaacgtcc tggccgtgca ggccatcacc 149760
tcactggtgc tcagtgcaat gactgtgcct gtggccggca acccagctgt aagctgcttg 149820
gagcagcagc cccggaacaa gcctctgaaa gctctcgaca ccaggtttgc ttgagttccc 149880
acgtgtctct gggacatagc aggtgctggg gacagtgggt tccccgctga agcgtccagc 149940
agcttcaacc aggccgtttt ccttcattgc tagaattgaa aacaccgtcc gtgtggcctg 150000
tgcaggagat gcagacccaa aggtggcctc ctggtcagtg agaagctgga aacgtgacag 150060
gaactgacgt ggggttattg agcatttagg ggaagacgtt agcagagcag gaatgagcag 150120
gcaactagta gaacacccac ttaagggctc acggacaggt gctcacttag gaagtgagtt 150180
tcatttggta ttacaccagg ttcctttagg caaagcggag ggaaagttct ggtgtttttc 150240
acttgtaaga ttttgaagga aacaaaacac tctttacctt ttttctaaaa tgtaggtttg 150300
ggaggaagct gagcattatc agagggattg tggagcaaga gattcaagca atggtttcaa 150360
agagagagaa tattgccacc catcatttat atcaggcatg ggatcctgtc ccttctctgt 150420
ctccggctac tacaggtacc tgagggaaag ggtgcggggg agcggttgta cttgggctag 150480
aatgagagaa gactggcatg ctcaccacac cagtgatgcg ggaagacctg agtgtggtct 150540
gagttggagg ctgtggtgct aaatacgctg ccccttttcat aagcaggagt cttagtcagg 150600
cccagggagg aagtaaaatc tggaaatgaa tgagaagcat tctctcctgc cagtcaagaa 150660
atgagaagcg aaagaattct cacgggctgt aagaccagca ggatttaaaa gttgaattag 150720
ttgcttatgt taagaactca accaagttca tctacacaag ctgaatctcc agcttttcct 150780
aagaaaccat gtgtggcagt ggctgcaggg cagggcacag ctgggcctga gcaccccgct 150840
ccctgcacct ctcccctccc tgggccctgc ctgtcactgc ccactctccc accaagcctt 150900
ccggttgtgt gcctgcccta tcacaggcat cggagcttgt cacctggttt aaaagaagag 150960
agttgtgtgg ggatttggga tgcacgtttt tcactcaaaa gtattttagc gtagagctct 151020
gtgattccgt agctatttag gagtttaagc accttgaagg ctttaattgc agaaagttct 151080
atgtggacgt gcaatgtgtt atacgcagtg tctatgagac tcaaatgttt attagggcgt 151140
tgaagtaaac tgagcacttg gagggccatg gatccagcct tcaaggagct cataagtcag 151200
gaggacccag gagcaatgac ctgtcataga aggcagaaaa gaggggcaca gaggtgggtg 151260
ggaggcatac acaggcagct cctggagctc caaggggagc aagtgcttcc agggaagggg 151320
gcgtggaggc ccctttggag gaggcaagtt gatctggggt ctggcagagg gttagctggg 151380
gacatttagc gggaggctgg tgcccgggaa ttggggggat gcccagcaga aagacatgag 151440
gaggctggcc tggggcgtgg gggggtgtga aaggttaagt gggggcatta tcctgctccc 151500
gctcctgccg gctgtatctg gtcagcctgg gcaccgaggt ggggttctgg aaggcactgt 151560
tcaccaaaat gcttatctgg gtcccccaga gagcttgcct gcctggactg tcggctcgcc 151620
tgcaactgct gactcctaag cttttgcagc tcagcccaca accagttcct attcacagag 151680
gtgggagctg aggggtgaca agtgactgct gcagtcttat ttgtcataga gaaaaagtga 151740
cagagtccag cttgcccact ggccctgcca gcttaactgg ttataaagtg acaaatcccc 151800
aagacccaca gggctctgca caacctgggc cctcctgcca gtggcggcga gggcaggtgg 151860
ctcacggctg ggtgcctgtc tgggcaggag ctgggctggt atggggtggg cctgcggccc 151920
tgcccccctg tgcagatcaa gactcagggt gctggtgttc acaggtgccc tcatcagcca 151980
cgagaagctg ctgctacaga tcaaccccga gcgggagctg gggagcatga gctacaaact 152040
cggccaggtc agtctcgcgc ccccgccgcc tggcctctgt ccgtttctgt cctcagactt 152100
tggcgcttga cacacccagg agaaaagctc agtgcacttt ttaaatgaaa ggaagttttc 152160
cttttttta aaaaaaaatt taatgttcat tgtttttatc tgttttattc ctaggtcccg 152220
caagcagagg aagcattagt tttgttttta tttatgttct gtattccaga aagtagttaa 152280
gagacctcac atgtagcgat agagatgtgt gtaagagaca gtgagagggc gtgacttgga 152340
cttaagcaag gaccgtgaga cacaaaaagg ggggtgagga cagagtggag tcagctgaaa 152400
tgctcaggag gaagtagacg ccatgaaggg ccatggtatg gggggccgca ggcgtggccg 152460
tgagtgtccc tggggccagc tcttgggggg ctccctgagt gtccctgtcc ctgtggccag 152520
ttctgggtgg gagccccgtg tgcaggcaga cagctcggcc acttcctagc aggtcacatt 152580
ggtctgtgct tctgtttcct cctcagataa gtgaagggat tcaagggtct gggtgtggtg 152640
gctaacacct gtaatctata acattttagg aggctgaggc aggaggctta cctgagctca 152700
ggaggttgag gctgcagtga gccatgattg caccactgca ctccagcctg ggcaacagac 152760
cagtactctg tcccttaaaa aaaaatgtaa acagaaacgt agggccattt gcatatgatg 152820
gcacatggcg tggagcccta caggtgtatg ctgggcgggg cccggctgtg ctggccgact 152880
tgcacctttc cctccacccc ggtgctgtgt ctttcgctca ccgggttcct gatttagtga 152940
aagcagttgt gcaggacagt tctctttgta gcttttgttt ctgtggaaat gggtcagaat 153000
atggtgttta gaaacactta tgagctctga gagtttcctc ttctgagttc ctggcctgca 153060
gccttcacag cagaaaccct gtgatgtcac aagcctgttt ctgttccctg ctctctgcct 153120
gtactgtcct gttttgtgcc tgccggtttc agtgacagga agcagggagc tactggacca 153180
gcctgtattt ttctagacat agttggaaaa agaagtccca ctcttctgtc ctttcacctt 153240
tgacagatgt ttccacccca agataagtga aaatgaccaa taggatgcac tgtatttttc 153300
atgaaagtgt ttctgaaggg caggctgaga gtgagaggcc tggggctcac tgggtgcctc 153360
tggccttgtc ctgggcccag ggacactggt ctgtgcccga ggtattccct atccccccaa 153420
ccccgctgca tttggccaca tccttcaatg tttgcgttgt gtccagcgtc cgcaaaccaa 153480
ctgtcatggg atcatactgg ggctgaagta cggtcccacc cctgccctgt ctggggctga 153540
agtacagtgc cacccctgcc ctgtctgggg ctgaaggaca gtgccacccc tgccctgtct 153600
ggggctgaag tacagtgcca cccctgccct gtctggggct gaaggacagt gccacccctt 153660
ccctgtctgg ggctgaagga cagtgccacc cctgccctgt ctggggctga aggacagtgc 153720
cacccctgcc ctgtctgggg ctgaaggaca gtgccacccc tgccctgtct ggggctgaag 153780
gacagtgcca cccctgccct gtctggggct gaaggacagt gccacccctg ccctgtctgg 153840
ggctgaagga cagtgccacc cctgccctgt ctggggctga aggacagtgc cacccctgcc 153900
ctgtctgggg ctgaaggaca gtgccacccc tgccctgtct ggggctgaag gacagtgcca 153960
cccctgccct gtctggggct gaaggacagt gccacccctg ccctgtctgg ggctgaagga 154020
cagtgccacc cctgccctgt ctggggctga aggacagtgc cacccctgcc ctgtctgggg 154080
ctgaaggaca gtgccacccc tgccctgtct gggatgttta gcccctagat gccactggac 154140
tgagccgcta cttgcttttg ggaaagaggg gtgggggtta ggggtctggg cgaggggagt 154200
gcaggggctc ctccttggcc tgagagctgt tcatacagac tcctcgccca ctccctgcag 154260
ggtgctgggt cccagggggg aaatggccct tggtgccaag aacgtgagtt ggggctagtg 154320
ccagtgatga tggagaacag ctttttatgg gcacacagcc cacagcactg tgccaagtgc 154380
tcgaggcttc ccgagaacca ggcagaaagg aggacagtcg aggtgtgctg actgcgtggt 154440
ggctgcgtga tctagagcgc gggtcacaaa ggcgcgaggg agctctggcc ttgggtttac 154500
cgcaatgact gccagtgcgg gagactggaa aaggaatctc acgtattggt tccgtgtttt 154560
ggggactcca ttcagatgtc acttaggagt gaaagcatcc cttcgtagag cctctttctg 154620
tgtcaccctc ctcagctgct cctggggttg actggcccct gattcatgcc tttagcatgt 154680
gctggagctt cccagcagct gtccagcccc tgccccaccc tctctgtggg ctcccttgcc 154740
cgtaacctgg ggtgtctgaa cgacccttgc taaggggcag actgttagac ggtaggcatg 154800
tgctgagtcc cagtggccac acccacccac caggagcctg gcactgtggc cgcagcactg 154860
agcagtgccc cgtttctgtg gcaggtgtcc atacactccg tgtggctggg gaacagcatc 154920
acacccctga gggaggagga atgggacgag gaagaggagg aggaggccga cgcccctgca 154980
ccttcgtcac cacccacgtc tccagtcaac tccaggtttt ccaatggcct ttttcttttt 155040
aacagaaatt tgaaatttct tatcagtcat ttgatttgtt tgaggtgctt cttgaaatga 155100
gcctctcatc tcatgtactt ggaaaatacc catctcgcat attccacagg aaacaccggg 155160
ctggagttga catccactcc tgttcgcagt ttttgcttga gttgtacagc cgctggatcc 155220
tgccgtccag ctcagccagg aggaccccgg ccatcctgat cagtgaggtg gtcagatccg 155280
taagtgagcc ttcccattcc cctcacacct gcacgtgcca cacgcaccac acacgccaca 155340
caccccacac acacacaccg cccacacaca tgccacttgc acacacaccc ctcatgcatg 155400
caacacacac acaggccaca cgcaccatag acaccacaca cacatgccac atgcacacac 155460
atacacggca tgcaccatac acacaacaca cacagcacac atgccacaca cacacgccac 155520
accacatgca ccacacacat gccacatgca cacacactcc acatgcatgc accacacaca 155580
cacacacaca ccacacacac cacatgcacc acaccacaca ggttacatgc acacaacaca 155640
cacatgccac gtgcacacac cccacacacc acatgtatgt gccacacaca gcacacaacc 155700
acacacatgc accacacaca tgccacatgt gcatgcacca gacacatggc acacactaca 155760
cacacgccac gtgcacacac cccacacaca tgtacgcacc acacacatgc cacacacaca 155820
tgcaccacac acatgccaca tgtacacaca tgtatataca caccccacac cacacacaca 155880
ccacttgcac accacgcaca cacaccacat gcgcacacac acaccacata cgccacatgt 155940
acacaccata cacacaccat acatgcacca cgtgtaccac gcacccacac agacacagca 156000
cacgcataca ccacacacac acgcacacat gcgtcccgca cagtaatgtc tcttgggtgt 156060
aagaacacga cttgccagta gtagcgttct ggatgcgttg cctggattct aacagcgcga 156120
ttctcccctt gccctcctgg ttttccacat ctccagcttc tagtggtctc agacttgttc 156180
accgagcgca accagtttga gctgatgtat gtgacgctga cagaactgcg aagggtgcac 156240
ccttcagaag acgagatcct cgctcagtac ctggtgcctg ccacctgcaa ggcagctgcc 156300
gtccttggga tggtaagtga caggtggcac agaggtttct gtgctgaagc cacgggggcc 156360
catctgcctt gggacctggt gttggccaga ggtgccgggt gcggctgcct ccttccaaga 156420
gttgacccga accggactcc acggcccacg tgagctgcag tgcttctcag atggaggggg 156480
ttcagcgacg gtcagtgcca ttcacaggtc actgtgatgt gggttgtggc ggccaagcca 156540
tggtttgggg tcccgtatcc ctgggcttat gacatcattg tagtagccca tccccacaga 156600
accacggtgt gtggtggcgc tgaggcatcg tagatggtgg aaatgctact ggcttcccca 156660
tgctctgccc tgaggcctga ctgcctcact ccccttctca gttatgttcc aggccccccg 156720
agcttcctgg ctggacagct tctctcctgg gggccgtttt gtcacagtga ccctgtgttt 156780
ctagtcccaa atctgggtgc tatagtctct ttttagcgtg gtggttgtct tagtcttttt 156840
tggctgctac cacaagttac cttagactgg gtaatttata aacagtggaa atttacttct 156900
caccgttctg gggggctggaa gttttcatgg tcaaggtgcc agcagatttg gtgtgtgatg 156960
agggctgctc tctgcttcat agatggcatc ttctggctgg gtcctcacgg tggaaggagt 157020
gaacaagctc cctcaggcct tttagaaggg ccccaatcca caagggctct cccatcatga 157080
cctcatcacc tcccaaggcc ccaccttctt gtactgtggc actgcaaatt aggtgtcagt 157140
gtaggagttt caggagggat agaaacattc agaccatccc agcggtcaag tgttcatcct 157200
cttgagttcc tccttattct gcttctggtt tatcaggatt cagccagtgc agcatggtac 157260
ctgtattctg tggcacatca ccacatggta tttgccaagt atccatcacc tgcacacgtg 157320
aaatcattgc ccgtgggtcc cgacatctgg cgaagcatat tcaaggatgg cagaactgtc 157380
agagctggca cctctggttc cttgtcatgt ggcattacct agtaatccat tttatgatag 157440
caatggaaac tcatttcttc aacaaacacc tgagtggctg ccgtgtgcca gccgtctggg 157500
gcccttggtg agaatggcat ggtggtgccc atcagggcct gcctagcccg tgctctggac 157560
gggctcctgt gtgtcaggaa cgacaatgct gtcatgacgg tgaatgattt tttttttgc 157620 catcactcca gccgctaaca tttgcggagc tcttcctccc gcacccccac ctgacaaggc 157680
caagggtgac cttggcccca ccctaggcgg ccaaggtcag aggttagctg gcttgtctgg 157740
gtcacacaaa atgcagcaga ggttgaggtg agcacatgtc cgtgacctgg agcctgactc 157800
cctctctgcg agtcttgact gctcttgcct agactctgtc ctccccgagc ccaaacgcca 157860
gtcatcttcc cttgtgggtg tccttcagcc tggtgccatg ctggtgactc agcagccgtc 157920
cagggagtgg aaacaattga gtgtgtgggt tccctgtgtg ggcatctctc ttcacggcga 157980
acaccctctg ggtgttgccc acacgatgtc aaagcggctc ttggaagggg tccttctcct 158040
ttgtgggaag tttcagctgc tgggctaact tgaattgtaa ctgtggtttt gtgctcaggc 158100
ccagatcccc ctaggcaagt gttgtgccat cagtaatcaa atgagaaata atcattttga 158160
aaagcagatc ctaaggcagg atggtcatgg acactcactc ccagctcttt gtgcactcat 158220
gctttctgga agatggccat cctctgtgaa ggttttcagc gcgtcatgct tggtacccac 158280
gtatccagag catgtcgttt tgaggtattt gcccaccgtt gtgaaatccg tgccacccga 158340
gagcaggtcc tgatgtgggg ctttcagaag tgggacctgg ggccgtacgc agtccttagg 158400
gaggggccgt gtggcgttgt gcgtgtgagg ggatagcaca gggtgaggtg ggggcccaag 158460
aaggaagtga cccacaaaga acagcctcct cttttggtcc ttgttcctgg gatggctggg 158520
agtggcttct gtgtcgtccg gccatttccc ctgcggagag gctcctacca ctgccgagaa 158580
cctcatcatt ccacaaaaac aagaggccgc ctggccatcc agcgctccat gggaattctg 158640
tgtccccata gtcttgggct gaaggagggt gacattcctt gctgacttct gcaggggtct 158700
cctcactgtt aaagagcaga ttgaaagtga agaacgtggg ctaagtgttt aggtcgatat 158760
ttaaccctgc taggttttgg atactaagtg aaattgaggc cattttggtt gaagttgaca 158820
gaaaccacta tcagggatcc ccaagactac cccaggcttt tctagaaaga ctctcagcta 158880
agatgtgtta tggtaaaagc acacaaaaca aaatcagcaa agaaaattag caagggcaga 158940
ggcccatggg gcgatgtccc gaggacacca ggcttgagct tccagaatcc tctcccagcg 159000
gggtcgtgca ggacgcactt aactccccgc acagtgagcc gtgacagcgc gtgtgcagtg 159060
tcgtcgccag gaaagcacac tagagactcg gtgccagggt ttttactggg ggctgggcac 159120
atgggcaccc tctgcctgcc tcgtgcccag actctggact cccggaggga aggcaagttc 159180
tcagcaccaa ccctggtgcc cacacaagca gctgagcaca gggagcccct cctcagtgag 159240
gatggtgggc accgtcccaa caccagccag gggccagcct tgcacacagg cctctcagga 159300
tggtctccgg cctgctgtgt agtctcttct gcacacaagc gtgagggcag cgccccccgcc 159360 tcggctgtgg ggaggagcca ctgggacgtg agctctggtg gcatgcagca gcttttgtct 159420
gtgtgtgcct aggacaaggc cgtggcggag cctgtcagcc gcctgctgga gagcacgctc 159480
aggagcagcc acctgcccag cagggttgga gccctgcacg gcgtcctcta tgtgctggag 159540
tgcgacctgc tggacgacac tgccaagcag ctcatcccgg tcatcagcga ctatctcctc 159600
tccaacctga aagggatcgc ccagtgagtg ggagcctggc tggggctggg gcgggggtct 159660
cagaatgagc tgtgaaggaa gcagcatcac cctctccaag tgcccaggct cctggccaga 159720
tggcaggcca ggtatcagtg ggaacccagg tgggtgccat ggctgaggtc agtgagacgc 159780
aagagcacag gtgcgtccta gaggcttcct cgggcacctc cagcgagctg gagctctcgc 159840
ctctgctgct gtctcatgtg gcgcttagca cactctccca cgtgcccatt cctgactctg 159900
ctctcgaggc catcggctct cattctctgc tcccagaacc ctgttattac ccaggctagc 159960
ctcctctctg caccttcccc gccctggccc agtacctccc tcttgtttcc actgtgattc 160020
cgacctcacc ttatcttaaa gctgctggac ggcaggttct gtacacacgt gtccttgaca 160080
aagcacggct ggtgccgcaa cccctcagcg agcaagtcaa gctcttcaca gcgatgtctt 160140
acaagcgcag agggctctgt gacaccctgg tctcaccgcc actcttccaa agtcgcagag 160200
gctttagcag agatgggccc agcctctctg agtcataggc ttctgcacac gggagctgtc 160260
tttagaggga gggtggaatt tcatcagcca ccccacatggg ggagttgagg gcaagaatta 160320
ggagcaaaga tgggaagggg tctgggagga atggccagtg atccccctttg acaagtgggc 160380 aggaaacggg ggctaggtca aagttgagtg gaagacctgg agggagacgg gaaggtctct 160440
gtaggcacag ttcagacagg agggaggtgt gagccagggc acatgccggt ggccgtctgg 160500
caggatttgg gacatgctgg agcagggaca gcggctcatc aggggccatt gccctcatcc 160560
aggccagagt gtcacaagcc cgtggggagg cccttctcgc ctgtcatcct tgctgggcag 160620
tgggtgctgt gctagcagga caggcggacg gctggcaact gtctctgcat ccctggagcc 160680
tggcataggg ccaagtcaca cggggcacag gcctgcaaat caggcacata tgttggtgca 160740
gtgacgtgat tttgggggc agccccagaa caggccccag acacaggcca aagccctgcc 160800
tgtgctggtg tgttgggctg ttctatggct cttgctgtgg gcatggagga ctcagggaag 160860
gagagttgag gtggtccagg agttgcgttt gggatgcaga gagcttgtgg catccaggta 160920
gaaatggtgc gtggggctga cctcagcacc atgggcagag gggccgtgtc acgtgcctcc 160980
gaggtggagg tgggaccacg tggtgacaga tatacgcatc actgggcacg tttttgtggg 161040
tgttgggggg catcgtattg gctcctctgt tcacagtggc cactcattca gtccctggct 161100
accaggtcct cactgtgcca tggggaaggc cggcgctgtc gggggatcac agaaggcagc 161160
acgtcatgat ggcatgtgcc atgaaggaaa agcacagggc actcaggaag tagaggggac 161220
tggcctgggg tgtgggaatc tagggcctcg ttgagggaca gagagaggaa gtgtgtggtg 161280
gccagcatgg aggtggccac aggggaggct gagttaggcc gagagggcag ggcgttgggg 161340
aggtagacgg gctcagccac tcagggagtg gtcaagcaga ggctgaaggg tcaggccagg 161400
ttgcaggggc ctgggggagc cactcagggt aggcgctccc gggagcccgc ctggcccata 161460
gctctacact cccgcgtggg gccggacatg ctgtgaagcc ctctccacgt tggatggggg 161520
tggctgagcc tggatgctgt ctcccgtttt cagctgcgtg aacattcaca gccagcagca 161580
cgtactggtc atgtgtgcca ctgcgtttta cctcattgag aactatcctc tggacgtagg 161640
gccggaattt tcagcatcaa taatacaggt gagtgggccc tggctgtctt cctctgcaca 161700
cggggagtgg gcttcccttc tcttttcctt gcaggatcat accagtgggc cagttttgac 161760
ttggtcggga ggaggcatga acacctgaga ctgtgcagcg attctttgac acagaggcct 161820
ttctccctgt gcagatgtgt ggggtgatgc tgtctggaag tgaggagtcc accccctcca 161880
tcatttacca ctgtgccctc agaggcctgg agcgcctcct gctctctgag cagctctccc 161940
gcctggatgc agaatcgctg gtcaagctga gtgtggacag agtgaacgtg cacagcccgc 162000
accgggccat ggcggctctg ggcctgatgc tcacctgcat gtacacaggt gagcatgtac 162060
acggtgccca taaggccagc ccaagtcctg ttcaagggag gcaggagcat gctcactcaa 162120
gggacctcga ctaggtgccc tctgatttca cacttctggt gttgccccaa gccggcccca 162180
tcaccttgca agaaaggctc tggagccccc agggctggag tacctggtca gggttgaccg 162240
tccctgtggt cactcatccc atgtggctga gctgggctgg gtcctgggca agcaaggggc 162300
tgatatcacc tgctttcaga tctccaggga ctcactggac ccctgtgtac aaagcactgt 162360
ctacagagcc tattgggttg tatagaggta accttcgtac tgaacacttt tgttacagga 162420
aaggagaaag tcagtccggg tagaacttca gaccctaatc ctgcagcccc cgacagcgag 162480
tcagtgattg ttgctatgga gcgggtatct gttctttttg ataggtaaga agcgaagccc 162540
catccctcag ccgttagctt ccctagaact ttggcctgaa gctgtgcttt tgtgtgtgtc 162600
tgctgatccc ctggcgctgt tgctggagtc ctgccagtga ttccccacca cagcctgacc 162660
atgggctgcc ttggctcagg gttccactgg cgagctggtg gtccttggac cccagcactc 162720
aggtgtagcg ttgaccagtt ccaaggttgt cccagtgcct gcccatctct cctgagggct 162780
cagggacagt acctggcagt tgggggtgtg gcagggggca ggaatgacca gcctctggga 162840
gggtggggca gaagcctgta cagtgaggag gagctggctc agcctggctg cctatcgtga 162900
gaggggagcc cacggggctg tgggaggggg gccgtggtgc ctgtgagcag ggtgaggagc 162960
agcggcagga ggatgaaggt ggaacccaca catgcatctt tgagacccgt gtggtcagtg 163020
gcttctgccc cccaccaccc cccactgctg tgcgtgcata gaattggctt ccctcacctg 163080
ctctggaagt gggttaggag cttggtaggg ctttttctca aggacaaggg cccctgattt 163140
gctctcaggc ctcagtcctg gcgacatggt ggatctggag ccttgttgca ctgccttgcc 163200
tgtgctctcc aatcagggtg gccagtgggg agccatttgg cttttctcaa gagcatactc 163260
aggtggacct tgctccactg tttgaccaga tgaggcattc tgaacagcca agcctgtgct 163320
ggtctgtttt catgttgatt tttttttttc ttttcttttt gagatggagt tttttcccttg 163380
tcacccaggc tggagtgcaa tggtgtgatc tcggctcact gcaacctccg cctcccgggt 163440
tcaagtgatt ctcctgcctc agcctcccta gtagctggga ttacaggcac acaccaccat 163500
gcccagctaa tttttgtgtt tttagtagag acggggtttc accgtgttgg ctgggctggt 163560
ctcgaactcc tgaactcaag tgatccaccc tccttggcct cccaaagtgc tgggattgca 163620
ggcgtgagcc actgcgcccg gcccccatgt cgatttttaa atgcacctct gcatcgttct 163680
tcagtcccca tatgctcact gagcaccact gcgactggca gacgggcaca gggaggcgcc 163740
acgaccagtc ctggccttca aggggcttgt ggtctagtgg gcccaatgct aggtggcgag 163800
tgctccaaag agtgtggtgc acgccttccg cttgaccgct ctccagacgc cacagggagg 163860
cacctcgcag ctgaccacag atttctctct gtggagcagt gtcttcagag cggctgccat 163920
gccactgctg ggcgagggtc tgcgggcggg tagagccagg agcacctgtg aggaagtgca 163980
ctgccatttt cgtagctgct tcccgtgtgt ctcagttaca cacggctggc atgtgtgcac 164040
tgatgagacg ggaacgtgat ggttgctttt cagcactgaa agggatactg ctcagggggc 164100
gtgtttcagg atctggttag ggaagaagca gcgagagcac agatggggcc ctgtgtggta 164160
acaagaaaaa agtcctggtt gacaacagtg ccacgaagcg ttagaacaca tagggatgtt 164220
tgtggagcat ttgcatgtgg aaagcagcaa aaacataatg ggaacgggtt cttttgttat 164280
gatttttaaa aatctctttt gtaacatcct tcccgctgcg ccgtttctgc atattccttt 164340
atgtagcttt caaactcctc ttaggagttc tggtccctac agggcgtggg agcccaggct 164400
ttacgtagct ttcaaactcc tcttaggagt tctggtccct acagggtgtg ggagcccagg 164460
gcctgtgccg agcagcctgc ctccacgagc tagacagagg aagggctggg gttttgcctt 164520
tttagtctca aaattcgtac tccagttgct taggctctga ctttccccac ttggaaagtc 164580
cctcacggcc gagggtccct cccagccctg atttcacatc ggcattttcc ccagtattag 164640
agccaaggcc ctccgcgggc aggtggggca gctgtgggag ctggtgccag tctctgacct 164700
gcgtccctcc tcccaggatc aggaaaggct ttccttgtga agccagagtg gtggccagga 164760
tcctgcccca gtttctagac gacttcttcc caccccagga catcatgaac aaagtcatcg 164820
gagagtttct gtccaaccag cagccatacc cccagttcat ggccaccgtg gtgtataagg 164880
tgaggttgca tgtgggatgg ggatggagtg ggaaagcctg gaggtggagt tgcctccgac 164940
ttcccagcag attcgccagc agagcccagc tcctccgctt taaagcagca atgcctctgg 165000
cccccacccc acccccgcca cccaggcgca gcaggtgctt cccgtccccc cagccctgac 165060
actcaggcac ctgcttgctc cttgcaggtg tttcagactc tgcacagcac cgggcagtcg 165120
tccatggtcc gggactgggt catgctgtcc ctctccaact tcacgcagag ggccccggtc 165180
gccatggcca cgtggagcct ctcctgcttc tttgtcagcg cgtccaccag cccgtgggtc 165240
gcggcgatgt atcctctctg ggtccctggt gctggccccg tttcccttgt caacaccgag 165300
gctcatgttt catgataagg ttttgaaacc taacctttgc aaaaacccca cagatgccag 165360
ggtgacaggc cctcagcccc agggaagtaa aatgctgaca ggggtacaga aaggagcacg 165420
tccagacatt tgctgaccag ggcctctcag aggggccggt gtatggcagg agggtcgcag 165480
ctgaggggcc tttctgtgga gggcctgggt gaggggagcg agggtgggcg gtggtctctg 165540
cagacgtccc gcccactcgc gggctctgtg tggctgggct tctcctgaca ctgcttctca 165600
ttagctttgg tcattgtgcc tcgatcgccc tctcggggaa aggcttaagt aaagatccag 165660
ttcccacccc cagatgctgg ctgccaggag tttccctttc cacagccctt ccccaagaca 165720
gaccacaaga gcctccaagc agcacagttg tcctggtgct gacagcacag ccttgcccgg 165780
cgtgcctggc acggctctgc cctcactgca ttggagcagg gctagtggag gccagcggaa 165840
gcaccggcca ccagcgctgc acaggagcca ggccaggtga gtgctgccga gtgggtgccc 165900
tgcctgcagg gcatccagcc agccaagggt tgcaggaatg gaggtggagg cgctgatgca 165960
gctggaggca tccaggtggc ccttccgggg ctctgctcgc tctccaggct ccctggaccc 166020
ctttgtagac tgtttcagga gaggaactcc caggtgagga cagggaggca gcattcccct 166080
catttgccgg ccttttttcct taactcctgc accagcctcc cacatgtcat cagcaggatg 166140
ggcaagctgg agcaggtgga cgtgaacctt ttctgcctgg tcgccacaga cttctacaga 166200
caccagatag aggaggagct cgaccgcagg gccttccagt ctgtgcttga ggtggttgca 166260
gccccaggaa gcccatatca ccggctgctg acttgtttac gaaatgtcca caaggtcacc 166320
acctgctgag cgccatggtg ggagagactg tgaggcggca gctggggccg gagcctttgg 166380
aagtctgcgc ccttgtgccc tgcctccacc gagccagctt ggtccctatg ggcttccgca 166440
catgccgcgg gcggccaggc aacgtgcgtg tctctgccat gtggcagaag tgctctttgt 166500
ggcagtggcc aggcagggag tgtctgcagt cctggtgggg ctgagcctga ggccttccag 166560
aaagcaggag cagctgtgct gcaccccatg tgggtgacca ggtcctttct cctgatagtc 166620
acctgctggt tgttgccagg ttgcagctgc tcttgcatct gggccagaag tcctccctcc 166680
tgcaggctgg ctgttggccc ctctgctgtc ctgcagtaga aggtgccgtg agcaggcttt 166740
gggaacactg gcctgggtct ccctggtggg gtgtgcatgc cacgccccgt gtctggatgc 166800
acagatgcca tggcctgtgc tgggccagtg gctgggggtg ctagacaccc ggcaccattc 166860
tcccttctct cttttcttct caggatttaa aatttaatta tatcagtaaa gagattaatt 166920
ttaacgtaac tctttctatg cccgtgtaaa gtatgtgaat cgcaaggcct gtgctgcatg 166980
cgacagcgtc cggggtggtg gacagggccc ccggccacgc tccctctcct gtagccactg 167040
gcatagccct cctgagcacc cgctgacatt tccgttgtac atgttcctgt ttatgcattc 167100
acaaggtgac tgggatgtag agaggcgtta gtgggcaggt ggccacagca ggactgagga 167160
caggccccca ttatcctagg ggtgcgctca cctgcagccc ctcctcctcg ggcacagacg 167220
actgtcgttc tccacccacc agtcagggac agcagcctcc ctgtcactca gctgagaagg 167280
ccagccctcc ctggctgtga gcagcctcca ctgtgtccag agacatgggc ctcccactcc 167340
tgttccttgc tagccctggg gtggcgtctg cctaggagct ggctggcagg tgttgggacc 167400
tgctgctcca tggatgcatg ccctaagagt gtcactgagc tgtgttttgt ctgagcctct 167460
ctcggtcaac agcaaagctt ggtgtcttgg cactgttagt gacagagccc agcatccctt 167520
ctgcccccgt tccagctgac atcttgcacg gtgacccctt ttagtcagga gagtgcagat 167580
ctgtgctcat cggagactgc cccacggccc tgtcagagcc gccactccta tccccaggcc 167640
aggtccctgg accagcctcc tgtttgcagg cccagaggag ccaagtcatt aaaatggaag 167700
tggattctgg atggccgggc tgctgctgat gtaggagctg gatttgggag ctctgcttgc 167760
cgactggctg tgagacgagg caggggctct gcttcctcag ccctagaggc gagccaggca 167820
aggttggcga ctgtcatgtg gcttggtttg gtcatgcccg tcgatgtttt gggtattgaa 167880
tgtggtaagt ggaggaaatg ttggaactct gtgcaggtgc tgccttgaga cccccaagct 167940
tccacctgtc cctctcctat gtggcagctg gggagcagct gagatgtgga cttgtatgct 168000
gcccacatac gtgaggggga gctgaaaggg agcccctcct ctgagcagcc tctgccaggc 168060
ctgtatgagg cttttcccac cagctcccaa cagaggcctc ccccagccag gaccacctcg 168120
tcctcgtggc ggggcagcag gagcggtaga aaggggtccg atgtttgagg aggcccttaa 168180
gggaagctac tgaattataa cacgtaagaa aatcaccatt ccgtattggt tgggggctcc 168240
tgtttctcat cctagctttt tcctggaaag cccgctagaa ggtttgggaa cgaggggaaa 168300
gttctcagaa ctgttggctg ctccccaccc gcctcccgcc tcccccgcag gttatgtcag 168360
cagctctgag acagcagtat cacaggccag atgttgttcc tggctagatg tttacatttg 168420
taagaaataa cactgtgaat gtaaaacaga gccattccct tggaatgcat atcgctgggc 168480
tcaacataga gtttgtcttc ctcttgttta cgacgtgatc taaaccagtc cttagcaagg 168540
ggctcagaac accccgctct ggcagtaggt gtcccccacc cccaaagacc tgcctgtgtg 168600
ctccggagat gaatatgagc tcattagtaa aaatgacttc acccacgcat atacataaag 168660
tatccatgca tgtgcatata gacacatcta taattttaca cacacacctc tcaagacgga 168720
gatgcatggc ctctaagagt gcccgtgtcg gttcttcctg gaagttgact ttccttagac 168780
ccgccaggtc aagttagccg cgtgacggac atccaggcgt gggacgtggt cagggcaggg 168840
ctcattcatt gcccactagg atcccactgg cgaagatggt ctccatatca gctctctgca 168900
gaagggagga agactttatc atgttcctaa aaatctgtgg caagcaccca tcgtattatc 168960
caaattttgt tgcaaatgtg attaatttgg ttgtcaagtt ttgggggtgg gctgtgggga 169020
gattgctttt gttttcctgc tggtaatatc gggaaagatt ttaatgaaac cagggtagaa 169080
ttgtttggca atgcactgaa gcgtgtttct ttcccaaaat gtgcctccct tccgctgcgg 169140
gcccagctga gtctatgtag gtgatgtttc cagctgccaa gtgctctttg ttactgtcca 169200
ccctcatttc tgccagcgca tgtgtccttt caaggggaaa atgtgaagct gaacccccctc 169260
cagacaccca gaatgtagca tctgagaagg ccctgtgccc taaaggacac ccctcgcccc 169320
catcttcatg gagggggtca tttcagagcc ctcggagcca atgaacagct cctcctcttg 169380
gagctgagat gagccccacg tggagctcgg gacggatagt agacagcaat aactcggtgt 169440
gtggccgcct ggcaggtgga acttcctccc gttgcggggt ggagtgaggt tagttctgtg 169500
tgtctggtgg gtggagtcag gcttctcttg ctacctgtga gcatccttcc cagcagacat 169560
cctcatcggg ctttgtccct cccccgcttc ctccctctgc ggggaggacc cgggaccaca 169620
gctgctggcc agggtagact tggagctgtc ctccagaggg gtcacgtgta ggagtgagaa 169680
gaaggaagat cttgagagct gctgagggac cttggagagc tcaggatggc tcagacgagg 169740
acactcgctt gccgggcctg ggcctcctgg gaaggaggga gctgctcaga atgccgcatg 169800
acaactgaag gcaacctgga aggttcaggg gccgctcttc ccccatgtgc ctgtcacgct 169860

```
ctggtgcagt caaaggaacg ccttcccctc agttgtttct aagagcagag tctcccgctg 169920
caatctgggt ggtaactgcc agccttggag gatcgtggcc aacgtggacc tgcctacgga 169980
gggtgggctc tgacccaagt ggggcctcct tgtccaggtc tcactgcttt gcaccgtggt 170040
cagagggact gtcagctgag cttgagctcc cctggagcca gcagggctgt gatgggcgag 170100
tcccggagcc ccacccagac ctgaatgctt ctgagagcaa agggaaggac tgacgagaga 170160
tgtatattta atttttaac tgctgcaaac attgtacatc caaattaaag gaaaaaaatg 170220
gaaaccatca gttgttgctg tgtgaggctt gctttgcttc atgagaacct agaccttgct 170280
gagctggagt cttaggaagc agtctcctaa gtgcttctcc agcaggggca gaaactgtcc 170340
caccagctaa catctggcat tatggagggt cccccaggca gctgccagca gggacaggcc 170400
ccgtgttttc tgtagccagg gatgaggaag tggccccagg gcatgggcct ggctgggtgc 170460
ttctgcaagg gccttcccaa accacagtac aggtggtctt cctgccctgc agatgggagc 170520
tgtgggagct gctggagctg ctggagcctt catggtcaag tgacatcata agcttatatg 170580
acatacacaa gcctcaggac ttggcccatg gcactgaagc aggtcatcag gcccagcaca 170640
gagactagag ctgtgttctc acagggccca ccacccttcc acctccttgg ccattgacac 170700
ctgcgtccct ggcccagctg ctcccaggta acccccaaag cagctggcac atcccacctc 170760
tggtgtggcc ggggctgctg tgtgtccgca gggcctgccc cgtctattct agcttgtttg 170820
tcctgtctga accagcgcct actccaagaa gcctctgctc agcccagcgg ggatgcttct 170880
aagctccgga cgagcctctc ggaagccttg gtgattggtg gtgtagtcat cttgggatgc 170940
agatgtctta ccaacctgca agaacaaaaa ccctgtggct tcctctggtg cagggtattt 171000
agtcaatgtt tgctgaggtc ccgtctggtt ctggctaatt ggcaggggtc gtccacccat 171060
tctttccctg ctctgctgtc tgtgccagga gagacggggg ccagtcggcc aaggggccag 171120
ctcctgctgc ctgctcctct tgggcacgtg cgggggcccc ctttctctga gcagggatag 171180
ggatcagtct gccggaggga tgtggtggac aggcctaaag catttggggc ggggcatgcc 171240
acttgagctc cctaaatctg tctcctcata ggtgacaccg ctccagggcc ccccagtggc 171300
ctctcctttc agagctacct aaattctggt cacttcagag aaatggagca ccccccttctc 171360
cctggtccag gtgtggacag cctggcacac tgagcacacc tggcatggct ggtaatttca 171420
gaaagaagag gggccggggt ccagtgggaa gcagcggtga acccctcgtg agtgggcttt 171480
gcagtccctc cccatgccac ggcagagctg ccctcaacac agccttcctc ttcctcatcg 171540
gagagcacac cctgtcccct tgccgagctg tgccctgtgc cttcggtggt atttgatttt 171600
ggctgctact ggctttgttg ggatctggaa gtcgcttccc ctgcgtggtg cgtggagcac 171660
tgtaagtcag atgagggaag tagccagggt gaggtgagta ccgggtggag ccgccactga 171720
agggactggg tagggggggcc ttgcctctac atgatgtgac acagccaacc gaggacagag 171780
gaagccccgt tcctgggggt gtggggtgca cccctcaggg aagcctgcag tggggcctga 171840
ggaaaggcat cctccgcgag cccacgagtc tggtccatga gcaccgtgac agtgtctgtg 171900
ggtagaggtg gacccggcct tgtgtcatca ccaggacctc ttttgggaaa ccatgtggac 171960
atcgcttgcg ggtcccccag gctctgcagc cccagcagcc t                    172001
```

<210> SEQ ID NO 3
<211> LENGTH: 10081
<212> TYPE: DNA
<213> ORGANISM: Mus musculus

<400> SEQUENCE: 3

-continued

```
gcactcgccg cgagggttgc cgggacgggc ccaagatggc tgagcgcctt ggttccgctt     60
ctgcctgccg cgcagagccc cattcattgc cttgctgcta agtggcgccg cgtagtgcca    120
gtaggctcca agtcttcagg gtctgtccca tcgggcagga agccgtcatg gcaaccctgg    180
aaaagctgat gaaggctttc gagtcgctca agtcgtttca gcagcaacag cagcagcagc    240
caccgccgca ggcgccgccg ccaccgccgc cgccgcctcc gcctcaaccc cctcagccgc    300
cgcctcaggg gcagccgccg ccgccaccac cgccgctgcc aggtccggca gaggaaccgc    360
tgcaccgacc aaagaaggaa ctctcagcca ccaagaaaga ccgtgtgaat cattgtctaa    420
caatatgtga aaacattgtg gcacagtctc tcagaaattc tccagaattt cagaaactct    480
tgggcatcgc tatggaactg tttctgctgt gcagtgacga tgcggagtca gatgtcagaa    540
tggtggctga tgagtgcctc aacaaagtca tcaaagcttt gatggattct aatcttccaa    600
ggctacagtt agaactctat aaggaaatta aaaagaatgg tgctcctcga agtttgcgtg    660
ctgccctgtg gaggtttgct gagctggctc acctggttcg acctcagaag tgcaggcctt    720
acctggtgaa tcttcttcca tgcctgaccc gaacaagcaa aagaccggag gaatcagttc    780
aggagacctt ggctgcagct gttcctaaaa ttatggcttc ttttggcaat ttcgcaaatg    840
acaatgaaat taaggttctg ttgaaagctt tcatagcaaa tctgaagtca agctctccca    900
ccgtgcggcg gacagcagcc ggctcagccg tgagcatctg ccaacattct aggaggacac    960
agtacttcta caactggctc cttaatgtcc tcctaggtct gctggttccc atggaagaag   1020
agcactccac tctcctgatc ctcggtgtgt tgctcacatt gaggtgtcta gtgcccttgc   1080
tccagcagca ggtcaaggac acaagtctaa aggcagcttt tggggtgaca cggaaagaaa   1140
tggaagtctc tccttctaca gagcagcttg tccaggttta tgaactgact ttgcatcata   1200
ctcagcacca agaccacaat gtggtgacag gggcactgga gctcctgcag cagctcttcc   1260
gtacccctcc acctgaactc ctgcaagcac tgaccacacc aggagggctt gggcagctca   1320
ctctggttca agaagaggcc cggggccgag gccgcagcgg gagcatcgtg gagcttttag   1380
ctggaggggg ttcctcgtgc agccctgtcc tctcaagaaa gcagaaaggc aaagtgctct   1440
taggagagga agaagccttg gaagatgact cggagtccag gtcagatgtc agcagctcag   1500
cctttgcagc ctctgtgaag agtgagattg gtggagagct cgctgcttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtattta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tcctttttgt taactggtga aaagaaagca ctggttccag   2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
```

-continued

```
gtactgagga acagtatgtt tctgacatct tgaactacat cgatcatgga gacccacagg   2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
tggtggactg cattccttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa gaacagctcc tactggctgg   2700
tgaggaccga actgctggac actctggcag agattgactt caggctcgtg agtttttttgg  2760
aggcaaaagc agaaagttta caccgagggg ctcatcatta tacagggttt ctaaaactac   2820
aagaacgagt actcaataat gtggtcattt atttgcttgg agatgaagac cccagggttc   2880
gacatgttgc tgcaacatca ttaacaaggc ttgtcccaaa gctgttttac aagtgtgacc   2940
aaggacaagc tgatccagtt gtggctgtag cgagggatca gagcagtgtc tacctgaagc   3000
tcctcatgca tgagacccag ccaccatcac acttttctgt cagcaccatc accagaatct   3060
atagaggcta tagcttactg ccaagtataa cagatgtcac catggaaaac aatctctcaa   3120
gagttgttgc cgcagtttct catgaactca ttacgtcaac aacacgggca ctcacatttg   3180
gatgctgtga agccttgtgt cttctctcag cagcctttcc agtttgcact tggagtttag   3240
gatggcactg tggagtgccc ccactgagtg cctctgatga gtccaggaag agctgcactg   3300
ttgggatggc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ttcatggacc tctgaagaag aagccaactc agcagccacc agacaggagg   3480
aaatctggcc tgctctgggg gatcggactc tagtgccctt ggtggagcag cttttctccc   3540
acctgctgaa ggtgatcaat atctgtgctc atgtcttgga cgatgtgact cctggaccag   3600
caatcaaggc agccttgcct tctctaacaa acccccccttc tctaagtcct attcgacgga  3660
aagggaagga gaaagaacct ggagaacaag cttctactcc aatgagtccc aagaaagttg   3720
gtgaggccag tgcagcctct cgacaatcag acacctcagg acctgtcaca gcaagtaaat   3780
catcctcact ggggagtttc taccatctcc cctcctacct caaactgcat gatgtcctga   3840
aagccactca cgccaactat aaggtcacct tagatcttca gaacagcact gaaaagtttg   3900
gggggttcct gcgctctgcc ttggacgtcc tttctcagat tctagagctg gcgacactgc   3960
aggacattgg aaagtgtgtt gaagaggtcc ttggatacct gaaatcctgc tttagtcgag   4020
aaccaatgat ggcaactgtc tgtgtgcagc agctattgaa gactctcttt gggacaaact   4080
tagcctcaca gtttgatggc ttatcttcca accccagcaa gtctcagtgc cgagctcagc   4140
gccttggctc ttcaagtgtg aggcccggct tatatcacta ctgcttcatg gcaccataca   4200
cgcacttcac acaggccttg gctgacgcaa gcctgaggaa catggtgcag gcggagcagg   4260
agcgtgatgc ctcggggtgg tttgatgtac tccagaaagt gtctgcccaa ttgaagacga   4320
acctaacaag cgtcacaaag aaccgtgcag ataagaatgc tattcataat cacattaggt   4380
tatttgagcc tcttgttata aaagcattga agcagtacac cacgacaaca tctgtacaat   4440
tgcagaagca ggttttggat ttgctggcac agctggttca gctacgggtc aattactgtc   4500
tactggattc agaccaggtg ttcatcgggt ttgtgctgaa gcagtttgag tacattgaag   4560
tgggccagtt cagggaatca gaggcaatta ttccaaatat atttttcttc ctggtattac   4620
tgtcttatga gcgctaccat tcaaaacaga tcattggaat tcctaaaatc atccagctgt   4680
gtgatggcat catggccagt ggaaggaagg ccgttacaca tgctatacct gctctgcagc   4740
```

ccattgtcca tgacctcttt gtgttacgag gaacaaataa agctgatgca gggaaagagc 4800
ttgagacaca gaaggaggtg gtggtctcca tgctgttacg actcatccag taccatcagg 4860
tgctggagat gttcatcctt gtcctgcagc agtgccacaa ggagaatgag gacaagtgga 4920
aacggctctc tcggcaggtc gcagacatca tcctgcccat gttggccaag cagcagatgc 4980
atattgactc tcatgaagcc cttggagtgt taaatacctt gtttgagatt ttggctcctt 5040
cctccctacg tcctgtggac atgcttttgc ggagtatgtt catcactcca agcacaatgg 5100
catctgtaag cactgtgcag ctgtggatat ctggaatcct cgccattctg agggttctca 5160
tttcccagtc aaccgaggac attgttcttt gtcgtattca ggagctctcc ttctctccac 5220
acttgctctc ctgtccagtg attaacaggt taaggggtgg aggcggtaat gtaacactag 5280
gagaatgcag cgaagggaaa caaaagagtt tgccagaaga tacattctca aggtttcttt 5340
tacagctggt tggtattctt ctagaagaca tcgttacaaa acagctcaaa gtggacatga 5400
gtgaacagca gcatacgttc tactgccaag agctaggcac actgctcatg tgtctgatcc 5460
acatattcaa atctggaatg ttccggagaa tcacagcagc tgccactaga ctcttcacca 5520
gtgatggctg tgaaggcagc ttctatactc tagagagcct gaatgcacgg gtccgatcca 5580
tggtgcccac gcacccagcc ctggtactgc tctggtgtca gatcctactt ctcatcaacc 5640
acactgacca ccggtggtgg gcagaggtgc agcagacacc caagagacac agtctgtcct 5700
gcacgaagtc acttaacccc cagaagtctg gcgaagagga ggattctggc tcggcagctc 5760
agctgggaat gtgcaataga gaaatagtgc gaagaggggc ccttattctc ttctgtgatt 5820
atgtctgtca gaatctccat gactcagaac acttaacatg gctcattgtg aatcacattc 5880
aagatctgat cagcttgtct catgagcctc cagtacaaga ctttattagt gccattcatc 5940
gtaattctgc agctagtggt ctttttatcc aggcaattca gtctcgctgt gaaaatcttt 6000
caacgccaac cactctgaag aaaacacttc agtgcttgga aggcatccat ctcagccagt 6060
ctggtgctgt gctcacacta tatgtggaca ggctcctggg cacccccttc cgtgcgctgg 6120
ctcgcatggt cgacaccctg gcctgtcgcc gggtagaaat gcttttggct gcaaatttac 6180
agagcagcat ggcccagttg ccagaggagg aactaaacag aatccaagaa cacctccaga 6240
acagtgggct tgcacaaaga caccaaaggc tctattcact gctggacaga ttccgactct 6300
ctactgtgca ggactcactt agccccttgc ccccagtcac ttcccaccca ctggatgggg 6360
atgggcacac atctctggaa acagtgagtc cagacaaaga ctggtacctc cagcttgtca 6420
gatcccagtg ttggaccaga tcagattctg cactgctgga aggtgcagag ctggtcaacc 6480
gtatccctgc tgaagatatg aatgacttca tgatgagctc ggagttcaac ctaagccttt 6540
tggctccctg tttaagcctt ggcatgagcg agattgctaa tggccaaaag agtcccctct 6600
ttgaagcagc ccgtggggtg attctgaacc gggtgaccag tgttgttcag cagcttcctg 6660
ctgtccatca agtcttccag cccttcctgc ctatagagcc cacggcctac tggaacaagt 6720
tgaatgatct gcttggtgat accacatcat accagtctct gaccatactt gcccgtgccc 6780
tggcacagta cctggtggtg ctctccaaag tgcctgctca tttgcacctt cctcctgaga 6840
aggaggggga cacggtgaag tttgtggtaa tgacagttga ggccctgtca tggcatttga 6900
tccatgagca gatcccactg agtctggacc tccaagccgg gctagactgc tgctgcctgg 6960
cactacaggt gcctggcctc tggggggtgc tgtcctcccc agagtacgtg actcatgcct 7020
gctccctcat ccattgtgtg cgattcatcc tggaagccat tgcagtacaa cctggagacc 7080

-continued agcttctcgg tcctgaaagc aggtcacata ctccaagagc tgtcagaaag gaggaagtag 7140
actcagatat acaaaacctc agtcatgtca cttcggcctg cgagatggtg gcagacatgg 7200
tggaatccct gcagtcagtg ctggccttgg gccacaagag gaacagcacc ctgccttcat 7260
ttctcacagc tgtgctgaag aacattgtta tcagtctggc ccgactcccc ctagttaaca 7320
gctatactcg tgtgcctcct ctggtatgga aactcgggtg gtcacccaag cctggagggg 7380
attttggcac agtgtttcct gagatccctg tagagttcct ccaggagaag gagatcctca 7440
aggagttcat ctaccgcatc aacaccctag ggtggaccaa tcgtacccag ttcgaagaaa 7500
cttgggccac cctccttggt gtcctggtga ctcagcccct ggtgatggaa caggaagaga 7560
gcccaccaga ggaagacaca gaaagaaccc agatccatgt cctggctgtg caggccatca 7620
cctctctagt gctcagtgca atgaccgtgc ctgtggctgg caatccagct gtaagctgct 7680
tggagcaaca gccccggaac aagccactga aggctctcga taccagattt ggaagaaagc 7740
tgagcatgat cagagggatt gtagaacaag aaatccaaga gatggtttcc cagagagaga 7800
atactgccac tcaccattct caccaggcgt gggatcctgt cccttctctg ttaccagcta 7860
ctacaggtgc tcttatcagc catgacaagc tgctgctgca gatcaaccca gagcgggagc 7920
caggcaacat gagctacaag ctgggccagg tgtccataca ctccgtgtgg ctgggaaata 7980
acatcacacc cctgagagag gaggaatggg atgaggaaga agaggaagaa agtgatgtcc 8040
ctgcaccaac gtcaccacct gtgtctccag tcaattccag aaaacaccgt gccggggttg 8100
atattcactc ctgttcgcag tttctgcttg aattgtacag ccgatggatc ctgccatcca 8160
gtgcagccag aaggaccccc gtcatcctga tcagtgaagt ggttcgatct cttcttgtag 8220
tgtcagactt attcaccgaa cgtacccagt ttgaaatgat gtatctgacg ctgacagaac 8280
tacggagagt gcacccttca gaagatgaga tcctcattca gtacctggtg cctgccacct 8340
gtaaggcagc tgctgtcctt ggaatggaca aaactgtggc agagccagtc agccgcctac 8400
tggagagcac actgaggagc agccacctgc ccagccagat cggagccctg cacggcatcc 8460
tctatgtgtt ggagtgtgac ctcttggatg acactgcaaa gcagctcatt ccagttgtta 8520
gtgactatct gctgtccaac ctcaaaggaa tagcccactg cgtgaacatt cacagccagc 8580
agcatgtgct ggtaatgtgt gccactgctt tctacctgat ggaaaactac cctctggatg 8640
tgggaccaga attttcagca tctgtgatac agatgtgtgg agtaatgctg tctggaagtg 8700
aggagtccac cccctccatc atttaccact gtgccctccg gggtctggag cggctcctgc 8760
tgtctgagca gctatctcgg ctagacacag agtccttggt caagctaagt gtggacagag 8820
tgaatgtaca aagcccacac agggccatgg cagccctagg cctgatgctc acctgcatgt 8880
acacaggaaa ggaaaaagcc agtccaggca gagcttctga ccccagccct gctacacctg 8940
acagcgagtc tgtgattgta gctatggagc gagtgtctgt tctctttgat aggatccgca 9000
agggatttcc ctgtgaagcc agggttgtgg caaggatcct gcctcagttc ctagatgact 9060
tctttccacc tcaagatgtc atgaacaaag tcattggaga gttcctgtcc aatcagcagc 9120
catacccaca gttcatggcc actgtagttt acaaggtttt tcagactctg cacagtgctg 9180
ggcagtcatc catggtccgg gactgggtca tgctgtccct gtccaacttc acacaaagaa 9240
ctccagttgc catggccatg tggagcctct cctgcttcct tgttagcgca tctaccagcc 9300
catgggtttc tgcgatcctt ccacatgtca tcagcaggat gggcaaactg gaacaggtgg 9360
atgtgaacct tttctgcctg gttgccacag acttctacag acaccagata gaggaggaat 9420
tcgaccgcag ggctttccag tctgtgtttg aggtggtggc tgcaccagga agtccatacc 9480
acaggctgct tgcttgtttg caaaatgttc acaaggtcac cacctgctga gtagtgcctg 9540
tgggacaaaa ggctgaaaga aggcagctgc tggggcctga gcctccagga gcctgctcca 9600
agcttctgct ggggctgcct tggccgtgca ggcttccact tgtgtcaagt ggacagccag 9660
gcaatggcag gagtgctttg caatgagggc tatgcaggga acatgcacta tgttggggtt 9720
gagcctgagt cctgggtcct ggcctcgctg cagctggtga cagtgctagg ttgaccaggt 9780
gtttgtcttt ttcctagtgt tcccctggcc atagtcgcca ggttgcagct gccctggtat 9840
gtggatcaga agtcctagct cttgccagat ggttctgagc ccgcctgctc cactgggctg 9900
gagagctccc tcccacattt acccagtagg catacctgcc acaccagtgt ctggacacaa 9960
aatgaatggt gtgtggggct gggaactggg gctgccaggt gtccagcacc attttccttt 10020
ctgtgttttc ttctcaggag ttaaaattta attatatcag taaagagatt aattttaatg 10080
t 10081

<210> SEQ ID NO 4
<211> LENGTH: 168002
<212> TYPE: DNA
<213> ORGANISM: Macaca mulatta
<220> FEATURE:
<221> NAME/KEY: misc_feature
<222> LOCATION: (8794)..(8848)
<223> OTHER INFORMATION: n is a, c, g, or t
<220> FEATURE:
<221> NAME/KEY: misc_feature
<222> LOCATION: (11952)..(12155)
<223> OTHER INFORMATION: n is a, c, g, or t
<220> FEATURE:
<221> NAME/KEY: misc_feature
<222> LOCATION: (13733)..(14137)
<223> OTHER INFORMATION: n is a, c, g, or t
<220> FEATURE:
<221> NAME/KEY: misc_feature
<222> LOCATION: (17299)..(17497)
<223> OTHER INFORMATION: n is a, c, g, or t
<220> FEATURE:
<221> NAME/KEY: misc_feature
<222> LOCATION: (18993)..(19355)
<223> OTHER INFORMATION: n is a, c, g, or t
<220> FEATURE:
<221> NAME/KEY: misc_feature
<222> LOCATION: (30628)..(32144)
<223> OTHER INFORMATION: n is a, c, g, or t
<220> FEATURE:
<221> NAME/KEY: misc_feature
<222> LOCATION: (37234)..(37641)
<223> OTHER INFORMATION: n is a, c, g, or t
<220> FEATURE:
<221> NAME/KEY: misc_feature
<222> LOCATION: (56357)..(56602)
<223> OTHER INFORMATION: n is a, c, g, or t
<220> FEATURE:
<221> NAME/KEY: misc_feature
<222> LOCATION: (66208)..(66275)
<223> OTHER INFORMATION: n is a, c, g, or t
<220> FEATURE:
<221> NAME/KEY: misc_feature
<222> LOCATION: (72472)..(72756)
<223> OTHER INFORMATION: n is a, c, g, or t
<220> FEATURE:
<221> NAME/KEY: misc_feature
<222> LOCATION: (82608)..(83314)
<223> OTHER INFORMATION: n is a, c, g, or t
<220> FEATURE:
<221> NAME/KEY: misc_feature
<222> LOCATION: (108856)..(108875)
<223> OTHER INFORMATION: n is a, c, g, or t
<220> FEATURE:
<221> NAME/KEY: misc_feature
<222> LOCATION: (131686)..(132275)

<223> OTHER INFORMATION: n is a, c, g, or t
<220> FEATURE:
<221> NAME/KEY: misc_feature
<222> LOCATION: (143992)..(145163)
<223> OTHER INFORMATION: n is a, c, g, or t
<220> FEATURE:
<221> NAME/KEY: misc_feature
<222> LOCATION: (147895)..(148388)
<223> OTHER INFORMATION: n is a, c, g, or t

<400> SEQUENCE: 4

```
atacaggcgt gagccaccgc acccagctgg aacttaattt ttttaaagat cgtgttgctc     60
tatcgcccaa gctggagtgc agtggtgcaa ccatagctca cttgcagcca caaattcctg    120
gtttcaggtg atcctcctac atcagcctcc caagaactgg gaactaacgg ctgtttctct    180
gctgtccttc tcaagagaag ggagggagac aatgctgggt ttccctttgg gacaggctct    240
gagacaaggt ggaggtgctg cttgtggcca cagagcaggg gactctgggt tgcaggtgtg    300
gcctggcttg agtaggcttt agtgggcttc tctctgcctg caccaccccc gggctgggtg    360
gttgtctctg aggccaaccc tactccctaa tgggcaggct ggacagctgc cctctctgtt    420
tgcccctcta ccacccaaaa ggcgggaggc tctggagacc aggaccctgc ctgcgccggc    480
ctgtgcccca ggcgtgaggg ggtgccccac agatctctgc tgagctgagg ctgaatggca    540
ccccttgggg gtcctgccag gtcagagcag ggtgctttcc catacagaaa cgcccccagg    600
tcgggactca ttcctgtggg aggcgtcttg tggccacaac tgcttctcgc tgcactaatc    660
acagtgcctc tgtgggcagc gggcgctgac catccgggcc tgcctcagac cctctcctcc    720
cttccggggc gctgcgctgg gaccgatggg gggcgccagg cctgtgggca ccgccctgca    780
ggggccgctc cagctcactg gggggtgggg agggtcacac ttggggtctt cagatggcgc    840
cgaccacgcg caatctctgc gctctgcgca ggggctcgcc caccctctcc ccgtgcagcg    900
agtccccagc aggctccccg cagggctgtc caggtgagcc tggctctggc cgcgggccag    960
tgtggcgggc gggcaagccc cgaggccacc tcggctcaga gcccacggcc ggctctcgcc   1020
cagctccaga cgtctgcgag ggttccattc cgcttgggcc ggcgccccgc gcgccgcgcc   1080
ctggccccgc ccctccctca tcccgccccc tctgcacccc acccctccct ggccccgccc   1140
tccgcgcccc acctctcatc ttcccgcccc gcccccagcc acgcccctca cggtcagccc   1200
cctcccctat ccgccccgcc tctcatcgtc tcgcctcgct ccgcccctca gccgtcccgc   1260
ccctcagccg ccctgcctaa tgtccccgcc cccagcctcg ccccgctccg ccccagcctc   1320
gccccgcccc gcccctcagg cgccctgcct gctgtgcccc gccccagcct cgccacgccc   1380
ctcgttacca tgtagtcccg ccccgtccct tccgcgtccc gcctcgcccc taccccttca   1440
cagcttcgcc ccaccccatt acagtcttgc cacgccccgt cccctgtccg ttgagccctg   1500
ctccttcgcc caggtggggc gctgcgctgt cagaggcttt ggtggctctg tgaggcagaa   1560
catgcgggcg cagggactgg ctggctccct ggccagtcat tggcagagtc cgcaggctag   1620
ggctgtcaat catgctggcc ggcgtggccc cgcctccgcc ggcgcagcgt cttgagacgc   1680
aaggcgccgc gggggctgcc gggacgggtc caagatggac ggccgcttcg gttccgcttt   1740
tacccgcggc ccagagcccc attcattgcc ccggtgctga gcggcgctgc gagtcggccc   1800
gaggcctccg gggactgcct agccgggcgg gagaccgcca tggcgaccct ggaaaagctg   1860
atgaaggcct tcgagtctct caagtccttc cagcagcagc agcagcagca gcagcaacag   1920
ccgccgccgc cgccgccgcc gcctcctcct cctcctcagc ttcctcagcc gccgcaggca   1980
cagccgatgc tgcctcagcc gcagccgccc ccgccgccgc ccccgccacc acccggcccg   2040
```

```
gctgtggctg aggagccgct gcaccgaccg tgagtttggg cccgctgcag ctccctgtcc   2100
cggcgggtcc cagcctacgg cggggatggc ggaatcctgc agcctgcggg ccggcgacac   2160
gaaccccccc ggccccgcag cgacagagtg acccagcaac ccagagccaa tgagggacac   2220
ccgccccctc ctgcggcgag accttccccc acttcagccc cggtcccgca cttgggtctt   2280
gtcctcccgc gaggggaggc agaacctcgt tgggacctgt cctgaattca cggaggggag   2340
tcacggcctc agccctctcg ccctttccag ggtgcgaaga gttggggcga aaacttgttt   2400
ctttttattt gcgagaaact agggcggggg tttaactgtg ttctgaagag aacttggaag   2460
agccgagatt tgctcagggc cacttccctc atctagtcag agagggaaga gggctggggg   2520
cgcgggacac ctcgagagga ggcggggttt ggagctagag agatgtgggg gcagtggatg   2580
acataatgct tttaggacgc ctcggcggga gtggctggag tggggggcgg ggagtgaggg   2640
cgcgtccaat gggagattta ttttccaagt ggcatttaaa acagcctgag atttgaggct   2700
cttcctacat tctcagggca tttcatttag ttcatgatcg cggtggtagt aacacgattt   2760
taagcaccac ctaagagacc tgctcatcta agcgcaagtt agtgtgcagg catttgaatg   2820
agttgtggtc gccaaataag tggtgaactt acgtggtatt aataaaatta tcttaaatat   2880
taggaagagt tgattgaagt ttattgcctg tttgtgttgg gaataaaact aacacgttgc   2940
tgagggggag gttaattgcc gagggatgaa tgaggtatac attttaccag tattgcagtc   3000
aggcttgcca gaatatggga ggtctgcaga ctccgtggac atctcatgtg ccagtgaaag   3060
ggtttctgtt cgcctcattg ctgacagctt gttacttttt ggaagctaga ggtctctgtt   3120
gcttgttctt ggggagaatt tttgaaacag aaaaagagac cattaaaaca tctagcggaa   3180
ccccaggacg tgggagtgtg tgctgagtgt ttagcaggat ttaggaagta ctccgctgca   3240
gttcaggcct ttctcttacc tctcagtgtt ctatttccga tctggacgtg tatcagatgg   3300
catttgataa gaatatctct attaagactg attaattttt agtaatattt cttgttcttt   3360
gtttctgtta tgatccttgc cttgtcttga aagtttaatt agaagaggag gatttggaga   3420
gcagtgttag cttatttgtt agagtaaaat ttaggaataa attcttctaa aggatggaaa   3480
aactttttgg atatttagag aaatttttaa acaatttggc ttatctcttc agtaagtaat   3540
ttctcatcct tccagaaatt taatgtagtg cctttctagg aggtaggtgt catagaagtt   3600
cacacattgc atgtatcttg tgtaaacact aaactgggct cctgatggga aggaagacct   3660
ttctgctggg ctgcttcaga cacttgatca ttctgaaaat atgccgtctc tttcctgtgc   3720
tgatttgata gaacctgcgt ttgcttatct tcaaaatatg ggtatcaaga aatttccttt   3780
gctgccttta caaaggagat agattttgtt tcattacttt attttaaggt aatatatgat   3840
taccttattt taaaaattta atcaggcctg gcaaggtggc tcatgccttt aatccgagca   3900
ctttgggagg cttaggcgga tgaatcacct gaggtcagga gttcgagacc agtctggcta   3960
acatggtgaa accccatctc tactaaaagt acaaaaatta gttggtcatg gtggcacgtg   4020
cctgtaatgc cagctacctg ggaggctgag gcaggaaaat cgctggaacc cgggaggcag   4080
aggctgcagt gagctgagac tgcgccactg cactccagcc tgggtgacag agcgagactc   4140
ttgtctcaaa aaaaaaaaaa ttattatttt tgcataagta atacattaac atgacacaaa   4200
ttccgtaatt acaaaagagc aatacttaaa atatcttcct tccacccctt tcatctgagt   4260
acctaacttt gtccccaaga acaagcacta ttacagttcc tcctgtatcc tgccagatat   4320
aatctatgca tattgtaaga tagatttaaa atgctgtaaa aataaaagta gtttacagta   4380
```

-continued

```
ataattttttt ttctttattt tttttgagat gtagtctcac attgtcaccc aggctggagt   4440
gcggtggtat gatcttggct cactgcaacc tccacctccc aggttcaaac gattctcctg   4500
cctcagcctc cagagtagct gggattacag gtgctcacca ccatgtccag ctgatttttg   4560
tatttttagt agagatgggg tttcaccatg ttggccaggc tggtcttgaa ctcctgacct   4620
cggaatccat ccacctcggc ctcccaaagt gctggggtta caggtgtgag ccactgcccc   4680
tggctagaat aataactttt aaaggttctt agcattctct gaaatcaact gcattaggtt   4740
tatttatagt tattttaaat aaaatgcata tttgtcatat ttgtatgtat tttgctgttg   4800
agaaaggagg tattcgctaa ttttgagtaa caaacactgc tcacaaagtt tggattttgg   4860
catttctgtt catgtgcttc agccaaaaaa tcctcttctc aaagtaagat tgactaaagc   4920
aatttagaaa gtatctgttt ttatggctct tgctcttttg tgtggaactg tggtgtcatg   4980
ccatgcatgg gcctcagtct aagtatgagc gtatgtgctc tgctcagcat acaggatgtg   5040
ggagttccgt gtggggctgg ccacagtctc agcaaatcta gcatgcttgg gagggtcctc   5100
acagtaatta ggaggcaact gatacttgct tctggcaatt ccttattctc cttcagattc   5160
ctatccggtg tttccctgac tttattcatt catcagtaaa tatttactaa acatgtacta   5220
tgtacctagc actgttctag atgcagggct cagcagtgag cagacaaagc tgtgccctca   5280
tgaagctttc attctaatga aggacataga caataagcaa gatagataag taaaatatac   5340
agtatgttaa taagtggagg aatgtcaaag cagggaaggg gatagggaaa tgtcagggtt   5400
aatcaattgt taacttattt ttattaaaaa aaaatttttt taagggcttt ccagcaaaac   5460
ccagaaagcc tgctggacaa cttccaaaaa aactgtagca ctaagtgttg acatttttat   5520
tttattttat tttattttgt tttgttttgt tttttgaggc agtcttgctt tgtcagccag   5580
gctgcagtgc actggtgtga tcttagctca ctgcaacctc tgcctgttgg gttcaagcga   5640
ttcttatgcc tcagcctcct gattagctgg gattatagac atgcaccgtc ccgcctgggt   5700
aatttttttt ttttcccccct gagacagagt cttgctctgt cgcccaggct ggagtgcagt   5760
ggcacaatct tggctcactg caagctccgc ctcccaggtt catgccattc tcctgcctca   5820
gcctcccagg tagctgggac tacaggcgcc tgccaccacg cccagctaat tttttgtatt   5880
tttagtagag atggggtttc actgtgtcag ccaggatggt cttgatctcc tcacctcgta   5940
gtccgccccc cttggcctcc caaagtgctg ggattacagg cgtgagccac cgcgcccggc   6000
ctgtaatttt tttttttttt ttttgagaca gagtcttgct ttgttgctag gctggactgc   6060
agtggtgtga tcttggcaca ctgcaacctc tgcctcccgg gttcaagcga ttctcctgcc   6120
tcagcttccc gagtagctgg gactacaggc acgtgccatc acgcttggct actttttgta   6180
tatttagtag aaacggggtt tcaccatgtt agctgagatg atctcgatct cttgacctcg   6240
tgatccgccc gcctcggcct cccagagtgc tgggattaca ggtgtgagcc actgtgcctg   6300
accacgcctg ggtaattttt gtatttttag tagagacggg atttcaccac gatggccaga   6360
ctggtctcga actcccagcc tcatgtgatc tgcctgccta ggcctcccaa agtgctagga   6420
ttacaggcat gagccaccat gactggccag tgttgatatt ttaaataggg tgttcaggga   6480
aggtccactg aggtgacagc tgttttttttg gggggagtgg tgggacaggg ccttgctctt   6540
taacccaggc tggaatacag catcacaatc gtagcttact gcagccttga actcctaggc   6600
tcaagtgatc ttcccacctt gacctcacaa cgtgttggga ctgtaggtgt gagtcaccat   6660
gcctggccag atgatggctt tgagtaaaga cctcaggcga gttaagagtc tagcgtaaag   6720
gtgtatggag taggggtatt ccagataggg ggaacaggtc caaagtcttc ctgtttgagg   6780
```

-continued

```
aatagcaagg gtgccatttt agttgggtga attgagtgag ggcgacattt gtagtaagag   6840
gtaaagtcca agaggtcaag ggagtgccat atcagaccaa tactacttgc cttgtagatg   6900
gaataaagat attggcattt atgtgagtga gatgggatgt cactggagga ttagaggaga   6960
ggagtagcat gatctgaatt tcattcttaa gtgaactctg gctgacaaca gagtgaaggg   7020
gaacatggac aaaagcagaa accagttagg aagccactgc agtgctcaga taagcgtggt   7080
gggttctgtc agggtaccgg ctgtgggcag tgtgaggaat gactggattt tgaatgcaga   7140
agcaactgta cttgttgaac tctgctaagt ataactattt agcagtagct ggcattatca   7200
gttaggtttg tattcagctg caagtaacag aaaattctgc tgcaatagct taaactggta   7260
acaagaaaga gcttatcaga agacaaaaat aagtctgttt ggggaaattc aacaataagt   7320
taaggaaccc aggctctttc tttttttttt tgaaatggag ttttgctctt gtcacccagg   7380
ccggagtgca atgatgcgat cttggctcac tataacctcc gcctcctagg ttccagtgat   7440
tcttctgcct cagccttcca ggtatctggg attagaggcg cacgcacacc accatgccca   7500
gctaattttt gtatttttag taggcacggg gtttcatcat gttggccagg ctggtctcga   7560
actcctgacc ttaggtgatc aacccgcctc agcctgccaa agtgctgaga ttacaggtgt   7620
gagccactgc actcggtcag aacccaggct ctttttttaca cttagcttgc aaacccttgt   7680
tctcattctt ttccctttgt atttttattg tcgaattgta acagttcttt gtgtattctg   7740
gatactggat tcttatcaga tagatgattt gtgaaaacat tctctcttcc tttggattgt   7800
ctttttactt tcttgatcat gtcttttgaa gtgtgaaagt ttttaatttt gatgaagtct   7860
agtttatcta gtttgtcctt ggttgctatg ctttgagtgt catatctaag aaatcattgt   7920
ctaatccaaa gtcaaaaagg tttacccgta tgttttcttc taagaatttt agagttttac   7980
atttaggtct gatccatttt gagttaattt ttatatgtgg ttcaggtaga agtccaactt   8040
cattcttttg catgtggtta ttcagttgtc ccagcacagt ttgttgaaga gactgtactt   8100
tccccatgga attgtcttag catccttgtt gaaaattcat tgtccttgat tgtatagatt   8160
tatttcttga ctctcagttc tacctattgg tctttatgtt gatcctgtgc cagtaccata   8220
cagtcttgat tactgaagtt tgtgtcacaa tttaaattca tgaaatgtga gttctccaac   8280
tttgttcttt ctcaagattg atttggccat gctgggtccc ttgcatttcc atatggattg   8340
taggatcaac ttgtcagttt ctacaaagaa gccaaggagg attctgagag ggattgtgtt   8400
gaatctgtag atcaacttgg ggagtattac catcttaaca gtattgtctt ccatctctga   8460
actgggcaaa ctttgtgtaa atggtcagat ttaggtattt caggctgtgt gggcacaatg   8520
tctctgtcac agctactcag ctctgccatt gtagcgtgaa atagccataa gcaatatgta   8580
tgagtgtctg tgttccagta taattttatt aatgacaagg aaatttgaat ttcgtgtaat   8640
tttcacctgt catgaaatat tatttggttt ttttggtcaa tcatttaaaa atgtaaaaac   8700
ttttcttagc ttttgaactg gccaaacata tgcaggttat aattttccca ctcctagatt   8760
aaaatatgat aggaccacct ttgaaaagca tgtnnnnnnn nnnnnnnnnn nnnnnnnnnn   8820
nnnnnnnnnn nnnnnnnnnn nnnnnnnnaa cactttggga ggccgagcca ggtggatcac   8880
ttgaggccag gagttcgaga ccagcctaac caacatggtg aaaccccatc tctactaaaa   8940
ataaaaaaat tagctggggg tggtggtggg tgtagggtcc agccctatgg ggcttagcgg   9000
gtgttctccc cgtgcgggga gacgagagat cttaagaaat aaagacacgg ccgggcgcgg   9060
tggctcacgc ctgtaatccc agcactttgg gaggccgagg cgggcggatc acaaggtcag   9120
```

-continued

```
gagatcgaga ccacggtgaa accccgtctt tactaaaaat acaaaaaatt agcggggcgc   9180
ggttgtgggc gcctgtagtc ccagctactc gggaggctga ggcaggagaa tggcgtgaac   9240
ccgggaggag gagcttgcag tgagccgaga tcgcgccact gcactccaga cggggcgaca   9300
gagcgagact cctgtctcaa aaaaaaaaaa aaaaaaaaaa agaaaagcat gttttttttt   9360
ttttgagatg gagtttcgct tttgttgccc aggctggagt gcagtggcgc gatctcgggt   9420
caccacaacc tctgcctccc aggttcaagc gattctcctg cctcagcctc ccttgtagct   9480
gggattacag gcatgtgcca ccatgcccgg ctaattttgt atttttagta gagacggggt   9540
ttctccaggt tggtcaggct ggtctcgaac tcctgacctc aggtgatctg cctgcctcgg   9600
cctcccgaag tgctgggatt acaggcgtga gccactctgc ccagccagaa agcatttctt   9660
ttttggctgt ttttttgttg tttttttttaa ttaactagtt ttgaaaatta tagaagttac   9720
acatatatgt tataaaaaca tctccaagca gcacagaaga tgaaaaacaa agcccttctt   9780
gcaagtctgt catctttgtc taacttccta agaacaaaag tatttcttgt gtcttcttcc   9840
cagattttaa tatgcatata caagcattta aatatgtcat tttttgttgg cttgactgag   9900
atcacattac atacgtattt ttttacttaa caatttgagt acaatgtgtc atggaaattg   9960
ttccatagca gtatctgtaa ttcttattaa ttgctgtgta atattgtaga atttcttttt  10020
aaaagaggac ttttggagat gtaaaggcaa aggtctccca ttattctggc tgtacaacgt  10080
tctggtgaca tattctctct accctgagag gtccccatac ccatcacctc catttcctgt  10140
aaataagtca accacttggt aaactacctt tgaatggatc cacactcaaa acatttagtc  10200
ttattcagac aacaaggagg aaaaataaaa taccttataa agcactgttt catatgtatt  10260
aaattggatc aatttgcgtg ctagaatgta tgttagagac atgatatgcc cataggtcct  10320
tgctatcacg gtgaggtctc agggacagca gtttggtatc atttggtatc tcataagcag  10380
actctgtctg cctgacttaa caaatcagag tctgcgtttt aacaggttca gtgagtgact  10440
tacatgcaca ttggagtttg ggaagctcca ctataggtgc ttagacctta cctttgttgt  10500
tgctaataac aatgcaagca tttgggagga agacctgtgt tgctcgtatg tgtccaggtg  10560
tagctgaggt ggccttgctt gtctgctgta gggccattga gcatttgcgt agctgtgatg  10620
aatgagctga ggtgagcctg cggagagctc ccagccattg gtagtgggac ttgcttagat  10680
gaactagaag gacctgagca tccactttgg ggaaaaacaa ccgaatgaag ggagaggcaa  10740
catgcagttt tatttagggt acgaaggaga gctgtggtta gaaggtgaca tttgagtgga  10800
aagggggcaa cccatgtgtg gagcgggaga agagcggtcc aggcagagtt aacagaaggc  10860
agaaatgctt tccatctttg aaaactagga aggatgccag tggctgaagt aagatgaagg  10920
acagaaatag gggatgaggc ttcgagagat gagaggttag agacgagggt cttgtgcacc  10980
aagataagct tgtgtggtca aaacaagtag tttcgttttt gtttttaaaa gatcactttg  11040
gctgggtgca atggttcatg cctgtaatac cagtactttg agaggctgtg gtgggaggat  11100
tgcctgaagc caggggacca gcgtagccaa catagcagca cctataaggt ctctacaaaa  11160
aacttttaaa aagtagctgg gtgtagtggt gtgtgcctgt agtcccagcc acccaggagg  11220
ctgaggaggc tggagggttg cttgagtcca gcagtttgag gctgcagcga gcaatgattg  11280
tgccactgca ctacagcctg ggcatgagag tgagaccctg tctctaaata tatgtgtata  11340
tataaaagaa aagatcactt tgacaacacc acatgctggt gaggatttag aaaaactagg  11400
tcacttattg ctggtgggaa tataatatag tacggccact ctggaaaaca gtttggcagt  11460
ttctcataaa actgaatgta caattagtat acaacccagc aactcctgca atcctgcgca  11520
```

```
ttaatcctag agaaatgaag ccttcatgtt cacataaaaa cctatactca agcgtgcata  11580
gcagctttac ccataatatc taagaactgg aatcagctca gatgtccttc tgcaggtgaa  11640
tggttaaact actcagtaat aaaaaggaat gatctactga tagcatgcaa cagtgtaggt  11700
gaagttatgc taatgaaaaa agccaatccc aaaaggttac atattatatg attctatgta  11760
tataacgttt tggcagtgac acagttttag ggatggagaa tagattagtg gttgcctggg  11820
gttagagatg gggttgtaga gtaggttagg ggtggcagag gagagaaaag agagggaggc  11880
gagtgtggtt ataaaaggac aacacagggg gatacttgta acagaaatgc tttgtctttt  11940
tttttttttt tnnnnnnnnn nnnnnnnnnn nnnnnnnnnn nnnnnnnnnn nnnnnnnnnn  12000
nnnnnnnnnn nnnnnnnnnn nnnnnnnnnn nnnnnnnnnn nnnnnnnnnn nnnnnnnnnn  12060
nnnnnnnnnn nnnnnnnnnn nnnnnnnnnn nnnnnnnnnn nnnnnnnnnn nnnnnnnnnn  12120
nnnnnnnnnn nnnnnnnnnn nnnnnnnnnn nnnnngctca ctgcagcctc tgcctctggg  12180
gttcaagcga ttcttctgcc tcagcctcct gagtagctgg gactacaggt gcacgccacc  12240
atgcccggct aatttttgta tttttagtag agacagggtt tcatcatgtt ggccaggctg  12300
gtcttgatct cctcacctca tgatccgccc acctcgccca cctcggcctc ccagagtgct  12360
gggattacag gcttgagcca ccgcgtccgg cctattttat tttttttgag acagagtctc  12420
actctgtatc ccagactgga gtacagtggc gcgatcttgg ctcactgcag cctctgcctc  12480
tggggttcaa gcgattctcc tgcctcagcc tcctgagtag ctgggactac aggtgcacgc  12540
caccatgccc ggctaatttt tgtattttta gtagagacgg ggtttcacca tgttggccag  12600
ggtggtcttg atctcctcac ctcatgatcc gcccacctcg gcctcccaaa gtgctgggat  12660
tacagggatt tttgtgtttt tcgtagagac agggtttcat tatgatggcc aggttggttt  12720
tgaactcctg acctcctgtg atctgctggc ctcgcctccc aaagtgttgg gattatagac  12780
gttgagccac tgcactcggc caaggaaaga gatgctttgt cttgagtgtg gtggtgtata  12840
gaaattgtat agaactaagg ctgggcacgg tggctcactc ctgtaatccc agcattttgg  12900
gagaacgagg tgggcagatc gtgagttcag gagattgaga ccatcctggc taacatggtg  12960
aaaccctgtc cctgctaaaa ataccaaaaa ttggccgggc gtggtggctc acgcctataa  13020
tcccagcact ttgggaggct gaggcgggtg gatcacgagg tcaggagatc gagaccatcc  13080
tggctaacac agtgaaaccc tgtctctact aaaaatacaa aagcaaaatt agccgggcgt  13140
ggtggcgggc gcctgtagtc ccagctactt gggaggctga gacaggagaa tggcgtgaac  13200
ctgggaggtg gaggttgcag tgagctgaga tcgcgccact gcactccagc ctgggcaaca  13260
gagtgagact ctgtctcaaa aaaaaaaaaa aaaaagaaat tgtatagaac taaatacaca  13320
aatgaacaac aataaaactt gaaactctaa gtaagatcac tggattgtat cagtgtcaat  13380
attctggttg tgataatgta gtatattaaa tagttttgca aagtgttacc attggggaaa  13440
actggataaa gggcacactg gatctctgtt atttcttaca actgcacgtg aaccaataat  13500
tatcttaaaa aaacttcaat tcaaaaaagt ctgccctgat ccagttggga ggctactgaa  13560
gtaatcaaag ctagacatgc tggtgtcttg tgactggtag cagtggtgat ggtaagtggt  13620
cagattctgg atctcttgga gaaagatctg acaagatttg cagattcttt aaaaaaaatg  13680
agattaggct gggcacggtg gctcacgctt gggaggctga ggagggcgga tcnnnnnnnn  13740
nnnnnnnnnn nnnnnnnnnn nnnnnnnnnn nnnnnnnnnn nnnnnnnnnn nnnnnnnnnn  13800
nnnnnnnnnn nnnnnnnnnn nnnnnnnnnn nnnnnnnnnn nnnnnnnnnn nnnnnnnnnn  13860
```

-continued

```
nnnnnnnnnn nnnnnnnnnn nnnnnnnnnn nnnnnnnnnn nnnnnnnnnn nnnnnnnnnn  13920
nnnnnnnnnn nnnnnnnnnn nnnnnnnnnn nnnnnnnnnn nnnnnnnnnn nnnnnnnnnn  13980
nnnnnnnnnn nnnnnnnnnn nnnnnnnnnn nnnnnnnnnn nnnnnnnnnn nnnnnnnnnn  14040
nnnnnnnnnn nnnnnnnnnn nnnnnnnnnn nnnnnnnnnn nnnnnnnnnn nnnnnnnnnn  14100
nnnnnnnnnn nnnnnnnnnn nnnnnnnnnn nnnnnnnttg ataatttata aaatgtgatt  14160
atagaatgct gtagtgtcct tgagtttaca tgcccttcct tacacttgtg tgcctgtgca  14220
gatgccttga tttcacaatt agaggaggct gactgagatt tgtttaattt tttttttttt  14280
tgaggcagag tcttgttatg tcccccaggc tagagtacag tagcgcaatc ttggtgcact  14340
gcaacatccg cctcctgggt tcaagcaatt cttctgcctc agcctcccga gtgcctggga  14400
taacaggtgc cagcccccac gcccagctat tttttgtatt tttagtagag acgggatttc  14460
accatgttga ctgggctggt ctcaaactcc tgacctcaga tatctgccgc cccagcctcc  14520
caaagtgctg ggattacagg cgtagccaca cctggccgtt tgttttaatt tttaaggtga  14580
cgttaaagtg actgcattta ccaaaagtgg ttgagaagcc aggactgttc ttatcctgtt  14640
tttccagttc ttgctcagag caaggtggtt tatttttcac ttaattacca tacttacttt  14700
tcatgtagaa caagtcagtt tgagttatca gttcatcatc taactaaatt ccatggggga  14760
aggaatagtt ttagtttctt aaacttccaa ggttgcttat tggacaaaat gagatagcaa  14820
ggcggtgttt ttaagttaga ttttttattt ctttggtaat ataattttct caaaaactta  14880
gtagtctttt agtttagttg tttttagttg gtcctatgtt ttgcatcccc cctctctact  14940
tttattttga tagtgccaat tgcgaagaca tctgaagcca taggtttggg tgggaaggcg  15000
gcacctttag cctgattatc tttgccaggc tgtttatctc cttttgcttg gctgagaagt  15060
cttaatagga ggcttattcc cagctacttg gggacataga agcggttagc tattgttcat  15120
gttttactga ggtctgtgtg gtatgttgac tgcagtcagt tactggtttt gagaattgaa  15180
ggcagcctgg tatatagagt aggtattata ttgtgtttct ttgaattgaa tttcctatct  15240
cttgtaatct ttgccatcat cttctgtgaa agaaaaaaag tttctatcaa actataccat  15300
tggttgtaag atgcagttcg gctttagtga tgctaacaca tgatccaaac gtgaaactga  15360
gtattggtga aatacagagg agatttaaag ccagaagacc tgggtttaaa tgctggctct  15420
atgacttcaa atctgtgtgt tcttgggcac gtcatggttg gcacttcaat ttcttctctc  15480
tgtaatgggg gaaatgaggc cagtcatggt ggctcatacc tatgatccca gcactttggg  15540
ggccaagatg ggaagatcgc ttgaggccag gaggttgagc aattgggcaa catagtgagg  15600
ccccgtctct acaaaacatt taaaaaaaat tagccaggcc cagtggtgca tgcctgtggt  15660
ccccaccact caggaggctg agatgggagg atcctttcag cccaggagtt taaggctaaa  15720
gtgagccatg attgtgctac tgtactctag cctgggcagt agagcaagat cctgactcta  15780
aaaaaaagta aaatgaaata aaatggggga aatgaactgc tttagtaaca tcatctgttt  15840
tttctgtgag cagtgtagct tgaaagccat tggtgaactc atgcactgtg cttccctgtc  15900
cagatcccca ttctgccccc agcatggagt ataacagttt attagtagta gtcgagaaac  15960
cctcattgaa tgaatgaatg agatgtagaa gtaagtggag tgggtaattg aacacatatt  16020
catttccttt tcttttttct tatttttaga aagaaagaac tttcagctac caagaaagac  16080
cgtgtgaatc attgtctgac aatatgtgaa aacatagtgg cacagtctgt caggtaattg  16140
cactttgaac tgtctagaga aaataagaac tttgtatatt ttcagtctta atgggctaga  16200
atattctgtg tcccagttat tttaaatgga ttcaaaaatc cttgaagaag gacccttttc  16260
```

```
ccatatttct ggctatatac aaggatatcc agacactaaa atgaataatg ttccctttc  16320
gtaatctttt atgcaaaaat taaaaccatt atggtaattg aacaacatgt ttatgtttag  16380
ttaacaccct tagcaactat agttatttta aaatcctgtg tggtttgata tttttgcgtt  16440
tattgtaaca gtgggaacag cacaaggcgg tccactttgt ctctctcatt ttgcagtttg  16500
ctgtcctgtt gtgctggtgc tcctagcagt ggctggagcc cacttctctg tgctttggga  16560
ttagtggggt catggggcat tgactggagg tcagctttcc ttgcttgatc tttctcactg  16620
gggtgaacta gcagcacctt cttttgtagc tgctttgctt ttggctatct ttctgaccgt  16680
tgttcctagc agctgtagat ggtaaatatg tttaggcctg tttccaatgg ctgagtagga  16740
gacatatgca cctatgatat ctgaattctg ttacccagat gggcgtgtgt gaaatagtta  16800
ccttgcttta ctttcccttg gaataaataa ttcatgttat tctcctggta gaagctagaa  16860
aaagctcttt atagtcagtc agaaaaaaat ttttagacaa ataatcttga ttttagtact  16920
gacaaaaatg tgtggtgatt cttttttta gtttttttg agatggagtt tcactcttgt  16980
tgcccaggct ggagtgcaat ggtgcgatct cggctcactg caacctccgc ctcctgggtt  17040
caagcgattc tcctgcctta gtctcctgag tagctggggt tacaggcatg tgccaccacg  17100
cccagctaat tttgtatttt tagtagagac agggtttctc catgttggtc aggctgatct  17160
caaactccca acctcaggtg atccgcccgc ctcagcctct caaagtgctg ggattacagg  17220
cgtgagccat ggcacctggt gattcatttg tttttttaaa aatttcctct tggccattgc  17280
ttttcactgt tttcttttnn nnnnnnnnnn nnnnnnnnnn nnnnnnnnnn nnnnnnnnnn  17340
nnnnnnnnnn nnnnnnnnnn nnnnnnnnnn nnnnnnnnnn nnnnnnnnnn nnnnnnnnnn  17400
nnnnnnnnnn nnnnnnnnnn nnnnnnnnnn nnnnnnnnnn nnnnnnnnnn nnnnnnnnnn  17460
nnnnnnnnnn nnnnnnnnnn nnnnnnnnnn nnnnnnntgt agaaatattg tgggaagaaa  17520
atgaaataac aaatgagcat gtgtcctgaa aataaaaata taaaaattct aagttagcat  17580
gctattgtag aatacaacac tatgataaaa gtagggaaaa aaaagtttga attccacgtc  17640
tgctgcctgt gtaagctggg tgactttaga taagctttaa cgtgtttgag ccttactggc  17700
tcatgtttga agtgtaatcc ctcgttacac agttcttgtg ggatcagacg atgcatgtga  17760
aacactgtga agaagtaact gcgatagatg tgttcattag ccgcctgaac gggaagcaca  17820
tcccattgcg atgcccatca tccaaagcta tatgttatct ttactttttt tgtttttttg  17880
agacagagtc tcactctgtc gcccagactg gagtgcagtg gcgccatctc ggctcactgc  17940
agtttctgcc tcctgggttc acgccattct cctgcctcag cctcccaagt agctgggact  18000
acaggtgccc gccaccacac ctggccaaat ttttgtattt ttagtagaga cagggtttca  18060
ctgtgttagc caggatggtc tcgatctcct gacctcgtga tccgcccacc tcagcctctc  18120
aaagtgctgg gattacaggc gtgagacact gtgcccagcc atcttcactt ttcttgtgaa  18180
atgatgactc taaatgtttg gcaaacattt ggtgattgtt catctgattt ccactatcca  18240
ggtctcagag aatataattt atctctgaaa gcttattgac ccaggaaaca agatctcttc  18300
caatctgagt acatcaggct ttattcttgt cattttgtct tttgagaatt ttcaaatgga  18360
attcatggaa tgttggctca tattcacata ttagtaaagt acgctgagac atcttaagat  18420
tgatttgtgg ttctatttgc catattaaat caaaataata actgttaatg gttttctttt  18480
ttttttttt tttttttgag acggagtctt gctctgtcgc ccaggccgga gtgcagtggc  18540
ccgatctcag ctcactgcaa gctccgcctc ccgggtttat gccattctcc tccctcagcc  18600
```

-continued

```
tcccgagtag ctgggactac aggcgcccgc tacctcgccc agctagtttt tttgtatttt  18660
ttttagtaga gacggggttt cgcccgtgtt agccaggatg gtctcgatct cctgagctcg  18720
tgatccgccc gtctcggcct cccaaagtgc tgggattgag ccaccgcgcc cggcctgtta  18780
atggttttca cattagtctg tctcttgttt ttatggagta atgctgagag ttcattatgc  18840
ttcttgttct acagaagagc atgttaaaag gatttttgg gatcagagag gttatccatg  18900
gtttcatagg atactctgta ctttgcaggg atttcagggt atatagccaa aggtgatatt  18960
ttatataaat atgttttatg gaaacttact gannnnnnnn nnnnnnnnnn nnnnnnnnnn  19020
nnnnnnnnnn nnnnnnnnnn nnnnnnnnnn nnnnnnnnnn nnnnnnnnnn nnnnnnnnnn  19080
nnnnnnnnnn nnnnnnnnnn nnnnnnnnnn nnnnnnnnnn nnnnnnnnnn nnnnnnnnnn  19140
nnnnnnnnnn nnnnnnnnnn nnnnnnnnnn nnnnnnnnnn nnnnnnnnnn nnnnnnnnnn  19200
nnnnnnnnnn nnnnnnnnnn nnnnnnnnnn nnnnnnnnnn nnnnnnnnnn nnnnnnnnnn  19260
nnnnnnnnnn nnnnnnnnnn nnnnnnnnnn nnnnnnnnnn nnnnnnnnnn nnnnnnnnnn  19320
nnnnnnnnnn nnnnnnnnnn nnnnnnnnnn nnnnncctgt agtcccagct actcagaagg  19380
ctgaggcagg agaatagcgt gaacccggga ggcagagctt gcagtgagcc gagatcgccc  19440
cactgcactc cagcctaggt gacagagtga gactctgtct caaaaaaaaa aaaaaacaaa  19500
aaaacaaaaa aaccaaaacc ttatgtatat tgtgaaaatg tagtctgctt taagctctct  19560
aaagaggtct aagttactgg ttcctaagta tggatgagca tcaaaatcat ctggaaaatt  19620
tgttaaaaat acaataatga aggtacctca ctgtcctttt tcccaaacac acttctgcat  19680
tctgtttgag taggtagggc ctacacattt ttcacaagta ttctcttggg aatacccagg  19740
aatgctcact tgagcaacct cttactaata ccatatactt tgataaagtg gctaggtaaa  19800
aataaatata taaaaatcca tcaatctccc atatattagc ataaatcagc tagaaaacag  19860
taatgtttaa agatctagtt cacagtagca ctgaagtatt gaattccaag aaattgataa  19920
gaaatatgca gaaactttat aaaaacttct gttaatgttt ctgaaagata taggtgacca  19980
ctttctagac aggaagattt tatatcatta agttgacttt tctctaaatt aacacagaaa  20040
tttaaaataa tcttgattaa aattctagta gaggtatttt tgaacttgtt cactgtaaga  20100
ataaatacat aactgcaaag aatatcttaa aatcatcact aggcccggtg tggtggccca  20160
cgcctgtaat cccagcactt ttggaggcca aggcaagcgg atcacctgag gtcaggagtt  20220
tgagcccagc ctgaccaatg tggtgaaacc ctgtctctac taaaaataca aaaattagct  20280
gggtgtggtg gtgcatgcct gtagtcccag ctacttggga ggctgaggca ggagaatcgc  20340
ttgaatccag gaggtggagg ttgtggtaag cctagatggc accactgcac cactgcctgg  20400
gtgacgagca aaattgtgtc tcaaaaaaaa aaaaaaaaaa gaaaaaaaga aaaagaaatc  20460
aacgctaata tggtgagact tgatatatgt gacattaaaa tagtgattgg acattagaac  20520
aggtatagaa cagaaagaag agtgtgtgta tctgtgtgga tttatgatgg gtgtagcata  20580
ttgtattagt agggaaatga gggaaatgat atatttcttt gactttggga caacattata  20640
tctctacctc atattgcaaa caagcataaa attctgatta attacctaaa tgtgaaaaaa  20700
tgaaatactt tcttcaaaaa atgtaatctt agtttgagga agactaacat tatgaaggaa  20760
aaacctgttt tgactggaat atagttcaat atgtcaaaat ccaccttcaa caaaattgaa  20820
agtaaattga acttggggaa agtattgata gcatgtagat caaaggttac tagcctgtgt  20880
aaagagcaat tataaatcat taagaaaaga ctgtcaaccc gtcggcacct tgttctccga  20940
ctcccagcct ccagaactgt gacgagtaag tgcctgttgt ttaaaacacc tagtctatat  21000
```

-continued

```
gtactatttt gttatagcaa ctcaagctga ttaggaccct agtaatcagt agactgagac  21060
taaaacaaaa ataagaacct tttttacctg tcaagttggc aaacattaag aatatgcaga  21120
tttttgtcag aggtgataca acctttaaga aggcaatttg ggaaaacata aagctttaga  21180
ttattaatgt gtctgatcta gggcacttac cctaggaaag tgtgtaatga tattggtgca  21240
ctgctgttca tcccattaga aaataaaaat aaccttaata gcttaccact aaaaggggga  21300
ttgaaaaatt aagatacatt tatttattta tttattgaga cagagtcttg cactgttgcc  21360
tgggccggaa tgcaatggtg cgatctcagc tcactgctac ctccgcctcc tgggttcaca  21420
tgattctcct gcctcagcct cccgagtagc tgggaataca ggctcacacc tccacaccca  21480
gctaattttt tgtattttta gtagagatgg ggtttcactg tgttgaccag actggtctcg  21540
aactcctgac cttgtgatcc atccccctcg gcctcccaaa gtgtcaggat tagaggcgtg  21600
agccattgta cctggccaga tacatttata caagagagtg ttagttaaca ttcatagatt  21660
tttttttct tgtttacttt ttattaaaaa aattttttt tagagacagg gtcttactct  21720
gtcacccagg ctgaatgcag ttgcacaatc gtagcccact gcagcctgaa ctcctgggcg  21780
gaagtgatcc ttctgcctca gccttttgag tacctggggg actttaggca gtgctgctat  21840
atatacctgg ctaagtttta aatgttttat agatgggatc ttgctatgtt gcccaggctg  21900
gtctagaatt cctgggccca agcaatcctc ccaccttggc ctcccaaagc actgagatta  21960
caggcattga gccaccactt ctgatcaata gatatttata tttgtgactg gaaaatatat  22020
taacaatgtg ttaaaaaatt cagttaaaaa ataatgaaag atttttgctt ctagctaaga  22080
tagaataaca aggacagcat ttatcttctt gccttgaaat agttgaaaat ggataaaata  22140
tatgtaacag tggttttcaa gttattgggc attaggcaaa gaagagtagt tatcacagga  22200
aaattaatgt ggagagccct acaatttcct tacattgctg cctggccatg gcaagaggaa  22260
aaactgaaag gaaactgagg ctgagccagt ggtttgctgg gttgaggagg cagagctggg  22320
agtccagaga tgcaaggtgg ctagagcccg tatggaaaaa taccagggaa gagagctgca  22380
gagggagctc cggagaactg cacagtaccc tctcatgtgt gtagctgagt attgatgagc  22440
acatgctggt gaggaaatga cccagggctg caggtagaac cacttaaaag gattagaagg  22500
aacaattgct gcaactcaca cagggccagg aagaatttct tttttttttt tttttttttt  22560
gtatttttag tagagatggg gtttcaccat gttagccagg atggtctcga tctcctgacc  22620
tcgtgatccg cccgtctcgg cctcccaaag tgctgggatt acaggcttga gccaccgcgc  22680
ccggccaaag ggccaggaag aatttctaat cacacaagtc ggagtggaaa acctcggctc  22740
tcatagagca gcaggtagag tactcagaag ggtttgcctg cctagcccca gactaagttt  22800
cgttactctg accccgccta atattaaaaa aagattaatt aaattaattg tttgcaacaa  22860
aagtaatata tttcagtgtt tataacgtgt agaagtgaat tgtatgacaa tagcataaag  22920
gctggaagag cagaaattga catgtatttg tgctggacag aataatgttc ccctcttttc  22980
ccaaaagata tcgagtccta atccctggaa cctgtaaatg ttactttata aggaaaatgg  23040
tttcatggtg tgattaaatt caggatcttg agatgagggg gctgtcttgg atgatttggg  23100
taggcactaa atgcaatcac atgtgtatgc aaaggaggca gagggagatt ttacatacac  23160
agagaaggcc atgtgaagat agaacagaaa gatttgaagg tgctggcctt gaaaattgga  23220
gtgatgaagc tataagccaa ggaatgcagt agccaccaaa gctggaagag gtaggagcaa  23280
ttctccttca gagcctactc cagagggaac gtggtgctgc cagttcctta atttcagctc  23340
```

```
agtgatacta attttggact ctggtctctg aaactgtgaa agaataaatt ttttttgttt  23400
gtttgtttaa gccacacagt ttgtggtaat ttgttacagc agctgcagga aactaattta  23460
tgctgcatgt gaaatggcat aatatcatta agatagattg tgataaaggt acatagtata  23520
aacaattaag caacaactaa aagcacaaca aggagttata gctaatgaac caaaaaagga  23580
gattagaatc ataaaaatag tgaatcccaa agaagccaga aataggggaa gaggcaaata  23640
aaggaaagaa agagcttgat ggtagattta aacctagtta tgtcaaaaag gacattaaat  23700
gtaaaagata tttttcggat tgaatggaaa agtaagaccc agtatatgct gctgcctgca  23760
agaaacatat tctaaatgta aaggcaaaaa tagcctacaa gtaacagaac agaaagaagt  23820
tcaccgtgct tacaagaatt agatgcaagc tagactggtt ctgttaatat cagacaaagt  23880
ggatttcaga gcaaaggcta ttgcctagga tgagatggtc gtttcataat aacgaagggg  23940
attcgttcat cagccgcaca taacaaactg aaatatttat gcacctgact acggagctaa  24000
aatacacgaa gcaaagccta acaactacga gtagacacag gcaaatccac agtgagagag  24060
atttcagtgg cttctctcag tgatttgtag aacacgtagc cataatatct ggatctagaa  24120
cagttgaaca acactgtccc tatgcaacct gattggcttt tacaggacac tccacccggc  24180
accagcagaa gagacactct ctcaagtgct cacagaatgt ctgccaagat agagcagatg  24240
ctgggccata aaacaagtct ctaaattaaa cgcattcaaa ttattcagag tacgttttcc  24300
gacctcagta tcattaagtt ggaatatatt ataggaagat aacctggaaa agcctcagat  24360
atgtggaaaa actcatttct aagtggccca tgggtcagaa gtgaagtcaa aagggaaaac  24420
tgaaaatctt ttggattgac tgatatgaaa acaatagatg tctatacttg tggggtgctg  24480
ttacagtata gtaaagggaa atttctagca ttaaatgcct gttttagtaa agaaagattt  24540
caaatcaatg acctcagctt ctaccttggg aaacttgaaa atgacaagca aatggaatcc  24600
agagttacca gaaaggccag gtacagtggc tcatgcctgc aattctgcca ctttgggagg  24660
ccaaggcagg cggattgttt gagactggca gttcaagacc agcctgggca gcatagggag  24720
actccatatc tacaaaaaac acagaaaatt agccaggtgt ggtggcatgt gcctgtagtc  24780
ccagctaacc aggagtctaa ggtgggagga ttgcttgagc ctgggaggtt gaggctgcag  24840
tgaactgtga ttgtgccact gcgctccacc ctgggcaaca gaatgagacc ctgtctcaaa  24900
aacaaaaaca gttactagaa gaatggacat catagagata agagcagaag tcagtaaaat  24960
agaaaacaaa aatacataga aaatcaataa aaccaaaagc tagttcatca agaacatcaa  25020
taaattggtg agactaatag gaaaaaaagt gaagtcacat attatcaata tcaggaatga  25080
gggagatgac agtagtatag attatataga tattaaaagg gctatatgag gcaggtgcgg  25140
tggctcacgc ctgtaatccc agcactttgg aaggccgagg tggacagatc acctgaggtc  25200
aggagtttga gaccagcctg cccaacatgg tgaaactccg tctctactaa aaatacaaaa  25260
attagctggt catggtgcca tgcgcctgta gtcccagcta ctcgggaggc tgaggcagga  25320
gaattgcttg aacctgagag gcagaggttg cagtgagctg agatggcgcc attgtgctcc  25380
agcctgggtg acagagtgag actccgtctc aaaaaaataat aataataaaa aggactatat  25440
gggaatatta tgaacaactt tatgccaata aatttgataa cttatagatt aaatggataa  25500
gttccttgaa agacacacaa actattaaag ctctctcaag aagaaataga taaactgatt  25560
agccctatat ctattttatt aaatttaaat gtaaaaatca atatttagtt actggaaaac  25620
ttttaagtgt ggttggaaat ggtatatgaa ctttttcaac tgaattttat gaaggctaat  25680
cacaggtaaa ggttttctga tgaaaattta gtgtctgaat tgagatgtgc tgtaaaaaat  25740
```

-continued gttgttatgt atcttaatca tttcttcaca ttaattacat gttgaaataa tactttgggt 25800
gtattgggtt aaatgaaata ttatgaaaat cttgcctgtt ttcttttttac ttttgatgtg 25860 tcacctggga aataaaaaag tgtgacttac attctgtttc tgttgacagt actgctttgg 25920
agtgcagtgt tggaatgatc tagcatttcg aagacctttc ctcccttcgt tattcagggc 25980
tgtattccac atagataagt ctgaaatact gctaagtggc acgttttgtt ttgtgctttt 26040
gtaagtttgt tgatcgttac tgatgtggac ctttggtgcc tcttaggctc atggctatct 26100
tccaaccatt gtttgcaatt tttacctaga gataaagaga aaaagagatt tggtttcaga 26160
gtaagttaga ttgagatcat gaaagagcaa tctcattttg atgcttcaaa aatagcacat 26220
cccccgtatt actgggattt gctattcttg ggcttacttc aagaacatcc ttgtgttgct 26280
ggtttggatg cttccgaatg ctgtgaagtc agtttcatgg acgtggctca tcagtttagc 26340
tctcttggct ttgtttaggc agttggagca tgatagcctg aacagcttct ctcaattaaa 26400
catttacaaa tcgtttacga atagtaaaca aactccaggt tttgtgactc tttgatagtt 26460
catctagcac aacaaaaaca caatgtgacc atgatcacct ggcatcttag ggtgaaatac 26520
tttggcccag actgaaagca aaattaaaaa ggggcaagag agatatactg ctgaactgat 26580
tttcaaggtt ccaagaatat cataggttaa gagtaaaagt aaacttttga cagagagcag 26640
cgggttttct gggattgaag tatctgaagt tttcaaacga aaatttaaaa agaaaaaatg 26700
agaattgcct tataagtaca atctcttctt ttttaaaaaa taaactttat tttggaatag 26760
ttttaggttt atcgaaaaaa attagggtag agagttttca tataccctac atccggttac 26820
cccagttatt atcttaatta agtgtgagac attttcatgt ttaatgaatc agtatcgata 26880
tgctgttaac taaagtgcag actttattaa gattttctta atttctatgt aatgtccttt 26940
ttctgttcca gaattccgtg caggacaccg gatacctcat tacatttcat tgtcatgtca 27000
ccttaggctc ctcttgacag tttctcttct tttttgctta gaaattctcc agaatttcag 27060
aaacttctgg gcatcgctat ggaacttttt ctgctgtgca gtgatgacgc agagtcggat 27120
gtcagaatgg tggctgatga atgcctcaac aaagttatca aagtaagagc cgtgtggatg 27180
gtgttctcag aaatgtcatt gttgtaggct aagagaagca gccatcgttg agtgttcttc 27240
tgtttggagc ccctgaggat gtctgcactt ttttcctttc tggtgtgtgg tttggaggtg 27300
ctctggtatc tgcccgcatt gcttgccaca cctgcctggt cagaaggaac tgtgttgacc 27360
cttgtgcctg catggtgcct aggtcaatga agggaaccaa tggtgaccac tggatgctcc 27420
tgggaaaatg tcactacagg taccagagaa gccagagcta tgcccacatt tttttttttt 27480
tttttttgag acggagtctc actctgtcgc ccaggctgga gtgcagtggc gcgatctcag 27540
ctcactgcaa gctccgcctc ctgggttcac gccattctcc tgcctcagcc tcccgagcag 27600
gtgggactac aggcacctgc caccgcgccc ggttaatttt ttgtattttt agtagagaca 27660
gggtttcact atggtctcga tctcctgacc tcgtgatccg cccgcctcag cctcccaaag 27720
tgctgggatt acaggcgtga gccaccgcgc ccggcgctat gcccacattt ctatgagtct 27780
cagttttctt aactataaaa tgggatcaaa gtttttgtgg catgcgtatg agtgtgtgtc 27840
tgtgtgagga ttaaatgcac taattgccac taccggatcc tcaaagtggt aagaagtatt 27900
cttattaatc atgacatcct cacactctta tgcagcaaga ttgatgggtg tggcactgct 27960
tctctttttc catcacatgg attccatgct atccttttgc ccagggaatc tttcctttgt 28020
ggccagcact ttgttgtttg gctcatcacg ctttctgtgg gcaggacgct ggcttctctg 28080

-continued gagtcttggg attctagctc cctctcttgt ccctagagtg gtcactgtct tctctctctg 28140
cttgcaattc ttgctttgct cgcatctcac tcatgcggtg acctgtatca gtttcacctt 28200
gttctccgtg cctgctggtc gttggcacca cttgcctgtg gatggcatcc catagcgtat 28260
ttagggcctg cttccccagt taagcttgct tttccacagg cctgaatatc cttgcttgct 28320
tctgttattc ccactggcag gaccacggcg gtctttttg gatgagacag ggtcttgctc 28380
agtcacccag gctggagtgc agtggctgat cacggctcac tgcagccttg agctactggg 28440
ctcaagctat catcctggcc tggcttcttg agtagctggg actacaggcg tgcaccacca 28500
tgcccagcta attttaaaaa ttatttgtag atatgggatc tcgccaggtt gcccaggctg 28560
gtcttgaaca cctgggctca agtaatcctc cctccttggt ttcacaaagt gccgggatca 28620
caggtgtgag ccactgtgcc tggcccttga tgtttcagtt cttgatattt gatcctcaga 28680
gtcagaaagt ctaaaaagag gactatccca ggttgccttg gttcacggca aatgggacgt 28740
taagagggca gagaaaacaa tatgaccaga aacgcttcta atattggtca tttaacgtgt 28800
aagtattgtt ctttttaaa cctccttcat ctttttctag ggattgctgg acacagtggc 28860
ttggtgtgtc tgagggctgt aggccatggc cctgggttgt ggttttaggt ctcaggtgct 28920
cttcctggtt gtctccttgc ttctttccca tttcctcttc tttgtttcca gccatttctc 28980
ccttttgctt aagtttggtg cagcagggtt tggctgctct cagattgctg cttcctcaga 29040
tgatgcagtt gccaggccca gtgggctggc agtgggatca ggatctgact aggtttgctc 29100
tcactgtggc agaggagggg caggcgtggg agagcacgtg tgaccccagg ccaggtgtag 29160
ggagcccagg catggtcact tagccttcag gtcctagact ttgtcttctc atgagtgtgg 29220
ctgtgtgtgt atggtgagaa ccaggttcta cgtagcccaa gaaaatgtag agaaatgcac 29280
tgggtatctg acatagcctg gcagcacgcc tccctcaagt aggttagtct caggcggtga 29340
agcatgtatg tccagcaaga acttcatatg tggcataaag tctccgttct gtgcggcact 29400
gacaaatcac caccgtcagg aggctgaagt aatttctgtc tagggaggca gggaaggctt 29460
cctggagaca gtagccaata ggtgaaaggg tagattggag accttcttaa tcatcaccgc 29520
ctcttggttc gaggggtgcc aggaagctgt ggaggctgag aggaggggga acccatctta 29580
tgctgccaga gagtgggaca ccctgagggt caggtcaagg ggttgtacct tgttgggtgg 29640
agaattaggg gctcttgaag acttttgatg tggtcagggg agtgtatcat ttaggaagag 29700
tgacctggta aggacgtggg atagaggagg acagaggtgg gagggagtct aggtgggagt 29760
gagtgggccc agcaggagtg cagggcctcg agccaggatg gtggcagggc tgtgaggaga 29820
ggcagccacc tgtgtgtctg cggaagcagg ggcaagagag aagaggccag cggcgcgccg 29880
ccatcaccca gcaactggcg tagattgtga gagcccattc cctgctttta ggaggggccg 29940
agttttagtt ttctcttata aaataaactt ggtatttgtt tacaaaacat ttgtaaagct 30000
aaatcaaggt ttgataaggc ttctagtttt atttaagaag taatgtttaa ataaatgtcc 30060
aattcgcttt gcttatttaa ggactttcag tacaaacttc aacaacagga tcaggattta 30120
aacatttctg agatgttatt acccctcaga atttcccaga acgtgatctg gttttgattt 30180
tcaagcttgc tgacccagta ggttaaccca caaattttac taagatacac ctcagtccat 30240
ttatatcgac tgcccatgtc acggtcaaag agatcatcga ctgatgtttg gcacagcttc 30300
ctccctcttg ggtgggcaag catttggaag agaaggctcc catgggtgag agtggggcac 30360
cagagtcttc cccgtcctgt cccctggctt gagaaaccct tctctaatgt ggactttgtg 30420
ccgttagcat cgttactggc ttgaagttga ccatgtggac ataatttctg gtttagcctc 30480
acaagtgagc aaggagggtt gagagatgtg ctgtgaggaa catggggccc ccgctggccg 30540
tgggctctgg gtcagggggg caggggacca tgggcatacc tgacagtgag gaggggccac 30600
acctgcagaa agcatgcggg actcggcnnn nnnnnnnnnn nnnnnnnnnn nnnnnnnnnn 30660
nnnnnnnnnn nnnnnnnnnn nnnnnnnnnn nnnnnnnnnn nnnnnnnnnn nnnnnnnnnn 30720
nnnnnnnnnn nnnnnnnnnn nnnnnnnnnn nnnnnnnnnn nnnnnnnnnn nnnnnnnnnn 30780
nnnnnnnnnn nnnnnnnnnn nnnnnnnnnn nnnnnnnnnn nnnnnnnnnn nnnnnnnnnn 30840
nnnnnnnnnn nnnnnnnnnn nnnnnnnnnn nnnnnnnnnn nnnnnnnnnn nnnnnnnnnn 30900
nnnnnnnnnn nnnnnnnnnn nnnnnnnnnn nnnnnnnnnn nnnnnnnnnn nnnnnnnnnn 30960
nnnnnnnnnn nnnnnnnnnn nnnnnnnnnn nnnnnnnnnn nnnnnnnnnn nnnnnnnnnn 31020
nnnnnnnnnn nnnnnnnnnn nnnnnnnnnn nnnnnnnnnn nnnnnnnnnn nnnnnnnnnn 31080
nnnnnnnnnn nnnnnnnnnn nnnnnnnnnn nnnnnnnnnn nnnnnnnnnn nnnnnnnnnn 31140
nnnnnnnnnn nnnnnnnnnn nnnnnnnnnn nnnnnnnnnn nnnnnnnnnn nnnnnnnnnn 31200
nnnnnnnnnn nnnnnnnnnn nnnnnnnnnn nnnnnnnnnn nnnnnnnnnn nnnnnnnnnn 31260
nnnnnnnnnn nnnnnnnnnn nnnnnnnnnn nnnnnnnnnn nnnnnnnnnn nnnnnnnnnn 31320
nnnnnnnnnn nnnnnnnnnn nnnnnnnnnn nnnnnnnnnn nnnnnnnnnn nnnnnnnnnn 31380
nnnnnnnnnn nnnnnnnnnn nnnnnnnnnn nnnnnnnnnn nnnnnnnnnn nnnnnnnnnn 31440
nnnnnnnnnn nnnnnnnnnn nnnnnnnnnn nnnnnnnnnn nnnnnnnnnn nnnnnnnnnn 31500
nnnnnnnnnn nnnnnnnnnn nnnnnnnnnn nnnnnnnnnn nnnnnnnnnn nnnnnnnnnn 31560
nnnnnnnnnn nnnnnnnnnn nnnnnnnnnn nnnnnnnnnn nnnnnnnnnn nnnnnnnnnn 31620
nnnnnnnnnn nnnnnnnnnn nnnnnnnnnn nnnnnnnnnn nnnnnnnnnn nnnnnnnnnn 31680
nnnnnnnnnn nnnnnnnnnn nnnnnnnnnn nnnnnnnnnn nnnnnnnnnn nnnnnnnnnn 31740
nnnnnnnnnn nnnnnnnnnn nnnnnnnnnn nnnnnnnnnn nnnnnnnnnn nnnnnnnnnn 31800
nnnnnnnnnn nnnnnnnnnn nnnnnnnnnn nnnnnnnnnn nnnnnnnnnn nnnnnnnnnn 31860
nnnnnnnnnn nnnnnnnnnn nnnnnnnnnn nnnnnnnnnn nnnnnnnnnn nnnnnnnnnn 31920
nnnnnnnnnn nnnnnnnnnn nnnnnnnnnn nnnnnnnnnn nnnnnnnnnn nnnnnnnnnn 31980
nnnnnnnnnn nnnnnnnnnn nnnnnnnnnn nnnnnnnnnn nnnnnnnnnn nnnnnnnnnn 32040
nnnnnnnnnn nnnnnnnnnn nnnnnnnnnn nnnnnnnnnn nnnnnnnnnn nnnnnnnnnn 32100
nnnnnnnnnn nnnnnnnnnn nnnnnnnnnn nnnnnnnnnn nnnnggtggg agaatcactt 32160
gaacctgggc ggtggaggtt gccttgagcc gtgatcacgc cactgcactc cagcctgggc 32220
aacaaagtga gacttcgtct caaaaaataa aaataaaaat gaaataaaat cagtccgggt 32280
gtggtggctc gtacctgtag ccccagcact tcaggaagct gaggcaggtg gattgcttga 32340
gaccaggagt ttgagaccag cataggcacc atggcaaaac gctgtctgta cagaaatgag 32400
ctaggtgcgg tggtgcacaa ctatagtccc agttacttgc gaggtggagg tgggaggata 32460
aatggagcct ggaaggttga atctacagtg agctgagatt gtaccactgc ccttcagcct 32520
gggcgagcaa gtaagaccct gtctcaaaaa aaaaaattat tgactatatc ttattgtcta 32580
taatccctcc tctgtgctat tgaataccag gttttgggcc cttatttcca tcactgaaca 32640
aacttcactc tattgagcag catgtgtgga atttcatctt tattcaataa ttaacagcta 32700
ggaggaaatg ctgtttgcta gactattgct ttacttttct tcaaaaggtt actctttatt 32760
agatgagatg ggaattaaaa atggtaactt actttatgtc tttataattg aagcccgcta 32820

```
gatcttaaag tagttaccag atgttttatg catttaaatg gccttttctc taaaaataga  32880
aagtaacaat gaaagaaaat gcttcgtttc tatgcaaccc tcttggtgac tagtgtgtgt  32940
gactcttaat gtgacactca ttgcaccccc tcagaatggt gcccctcgga gtttgcgtgc  33000
tgccctgtgg aggtttgccg agctggctca cctggttcgg cctcagaaat gcaggtaagt  33060
tgtacattct ggatgttgat ttttgttggg ggccagctgc tactgatcct ttatgtctca  33120
gctcagatgt catttcagaa atctgctctg ccccttccaa attgcagtcg accttgccct  33180
gtttatgttt ccgtcatagc actaatccgt gtcagaaagt gtcacgtaca gtctgtgtgc  33240
ttgttcattt tctatcccac cctcccccaa gagacttatg ggatgtgtgc cccaggacag  33300
caggggtctt actgtcttat gctctgttgc agcctaaaca gcagtaacag tgtctgcaca  33360
tagtacttgc ttaaatgatt cttgccaaat tgttgaaggt tgaggtacca gtttcattat  33420
tgctgactat aggagttaca gcaaaatatc catttgtcta ttacatgagt taaaaatatg  33480
gttgtttcac tatgaatagt tttgtctagt caaaacagtt gtgtcttaac ggattgagaa  33540
acaaaagcag gaccactttt catcagctcc ctcctcctta acctgcagta tacgctgatg  33600
ctgatgtcct gtagaccctc agctccatcc tgagtcactg ggaacgtggt ctaaaccctc  33660
attattagta tgaactgagt ttcaataaga atctcacatg ggtcgggtgt agtggctgat  33720
acctgtaacc ccagcacttc aggaggccaa ggcaggtgaa tggcttgatc cagactaggc  33780
aatatggtga aaccccgcct ctacaaaaaa tacaaaaatt agctgggcat ggtggtgcgt  33840
gcctgtaatc acagctactg gagaggctga ggtgggagga tcagttgagc ctgggaggtg  33900
gaggtcgtgt tgagccaaga tcacatcact gcactccagc ctgggcaaca gagtgagacc  33960
tgtctcaaaa aaacaaaaaa caaagaaaca aaaaaaagct tatatgggtg cagaggtata  34020
atcactaagg aaatttcttt ttgtgtagtc tttttctttt tactgtcatt tcaaaaaatg  34080
tgttatattt ctgaagtaac acatccaggt tctccacata gcagccaaag tgaccttaaa  34140
gaacataatt gggtcttgtc attcccttat ttaaactctt gtgcccgttt cccagtgccg  34200
tttagattga ttccagactg gtaactggct ccgtcacctc agacactctg cattgactca  34260
ttagcctgat cagttcttca gatgagtcag gtttttcttc ctcctgatgg tttgtttgtt  34320
ttgtttattc ccctcagttc tcagcaaaac agtcatttcc ttagggaggt ttccctagcc  34380
tccctgtctt tccctgtccc aggagcctgg tggtgtggtc actgccctct gaggccctgc  34440
ttgttgccag gctctgccac tagagggcag ggctgcacca ctcctggcac ctcacacctg  34500
gcctgccctg tcagtgtttg ttgggtgaat tcctgtgatc tgtgactcac tgctctgtgt  34560
cctacacatt ctgcttttct tctcccctca caataccatt tataattctc ctttttcagg  34620
aaagctttat ttccattaaa acatttttgt ttttaaaatg gtattttctt acactattat  34680
tttctaatta aaaatgagtg ttttggcagg gcgtggtggc tcacccctgt aatcctagca  34740
ctttgggagg cccagatggg cggatcacaa ggtcaggaga tagagaccat cctggctaac  34800
atggtgaaac cccgtctcta ctaaaaatac aaaaaaaaat taggcgagtg tggtggtggg  34860
cgcctgtagt cccagctacg tgggaggctg aagcaggaga atggtgtgaa cccgggaggt  34920
ggagcttgca gtgagccgag atcacgccac tgcactccag cctgggcgac agagcgagac  34980
tccgtctcaa aaaaaaataa aaataaaaaa aaaaaaataa ataaaaagta aaaaaaaaaa  35040
agagtatttt aagaagtatt acgatttact gcaaataatt tttaaaccca gccttttaga  35100
tcctctgtga tcataagaga aatgaaggat gtctcccgac acttgagctt catccacatt  35160
tcattctctc gttctttcag ctgagctttg cccatcccca ttagggaccg tttggcatat  35220
```

```
gaaactggct tttccctaac agggaatgaa ttgcttctat ttctcctgaa ggagagctgg  35280
aggaatgact tgcgttcttt tgcatacaca ggccttacct ggtgaacctt ctgccgtgcc  35340
taagtcgaac aagcaagaga cccgaggaat cagtccagga gaccttggct gcagctgttc  35400
ccaaaattat ggcttctttc ggcaattttg caaatgacaa tgaaattaag gtacgattat  35460
tgcctcagat cacaaacatg tgagtgacgc tgtgagtgag tctgtggagg gttacggctt  35520
ctgagcaggg agtcatgtgg gagcgcttct tagagtatgt tgtatgtcgt aatttagact  35580
accgtcattt gtgttatttt tgaggcacct aaagacttct ttccacttct gatttcttac  35640
tgtggggtga agagttgaat tgggagatgg tttatagatg cacattcaaa aggcatattt  35700
ccagagcaga ttggttttca gtgtattaga gtgactgttt aacctagctg tggaaagatg  35760
gctgtgccag gactgcaggt aggagaaagc tcactgacga ggccttgtgg gtctgaacat  35820
cctgcagcta tcagggcctg ttggctccct gttgtgcatt ccaacaaacc accttcaaac  35880
ccactttagt gtttgtttat aatgtccaga aatagtgacc ctgtcacatg ctctacagat  35940
tacaggattc ctagcctctt ccttttggt gggtcagtcc tgggtttgag cccaagtggc  36000
cctcttggaa ggtgatgata cacagtgggt agagtggaat cagatggact tggattagaa  36060
ttctgtccgc tttactggtt cttttcctct aggcaaacta tccaacagct ctaagctatt  36120
tccttcgtat tctgaaaact aagccttaat gggacccata tcgggcaatt ctgagagtga  36180
aataaatgaa tatgtgttag cgtgtagcat agtcgcccac aggaagggct tagatgttag  36240
ctgctactgc tcttattagc tgaatgactt ggaataaagt gttagcctct ctcatgtttt  36300
tttctctgag ctttgaagtt ttcttgttaa tactaaggag atattcaaac tagtcatggg  36360
gttttggaat gacgaaggga gatcatgaat ctaaagaatt tagtgtggta attcatcatg  36420
ctcagtaaat ggtagctgct gcttgctgtt atttttatta ccatctcttt ggagtgggag  36480
taggtctcct ttgtggtcag aggctgtgag agctccgcag cgccagtctg cccgtcagta  36540
caccgggctc tgatgaaggc agttccctct gtggtatctc tggctgtcag agctcagatg  36600
atagatggtg tttttgtact ctcagttctc atcattttca tgatttcgat cactatttga  36660
gtatgatgat gctaacactt tgttgaacat agagtccatt aattacttcc ttcctgaacc  36720
ttaggtattt aaaaaaatct attctgctac ctctctgctc atttatgatt attcagattt  36780
attatcaaga gcctggtaca gtggcttgtg cctataattg tagctacatg ggaagctgag  36840
gtaggaggat tgctggaggc caggagtttg agaccagcct gggtaacatg gtgagaccct  36900
atcgctaaaa aatgaaaaaa gttagctggg catgatggca cgtgcctgtg gtcctagcta  36960
ctcaggagac tgaggcagga ggattgcttg agcccaggag ttggagttcg aggctatact  37020
gagctgtgat tgtgccacca cactctggga tgggtggcaa aagaagatgc catttcttca  37080
aaacaaaaca aaacaaaaaa aggtattatc ggtgaaattc aatagtacca acaggattat  37140
aaacaaagat agttctcttc ctacttttc tcttaatcct tgtgtctcag aggcaaacat  37200
aactcttagt gtttcttcca atatttactt cgannnnnnn nnnnnnnnnn nnnnnnnnnn  37260
nnnnnnnnnn nnnnnnnnnn nnnnnnnnnn nnnnnnnnnn nnnnnnnnnn nnnnnnnnnn  37320
nnnnnnnnnn nnnnnnnnnn nnnnnnnnnn nnnnnnnnnn nnnnnnnnnn nnnnnnnnnn  37380
nnnnnnnnnn nnnnnnnnnn nnnnnnnnnn nnnnnnnnnn nnnnnnnnnn nnnnnnnnnn  37440
nnnnnnnnnn nnnnnnnnnn nnnnnnnnnn nnnnnnnnnn nnnnnnnnnn nnnnnnnnnn  37500
nnnnnnnnnn nnnnnnnnnn nnnnnnnnnn nnnnnnnnnn nnnnnnnnnn nnnnnnnnnn  37560
```

```
nnnnnnnnnn nnnnnnnnnn nnnnnnnnnn nnnnnnnnnn nnnnnnnnnn nnnnnnnnnn  37620
nnnnnnnnnn nnnnnnnnnn nggagtacaa tgacatgatc ttggctcacc acaacctccg  37680
cctcccgggt tcaagcgatt ctcctgcctc aatctcctga gtagctggga ttacaggcac  37740
gcaccaccat gctcggctaa ttttgtattt ttagtagaga cggggtttct ccagattggt  37800
caggctggtc tcaaactcct gacctcaggt tatccaccca cttcagcctc ccaaagtgct  37860
gggattacag gcatgagcca ctgcacccgg caacttccac atttctcagt aacatgcttc  37920
tactgctttt tttttttttt ttttttcaat tttagacatt ttttactttc acactataat  37980
tctatcagaa ttcagtatgt acattattat acctaagtaa atagtcatgg ttggttgtgt  38040
attatatttc tttgtatttc ttatttgatg agagagctgt gttttttgct gtgggttgaa  38100
actgtggaga gaggacatgg ggaggggaag gaagacagat gaagttggtg actgtacctt  38160
cctggccata gctgggttct cagcaccctg ggatctgctg atcacctgct cgtaggccaa  38220
gcccctagcg aagttctagg tgacccagtg ctggggatgg gggggtcacc tgcaaggtct  38280
agtcatggag gtgggggcta cagtgttggc ttgtgctggg gccagcatcc ttaggaatgc  38340
atcttggagg aggaggagac agccacccac ttcttgactg gggccttcag cagtgccagc  38400
ttcttgggca gactggtgct ggctttcatc accacatcgt gttcaatctt cttccagatc  38460
ctgacttcta ggttcacctt tccttagacc ccggttcctt tcagaggctg tcgctctgcc  38520
ttgctctttg ctggcttgtg ccttgattat atgtctttgt acaacttttt gttttcctgg  38580
agttaatcct cacatctgtt ttcctagagt gaattgttac ctttatatca cttgcttatt  38640
attctttgac cttttttttct tctcacacct tccaacttct ttgtaaaatg tgtttagtac  38700
aatttttcat gacaggtaat ttaccaaatc agtttttccc cagtgcagtc atccatcttg  38760
agttacccag ctcgctgccc cagtctgggc ggattgctct tcaggtctgt tgtacacttg  38820
tatcctagga cttctctttg ccatcagcct ggaatttcct ttgcagttct cctgttggat  38880
gcccagttcc tacatgccat atgtttatct ttctatcctc tagtagcttt gtgagagaag  38940
atgaatggga ggtaaattgt ttggagtttt gcattcataa aaatgccatt ttttctcgcg  39000
tacacttggc tgagtatagt gttctggggt agaaatcatt tttcctcaga aatgtgaagt  39060
ctttccccgt tgtcttaaag tctccaacat aacccaattc cttaacccat gaatgtgctt  39120
ttctctggaa gctttccatt tttggggagg tgaagtgcta ggtacttagt aggcctttta  39180
ttttttattt ttatttgttt tttgaggcgg agtctcactt tgtcgccgag gctggagtgc  39240
agtggcatga tctcggctca ctacaagctc tgcctcccag gttcacgcca ttctcctgcc  39300
tcagcctcca agtagctggg actacaggcg cacaccacca cgcccggcta gttttttttt  39360
tgtattttta gtggagacgg ggtttcaccg tgttagccag gatggtctcg atctcctgac  39420
ctcgtaatcc gcctgcctcg gcctcccaaa gtgctgggat tacaggcgtg agccaccgcg  39480
cccagccagt aggcctttta atttggaaac ttatatactt cagttctggg aaaattttct  39540
tacatttctc tgataaattc ttgcctttta ttttctgtgt tctctccttc tgaaattagt  39600
tagttggatg ttggtcctcc tgggttgact cacatcttac ctttttcttt ttctggtact  39660
ttttagatat ccatctcaaa ctcttctatt cagtgttatg tttttaactt ctttcttttc  39720
tttgtctctt gatggggtct tgctttgttg cccaggttga ggtgcagtgg tgcaatcata  39780
gctcactgca gcctccaact cctgggctca agcaaccgtt ctgccttagc ctcccaagta  39840
gttgggacta caggtatgca ccaccatgtc cagctatttt ctttactttc tttctttttt  39900
tttttttttt ttgagatgga gtgctgctct gttacccagg ctggagtgca gtgatgcgat  39960
```

tttggctcac ttaagcctct gcctcccagg ttcaagcaat tctcctgcct cagcctccta 40020
agtagctggg attataggtg tgcaccacca cgcccggcta atttttgtat ttttagtaga 40080
gacggggttt cgccatgttg gccaggctgg tctcaaacac ctgacctcag gtgatccacc 40140
tgcctcagcc tcccacagtt ctgggattac aggcgtgagc ccatcattaa atctttaaat 40200
actagtatct gtaagtcttt tcctcttgag tcagccagta tccctggaag gaaattcctc 40260
attttcctgc ttggagacta taagcttggc tgtgtttatc ctgcaaccgg ggactggaag 40320
gggatggaag gggactgaca ctgttgctgg tcagggcgcc ctctttttgt tttctgtatg 40380
catctcacat ctgtcctcag ttatgtaaac acctcttgag attatccctc tcagtctttg 40440
ctggaggtgg ggaaggggct gcttcctggg ctgccttgga ttggagggga gacctcaggc 40500
gagtgggtgg gaatttgccc aaggagccat gagacaagcc actgttccac cctctccgtc 40560
cctccacttt cagatgtatg tggtgcctcc aaagcccgag tgcttcttgg agttctgtgg 40620
cttgaataag cttgcttttc actggtatcc ctcatacctt ctcccccatc cccagcaaag 40680
cttgcatttg aacttcttcc catgggctaa caaatcagtc agttatgtag cccttgttac 40740
tttttagctt ccgaagtttt gttgacacac gtagtctgct agtgtccctg ttctgttctt 40800
tctgtccgtg tacatttatg ctttatacaa cttctttaca tgattttcgt ggggtttctg 40860
ggtagcagag cttcacatgt tcaatccagc atgttggatt agaagtctcc caccctctgg 40920
tgtattctca ttctcagaat tacctgccaa acaccgatac tcccttgttt ttccttttcc 40980
tgacaggaaa tgtacatacc agacaggaca gaaatcatta gtgtatccct tggtgaataa 41040
ccacaaagtg atcttaccct cgtaaccacc acccaggtca agacagagta ttaccagcac 41100
tcagaagcct cacccccatc ctcccatcac tgcttcttcc ttcctcccca aggtcatgac 41160
tgtcctggct tctaatgcca gagtctgttt ttaaattctg tgtacataga ccatatagta 41220
tgtattcttt ttgtctggtt tcttttgctc gacagtaatt tcttaagagt cttctatatt 41280
atcgtgtgta ttagtagttc ctgtagtttt aggagcttca tagcattcca ttgtaggtat 41340
ataccacagt ttattcattg tgttatcact gggttgtttc tagttcttgg ctattgtgag 41400
caatgctact gtgaccactc tcaggtgttt tttttggagc acatgtgcag gtttccatca 41460
tgcgcagcta gaggtggagt tgttgggtga tagggtgtat gcatgtcagc tgcagcagaa 41520
actgccaaat agctttcctg agtgcttgta ccagctcacc ctttggttgc tgcgtatggg 41580
gactccggga gctctggtcc tcgctagcac ttggaattgc tgatgctttt acttttagcc 41640
ttcctgatgg gtattttctg gaatcacatt atgattttaa tttccgttcc ttaaagtacc 41700
cttgactctg aagtttaatg attaatgcat ctcttccttt ttgaagtact ctgaaaggta 41760
tgttgtgcat gtgttgaaaa ctggagctat ctagtctaaa atacagtgta cctcctccct 41820
gtttgaagag ttgtagcatg gcctcggggc ctcctgttag gtgccttgga gaagggattc 41880
ttgggattgt agagattaga cctgaggagg ccccttggag ctctcagact aaattttgtt 41940
ctttattatt ccaaactatt taagctcacc gtgtgctgac tcatcataat aatgagtagc 42000
tctcattgtg cttgtatatt tggaccaata gaatgatttt tttttttga gacatagtct 42060 tgctctgtca cctaggctgg agtgcaatgg cacaatcttg gctcactgca gcctctgcct 42120
cccaggttca agcgattctt gtgcctcagc ttctcgagta gctgggactg caggtgtgta 42180
ccaccatgcc tggctaatgt ttgtattttt agtagaaacg gggtttcacc atgttggcca 42240
agttggtctc aaactcctga cctcaagtga tctacccgct taagcctccc aaagtgctgg 42300
gattacaggc gtgagccgct gcgcttggcc aaagtagttt tttaagatgt gaatatcttt 42360
tcttgcagct aaaaaagttt gtcagagata attctacttt attctccagg tggtttttca 42420
gggagaaatt ggaggcagta aaccacgggg ggagtcctgt ggcttggtgg gtgggtgggg 42480
gaggtgtggc tggggtgggg agaagtcctg tggctcgctg ggtttggggg gagctgtggc 42540
tggggtgggg agaagtctag tggctggggt ggggagaagt cctatggctc ggtgggtggt 42600
gggggagctg tggctggggt ggggagaagt cctgtggctc ggtgggtggt gggggagctg 42660
tggctggggt ggggagaagt cctgtggctc ggtgggtggt gggggagctg tggctggggt 42720
ggggagaagt cctgtggctc ggtgggtggt gggggagctg tggctggggt ggggagaagt 42780
cttgtggctg gggtgggggg cagtcctgtg gctggtgtct catcatgtgc ctaacagtgt 42840
ccagaggtct cgtgtaaatt ccctgggagt cgataagcct ctgagaaaca gatgatgcta 42900
accacgctgt ggaagagaaa cttgtttata aatcagatgt ccgttactgg tttactgctt 42960
gtttgcccag gcatagctcc gacagagtcc ccgactcata gtgattgctc agtgcgtgct 43020
gaacaatgat tggaatcaag tcatggctca gagcatagtt ttgaataatg ggaaattgat 43080
gttcttaagt aacatagtca ccaagataat gcaactagat gagtcacccc ttttcaattt 43140
taggatattt ttatcaagat ttaagtggtc atcattagaa ttatagcagt ttctcctttg 43200
gattgttcta gaggcccagt gagaaagtat tccctaattt ctcaggagaa cagttgtggg 43260
tagtgtgctg tcatgtccag ttaaattgca gacgtttccg gttgaagata ttccagtcct 43320
gagaactttg tgacattagc aggactttta caagccatct cttagggtgg ggcattactg 43380
tagttggctg gtactctttt ctccttaact ttgtcatttg ttgatttttt tttttaact 43440
gtccccaaac actgtgggca gacagtatct agaattgagg cctccacccc tgcagagagg 43500
acgtggatgc tgagcagtcc ccgagtgaag attataaaga agcaaataga gtacacgtgt 43560
ctgtgaactg ttcttgagtc tcccaaattc ggggtacttc tgttcagcta taggaaaagc 43620
ctcaaactgt ttatactttg caagaattgg aaacttctaa ttcaagttaa gttttacgga 43680
atgcatggta agcttcatag gagcttcatc ttttatctgc ttggactttt gcttctatag 43740
gttttgttaa aggccttcat agcgaacctg aagtcaagct cccccactat tcggcggaca 43800
gctgctggat cagcagtgag catctgccag cactcaagaa ggacacagta tttctatagc 43860
tggctactaa atgtgctctt aggtaaggtg gaggcataca ggtggaaggg tctccagcat 43920
gtattcatga tagacctttg aaataattaa aatcagatga tccctcagct tctagaccag 43980
gctatttggc actggttgac tgaatgtgaa ctgcattggg actgctgtga gcacgcatgg 44040
gtctctgtga ccctgcagat gcagccatgc ccagggacac ctagctgggc agtgggtgtg 44100
ggctggtgtg agccctgcct gccacccagg gcctggtcct ccgtctgtgc cggccctgac 44160
tacggtgagt ctgtgaggct tgagactgtg ccttgggtcc ctgtgggttc tctgtaggtc 44220
agttgacagt ttctcctgtt gtttgggtaa ctgtggaaat gaacactggc aagtgctgaa 44280
gtgagcactg gacgcgtgat atggaccctg ccaagccagg gatatgggtg tgtagccact 44340
cccagtgggc ctcatggtgt actcgttcac ggtcatgttt gtgccatatt gatctcttgg 44400
gatctcttct tttttaacaa attaagcggg gaatctccaa acagtgagtt ggatgttaag 44460
atatcttgct gctgccccca caggcttact ggttcctgtc gaggaggagc actccaccct 44520
gctgattctt ggcgtgctgc tcaccctgag gtatttggtg cccttgctgc agcagcaggt 44580
caaggataca agcctgaaag gcagcttcgg agtgacacgg aaagaaatgg aggtctctcc 44640
ttctgcagag cagcttgtcc aggtaggagc acagggttta ctctaggcct ggcatgtgaa 44700
caactgacat ttgaagaact gattactttg gaagagaagc ggcagaaccg agggttagag 44760
gtgtggactc tggagctgtg ctgctcggtt ccgaccctag gtgctgacct ctagctgcct 44820
tccttctgta tgccattgtc accgtgagtc agatgcaggt gatgcctctt caggtgccac 44880
tctgtttcta aaaccagagg tcacgatatg tgttcataca cccagtaaat actgattgag 44940
cacccactgt gtgctcgggt ctggggtagg tgctgggggt cctgtggtga atatttccgc 45000
tgcagcctct gccctgtgga gcctgtggcc tggtgcactg gtcgaggcag ggtggtatgc 45060
cccctcaggg aggtggggac gtggtccttc ggggtgtcag aacaaaatgt tggaacttct 45120
ctttccaatg cagagaaacc ctgcagtaat tctaatgtac tgtgattggc agttgacttc 45180
agttctttgt agcgtgctta ctcaggttat tttcactaac tgtgtaacag tgcagcctca 45240
ttttaagcaa ttgaattttt tgaactttac ttaaaatatt aggtcagggt ttttattgtg 45300
cttaacatgt gccatttagc taaattttgt aggatataaa attgtaagtg acttaaaatg 45360
attcttgcat agaatcatga attgaagata atgctaataa tttaagcact gagttaggta 45420
gtgtttgtga agtgcttaga atgcttcctg gcacatgtga aggccatgta agtgctgctt 45480
attgataaac agctgagcaa gagtgaactc taagaaatga atggggctga gagttctatt 45540
ccacccagct gccctttggt tattttacag aataaaagca gagtctcatg ggatatgaca 45600
tttaattata tttccttcac aaaaaacact gctgaatatt ttgtggagta aaaagggtgt 45660
agccatggca ataatacatt taaaatatag tttatttcat ctttacctta cctgtttttt 45720
ttttttaagc tagctttata ttgagaattg catacatgca aaagtatcaa gtcatgacca 45780
gttacatttc atttataatc ctacttctcc cttttttttt ttattatttg gaagcaaacc 45840
acaatcatcc tcttacttca tctataggta tttcagtatc tctatagatg aggactcttt 45900
tttattttta aaacttaatg atggtcaggc gcagtggctc atgcctgtag tcccagaact 45960
ttgggaggcc aaggcgggca gatcacttga gcctaggagt ttgagaccaa cctgggaaac 46020
atggtgaaac cccatgtctt taaaaaaaaa aaacaaagtc agccaagtgt ggtgatgcat 46080
gcctgtagtc ccagctactt gggaggctga gatgggagga tcacatgagc ctggaaggtc 46140
gaggctgcag taagccatga ttgtaccact gcactccagc ctggttgatg gagcaagatt 46200
ctgtctcaag aaaacaaaac gaaactccaa aacaatgtca caaaacagtg ccattgttag 46260
acctgaaaat attaaacatt tcctacatca aatacccact aactcattgt caatttttct 46320
ctctactctt ttggaatcag catataaata aaattggttg ataaggattg taaatctctt 46380
tgatcaactg gttctcctcc atccgaattt ttttttccct ttagagttca tttattgaga 46440
aaccagatta tttgtcttct aagttttcct gtggtctgat atactgctta catctccatt 46500
gtgtaaatta acaccttttt ctgttctctg tatttcctgt acatcaataa ttggaggaaa 46560
aacctggtca gatttagtgt atattttata tctgagttca gtatttcgta tataatattt 46620
taaggtaaga gtatactctt ttaaaaagtg ttgagactat atgctcaatt ttttttaaca 46680
gatgcttttg aaaaggctgc ttgatcataa aagtttagag accattggtc tgttgggaga 46740
agcaaataat tacgaaacag tttagcaagg ttaaggtgca catggtaggg cctggagagg 46800
ttcagtcgtg agccgtcact gatgggcacg tggaatctga cccggcacag agagctggga 46860
gaagacagga gctttataga cagaaaacgt ggtctttgcc aagtcccggg agtgaaagag 46920
tgagagaatg ctcacagcac atgagtgtgg gtgcgtagac agagcaacgg tgggtcctga 46980
aaaggcctcc aggctttctc atagattagc aagagtgttg gttatggagg tcagaaggag 47040

```
gtcgaaactg tgttaaattg ggattgcagt aatcctggaa ggacagagat agagggtgaa  47100
ggggaaaaaa gggtatggat gtgagactta attgctgatt ttcttaatac ctttctccaa  47160
agtaaataaa tgatatggca catttttgaa ctagcaaact ctagatatga ttatctgtat  47220
aacatatctt actccatctt cttttgacta ataactgttc ttaattaaat tactgtgaga  47280
tgttcaattc agcaaatgta gtttggctaa ctatatttaa ttagaattta atataatcct  47340
aggcctggcc aaactattaa gcaagtgtgg gcaaaatatt gataatttta gatatgcagg  47400
agctcagttt ctttctatgt gtgctttttg aaaaagaaag aaattgaaaa atagaggaag  47460
ccctgaaatc caagaaacaa agtctctcat ctaggcatgc aataaaagca attctaggat  47520
gattgttgtt cggcatgtag tttgttagaa aacattcttc ttgaataaat agtatgccta  47580
agaaagtggg cagagggaag gcatatgcat atattattaa caaggaggga gaaaaaggca  47640
attagtaacc atccatagga gagccagcaa gatttataaa ggaaatttgt gatccaagta  47700
tgaagcaaaa taagatgcat aataaatttt aagcaagtaa tagattacag taagagaacc  47760
catttgacca ttaattttgg ggcattttct ttcaaatgac atggagtagt aatgaaatat  47820
ttctttcttt ctgagtctag gttattgtga ctggactcag aaagaaagat ttcattattg  47880
cagtgaataa catttttgaa cattattcat aaattatgca gtgaataaca tttatgaaca  47940
catgatacat aagatacata ctgtttattt ttaattaagt ttttcagctc aacttctcgg  48000
cagggaacat taaatgtaaa tagtgttacc tagtagcatg taaatggaaa tctccatagt  48060
atgaaagcag tgctgttgct aacagaattt aggaggcgac agatgaggtg aaggaaatgt  48120
gggtgccgat ttccttatta cattgagagg agccaggaga ttctttgttc aaaatagatg  48180
gcttaagaag tcaaggtata agctgattac ctagagcagg tacccacaaa tgttttgtgt  48240
aaggggccag atagtaaata ttttcagtct tgcaggccat tccaagtctg tggcaactag  48300
gccccactac cttcgtagca cgaaagcagc cacaggcagc ccataaacgt ggctgtgttc  48360
cagtgaaact ttatgtacaa aagcaggtgc gggccagacc tgacctgtgt actgtggttt  48420
gatgacctgg gattcagggg tataggagtt accatcagag gagctgaaag tgagactttt  48480
tactttatac tcttctacac tgtctgattt tttaaaaaag aaacatatgt attttataat  48540
attgaagatg gggttggcaa atagcaaata aaaatacagg atgccagtga aatttgaact  48600
tcagataaat tatgagtaat tttatgatgt aagtatattc caaatcctgt gggacataca  48660
ctacaaaatt atttgttgtt tctttacaat ttaaatttaa ctgggtgccc ttgtctttta  48720
tctggcaact ctaattaaag ggaaaaagaa taaattcatt atgttcatat aatgtgatac  48780
agcaggggtc cccagccccc acgctgcgga gcggtattgg tccatggcct gttaggaact  48840
aggctgccca gcaggaggtg agcagcaggt gagctggcat tcccacctga gctccgcctc  48900
ctgtcagatc agtggcagca tttgattctc atagtgcaaa ccctattgtg aacagcacat  48960
gtaagggatc tagattgtgt gctccttatg agagtctact gcctgatgat ctgaggtaga  49020
acagtctcat cttgaaacca tcccctggcc ctgtggaaaa attgtctccc atgaaaccag  49080
tctctggtgc cagaaaggtt ggggagcact gtgatatagt attgaaagtg ctgataaatg  49140
tggctactgc ctttaaaatg tctggtagct ctttctcagt ggcactcata atagtgtttt  49200
ttgattttta aatgtgtgtc aagctaactc tcccctcagt gtatgctgga ctttattttc  49260
cctttcctag tcaccagttt tgggaaatag agatcttcat tctcatgctg cttctctagt  49320
ggaagtgctc catttatttt taaggaatga atataacaat gaaaaaatca tgggaattca  49380
gaaaacaaca tggaaggtaa cgatcacatt ggtagaagtg atagggaaat atttaggggg  49440
```

```
agaaattaag gtgtaaactt tgccaacgaa gtcctgttaa aaaaaaaaaa gtgaagctta  49500
ggatgcattt tataaactct gaccagaaca cctgtgtttc tctgtttcta ggtttatgaa  49560
ctgacgttac atcatacaca gcaccaagac cacaatgttg tgaccggagc cctggagctg  49620
ttgcagcagc tcttcagaac gcctcccccc gagcttctgc aagccctgac cacagtgggg  49680
ggcattgggc agctcaccgc cgctaaggag gagtctggtg gccgaagccg tagtgggagt  49740
attgtggaac ttataggcaa gttattagta aggtctactc ttacagttaa cttttcagtg  49800
atactagtta ccctctattg atgatgggcc tgccctgtgc taagcagtct gcattgcatc  49860
ttccttgcca aaacttataa tacagatttc atctttattt tataaatagg ggagttgggc  49920
tgggtgtggt ggctcaggcc tgaaatttca gcactttgga aggatcactt cagcccagga  49980
gtttgagaca gcctggccaa gtgagaccct gtctctccaa aaaaaaaaaa aaaaacaaaa  50040
actgggcatg gcggcacgtg cctgtagtcc cagctgcttt ggaggctgag gtggtaggat  50100
tgcttaagcc caaaaggttg aggctgcagt gagttgtgat ggcagctgca ctgcagcctg  50160
gtgaccgagc aagatgctgt ctcaacaaaa tttaaaaatc aaagaagaga attaaagttt  50220
agaaggttag gtggcaaaat gaggccacac atttaaagcc cctcctcctg attctttctc  50280
taccttgact gcctcctgtg gtggttcagt tgctgagaaa tgaaaacagt agggaaggcc  50340
gggtgcggtg gctcaagcct gtaatcccag cactttggga ggccgagacg ggcggatcac  50400
gaggtcagga gatcgagacc atcctggcta acaccgtgaa accccgtctc tactaaaaaa  50460
tacaaaaaac tagccgggcg ccgtggcggg cgcctgtagt cccagctact cgggaggctg  50520
aggcaggaga atggcgtaaa cctgggaggc ggagcttgca gtgagctgag atccggccac  50580
tgcactccag ccggggcaac agagcgagac tccgtctcaa aaaaataaaa acaaaacaaa  50640
acaaaaaaaa aaaaaaaaag aaaatccatc tgtccccagc tctgcatctg cctccactgc  50700
ccagtctgct cctctccatg cgcttggggc tgggccctgt cccaccatgc agtgctgccc  50760
tggagcagtg agcttagtgg gtcctttctg gcatgagagc tgcctttggg agctggagtg  50820
ggtgggaatc tctgaatccc agcctctacc gctgggtctg gtgcctagca ggctatggat  50880
aagcttttgc tgactctagc ctcccctagg ccactgcagc gtggtcggtg tagtgcactg  50940
cgtgtgcagc atggccttta ctcacagcct ccacattaga gagaatctga ctgaagtctc  51000
gttgctgcct cgtgtgagca taaatgtttg ccggaaccat gagcaggaaa tattaatctg  51060
ccttgtttcc tgtcctttac actgaagaat ctttttctgt atgggatgca tgccttacaa  51120
ataatgagtg gaaatactca tcgctaatga aaagttatac ctgattgtta gtctaccaaa  51180
taatctgaga tttctaatac ttttaatttg gcttttaaaa tgcaatttat cttagctttt  51240
ttgacttctt aggtcatatc tttagaacta tgtatttgaa tgttaatgta attttcatat  51300
tgaaattaaa atgttgaact gtgatgttaa gtgcttcctg tggaaataca ttcacatttg  51360
attcaacttt gaatcaagct gtttgaagat tttcacattt cttctagatt ttatcagctt  51420
gttactttat ctgtcacttt ctgtgattta cagctggagg gggttcctca tgcagccctg  51480
tcctttcaag aaaacaaaaa ggtgattatt tcagaaatca gagtcttgtg ttgaatctta  51540
ctgatttcct tgtatttctg taatgtaatg tatcttgtat ttcttgtaat actgtattgg  51600
actctgtgta tgtatatatc ttctcagtgg agtgattgta tgtgtgaatg ttgctggaat  51660
ctgataacaa ggcctgaata gttttatagg gtggctttta acagttactt tcatatcaga  51720
attgctttgt catacatttt gaatgcatca taaatttcta atgttcgggg tcagcagact  51780
```

```
ttttctgtaa agggacagag tgcaaacatc ttagctttat gagccatatg gtctcttttg  51840
caaccattca gctctgccct gtggcaggaa tgcagttgca gacaatacac gagctactgg  51900
ccagccatgt tccagtagaa ctttacttac aggaacaggc aggctgtagt ttgcccatac  51960
ctgccttagg gaatgtgttg ttatatttta tgaagttaac ttaccttccc agtgaatttt  52020
gtttagcatt agtcaggaat attattaagt agcttctttt ccagcctggg caatgtcatg  52080
agacccggtc tctaccaaaa caagaccaaa caaaaaaaca gccaggcatg gtggcatgtg  52140
cctgtagcct cagctgctgt tctggaggct gaggcaagag gattgtttga gcccaggagt  52200
ttgaggtcac agtgagctgt gatcatgcca ctgcactcca gcctgggcaa cagaatgaga  52260
cctcgtgtcg ttaaaaaaaa caacaaaaaa agtttccttt gttggactgt tttaatttgg  52320
acctggttat catttttcag ccatatctaa ctttgtacat atcagaatgt tctgataaag  52380
cttaactttt attaaagtgt ttctgatagt tttggtacac attatcattt gcaatgccag  52440
ttattttctt ttccagtggg gatttgcata ggaaaaaaat tgctgtcact ttctattttg  52500
aaatcttaaa agactgatcc ttttttgtgt catgatttga gtgtttaatt gagagcctaa  52560
tgcctaatat tatttgcagt attgaatggg atcttaacag gaataacatt ctagccttca  52620
ttgaattaag taaacatttc ttgaaagaac ttggaatcta taatatttgg gtcatcacag  52680
tatgagatac ttaatcaaat ttgagatttt agtgaaacat tgttgaaaag ccaaaaagat  52740
tctaggaaaa attcatctct atattcttga attaggagag attttcggac ctgtgactaa  52800
gttactctga cacttgtttg tttcttagtc actcttccca gtggcagtga aaaagaagat  52860
gactggttca cattgttgag attagtttat cctcttctgg ctaggacatg ggatatatcc  52920
tgtctctttt aagccctttt ggtatttttt cccccattta gagctgtgtc ttcaaactgt  52980
tttgttatag ctggaaaatc cttttttttaa gtgaaatctg cccaaattat aagacagatg  53040
aaagtagagt tgtgttggat ataggattag ggtgcaagtg gcgggggtgt cctggagcct  53100
ctcttctgag ggcagcctag cgcttgtgcc tttgaggaaa ttaccctggg gatggtctat  53160
ggaacatatt tgcaaaccac tgatttgaaa gatagagatg gcttttgtta agatctgaat  53220
tcaccttttt ggcattttat ttgatttctc aagggaaaga acttattttg taataaagtt  53280
tccttttatt tagtagatag gccaagttgc tgtgttaatt taacctagag tttgggtttc  53340
ctttgctaat ttttttcacc tttaatgtca catcattgta aatttgtgga agttatactt  53400
ctgacttatt ctttgaagag cagaaattag aaatttccaa taattatttt gatagtgtca  53460
tttaatgaca ttaatatgta atgtagccac aaagatttaa tgagttcagt taagtcatat  53520
taagactgtt ggtttcattt gttttcatta atgtaattct gaagatgaac aataaaatgt  53580
atttttagaa ctttcaagtg aaatattatt tcatccttcc agatcatata atgcttgagt  53640
tctgattgtt aatcataaag tcaagaaaat taaaagataa taaaatgaaa gtgactttta  53700
ggtgttagag ttttatgtac aaattctggt gtgtcattgg agctatcaca tgaatatttc  53760
aaaggccaat agcattgggt ctttacagtt aaaacttact atttttaagt ttaagtagta  53820
ctatagatta tttaataatc gaaatcaata aatattaatt attaaaatgt tttgtggtat  53880
actttgagaa tcattgcttt taactttttc catataggtt tattaacttt aatagcattc  53940
taaacataac atctctacat tctttgtgtt taatactgta gaggtataaa aatacttata  54000
tatgatgata aaccatatta gagtaaatta aatattctta tgagtttcat tttagagtgc  54060
atttacttaa ttttgaaatc cttattttta gcaaactaaa ggaatgttgg tacattattt  54120
actaggcaaa gtgctcttag gagaagaaga agccttggag gatgactctg aatcgagatc  54180
```

ggatgtcagc agctctgcct ttgcaggtag ttctcactag ttagccactg atgtggacct 54240
tcactctctg ccgtccaccc catgcccttc ctgcctgtcc ccctgcacct ggtggacagc 54300
acaactgggg gcagcagtgg acccaggttg cttaaatggg ggatatttgg gcttctttca 54360
taatacttac tctgaagctt gtgtgtctgt ggtgtttgca tcatatattt gctgttttct 54420
gtggtttaga ctgttttaaa attaggttta tgctccttga gcatagggct ttgtgagtag 54480
ggatggcacg ttgaaacgtc tcatgagttg gatgggttat gctgggggtt ggaaatggga 54540
tgaaaaattg tgggatgaaa aattgcctat ggatagttta acttgaaaga atctgccttt 54600
gtttacagat agttatcttt tttttttttt tttgagataa agagtctcac tctgtcaccc 54660
agtgccgata cccaatgtca ctggcatgga gtggtgtgct cttggcgcac tgcagcctcc 54720
gccttctggg ttccagccgt tctcctacct cagcctccca agtagctggg actacaggtg 54780
cccgtcacca cggctggcta agttttgtat tttttgtaga gacgaggttt taccatgttg 54840
accaggctgg tcttgaagtc ctgacttcaa gtgatccgcc tgtctcagcc tcccacagtg 54900
ctgggattac aggcgtgagc cactgtgcct ggccagttac agacagttat ctaatgaaat 54960
tctctgtgta ctttataaaa gataaggatt aacttaaggt actaataact ggattatatg 55020
agggtggttt tggttgtata atcctatcta aaagaatatt ttagctgtaa ctgaaagtaa 55080
gacttaaata tttagggagg aaaatctgaa taattctagt agtaattatt tacaaaataa 55140
aaatagattt tatttttgat tacacaaatt aaacaacaat aaaacatcac agcgatctag 55200
actagtataa aggtcacacg cttaccaacc caaccgcccc aggagtgacc actgccaaca 55260
gcttcgtgtt gacctttttg ccatgatttc tatatagtct tttttgtttt taaatggtaa 55320
ttaaaaaagt caactaggaa aatgtgttag aagtttatct tccaggagaa taataggact 55380
ggagtcgaga tcttgaacgt ggcttggaag aaggcaagcc caccccagag agattacagt 55440
tgttcgggac cactgcttgc ttagaggacc tgcgtgtctg ggaccgccta gttttgtgcc 55500
cctgactagg ctgcccctta attacgaacg tctttataaa ttgccctagc cagggcttgg 55560
agtagttggt taagaacttg aacttcagtt tttgcagtga aacaccgttt gagaatatta 55620
ccttctgata agccttattt tattaagatg ggtactgtag cgagaggcag tgtgagtggt 55680
acatgaggga tgcactgctg tcctgcattt cactgtcttc aggatgctat gcagtgatga 55740
catttggaaa catttcatca aacattccat caaatggaaa cattggatga cagtggaact 55800
ttgtgttatt ttgcaagcct ttgattccat attgaatgtt ttctctcgcc atttgacaaa 55860
tgagtgtttc tctgtcttca gcctcagtga aggatgatat cagtggagag ctggctactt 55920
cttcaggggt ttccactcca gggtcagcag gtcacgacat catcacggag cagccacggt 55980
cacagcacac gctgcaggcg gactcagtgg atctggccag ctgtgacttg acaagctctg 56040
ccacggatgg ggatgaggag gatatcttga gccacagctc cagccaggtc agcgccgtcc 56100
catctgaccc tgccatggac ctgaatgatg ggacccaggc ctcctcgccc atcagcgaca 56160
gctcccagac caccaccgaa gggcctgatt cagctgtcac cccttcagac agttctgaaa 56220
ttgtaagtgt gcggaggggc ctgccatctt ttattttta tttgagacag agtctcactc 56280
tatagtgcag tggaggccgg gcacagtggc tcacgcctgt aatcctagca ctttgggagg 56340
ccgaggtggg cagatcnnnn nnnnnnnnnn nnnnnnnnnn nnnnnnnnnn nnnnnnnnnn 56400
nnnnnnnnnn nnnnnnnnnn nnnnnnnnnn nnnnnnnnnn nnnnnnnnnn nnnnnnnnnn 56460
nnnnnnnnnn nnnnnnnnnn nnnnnnnnnn nnnnnnnnnn nnnnnnnnnn nnnnnnnnnn 56520

```
nnnnnnnnnn nnnnnnnnnn nnnnnnnnnn nnnnnnnnnn nnnnnnnnnn nnnnnnnnnn  56580
nnnnnnnnnn nnnnnnnnnn nnccacccat cttggcctcc taaagtattg ggattatatt  56640
tgtgagctac catgcccaac cctactgtct gccatctttt gagctcttcc ctggagaccc  56700
agacctgaac cctcctgctt gttctcttct tgtctaatac ccctaatgac agcgcagctt  56760
agatcactag tggagagctt gacctcatct gataccttca ctgaagggaa cagcttagtg  56820
tcttttccac tgaacactga ggtaaaaaat tggaatagtt gattatgtga actctgctaa  56880
aattgagtgc attttacatt ttttaaggcc tttttaggcc ctggttaaat aattattttt  56940
aaaaatcctg aaggagccta ttataaacag atctgtggtc ttaatgaaat gtgattaata  57000
ctgtgcatta ttttaagaac ttttgacttt tcaaaaaact tttacaacat ttcccatttt  57060
atagcagcat aggtgtaagt acctctcatc cctgagttag tggacaagaa accctcatgg  57120
atagtctaat aacgtttggt acaagtctat gttgttttat actccatttt attttcagtt  57180
ttaaaaactg gttaaatatg tgtaacataa aatctacctt cttaaccatt ttttacgtat  57240
gcagcttgct ggaataaata attaaataat gtcatggaat catcgctcca cccatctgtg  57300
taacctttttg atcatgtgac actgaagctc tgttcccatt gaactctcta ttcctccttc  57360
cccgccaagt ccctggcaac caccattctt ctttctgtct tctgaatttg actactttag  57420
gttctcatat actttagggt cacaccgtat ttgttttagt tagcataacg tccgcaaagc  57480
tcatgcatat tgtagcctgt gttgaacttc ctaatgtttc aggccaaatg ctattccatt  57540
gtatggatag gccacatttt gcttttccat ttctctgtcc atggacactt gtattgcttt  57600
catgctttag ctattgtgaa tcgtgctgtt atgaacatgc gtgtacaaat gtctcctgga  57660
gactctgctt tccatttttt tggctaaata cccagaattg gagttgcttt tacattctga  57720
ttttaattta aaacatttat atcattgagt gttttactta atagtataat agttagcaaa  57780
ctaatatttt ggtaataatt tgctggtagt tttagagtcc attgctcagt ttttttaggt  57840
aaattacaca ggacatttca agtggacgtg gaacaacttg tgatatggaa tcatgcccca  57900
agctgatggc taaacatacg aaataccatg ccctaaattt agtagattta gtctttgcaa  57960
tttaggagat aacctgttat attgttaggt ttttgtctaa aagctttgtc ctcatatttc  58020
caacttgctg taaaatttgt tcgtgaagac aaatattttt gtatgggttt tttcttttttt  58080
atattaaaaa gaaatgtcca cattggaatt tttttggagt ttttagagct aatagagctt  58140
ttcataatgt agtgggaatg agtgatcagt aagctcttag cagtttccat gcacacattt  58200
ctgtgcattg aaataaatga cagatgagta catttgtgtt ctgtgtgtaa aacgtgctct  58260
ttcttcgttg catttccatg ttggagggct tgtctcttgg tgatcacact tcaaaattct  58320
cacagccccc cttgaaccgt ttaggtgtta gacggtaccg acaaccagta tttgggcctg  58380
cagattggac agccccagga tgaagatgag gaagccacag gtgttcttcc tgacaaagcc  58440
tcggaggcct tcaggaactc ttccatgggt atgtggacca caggtgacgc gctacaaagt  58500
ggtcttgtat tcaggcctgg acatcttaat tatatctttg ctctcaagaa gaaatccttt  58560
gatattgttt tctgagttct gaatagctga tgaaaatgac caattgagga ataatcatac  58620
tttttcttca tctaaatctt acgcttttga gttatcttag cataaatgta taattgtatt  58680
ttaagtggaa atttgtcact taatcttgat ttctctgttt ttaaagccct tcaacaagca  58740
catttattga aaaacatgag tcacagcagg cagccttctg acagcagtgt tgataaattt  58800
gtgttgagag atgaagctac tgaaccgggt gatcaagaaa acaaggtgag ggacataggc  58860
ttgagacaac ttggtgtttc tgagcttgtg tgaggattta aaatcgccct ggctactatc  58920
```

-continued

```
tactttattg ctttcccatc cctgggcctt taaatttccc ctttaaatac cagctcttcc  58980
caggcctgtt gttttccgcc tttcaggtgc tactgacagc gttaagaatt gcctgagttc  59040
tgcctccttt gagagtgtgc cccagagaaa tctattctgt actgagtgtt tccttgtctg  59100
atttcttggg ccattcattt gatggctgcg tatggccttg caccatgttt tggttctatt  59160
gaactgtttt aaaagtctct gtttatatta cctttttaca tgtaaatgta actgtcttca  59220
cttttaattg ctcaagggca aggaatagcg tttcacagtt tctcccagca atcagaatta  59280
cagcctttgg catctccctg tctaccaggc ccagttcgtc ttagctttgg gcttccccag  59340
gctgttacct ttccctgagt agcttctgct tgtcctgtag aagaccactc atgctttgct  59400
tccagagcag ccttttctga atgcctggtg tcaggtgcct tcttactgtg cccaccctcc  59460
ctgcatgctg catttatccc ctgccacagc cctgggaccc tgtgtccagc tgcctctgac  59520
ttgtctgttt ctgcttggtc atggtctctg tgaggtcagg tgtgcatatg agcacagacc  59580
agggcatctc tttatcccca gcacccagtg taagtgctac tctaggacta tttgttgaat  59640
gaactaatgc atgaatgtat tggttgagta tgagacaaac aagtgtcact gtctcctttc  59700
tagccttgcc gcatcaaagg tgacatcgga cagtccactg atgatgattc tgcacctctt  59760
gtccattgtg tccgcctttt atctgcttcg tttttgctaa cagggggaaa aaatggtgag  59820
tacaaaaggg gacgtgcaga gttgaaggaa ataactaggt ttcagaggtc aacttggtgc  59880
ccgtttagta ctgtgtgtag cagaggcagt agaatctgag gatgagtttg gttttcacta  59940
gccaagggga agggaggaaa tgatgggagc aggtaggtta ctgggtctgg ttttgttcat  60000
ttgaaaacaa tctgttgttt gaggctgaag gtggcttggg tgatttcttt gcagtgctgg  60060
ttccggaccg ggatgtgagg gtcagcgtga aggccctggc cctcagctgt gtgggagcag  60120
ctgtggctct ccacccagaa tctttcttca gcaaactcta taaagttcct cttgacacca  60180
cagaataccc tggtatgtta aaagttcaca tcttattttc tcagatttaa tcattattgt  60240
aaaaacgatt tcagtattga ctattttagt tttagagcgg tgttttgagt ttatttggga  60300
ttttttttt tttttgagac ggagtctcac gctgttgccc aggctggagt gcagtggcgc  60360
gatctcggct cactgcaagc tccgcctcct gggttcacgc cattctcctg cctcagcctc  60420
ctgagtagct aggactacag gcgcccgcca ctgcgcccgg ctaatttttt gtatttttag  60480
tagagatggg gtttcactgt ggtctcgatc tcctgacctt gtgatccgcc cgccttggcc  60540
tcccaaagtg ctgggattac aggcttgagc caccgcaccc ggcctatttg ggatatttga  60600
cccgcgttgt agctcttcag aaaacacatg aatagtgaag ttctttgttt catggtttct  60660
ctttagatga aatccgtaga ggaaaaaaat agaaacctca gcacgtaaga gccaacttat  60720
atacgcatcg gatttaaacc taaagcacaa attgtgcatg gtcacggtgg cgctgagtca  60780
cactcagcca ggccaggcat tcacactcag ggtgagtggg caccaggact ggctgaggca  60840
gcagtggacc cgtgtctgca ccctgcccat gcttattgtg gagccttctc gctcgctctc  60900
tttctttggg tgagagggta cacttgtgtt tttgaattta tatgaggtaa gggtttatat  60960
atagggtttt ttctaatctt tttttaagtg gaatctggaa ttttaatcag atttactatc  61020
tgacagccta gaattataat ccagaaagtc tgtggtattg aggacatatt ggcaatatga  61080
tgaatctgta atccttaaat cctgaaactt tttttttttt ttaatcactt agggttatta  61140
tagtgaagtc atttctgaat ttggatcttc tcttcatacc tctttttctc tttcctgaga  61200
attaagcttt tgttttgagt tagaaagttg atagtaggaa attgttccat ggctgggcaa  61260
```

-continued

```
tttatctcca cagaggaaca atatgtctca gatatcttga actacatcga tcatggagac  61320
ccacaggttc gaggagccac tgccattctc tgtgggaccc tcatctgctc catcctcagc  61380
aggtcccgct tccacgtggg agattggatg ggcgccatta gaaccctgac aggtagtggc  61440
cagtttttca gctgtgtttt ttctagatat ccttactaag gtttccgttt ccatgacgat  61500
gtttgtttct gttcttctgt caggaaacac attttctttg gcggattgca ttcctttgct  61560
gcggaaaaca ctgaaggacg agtcttctgt cacttgcaag ctggcctgta cagctgtgag  61620
ggtgagcgcg atctctgtgg agccattgct tcacttagtg ggcattttat cattgctgca  61680
attacaattg gagcttaata ggaaatattt ccatacactc taaagctgta accagtaata  61740
tccaccatgt atccatctct tagctttaga aagaaaacat tgccagtaaa gttaatgctt  61800
cataaacttc agtttaagtt ttaattctca gaatatttgt ttgaaataga cttcttccta  61860
aaggatatat ttagaaataa cctatcatta catgtaaagt ctgttgaata tgctgggcac  61920
ggtgactcat gcctgtaaac tgagcacttt gggaggccaa ggtggaagga ttgcttgagc  61980
ccaggagttc aagactatgg gcaacatggt tgatcctgtc tctacagaaa attaaaaaga  62040
aaaaaaaaaa ttaactgggc gtggtggtgc atacctgtag tctcagctac tcgggaggct  62100
gaggtggggg gattacttga gccccggaga tgaaggctgc agtgaggcat ggctgcatca  62160
ctgccctcta gcctgggcaa cagagtgaga ctgtctcaaa aataatagta ataataatcc  62220
gttgaattaa aaaaaacccc aaaaaccact gtgttaggcc catggtgtag taagagttaa  62280
agtgagcctt agggattatt tactcaacct ctgtgtttgt atgaagtgga atggccccag  62340
ttctttaagt gatagcatgt tgaacctttc cataccagct ggctcgtaag tcacaactgg  62400
ccagtcaaca agagtcaaaa ttaactagta aaaatcaaag caaaaaactt agaattgtcg  62460
aatttgtgcg atacctcccc cttttaaaat gtcatgcctg acagtaattt ttccctagtt  62520
tccaggtttt gtttcagtca attgtgtctg tcttgagcag aaggaagcgt gctaacagct  62580
cagtctcatg gctagctggg ggtctatgtg tcagccatgc atgtgatggt gcccctgggt  62640
gcctgaggct gcaggggagg ggtacagcag taggggcctg ttctgttctc ccgtgccttg  62700
gagtacatag tgatatagtg gggtggtcct tggtgtaggt ccctcgttcc taccctgggt  62760
ctgcgattta tttagaagtg gtgttggagc tgtgcggcag gcccctttgt aactgatcaa  62820
tgtttgtgaa gttgccgttt gagaattgaa accatgacat aagcagaaat ggaagaaaag  62880
aaccagttat ttgaaaggga cacattcact tttaagcttg tatttactga gataaaatat  62940
ataccatcag tgttcttgag aggtgtggga aaagtgcaac atcctggttg cagttaaacc  63000
cagaacgttg tgtgttgaag actgacagtt ctcaaaccgt caagacgcgg gtactgagtg  63060
ggactaacct gctgccctct tgcctcggac cttgtgttcc agcattgtgt catgagtctc  63120
tgcagcagca gctacagtga gttaggactg cagctgatca tcgatgtgct gactctgagg  63180
aacagttcct attggctggt gaggacagag cttctggaaa cccttgcgga gattgacttc  63240
aggtaagtga gtcacgtcca ttagatttca tgaactaagc tcaattgaaa gtcctggggt  63300
cacttggtat aaggaatgat gttatcaagt accctgccca tcagaaatct gagcggttta  63360
ggtagatgac agtgattttc tccccccagt ggctttttgc tgaacctcgc cctatgcgtg  63420
gattttattt tattttatta tttatttaga gacatgatct tgctctgttg cccaggcttg  63480
gatgcagtag cacagtcata gctcactgta gctttgaact ccaggactcg agtggtcctc  63540
ctgcctcaga ctcccggtta gctaggacaa taggtgtgtg ccatcacact ggctaatatt  63600
ttattttttg tagaaatggg gtcttgctct gttgcccagg ctagtctcat ctcctgagct  63660
```

```
caattgatcc tccaatcatg gcctcccaaa gtgctgggat tacaggcatg agccactgtg  63720
cctggcctag aattttaaaa gataaataga agagtagttt tttttttttt tttggatagt  63780
cctagtcatt taagtgttct ggatagtagg aataaaagag cttagaattt ttcatctttg  63840
tcttaaactt tttaaaaaat gtagcttatg ttaattctgc ttgttttaaa agaatatact  63900
catcattata ctgaacctag gtaagacagc tggtttatat tttgttgcaa ttaaaaaatg  63960
tgagctgtgg ttgcagtgag ccaagatcgt ggccattgca cttcagcctg gcgacagagc  64020
gagactccgt ctcaaaaaaa aaacaaacca aaaaacgtga gctgtgttgg aactttcatt  64080
ttctaagagt aaagttttgg caggagaagt tttctgtcag tactttattt tagaagggaa  64140
atttttataa ttcaggtgtt ttgtttttgt ttttgttttt ccccccaagc caccttttat  64200
agagcccttg tgggttattt tatttaatcc ttagaatgtt tataaatctg ggactgttct  64260
cggctccacc cacagatagg ggcgctgagc atgcgtgagt gggcagcaag atagcaggtt  64320
atggagggcc cagctcgccc cttctgtggt ttgagccagt tctgtacggg acttacagag  64380
tgttttgaaa tagtatttat tttgaagaaa aagaaaaaca gtttactgag tgctatctta  64440
ttgagtctgg agttgtgaga ggaatgccac ccctatttgt ttgaagccat cggccttttc  64500
tgttgtcttg agtaagtgct gcccaagggc cttccagggc gcctgactga gcctgctctg  64560
aagcaagctg gcggaaagtg tttactgagt aactaaatga tttcattgtt aaatgtgctc  64620
ttttgttagg ctggtgagct ttttggaggc aaaagcagaa aacttacaca gaggggctca  64680
tcattataca ggggtaagcg gcttattttt gtgagatact gttttacctt aaggaggtga  64740
aagtgaggct ttccttgtgg aatttctcta aatgcattca tcgtatttta gatctgttta  64800
tttcacagtt tatatcatga aagttataat tgtgtcacat ggatttaagt ctagcaatgt  64860
tgagttcttt ctcactagct ttccaaaata tcttacctaa aatttagtca aatacaagat  64920
tatgtttatt tttattatcc ttctctctaa agcttttaaa gctgcaagaa cgagtgctca  64980
ataatgttgt catccatttg cttggggatg aagaccccag ggtgcgacat gttgctgcag  65040
catcattaat taggtattta ccagtatttt atctctttta cttttttggt tgaagtacta  65100
aaaggtatga acatggaaag agagggaaga attcaaagga tgtagagcag tattcctgaa  65160
tctgagctca tttcagctat tctgttctta aactatcaag aaaaaaaaat ccaaaaaagt  65220
ctaaaattat aattaaaaaa acaaaatact aaccatccat tgtaaaaagt aatgcatttt  65280
cattgtaaaa atttggacta tagagaatag cactaagaag aaaaaaaatc accttcaatt  65340
ctgctaccac ctggaagtaa tcgctgttaa tattttgctg tatacttttt atgagtttct  65400
tattcaaaat ggggtcaaaa ttacatgcaa ttgtgtaacc taattttcac tgaatatttt  65460
attagcattt ttctgttatg aaacagtaat tttagttatg ggtcattgtt ttactatgtg  65520
attgtgataa aattttacat aaattttttt tggaaattaa ctattgtaca taaatgtgta  65580
taattttctt tttccgagaa ttcctggaag ttgagttagc agcccaggct ttgaattttt  65640
tttttttttt gagacagagt cttgttcgtt tgcctaagcg cgatctcggc tcactgcaac  65700
ctccgcctcc caagctattc tcctgcctca gcccccccgag tagccgggat tacaggtgca  65760
caccaccaca cccagctaat ttttgtattt ttagtagaga cagggtttca ccagattggc  65820
caggctggtc tcaaactcct gaccccatga tccacctgcc tcggcctccc aaagtgctgg  65880
gattacaggt gtgaaccacc atgcctggcc aggctttgaa tttaaaaaaa attttctaat  65940
agctttatgg cggtataatt tacatttctt gaaacctact cgttttgagt gtatagtaaa  66000
```

-continued

```
cttcaatttt atcacatttc tatcacccca aaggtccttg ggcccattgc agtaacctcc  66060
ggttcccgcc cccattccta ggcagccact catctatttt ctgtccctta agatttgtgt  66120
tttcgtcagg cacggtggct cacgccttta ctcccaccac tttgggaggc cgaggcaggt  66180
ggatcatggg gtcaggagtt tgagaccnnn nnnnnnnnnn nnnnnnnnnn nnnnnnnnnn  66240
nnnnnnnnnn nnnnnnnnnn nnnnnnnnnn nnnnnaccct gtctgtacta acaatacaaa  66300
aattagtcag gtgtggtggc gggcatctgt aatcctagct acttgggagg ctgaggcagg  66360
agaatcgctt gaacgtggga ggcgaagttg acagtgagca gagatcgtgc cactgcattc  66420
cagcctgggc agcagagaga gactctgtct gaaaacaaag atttgtattt tctggacatt  66480
ttatagaact ggggtcatag tataaatgga cttttgcatt tggcttcttt cacttaattt  66540
tgagattggg tcttgtagca tgtatcggta gtttgttcat ttttattggt gagagtatta  66600
tatgaataat accatatttt atctatccat cagatggata ttattgagtt catgttttgg  66660
ccaatttatg aattatggta ctgtgaacat ttgcctacaa gatttgtata ggcatgtttt  66720
catttctctt gagtggataa cctagaagtg gatttttaaa taatttttgg tacttactgt  66780
gaaactgctc ttcagaaaca taccatcgtt tgtcctttct ttcttgtctt tctctttctt  66840
tctttctttc tttctttctt tctttctttc tttctttctt tctttctttc tttctttctt  66900
tctttctaca tagacacatt ttaagaaaaa tttcagtagt ttttggggta caagtggttt  66960
ttggttacat ggctgaattt tggttgcatg gtgaagtctg agattttagt atacttgtca  67020
cccaagtagt gtatcttgta cccaatatgt agttttctgt ccctcacctt cctcccagcc  67080
tcccgccttg tgagtctcca atgtgcatta taccactctg tatgcccttg cgtactcaca  67140
gcccagctcc cacttctgag aacatactgc agaaacatac caaaggatac tcccactgcc  67200
agaatgtgat tgtgcctgat tcttctcacc aataaatatt tcaaaaaaag ttaaatatat  67260
atcagttttt tgggcagaag ttgatacttc tctttatttt ttattttttt ttgagatagg  67320
gtctcactct atgatgccca gactggagtg cggtggtgcc atctagctta ctgcagtctc  67380
tgcctcccag gttcaagtga ttctcccacc tcagcctccc aagaagctgg aattacaggg  67440
gagagccact actgccagct aatttttgta tttttggta gagatggggt ttcaccatgt  67500
tggccagact ggtctcaaac tcctgacctc aagtgatcta cctgccttgg ccttccaaag  67560
tgctgggatt acaggcgtga gctaccacac ccggctgata tttcttttta aaataactta  67620
ccttcttttg aaagtaatac atgttaaatg aacaaaattt aaggaaaata taaaaaagga  67680
aataatcttt ataatgaaac tactgaaaga aaaccaaaat tacattttgg tgcatattct  67740
ttttcgtttt catcattgta atttgcattt ctttgattac ttgtgagaca cacttttcat  67800
ttacttaaag gttcgtatga cttgcctgtt cagaaatttt gcagctttac catttctgc  67860
aaatgatagc aacttctttt tatttttta tttttatttt tatttttatt tttttttttg  67920
agacggagtc tcgctctgtc gcccaggctg gagtgcagtg gctggatctc agctcactgc  67980
aagctccgcc tgctgggttc acgccattct cctgcctcag cctcccgagt agctgggact  68040
acaggcgccg ccacctcgcc cggctagttt ttgtattttt tagtagagac ggggtttcac  68100
cgtgttagcc aggatggtct cgatctcctg acctcgtgat ccaaccgtct cagcctccca  68160
aagtgctggg attacaggct tgagccaccg cgcccggccg caacttcttt ttatttgttt  68220
gtttgtggtg acagagtctc gctctgtcac ccaggctgga gtgcagtggt ggaatcttgg  68280
ctcattgcaa ctattgcctc ctgggttcaa gcgattttcc tgcctcagcc ccccaggtag  68340
ctgggattac aggaatgtac caccatgccc ggccaatttt tatatcttta gtagagatgg  68400
```

```
ggtttcgcca tgttggccag gctggtcttg aactcctggt ctcaagcggt tcccctgtct  68460
cggcttccca aagtgctggg attacaggtg tgagccaccc tacccagcca atagttactt  68520
cttatattcc agaaaaaatt gtactcatga tcaagtctcc atgaggaaaa agactttaat  68580
taaagatatt gcagtttgca gaccaatatg ataaaatagt tgattgtttc taaaagtatt  68640
actgagtaat gatggcagat ataagccctt ttgtttttgt aggaaaatgt tacccatgtt  68700
ctgcatttga attcagttta gatttgttag gaatctcagc ttaagctttg ccatctggga  68760
gtgtttggga caattttgca gacagaattg caaaagtgcc taagggatgc aactggcact  68820
cagacctgct ccttgctcag tactctgtgg acagatgttc agcgcttgtt gatgttgatt  68880
aaaaggttta gaaagagaac tttcaaagtt ggtttttaat taaagcattt aatagtgtga  68940
ataaaaaggg acttaatttt atgacagaca aaagaaagta cagcacctgg cggggcgcgg  69000
gggctcacgc ctgtaatccc agcactttgg gaggctgagg caggtggatc atgaagtcag  69060
gagttcaaga gttcaagacc agcctggcca aggtggtgaa accccgtctc tactaaaact  69120
acaaaaatta gccaggtgcg ttggcaggca cctgtaatcc cgctactcag gaggctgaga  69180
caggagaatc acttgaacct ggatggcaga ggttgcagtg agccaagatt gtgccactgc  69240
actccagcct gggcaacaga gtgagagtct atctcaaaaa aagaaaaaag aaaatacagc  69300
acccagttat gtcagagtgg gtgcatcaga gagtgaccct gagattggag acgatgctgt  69360
cacgtgcttg aagaatgcta cctgagaaag ggggcgagaa gtggtgtttg ctggtaacca  69420
gaggtgttgg cttagccacc tgcagggagg gtggtctatc acaggtgagt ttcatctact  69480
ttcttaagca aatcaacctt acttttgtgt taggcttgtc ccaaagctgt tttataaatg  69540
tgaccaagga caagctgacc cagtagtggc cgtggcaaga gatcaaagca gtgtttacct  69600
gaaacttctc atgcatgaga cgcagcctcc atctcatttc tccgtcagca caataaccag  69660
gtatgctgac ccagtggcgt cctcacattg ttgggaaaat gccctttcct gatgcctttc  69720
tttaggcttt aattgaaaac attttatttt ctagaaaaaa gctttagctc aggatgtttg  69780
agtgtaggtc attcctttga taggatattg tcattctgag gattgaccac accacctctg  69840
tatttaagcc ctgccacaat cacacagctg tgacactata aatcttttaa tcgtttatta  69900
catttaatgt gctgacagtt atatttttgt gtgtgacact tacgtattat ctgttaaaaa  69960
attttcactt tagttgtgtt acctttaaag aggattgtat tctatcatgc ctgttgattt  70020
gtaggtgagc gggctattaa agtcagtgtt atttagggct atccactagt tctgtgattt  70080
gcaatgactc tccttcacat ttgttgtgga gcttttgaat atagcgtcaa atggccacat  70140
atatcccatg cttacctgat tcttaggtga gtaggacaga gtgctttaat gaagctataa  70200
tcttcagaat tctagcttgc aaaggagatt gcagaaggat aagacttgtg cttttcaatt  70260
ttgtctttta aatgttattt taaaaattgg ctttatatga tactcttttt ctgctgagta  70320
acggtatttt acagaacttg gactagatga cttctaagct taaatgatca cttgatgctt  70380
tttttctgaa ttaggaactc agcttacaca tttcaaagtc ataattcctg aatacataac  70440
atcttttttt catgtaaaga ctgctttaaa aaacacatgg aaggtcgggc gtggcggctc  70500
acacctgtaa tcctagcact ttgggaggcc caggcgggca ggttgcctga gttcaagagt  70560
tcaagaccac cctggacaac atggcaaaac ctgcctctac taaaacataa aaaattagcc  70620
gggcgtggtg gtgggcacct gtaatcccag ctacttggga agctgggga tgagaatcac  70680
ttgagccctg gaggcagagg ttgcagtgag ccaagatggt gccattgcac tccagcttgg  70740
```

gctacagagt gagactgtgt ctcaaaaaaa aaaaaaaaaa aaaaaaaaag ccacaaaaca 70800
acaacaacaa aaacacacgg aaacatttta tttggccacc ttagtatttc cccttcagat 70860
aattcctttg tttaaactca gaactggcat tttctctctt tgaaaagatt caggacaaat 70920
actcctttaa gataagcaga aacagtgaaa gagtatttga ttatcaggaa tttgataggc 70980
ttagaataaa ttgttgcttc ttaatgtcat ttcagaagat gaatattaat agatgccaac 71040
tgagatatca ttaaaattgg ttactactac tttgaaaagt ttcccagttc caaacttcag 71100
caggcctctt cacaattcaa cagtgcttaa ttgggacttg tgtgatagat acgattccca 71160
attgtgtagc agagtgtgct gcttagctac ctattctgtt agcattcgtg tgttaactta 71220
aaatcataat ctccttagtt ttgttgagtg tctctgtgga tgagacactg tgagggatac 71280
aaaatcagat tggctttatt caaaccattg ggtattattt tttatttttt gccttttttc 71340
catgtgttct aaaggaatta gagtttgaat ataactataa tgggggatag aaatttacat 71400
gtgccatgaa gggaatgcag aaaagtgcca tgggagctca gaagtggaga aaggaatttt 71460
ttttcttgga agcaggagta acttcatgaa gcatttattt caacttagag atagtaggca 71520
atgctgtaag gggagtgtgg ctgcagcgaa agtgtttggg gcagactggg aggaagggag 71580
ggaataaatt cagccattgt tatggcataa tgatcaaaat ttattttcag cccctctttc 71640
acttaaaagt tgagactgct taacttcttt taatctttaa tcttaaactt ttaaatgcca 71700
tttgatcttt aaaaagatat gttttaatag tatattttaa gtctctgtat ttttcttatt 71760
agaatataca gaggctataa cctactgcca agcataacag atgtcactat ggaaaataac 71820
ctttcaagag ttattgcagc agtttctcat gaactgatca catcaaccac gagagcactc 71880
actgtaagtc tctttcttga ttggtcttaa tgaaattata ataattttc gtgacttgta 71940
tggccagtta gttttatggt catcttatgg tgaggtgctt gtattagagc tcttacttat 72000
ctgtggggct tgctaagaaa ttgtgtttct gtgaaaagga tcttagctta ctccaggaat 72060
gtaaataact atttttttct gattattaaa gtaatacatg ccaaaagtta aaaaattcag 72120
ccaatttagg aagacataaa aatgaaaata agccaggcgt ggtggctcac acctgtaatc 72180
ccagcacttt gggaagccga ggtgggggc tcacttgatg tcaggagttc gagaccagcc 72240
tggccaacat ggtgaaaccc atctctactg aaaatacaaa aattagctgg gcatggtggc 72300
gggcgcctgt aatcccagct actcgggagg ccgaggcagg agaatcactt gaacgtggga 72360
ggcagagctt gcagtgagcc gagatcgagc cactgcactc cagcctgtgc aacagagcga 72420
gactttgttt ccaaaaaaaa aaaagagaaa gaaaactact gtcacctgca tnnnnnnnnn 72480
nnnnnnnnnn nnnnnnnnnn nnnnnnnnnn nnnnnnnnnn nnnnnnnnnn nnnnnnnnnn 72540
nnnnnnnnnn nnnnnnnnnn nnnnnnnnnn nnnnnnnnnn nnnnnnnnnn nnnnnnnnnn 72600
nnnnnnnnnn nnnnnnnnnn nnnnnnnnnn nnnnnnnnnn nnnnnnnnnn nnnnnnnnnn 72660
nnnnnnnnnn nnnnnnnnnn nnnnnnnnnn nnnnnnnnnn nnnnnnnnnn nnnnnnnnnn 72720
nnnnnnnnnn nnnnnnnnnn nnnnnnnnnn nnnnnnttta gtagagatgg ggtttctcca 72780
tgttggtcag gctggtctca aactcctgac ctcaggtgat ccacccgcct tggtcaccca 72840
aagtgctggg attacaggcg tgagccacca cacccgtctt tacattttta taataataat 72900
ttatgttgct gatattagaa aagaaccata atatccaaga attcaagaac aattaaatta 72960
tgtacatatg ctagtgtata gtgtgatgct ttggagaatt tttaacaatg tggagatata 73020
taatctgaat tgtagtattg agtgaaaaaa ggcagaatac aaacctagta gggggtatag 73080
tcggatttca gttaagaaaa ataatattta catatataca ttcctcacat tggcagataa 73140
tcaccaagat acattttggg attgtggatg atttttgtgt tctttatatt tttcaggtat 73200
tctcaaattt tctaaaatga gcaagtataa cttttgtcat cagaaaaaat aatatgcaaa 73260
agtaatgtta atttgttggt gaccaggtta aaccttttta tttttattat tattttttga 73320
gatagagtct cgctctgttg cccaggctgg aacgcagtgg tgtgatcttg gctcactgca 73380
gcctctgctt cccgggttca aacgattctc cagccccagc ctcctgagtg gctggaatta 73440
caggtgcagg gcaccacacc tggctaattt ttgtattttt agtagaggtg gggtttcacc 73500
aggttggtca ggctggcctc gaactcctga cctcgtgatc caccctcctc ggcctcccaa 73560
agtgctggga ttacaggtgt gagccgctgc acccagccaa acctttttat tttatttgac 73620
aaaagaaata cttgcatgtt atagaaaact aaatattgtt tgggctgtct gcagtatggt 73680
cttctcttga tttgttcaaa atattgtaaa ctttgatttg ttcaaaatat tgtaaacttt 73740
gcttattttt tttgttcttc ccttgctttg ttcaaaatat tgtaaacttt acttattttt 73800
ttttgttctt cccttggttt gttcaaaata ttgtaaactt tgcttattta tttttattgt 73860
ggctgacatg tgtcagacac tgttgtaggc ctgggatgta aaaacaggat tcctgccctt 73920
acggtctctg gaggctggtc agggagatga tgtggtcagc tggagctccg ctcctaaggt 73980
tgtgcagggg cagttgagag gcggaagggt gggacagcat ttcaaggtgt gggcagcaca 74040
ggagtctctc ttcattggga tataattgcc attccgataa catgtatttg agttgtctaa 74100
agtaggaagt tgtaccatgg tgggacagat atctcatggt tatcatacac agatctcagt 74160
tctcattgtt tgtacttttt ataaagggta aaaggagata taattcaata aacctttgtg 74220
gtgtttgggt gtgattttat tgtttctttg ttctatagtt tggatgctgt gaagctttgt 74280
gtcttctttc cactgccttc ccagtttgca tttggagttt aggttggcac tgtgggtatg 74340
tattttcctc agtatgtatt aatagttgtc tacaacagta taatataaac gtagttatta 74400
ggatgccctt tttctttctt tttaagtctt ttatcagttt ggcttttgca aaaatatctg 74460
atagaatact tgtttctgct gtattagttg tgtgagacta gtgacaggag ctgtgggaat 74520
tgaatgccaa atgttcttag gcatttttgg gaatttgagg gtgtgatctt caagttcatc 74580
taggggaatt ttcatatgct ggcaaaatac ttttctcatt agcttgattc tttccagaat 74640
tatttgctgc atattagaag tttaggaacc ttttttcact taaatgtgat ctaacatatg 74700
aaatggtgat gatttaggaa ctactgtact tacattaaca gcttttactt aaaaatgatt 74760
ttcccccagt agatgaccct actcacatct gggaaataat ttcaagtctt ctccagcatt 74820
caggaataag ctttcattct gtgtatcaat tactgagaat gattttggtg actcacatca 74880
catttgagaa gtaaacctgt agatttcttg tgtgtgtcag tgaataacca gctgacattt 74940
gcttgaagtg gattacattc tctgctctag aatgattgct ttcccgcctt cctcacatat 75000
agactgagca actatggttt ctagtcatag gtccggcact agacttgact tctgagcaac 75060
tttggcattg gagtaaaatg tattaattta aagaaagcta aaaattcatt caagtaaaca 75120
tacagttcta atacttttta aagtttaaaa tatagatagg tttaagtgat aaaaaaatat 75180
gagtagacac cataatcctc atttctgtat ctgttcacaa ggggttgata tttatgagtt 75240
ctattctcca tacccattct gtgttctctt aatcctcagt cagcacctca ggtggttggg 75300
attcagttct tggtagtttg acttatactc tcttttctag gggattgagc cctgggtagt 75360
cctccttata tgagattgca atttgtcttc caataacttt tactacaaga tatggggtat 75420
taaaggatgc cattggggaa ccaagataat attagtatca ggaaaactaa ccacgtcaga 75480
cctgccccat tgggtatcaa gtatactatt tttccatagt aataaagagc tcaccccagc 75540
caattctctt ttattttgga cctgtttatt caatggcatt aagatgccca aatgtctggg 75600
tagctatctc atctccaatt cagcagaacc attgtcatat gccctagtgg aagcattcct 75660
tcattggaca cttaggcccc agtactttta ttcagatcta ctacctgatt tcatttctca 75720
aatgattttt atggagcttt aatttatagg aaagttgtta gttgattaac agtaaaacag 75780
tttctgagct ggtataaaac atattgtgac acgcttttct cttggaattg caagagaaag 75840
gaagactgtt gtttgcttga aatttttcta taatttgacc ttgcaaatgt ctgcttccag 75900
agtgcctcca ctgagcgcct ccgatgagtc taggaagagc tgtaccgttg ggatggccac 75960
gatgattctg accctgctct cgtcagcttg gttcccattg gatctctcag cccatcaaga 76020
tgctttgatt ttggccggaa acttgcttgc aggtactgag ttgaagcagg gactccgagg 76080
cttggatttt gatttcctta gggggaatgg gggtggtgag catatgaggg gaaaatacta 76140
aaaggtcatc gccagtgatg gcttgtccct ttagtcaaat ttcagatgtt acctatatgc 76200
acaaacacat gcagctgttc tgtgctgagt attttaaagt ggcctcttcc cagtatggcc 76260
cctcagttaa ctacaaataa actcattttg aatttcatct tagtgggcac catatgccag 76320
tactgcctca ggcactggga tggtaagaaa gtataaagta tggactccat tctcaagttg 76380
gttttagatt agaggggata catgtaaaca gaagtgcagt ggtcacacag agtggccatg 76440
atcactctcc ttgggcagat ttatgggctg ataggaaagg gcacaacagg gagagggtgc 76500
agcaccgtgg cgatgataat ggaggatgtg gccagcaagg aagacgcagt ccattgaaat 76560
tgattttggg agaagttgcc aatctccatg aaagaatcgg gacctgtgtt ctttgcttta 76620
ggaggctata ggagagtttc gtgaaaggga ctaaaagatg agtattttaa taagatcatt 76680
cagccaactt gaatgtgggc tggaggagaa ggtagagaga ctcaggagat taatgttgac 76740
gctaaggcaa gagatgggga gtctaaacca agataatggc tttgggattg tagggaagac 76800
actgatcgta agagaatgaa ggaggcagaa ttgccaggcc tgggtcacca actgaacttc 76860
ggttgtgaag accaagaaac ctgggatgac ttcacatcct gggcaggtgt gtggtagtga 76920
cagtcatgga aattgggaac acagatttgt ggggaagaca tcagtttgag tttgagtttg 76980
agtttgagtt tggcttatcc gttgaatatc agacacagat gtctggccaa ctctcaacat 77040
agattagggt cttaaatgac ttcagttccc caagcaattt gtccttccca tactgttggg 77100
ctagagaggt aatatctatg cccatatcac agccagtgct cctaaatctc tgagaagttc 77160
atgggcctct gaagaagaag ccaacccagc agccaccaag caagaggagg tctggccagc 77220
cctgggggac cgggccttgg tgcccatggt ggagcagctc ttctcccacc tgctgaaggt 77280
gatcaacatt tgtgcacatg tcctggacga cgtggctcct ggaccggcaa taaaggtaat 77340
gtcccactta ggtgctggat taatatagcc ttaatgactg tgggtttcca gactatcttt 77400
atttagtaat ctgtctcttc tttattctct tttactttaa atgaacaaaa ttgctcagat 77460
tgtgacacta aatttaacat caaaatgtga ccatgtggcc gggtgcagtg gctcatgcct 77520
gttattccag tactttggga gactgaggtg ggcagatcac ttgaggccaa gagttcaaga 77580
ccagcctggc caacatcaca aaaccccatc tctactaaaa atacaaaaaa attagttggg 77640
cgtggtggca catgcctgta gtcccagcta cttgggaggc tgaggcaaga gaattgcttg 77700
aacctgagag gtggagtttg cagtgaacct tgattgtgcc actgcattcc agcctggatg 77760
acagagtcag gctctgtctc aaaagaaaaa aaaaatgtga ccatgtgttt tacagctcct 77820
ttggtatcat cagtcactgt taccccctaag agggaaatac atagctttag ttttaggttt 77880

```
ccatcattag ccaagaaagc tcagaattgg ttttcctggc taaagtacct cattgctgtc  77940
tccttaaatc ttagttaatg gctactgtcc tggctagcat agttatagag catgtccatg  78000
gttgtagaat gttctgccaa tctcagggac agttttgctt ttctgtgaag caataaaatc  78060
aacttcaaaa caaatgttaa ctgtttgcac aatggattta agatagacca gttcacatac  78120
tttttttttt ttttgagacg gagtttcact cttgttgcct aggctggagt gcaatggtgc  78180
gatctcaggt cactgcaact tctgcctcct gggttcaaac gattctcctg cctcagtctc  78240
tagagtagct gggattacag gcatgcacca ccacacccag ctaatttttt tgtattttta  78300
gtagagacgg ggtttcacca tgttggtcag gctggtctca aactcctgac ctaaagtgac  78360
ctacccgcct tggcctccca aagcgttgag attacgggca tgagccacca cgcccagcct  78420
aagatagacc agttcactta ctgttatatc tgtttactct ctctttgctg tgtcttctac  78480
ctttaaaaat ctccccacta acttcccatt ctcctttagc tgccatcagt cacttccctt  78540
ctctgcaaac atctctggag agtctcagcc tcagcccaca gagcttccca ctgctctgag  78600
gtggaccttg tttgtaagac ttcttggccc tcttggcctg gaccctgtct actacttcag  78660
ccatccttcc ttaaccatcg ctagtggttt ttgttgccac cctccatagc agcgtttccc  78720
ttccagatca tgtctttaca tctctgggca ctgctctggt cctgcctgcc tttccctctc  78780
tgtaccctgc aggccgctgc cgccatcttg agtgtcctct tcacttggct ttcagagggc  78840
ccacagagtt tcccactgct ctgaggtggg ccttgtttgc aatacttctt ggccctcttg  78900
gattactgca ctagcctttt gttttggaaa cagcattttt aaaaaaattt aattttattt  78960
ttttgagata ggatgtcact ctgttgccca ggctggagtg cagtgtcatg atcgtagctc  79020
gctgtggcct tgatctccca ggctcaagtg atccttctgc ctcagcctcc tcagtagttg  79080
ggagtacagg tgtgcaccac catgcccagc tagtttttttg atttttttttc ttttttcttt  79140
tttttgaga cagagtctca cactgtcgcc cggactggca caatcttggc tcactgcaac  79200
aacctccacc tcccaggttc aggtgattct cctgcctcag cctcctgagt agttgggatt  79260
acaggcgcct gccaccacaa ctttttgtat ttttaggaga gacggggttt caccatgttg  79320
gccagtctgg tctcgaactc ctgatctcgt gattcgccta cctcagcctc ccaaagtgct  79380
gggattacag gcatgagcca ctgctcccag ccaggaaaca gcattcttga gataattcat  79440
ataattcacc catttaaagt atataattca ttctctttag tatgcccaca gagttgtgca  79500
gccatcacca gaatcagttt tagaacccac aaaggaactc tgtacccttc acccaaaacc  79560
ttccatgccc ccagctgcag gcagccactg acctaccttc tgtctctgtg actctgcatc  79620
ttctggacat tactgtggat gggctcatac agtcagtgag cttgtgactg gtgccttcta  79680
ccaagcaggg ttttcagtgc agtagccttt ctttcttttt tttttttta aattgagacg  79740
gagcttctgc ctcccaggtt caagcgattc tcctgcctca gcctcccaag tagctgggac  79800
tacaggccca tgccaccatg cctggctaat tttttttttt tttttgtatt tttagtagag  79860
atggggtttc accatgttag ccaggatggt cttgatctcc tgacctcatg atccgcccac  79920
cttggcctgc caaaatgctg gaattacagg cgtgaaccac cacacctggc taacctctca  79980
tgtactgtct gcggttcttc cctgatgcct tccagtccat gcacccgatt gtagcccctc  80040
atcctattat ggtttaaggt gactgtctta gtcaccatgg gttgccataa caaaatacca  80100
tagcctgggt ggcttcaaca acagaattta cttctcacag ttctagaggt taggaagttc  80160
aagatctagg actttcacct tgccctcaca tggtgagggg gtgagggagc tctctggtgc  80220
```

-continued

```
ctcttatatg tggacgctaa tctcattcat gagggtctgc cctcatgccc cagtcacctc  80280
tcaaaggccc cacctcctaa taccatcacc ctggtaatta agtttcagtg tatgaatttg  80340
ggggactata gacattgaaa ccataacaag cacttttcta aaagatcagg gagtgagtaa  80400
gtaccagagc taggacctca attccacctc tcggtcatct tgccttcact ctgctccatg  80460
atggctgcct cctagagtga tgggagcctc catgttttat attctctcat gtgttgtgta  80520
ttggagagag ttcagacttt atgaatacat ctggatttgt tgacttctag ctttgctggt  80580
aaccagctgt gaccttgagt aaattacttc atctctgagc ctgtttcctc tttttgaaaa  80640
gggagtttaa aatgctgttt tgggttgggc atggtggctc atgcctgtaa ttccagcact  80700
ttgggaggct gagatgggag gatcacttga gcttggagtt cgagaccagc ctgtgcatca  80760
tagtgtgaga tcctgtctcc tcaagaaatt aaaaaattaa ctgggtgagg taacgtgtgc  80820
ctgtgggccc atctactctg gaggctgagg tgggaggatt acttgagcct gggaggttga  80880
ggctgcagtg aactatgatt gcgccccatc ccgggtggcg agtgagaccc tatctcaaaa  80940
aaaagaaaaa aaaatgctgc tttgcacccc tttctcatgt catggtgtca tggctaacat  81000
cgaatgccct ggttgtttgc tgttggaagg cgtgggccta ggggctccct gaggactcct  81060
tccatcttca attcgttctc tgtgtacctg ttagcaagtt gtgggccagt ccctgccatg  81120
taccattgtg tgggtaaaag taaataaaat gtgtacagtg tctgaactgt acatataggg  81180
gtccaagaac aaaatgaatg acatgggtta gctctttcta ataaatggta aaaccaaata  81240
ttctaatttt cagttttgtt atacttccat cacatgtttt tgttttttgt ttttgttttt  81300
ctattttagg cagccttgcc ttctctaaca aaccccccctt ctctaagtcc catccgacga  81360
aaggggaagg agaaagaacc aggagagcaa gcatctgtac cgttgagtcc caagaaaggc  81420
agtgaggcca gtgcaggtag gaaacagtgt ggggaaggga gggacaggag tgcagcatct  81480
gtcatgtagc aacataggat ttaagtaact tggtgtttta gagaaatata atacacatca  81540
gtaaagtgag agaaggtttc tccaggtgcg gttcaagata ttagaaacta atgactaata  81600
tacacagacc accttttggt ctgaagcatc tctaagtgcc acctgctgac acgcagcccc  81660
tgcagcctcc aggcttccag ccccagcacg gagcctcact ctcctgtgct tccctggttg  81720
cgggtgaggg ctggagaggc ctcctgattt tcagtaaggg aagtggtgta gatgcttagg  81780
aatagatata gtgagtgaaa aaattgattc tgatatgtca aaatttctga ttggaaatgg  81840
aatatttaca tttggaagaa ctaaaggaga gagaaagtgg ggataaagtc atctgagttg  81900
gaggagctta aaccatgcac aagtttggag gaccttttttt taacccatga aaaggtcaga  81960
acagaagggg ctaggattta gttgtgactg cagtttttcg aattcccatc catactgctc  82020
ttggagggca gtggcagggg caggagagga gcctggcaaa gcatgaagtg actgctgctg  82080
cctctgctat ctgggtcgcc tggctgcctg tctgtacagt ctccctccaa acccattctc  82140
tcgctgtctc ttggtgccca ggggccagtg atggttctcc cgtttgtttt gtgtatatag  82200
catttatatc aaggctattt atttatttag agacagagtc ttgctctgtc gcccaggctg  82260
gagtgtagtg gtgcaatctc ggctcattgc aagctccgcc tcccaggttc aagcaattct  82320
cttgcctcag cctcccaagt agctgggact acaggtgtgc accactacac ctggctaatt  82380
ttttgtattt tttttagtag agacagggtt tcaccatgtt ggccaggatg gtcttgatct  82440
cctgaccttg tgatccacca acctcagcct ctcaaagtgc tggaattaca ggcatgagcc  82500
actgcacctg gcctatttat ttatttttaa ttgacaaaat tgtatatgtc tgtagtatac  82560
aacatgatgt ttgaaatatg tatacattgg ccaggcgcag tggctcannn nnnnnnnnnn  82620
```

nnnnnnnnnn nnnnnnnnnn nnnnnnnnnn nnnnnnnnnn nnnnnnnnnn nnnnnnnnnn 82680
nnnnnnnnnn nnnnnnnnnn nnnnnnnnnn nnnnnnnnnn nnnnnnnnnn nnnnnnnnnn 82740
nnnnnnnnnn nnnnnnnnnn nnnnnnnnnn nnnnnnnnnn nnnnnnnnnn nnnnnnnnnn 82800
nnnnnnnnnn nnnnnnnnnn nnnnnnnnnn nnnnnnnnnn nnnnnnnnnn nnnnnnnnnn 82860
nnnnnnnnnn nnnnnnnnnn nnnnnnnnnn nnnnnnnnnn nnnnnnnnnn nnnnnnnnnn 82920
nnnnnnnnnn nnnnnnnnnn nnnnnnnnnn nnnnnnnnnn nnnnnnnnnn nnnnnnnnnn 82980
nnnnnnnnnn nnnnnnnnnn nnnnnnnnnn nnnnnnnnnn nnnnnnnnnn nnnnnnnnnn 83040
nnnnnnnnnn nnnnnnnnnn nnnnnnnnnn nnnnnnnnnn nnnnnnnnnn nnnnnnnnnn 83100
nnnnnnnnnn nnnnnnnnnn nnnnnnnnnn nnnnnnnnnn nnnnnnnnnn nnnnnnnnnn 83160
nnnnnnnnnn nnnnnnnnnn nnnnnnnnnn nnnnnnnnnn nnnnnnnnnn nnnnnnnnnn 83220
nnnnnnnnnn nnnnnnnnnn nnnnnnnnnn nnnnnnnnnn nnnnnnnnnn nnnnnnnnnn 83280
nnnnnnnnnn nnnnnnnnnn nnnnnnnnnn nnnngcactt taatatttag tatcggttta 83340
atgataatgt ttgtgccctt actgtcttta aaacattttt acgtcatccc tgtttgatta 83400
cttggtgtgc tcatgaagtt gttggccact agggaatctt aggctcagag aggttctgga 83460
attggtcagt ggtccttgaa ttagccgctc ctatgattct ctaactgatt tctcaaaaag 83520
caaacaagca accacagcaa aacagctgtg cacaccactc ttcttatttt gttattgttt 83580
tagtacttag gccgtactta tgtttgttag tcagtttctc attacttcta gttaatcaaa 83640
agatcagagg caatatttga gtattttcat actagaatgc tttaaaaaaa gtcattattg 83700
gccgggcgcg gtggctcaag cctgtaatcc cagcactttg ggaggccgag acgggtggat 83760
cacgaggtca ggagatcgag accatcctgg cgaacacggt gaaaccccgt ctctactaaa 83820
aaatacaaaa aactagccgg gcgagatggc gggcgcctgt agtcccagtt acttgggagg 83880
ctgaggcagg agaatggcgt aaacccggga ggcggagctt gcagtgagct gagatccggc 83940
cactgcactc cagcccgggc gacagagcga gactccatct caaaaaaaaa aaaaaaaaaa 84000
aaaaagtcat tatttccagt aatctcttta aaacttggca agttattttg atctaaaagt 84060
ttatcttttg tgtgcacatt tttaaagctt ctagacaatc tgatacctca ggtcctgtta 84120
caacaagtaa atcctcatca ctggggagtt tctatcatct tccttcatac ctcaaactgc 84180
atgatgtcct gaaagctacg cacgctaact acaaggtatg ggcctctgca tcttttgaaa 84240
atatatatgc ccacatactt atgtctaatg gatcgttgat gtttttctta tgatttgtag 84300
gacgtataag ccctttgaga tatgagttac aattcgtgtt ttcaagtttg tctttcagct 84360
ttgtttatga tagcatctgt catacaggtg ttttggattt tcatattgtt tgtactcaca 84420
gctaagattg attacgtgag agagctagga tgtgcagcca ggttattggg ggaagtggcc 84480
tcggtggagt ctggagggat ctgtgtacag gcttccttcc ctcctgtgag gctcacacaa 84540
aaatacagca acctgctggt cctgcaggtc ccctctgcct aacatgagcc acaattccag 84600
actcacagaa gcaggcgttc agcataaacc acgtgtttca aatagtctgg gcgttgtgag 84660
ccacttgtta tcagctaggg aaagttttta tgtcagtgta aggaactgtt gaccagataa 84720
ccccaagagc cggcctttct gtctagggat gttttagttt tctagttcat tttttttttt 84780
ttaactttaa aattttctat tcatctgcaa tttgttagat atgaagtacg catctaattt 84840
aattttggtt ttggttgtcc ccaatgctgt ttacagaaga atttttttgc actaattggc 84900
ttaagttact tacattctca tagttctcta gtttcatttg ccattttgtt atatcaatct 84960

```
atctgtctgc tcatctatta gaagcatcct ttttttcctg ttgtagacag tctcgctctg  85020
tccccaggct ggagtgcagt ggtgcaacca tgcctcactg cagtctcaac ctccagggct  85080
caagtgatcc tcccacctca gctcctgggt acctgggact acaggcatgt gccaccatag  85140
ccagctgctt tttacatttt ttgtagagac agggtctccc taagttgcct gggctggtct  85200
caagttcctg gcttaagtaa tccttcctcc ttggcctccc aaagtgctgg gattacaggc  85260
gtgagcaact gcacctggct agaagtatac ttcttagtta ttatagcttc atggtattta  85320
tgatgggatc agttctcctg ttctttagaa ttttctggat attcttcttt gttgattttg  85380
ggatgtgaac aatagaatca acttctactt gtaggttgat ttagggagaa cttatacctc  85440
agatgttaag ttaccctgtc cagaatgtgg gatgctttcc tatttgttca aaacgtttta  85500
aattacctca gaagcacatg aaatttaaag gattttaaaa aaaactttaa agattatttc  85560
acatagctct tgcacatttc ttggtaaatg aatcctcagg tgttcttctg tttttgttac  85620
taatagatac ttctcatggt tgtttttttt tttttttcc tgaaaatcat ttgtcaaact  85680
tatgtggctt cttttctgaa ggatgtttga taattttgga agatataaaa gtcttcatat  85740
tttacaaggt ttggagtctc tttaagctgc gtggttctca cgtcagctcc caaagcagaa  85800
gacggcatgt cgaaaaatgc catagagaag ctacttcttt tccacctgtt ttcagctcat  85860
atcatcttga atttcggggc acctttctat gctcctagtg cttgctgtct gtttattatt  85920
ttccttcctg aataccctga actccagcat gttctgctgt aattctggcc tccctggcgt  85980
cttggactcc tgtttccttt gctctgtcat ccccacggtc agctcctgct gcgcagcttc  86040
tcagctgaac tgtttggagt ggctggcggg tcttgctgga tctttgagta ttgcctctgg  86100
tttccttggt tccttctgct gagttgctca gcgtctccac tccccatttc tcgtgtggcc  86160
cttcctgctc tcctctgatt ccttttgtct tccctggttt cttgctttgg ttttcagtct  86220
ccgcagaact tttgccactc ttctgaaaac ccggaggctt tttcatctta attctcattt  86280
catgacctct tttcccttat ttgagaggta gaccttccca tggtgagctt ctctttccag  86340
aattccatgt cttcttttcc ctcccactta cctgttgtcc aggagaggtc agattgctgt  86400
gcgcattgga gaagaaccct ttcttccctg ggctcttcat ttcacatgac atcaccacat  86460
cacctcatcc cttggaccct cagtggtggc actgctggat ttttctttcc tttggctggc  86520
cttggggcac acccaggttg accctagctt agtcatggta tttagatcaa ctcacatttt  86580
cagtttctgt gtctgtctct tgcctgcttc tgactttgcc cagagaaagc tttttcacaa  86640
gggttcttag atttacgagc accttctttc ctgaggcagt gtttttgcca atatttattt  86700
tcctagtcag tctcgcctta cctttcttgt tatacatgat gtctttggtc ctgacccatt  86760
ctctgagtct gtaaaataga attgctgtat aatttaatta catgaaatcc tttagaatct  86820
taatacatct tacaccaggt gtaacatttt atgatatcca aattgaacaa ccctgtgtga  86880
atttgacagt gatttctccc agggatccta atgtataagg aataggactt tgtattttct  86940
attttttgat ataccacata ccagatactg atcatgatgg acatttaacc cttttttttct  87000
cattaggaaa gaaagttagg aattacatct ttcagtagtg ccagtgtgac ctgaaagatg  87060
cctttgaaag agtagttttt gtatagctat ctgaaaggaa tttctttcca agatattttc  87120
ccagtgctga caacaaacac gcagacacgc cctacaaggt caatgtacag cgccgcacag  87180
tggaggcgtc tgccgcagcc gttaatgttt gtatctttgg ttgtacttta cgagatcttg  87240
acggggccag taaccgtgtg ttctctcctt caccttctca aggtcacctt ggatcttcag  87300
aacagcacgg aaaaatttgg agggtttctt cgctcagcct tggacgttct ctctcagatt  87360
```

ctagagctgg ccacactgca ggacattggg aaggtctgtg tcttgttttg acgtgcgtcc 87420
tctgggctga gttcatctag gatggagtcc ggttctccag ggtgcctccg ggagactcct 87480
ccctgcgcca cggacttgca tcacaggacc cgagtctgac tctgccttag ccatgaagtt 87540
tggggggaag gttctatttg tattctgttt ttgtctgtta tcacgtatta gcttagaccc 87600
agtttagttt agaaaattgg tgggtttaaa aatgtgttta tagagtcctt tatttcttaa 87660
tttgaccttt tcaagtggaa aggggcaaaa cagacagatg agggggcggg gcgggaggtg 87720
tgacttgctc ttttgtgcct gaggaagtaa cagagctggg gttgacagtt atattctctg 87780
gttttatgtc caggaatttc ccctgccgca cccctagttg atagcgaaaa tgttcaaaac 87840
tatgagaaag ttagaatgct gtggtaaaca ctctattatg tacacacaac ccagcttctg 87900
cagttgtttg cgtttggcta cgtttccttt ctatgtatat agccatctct ccatttacca 87960
gtacatctta ctttataatg cattttaaaa ggagtgacag atgcctccct ccaccaaatg 88020
tgtgtcttca cgtgaaatac agtatgtctg atgcacttca tttgttctta tgtctttgaa 88080
tctttttatc tggacatgga cacaaggtta cctagtttta atcgttacat atgttagtgc 88140
ttcttctctg ttattcctca tgtttttccc atgtatctat ttagtgtgcg cagttgtcat 88200
ttttaatggc tatctagtgt cctgctgtgt tgatactcca tcgttccctt agagtaaaac 88260
ttgttgagac ttcagtaatg tcacctgctc agtgagactt tcctggccat cctttcaaaa 88320
cttgcttctc tctgtactct cttttcctgt tcatttttct ctttgaccca tagcatcgtc 88380
taacagtcaa ccttaaaata aataaataaa taaagacttc agagaaatgt ccaaatacat 88440
ggagtcagtt tgggaatgag aaatgaggat tataatccgg gatgcacggc atgtccggct 88500
gccagtgcct ctggtgaagg aaggggaagg ggaagctgtt attgtcagaa agggagagaa 88560
tcacataggc tccctggaag cagagttcgt tggctccaga ggctgaaagc cagagttgtc 88620
gtcattcact ggtggaattg taggcaccgg gcaggtgttc agttgagagt attttaactg 88680
aattgctgca gtcctccaga atggctagtg ataaatctgg tcatagaaac atgtattcac 88740
gtggaacatg caagccatgc acagcagata tgtaaaggat gtacgggaag ggtttcttct 88800
agggttgttg gaaagtcttt ggaaacagct ctaacctggg gcacataagc atgaacccca 88860
tctccctttg tgctttccta gtccaatttt gtctgggtct gacaaagtga tttgatccct 88920
gtatctgcaa ctttcacaaa acatactatt tatttatttt acttccttgt cttttcagtg 88980
cctatagcag tgcctggaag attgtggaat ttagtgaaca tttgttgaat gaatagatgt 89040
tcttgttaaa aatgagtttt agtgtctcat ttatcttaca tccacactgt ggtggagcca 89100
tattagccca tttcacgcca taactggaag ctgaaagatg tgacattctt ggggccagat 89160
aagtcagtgg cagagcctga gttaagtctc atagattttc ttttttcttt ttcgtttttg 89220
gtggctagct ttggttttat ttttatttat ttatttattt ttattatact ttaagttctg 89280
ggttacatgt gcagaacgtg cagttttgtt atataggtat acatgtgcca tgatggtttg 89340
ctgcacccat caacctgtca cctacattag gtatttctcc taatgttatc ccttccctag 89400
tcccctcacc ccgatgggcc ccggtatgtg atgttcccct ccctgtgtcc atgtgctctc 89460
attgttcaac tcccacttgt gagtgacaac atgcagtgtt tggttttctg atcttgtgat 89520
agtttgctga gaatgatggt ttctggcttc atccatatcc ctgcaaagga cattaactca 89580
tcctttttta tggctgtata gtattccatg gtgtatatgt gccacatttc ttaatccagt 89640
ctatcatcga tggacatttg ggttggttcc aagtctttgc tgttgggact agtgccacaa 89700
taaacatacg tgtgcatttg tctttattgt agaatgatat aatcctttgg gtatatgccc 89760
agtaatggga ttgctgggtc aaatggtatt tctagttcta gatctttgag gaattgccac 89820
actatcttcc acaatggttg aactaattta cactcccacc aacagtgtaa aagtgttcct 89880
atttttccac aacctctcca gcatctgttg tttcattaat ttttaatgat cgccattcta 89940
gctggtgtga gatggtatct cattgtgatt ttgatttgca tttctgtaat gaacagtgac 90000
gatgagcatt tattcatatg tctgttgact gcataagtgt cttcttttga gaagtgtctg 90060
ttcatatcct ttgtccattt ttagatgggg ttgtttgctt ttttttttt tttgtaaatt 90120 tgtttaagtt ctttgtagat tctggatatt agccctttgt cagatggtta gattgcaaaa 90180
attttctccc attctgtaag ttgcctgttt actctgatga tagtttcttt tgctgtgcag 90240
aagctcttta gtttaattag atcccatttg tcaattttgg cttttgttgc cattgctttt 90300
ggtgttttag acattaagtc tttgcccatg cctatggcct gaatgttatt gcccaggttt 90360
tcttctagga tttttatagt cctaggtctt atgtttaagt ctttgatcca tcttgagttg 90420
atttttgtat aaggtgtaag gaaggggtcc agtttcagtt ttcagcatgt ggctagccag 90480
ttttcccaac actatttatt aaatagggaa tcttttcccc attgcttatg tgtgtcagat 90540
ttgtcaaaga tcagatgctg gtagatgtgt ggtgttattt ctgaagcctc tgttctgttc 90600
cattggtcta tatatctgtt ttggtaccat gctgttttgg ttactgtagc cttgtagtat 90660
agtttgaagt caggtagcgt gatgcctcca gctttgttct tcttgcccag gattgtcttg 90720
gctatgcagg ctcttttttg gttccatatg aagtttaaag tagttttttc caattctgtg 90780
aagaaagtca gtggtagctt gatggggata gcattgaatc tataaattac tttgggtagt 90840
aaggccattt tcacaatatt ggttcttcct atccatgaac atggaatgtt tttccatttg 90900
tttgtgtcct ctcttatttc cttgagcagt ggtttgtagt tctccttgaa gaggtccttc 90960
acatctctta taagttgtat tcccaggtat tttattctct tagtagcaat tgtgaatggg 91020
agttcactca tgatttggca caatctcagc ccactgcaac ctttgcctcc tgggttcaag 91080
gaattctcct gcctcagcct ccagagcagc tgggattaca ggcacctgcc accatacctg 91140
gctaattttt tgtattttta gtggaaacgg ggttttacca cattggccgg gctagtctcg 91200
aactcctgac ctcgtgatcc acccacctca gcctcccaga gtgctgggat tacaggcttc 91260
agcaactgcg cccagccaga ttttcagatc tccctctctt tgccctaaac cactgtgctt 91320
aataagaatt ctttagtggc cagcagtctc catgtgtaac acattgtagc aaaatggaaa 91380
atattacatg ttttaaattt gagtgtgaga tatactgaaa taaaaatcat ctaaatgaga 91440
ttctttaaat aataagattt tcttttttgt atgtgggttt ttttttaaca ttattattat 91500
gactgtcgta tatagaaatg gctgttttca actacagtca gtgaatgtat caaatgctgc 91560
cttatccaaa taataaaagt aaatgattaa caagtcacaa tttagtgaag attgatgtta 91620
gttgatcttt atattcctga attagccaca tggttgtgtg tgtgtatata tgtttagagg 91680
tacatataga taataagctc atctctgaaa atttttacat ttggcataag aataactgga 91740
taattaagca tcttattctc tggcctgtgt ctttacagtt aaaggtagat ttactcacct 91800 ctccttttt gtttttctca gttcatcttt tttgctattt catgacggag gcccatttta 91860
cctttctcgt atatcctttt gtttgtactt tggaagcctc acctgcttaa ttgttgagtt 91920
tttaatctgt ggtcttttag aggaggatgt gtagggtaga agctttcaca ggttcttctt 91980
tgcacttggc ccttggctgt tttgaggaat ctccctcact aactcacagc atagcaaggt 92040
ttgagatctc ttctgccaca cagcagttcc caggcagctg gaaagatatg cagatgctca 92100
gattgtcagg ccagccttga gatatacaaa ctactgagcc ttatctgtga ccttgcttag 92160
gtgaaggcat cagagcccct gcaccgacat gtgtaggcct ctggatgtgt gcggggctgg 92220
gtgttggggt ctgagcacaa gtgtagctgg agaggtgagc ttgttgtggt gacgggtatg 92280
agcaagtttt cttcagactt ctgtgagttt acctcgttcc aggatttaaa ggcacagaga 92340
ccttagaatt aaaatagaat cattttcttt ttctaaatag caacactagg aataaaaaat 92400
aataattcca cattctttac aggtaatgtt ttgtttttct tgtcttctaa tccttattta 92460
ttctgtactt atttttatac gtatttgaaa tgtattatgt gttggagttt tctttttgca 92520
ttatattata cacggttttt catgtaactc cttactgttc cattttatat gttttgtctg 92580
gtttatttta agactttatc agcaaatcgg gaaaccgtct ctacaaaaac aaaaacaaaa 92640
gcaaaaatag ttggccacag tggcatgcgt ctgtggtccc agctactcgg ggctgaggtg 92700
ggaggattgc ctgagcccgg gaggttgagg ctgcagacaa ccatggtcgt gtcactgcac 92760
tccagcgtgg gtgacagact ttatactgtc tgtttggggt gatttggtaa tgatatgccc 92820
tgatgtagtt tttttatatc ttgtgtttct tgtgcctggg tttattgagc ttgggtctgt 92880
ggcttcatag tatttttaaa gtttggaaaa ttttagggca ttatttcccc aaagattttt 92940
ttctgccctg ttcccctcct ttttttcctc tcttaaaggg gctgtgattt cctgaatgat 93000
tgcttagtgt tgtcccatag cttattgatg ctcttttcag tgtttttttgt gttttctgtt 93060
ttctatagtt tctattattg tatttgcaag ttctctaact tttcttctac gatgtctaat 93120
gtgttgttta tctgttaatc tattgttaat cctgtccagt attttttttt ttttttttgaa 93180
acagtctcac tctgttgccc atgctggagt ttagtggtac aatctcggct cactgcaacc 93240
tccacctccc aggctcaagc aattgttctg cctcagcctc ccaagtagct gggactacag 93300
gcacgtgcca ccacacctag ctaatttttg tatttttatt agagatgggg tttccccatg 93360
ttggccagac tggccttgaa ctctgatctc aggtgattca tccacctcgg cctcccaaag 93420
tgctgggatt ataggcatga gctaccttga ctggcccctg ttcagtgtat atcactaatt 93480
gtgtttttat ctatataagt ttgatttagg tcttttaaaa atttctccct gtgtctctac 93540
ttagctttgt gaacacagtt gtaataactg ttttaatatc tttctctgct agttctaaga 93600
tcttctaata acttcctggt tctcggtgtt tttgattggt ctattgatgc tccttgttgt 93660
ggattgtgct ttcctgcctc tttgcatcgc tgccaatttt tggttggatg cccaacattg 93720
tgaattttac tttgctggat gctagacatt tttgtgttca cagagatctt cttgagtttt 93780
gctctgaggt tagttgagtt acatgtagat ggtttactct tttgggtctt gctttataat 93840
gagtactcta cctaatgaac cagaaagttc gggttttcca gtctgcctgc tgagaacggt 93900
gactgtttct agccctgtgt gagtgcccga gcgccgctcc ctctgatcct ttctgatgct 93960
tccctctgtg gcctcaggga gtttcctcac acacacagtt ctgctgagta ctcgaggggt 94020
ccttccccga tctccaaggc tctctctgtc ttgttctctc ttctctggtg ctctgtccta 94080
taaactgtgg ctatcttggt ctccttagat tctcagcacc tcttcaattc agagggttgc 94140
ctgtccctcc tccttgtgcc acagcctagg aactctctta aagaagtgag gtggggcagc 94200
tgtggggctc actttgtctc tcgtctccca gggatcactg tccttcatgg ctgatgtcca 94260
atgtcttaag gactctggat tttgtctgtt ttgtttttttg gttggctttg tttgtttcaa 94320
acaggagggt aaacccagtt cctcactctc attgtgctca gtactggaag tctcgctctg 94380
ttatattgga tattagtatt tgtagcagag ccctggttcc ctggtacttg gggagctctt 94440
gaaaggccag aaacagcatg ctttctcacc tttcccaggg cttccgtttc tggtgcacac 94500
aaagcattcc atacacattt gttaaagttc tttgttagac aaatagtgat tcacaggctc 94560
tatttgtaat tttttcagta agcatgtatt agatatctgc tgggagctag tagaaacaaa 94620
aagtgacatg tgacaaattc aattctgaca agaacaacct taaacattta gaatataatt 94680
tgagtaaatc agaattttaa aaatgtgtgg cccttgaata tttgaaacca acaagaatct 94740
attgcttatt agtagaggat attttgttga acaagtggag agagaggcat tttcagtcta 94800
actggtgttg gcttttagca gctgttggaa accggttcat gattagccag gcagtggtga 94860
aacaggctgt gcattctgaa tgcctagatt ggtggcactc ttcgagttag catcttcttc 94920
tttcttcttt tttttgagat ggactttcac tcttgttgcc caggtaacaa ctccagtgca 94980
atggtgccat ctcggctcac tgcaacctct gcctcccggg ttcaagcgat tctcctgcct 95040
cagcctccca agtagctggg attacaggtg tgcgccacca tgcctgacta attttgtgtt 95100
tttagtagag atggggtttc actatattgg tcagactggt cttgaactcc tgacctcaag 95160
tgatccacct gcctcgacct cccaaaatgc tgggattaca ggtgtgaacc actgctccca 95220
gccccttctt gattcttgta aaggacattg ggtgctgtac accttgttat agatgttgat 95280
aaaaattctt gtgagaatag taacgttaag gtagttgttt ggtcattttt gtctatcagt 95340
ataagataat tctaggactg atttgtggta aatcacacat tgctgtatca tagttgtgtt 95400
cactgaacat attcaggggc tttacagatg cagggctctt agctgctttg cgcacttctg 95460
aattcctgcc ctgagaacag gactggatac ctagtagacg ataggtattt gataacagtt 95520
taatgaatta atgagtgaat gaacagatac gtaggtatgt gaaagaatgg ttgtaatgta 95580
tgtaacttgg atttcaagac ttactctgtt caaataagaa atggaaaact ttcctctgat 95640
tttgctctac tatttacact ctttaaatgg aagttatctt gtacctttga tttctgtcta 95700
ggattcgtac aataatgggt catctctgag tcacttacgg tctcactgtt ctttccacag 95760
tgtgttgagg agatcctagg atacctgaaa tcctgcttta gtcgagaacc aatgatggca 95820
actgtttgtg ttcaacaagt aagagcttca ttcttttcct attctgttaa gactttcagg 95880
tatgacgaca aaatgctgct actccttaag cagcaggtgc tggtggcgta atcagctggg 95940
aggattgtgg ggtccagcat agcacttttc ggctcattcc atgattgagc caagaggccg 96000
accttcccgt cattccccag gaggacgagg tctgtcattg tggagagcaa aggacatcag 96060
aagctcccct gcatcctcac tcgttaactt ccagtccctc ggggtttttg tttagcgtgc 96120
tcaatctcat ttagaatcgc aaggaaaccc aaaactctta tttaaggtac aaacagcact 96180
tcatacaata tctcgccgag gtaataatag tgattcacag gaagaatttc acattgtgaa 96240
tctttgctaa tgtatccagt tatttacaga tggatttgat atttgtgtgg gagattctta 96300
aagtgttgtt catgccacgt tgtttgtgct tcaatttttt cactatagtt gttgaagact 96360
ctctttggga caaacttggc ctcccagttt gacggcttat catccaaccc cagcaagtca 96420
caaggccgag cacagcgcct tggctcctcc agtgtgaggc caggcttgta ccactactgc 96480
ttcatggccc cgtacaccca cttcacccag gccctcgctg acgccagcct gaggaacatg 96540
gtgcaggcgg agcaggagca cgacacctcg gggtaacagt tgtggcaaga atgctgtcgt 96600
tggtggaagc acaaaagagc aagcaggaaa tactttgtaa aagaataaaa acgaaaaatg 96660
ttagccaaca tcttctaata gtctgctgta ttcaaagaac tctaggaaat atggttgatg 96720
caaagatgat ttaaggcata gcccggcctt tcaagaagtg tgtggccagt gagtgagatg 96780
ggcttgggac ttacacatct cagaggtggg ggtagaggag gaggaacact gagtgggctg 96840

```
agaagcagcc agctttcatt gccaaagtgt gtcagcaaac cagaaggcag ttcataatgt  96900
ccccacccgt tcaaagcaca ggccctgtag agtggtgtgg catgtgttgg tggcactttt  96960
caggcctgta acaaggatga aagaacagct tcattgcagc acagtagtgc tggtattcag  97020
aggtatatga aggtcatgga agcatcttgg atatgttacc ttgtgttttg tcaactttat  97080
gactagaaat ctctttttac ttaaatttat gtttgtgtct ttaatgcctg gaatacagga  97140
cttcttaaat tgccataagt atcaacaggt atttgagtta ctaatctgta tagtagcaat  97200
aatagaatcc cttgtttttc cttttataaa tgtaatgatt aaatagctac aattgaaaca  97260
ctagagtcag gagtcaagga aaatacccat gttccaggct gtatgttagt gatgtactca  97320
ctgtgtattc cagtttcagg aataagtctg tttcaatgct ttctgtaacc atttggggta  97380
ttaataagca agtgagtgta tgcatgtttg ggttaatttc atatatgtgt cttagaaagg  97440
atatcattga tgtaaatatt ttcaaggctt atcctccaaa aaaatcctgt gatttcttct  97500
aaattactga tcttttaaat gaccttcacc tttctctcaa gtctcactta agactgggct  97560
gagtagtcag tttcctgtag cagtaaaaag ctcagacttg agtagccttc cacaggtgac  97620
gagacttgat ggctgtcagg cagctgtaaa ctgtaaatag agtgtcatta tctcgagagg  97680
gtgatgctgc cacactgagt ggcctttcaa gttgtttctc agtctgacat gttctgatcg  97740
tgtgaatgtg aaattggttt gaacaggagt atatctgagt gcagaggaga ttatttaaag  97800
atattctcat tgtctgcttc ccttctattc ccatttggca gatggtttga tgtcctccag  97860
aaagtgtcta cccagttgaa gacgaacctc acaagtgtca caaagaaccg tgcagataag  97920
gtaaatggtg ccgtttgtgg cgtgtgaact caggcgtgtc agtgctagag atgaaactgg  97980
agctgagact tcccaggtat tttgcttgaa gcttttggtt gaaggctcac ttacggattc  98040
tttctttctt tcttttgttt ttttatagaa tgctattcat aatcacattc gtttgtttga  98100
acctcttgtt ataaaagctt taaaacagta cacgacaaca acatctgtgc agttacagaa  98160
gcaggtttta gatttgctgg cgcagctggt tcagttacgg gttaattact gtcttctgga  98220
ttcagatcag gtttgtcgct tttaatcttt catccatcat acctgtacct aatttagtac  98280
aaaattaccct gaaagacact gaaatctact ttaaagaaat gtgaactgtg tttccccacc  98340
ccccatcaat tgctgctgct tatgtttttc atgcacttag ctagtacaag gcccggggca  98400
tagccagcct cagcaagtcg gcatccttgc cccagctccc tggactcaag gctaacctgg  98460
ggttggctgt tagggatttc caaaggtttg tcccatccac tcgcctcccc tccaaaataa  98520
gtttgaattt aaattgtgag atttaattaa gatttattgt ttggggaaca tttttgcaaa  98580
atctagagag ttagtttaaa tggattatca attatgacta taattgatca tctgcagttt  98640
caggctatct aacaggttag cttacctctt taaaaaggaa tggaatttag ccggacagta  98700
actgagaccc acgctcctgg agtccacgtg ggagccgcgt ggctctgcac aaacaagcat  98760
ttgcactctt cccctcttgg ctgcgttgcc ctcctcctgc agttgctgtg ggcactagat  98820
tctggctagt catgtccctt catgatgcac agtttcctca agattcgtgc cagttaaatc  98880
actgcctttt catagtcaaa atttaactgt catctttgac ccatgatctt gggctacttc  98940
cttatgtggg gtaggaatat ttttgagata gaaatattac acttctctgt ttccttctag  99000
acaaaaatct gttaattctg ttagtaccgt gactcatctg aaagggtctg tttccctagg  99060
agaactgagg gcacgtggtc aacactgatt tcccaccatg ggtattgagg tggggtctgc  99120
tttttttgt tttgtctttt tttttttgag acggagtctt gctctgtcgc ccaggctgga  99180
```

```
gtgcaatagt gccatctcag ctcactgcaa cctccacctc ccgggttcac gccattctcc  99240
tgcctcagcc tcccaagtag ctgggactac aggcacccac cacttcgcct ggcttatttt  99300
ttgtagagac cgggtttcac catgttagcc aggatggtct ctatctcctg acctcatgat  99360
ccacctgcct cggcctccca aagtgctagg attacaggcg tgagccaccg tgcccggcct  99420
ggggtctgct tttaatgaaa gaggcatcta ggggtgggct ttgccttggc ttgatgcttt  99480
gaacctttgt tcacaaaacc tatctgaaga aaatctgtct cagtgggcca ttgctctcct  99540
caggaaacat gcattgggaa cttcttttcg tttcctttga cactaggagg ctgcctgggg  99600
agaagccctg gtctatggct atgggcaagc aggggctgag aggagcaggc tctcagtggg  99660
gcagggtacc ccaagggaag ccagaaccct gatttgttcc attctagtga gaacaaagac  99720
tacagtctac cttttcttca gaatttccca gttctaactg ggcatggtgg cacacctctg  99780
tagtcctagt tactgaggag gctgaggcgg gaggatcact tgagtccagg agtttgagtc  99840
cagcctgcac aacatggcaa ggcctgtctc taaaataata gtaataatca taatctctag  99900
ttctagccgg gcacagtggc tcatgcctgt aatcccagca ctttgagagg ccgaggcagg  99960
taaatcattt gagctcagga gtttgagaac agcctggcca acatgatgaa accccatctt 100020
tactaaaagt acaaaaatat tagctgggtg tggtggcagg tgcctgtaat cccagttact 100080
tgggaggctg aggcaggaga atcacttgaa cccgggagat ggaggttgca gtcagctgag 100140
attgtgccac tgtcctccag cctgggcgag acagagcgag actgtgtctc aaaataataa 100200
taacaacctg tggttctgac tcgtcatggg taggaactga ttttctcatg tggtagttac 100260
agactatggt ctccttgggc ctgtctttag tagggaaaaa aggcaactcc ccactctaac 100320
ataaaatggg tggacttgaa tgttttatca aattctttct ttagtcgttc tactggagct 100380
ttttcttcaa tgtagaatat tctgttgctt tattatattt gtctgcaatc tccatgtgat 100440
atttccatgt tgagggagga cagccttgag gctccccccgt gctgcctgcg gccctgcagg 100500
catgtggaat tcatctttgg cctgtgcttt cttctgggtc ccggtgcccc tgcccgcgag 100560
gctcatgtcc agctgcccct ttgtggtggt gtgaggtcat tcctgctgtg agcgctctgg 100620
tttcatgttt gttccgattg cctttcatca gccgatcccc tttctcccag ttcttaagat 100680
tcaatacagt gacagtttta tgaacaagaa tagaactaga acagacaagc cattgaactc 100740
tatgctgata atgatttacc gagcacctgc tgtatgtttg cattccgcgc agaggctctg 100800
agaaagccgg gccatgtgct ccatgcttta tcggtggaag ctcctcatca ggttgggaaa 100860
gctgacagct gcgtagaata ccagtgtgac acaaagctgg ctcccgtgcg gcccttgcgt 100920
gttgcctctc agatggtggg aggaagaagg tcgactcctt tggggatctt actaccaaac 100980
cagtttcagg gaatctgcta ccctgtctgc cattaatggg aacagatgag tccccaaggt 101040
gtacttctgg gtattgtctg atgtcgcttg gaatttatta cttgtttttc caatgaggtt 101100
tcacctcagt gtgtagtaaa gttgttgagg ggattcctgg aggtgttcta cagttatcta 101160
ggctgatttc agaatagagt tatgcttata gtccaattta tcagctgtca agaaattcat 101220
ttaaaatttg tgcagataag caggaggaaa agaaacctgg tttttacgtt ttaatcctat 101280
tattgatgta aaattttact ttccttcccg taggtgttta ttggctttgt attgaaacag 101340
ttcgaataca ttgaagtggg ccagttcagg taatagcatt ttgttatttt agagtttttt 101400
ctccttcttg tgtacttaca tgtaatttag gttattaaga tgaatgttta aactactgtt 101460
aggcattttt gctgttttct ttaaatggaa atctgattaa catgctgtgc atttttgctt 101520
ctcttaaaaa ttaatgtata tctcaagact tgtttggaag tagttacata tctgaaaatt 101580
```

ccatatgttg tcagttttca ttgcacattt caaagcattt aattatgttg acagatggcg 101640
gaatgaaatc ttgtggtgga gcactagttt ttaaatcttc ttagagaaag cagtttttat 101700
ataaggttgt ctttagtaat tattatgcac ttgtattctc tgcagctttt ttttgctaga 101760
tgttgaggtt ttaatacttc ttgctagtcc attacaggtt tataatgatt gaaagttaaa 101820
attctttagt acctgaaata cttaataaat actgtagtta ggaaaactta gtgcagaagg 101880
aaagtgttcc cagattccct ggggtctgga agcatagcgt ttgttctaat cacgtgacac 101940
ctccactgtg ttttggggca agttactttt tctcttttga gtttcaattt ctacaagagc 102000
aaaggggcag agagagctag ggagattgta gctgctgtgc ctctgtgccg tcaggtgcct 102060
tctacctgct ccctctgaac ctttacacct gtcccggctc tgcacaaggg cacagatggg 102120
atgcactgtg gcagggatgg gcttagagta gatcactgac acctgttagc ttcatgtgcc 102180
ctcatgaatt attttatgtt gcttatattg atatgtatct taattttaaa agaaaggtct 102240
aaatggatgt ttttgtttct agggaatcag aggcaatcat tccaaacatc tttttcttct 102300
tggtattact gtcttatgaa cgctatcatt caaaacagat cattggaatt cctaaaatca 102360
ttcagctctg tgatggcatc atggccagtg gaaggaaggc tgtgacacac ggtaatggga 102420
cacatctttc actgtcgtct tcagtgtcac gatgtgcttg gcagtgttcg ttttcttttt 102480
tttgttgttg ttgttttttt ttttttgaga cggagtctcg ctgtgtctcc caggctggag 102540
tgcagtggcg tgatctcggc tcactgcaag ctccgcctcc cgggttcacg ccattctccc 102600
gcctcagcct cccaagtagc tgagactaca ggcgcccgcc accacgcccg gctagttttt 102660
tgtattttta gtagagacgg ggtttcacca tgttagccag gatagtctcg atctcctgac 102720
ctcgtgatcc acccgcctcg gcctcccaaa gtgctgggat tacaggcttg agccaccgcg 102780
cccggccggc agtgttcgtt ttcatacacc cactttcaac tttgtcagtg gcggccgtgt 102840
gcgtctcagg ctctgcatat gtgtctgtgt gtctgtgtat gtgaatgtac tggttagaga 102900
cgtttcaaaa gagaagagag catattcttt actctcagca atttgtaatc ttctcaggga 102960
aaaaaagttc aagaaacagt aagatagcct aaggtacaga tagattctga atataaagtt 103020
cctgttcatt cacacgaaac actaaaagtt cttcacctga tcttagccca aaggccgaga 103080
agcgatgaaa cactaaaaat tcttcagtcg aacttgctgt gaattaaatt ttgatctctc 103140
atccaggtgg tattggagat acagtttgac ttgggttcag ggctttctgt tttgcctgat 103200
gattattttg ctggagctta aataaagaca gggctccagg agatggccag ctgtgcaagc 103260
ccccagcctg tggaaggagc tagcctggtt ttatgaatga gctgtaaatc tttctttgag 103320
ctttttgaac tggtcttcca gcattgccct attgacccct ccctgactcc tttgctggaa 103380
tccgtaggct tttgaacttt gacagggaca catcctaaga cccttgcaaa cccctagatg 103440
tgagaatggc actactacat agagtctttt ccactcagcg tgtgtgcaga agaacatcaa 103500
ccatgctgtg tggcgaggca gggccttggc tgacctctca gtcaaggcct tagctttaca 103560
gagctaagcc agttagtctt tgccatggct tcacaatggc ttcaggttca cactgccaaa 103620
gtatagatta ttaaaggcat aggtgtttgg tttcctgcac ttggagggtc tttggacaga 103680
aaatcagtag gcagccaaag ccagtacttt gcgctgggaa gcttggtcgt ctgtgagagg 103740
gtcagagagg atacccatgt gtgcgcacca ccgaagggtc agtgagtctc agggctctgc 103800
gtgcatgtct cagggctgga gagagtgtgt cactgagagg tcagagtgtt tgtgcgtgtg 103860
tgtcaaagag ggttgcagtg tgcccttcac tgaggggtca gagggtgcct cacgtgtgtg 103920
tatgtgtgtg tgtcactggg tcagtgagtg ttcttgtgtg tgcatgtcac tgagaggtca 103980
gagggtgcct ttgtgtgtgt gtgctcatgt gtgtgtgcgt gtcactgagg ggtcagtgtt 104040
cctgtgtgca catgacattg agggtcagag tgtgcctctg tgtgcgtgtg ctcgtgtgtg 104100
catgcgtgac acctccactg tgttttgggg caagttactt tttctctttc tcttttactt 104160
ggtcatctgt gagagggtca gagaggatat ggtcctgtgt gcgcatgaca ctggggcaga 104220
gtgtgcctct gtgtgtgtgt gtgctcctgt gtgtgtacgt gtcactgagg ggtcagtgtt 104280
cctgtgtgcg cgtgacactg aggggcagag tgtgcctctg tgtgtgtgtg tgtgctcctg 104340
tgtgtgtacg tgtcactgag gggtcagtgt tcctgtgtgc gcgtgacact gaggggcaga 104400
gtgtacccgt gtgccaatga aaggcatttc ttattttttt ttatatgtgg tcacagtaga 104460
ccaattaatt tattttgact cctgttttag accaaaataa gacctggggg aaagtccctt 104520
atctatctaa tgagagagtg agtttactta aaaaagcata ataatccagt ggctttgact 104580
aaatgtatta cgtggaagtt tttattgtct tttcagatga atcaaataga ttattctcga 104640
gaccaggaat ggtgctgttt tggttatttg ggaagtttta tcattttcaa attgaccttt 104700
gaatttgagt cacctttttt cagaagtggt gttaaattac aggagcccta ggtttttttt 104760
ccttttttag aagccatcac aaaatgatcg gtgttcagag gaaaagcttt gatcttccac 104820
aatggtataa tgattgataa ccttaattca tctcttacca taaaccaagt atgtgtaagg 104880
gttttcttta tttcttgata tcattttgta gatgttgaga gcagttttcc aaatgtaatt 104940
tccatgaaat gcctgatgag ggtacccttt tgtccccaca gccataccgg ctctgcagcc 105000
catagtccat gaccttttttg tattaagagg aacaaataaa gctgatgcag gaaaagagct 105060
tgaaacccaa aaagaagtgg tggtatcaat gttactgaga ctcatccagt accatcaggt 105120
aagaggaatg tgtgttggaa ctgtcgtgga tactttattg acccgtacag atggaaggaa 105180
gtgccatgtg gtaacactca ctgttaaccg tgctactttg aactaggttt gagctttctg 105240
aggcctgggg agatgctggg gcagcggcgg gtgcaggggg aggtgggggc gggggacagg 105300
cgtggtggca ggaggtatca ttggtgttta tccttccttt tttttttttt tttttgagat 105360
ggagtctcac tccgttgccc aggctggagt gcggtggcat gatcttggct cactgtaagc 105420
tccatctccc gggtttaagc gattctcctg cctccacctc ccgagtagct gggattacag 105480
acatgcacca ccatgcccag ctaatttttt tttttttttt tttgtatttt tagtagagat 105540
ggggtttcac catgatggcc aagctggttt caaactcctg acctcaagtg atccgcctgc 105600
ctcggcctcc caaagtgctg ggattacagg cgtgagccac cgcgcccggc ctggtgttta 105660
tctttaaagt gggtacagcc acaggggttc acctgactcc tggtctgaga gtcacaagat 105720
cgttcaagat agtgaggccc tcttttccaa aacaaggacc aaaaatcagt tgacagtgtt 105780
ggtcaagatg gtagaaacct aaaatgatag aaatctcaac tctgaaataa aaactttatt 105840
tgcatattta tttaccacta ttttgacata gggctaaggt ctttttcttt gagctagttt 105900
ctggttttgt tttcttaagg tggcataaga attcaaagac attttgagga aaactgagtg 105960
tagaaatctc tcttttttaa tgacttctct tttctttcag cttgtactgt tgtgtagccc 106020
tcgcttattt tgtcaattct ttttagctgt ttgtctttga atctttatga agccatagct 106080
tttctcataa gaagcagcac tttctttgtt cattcatatt ttaattaact cctgtagtat 106140
ttaaatactt aatgcctaat taaatcacat aattgcaatg caaaagtaca tgtatcataa 106200
agaggtctga aaatgagcaa ctggcaagca ggtggctgca ggcagagctg gctgggtggg 106260
tgggtgtcct ggagaagagc tcatcagctg catgttcagt gagctctgga tatctctgtg 106320
taaaaatgat cactaataaa cttgtgctca actgtgcaca cttccggaaa ggagatgctg 106380
ttcagtagat tgcctctgca gagaacacag aattgaaggg aatttccaca aaggcggtga 106440
gccgcctgca gaatagttta gtcaaggctg tgtttgaatt ttgccaaaga ttaatataca 106500
tttatttttt tcatgctgtg ccttttctct gattgtgaaa tattataaat tctatccaaa 106560
taacaatgat ggcaagtcct cctgagcaaa gtgtgcagct tgcatgtgtc ctagaggaac 106620
tcgtgtttcg ttctgattcc cctgcatttc tcatgtcata gagtggggat tgcatccgtg 106680
tccccctgtc ctcgtgggga tcacatctgt ttggatccta gagtcttcaa gctgagctgg 106740
gacaagtgta acagatggac acatgggggt ggaaaggcgc ctctaggcag cagactctct 106800
aattgtgcac actcttatag gtgttggaga tgttcattct cgtcctgcag cagtgccaca 106860
aggagaatga agacaagtgg aagcgactgt ctcgacagat agctgacatc atcctcccaa 106920
tgttagccaa acagcaggtt tgtccccgca gccttggctc gttgttgcat agtgatggta 106980
gcttaaggtc cttgtgaaag gtgggtggct ggaatcagct cttccttcaa tcctaatctg 107040
tgctttgata gcagttctcc atgctagtca tggggcaact gacttcattt cttctcataa 107100
tgccatctca ggttggtatt gcccacctcc tttacggggg gaactcatga ctcagagagg 107160
ttatggaggc gatcaggcag cacacagctt tagagtgctg gggtgagggc gggccaagtc 107220
tgactctaaa gcccgaaccc ttacctccta tactgcctcc tgcattctgg tcaacgcagt 107280
gttttatttg gtggttacat ttttgttttt gttaccttac tacttgtaat ttagcagttt 107340
tcctttcctt tcctttccct tcctttcctt tttccttctt tctttccttt ctgacagggt 107400
ctcgctctgt cactcaggct agagtgcagt cgtgtaatct cactgcaact tccgcctccc 107460
aggttcaagc aattctccca cctcagtctc ccgagtagca aggaccacag gtgtgcacca 107520
ctacacctgg ctagtttttt gtatttttag tagaggcgag gtcttgctgt gttgcccagg 107580
ctggttttag actcctgggt gcaagtgatc caccaacctt ggcctcccaa agtgctggca 107640
ttacaggtgt gagccacctc acctggccta ttcatcacta atcagaattt ctatgatcaa 107700
atgacatgaa ttgttgtttc cacaaatgca gtggaaggaa atggcctggc agtaccaatt 107760
ttggaagcaa caggccccca gtcaggcaca ggacactgtg cccccagtgt agcagcatct 107820
ctatctcaca gagaaggtgg tgcgtcctcc tcaaggcagc tccgccagaa aatctcatga 107880
gcggcctggc acggcttgag gttgcctttt aaatggactc agcaaataca tgtttgttca 107940
tcttgattat acacaataaa caactactct gtatagtaca agtagtccgt ggtttttttgc 108000
atttgattta aaccagagac atgtgatatt gatggttact gccttcatga ctgcaccccc 108060
atcctgattt cataatagaa tgttatcctg agaccagtta gacaatggaa cagggatctt 108120
ggcttctggt gagactgaca gcagttttag cgtggtcagg gtctccctgc ccacagatgg 108180
tgttagaatg gtgctctgga agctttattc cattatcttc tgtgcataat ctgagtagag 108240
tggagattga aggcctgaat gcatagtaaa tatctgactt aatttctgcc gcaatggaaa 108300
ttgtgcgata aaacatttat gaaatgcgta gcacagcccc ggccaggtag ctcagcacag 108360
gagcctgttg cattcagaag tagtgctaga tactatcctg ttactggcag tacatacatc 108420
agtgatcaga gcagattcaa gaaagacccc ctgccttctt ggagtgaagg ttttgttggg 108480
atggggtgag gggacagaca atagaaaaac cagtgagtga agtctctacc atggcagctg 108540
atcagggacg ctgtacagaa gaatcccgga gggaagagag ttaggtggtt tcggcggcgg 108600
agtggcattg ttcagttggt gatgagaaac gttgtggtga tctggtgaca tttgagtgaa 108660

-continued tttgcagaaa ggaaagatac aagcctagga gatacctggg ggaggagcat tccaagaaga 108720
gcaaacagct gcaaaggccc tggggggaac gtgctgttag ggtaaaagca atgggggtgg 108780
aggagtgggg cagctatgcg gagggaaggg agcgaggcct ggtggggtga ggccagcatg 108840
gaggagcctg agaggnnnnn nnnnnnnnnn nnnnnctccc aaagtgctgg gattacaggt 108900
gtgagccact gcaccccggc ctgttttttt tagagacgga gtcttgctct gtcgcccagg 108960
ctggagtata gtggtgcgat ctcggctcac tgcagcctcc gcctcccgga ttcaagcgat 109020
tctcctgcct cagcctcctg agtagctggg actacaggcg tgtgccactg tgcctggcta 109080
attttttgta gagacggagt ttcaccgtgt tagccaggat ggtctcaatc tcctgacctt 109140
gtgatccgcc cgtctcagcc tcccaaagtt tacaggtgga ttacaggtgg ctcccacacc 109200
gagccaagag tttgcatttt taacaaattc ccaggtgata ctaatgctgc ttttctggga 109260
ccacactttg agactcagtg atagaaagat ttattggtag gatagtaaaa taggagtaat 109320
tttttttttc cacaaaattg gcaattgggg gaaatttaat cttccttttt tctttagcta 109380
tgacttattt attctgttta ttttaggcat ctgtgagcac tgttcaactg tggatatcag 109440
gaattctggc cattttgagg gttctgattt cccagtcaac tgaagatatt gttctttctc 109500
gtattcagga gctctctttc tctccatatt taatctcctg tccagtaatt aataggctaa 109560
gagatgggga cagtaattca gcactagaag aacacagtga agggaaacaa ataaagaatt 109620
tgccagaaga aacattttca aggtatgctt tctatctgag cctgtaacta acccatgcct 109680
tttgggaagt cacttggtat ttcatgatca gttaagtctg gaataacacc tggtctcgct 109740
tcagttctga gctgggtaaa gaagtctgta tcagtgtaat tttctaatcc atcctggctt 109800
atctgtggct cctgtttcat acctctcttg aggttctgtc atgttctgtc tcttgtcctc 109860
agcagagatg ctacagcagt ggcttgctca ggtaggacag ggcagtgggg tggctgtcct 109920
gggggcaggc agtaggcgtg cattgccttc agggaagtta aaacccaaga gaagccacag 109980
aaagtgaatc ttatattctc accatgtgcc ggcagtttta cacgctgtca gtaataaaat 110040
acttctccct gcaaggcaga ctgcctccag taaatacctg tagtatcaaa tcctgtcttc 110100
cctcataaat tgttgggaag ctccctcagg acagtggtca ggcactcgta aatgcttgct 110160
gcctagatgg gtccctctcc acctctgctg gattctgagc attcactgag ttagagctgc 110220
tgctgcaaat gtgctacttc tgcctgagtg gctgtgactt catgcagccg tcatttggtt 110280
tgtcgtcagt gaagatgccc tgtgttgtcg atggagataa gcccagtaag cctgctgggc 110340 accttttgt ttgcgggttc agcaggcagc ccgtggcttt ccctctgttg cattgaagca 110400
gctggctaaa actgatggta cattaaattc ctatgacaga tgatcagctt gtatttgtgt 110460
aatggtgtac agtttacaaa gcttaaaaaa atactacctg ccatttcatc ctcagcgagg 110520
aaggtgatac acagagagga aaagtgactg tatccaaggc gatggtgtta cgcgtttcac 110580
tttaacggtt taatgtactt tacttctatt tttactttat atttaccaca tatattttca 110640
tatatacttg gcataagtgc tttatagtag tcacctaatt cactgtcacc ctttttgttt 110700
cttggaaggt ttctattaca actggtgggt attcttttag aagacattgt tacaaaacag 110760
ctgaaggtgg aaatgagtga gcagcaacat actttctatt gccaagaact aggcactctg 110820
ctaatgtgtc tgatccacat cttcaagtct ggtaggtaaa tcacattagt cttcctcgag 110880
tatctcaatt ccccattctg cactgtacgc tcttagagtg taggagctat gctgcccggt 110940
agaaactctg tcttgcccag agtgccagtt gaaaatgttt gttgctataa gagtcagcct 111000
gatccatatg acccagcagt tctactcttg ggtatgtacc caaaagaatg gaacgcaggg 111060
tggtgaaaag atgtttgcat gccagcgttc atagcagcgt tattcacagc agctaaaatg 111120
tggaagcaac tgaagtgtcc attgatggac gaatggataa gcaaaatctg gtgtatactt 111180
agagtggaat attattgaac cttaatattc aataacctta aaggacattc tgacacgtgc 111240
tacaacatgg gtgaccccta aggacattat gctaaatgaa ataagccagt cacaaaagga 111300
caaatactat gtgattcctc ttatatgagg gacctggagt acttaattca tagatacgga 111360
cagtagagtg gtggttgcca ggggctgcgg gggaggggag ttgtttttac aagatgaaaa 111420
gagttattct agaaacgaat ggtggggatg gttgtataac agtgtgaatg tatttaatgc 111480
tactgaactc tacagttaaa aatagttaag atgagccagg tgtaatggct catgcctgta 111540
atccaagcac tttgagaggc caaggcagga ggactgcttg agccaaggag tttgagacca 111600
gcctcagcaa catggcaaga ccccatctgt acaaacagac tagccaggga tagtggtgtg 111660
cctgtggtcc caactactca ggacactgag gctggtggac cgcttgagct caggaggtca 111720
aggctctagt gaagtatgtt catgcctctg cactccagcc tcgactacag agtaagaccc 111780
tgcctcaaaa aaacaaagca agacaagacc caaaaatggt taagacgggc caatcacact 111840
ggcttactcc tgtaatccca acacttcggg gggtcaaggt ggaaggatca cttgaagcca 111900
ggagcttgaa accagcctga gcaacatagt gagaccccta tctctacaaa gaaaataaaa 111960
aactagctag gtatggtagg cacatgcctg tagtcccagc tacttgggag gccgaggcgg 112020
gatgatcgct tgagcttgag accagcctgg aaaacatagg aagagactcc atctccacaa 112080
aaataaaaaa aataaaaaaa ttatccaggg gtagtgacgt gagcctgagc ccaggaggtc 112140
aagctgtagt gagccacgat cgtgccactg cactccaacc tgggcgagag atcgagacca 112200
tgtctctaaa gaaagaaaat tacaaggaca gtgaacccaa gaaagtcagt tgtgcagcaa 112260
gcatagaaag caaccagtcc aaattaggac agtgtgtttt ccaagaagaa cgatcatttg 112320
tcatgagaat gctttgcttt aaataaatga gtaaataggt agaagactag ttctagggga 112380
taggcacgtc tttcttctct caacaagaaa aaagaaaggc aattctaatc tctaggaaaa 112440
gcaaatagca ttaagtcatg gtccaaatat gaggcaaacc aaaatatggc ttgatttttc 112500
agcagttgat ctgttggaag cccttgatat taaaaaggtt ctcctttaag cagtttaggg 112560
gtcatgatca aagacccata gaaagagatg ccatcctttt aggatccttg gctctcttgg 112620
gaactgtatt cacgtagtca taatgtaagt attgcttgag ctttcatttt tggaatcaat 112680
atgtgactga aacactgaag acttactgac ttaattatgg tttcagaaca gaatgaaaat 112740
gtcttcagtt ctgatgaata taaaaggaaa actaaccaag ttaatttggc aagtagatgg 112800
tagagatggg gtgggaatgg aaggggcact aaaatcctta cctagcattg ttggagttac 112860
atgattacat catctgaagt tgacagacca aaatatagag gcttcaaagg tatccagata 112920
gagctaaaca tgtaactcag attgttagga ggtagtataa atgagccaaa tctcctcttt 112980
attaccgtag agttaatggg taatgtctaa agttgtctga agtctgtaaa tcatgacaaa 113040
ttatgatgtg gtgattgtat tcaacagtct ttcagttgca gggataaaac cccaatttaa 113100
actagagtaa gagaaagaat ttgttggttt gagctcctgg aaagtgcagg caagggtagt 113160
tggtaggact gcatctagtg ttataattct atggtctgca ttgtatattt atgcatatca 113220
gctctgcttt cttctcttaa tttgtatact tttaaaattt tattttaaag atagggtctc 113280
actttgtcgg ctacgctgaa gtgcagtggt gtgaagtgca gtgcgaggct cgctctagcc 113340
tcgaactcct gggctctaga gttcttcctg cctcagcctt ctaaggagct gagacaatag 113400
gcattcacca ccatggctgg ataggtttta aaattctttt gtagaaatgg aggccttgtt 113460
atgttgccca ggctggtctt taactcctag cttcaggcga tcctcctgcc tctgcttccc 113520
aaaatgctga ggttataggt gtgagccacc gcgcccagtc tcatctctgc ttcctgtctt 113580
agcccctcaa gtaggcatgt gattggcctt gcataagtca tatgggtgac cataaaccgc 113640
tgaatgctct ggtccacctg ggccaaatgg gagactggac agcattccat tgacgaggag 113700
gtggggcttg tctccgggag taagggagag gagcgcatgc agtaactgat ggtctgctgc 113760
acgggatagc ggcgcatcag ttagaatttt gaaggtaact accagaactg aaaacagaaa 113820
agataacaag tagttgcctt aaaaagggat ggggcagggt gcttttgtga tcagaaactc 113880
ctttctctta ttggattttt gtacacattt tgcggacata cccttagagt aaagataatt 113940
agcattttca gccttggtcc atttgaggag tggcccgcct ccctgctagc aggctctggg 114000
tctgctaggt tcagttgagc atcctggctc ttgcctgcat ggaacttaca gtcagtgcgt 114060
cagtatcaca agtcttaata tttcctatga aggaaaacaa tagtgcagtg acagacaaaa 114120
tgggtgggcg ggcagaggca ggatttccga gggggagaag tagctagctt tttgcagaga 114180
aatgttccgg cacccgagag agcagctgag agtgcaggca ggcaggaggc gagtggggcc 114240
tggccgcaca gcgtcacaga gtcccagaga aaggggcctc ttcatggcca ctgcattcag 114300
ctgctgtcac cctccacaca agccatggcc aaaatttaat tttgataatg gactctagtt 114360
tttgagcctt acttgctatt attgaaagaa ttttcttgtt tctttttaaa gatcttcaga 114420
ttatgcttca ctgaccactg taataagttt aaagttgaga aaatatgcct tgttaatgaa 114480
tgataggtca attttagtat attggtcatt ttaatatttt gccaccagtt ggtttgaatc 114540
tgatgccagg aggagacagc ctcatttctt tttttttttt tgagacggag tctcgctctg 114600
ccgcccaggc tggagtgcag ggccggatc tcagctcact gcaagctccg cctcccgggt 114660
tcacgccgtt ctcctgcctc agccgcccga gtagatggga ctgcaggtgc ccaccatctc 114720
gcccggctag ttttttgtat tttttcagta gagacggggt ttcaccgtgt tcgccaggat 114780
ggtctcgatc tcctgacctc gtgatgcgcc cgtctcggcc tcccaaagtg ctgggattac 114840
agacttgagc taccgcgccc ggccgagaca gcctcatttc taaggactag tcttgccttt 114900
gtgggataag ggtggtgtgt tctgtgtctt tctacatgtc cgagcgatct ctgcagctca 114960
aaggtgttca ctgtcttatt gtgctgattt cctcttcttc catctcaaaa ttgaggcaaa 115020
atactttcac tattgaagtg ttgtccagta gaacttccag cagagacggg atgtctgcac 115080
tgtctaattt agttgccttt agccacgtgt ggtgttccat acctgaaatg tggctggtct 115140
gattgggtag cttaatttat aattttattt aattttaatt aagtttgaac agctctgtgt 115200
ggatagtggc tcctgtatga aactgcaggt ctgttgagaa gcatctttac tggagagagt 115260
ggagggcttg gagggggcac atgggtttcc tgctgctatc tttgacctta tttaattggc 115320
ccaacatttg caagtaagtt gtctgtgcgt gtatatataa atgtctgttt ctgtcttctt 115380
gtttcgtttg actgcattta tttgaaagac actaggtggc agaattactg tatttggttg 115440
gtttaaagat aagagttgaa gtaatccgtc ttgtgttttt atatcggtaa ggtgtgttta 115500
gcatgtaaaa ttggtaattc gtattcacgt actgcttaaa caaaggctaa gaattccacc 115560
catacactga aaatggagac ctttgaattt gtccatttca ggcattactt cttaaacaat 115620
acctggttca ggaactagtc agaatggcac ccttgacttt tagtttcctg cttttccttt 115680
tgttggggga ggagggtatt tagctcaaag gtgtgtgcct atttcagatt ccatctagga 115740
gaagcagaat agccaagaca gatacctgtc ctcctgttta caacatttgg ggtaaccagc 115800
atccctctcc tttggtccaa gatagacggg tttagaaaca gatgatggta ccagaggccc 115860
cgggggtgga agcatcagct ttgtttgttg tccatgtggc tggattagag ctgtctggct 115920
ttgtagcctc aacacggccg tccagctttg ctcagtatga ttttcaagga cacatcttgt 115980
gcccttccct gcctgccatc cagaccatac ccagtcaggg tggcaggaac tgctgcccct 116040
tcctccctga gtcctggtcg tgggtggtgg agaggtacca tgaccctcac ggaggcctgc 116100
tcacccttcc tctgcggcag aggcgatggc tgcacgacag ctctttccct gtcctttcca 116160
aagcgtccat ggttccactt gatggggcaa agcaggaata ctggaagaga aagtggtcct 116220
ttctatagta ataaagttga cattgattca agttcaccct tggggaaagg acagggccac 116280
taacaattat aatgctggaa gcagtggaat tttctcatgg gtatatagta ggtttaattt 116340
taattatccc agttaattct tagaacagct ctgtgaagta tttccccctt tctgcttgag 116400
ttctaaaaga tcctatgcca aaaccaagaa tgaaaaccca agcattcttt cttgctcatc 116460
gatctttctc tcatcgggcc acttcttggg ttgttagtgg tgaatgtagc cgctggcaat 116520
tgcagaatac ccaccatggg ccccagtcac tgtgtggcgt ggattagagg tggttctctc 116580
catgtcatag ccgaacaagc ccagcccaga gaggtttctg ccctaggagc tcttgatggt 116640
ggaattggga tgcgatccca catcctgcct gtgttttgaa agcagcattc ttcatttcca 116700
gttcctgctt ccgttgttcc ttttagtatt tctttgttta actcacgaaa tcaggacttg 116760
gggagctgct gcgtgcagct gtagctgttt ctctgggtgc agcctgcatc caccttcctg 116820
ccccctcct tactgccatc gtggtctctg ggcacttggt ccctttctct tcccccgagt 116880
ccctttggct cccctgtgcc acccttgtga tccacaggct ctgccttctt tctgtctgag 116940
actgctgctc atcactaccc gggaccttag gaagggaggt tcctccgaga agcatcttct 117000
aatctcagcc acgttctcaa tgccgctgtt ggctttgtta aataatggta gctactgtaa 117060
caaataaacc aacatttcca tggcttcaca ccagagaagg ttgtttcttg gttttatgac 117120
aatgtgttga gggtgtttct ggttcacgga tggttttcct ccatgtggga attcggggac 117180
ccaggctcct ttccttcttt tggttctctt ctctgggcct ccacatcctc tgtgtctagt 117240
tggggacaag gagagggaag gtagagaaga aggctctgtg gccttggaca agtgacatgc 117300
atgcctttgc tggtgttctc tgctggtggt gggtcacagc cccaccccgt acgaggggac 117360
tgggagacgt cgtcctgctg cctcccagca gcaagcagca ctgtggtctc tgatgtgttt 117420
tctatgagga taaaaacagg cgattccagg atgagtaaag tcagggaaac ccttggaagg 117480
aggtgaccag gcaggtgtca ccatgggatt agtggtggct tcagaatgag ccgccaagag 117540
tgcagtgcct tctaaagctt ttgctattct gatatgccca caccatgccc agcaggtgtc 117600
tgccttgctc tccgcagaga gagtgatgaa tccttctcgt gaacctctgt cccgttcttc 117660
ctccctccac ctggaaggga ccctgggttc cttgaaacat cccggtggaa caggggacct 117720
tctgtcctgt ccctaagctc agcctcatcc tcctgccagc ttcccaaccc ctcttatgtc 117780
tgcttcctca cgccacatcc ttctggattc tctggaattg aattttgcct ttgatgctta 117840
tttaaaaata tccattgcag gccaggtatg gtggctcaca cctgtaatcc tgtgcacttt 117900
gggaagccaa ggcgggcaga ttgcttgaac ccaggagtct gagattagcc tgagcaacat 117960
ggtgaaatcc tgtttataga gaatacaaac agggcatggt ggcgcacacc tatactccca 118020
gctagacagg atcgactgag ccctggaggc cctggaggcc gaagctgcag tgggctgtga 118080
tcgtgccact gtattcccgt ctgggcaaca gagtgagacc ctgtctttaa aaaaaaaaaa 118140
aaatccattg catacttcac cacagtgaaa cgtgtgtctt atctttcctt tccggcctgt 118200
agctgctctt ttgcacttat agccgcacta agtcaacctt aaattaaaag caaaccagca 118260
cttcctgtgc tcttctgctt ccttcatgag ggtccctccc tctgtgtacg ctccattctc 118320
attgccccgg tggtttgttt ccctcttggt tctcaagctg tggcagcctg cctcttatca 118380
tctttactga aaagtccttt gcagaggctg cctgtgttct ttctttctcg gtccctctca 118440
tcctgggccc cccagcttga tgctgtgggg ctgccctctc ctcactcagt agcttgcagg 118500
gtcttctctg tctagccact taattggttg tgttccccga gttgctgtcc gtggtctctc 118560
gtcactgttt tctctgtgtc tctgcctctc tcctcggcct tggtaggtct ctcccctttg 118620
tgaccctggc tgttgctctc gtggacaact ttctcttgct ggtccgcgta gtcctggcat 118680
ccagcttctc aacatgggac ttgtcctgcc agtacctcag acttacgctg aaaattgaac 118740
tagcaccact gtcactctcc aggacctctt cttgttaatt aggtcattag ggatgttcga 118800
aatcccagca tcattgtcca ttcctcctcc tgccagccca gggaccctga ccttacctcc 118860
tcctctccat ctaccgggag gtggctctca gagtccgtct catcttccac ccgaacttcc 118920
ctacagactc cccgctgccg ccccaggggc tgagcacttc ctccgtgcct cgtgcagcgc 118980
tgagcccttt acctgggttc tcctgtttgc tccttattgc aaccctgtgg acagatactg 119040
ctcttaattc catcttaaac ctgaggaagc tgaggcccca ggtaaggtgc atccaaggtc 119100
actcaggtag taaactgtag agccacgatc cgaaccaggc agtctgattc ggagcctgtg 119160
ttgacactca gccacctaga acacagctca gattgtgggt ttctattacg tgttcaaaac 119220
cgccacatcc cgggtctgtc cctgcacgtg ccctgtggcc tggctgcatc ttcttgaagg 119280
cagcgcatgc gtcttcactc aaggggccca tgcaggaaag agggccccac agaaggacga 119340
ggccagtgca gaatgggctg gaggggacga tgctgactgt gaagcaagtg tagagaaatc 119400
ccaggaaacc tggaggaacc agagacaggg cattagaact catcgttgtg acctggtctg 119460
tattctctga gtgtgctgct gcttttagct cgcttcctta gtctcaggtt gtagtttaag 119520
gcattgtgga gccctaaaaa gcctctactc tgtttttgcc tgtttcggga ccctttcact 119580
tcggggatgt gttgaatttt ttgtttttgt tttttaattt tttgagatag agtcttgctc 119640
cattgcctag gctggagtgc aatggcacaa tcttggccca ctgcagcccc tgcctcctgg 119700
gttcaagcga ttcttgtgcc tctgcctccc aagtacctgg gattacaggc gcccgccacc 119760
acgcctgacc aatttttata tttttagtgg agacagagtt ttgccatgtt ggccaagctg 119820
gtctcgaact cctgacctca agtgatccac ccacctcggc ctcccaaagt gctgggatta 119880
taggcatgag ccaccatgcc cggcctgaaa tttaatcaga aataaaattt tgaccccaac 119940
aatgatgcta ggaggcccag atctggggga gagggcaacc ttggccagat gggcctgtct 120000
ctgtttccca agtcttgctg cctctccctg ctgtgctttg cagcctgtgc atgtctctgt 120060
gcctctgatc ttgttcatcc agaggagagg atagaatcaa gtcatgattc ctggagccct 120120
gagaagaatg ctgtggagaa acttgcaggt agactctaac tgagtgtgtg gctgaggtgc 120180
cagcattgtg tgtggggagg ctgaccgctt ggcctgccca ggcccaggat gctccatggc 120240
cgggcacaga ggcaacttgg ctgtcaggtg tcaggagcct gcagagagca cacagcctgg 120300
accgcagggc gctgcccatg ttcttccagc acctgtcctg cttgctcacc tggcctctta 120360
cagcatttct gtccctcagt tcttagcaag cccaggagct gttcaggttg gcaggtgccg 120420
agtgctgttc ctgcctgtgt agctgtggct cagtcctgtg gggggccccg ctgtggcctg 120480
agtgcagtga ttcgaggtgc cgagtgttcc ctgactcgtt ctgcaggagc tgtgttcaga 120540
ctttcacagc tcttggcttg gagcttctgg agggcttggc attgccaacc agtgcagggg 120600
tggacagtgg gagaggagga atgctagctt tcttgaccag tccattaaat aaatgggata 120660
ttggccgggc acggtggctc acgcctgaat cccagcactt tgggaggctg aggcgggtgg 120720
atcacgaagt caggagttcg agaccagcct ggccaacatg gggaaacccc ctctattcta 120780
aaaatacaaa aattagctgg gcgtggtggc agacacctgt aatcctagct actcgggaga 120840
ctgaggcagg agaataggtt gaaaccagaa ggcggaggtt gcagtgagcc aagatcatgc 120900
cactgtactc ccacctgggc aacaagagtg aaactccatc tcacaaaaaa aaaagcagaa 120960
tgtctgtttc tgcttagaaa aatcagaatt ttctaaatgc caggtgcttt gaatatgtaa 121020
gtatgggaaa caactcagcc tgtttcattt ttatgtaaaa tctccacgta gccatgtggc 121080
actggaccga gatgaaagca aagacatttc tccttctgaa ctttgtttct aggaatgttc 121140
cggagaatca cagcagctgc cactagactg ttccgcagtg atggctgtgg cggcagtttc 121200
tacaccctgg acagcttgaa tttgcgggct cgttccatga tcaccaccca cccggccctg 121260
gtgctgctct ggtgtcagat cctgctgctt gtcaaccaca ccgactaccg ctggtgggca 121320
gaagtgcagc agaccccgaa gtaggttcat aatgcccaca gcccagggcg ctggcccagc 121380
actctgtcct gagactccca gtaacctgag attgggccac cgttacagca ttttcatttt 121440
ccattttttg tgagggcttg taaaatttct gctgcatatt aatattcctt tcatggacag 121500
catattgtag agacaaacat gcggtccagc caaaggcatt cagaatagca attgctttct 121560
aaatgtgatt ttctttggca agttctttga caccattcca tcttgtggat tatgcttgtc 121620
atgctgtgtg gctcctacta agttctagtc cttcagttgg ttccatagcc agacatgttg 121680
caatgtctta acttcattat aaattaaatg tggttctggt tattcttaga taatggagta 121740
acgatttagc aaatttcaaa acctcttgga aatattattt gaccattcaa aaagacttac 121800
taagtctctc attatgggtg gccctctttt tgtaaaaggt tttcaggctt aagctccatt 121860
tctaggtgct ccaacactct gttatttgta tacacgtgga aataaaagct gtgacatccc 121920
cgccctagct gaatcctcag cacagtgttt ctggaaggct caagatccca cactggggaa 121980
aagaagttcc agagagaaaa gagggcaggt gctgccgtgc ctctctgctc agtatggata 122040
ctgggccatg tgcggccagg gcttgcagta gggccagttc atggcactca gctggaaagt 122100
ccactgttgg cgggcattcg taaccatcca ctctgtgccg tatgtagtgg ggtgtggcat 122160
ccaagtattt gaaatcagcc gcgtgcagag aaatcagccg cggatgcagc agatcactct 122220
ttttctgaca ggcctgctca ctctgatgtt atatcagaaa gctctgaatc tgggaattgt 122280
gttccctgaa ttggaataac agaaatgctt agatgatcag tgtttaaaag aaataaacca 122340
aaggtaaatt tagtttggaa ttcagcaagc gtcttcattc agccctctga gggcaaacta 122400
cagcttttca taaatgtagg taaattctct gtttcttgac cccttctgac ccagttttcc 122460
tttataacct tctgtattgt tccattatcc tgaaataaca ttaatagatt aggctgggtg 122520
tggtggctca tgcctataat cccagcacct tgggaggcca aggcgggagg atcacctgag 122580
gccaggactt cgagaccagc ccagcctggc caacatggtg aaaccctgtc tctactgaaa 122640
ataacaaaaa ttagccaagc gtggtgacag gtgcctgtag tcccagctac tcagaaggct 122700
gaggcaggag aattgcttga acccaggagg caaaggttgc agcgagctga gatcacgcca 122760
ctgcactcta ggctgggtga cagagtgaga ctccatctca aaaaaaaaaa aaaaaattaa 122820
tggatcaatg gatttttaac ctaatagtta aattaaaaaa atatcattct ttaatggtaa 122880
tgtaaaggta aaattaagag aagataatat gtaacaagca ttttagtatg tgagtgtcca 122940
aggtctccct gtggtggaag gaaaaaataa atccccataa gtgtccacga tgctcataga 123000
gagcagagct gttccggttt aaaccgctgc tcttaggact gtgtttttcc agctatgggt 123060
ggtgggggat gagtaccttt ttatttccat gagatgagaa aaatgaatta ctagaagtat 123120
gaagcacaaa acacagctgc tcttttttta tctggactca gcagctataa aattgctcta 123180
tccagttgca gaagttcctg ctgcttaccc ttgatgcccc ctcggttagt gtgcatctcc 123240
tttcaggctg gctcccagat gggagctggc tccaggcgac actgggtgct ctgctccagg 123300
aggtccttgt gtgggcccta ccccggccta gcccctctct tatggactct gtcaccatgg 123360
gtttgattca ctcaatctgt cttacctttt ggtgagctgt tagagtcctg cctatacttc 123420
agcacttgtg ggtgtgttgt ggtacacatg acatgttggt cacttcccag ctcatcttgt 123480
tctgagtcac cctggatttg gtacgttcat tcgccactag tagctggcgg tatatggcct 123540
gcgatttgga ggacttgtgc tgctacaaat tggggctgaa tttgagttga cactggccct 123600
tctttatgtc tactgctaat atttgaattg caaatgctgc ctcttctctt tcagaggctc 123660
attaccctat agctgtatta ttgcaaagta cataattaca gcttgagtgt aagtcacgct 123720
gggctggcag gacagccaac tgagaaaggg caagtttcct gttagttttc acattgacac 123780
ataatttaca atacagtaga atgtactttt gtatcaactg tagtcagtaa cagccccctc 123840
ccccaaccac ataagatata gagcagtgct gtcgcttcac atagttccct cttcctctgc 123900
catgtcccgc cctccccagg tctaaccacc aatccgtgct ctattcagcc cattgcagag 123960
ggtcatagaa atagaatcta caggctgggt gtggtggctc atgcctgtaa tcccagtgct 124020
ttgagaggct gaagtggaag gatcacttga ggctaggagt tcgagactag cctgggctac 124080
ctagcaagac cccatctcca gaaaaaaaaa atttgaaaat tacaagcatg tccctgtagt 124140
tccagctgct tgggaagctg aggcgggagg atctcttgtt gaggttacag tgagctatga 124200
tcgtgccact gtgctccagc ctgggtgaca cagcaagacc ttgtctttgg gaaaaaaatt 124260
aagaaagaga tggaaccaca cagtgtgcag ccttttgagt ctggcccctt gcagtgagcg 124320
gtgtctaccg tcatgcgttg cacacgtgtt ggtggctggc ttcttgtgac tgctgagcat 124380
tatatggctg ggctgtagat tgctttcact tcaccagttg ggaaacagag aaaaggcagt 124440
ttttaaaaag tttaaatctg tagaattttg gtttttacca gttctcttct aaatcctgag 124500
ggattacagg aaaagttgtt gtatttcaga atattcttag cttgatgtga cctctctccc 124560
tgttaaggcc ctttgctgca atgggaagga cgtcgtcctc ggtcagaccc tgaaggtcag 124620
aggggcactt tgggagtgtg tcaacatttt aactgtatgg actagagcca agagtctcaa 124680
gatttataat tcccacctat tcaaaaagaa aaaataataa taataaagtg agaagaagtc 124740
aatgtaaagt gaaataacct gtgttggtgg ggaagaagtg tttttaaaca gaatttccat 124800
aatgtatacc ctgaacgtgt ttagagtggt gatgtttcat tgggaaacga acagtaaaac 124860
atgaaagcag ggagattttc tttctggcag ttggcaactt tcatggcaga tggggaattt 124920
gaaaagcaat tgctcaatta tcaaacatag ccagtgtgag ttctgaaata aaggtgctga 124980
ttgaatgtgc agctttatgg tggattttgt cattcaggca agcattttaa ttttctgcct 125040
gttaaattct gttttcttta gtttttcata tgtggtttat tgtagcttgg gaatagataa 125100
ctgagagtat atattacaca tacaacattc tgatatggca atatttaaac caacttgtct 125160
gttttagaac tagaattaaa cataatcatc ttcagtattt tgcaaataag ctcactgcca 125220
tccagaaaca ttgtcaatgc atctgttgct ccttctagaa gacacagtct gtccagcaca 125280
aagttactta gtccccagat gtctggagaa gaggaggatt ctgacttggc agccaaactt 125340
ggaatgtgca atagagaaat agtacgaaga ggggctctca ttctcttctg tgattatgtc 125400
gtaagtttga aatgcctgta aacggggttg agggaggtgg ggaccgggag aacatcctga 125460
gtagatgaca cttgcctgga ccctctggaa cccagactgc ccagtgtcct gccagctcca 125520
tcaaaactaa atctggaatg aatgtttact tctgctctga catataattg gagaccgggc 125580
ctggccttcc agtcactgga ttctaagctg gactgtgaga gttgatgcag ctgactcatt 125640
tatcaaatgc ccagctattg gcttcacgcc tacacgatgc tgggcatatt tgttaattca 125700
agggaagcaa tggaataata ataactaatg atttgaaaaa caagataagt gcattgacta 125760
tagtggggtt ctgattttaa attttttaaa aaagtaatac caggagcagt ggcttacgcc 125820
taaattctag caactcgaga ggctgaggtg gaaagatcac ttgagcccag gagtttgaga 125880
caagcctggg ctacggtgta agacccccat ctctaaaaaa ataaaaaatg aaaaattatc 125940
caagtgtggt ggctcgtgcc tgcaatcaca gcttcttgag aagctgaggc cagaggatgg 126000
ctagagcgtg ggagttcgag accagcctgg caacacagag aaaccctgcc cctaccgaaa 126060
gaaagaaaaa ttagcctgat ggtggtgcgt gcctgtggtc ccagctacct gagagactga 126120
gaagggagga ttgcttgagc ccagaagttt gaggctgcgg tgagccgtga ctgtgtcact 126180
gcactttagc ctgggtgaca aggcgagacc cctgctctaa aaaacaattt ttttaagtta 126240
atttgtagaa aaggtgttag atgttcattg ccgtatttta tgatggattc ctgtttaaat 126300
gccattctct taaaaaaaaa aaaataactt gtaggagttt ttaaccgtaa aattagcatc 126360
acatgtttac catggagaat ttacaaaaaa caaacagagg aaaataaaac ctctgtaatc 126420
atactactca gagataactt gctgttagat ttcggtgtag atctaatact ttttctgtat 126480
ttatattaaa aatacttaaa acatatacat ttctttgtta caaacatggt atcttataga 126540
tagtgctgtc acatagcaaa acagtgttaa atattctgaa tcagaaaagg aagccgactc 126600
tccaactgaa agaggtgtta tcctagagac tttttctggt gatggcaatt tgttaatatt 126660
cactttttgc tttacattct gtattgaaat agtttttctg ttttgttcta cttttaagga 126720
taatataatt gtatcatgct gtttttcaca gaaatgtaag aaaaaaagat attaattttg 126780
taagttaata gaggttgagc atcccaaatc caaaaatctg aaatcccaga tgctccaaat 126840
tctgaagctt tttgagtgct gacattatgt tcaaaggaaa tgttcattgg aagatttcag 126900
atttttttgat ttagggagct caacaaataa gtataatgca catattccaa aacctgaaaa 126960
aaatcctaca ttcagaatac ttctgatccc aaacatttca gataagggtt attcaacctt 127020
tactgtcaga tgatcccaaa tgaaaaatat taatcgttaa ccaaatgtca aggaattgat 127080
cacattttac agtttctgcc taggattatg aatcaagatg aaaaggctct gcgtgtttaa 127140
aaatatatat atttttattt tcttataaat cttaaatgta tcaacactta agatgtattt 127200
gatatgtgga atccattcat attttggatt aaacaattct gtcaagaccg tggcagtgat 127260
agaggatttt tttttcccac tgaactatca caaaattgga aaaagagtaa ttggagaacc 127320
ccactggctt ggccagctcg aagccccgga gggggcaggc agtgctgtgg atgggagcgt 127380
cgcagtacca cgctgcccct cctgcccatg gatctctgag gcctgccttt gtcctttgac 127440
ccttggccat ttgttagtgt ctctgagagc tggactgctg taccctactt ccccaggggg 127500
gcctgacttc acacagcctc tgctgcagtg cgtggttgga ggtgacggcc ttggtaaatc 127560
cagtttcctg cctcctcaat tatttgtgct catacactgt atattttta gtgaggttta 127620 tatttgagat gtgttttctc cttcttaccc tttctggcct ttctatggat taatacctgg 127680
tctcttcttg tgtacttgaa agtgaatctc tcatcgtatt tttccttagt gtcagaacct 127740
ccatgactcc gagcacttaa cgtggctcat tgtaaatcac attcaagatc tgatcagcct 127800
ttcccacgag cctccagtac aggacttcat cagtgctgtt catcggaact ccgctgccag 127860
cggcctcttc atccaggcaa ttcagtctcg ttgtgaaaac ctttcaactg tacgtcttca 127920
tcctgccaac aattgccagt tgcagttttc tctgccttaa aaatggagta ttgaaatttt 127980
taactttaat ttctgactgg caaaatagtc atcttttgtt cttttccttc tcgctgttag 128040
ccaaccactc tgaagaaaac tcttcagtgc ttggagggga tccatctcag ccagtcggga 128100
gctgtgctca cgttgtatgt ggacaggctg ctgtgcaccc ctttccgtgt gctggctcgc 128160
atggtcgaca tccttgcttg tcgccgggta gaaatgcttc tggctgcaaa tttacaggta 128220
ttgggaaaag aaaccctgat attgatttat attgaaaatt tagcaggcca agcaaaacag 128280
gtggctgcct ttttcctcca taggtgtggt cttgacacgg tcaccaatag aaacatggaa 128340
atatctgcaa acttgccatt cctcgtgtgt ctgatctgtt tcttgaactt ttttctagtc 128400
tgtccttact aggatgaact gtacacatca gtttatcctt tttaaatgag catgaggtta 128460
ttttgggttg tacagtgtca caaacacact aatgtgtttt tgtctattag agcagcatgg 128520
cccagttgcc aatggaagaa ctcaacagaa tccaggaata ccttcagagc agcgggctcg 128580
ctcagaggta atgctggaaa cacaggtcat ccttgtgtta ggagaaccca ggatataaaa 128640
gatatagatt tgtgcgggaa taaattcaca ggacaagaaa ttgatgtgcg ttataggtgg 128700
gtttgctgca gaagtgccat aatagaaagc ttcctacttt taaaacaacc agatctcact 128760
ttatatggag taaaggacaa ccagcaggat cacgtctatg acatgagtgg aggcagtttg 128820
cactcctttt ggctgtttga gaggtagtat ttagaatgcc tgtattcact gtcctgtgat 128880
gagtgggaaa ataggttatc agctttatct tagcaaaatc aaagcatatc atctaattgc 128940
taaacaagag ttggcaaatc tgaaagacat tactgaatcc ttggcatgca ggacttacat 129000
ctgcatcccg ttgccatttt ttctcttcaa agcatttaat cacttagttg tgtttgcaaa 129060
gtcttttaga agcctttatc agaaatcctt acatctccta tgtgagtgta tttccatgac 129120
tgcaaaataa gttaaacttt tacctttttt cttcccttgg tgggggcgga aattgtgtgt 129180
gtgaaaggga aagagagaca gcagagaagg agaatataat tatcatgctg tgtcctttga 129240
gctgaaattg caaaaaagaa aacacacaca cacatgcttt gatttcagtc ttaagagtac 129300
cttgttgatg gtgtttttaa atgggattgg gcacaattag gtggacagtt tggggcgatt 129360
tttcggtctg tagggccaag ctgttttgta atttgcttta taaagttgtc actctcatag 129420
catatggtgg cagataaact attattactt tttgacccta gacttagtct tcagtccaga 129480
tgagggagat taaaagatta taaatatctt gtgccagatg aggtgatttt attttgaaat 129540
gaccataaat tcctatcagt tgtcttactg ggatatttga tagtggagtt tgtgcatttg 129600
agtcttagat gatctgtttt acgtttatta agaaagcctt tattagcttt tataccatgt 129660
atggactgtt gcaatgtttg agtataaatg aaatttctgg acaatattaa tggagtacaa 129720
actgtgatac cttagaagta aactagggcc tgcgtttata tcatgacctg tttgagtgtt 129780
gatgagaaaa tagctgtgaa gaaaaagttt taaacaagtt tcattttcct ttaagaagcc 129840
actaatagtg catccttagg gtgtatattt ctagaatcct agtgtgcaga gtttagacta 129900
agactaaaaa aaaaattgca ctgtaatttc ctttttgttt gtattttaga caccagaggc 129960
tctattccct gctggacagg tttcgtctct ccaccatgca agactcactt agtccctctc 130020
ccccagtctc ttcccacccg ctggacgggg atgggcacgt gtcactggaa acagtgagtc 130080
cggacaaagt aagtgtccag cgtgtctgca tgcgaggcac agggcagagt gcctctgtca 130140
cctgaggcag atacagagag tgcagaggag gtgcggtgga cccaaggagt gctggcgctc 130200
tgctcggctc aatgaagccg tggttagaga cctgggggga ccatcaatgt ccgagggagc 130260
aaagcagtgc tgatgtggga ccgtttcggt aggagtgcga ggtgagtcgt tagtgggtga 130320
ctcaagggaa agtcaattgt ggcctgcagg cccctgactg cacaggcctt caagcacatg 130380
tcagtgcatt tagcctccct ccatcgcctc ataccttctg gccacctgtg agttgcactg 130440
ccactgccag ccatactggt atgttgtcag cacctccact gctcatacct caccgttagg 130500
gaccacttgg ggccttggta gagccttggt actctacttt cctggagaga gttcagctta 130560
tgaatatgaa tttagatttc aaaaaccagc agcccaagta taagaaagcg aaggttcagt 130620
cctgccgcct taggctctat ttgctaagca tctgccctgc cctgccctgg ttgctgggaa 130680
gagatgagca aagcagacag cccaggagag gatggcaaag gggccgctaa cccttagtag 130740
tttagctata tttggaagga ctattagaaa ttcaccaggt gaagggggag gccgtgagag 130800
tacccaggta ggtaacagaa gtccaaagag gaagacctgt ggtgtggtga gctgtatagc 130860
cacaacatgc cggccggagg ccctctcagt tagcctagtg cagtgttccc aagcactggc 130920
ctaggcctgt agctccaggg atgtgaagtc cccttgaacg ccacccatca tgttcccctt 130980
attcatcttt ttcttcccag gactggtaca ttcatcttgt caaatcccag tgttggacca 131040
ggtcagattc tgcgctgctg gaaggtgcag agctggtgaa tcggattcct gctgaagata 131100
tgagtgcctt catgatgaac tcggtacggg gggagcagcg gaagcaagga atcctcagct 131160
tttcttgtga cttccaagtg ggatttgtct cctcatgtga cccacttgtt gacaacacat 131220
gttgaggact ccactctgga tggggacggg atgacggaga gactccactc tgaatggggc 131280
tgggaactgg ggaggactcc atttcagggg gccgggacat gggggatatg ctgatcgaga 131340
ttgtttcagc cacattagaa tccaaggagg caagtcgatt tcactcaacc tttcatgcat 131400
ttaaagaaaa tggaggtggt cttagattac agtcatttca ctggtttgtt ctcatggcag 131460
tgaggaaggg tattgggatt ggtgtctgtc ttaattcagg atctttgaga agatggagag 131520
cactccctca gggattagga gagactcgag atggaaatga agattttact acttacaggt 131580
cctggcgggt acatggcatg cccagaggcc cctcacacgt ggaagttggg ggcatgtgag 131640
ggaatgaagt gtggtcctgg gcactagggt gggggacctg agcggnnnnn nnnnnnnnnn 131700
nnnnnnnnnn nnnnnnnnnn nnnnnnnnnn nnnnnnnnnn nnnnnnnnnn nnnnnnnnnn 131760
nnnnnnnnnn nnnnnnnnnn nnnnnnnnnn nnnnnnnnnn nnnnnnnnnn nnnnnnnnnn 131820
nnnnnnnnnn nnnnnnnnnn nnnnnnnnnn nnnnnnnnnn nnnnnnnnnn nnnnnnnnnn 131880
nnnnnnnnnn nnnnnnnnnn nnnnnnnnnn nnnnnnnnnn nnnnnnnnnn nnnnnnnnnn 131940
nnnnnnnnnn nnnnnnnnnn nnnnnnnnnn nnnnnnnnnn nnnnnnnnnn nnnnnnnnnn 132000
nnnnnnnnnn nnnnnnnnnn nnnnnnnnnn nnnnnnnnnn nnnnnnnnnn nnnnnnnnnn 132060
nnnnnnnnnn nnnnnnnnnn nnnnnnnnnn nnnnnnnnnn nnnnnnnnnn nnnnnnnnnn 132120
nnnnnnnnnn nnnnnnnnnn nnnnnnnnnn nnnnnnnnnn nnnnnnnnnn nnnnnnnnnn 132180
nnnnnnnnnn nnnnnnnnnn nnnnnnnnnn nnnnnnnnnn nnnnnnnnnn nnnnnnnnnn 132240
nnnnnnnnnn nnnnnnnnnn nnnnnnnnnn nnnnngagaa acctcctggt gctttagccg 132300
tgcgttgata cacagcagat gggagggaag tgggcacccg ggaggacaaa tgcatgtaga 132360
ggctgggggt ggaggcaggt gttcatgaaa agagacctta cagggagggc aacacaacag 132420
tgtgttctga tgtactgaag agctagactg aaaagaacag gagaattcac ccaaaatcca 132480
tttactaaaa ttgtttatcc ttttttttt tgagacgaag tctcgctctt gtcccccagg 132540
ctggagtgcg atggtagatc ttggctcact gcaacctctg cctcctggat ttaaacaatt 132600
ctcctgcctc agcctcccga gtacaggcat gcgcccacca cgcccggcta atttttgtat 132660
ttttagtaga gacgcggttt caccgtgttg gccaggcttg tcttaaactc ctgacctcag 132720
gtgatctccc tgcctcagcc tcccaaagtg ctgggattac aggcctgagc cactgcgccc 132780
ggcctaaaat tgtttatctt aagattcatg cagtgaaaac taacttactg agtgataaat 132840
ttgcttagtg atctgtttat taggttttct aaatttgcta attgggcttt gaacagctgt 132900
aaaagttctg actgtaaaag aaagctgcaa cttttggcat tcatgatgct tttctgaata 132960
ttaaactaag atagatgttt tacctgaaga attggccccc aatcttataa atggctaaac 133020
aaaaaaggtt gctaaaacat aatccaaatt gtcataggaa ataccatttt tccaaccaaa 133080
attttgtcat tcatatggct acttttactt atttcagctg catttgacca tctttttcaa 133140
acttcaggga tggctggtgt atcaccgaga tcttggatga cactttagct ttgattttct 133200
gtttttatga attaaaattg tcataccaaa atttttactt caagcaaatc caagagcata 133260
aaaaattaaa atatcactta aagtaccaag agagaacaga aatatatttt actaagcgta 133320
cgttgaatga agttgttcaa atatttgtaa caggcataga gtagaatttt cttaaaaaca 133380
tttttgatgg tataccaatc tgtgttttct cagaaacatt tgccttattc tttttctgt 133440 tgtgtttttc ttacctgatt gaaagctcct aatctgttgt tattgtttgt ttaaccttta 133500
atgctctgat ttcaggagtt caacctaagc ctgctagctc catgcttaag cctagggatg 133560
agtgaaattt ctggtggcca gaagagtccg ctttttgaag cagcctgtga ggtgactctg 133620
gcccgcgtga gcagcaccgt gcagcagctc cctgctgtcc accacgtctt ccagtccgac 133680
ctgcctgcag agccggcggc ctactggagc aagttgaatg atctatttgg taattaaaat 133740
taaaatttat cttattttta gaaaggttcc agggccagta tagtactttg caccaagtaa 133800
atatacaata aaggcggtgg atctaataca gcgaaagcgt ttacagaggc agctaaagag 133860
cagcactggt ggcctcagcg cagaatttct tcctgcgtgt ttgccacttt gccgttcatt 133920
gacgtggtca cggacatagg gctctaagcc cttgaggaag gctgggccag acctcagggg 133980
agatgcagcc ccaaactaca tgcagtcatg tggatggatg cgtagatgtg ccattgagga 134040
gcaatgtctt gtgctttcat cagattctca aagaattgct tgactgcctt tcgaaggtgt 134100
tgcatctgtg ctcatgtttg cacccaccca cgagggcctt ctgtttcagg ggatgctgcg 134160
ctgtatcagt ccctgaccac tctggcccgg gccctggcac agtacctggt ggcggtctcc 134220
aaactgccca gtcacttgca ccttcctcct gagaaagaga aggacaccat gaaattcgtg 134280
gtggcaaccc ttgaggtaag aggcagctcc ggagctcatt gttgctgtgg gaggggacac 134340
ggggctgaca ctggagaggg taaagcagtt ttatttgaaa agcaagagct ctgaccaatc 134400
cagtcactat tctgtctcag cctggcagta agtcttgtca ccgtcaagtt attgtagcca 134460
gccttcaccc ttgcctcgcc actcctcacg gtggcctgtg aggtcagcca ggtccccttc 134520
tcatctgcac ctccagtgtt atgtggatcg taattttaga gacttgaaaa ataaccatct 134580
gtaggtactt tgtgtcttaa gttggcctgg acatgtcagc caaggaatac ttggtttgtg 134640
ttagtgcttg taattagccc ccaaaacatg tacacattct ggatgcatta aactcaggcc 134700
tgtatcctta aagggccatc tctgtgctgc ctgccctcag cagggacaca ctttgcagac 134760

-continued ccacagaggc tccgcctcca cctcacacca aagaaaggga ggagtccaaa gggcatcagt 134820
gccgttactc acaaaatgat aaatacaccc ttattctgaa ccaggtggag tcagatggtt 134880
tgtgatccct gtcctttagg tttcagctta gtggggaagt gggaaagcca gcgtgtgatc 134940
acagcacagg gtgattgctg ccgattatat tatgtgcctg ctgtgtgcag gacaacatac 135000
tttacacgca tcatcttatt tgactctcac aactccctgt gagataggct ctgttactcc 135060
catttgacag gtgaggagag caaggcttag agaatttcag tgacttgccc aggtccactg 135120
agctaggaag tagccattct ggcgtttgaa ctcaaggcct gctatcccta gaacccacgc 135180
tctcaaattc aacctctgag gctatgccag aggcaagccc cagtgctgtg ggcgccccag 135240
ggaagaacct ctggcctggt ggccacgtag cccaggagag atgtctacag gagcccacag 135300
cgctgaagga gagaagggca gcagagttaa gggggcattc tggcagagag gggactggca 135360
ccttggggaa tagctgggtc aggactgaat gtcatggagt caggtcagag ctgtccttct 135420
ggagggcaag ggcatctgga cctgcttccc ctcaatgctt tggacggttc caccacaact 135480
gattcacacg gcctccccaa atgaaggtac acgagcgggc attctgtgac ttggtacttc 135540
cctttaggcc ctgtcctggc atttgatcca tgagcagatt ccgctgagtc tggatctcca 135600
ggcagggctg gactgctgct gcctggccct gcagctgcct ggcctctgga gcgtggtctc 135660
ctccgcagag tttgtgaccc acgcctgctc cctcatccac tgtgtgcact tcatcctgga 135720
ggccggtgag tccccatccg tgaacaatgg gttcctatcc tagttcctgt ctagttcacc 135780
atgtttatat tttgtgctgc ctgtttgcca ggtactaagc taggaattgg ggatggagag 135840
gtagataaaa tacgcattag gaagggctgg gctccatctc tttttttttt tttttttttt 135900
tgagacggag tctcgctctg tcgcccaggc tggagtgcag tggccagatc tcagctcact 135960
gcaagctccg cctcccgggt tcacgccatt ctcttgcctc agcctcccga gtagctggga 136020
ctacaggtgc ccgccacctc gcccagctag tttttcgtat tttttagtag agacggggtt 136080
tcaccgtgtt agccaggatg gtctcgatct cctgacctcg tgatccgccc gtctcggcct 136140
cccaaagtgc tgggattaca ggcttgagcc accgcgcccg gccggctcca tctcttactc 136200
tccaatatat tggagtctac actggaattt aacttgaatt tgctttttta gtcattttat 136260
ttagattttg gaatttcagc tttcatcaaa attacttcta aattttatgt ctctgtgatc 136320
tttggtctta gctgactgtt ttatgcattt agtcttatat gatcgaaagg ttagtaagat 136380
tacgttcaga agattgtttt ctgttcaaat gcttgtttct atactgcact ataatattaa 136440
cgtactgtaa aataaaagtg gcttattctt ttcaaggaac agtatcctca acaagggtta 136500
ttagccacaa tttttaaaaa attggacatc atggtttaca tgttggaggg cattttgaag 136560
ctttgtattt tcaaattaaa cattatagag tgatgttttg atgtttcata attgttttca 136620
tctgtgcatt tgtggccagc ttgaaaacaa agatccaggg attaatactt aaaagccaga 136680
cttcttgggg gttatagaga tgattttggt agtaatgaat cttgagccgt ctgataataa 136740
cctcggggtg agagatggcc aacaggagag agtcgaggga cttacaaatc tgaatgaaat 136800
ctgaagtaca aatcttcaga catatgccac taaccaagag attggtacct cagtctaata 136860
ttgtctgttt gtctaaaatt ggttctaaga aatctaggct catctgtcta tccctttgaa 136920
cttttgtgag gctgcacaaa tgtaaaattt tgaatgaaaa gcactgatgg aagtctgtgg 136980
aaattcttct gtttgttctg ttgtaatttt agttgcagtg cagcctggag agcagcttct 137040
tagtccagaa agaaggacaa ataccccaaa agtcatcaga gaggaggagg aggaaataga 137100
tcctaacaca cagagtaagt ctcaggaccc attctttctt acatgtggtt cctccaagac 137160
ttaaaagtca ttcacagaga cgtgcgccgt ggtgagtgtg cactcctgga agcgcaccgt 137220
agctcggctg tgtcctgctg ctcctccctc gccgtgggag gctttagtcc attgctttgc 137280
cacactcttt tgtttcaccg tatccctgtg catgcggctg tttctgaccc tacagagcag 137340
ctgggatgcc tctgggggag cccttccccg ctccagcact tccacatgcg gttactctgg 137400
gctcctggag ggcagggagc aggtttgtct tctctgtgtt ctcagaaatt aatgcttggc 137460
ccctggtcag caagcagcaa ccttttgttg agtgatactg aataaataca tgtttcccac 137520
atgagtattc agtaacctca gtgtcaggtt caggcatctg ttttggtgga tatttaaaag 137580
aaaattccac ttttcctaca gaaaaaaaaa aataaataaa tctaaatccc agtgatttaa 137640
gccagttata gacttagaca tatactacgg cttttcatgc cctttcctcc cagttctaga 137700
gtagtatttt actaggaaaa tggtggcaat gcctgttgag aggaaaagtt tttggccaag 137760
tgtctttcgt tcttgccagg ggccctaggc tgctggggct acttcagttt ctttagccca 137820
gtgtctggca gggaatgctc cctgtagcct gtcccacaga ggcaggggtg cctcacctgg 137880
ggcctgtcca cgcattttac acagcaccct tacttggagc atcaggcatc ttttccgcgt 137940
tccgtggctc aggaaacaca ccttttcaat catgagttcg ccagtgcttt tgggcttttt 138000
ctcccagctt ttgtgcaatc ctagttatgg atggagtttt cctgccttta gtcttctgca 138060
tagtactttt ttcttctggt tcccggttcg aggttttgta attaaagaat gacccagaag 138120
cagtggcatt ttcttttctt ttctttcttt tttttttttg agacagagtc tggctctgtc 138180
gtccaggctg gagtgcagtg gccggatctc agctcactgc aagctccgcc tcccgggttc 138240
acgccattct cccgcctcag cctcccgagt agctgggact acaggcgccc gccacctcgc 138300
ccggctagtt ttttgtattt tttagtagag acggggtttc accgtgttag ccaggatggt 138360
ctcgatctcc tgacctcgtg attcacccgt cttggcctcc caaagtgctg ggattacagg 138420
cttgagccac cacgcctggc cagcagtggc attttcatac acagccaagg tcttctctga 138480
atttttatct cgaacctctg tgggtccttc aggcttcagt ttgtgatttc atgatttctt 138540
gttgctacct aaggaatatg aaaacaccca cctccctact ctgcgtcttc cagccgatgg 138600
cacctcaggc tcttggtcct gtgcttctgt ggcgaggata agaatagtgc caaccatgtg 138660
gattgagata gatcagttag tccatccatg tcaagcacct ggaatggatg acagtcttgt 138720
tgtgaatact caacagatgc taccatgact ttagttagat ttccattgct ttgaaacagt 138780
tgagacatct cagagctttg agccagagca gtgggccctg atgcaggttc tgtttggttg 138840
aagatgattg tgcttattcc ctgtggccct tgtagaccgg agtgggaagc ttgcttgatt 138900
ttaatcacct cgataggatc ttacttctta aaggtcatcc aataaataat gagccaactc 138960
attagcctgg ggcttaattg cttaagtcca atgagaagtc attctctatc ctaggaagtt 139020
gcccaaactg tagaatctcg tggcctgtgg gtagtagcca cttactacac attcactgac 139080
tcaacgaatc atatttttag tagatacaat attctagact caagacacca tgatgtggat 139140
cttcccaggg gtgtgacgtg ttcctcggcg tctgccttgg gagtttccat ttccatcaga 139200
accatgcccc agggccctca aacactctga tctaggaaag ccagtgaagc aaggatgaca 139260
gcgtggccct ttgataccag ctgagggaca gacacaggtc ctgggagacc agagaaagac 139320
aaggggcaga ggaagtgtcc tagagggtgg gccagagggc tgggaacgaa ggccagagct 139380
caggttcagg accattccag caatcccagc agaaaatggg gaggattgta tggtataggc 139440
ggatatgaag gaggtagact ctgcaagctt tcagtggcca actcattcta ggtgattcca 139500

-continued caattacagc ttgagcagct gcttgtcggt catgcttctt acactgggca agtagaatgt 139560
gtttttaaa aagtcttctc ttaaccattg cttgtttaga tccgaagtat atcaccgcag 139620
cctgtgagat ggtggcagaa atggtggagt ctctgcagtc ggtgttggct ttgggtcata 139680
aaaggaatag tggcgtgccg gcgtttctca cgtcagtgct caggaacatc gtcgtcagcc 139740
tggcccgcct gccccttgtc aacagctaca cacgtgtgcc cccactggtg agtctggtcg 139800
ttccgtgtag aagaccaagt acggtgaaac gcatgggtaa gccctgggct gggcacaccg 139860
gagagggcag ggcagagtcc ccgcggccca gaggctgcca gctgtggttc tggtgccagc 139920
tgtggttctg gtgccagctg tggttctggt gccagctgtg gttctcgtgc caggctgctt 139980
tcctcaggca ccgtatgtgg aggtcgctag tagaaatact gggttttcta aaatgaagtg 140040
aggccccaca tccctaagag attagtgtta gacttgattc taaagcaact agaccacttt 140100
gcttactggt agaccagaaa ccacactccc tcgagtgagt gagattttcc tttggaaata 140160
attcatgttt ttctacacaa ttttgctgtt gtcttcagaa tcggtttaaa gtaggtgtta 140220
ttgctgggca cagtaactca tgcctgtaat cccagcactt tgggaagcca aggcgggcag 140280
atcacttgag gtcaggagtt tgagaccagc ctggccaaca tggtgaaacc ccgtctctac 140340
taaaaataca aaaattagcc aggtgtggtg gtgtgcacct gtaatcccag ctactcagga 140400
gactgagaca ggagaatggc ttgaacccag gaggcggagg ttgcagtgag ccgagatcac 140460
gctactgcac tccagcctgg gcaacagagc aatattttgt ttcaaaaaaa aaaaaaaaaa 140520
aaaaaaaaaa aaagtaggtg ttattgatca ggatgcttgt ttcagataac gaagagctta 140580
gcttgaggag agtgagggtt gatggaaggg gactggcttc tgctcagtga aatggcatca 140640
tcccccacca gcctgctgaa gtaagatgat gggacctgtt ccttagggac tgcagcatcc 140700
tcaggcaaga aagaaaggcc gaccggcagg gtgtgagcca gcaggtatag gtcagtgaca 140760
atggagctgg gtcccaggga agaggcttgt ggctgcttga gaagggcgcg tgcccgtctg 140820
cgtgcgcgtg tgtgtatgta cgctggagag tctggggagg cttgctccaa ggacacagta 140880
tttgatcctg agacatgagg agggttctgc cgcaggcgat gaaggtattc agatggagag 140940
ctcattcgga agaagaggcc agggcctggt ggtgctggaa gcagttgcag aacagggagt 141000
tgtaagcttt cctaggaaga gcagcaggag tgctggagaa gcaggccacc cttgctgcat 141060
gggggttgct cttggcccca ctcttggtgc acggcgagtc actgtgagtt cgttagcatc 141120
tggttctgaa acagtaactg ctcctttgga ggggctcggg gagaccatgt aggagggcac 141180
agtcaagagg tcatgctatc tggaacacac ttgaggatat gccaggacgg actgcatgct 141240
gtagataaaa ttcctctagc aagctcttaa ccggcattga ggagttccct gagtgcggtc 141300
atctggaagg cagctgtgaa aggcactgca gtctcccccc gggcaggtac caggagcaca 141360
ggggagcaga actgatttaa agagagggct ttcctgtggt gaggtgagag atgagctggt 141420
cattatcata gaacccctct gcctgtgtgc agatgcgctg tgggaatcct ggggttccgt 141480
tgggtcctct gtcacctcac tgaaggcatg tcagctgagc tggccagacc ttcagctgat 141540
cctgccactt gaacagcatc aagcctgcct ctggattctt ctgtgcacgg tgcttgtcta 141600
atcacctcat gcacagagaa ctgtacttca gagtttacag aaataagctg tatggttcat 141660
tttcgtgcct gcttgccaac aaacatatct gagctgaact tcattgaacg cctgccttta 141720
ttctaacaca ccatctgctg tttgtgggcg aggggtgctg tctctaactc ctgcctgcct 141780
ctcccagcat ccctgagtgg ggtgtgccag cagcctcagg gtgaggacag gaagtgggag 141840
ggcagagcag atttggaagg gccacttgat ggggaaggaa gtcccaggaa gcagttggag 141900
ctgttttctg ggggagaagg tgccagcttg gggacagtgt tgtagtgagg aggaagccca 141960
gtggagagaa gtggggcttc ctgcttcctc acagtgtgtc tgtcctgact cagctcgggt 142020
gatgtcactt ccttttcatc ttctcaggtg tggaagcttg gatggtcacc caaaccggga 142080
ggggatttg gcacagcatt ccctgagatc cccgtggagt tcctccagga aaaggaagtc 142140
tttaaggagt tcatctaccg catcaacacg ctaggtactc ttggggcctc tttcaggtca 142200
ccatcgtcgg gcatgtaccg ggaggaaatc cagagcccca gtactgggat cttctcattt 142260
gactccagaa aagatttaag catgataata atacaaacct gtgtgaatac attttgcagt 142320
gtcagcaaaa ctccttttac tgagaaaata gatcccagtt cctgtgtttt gtggcttgaa 142380
tcccagcttt ttatattctg ggcttgtttg aagtcaggaa agattcatgt gtaacagaca 142440
acgtgaggcc aaattctgcc ttcgattttg catttaggct caacagtggc agcgcttgtc 142500
tcggagtgtg ttctcgtgtt caccagtctg atcctgttgt gtctcactgg tgcgttttct 142560
cacatgggaa caagcagacg ggagcagatg gagtcaagtc tcttagcact cgccttcctc 142620
agagcctaga ggcagcatgg ggagaaagcg ggcttggggc tcagacagtc ctggtctgct 142680
tccagccctc tgtagctgag cagcgcggaa caagtccttc taacctctag agaccctcag 142740
ttttgtcaaa tgtaaaatgg gagtcacgtc tatttcatag aattgttgca gatttagaaa 142800
ttacatttct tttttttttt tgagacggag tctcggctct gtcacccagg ctggagtgca 142860
gtggcgcgat ctcggctcac tccaaactcc gcctcctggg ttcacgccat tctcctgcct 142920
cagcctcccg agtagctggg actacaggcg cccgctgcca cgcctggcta atttttgta 142980
tttttagtag agacagggtt tcattgtatt aaccaggatg gtctcgatct cctgacctcg 143040
tgatccgccc acctcggtct cccaaagtgc tgggattaca ggagtgagcc accgtgcctg 143100
gcctagaaat tgcatttcta aacaagtgtt agcccttatt tctaaataag tgtcgaaatg 143160
aataagtcac cactttcgcc cctatttgat ggcaagaggt gtgatcttgt ggtgggattg 143220
taatcagtca gtcctcagtg actgtgccct gctgtggtgt ttcctggaaa gttcttgtct 143280
tgtcctagaa agtctggcag gggcaccctg tctccactgt ccagtcttct ccccaggccc 143340
ttcaggcttc tgcaaatttg aggcttgttt tcatcccaga aggttctggc agcagacgcc 143400
ttgcgtctac tgtccccttt agttaattag ataattcaat gtccaaaggg aaccctgagc 143460
aggaacctca agccagctgc ctcacggagc tcctcctctt cctcactgtg aagattggtg 143520
tcagtggcct cctggtctcc cccttgccta acacgagctc ctttgcttac ttgggtgccc 143580
ttgcccttga actccccggc agacgtgcgt gacccaagac tgtgctacag tccttgtttt 143640
tgttcatgct catcttcttc ttggttcatt gttttccctg taatgtcaat tgttttattt 143700
gtctgtatct gtgtctgaat cagtcctgca cgctctcctt ctctctgtct tttgttcttt 143760
ctttacccag tttatcacag ggaccccga tgtccatttc tctagttctc ctgtcctaag 143820
caccccatcc tgtctttctg gccttatcac aagtggcgtg tctgcctcag acatcatgat 143880
gggggcatga agcacagctg tcagaaacaa ctgttcgtta ggtacactcg aattcagctc 143940
atcaatagga atggagggtc tatcagatgt gttttcactg aatccctgtt cnnnnnnnnn 144000
nnnnnnnnnn nnnnnnnnnn nnnnnnnnnn nnnnnnnnnn nnnnnnnnnn nnnnnnnnnn 144060
nnnnnnnnnn nnnnnnnnnn nnnnnnnnnn nnnnnnnnnn nnnnnnnnnn nnnnnnnnnn 144120
nnnnnnnnnn nnnnnnnnnn nnnnnnnnnn nnnnnnnnnn nnnnnnnnnn nnnnnnnnnn 144180
nnnnnnnnnn nnnnnnnnnn nnnnnnnnnn nnnnnnnnnn nnnnnnnnnn nnnnnnnnnn 144240
nnnnnnnnnn nnnnnnnnnn nnnnnnnnnn nnnnnnnnnn nnnnnnnnnn nnnnnnnnnn 144300
nnnnnnnnnn nnnnnnnnnn nnnnnnnnnn nnnnnnnnnn nnnnnnnnnn nnnnnnnnnn 144360
nnnnnnnnnn nnnnnnnnnn nnnnnnnnnn nnnnnnnnnn nnnnnnnnnn nnnnnnnnnn 144420
nnnnnnnnnn nnnnnnnnnn nnnnnnnnnn nnnnnnnnnn nnnnnnnnnn nnnnnnnnnn 144480
nnnnnnnnnn nnnnnnnnnn nnnnnnnnnn nnnnnnnnnn nnnnnnnnnn nnnnnnnnnn 144540
nnnnnnnnnn nnnnnnnnnn nnnnnnnnnn nnnnnnnnnn nnnnnnnnnn nnnnnnnnnn 144600
nnnnnnnnnn nnnnnnnnnn nnnnnnnnnn nnnnnnnnnn nnnnnnnnnn nnnnnnnnnn 144660
nnnnnnnnnn nnnnnnnnnn nnnnnnnnnn nnnnnnnnnn nnnnnnnnnn nnnnnnnnnn 144720
nnnnnnnnnn nnnnnnnnnn nnnnnnnnnn nnnnnnnnnn nnnnnnnnnn nnnnnnnnnn 144780
nnnnnnnnnn nnnnnnnnnn nnnnnnnnnn nnnnnnnnnn nnnnnnnnnn nnnnnnnnnn 144840
nnnnnnnnnn nnnnnnnnnn nnnnnnnnnn nnnnnnnnnn nnnnnnnnnn nnnnnnnnnn 144900
nnnnnnnnnn nnnnnnnnnn nnnnnnnnnn nnnnnnnnnn nnnnnnnnnn nnnnnnnnnn 144960
nnnnnnnnnn nnnnnnnnnn nnnnnnnnnn nnnnnnnnnn nnnnnnnnnn nnnnnnnnnn 145020
nnnnnnnnnn nnnnnnnnnn nnnnnnnnnn nnnnnnnnnn nnnnnnnnnn nnnnnnnnnn 145080
nnnnnnnnnn nnnnnnnnnn nnnnnnnnnn nnnnnnnnnn nnnnnnnnnn nnnnnnnnnn 145140
nnnnnnnnnn nnnnnnnnnn nnnagaaaat aaggcagcag actggtgttt ctttcttttt 145200
tttttttctc ctaccttatt ttgagagagt agccagatgg tgtcttgact gatattccag 145260
agcagggaca aagcccactg aggtttgggg gctgcaatta ccaatggctg gaatgcattt 145320
gattacggtg cgttccatgt taaggatcaa taagattgtg ctctttctgg aaagtatctt 145380
ttagttttat ttattggtat tcagaggagt gtaggttgaa ttaaaatgaa aaggcatttt 145440
ataaaggccg tgagtagtac atggtttcat ttttctaatg tcttgcagag attttattag 145500
gcttctcgaa gtgttcacgt acattacgtt aatgtgatac taagagtaac tgtactctgg 145560
cacagcgaag ccagcagaat gggaagttgt ggaatgcagg cccttgattc tgatagaagg 145620
tgtggtatga actcgcagaa atgacagttt ggagggtaga catatgtcac aagtcatcaa 145680
gattgtcttt aaattcatcc atagaagcta acaggttgtc ataagcaaag cctctaaaat 145740
gtatgaggga attcaaggat aatttatcaa aaagtaattc atgtttggag ttttgtgccc 145800
aaaggagtcc ttgatttgaa aaatgggtgt ttgcccatca gattgtttca gggtccgtat 145860
gtgcagaggc cgtgcctcgt gccccgtgag ctcagcctga cagaagtccc ttggtagcac 145920
ttagggactt ggttagcact tcttcccttt gaggcagggt ggactctggg ttctgcattc 145980
agagctggct gtgggtgtct tgctgttctt gttgacctgt gggctctcct tccaggaaga 146040
cacagagagg acgcagatca acgtcctggc cgtgcaggcc atcacctcac tggtgctcag 146100
tgcaatgacc gtgcctgtgg ccggcaaccc agctgtgagc tgcttggagc agcagcctcg 146160
gaacaagcct ctgaaagctc tggacaccag gtttgcctga attcccacgt gtctccagga 146220
catcatgggt gctgcggaca gtggggtccc cgctgaagca tccagcagct tcccccaggc 146280
tgttttcctt tgttgctaga attgaaaacg ctgtccatgt ggcctgtgca ggaggtgcag 146340
acccaaaggt ggcctcttgg ccattgagga gctggaaacg cgacgggaac tgacatgggg 146400
ttattgggca tttaggggta aacattagca gagcaagaat gagcgggcaa gtggtagaac 146460
acccacctaa gggctcatgg acaggtgctc acttaggaag tgagtttcgt ttggtattac 146520
accaggttcc tttaggcagg gcggagggaa agttctggcg tttttcactt gtaagatttt 146580
gaaggaaaca aaacactctt tacctttttt ctgaaatgta ggtttgggag gaagctgagc 146640
attatcagag ggattgtaga gcaagagatt caagcaatgg tttcaaagag agagaacatc 146700
gccacccatc atttatacca ggcgtgggat cctgtccctt ctctgtcccc ggctaccaca 146760
ggtacctgag ggagagggtg gggggtggct gtacttgggc tgggatgaga aaagactggc 146820
gtgctcacca caccagttat gcaggaagac ctgagtgtgg tttgagttgg aggctgtggt 146880
gctaaatagc tgccccattc ataagcagga gtcttattca ggcccaggga ggaaataaaa 146940
tctggaaatg aattaggagc attatctcct gccagtcaat tctcacgggc tgtaagaaca 147000
gcaggattta aaagttgaat gagttcctta tgttaagaac tcaaccgagt tcatctacac 147060
aagctgaatc tccagctttt cctaagaaac caggtgtggc agtggctgca gggcggggca 147120
cagctgggcc tgagcacccc gctccctgca cctctcccct ccctgggccc tgtctgtcgg 147180
tgcccactct cccaccaagc ctgccagttg tgtgcctgcc ctatcacagg catcagagtt 147240
tgtcacctgg tttaaaagaa gggagttgtg tagggatctg gggatgcaca tttttcactg 147300
aacagtattt tagcatagag gtttgtgatt ccctggttat ttaggagttt aagcacctta 147360
aaggctttaa ttgcagaaag gtctatgtgg acatgcaatg tgttatacgc agtgtctatg 147420
accctcaaat gtttattagg gtattgaaat aaactgagca cttggagggc catggatcca 147480
gcttcaagga gttcataggt caggaggacc caggagcaat gacctgtcgt agacggcaga 147540
aaagaggggc acagaggtgg gttgggggca tacacaggca gctcctggag ctccaaggag 147600
agcaagtgct tccagggaag ggggtgtgga ggctccttgg gaggaggcga gttgatgctg 147660
gggtctggca gagggttagc tggggacatt cggctggagg ctgttgtctg ggaattgggg 147720
ggatgcccag cagaaagaca tgcggaggtt gtttggcctg gggcgtgggg ggtgtgagag 147780
gtcgagtggg ggcattatcc tgctcccgct cctgctggct gtatctggtc agcctgggca 147840
ccgaggcggg ttctggaaag cactgttcac agatgcttat ctgagtcccc cagannnnnn 147900
nnnnnnnnnn nnnnnnnnnn nnnnnnnnnn nnnnnnnnnn nnnnnnnnnn nnnnnnnnnn 147960
nnnnnnnnnn nnnnnnnnnn nnnnnnnnnn nnnnnnnnnn nnnnnnnnnn nnnnnnnnnn 148020
nnnnnnnnnn nnnnnnnnnn nnnnnnnnnn nnnnnnnnnn nnnnnnnnnn nnnnnnnnnn 148080
nnnnnnnnnn nnnnnnnnnn nnnnnnnnnn nnnnnnnnnn nnnnnnnnnn nnnnnnnnnn 148140
nnnnnnnnnn nnnnnnnnnn nnnnnnnnnn nnnnnnnnnn nnnnnnnnnn nnnnnnnnnn 148200
nnnnnnnnnn nnnnnnnnnn nnnnnnnnnn nnnnnnnnnn nnnnnnnnnn nnnnnnnnnn 148260
nnnnnnnnnn nnnnnnnnnn nnnnnnnnnn nnnnnnnnnn nnnnnnnnnn nnnnnnnnnn 148320
nnnnnnnnnn nnnnnnnnnn nnnnnnnnnn nnnnnnnnnn nnnnnnnnnn nnnnnnnnnn 148380
nnnnnnnntt gcagtgagcc aagatcacgc cattgcactc cagcctgggc ggcagagcga 148440
gactctgttt caaaaaaaaa aaaaaaaaaa aaaaaatctt taatgttcat tgtttttgtc 148500
ctttttattc ctaggtccca caagcagaga aaatattact tttgttttta tttatgttct 148560
ttattctaga aagtagttaa gagacctcac atgtagtgat agagatgtat ataagagaca 148620
gtgagagggc ctgagctgga cttaagcaag gaccgtgaga caccaaaagg ggtgaggaca 148680
gagtggagtt agctgagatg ctcaggagga agtagatgcc atgaagggct ctgttgtggg 148740
gggctgcagg cttggccctg agtgtccctg tggccagttg ttgggggggg cccagtgtgc 148800
aggcagacag ctcggccact ttgtggcagg tcacgttggt ctgtgcttct gtttcctcct 148860
caggtaagtg aagggattta agggtccagg tgtggtggct cacacctgta atgtataaca 148920
ttttaggagg ctgaggccgg aggctcacct gagctcaggc ggttgaggct gcagtgagcc 148980
atgattgcac cactgcactc cagcctgggc aacagaccaa tactctgtca cttaaaaaaa 149040
gtgtaaacag aaacacaggg ccatttacat atgatggcac atggcaggag ccccacaggt 149100
gtatgctcag gggagggccc agctttgctg gctgacttgc acctatccct ccaccctgtg 149160
ctgtgtcttt cgctcactgg gttcctggtt tagtgaaacc agttgtgcag gacggttccc 149220
ttggtagctt ttgttgcagt ggaaatgggt caggatatgg tgtgtagaag cacttatgag 149280
ctctgagagt ttcctcttat gacttcctgg cctgcagcct tcacagcaga aaccccatga 149340
tgtcacacgc ctgtttctgt tccctgctct gtgccctgta ctgtcctgtt ctgtgcctgc 149400
tggtttcagt gacaggaggc agggagctgc tggaccagcc tgtatttttc tagacatagt 149460
tggaaaaaga agtcacgctc ttctgtcctc tcacctttga cagatgtttc cacctcaaga 149520
taagtggaca tggccaatag gacgcactgt acttttcctg gatgtgtttc tgaagggcag 149580
gctgagagtg agaggcctgg agctcactgg gtgcctgtgg ccttgtcctg gccccgggga 149640
cactggtctg tgcccgagat actccctatt ccccacgccc cactgcattt gcccacatcc 149700
ttcgatgttt gccctgtgtc caatgtctgc aaaccgactg tcatgggatt atactggggc 149760
tgaagtatag tgccacccct gccctgtcgg ggacgttcag ccccagatgc cactggactg 149820
agccactgct tgcttttagg aaagggggtg ggggttatgg gtctgggctt ggggagcaca 149880
ggggctgctc cttggcctga gaattgttca tacagactcc ctgcccactc cctgcagggg 149940
tgctgggtcc caggggggaa atggcccttg gtgccaagaa cgtgagttgg gcctagggcc 150000
agtgatgatg gagaacagct tttatgggc acacagccca tagcactgtg ccaagtgctc 150060
gaggctccca gagaagcagg cagaaaggag gacagtcgag gtgtgctgag cacgtggtgg 150120
ctgtgtgatc tggagcgcgg gtcacagagg cgcggggacg ctctggcctg gggtttacca 150180
caatgactgc cagtggcgga gatcggaaaa gaaatctcac gcgttggttc cgtgttttgg 150240
ggggttccgt gttttggggg gttccgtgtt ttggggggtt ccgtgttttg gggactgcat 150300
tgagatctca cttacgagtg agagcgtccc cttcgtagag cctctttctg tgtcgcctcc 150360
tcagccgctc ctggggctgg ctgactcctg atccaggccc ttagcgtgtg ctggagcttc 150420
ccagcagcag tccagccccc accccaccct ctctgtggac tcccttgcct gtaagctggg 150480
gtgtctgaac gacccttgca aaggggcaga ctgttcaacg gtaggcatgt gctgagtccc 150540
ggcggccgca cccgcccacc aggagcctgg cactgtggct gcagcgctga gcagcaccct 150600
gtttctgtgg caggtgtcca tacactctgt gtggctgggg aacagcatca cacccctaag 150660
ggaggaggaa tgggacgagg aggaggagga ggaggccgac gcccctgcac cttcatcacc 150720
acccacgtct ccagtcaact ccaggttttc caatggcctt tttcttttct acagaaattt 150780
gaaatttctt atcagtcatt tgatttgttt gaggtgcttc ttgaaatgag cctctcatct 150840
tctgtaccca gaaaacaccc atcttgcata ttctacagga aacaccgggc tggagttgac 150900
atccattcct gttcgcagtt tttactcgag ttgtacagcc gctggatcct gccatccaac 150960
tcagccagga ggaccccggc catcctgatc agtgaggtgg ttcgatccgt aagtgagcct 151020
tcccattccc ctcacactgg cacatgccac acgcaccaca cacgctgcac acacagacac 151080
gccacaccac acgtaccaca tgcaccacac acacgtcaca tcacacatac cccacatgca 151140
cggaacacac acacgccaca tgcacacgta ccccacatgc atgcaccaca cacacacacc 151200
acatgcacac gtaccccaaa tgcacgcccc atacacctca catgcacaca taccccacat 151260
gcacacaaca cacacatgcc acatgcacac gtaccccgca tgcacacaac acacacatgc 151320

-continued cacatgcaca cataccccac atgcacacaa cacacacacg ccacacgtgc acacacatac 151380
accacatgca ccacgcacag cacacatgcc acacgcacac acacaccaca cacaccccac 151440
acagcccata caccactttc atgcaacaca caccacacac aatgccacac tcgccacatg 151500
cacacacacc acatgtacat accacacaca tgccacacgc accacacaca tgccacatgc 151560
accacacaca tgccacacca cacacaccac acacaatgcc acactcacca catgcacaca 151620
caccacatgt acataccaca cacatgccac atgcaccaca cacatgccac atgcaccaca 151680
cacaccacac acatcacata catgcaccac gtgtactatg tacacacaca gacacaccac 151740
acgcgtacac cacacacaga cgcacacacg cgtcccgcgc agtcatgtct cttaggtgta 151800
agaacacgac ttgccagtag cggcgttctg gatgtgttgc ctggattcta actgcgctac 151860
tctccccttg ctttcctggt gttccacatc tccagcttct ggtggtctca gacttgttca 151920
ctgagcgcaa ccagtttgag ctgatgtatg tgacgctgac agaactgcga agggtgcatc 151980
cttcagaaga cgagatcctc gctcagtacc tggtgcccgc cacctgcaag gcagctgccg 152040
tccttgggat ggtaagtgac aggtggtaca gaggttcctg tcctgaagcc atgtgggccc 152100
atctgccttg ggacctggtg ttggccagag gtgccaggtg cggctgcctc cttccaagag 152160
ttgacccgag ccggactcca cagcccacgt gagctgcagt gcttctcagc tggagggggt 152220
tcagcgacgg tcagtgccat ccacaggcca ccgtgatgtg ggtcgtggcg gccaagccat 152280
ggtttggggt cccgtgtccc tgggcttgtg acatcattgt agtagcccat ccccacagaa 152340
ccatggtgtg tggtagcact gaagcatcgt agatggtgga aacgcgactg gcttccccat 152400
gctctgccct gaggcctgac tgcctcactc cccctcagtt atgttccagg ccccccgaac 152460
ttcctgactg gacagcttct ctcctggggg ccattttgtc acagtgaccc tgcgtttcca 152520
gtcccaagtc tgggtgctat agtgtcttct tagcatggtg tttctcttag tctatttcgg 152580
ctgctaccac aaggtacctt agactgggtg atttataaac agtggaaatt cacttctcat 152640
agttctgggg gctggaagtt catggtcaag gtgccaacag atttggtgtt tggtgagggc 152700
tgctctctgc ttcatagatg gcatgttctc actgggtcct cacggtgaaa ggagtgaaca 152760
agctccctca ggcctttcaa aagggcccca atccacaagg gctcacccct catgacttca 152820
tcaccacccg aggccccacc ttctagtact gtggcactgc aaattagttg tcagtgtaag 152880
agtttcgggg gggatacatt cattcagacc atcccaaggg tcaagtgttc atcctcttga 152940
gctcctcctt attctgcttc tggtttatca ggattcagcc cgtgcagcac ggtacctgtg 153000
ttctgtgggc acatcaccac atggcatttc ccaagcatcc atcagctgta cacatgaaat 153060
cgctacctgt gggccccgac tgctggcaaa gcctattcaa ggatgtcaga actgtcagag 153120
ctggagcctc tgggtctttg tcatgtggca ttacctagta atccatttta tgatagcaat 153180
agaaacgcgt gtcttcaaca aacacctcag tggctgccgt gtgccagccg tctggagccc 153240
ttggtgagaa tggcatggta gtgcccatca gggcctgctt accccatgct ctggatgggc 153300
tcctgtcagt aacaacgctg tcgtgacagt gatgatgttt ttttgccgtc actccagctg 153360
ctaacatttg cggagctctt cctcctgcac ccccacctgac aaaggcaccc taggcggcca 153420
gcgtcagagg ttagctggct tgtctgggtc acacaaaatg cggcagaggt gggactgagc 153480
ccatgtctgt gacctgaagc ctgactccct gcgagtcttg actactcttg cctggactct 153540
gtcctccccg agcccaaact ccagtcatct tcccttgtgg gtggccgtca gcctggtgcc 153600
gtgctggtga cttggcagcc atccagggag tggaaacaat gaacgcgtgg gctccctgtg 153660
tgggcatctc tcttcactgc gagcaccctc tgggtgttgc ccacatgatg tcaaagcggc 153720
tctcggaagg ggtccttctc ctttatgggg agtttcagct gctgggctaa cttgaattgt 153780
aatgtggttt tgtgctcagg cccagagctc cttaggcaag tgttgtgcca tcagtaatca 153840
aatgagaaat aatcattttg aaaagcagat cctaaggcag gatggtcatg ggcactaatt 153900
cccagctctg tgcatctttc ttgaagacgg tgatcctctg tgaaggtttt cagcatgtca 153960
tgcttggtac cagcgtatcc agagcatgtc attttgaggt atttgcctcc tgttgtgaaa 154020
tccgtgccac ctgagagcag gtcctgatgt gggactttca gaggtgggac caggggccgt 154080
gggagcgcag tccttaggga ggtgccgcgt ggcgttgtgt gtatgagggg atagcacagg 154140
gtgaggtggg ggcccaagaa ggaagtgatc caccaaagaa cagcctcttt cggtcctcat 154200
tcctgggatg ggtgggagcg gcttctgtgt cttccggtca tttcccctgc ggagaagctc 154260
ctgccactgc caagaacctc atcttgttcc acaacaagaa gaggctgcct ggccatccag 154320
cgctccatgg gaattctgtg tccccatagt cttgggctga aagagagcga cataccttgg 154380
tgacttctgc aggggtctcc tcactgttaa agagcagatt gaaagtgaag aatgtgggct 154440
aagtgtttag gtcgatattt aaccccatta ggttttggat actaagtgaa attgaggcca 154500
ttttggttga aggttggcat aaactactat cagggatccc caagactacc cccaggcttt 154560
tctagaagga ctctcagcta agatgtaata cagtaaaagc acacaaaaca caatcagcaa 154620
accaaatcag caagggcaga ggcccatggg gcggtgtccc gaggaaacca ggcccgagct 154680
tccagaatcc tctcccggcg gggtcgtgca ggacacactg agctccccca gagtgagccg 154740
tgacagcgtg tgcagtgtcg tcaccaggct caagcttcca gaatcctctc ccagtggggt 154800
cgtgcaggac gcactgagct cccccagagt gagctgtgac agtgtgtgca gtgttgtcac 154860
cagggaagcc cactagagac tcggtgccag ggttttgact gcgggctggg cacgtgggca 154920
ccttctgcct gcttcgtgcc catactctgg actcccagag ggaaggcaga ttctcagcac 154980
aaacaccgtt gcccacacaa gcagctgagc acagagagcc cctcctcagt gaggatggtg 155040
ggcaccgtcc cgacaccagc caggggccag ccttgcacac agacctctca ggatggtctt 155100
gggccgtgca cacaagcatg agggcagcgc accgcccccg cccctccttg gctgtgggga 155160
ggagccactg gggcgtgagc tctggtggca tcagcagctt ttgtctgtgt gtgtctagga 155220
caaggtcgtg gcggagcctg tcagccgcct gctggagagc acactcagga gcagccacct 155280
gcccagcagg gtcggagccc tgcacggcat cctctatgtg ctggagtgcg acctgctgga 155340
cgatactgcc aagcagctca tcccagtcat cagtgactat ctcctctcca acctgaaagg 155400
gatcgcccag tgagtgggag cctggctggg gctaggacgg gggtctcgga atgagctgcg 155460
aaggaagcag catcaccctc tccaagtgcc caggtccctg gccagatggc aggcaggtgt 155520
cagtgggaac ccaggtgggc gccatggctg aggttggtga gacgcaaggg cacaggtgtg 155580
tcctagaggc ttcctcgggc acccccagtg agctagagct cctgcctctg ctgctgtctc 155640
atgtggcgct gagcacattt ccccatgtgc ccattcctga ctctgctcgc gaggccagcg 155700
gttctcattc tctgctctca gaaccctctc ctcattaccc aggccagcct cctctctgca 155760
ccttccccgc cctggcccag cacctccctc ctgtttccac tgtgactccg acctcacttt 155820
atcttaaagc tgctgggcgg caggttctgc acagatgtgt ccttgacaaa gcacggctgg 155880
tgccacaacc ccttaacgag caagtcaagc tcttcacaac gatgtcttgt gagtgcggag 155940
ggctctgtga caccctggtc tcacctccgc tctcccgaag tcgcagaggc tttagcagag 156000
atgggcccag cctctctgag tcacaggctt tagagctgtc tgtagaggga gggtagaatt 156060

-continued tcatcagcca cccacatggg ggagttgagg gcaagaattt ggagcaaaga tgggaaaggg 156120
gctgggaaga atggccagtg atcccctttg acaagtgggc aggagatggg ggccgggtca 156180
aagttgagtg gaagacttgg agggagatgg gaagatctct gtaggcacag ttcagacagg 156240
agggaggtgt gagccagggc actggctggt ggctgtctgg caggatttgg gacatcctgg 156300
agcagggaca gtggctcaac aggggccatt gccctcatcc aggccagagt ggcacaagct 156360
tgtggggagg cccttctcgt ctgtcatcct tgctgggcgg tgggtgctgt gctagcagga 156420
cgcaggacag gcggacagct ggcaactgtc tctgcatccc tggagcctgg catagggcaa 156480
gtcacacggg ggacacaggc ctgcaaatca ggcacatgcg ttggtgcagc gaggtgattt 156540
tggggggcag ccccacaaca ggccccaggc acaggccaaa gccctggctg tgctggcgtg 156600
ttgggccgtc tatggctctt gctgtgggca tggaggactc aggaaaggag agttgaggtg 156660
gcccaggagt tgcgtttggg atgcagagag cttgtggcat ccaggtagaa atggtgtgtg 156720
gggctggcct cagtgccatg ggcacgggct gtgtcacatg cctccgaggt agaggtggga 156780
ccacgtggtg atggatataa gcatcactgg gcacatttct gtgggtggag gggggcatct 156840
tactggctcc tctgttcaca gtggccactc attcagtccc tggctaccgg gtccccattg 156900
tgccatgggg aaggcaggtg ctgtcggggg atcacacaag gcagcacgtc atggtggaat 156960
gtgccacgaa ggaaaagcac agggcactca ggaagtagag gggactggcc tggggtgtgg 157020
gaatccaggg cctctttgag ggacagagag aggaagtctg tggtggccag tatggaggtg 157080
gccacagggg aggctgggcc aggccgagag ggcagggcgt ggaggaggta gacgggctca 157140
gctatccagg gaggggtcga gcagaggctg aagggtcagg ccaggttaca ggggcctggg 157200
gagccacaca gggtaggtgc ttccgggagc cagcctggcc cgcagctctt cactcccgcg 157260
tggggccggg catgctgcga agccctctct acgttggatg ggggcggctg agcctggctg 157320
ctgtctcccg ttttcagctg cgtgaacatt cacagccagc agcacgtact ggtcatgtgt 157380
gccactgcgt tttacctgat tgagaactat cctctggacg tagggccaga attttcagca 157440
tcaataatac aggtgagtgg gccctggctg tcttcctctg cacacgggga gtgggcttcc 157500
cttctctttt ccttgcggga tcataccagt gggccagttt tgacttggtg gggaggaggc 157560
atgaacacct gagaccatgc agcgacagaa acctttctcc ctgtgcagat gtgtggggtg 157620
atgctgtccg gaagtgagga gtccaccccc tctatcattt accactgtgc cctcagaggc 157680
ctggagcgcc tcctgctctc tgagcagctc tcccgcctgg atgcagaatc cctggtcaag 157740
ctgagtgtgg acagagtgaa cgtgcacagc ccgcaccgcg ccatggcggc tctgggcttg 157800
atgctcacct gcatgtacac aggtgagcag gtacacagtg cccgcaaggc cagcccaagt 157860
cctgttcaag ggagacagga gcatgctcgc tcaaggaacc tagactaggt gtcctctgat 157920
ttgacacttt tagtgttgcc ccaagctggc cccatcacct tgcaagagag gctctggagc 157980
ccccagggct ggagtacctg gtcagggttg accacccctc tggtcactca tcccatgtgg 158040
ctgagctgtg ctgggtcctg ggctagcgag gggctcacat cacctgctgt caggtcttct 158100
ccagtgattc attggactcc tgtgtacaaa gcactatcta cagagcctgt tgggttgtat 158160
agatgtaacc ttcgtactga acacttttat tacaggaaag gagaaagtca gtccgggtag 158220
aacttcagac cctaatcctg cagccccaga cagcgagtcg gtgattgttg ctatggagcg 158280
ggtgtctgtt ctttttgata ggtaagaaac gaagccccat ccctcagccg ttagcttccc 158340
tagaattttg gcctgaagct gagcgtttgt gtgtgttggc tgatcccctg gcgctgttgc 158400
tggagtcccg ccagtgattc ctgaccacag cctgaccgtg ggctgccttg gctcagggtt 158460

-continued ccactggcga gctggtggtc cttggacccc agcgctcagg tgtagtgttg accagttcca 158520
aggttgtccc agcgcctgcc catctctcct gagggctcag gcaccgcacc tggccgtgtg 158580
gggtatggca gggggcagga atgaccagtc tctgggaggg tgcggcagaa gcctgcgcag 158640
tgatgaggag ttggctcagc ctggctgcct gtcgtgagag gggagcccac gggggtctgt 158700
gggaggggggt ccatggtgcc tgtgagcagg gtgaggggca gcagcaggag gaggaaggtg 158760
aaacccacac atgcatcttt gagacccgtg tggtcagtgg cttctcctcg ctacccctcc 158820
gccccactgc tgtgcgtgaa ttggtgttga gaattggctt cgctcccctg ctctggaagt 158880
gggttaggag cttcgtaggg ctttttctca aggacaaggc tccctgattg ctctcaggcc 158940
tcagtcctgg cgacatggcg gatctggggc gttgttgtgc tgccttgcct gtgctctcca 159000
atcagggtgt cccagtcctg gcgacatggc ggatctgggg cgttgttgca ctgccttgcc 159060
tgtgctctcc aatcagggtg tccagtgggg agccatttgg cttttctcaa gagcatactc 159120
aggtggactt tgctctattc tttggccaga tgaggtgttc tgaacagctg agcctgtgct 159180
tgtctgtttt catgtttttt ttttttttttg agatggagtt ttgcccttgt cacccaggct 159240
ggagtgcaat ggcgcgatct cggctcactg caacctccac ctcccgggtt caagcgattc 159300
tcctgcctca gcctcccaag tagctgggat tacaggcacg tgccaccacg cccagctaat 159360
ttttgtgttt ttagtagaga cagtgcttca ccgtgttggc cgaactggtc tcgaacttct 159420
gaactcaagt gatccaccct cctcggcctc ccaaagtgct gggattgcag gcatgagcca 159480
ccgtgcctgg cccccatgtc gattttaaaa cgcacctctg catcattctt cagttcccac 159540
atgctcactg agcaccacca cagctggcag acggacacag ggaggcgcca cgaccagtcc 159600
tggccttcaa ggggcttgtg gtctagtgga cccagtgcta ggtggcgagt gctccagaga 159660
gcgtggtgta tgccttccgc tctaccgccc tccagacgcc gcagggaggc accttggagc 159720
tgaccacaga tctccctccg tggagcactg tcttcagcgc agccgccatg ccactgctgg 159780
gcgagggtct gcgggcgggt agagccagga gcacctctga gaaagtgcac tgccgtttct 159840
tggctgcttc ctgtgcatct cagttacaca cagctggcat gtgtgcactg atgagacagg 159900
aacatgatgg ttgcttttca gcactaaaaa ggatactgct cagggggcgt gtttcaggat 159960
ctggttaggg aaaaagcagc gagagcacag atggggccct gtttggtaac aagaaaaaag 160020
tcccggttga caacagtgct acaaagtgtt agaacacata gaaatgttta tggagcattt 160080
ggatgtggaa agcagcaaaa acataatgag aaggggttct tttgttagga tttttaaaaa 160140
tctcttttgt aacatccttc cggctgcacc atttctgcat attcttttat gtagctttca 160200
gactcttagg atttctggtc actgcagggc gtgggagcca gacagagcct atgcctagca 160260
gcctgtcttc acgagctgga cagaggagga gctggggttt tgcctttttta gcctcaaatt 160320
tcatactcca gttgcttagg ctctgacttt ccccacttgg aaagtccctc acggccaagg 160380
gtacctccca gccctgattt cacatcagca ttttccccag agccaaggcc ctccgcgggc 160440
aggtggggca gctgtgggag ctggtgccag gctctgacct gtgtccctcc tcccaggatc 160500
aggaaaggct ttccttgtga agccagagtg gtggcgagga tcctgcccca gtttctagac 160560
gacttcttcc caccccagga catcatgaac aaagtcatcg gagagtttct gtccaaccag 160620
cagccatacc cccagttcat ggccaccgtg gtgtataagg tgaggttgca tgtgggatgg 160680
ggatggagtg gggaagcctg gaggtggaat tgaccccgac ttgccagcag attcgccaga 160740
agaacccagc tcctcccctt taaagcagca atgcctctgg cccccacccc acccccacca 160800

-continued cccgggcaca gcaggtgctt cccgcccccc agccctgaca ctcaggcgcc cgcttgctcc 160860
tggcaggtgt ttcagactct gcacagcacc gggcagtcat ccatggtccg ggactgggtc 160920
atgctgtccc tctccaactt cacacagagg accccagtcg ccatggccac atggagcctc 160980
tcctgcttct tcgtcagcgc gtccaccagc ccatgggttg cggcgatgta tcctctctgg 161040
gtccctggtg ctggccccgt ttccctcgtc aacaccgagg ctcatgtttc atgataaagt 161100
tttgaaacct aacctttgca aaagccccac agatgccaag gtgacaggcc ctcagcccca 161160
gggaagtaca atgctgacag ggatacagaa aggagcacat ccagacattt gctgaccagg 161220
gcctctcaga ggggcccgtg tatggcagaa gggtcgaagc tgctaagggg cccttctgtg 161280
gagggcctgg gtgaggggag cgagggtggg cggcggtctc tgcagacctc ccgcccactc 161340
gcgggctctg tgtggctggg cttctcctga cactgcttct cattagcttt ggtcattgtg 161400
cctcgatcac cctctcgggg aaaggcttaa gtaaagatcc agttcccacc cccagatgct 161460
ggctgccagg agtttccctt tccacagccc tcccccaaga cagaccacaa gagcctccga 161520
gcagcacggt tgtcctggtg ctgacagcac agcctcgccc agtgtgcctg gcgtggctct 161580
gcccgcactg tactggagca gggctcgtgg gggccagcag gacagcagga gcatcggcca 161640
ccagcgctac acaggagcca ggccaggtga gtgctgccga gtgggtgcct gcctgcaggc 161700
ctcctgcttc cttggccagc tctgcccagc tcacttctgc cctgctggcc ttccagcagg 161760
gtgtccagcc agccaagggt tgcaggaatg aaggtggagg cgctgctgca gctggagcca 161820
tccaggtagc ccttccgggg ctctgctggc tctccaggct ccctgggccc cttcgtaggc 161880
tgtttcagga gaggagctcc caggtgagga cagggaggca gcattcccct catttgccgg 161940
cctttttcct taactcctgc accagcctcc cacatgtcat cagcaggatg ggaaagctgg 162000
agcaggtgga cgtcaacctt ttctgcctgg ttgccacaga cttttacaga caccagatag 162060
aggaggagct cgaccgcagg gccttccagt ctgtgtttga ggtggttgca gctccaggaa 162120
gcccatatca ccggctgctg acttgtttac gaaatgtcca caaggtcacc acctgctgag 162180
cgccatggtg ggagagactg tgaggcggca gctggggctg gagcctccag aaatctgcgc 162240
cctgtgccct gcctccaccg agccagcttg gtccctgtgg gcttccgcac atgccgcggg 162300
cggccaggca acgtgcgtgt ctctgccata tggcagaagt gctctttgtg gtacagtggc 162360
caggcaagga gtatctgcag tcccggtggg gctgagcctg aggccttccg gagagcagga 162420
gcagctgtgc tgcacgccat gtgggtgacc aggtcctttc tcctgatgct cacctgttgg 162480
gtgttgccag gctgcagctg ctcttgcatc tgggccggaa gtcctccctc ctgcaggctg 162540
gctgtgggcc cctctgctgt cctgcagtag aaggtgccgt gagcaggctt tgggaacact 162600
ggcctgtgtc ttcctggtgg ggtgtgcatg ccacgccctg tgtctgtatg cacagatgcc 162660
atggcatgtg ctgggccagt ggctgggggt gctagacacc cagcaccatt ctcccttctc 162720
tcttttcttc tcaggattta aaatttaatt atatcagtaa agagattaat tttaacgtaa 162780
ctctttctat gcccgtgtaa agtatgtgaa ttgcaaggcc tgtgctgcat gcgacagtgt 162840
tcggggaggt gggcagggcc cctggccacg ctccctctcc tgtagccact ggcatagcct 162900
tcctgagcac ccgctgacat ttccgttgta catgttcctg tttatgcatt cacaaggtga 162960
ctgggatgta gagaggcgct agtgtgcagg tggccacagc aggactaagg acaggccccc 163020
actgtcctag gggcatgctc gcctgcagcc cctccttctt gggcacagac aactgttgtt 163080
ctccacccac attagggaca gcagcctccc tatcagctga gaaggccagc cctccctggc 163140
tgtgagcagc ctccgctgtg tccagagaca tgggcctccc actcctgttc cttgctagcc 163200

-continued ctggggcggt gtctgcccag gagctggctg gccggtgatg ggatctgccg ttccatggat 163260
gcatgcccca agggtgtcac tgagctgtgt tttgtctgag cctctcttgg tcaacagcaa 163320
agcttggcgt cttggcactg ttagtgacag agcctggcat cccttctgcc cccgttccag 163380
ctgacatctt gcacggggac cccttttagt caggagagtg cagatctgtg ctcattggag 163440
actgccccac tgccctgtca gagccgccac tcctatcccc aggccaggtc cctggaccag 163500
cctcttgttt gcaggcccag aggagccaag tcattaaaat ggaagtggat tctggatggc 163560
cggctgctgc tgacatagga gctggatttg ggagctctga gatggggcag gagctctgct 163620
tcctcagccc ttgaggcgag ccaggcgagg ttggcgactg tcatgtggct tggtttgctc 163680
atgcctgttg atgttttggg tattgaatat ggtaagtgga ggaaatgctt ttctggagtc 163740
tgtgcaggtg ctgccttgag accctcaagc ttccacctgt ccctctccta tgtggcagct 163800
gaggagcagc tgacatgtgg acttgtgtgc tgcccacata catgaggggg cgctgaaagg 163860
gagcccctgc tcaaagggag cccctcctct gagcagcctt tgacaggcct gtatgaggct 163920
tttcccacca gctcccaaca gaggcctccc ccagccagga ccacctcgtc ctcgtggcag 163980
ggcagcagga gcggtagaaa ggggtctgat gtttgaggag gcccttaagg gaagctactg 164040
aattttaaca agaaagccac cattcttccg tattggttgg gggctcctgt ttctcatcct 164100
agcttcttcc tggaaagcct gctagaagct ttgggaatga ggggaaagtt ctcagaaccg 164160
ttgctgctcc ccacccacct cccctgcagt aagttatgtc aacagctcgg agacagaagt 164220
atcacaggcc agatgttgtt ctgctagatg tttacatttg taagaaataa cactgtgaat 164280
gtaaaacgga gccattcccc ttggaatgca tatcgctggg ctcaacacag agtttgtctt 164340
ccttttgttt acgacgtgat ctaaaacagt ccttagcaag ggctcagaa caccccgctc 164400
tggcagtggg tgtcccccac tcccaaaggc ctgcctgtgt gctccagaga tgaatatgag 164460
ctcattagta aaatgacttt acccatgcgt aagtcaagta cacgtgcacg tgcatatgga 164520
cacatctgta gttttataca cgcacatctc aagacagaga tgcatggcct ccaagagtgc 164580
ccgtgtcggt tcttcctgga agttgacttt cctcagacct gccaggtaaa gttagctgtg 164640
tgacgggcgt ccaggcgcgg ggcttggtca gagcagggct cattcatggc tcactaggat 164700
cccaccggag aaaacggtct ccatatcaac tctgccgaag ggaggaagac tttgtcgcgt 164760
tcctaaaaaa cctatggcaa gcaccaatca tattatccaa attgtgttga aaatgtgatt 164820
aatttggttg tcaagttttg ggggtgagct gcggggagac tgcttttgtt ttgctgctgg 164880
taatatcagg aaagacttta atgaaaccag ggtagaattg tttggcaatg cactgaagcg 164940
cgtttctgtc ccaaaacgtg cctcccttcc gctgcgggcc cagctgagtc tgtgtaggtg 165000
acgtttccgg ctgccaagcg ctctttgtta ctgtccaccc ccatttctgc cagcacacgt 165060
gtcctttcag gaggaaaatg tgaagctgaa accccctccag acacccagaa tgtagcatct 165120
gagaaggccc tgtgccctaa aggacacccc cgccccccacc ttcatggagg ggtcattcca 165180
gagccctcgg agccgatgaa cagctcgtcc tcttggagct gagctgagcc ccccacggag 165240
ctcgggacgg atagtaaaca gcaataactc ggtctgtggc tgcctggcag gtggaagttc 165300
ctccccctga ggggcggagt gaggttagtt ctgtgtgtct gtggggtgga gtcagcctgc 165360
tcctgctacc tgtgagcatc ctgcccagca gacatcctca cccggctttg tccctcccca 165420
cttcctccct ctgcggggag gacccaggac cacagctgct ggccagggta ggcttggagc 165480
tgtgctccgg aggggccacc tgtgggagcg agaagaagga agatcttgag agctgccgag 165540

-continued gcaccctgga gagctcagga tggtccaggc gagaagagga cactcgctcg ccaggcctgg 165600
gcctcctggg aaggagggag ccgctcagag cgccgcatga caactgaagg caacctggaa 165660
ggttcagagg ccactcttcc cccgtgtgcc tgtcacgctc tggtgcagtc caaggaacgc 165720
cttcccctca gttgtttcca aaagcagagt ctcccgctgc aatctgggtg gtgattgcca 165780
gccttggagg attgtggcca acgtggacct gcctacggag ggtgggctct gacccacgtg 165840
gggcctcctt gtccaggtct cattgctttg tgctgtggtc agagggactg tcagctgagc 165900
ctgagctccc ctggagccag cagggctgtg atgggcgagt cccggagccc cacccagacc 165960
tgactgcttc tgagagcaaa gggaaggact gacgagagat gtatatttaa tttttttaac 166020
tgctgcaaac attgtacatc caaattaaag gaaaaacatt gaaaccatca gttgttgctg 166080
tgtgaggctt gctttacttc atgagaacct agaccttgct gagctggagt cttaggaaac 166140
tgtctcctaa gtgcttatcc agcaggggca gaaactgtcc caccagctaa catctgacat 166200
tacggagggt cccgcaggca gctgccagca aggacaagcc ctgtgttttc tgtagccagg 166260
gatgaggaag tggccccagg ggcctggctg ggtgctgctt caagggcctt cgcaaaccac 166320
agtacaggtg gtcttcctgc actgcagatg ggagctgtgg gagctgctgg atccttcatg 166380
gtcaagtgac atcataagct tatatgacac acacaagcct caggacttgg cccatggcac 166440
tggagcaggt catcaggccc agcagactag agctgtgttc tcacagggcc catgaccctt 166500
ctagctcctt ggccattgaa acctgtgtcc ctgacccagc tgctcccagg taccccccaa 166560
agcagctggc acatcccacc tctggtgtgg cctgggctgc tgtgtgtccg cagggcctgc 166620
cccgtctgtt ctagcttgtt tctcctgtct gaaccagcgc ctactccaag aaggctctgc 166680
tcagcccagc ggggatgctt ctaagctcgg cccagcctct gggaagcctt ggtggtcggt 166740
ggtgtagtca tcctgggatg cagaacgaaa acctgcaaga acaaaactgt ggcttcgtct 166800
ggtgcagggt atttagttac tgtttgctga ggtcctgtct ggttctggcg aatgggcagg 166860
ggtcgcccac ccattctttc cctgctctgc tgtccgtgcc aggagagacg ggggcctgtt 166920
ggccaagggg gcagctcctg ctgcctgctg tccttaggca cgtgcaggga ccccctttct 166980
ctgagcagga tggggatcag tctgccagag ggatgtggtg gacaggccca gccgggtaaa 167040
aaattccccc agttgctcaa agcatttggg gcggggcatg ccacttgagc tccttaaatc 167100
tgtctcatag gtgacaccgc tccagggcgc cccaggggct tctcccttca gagctaccaa 167160
agttctggtc acttcagaaa aatggagcac ccccttctcc ctggtccaga tgtggacagc 167220
cagacccttg gcacacctag cacacctggc atggctggta atttcagaaa gaaaaggggc 167280
cggggtccag tgggaagcag tggcgaaccc ctcatgcgtg ggctttgcga tccctccccc 167340
tgccacggca gagctgccct cagcacagcc ttcctcttcc tcatcggaga gcacaccctg 167400
tccccttgcc ggggctgtgc tctgtgcctg cagtggtatt tggttttggc tgctactggc 167460
tttgttccaa agaggatctg gaagtcgctt cccctgtgtg gagcgtggag cactgtgagt 167520
cagatgaggg aagtagccag ggggaggtga gtacccggcg gagccgccac agaaaggact 167580
gggtaggggg ccttgcctcc acgtgatgtg acacggccag ccgaggacag aggaagcccc 167640
gttcctgggg gtgtggggtg cacccctcag ggaagcctgc agtggggccc aaggaaaggc 167700
gttctctgcg agcccacgag tctgctctgt gggcaccgtg acaatgcccg tgggcagagg 167760
tgggcccggc cttgtgtcgt caccaggacc tcttttggga aaccatgtgg gcatcccttg 167820
cgggtccccc aggttctgca gtcccagcgg cctggctgcc tgttgggcac atggcttgag 167880
ccgcccagag ggcccagccc tgttggcagc cacatcctct ggaggccctg ccggtggggc 167940
tggctttctc taccccacac caggcctcca agtatactgg tcgggggtgt ctgggccctg 168000
gg 168002

<210> SEQ ID NO 5
<211> LENGTH: 10295
<212> TYPE: DNA
<213> ORGANISM: Rattus norvegicus

<400> SEQUENCE: 5
gcactcgccg cgagggttgc cgggacgggc ccaagatggc tgggagcttt ggttccgctt 60
cggtctacct cgtagagccc cattcattac cttgctgcta agtggcgctg cgtagtgcga 120
ataggctcca agccttcagg gtctgtcctg tcgggcagga ggccgtcatg gcaaccctgg 180
aaaaactgat gaaggctttc gagtcgctca agtcgttcca gcagcaacag cagcagcagc 240
agccgccgcc gcaggcgccg ccaccaccgc cgccgccgcc gcctcaaccc cctcagccgc 300
cgcctcaggg gcagccgccg ccaccaccgc cgctgccagg tccggccgag gagccgctgc 360
accgaccaaa gaaggaactc tcagccacca agaaggaccg tgtgaatcac tgtctaacaa 420
tatgtgaaaa cattgtggca cagtctctca gaaattctcc agaatttcag aaactcttgg 480
gcattgctat ggaactgttt ctgctgtgca gcgacgatgc ggagtcagac gtcagaatgg 540
tggctgatga gtgcctcaac aaagtcatca aagctttgat ggactctaat cttccaaggc 600
tacagttaga actctataag gaaattaaaa agaatggtgc tcctcgaagt ttgcgtgcag 660
ctctgtggag gtttgctgag ctggctcacc tggttcgacc tcagaagtgc aggccttatc 720
tggtgaatct tcttccatgt ttgacccgaa caagcaaacg accggaggag tcagttcagg 780
agactttggc tgcagctgtt cctaaaatta tggcctcttt tggcaatttc gcgaatgaca 840
atgaaattaa ggttctattg aaagctttca tagcaaatct gaagtcaagc tctcccactg 900
tgcggcggac agcagctggg tcagcagtga gtatctgcca gcactctagg aggacacagt 960
acttctacaa ctggctcctg aatgtgctcc taggtttgct ggttcccatg gaggaagacc 1020
accccactct cctgatcctt ggtgtgttgc tcacactgag gtgtctagtg cccttgctcc 1080
agcagcaggt caaggacaca agtctaaagg gcagctttgg ggtaacacgg aaagaaatgg 1140
aagtctctcc ttctgcagag cagcttgtcc aggtttatga actgactttg catcacacac 1200
agcaccaaga ccataatgtg gtgacagggg cattggagct cctgcagcag ctcttccgta 1260
cccctccacc tgagctgctg caagcactga ccacaccagg agggctcggg cagctcactc 1320
tggttcgaga ggaagccggg ggccgaggcc gcagcgggag tatcgtggag cttttagctg 1380
gagggggttc ctcatgcagc cctgttctct caagaaagca aaaaggcaaa gtgctcttag 1440
gagaggaaga agccttggag gatgactcgg agtccaggtc agatgtcagc agctcagcct 1500
ttgcagcctc tgtgaagagt gagattggtg gagagctcgc tgcttcttct tcgggtgtct 1560
ccactcccgg ttctgtaggt cacgacatca tcactgagca gcctcgatcc cagcacacac 1620
ttcaagcaga ctctgtggat ttgtcaggct gtgacttgac cagtgctgct actgatggag 1680
atgaggaaga catcttgagc cacagctcca gccagttcag tgctgttcca tccgaccctg 1740
ccatggacct gaatgatggg acccaggcct cctcacccat cagtgacagt tctcagacca 1800
ccactgaagg acctgattca gctgtgactc cttctgacag ttctgaaatt gtcttagatg 1860
gtgctgacag ccagtattta ggcgtgcaga taggacagcc acaggaggaa gacgaggagg 1920
aagctgcagg tgttctttct ggtgaagtct cagacgtttt cagaaactct tctctggccc 1980

-continued

```
ttcagcaggc acacttgttg gaaagaatgg gtcatagccg gcagccttct gacagcagtg   2040

ttgataagtt tgtttcaaaa gatgaggttg ctgaagctgg ggacccagaa agcaagcctt   2100

gccgaatcaa aggtgacata ggacagccta atgatgatga ttctgctcct ctggtacatt   2160

gtgtccgtct tttatccgct tcctttttgt taactggcga aaagaaagca ctggttccag   2220

acagagatgt gagagtcagt gtgaaggccc tggccctcag ctgtattggt gcagctgtgg   2280

cccttcatcc agagtcgttc ttcagcaaac tctacaaagt acctctcagt accatggaaa   2340

gtactgagga acagtatgtc tctgacatcc tgaactacat cgatcatgga gaccctcagg   2400

tgcgaggagc tactgccatt ctctgtggga cccttgtcta ctccatcctc agcaggtccc   2460

gtctccgtgt tggtgactgg ctgggcacca tcagggccct gacaggaaat acattttctc   2520

tggtggactg cattcccttta ctgcagaaaa ctttgaagga tgaatcttct gttacttgca   2580

agttggcttg tacagctgtg aggcactgtg tcctgagtct ttgcagcagc agctacagtg   2640

acttgggatt acaactgctt attgacatgc tgcctctgaa gaacagctcc tactggctgg   2700

tgaggactga actgctggaa actcttgcag agattgattt caggctggtg agtttttttgg   2760

aggcaaaagc agaaagttta caccgagggg ctcatcatta tacagggttt ctaaaactac   2820

aagaacgagt actcaataat gtggtcattt atttgcttgg agatgaagac cccagggttc   2880

gacatgttgc tgcgacgaca ttgacaagac ttgtcccaaa gctgttttat aagtgtgacc   2940

aaggacaggc tgacccagtc gtggctgtag caagagatca aagtagtgtt tacctgaagc   3000

tcctcatgca tgagacccag ccaccatccc acttctccgt cagcaccata accagaatct   3060

atagaggcta cagcttacta ccaagtgtaa cagatgtcac catggaaaac aacctctcaa   3120

gagtcgttgc cgcagtttct catgaactca ttacgtcaac tacacgggca ctcacatttg   3180

ggtgctgtga agccttgtgt gttctttcag ccgcctttcc agtttgcact tggagtctag   3240

gatggcactg tggagtgccc ccactgagtg cctctgatga gtccaggaag agctgcactg   3300

ttgggatggc ctccatgatt ctcaccttgc tttcatcagc ttggttccca ctggatctct   3360

cagcccatca ggatgccttg attttggctg gaaacttgct agcagcgagt gcccccaagt   3420

ctctgagaag ctcatgggcc tcggaagaag aaggcagctc agcagccacc agacaggagg   3480

agatctggcc tgccctgggg gatcggactc tggtgcccat ggtggagcag cttttctccc   3540

acctgctgaa ggtgatcaat atctgtgctc atgtcttgga tgacgtgact cctggaccag   3600

caatcaaggc agctttgcct tctctcacaa acccccccttc tctaagtcct attcgacgga   3660

aagggaagga gaaagagccc ggagaacaaa catccactcc gatgagtccc aagaaaggtg   3720

gagaggccag tacagcctct cgacagtcag acacctcagg acctgtcaca gcgagtaaat   3780

catcttcact tgggagtttc taccatctcc cttcctacct cagactgcat gatgtcctga   3840

aagccactca cgccaactat aaggtcacct tagatcttca gaacagcact gaaaagtttg   3900

gggggttcct gcgctctgcc ttggacgtcc tttctcagat tctagagctg gcgacactgc   3960

aggacattgg aaagtgtgtt gaagaggtcc ttggatactt gaaatcctgc tttagtcgag   4020

aaccaatgat ggcgactgtc tgtgttcagc agctattgaa gactctcttt gggacaaact   4080

tagcctcaca gtttgatggc ttatcttcca accccagcaa gtctcagtgc cgagcacagc   4140

gccttggctc ttccagtgtg aggcccggct tatatcacta ctgcttcatg gcaccataca   4200

cgcacttcac gcaggctttg gctgatgcca gcctgaggaa catggtacag gcggaccagg   4260

agcacgatgc ctcagggtgg tttgatgtac tccagaaagt gtctgctcag ttgaagacga   4320

accttacaag tgtcacaaag aaccgtgcag ataagaacgc tattcataac cacattaggt   4380
```

-continued

```
tatttgagcc tcttgttata aaagcattga agcagtacac cacgacaaca tcagtacaac   4440
tgcagaagca ggttttggat ttgctggcac agctggttca gctacgggtc aattactgtc   4500
tactggattc agatcaggtg ttcatcgggt ttgtgctgaa gcagtttgag tacattgaag   4560
tgggccagtt cagggaatca gaggcaatta ttccaaatat atttttcttc ctggtactat   4620
tatcttatga gcgctaccat tcaaaacaga tcattggaat tcctaaaatc atccagctgt   4680
gtgatggcat catggccagt ggaaggaagg ctgtcacaca tgctattcct gcgctgcagc   4740
ccattgtcca tgacctcttt gtgttaagag gaacaaataa agctgatgca gggaaagagc   4800
ttgaaaccca gaaggaggtg gtggtctcaa tgctgttacg actcatccag taccatcagg   4860
tgctagagat gttcatcctc gtcctgcagc agtgccacaa agagaatgag gacaagtgga   4920
aacggctctc tcggcaggtc gcagacatca tcctgcccat gttagccaag cagcagatgc   4980
atattgactc tcatgaagcc cttggagtat taaatacctt gtttgagatt ttggctcctt   5040
cctccctacg tcctgtggac atgcttttgc ggagtatgtt catcactcca agcacaatgg   5100
catctgtaag cactgtgcag ctgtggatat ctggaatcct agccattctg agggttctca   5160
tttcccagtc aaccgaagac attgttcttt ctcgtattca ggagctctcc ttctctccat   5220
atttaatttc ctgtccagta attaacaggt taagggatgg agacagtaat ccaacactag   5280
gagaacgcag tgaagggaaa caagtaaaga atttgccaga agatacattc tcaaggtttc   5340
tcttacagct ggttggtatt cttctggaag acattgttac aaaacagctc aaagtggaca   5400
tgagtgaaca gcagcataca ttctattgcc aagagctcgg cacactgctc atgtgtctga   5460
tccacatatt caaatctgga atgttccgga gaatcacagc cgctgccact agactcttca   5520
ccagtgatgg ctgtgaaggc agcttctata ctctagatag cctgaatgca cgggtgcgag   5580
ccatggtgcc cacacaccca gctctggtac tgctctggtg tcagatccta ctgctcatca   5640
accacactga ccaccgatgg tgggccgagg tgcagcagac gcccaagaga cacagtctgt   5700
cctgcacgaa gtcactaaac ccccagatat ctgctgaaga ggattctggc tcagcagctc   5760
agcttggaat gtgcaataga gaaatagtac gaagaggggc ccttattctc ttctgtgatt   5820
atgtctgtca gaatctccat gactcagaac acttaacatg gctcattgtg aatcacattc   5880
aagatctgat cagcttgtcc cacgagcctc cagttcaaga ctttattagt gccattcatc   5940
gtaattctgc agctagtggt ctttttatcc aggcaattca gtctcgctgt gaaaatcttt   6000
caactccaac cactctgaag aaaacacttc agtgcttgga aggcatccat ctcagccagt   6060
ctggtgctgt gctcacactg tatgtggaca ggctactggg cacccctttc cgtgcgctgg   6120
ctcgcatggt cgacaccctg gcctgtcgcc gagtagaaat gcttttggct gcaaatttac   6180
agagcagcat ggcccagttg ccagaggagg aactgaacag aatccaggaa cacctccaga   6240
acactgggct tgcacaaaga caccaaaggc tctattcact gctggacaga ttccgactct   6300
ctactgtgca ggactcactt agccccttgc cccagtcac ttcccaccct ctggatgggg   6360
atgggcacac atccctggaa acagtgaatc cggacaaaga ctggtacctc cagcttgtca   6420
gatcccagtg ttggaccagg tcagattctg cactgctgga aggtgcagag ctggtgaacc   6480
gtatccctgc tgaagatatg agtgacttca tgatgagctc ggagttcaac ctaagccttt   6540
tggctccctg cttaagcctt ggcatgagcg agattgctaa tggccaaaag agtcccctt   6600
ttgaagcggc tcgtagggtg actctggacc gggtgaccaa tgtggttcag cagctgcctg   6660
cagtccatca agtcttccag cctttcctgc ctacagaacc cacagcctac tggagcaagc   6720
```

-continued

```
tgaatgatct ctttggtgat accacatcat accagtctct gaccacactt gcccgtgccc   6780
tggcacagta cctggtggtg ctctccaaag tgcctgctcc tttgcacctt cctcctgaga   6840
aggaggggca cacggtgaag tttgtggtaa tgacacttga ggccctgtca tggcatttga   6900
tccatgagca gatcccactg agtctggacc tccaagccgg cctagactgc tgctgcctgg   6960
cactgcaggt gcctggcctc tggggggtgc tgtcctcccc agagtacgtg actcatactt   7020
gctcccttat ccactgtgtg cgattcatcc tggaagccat tgcagtacaa cctggagacc   7080
aacttcttgg tccggaaagc aggtcacata ctccaagggc tgtcagaaag gaggaagtag   7140
actcagatat acaaaacctc agtcacatca cttcggcctg cgagatggtg gcagacatgg   7200
tggaatccct gcagtcggtg ctggccctgg gccacaagag gaacagcacc ctaccttcat   7260
ttctcacagc tgtgctgaag aacattgttg tcagtctggc ccgcctcccc ctcgttaaca   7320
gctatactcg tgtgcctcct ctggtatgga aactcgggtg gtcacccaag cctggagggg   7380
atttcggcac agtgtttcct gagatccctg tagagttcct ccaggagaag gaggtcctca   7440
aggagttcat ctaccgcatc aacaccctag ggtggaccag tcgtactcaa ttcgaagaaa   7500
cttgggccac cctccttggt gtcctggtga ctcagccctt ggtgatggaa caggaagaga   7560
gcccaccaga ggaagacacc gaaaggaccc agatccacgt cctggctgta caggccatca   7620
cctctctagt gctcagcgca atggctgtgc ctgtggctgg caatccagct gtaagctgct   7680
tggagcaaca gccccggaac aagccactga aggctctcga taccagattt ggaagaaagt   7740
tgagcatgat cagagggatt gtagaacaag aaatccaaga gatggtttcc caaagagaga   7800
atactgccac tcatcattct caccaggcat gggatcctgt cccttctctg ttaccagcta   7860
ctacaggtgc tcttatcagc catgacaagc tgctgctgca gatcaactca gagcgggagc   7920
caggcaacat gagctacaag ctgggccagg tgtccataca ctccgtgtgg ctggggaaca   7980
acatcacacc cctgagagag gaggaatggg atgaggagga ggaggaagaa gcggatgccc   8040
ctgcgccaac atcaccacct gtgtctccag tcaattccag aaaacaccgt gctggggttg   8100
atattcactc ctgttcgcag tttctgcttg aattatacag ccgttggatc ctgccatcca   8160
gtgcagccag aaggacccct gtcatcctga tcagtgaagt ggttcgatct cttcttgtgg   8220
tgtcagactt attcactgaa cgtacccagt ttgaaatgat gtatctgacg ctgacagaac   8280
tacggagagt gcacccttca gaagatgaga tcctcattca atacctggtg cctgccacct   8340
gtaaggcagc tgctgttctt ggaatggaca aaactgtggc agagccggtc agccgcctac   8400
tggagagcac actcaggagc acccacctgc ccagccagat cggagccctg catggcatcc   8460
tctatgtgtt ggagtgtgac ctcttggatg acactgtaaa gcagctcatt ccagttgtta   8520
gtgactatct gctgtccaac ctcaaaggaa tagcccactg cgtgaacatt cacagccagc   8580
agcatgtgct ggtgatgtgt gccactgcat tctacctgat ggaaaactac cctctggatg   8640
tggggccaga attctcagca tctgtgatac agatgtgtgg agtaatgctg tctggaagtg   8700
aggagtccac cccctccatc atttaccact gtgccctccg gggtctggaa cggctcctgc   8760
tgtctgagca gctctctcgg ctagacacgg agtccttggt caagctaagt gtggacagag   8820
tgaatgtaca aagcccacac agggccatgg cagccctagg cctgatgctt acctgcatgt   8880
acacaggaaa ggaaaaagcc agtccaggca gagcttctga ccccagccct gctacccctg   8940
acagcgagtc tgtgattgta gctatggagc gagtgtctgt gctctttgac aggatccgca   9000
agggatttcc ctgtgaagcc agggtcgtgg caaggatcct gcctcagttt ctagatgact   9060
tctttccacc tcaagatgtc atgaacaaag tcattggaga gttcctgtcc aaccagcagc   9120
```

```
catacccaca gttcatggcc actgtagtat acaaggtttt tcagactctg cacagtgctg   9180

ggcagtcatc catggtccgg gactgggtta tgctgtctct gtccaacttc acacaaagaa   9240

ctccagttgc catggccatg tggagcctct cctgcttcct tgtcagtgca tctaccagcc   9300

catgggtttc tgcaatcctt ccacacgtca tcagcaggat gggcaaactg gagcaggtgg   9360

atgtgaacct tttctgcctg gttgccacag acttctacag acaccagata gaggaggaat   9420

tcgaccgcag ggctttccag tctgtgtttg aggtggtggc agcaccagga agtccatacc   9480

acaggctgct tgcttgtttg caaaatgttc acaaggtcac cgcctgctga gtagtacctg   9540

tggaacaaga ggctgagagg aggcaactgc tgtggctaca gcctccaggg gcctgcacca   9600

agcttctgct aaggctgcct tggacgtgca ggcttccact tgtgtcaagt ggacagccag   9660

gcaatggcag gagtgctttg caatgagagc tatgcaggga acatgcacta tgttggggtt   9720

gagcctgagt cctgggtcct ggcatcactg cagctggtgg cagtgctagg ttgaccaggt   9780

gtttgtcttt ttcttagtgt tgccctggcc atagttgcca ggttgcagct gccctggtat   9840

gtggaacaga atccgagctc ttgtaagatg gttctgagcc cccctgtccc actgggctgg   9900

agagctccct cccacattta cccagcaggt gtacctgcca caccagtgtc tggacacaaa   9960

gtgaatggtg tgggggctgg gaactgggac tgccaggtgt ccagcatcat tttccctttc  10020

tctgttttct tctcaggagt taaaatttaa ttatatcagt aaagagatta attttaatgt  10080

aactcttcct atgcccgtgt aaagtgtgtg acttggcaag gcctgtgctg catgtgacaa  10140

agtttatgga agtggatgcg ccttctggcc accactctct ctcctgtagc tactcagtct  10200

agtcgggcag gtccctcatg tagccctccc aacaccctat ggcacttgca cttcacacgg  10260

ctccttttc ttatgcattc catttgacta gcaca                               10295
```

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6

```
tagcattctt atctgcacgg                                                  20
```

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7

```
acccgtaact gaaccagctg                                                  20
```

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8

```
ttccctgaac tggcccactt                                                  20
```

<210> SEQ ID NO 9

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ctctgattcc ctgaactggc 20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gcctctgatt ccctgaactg 20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
tgcctctgat tccctgaact 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ttgcctctga ttccctgaac 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
attgcctctg attccctgaa 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tggaatgatt gcctctgatt 20

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
gtttggaatg attgcctc 18

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ccaatgatct gttttgaatg 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gccttccttc cactggccat 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctgcatcagc tttatttgtt 20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cctgcatcag ctttatttgt 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agctcttttc ctgcatcagc 20

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
gtaacattga caccacca 18

<210> SEQ ID NO 22
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 22
ctcagtaaca ttgacaccac 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
atgagtctca gtaacattga 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tccttgtggc actgctgcag 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttctccttgt ggcactgctg 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tcattctcct tgtggcactg 20

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
attctccttg tggcactg 18

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
cgagacagtc gcttccactt 20

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
tgtcgagaca gtcgcttc 18

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ttgcacattc caagtttggc 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tctctattgc acattccaag 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tttctctatt gcacattcca 20

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
tctctattgc acattcca 18

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gcagggttac cgccatcccc 20

<210> SEQ ID NO 35
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 35
accttatctg cacggttc 18

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ctctctgtgt atcaccttcc 20

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
ctccgtccgg tagacatgct 20

<210> SEQ ID NO 38
<211> LENGTH: 23
<212> TYPE: DNA
<213> ORGANISM: Artificial sequence
<220> FEATURE:
<223> OTHER INFORMATION: Primer

<400> SEQUENCE: 38
ggaaatcaga accctcaaaa tgg 23

<210> SEQ ID NO 39
<211> LENGTH: 29
<212> TYPE: DNA
<213> ORGANISM: Artificial sequence
<220> FEATURE:
<223> OTHER INFORMATION: Probe

<400> SEQUENCE: 39
tgagcactgt tcaactgtgg atatcggga 29

<210> SEQ ID NO 40
<211> LENGTH: 21
<212> TYPE: DNA
<213> ORGANISM: Artificial sequence
<220> FEATURE:
<223> OTHER INFORMATION: Primer

<400> SEQUENCE: 40
gtctgagcct ctctcggtca a 21

<210> SEQ ID NO 41
<211> LENGTH: 19
<212> TYPE: DNA
<213> ORGANISM: Artificial sequence
<220> FEATURE:
<223> OTHER INFORMATION: Primer

<400> SEQUENCE: 41
aagggatgct gggctctgt 19

<210> SEQ ID NO 42
<211> LENGTH: 30
<212> TYPE: DNA
<213> ORGANISM: Artificial sequence
<220> FEATURE:
<223> OTHER INFORMATION: Probe

<400> SEQUENCE: 42
agcaaagctt ggtgtcttgg cactgttagt 30

<210> SEQ ID NO 43
<211> LENGTH: 21
<212> TYPE: DNA
<213> ORGANISM: Artificial sequence
<220> FEATURE:
<223> OTHER INFORMATION: Primer

<400> SEQUENCE: 43
cagagctggt caaccgtatc c 21

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
ggcttaaaca gggagccaaa a 21

<210> SEQ ID NO 45
<211> LENGTH: 26
<212> TYPE: DNA
<213> ORGANISM: Artificial sequence
<220> FEATURE:
<223> OTHER INFORMATION: Probe

<400> SEQUENCE: 45
acttcatgat gagctcggag ttcaac 26

<210> SEQ ID NO 46
<211> LENGTH: 25
<212> TYPE: DNA
<213> ORGANISM: Artificial sequence
<220> FEATURE:
<223> OTHER INFORMATION: Primer

<400> SEQUENCE: 46
aggagaaaaa caaagaacac cagaa 25

<210> SEQ ID NO 47
<211> LENGTH: 25
<212> TYPE: DNA
<213> ORGANISM: Artificial sequence
<220> FEATURE:
<223> OTHER INFORMATION: Primer

<400> SEQUENCE: 47
caattagggc aactcagaaa tagct 25

<210> SEQ ID NO 48
<211> LENGTH: 22
<212> TYPE: DNA
<213> ORGANISM: Artificial sequence
<220> FEATURE:
<223> OTHER INFORMATION: Probe

<400> SEQUENCE: 48
ccaactggtc ccccagccaa ga 22

<210> SEQ ID NO 49
<211> LENGTH: 21
<212> TYPE: DNA
<213> ORGANISM: Artificial sequence
<220> FEATURE:
<223> OTHER INFORMATION: Primer

<400> SEQUENCE: 49
cagagctggt gaaccgtatc c 21

<210> SEQ ID NO 50
<211> LENGTH: 21
<212> TYPE: DNA
<213> ORGANISM: Artificial sequence
<220> FEATURE:
<223> OTHER INFORMATION: Primer

<400> SEQUENCE: 50
ggcttaagca gggagccaaa a 21

<210> SEQ ID NO 51
<211> LENGTH: 26
<212> TYPE: DNA
<213> ORGANISM: Artificial sequence
<220> FEATURE:
<223> OTHER INFORMATION: Probe

<400> SEQUENCE: 51
acttcatgat gagctcggag ttcaac 26

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tcctagtgtt acattaccgc 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ctcgactaaa gcaggatttc 20

<210> SEQ ID NO 54
<211> LENGTH: 17
<212> TYPE: DNA
<213> ORGANISM: Artificial sequence
<220> FEATURE:
<223> OTHER INFORMATION: Primer

<400> SEQUENCE: 54
tggtccccca gccaaga 17

<210> SEQ ID NO 55
<211> LENGTH: 18

-continued

```
<212> TYPE: DNA
<213> ORGANISM: Artificial sequence
<220> FEATURE:
<223> OTHER INFORMATION: Primer

<400> SEQUENCE: 55

cccaccgtgt gacatcca                                              18


<210> SEQ ID NO 56
<211> LENGTH: 26
<212> TYPE: DNA
<213> ORGANISM: Artificial sequence
<220> FEATURE:
<223> OTHER INFORMATION: Probe

<400> SEQUENCE: 56

agctatctcc gagctgccct gattgg                                     26
```

MODULATION OF HUNTINGTIN EXPRESSION

SEQUENCE LISTING

The present application is being filed along with a Sequence Listing in electronic format. The Sequence Listing is provided as a file entitled BIOL0113USC3SEQ_ST25.txt created May 15, 2017, which is 488 Kb in size. The information in the electronic format of the sequence listing is incorporated herein by reference in its entirety.

FIELD OF THE INVENTION

Provided herein are methods, compounds, and compositions for reducing expression of huntingtin mRNA and protein in an animal. Such methods, compounds, and compositions are useful, for example, to treat, prevent, or ameliorate Huntington's disease.

BACKGROUND

Huntington's disease (HD) is a devastating autosomal dominant, neurodegenerative disease caused by a CAG trinucleotide repeat expansion encoding an abnormally long polyglutamine (PolyQ) tract in the huntingtin protein. The Huntington disease gene was first mapped in 1993 (The Huntington's Disease Collaborative Research Group. Cell. 1993, 72:971-83), consisting of a gene, IT15, which contained a polymorphic trinucleotide repeat that is expanded and unstable on HD chromosomes. Although CAG repeats in the normal size range are usually inherited as Mendelian alleles, expanded HD repeats are unstable through meiotic transmission and are found to be expanded beyond the normal size range (6-34 repeat units) in HD patients.

Both normal and variant huntingtin protein are localized chiefly in the cytoplasm of neurons (DiFiglia et al., Neuron 1995, 14:1075-81). As a result of excessive polyglutamine length, huntingtin protein forms aggregates in the cytoplasm and nucleus of CNS neurons (Davies et al., Cell 1997, 90:537-548). Both transgenic animals and genetically modified cell lines have been used to investigate the effects of expanded polyQ repeats on the localization and processing of huntingtin. However, it is still unclear whether the formation of aggregates per se is the essential cytotoxic step or a consequence of cellular dysfunction.

HD is characterized by progressive chorea, psychiatric changes and intellectual decline. This dominant disorder affects males and females equally, and occurs in all races (Gusella and MacDonald, Curr. Opin. Neurobiol. 1995 5:656-62). Symptoms of HD are due to the death of neurons in many brain regions, but is most apparent in the striatum, particularly in the caudate nucleus, which suffers a progressive gradient of cell loss that ultimately decimates the entire structure. Although the gene encoding huntingtin is expressed ubiquitously (Strong, T. V. et al., Nat. Genet. 1995, 5:259-263), selective cell loss and fibrillary astrocytosis is observed in the brain, particularly in the caudate and putamen of the striatum and in the cerebral cortex of HD patients (Vonsattel, J-P. et al., Neuropathol. Exp. Neurol. 1985, 44:559-577), and, to a lesser extent, in the hippocampus (Spargo, E. et al., J. Neurol. Neurosurg. Psychiatry 1993, 56:487-491) and the subthalamus (Byers, R. K. et al., Neurology 1973, 23:561-569).

Huntingtin is crucial for normal development and may be regarded as a cell survival gene (Nasir et al., Human Molecular Genetics, Vol 5, 1431-1435). The normal function of huntingtin remains incompletely characterized, but based upon protein-protein interactions, it appears to be associated with the cytoskeleton and required for neurogenesis (Walling et al., J. Neurosci Res. 1998, 54:301-8). Huntingtin is specifically cleaved during apoptosis by a key cysteine protease, apopain, known to play a pivotal role in apoptotic cell death. The rate of cleavage is enhanced by longer polyglutamine tracts, suggesting that inappropriate apoptosis underlies HD.

Antisense technology is emerging as an effective means for reducing the expression of specific gene products and may therefore prove to be uniquely useful in a number of therapeutic, diagnostic, and research applications for the modulation of huntingtin expression. (See U.S. Patent Publication Nos. 2008/0039418 and 2007/0299027)

Antisense compounds for modulating expression of huntingtin are disclosed in the aforementioned published patent applications. However, there remains a need for additional such compounds.

SUMMARY OF THE INVENTION

Provided herein are methods, compounds, and compositions for modulating expression of huntingtin and treating, preventing, delaying or ameliorating Huntington's disease and/or a symptom thereof.

Figure 6:
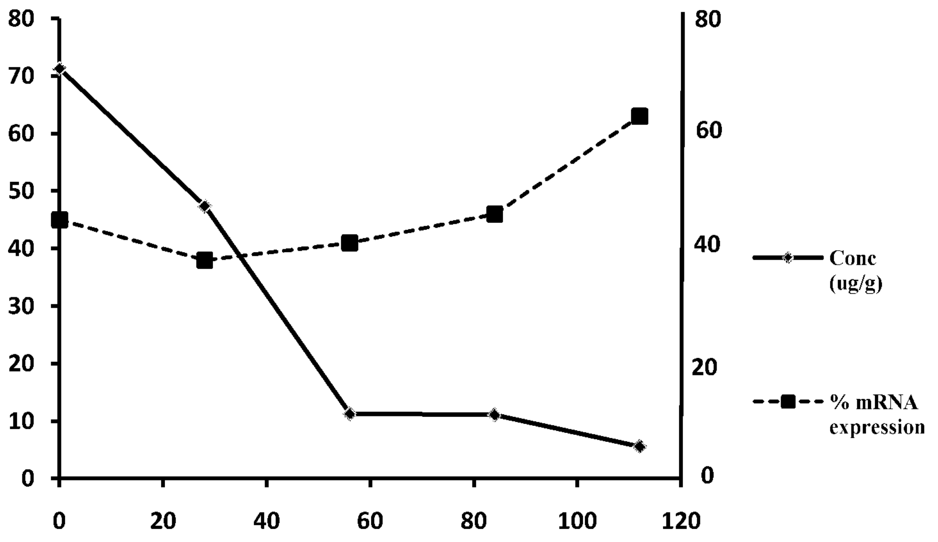

FIG. 6: Comparison of huntingtin mRNA expression in posterior cortex tissue and ISIS 443139 concentrations at various time points. BACHD mice were administered intracerebroventricular infusion of 50 μg of ISIS 443139 for 2 weeks, and huntingtin mRNA expression as well as the concentration of the antisense oligonucleotide in the tissue were measured. The duration of action (as measured by htt mRNA expression) of ISIS 443139 (dashed line) was observed to be longer even after the concentration of the oligonucleotide (solid line) in the tissue.

Figure 7:
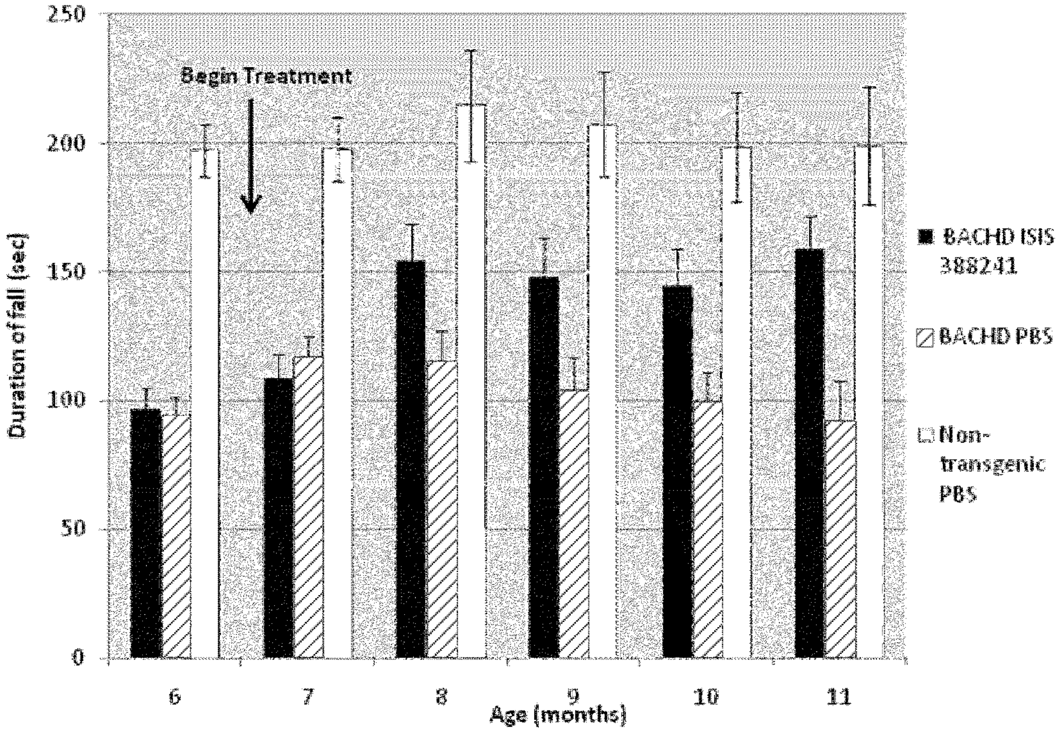

FIG. 7. Effect of antisense oligonucleotide treatment on the motor performance of BACHD mice using the Rotarod assay. BACHD mice were treated with 50 μg/day ICV of ISIS 388241 or PBS for two weeks. Control groups of non-transgenic littermates were similarly treated with ISIS 388241 or PBS. The accelerating Rotarod assay was then performed. Animals were placed on the Rotarod at a speed of 2 RPM; the Rotarod accelerated to 40 RPM over 5 minutes. The duration to fall was recorded. Baseline values at 6 months age were taken before the treatment and the time points given are the age of the mice at which the assay was conducted. The bars represent the duration to fall in seconds by BACHD mice treated with ISIS 388241 (black); by BACHD mice treated with PBS (hashed); and by non-transgenic littermates treated with PBS (white). ISIS 388241-treated mice displayed increased duration of fall and, therefore, improved motor performance on the Rotarod, compared to the PBS control.

Figure 8:
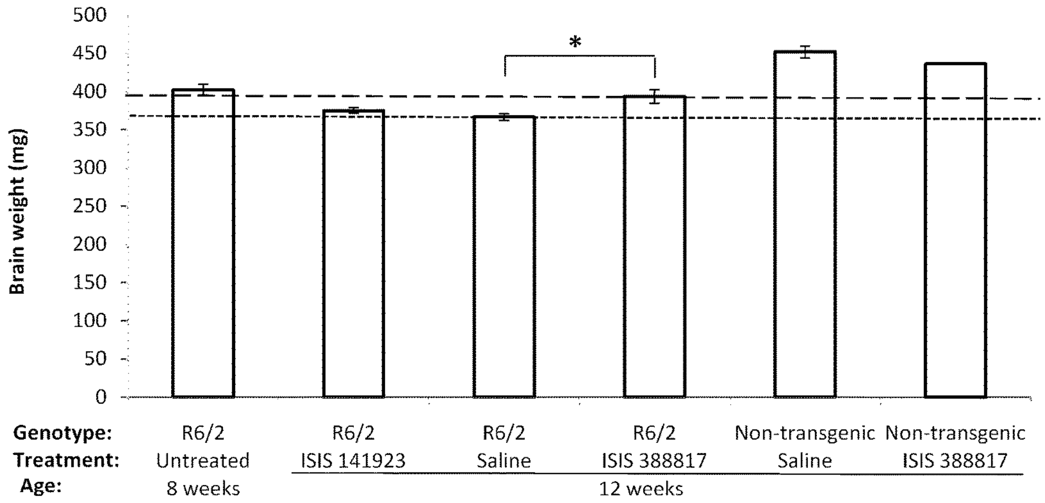

FIG. 8. Effect of antisense oligonucleotide treatment on brain weight of R6/2 mice. Six-month old R6/2 mice were treated with 50 μg/day ICV of ISIS 388817 or control oligonucleotide ISIS 141923 or PBS for 4 weeks. Control groups of non-transgenic littermates were similarly treated with ISIS 388817 or PBS. A control group of eight-week old pre-symptomatic R6/2 mice were included in the study and not given any treatment. The bars represent the brain weights of eight-week old untreated R6/2 mice; R6/2 mice treated with ISIS 141923; R6/2 mice treated with PBS; R6/2 mice treated with ISIS 388817; non-transgenic littermates treated with PBS; and non-transgenic littermates treated with ISIS 388817. There was an increase in brain weight of R6/2 mice treated with ISIS 388817 compared to the PBS control.

Figure 9:
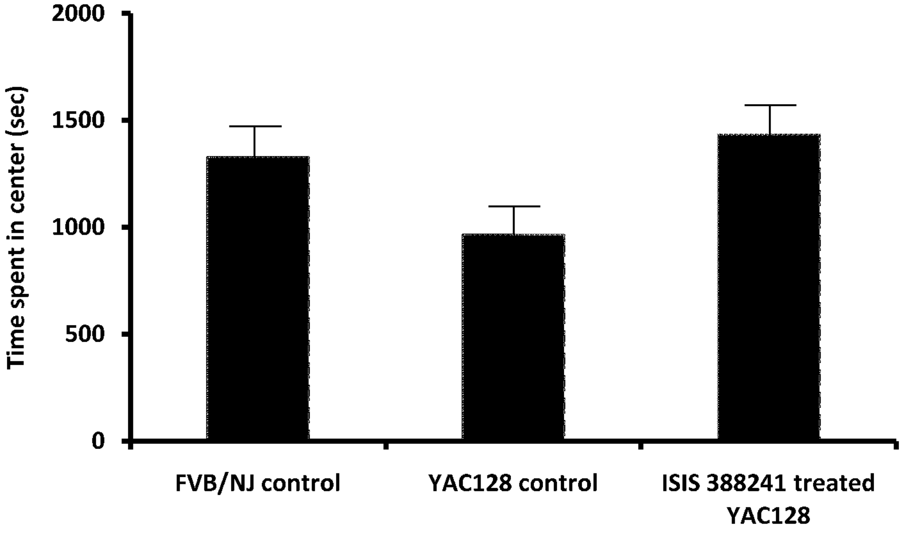

FIG. 9. Behavioral characterization of antisense oligonucleotide-treated YAC128 mice using the Open Field assay. Five month old YAC128 mice were treated with 50 μg/day ICV of ISIS 388241 or control oligonucleotide ISIS 141923 or PBS for 14 days. A control group of non-transgenic FVB/NJ littermates were included in the study and not given any treatment. Mice were placed in an open field arena that uses photobeam breaks to measure horizontal and vertical movement over a 30 min test session. Data was analyzed using Activity Monitor software to examine total ambulatory movement within the arena and movement within the center of the arena as a measure of anxiety. The bars represent time in seconds spent at the center of the field by FVB/NJ mice, YAC128 treated with PBS, and, YAC128 mice treated with ISIS 388241. YAC128 mice treated with ISIS 388241 spent more time in the center and were therefore deemed less anxiety-prone than the PBS control.

Figure 10:
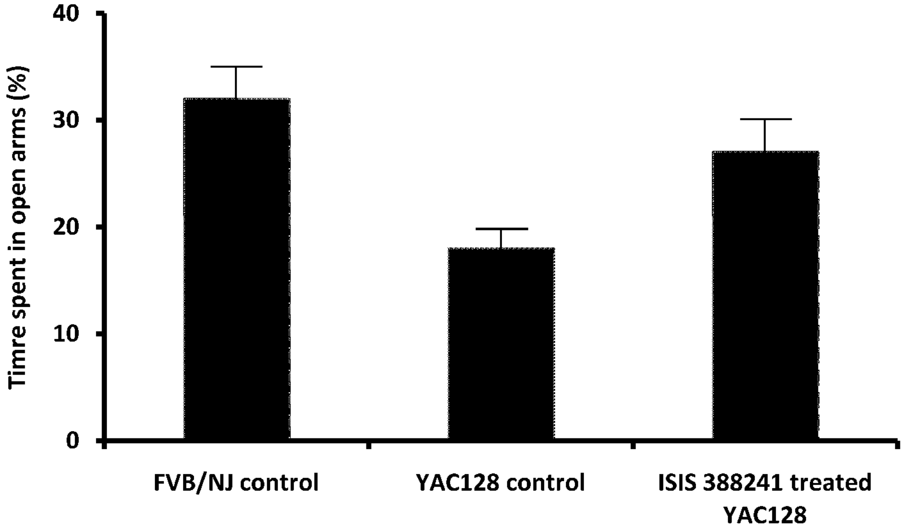

FIG. 10. Behavioral characterization of antisense oligonucleotide-treated YAC128 mice using the Elevated Plus Maze assay. Five month old YAC128 mice were treated with 50 μg/day ICV of ISIS 388241 or control oligonucleotide ISIS 141923 or with PBS for 14 days. A control group of non-transgenic FVB/NJ littermates were included as untreated control. Mice were placed in the center of an apparatus which consisted of two open arms and two closed arms each measuring 65×6.25 cm and elevated 50 cm above the ground. The location of the mice on the apparatus and amount of time spent in the open arms was recorded over a 5 minute test session as a measure of anxiety. The bars represent the percentage of time spent in the open arms by FVB/NJ control, YAC128 treated with PBS, and YAC128 mice treated with ISIS 388241. YAC128 mice treated with ISIS 388241 spent more time in the open arms and were therefore deemed less anxiety-prone than the PBS control.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to huntingtin is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Huntingtin nucleic acid" means any nucleic acid encoding huntingtin. For example, in certain embodiments, a huntingtin nucleic acid includes a DNA sequence encoding huntingtin, an RNA sequence transcribed from DNA encoding huntingtin (including genomic DNA comprising introns and exons), and an mRNA sequence encoding huntingtin. "Huntingtin mRNA" means an mRNA encoding a huntingtin protein.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting huntingtin expression.

Certain embodiments provide antisense compounds targeted to a huntingtin nucleic acid. In certain embodiments, the huntingtin nucleic acid is any of the sequences set forth in GENBANK Accession No. NM_002111.6 (incorporated herein as SEQ ID NO: 1), GENBANK Accession No. NT_006081.17 truncated from nucleotides 462000 to 634000 (incorporated herein as SEQ ID NO: 2), GENBANK Accession No. NM_010414.1 (incorporated herein as SEQ ID NO: 3), the complement of GENBANK Accession No. NW_001109716.1 truncated at nucleotides 698000 to 866000 (incorporated herein as SEQ ID NO: 4), and GENBANK Accession No. NM_024357.2 (incorporated herein as SEQ ID NO: 5).

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, or at least 12 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, or at least 12 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, and 32. In certain embodiments, the modified oligonucleotide comprises at least 9, at least 10, at least 11, at least 12, at least 13, at least 14, at least 15, at least 16, at least 17 or at least 18 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14, at least 15, at least 16, at least 17, or at least 18 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 12-30 linked nucleosides wherein the linked nucleosides comprise at least an 8 contiguous nucleobase portion that is complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828, 4928-4947 of SEQ ID NO: 1. In certain embodiments the region is selected from 4384-4403, 4609-4628, 4610-4629, 4860-4877, 4862-4881, 4925-4944, 4928-4947, 4931-4950, 4955-4974, and 5809-5828 of SEQ ID NO: 1. In certain embodiments the region is selected from 4862-4881, 4609-4628, 5809-5828, 5809-5826, 5801-5820, and 4955-4974. In certain embodiments, the modified oligonucleotide has at least a 9, at least a 10, at least an 11, or at least a 12 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

In certain embodiments, the modified oligonucleotide consists of a single-stranded modified oligonucleotide.

In certain embodiments, the modified oligonucleotide consists of 20 linked nucleosides.

In certain embodiments, the nucleobase sequence of the modified oligonucleotide is at least 90% complementary over its entire length to a nucleobase sequence of SEQ ID NO: 1, 2, 3, 4 or 5. In certain embodiments, the nucleobase sequence of the modified oligonucleotide is at least 95% complementary over its entire length to a nucleobase sequence of SEQ ID NO: 1, 2, 3, 4 or 5. In certain embodiments, the modified oligonucleotide is at least 99% complementary over its entire length to SEQ ID NO: 1, 2, 3, 4 or 5. In certain embodiments, the nucleobase sequence of the modified oligonucleotide is 100% complementary over its entire length to a nucleobase sequence of SEQ ID NO: 1, 2, 3, 4 or 5.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one bicyclic sugar comprises a 4'-$CH(CH_3)$—O-2' bridge. In certain embodiments, the at least one modified sugar comprises a 2'-O-methoxyethyl.

In certain embodiments, the compound comprises at least one at least one tetrahydropyran modified nucleoside wherein a tetrahydropyran ring replaces the furanose ring. In certain embodiments, the at least one tetrahydropyran modified nucleoside has the structure:

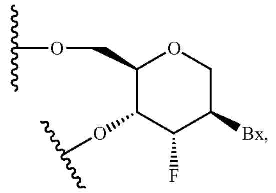

wherein Bx is an optionally protected heterocyclic base moiety.

In certain embodiments, the compound has at least one nucleoside comprising a modified nucleobase. In certain embodiments, the modified nucleobase is a 5-methylcytosine.

In certain embodiments, the modified oligonucleotide of the compound comprises:

(i) a gap segment consisting of linked deoxynucleosides;

(ii) a 5' wing segment consisting of linked nucleosides;

(iii) a 3' wing segment consisting of linked nucleosides, wherein the gap segment is positioned between the 5' wing segment and the 3' wing segment and wherein each nucleoside of each wing segment comprises a modified sugar.

In certain embodiments, the modified oligonucleotide of the compound comprises:

(i) a gap segment consisting of ten linked deoxynucleosides;

(ii) a 5' wing segment consisting of five linked nucleosides;

(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:

(i) a gap segment consisting of eight linked deoxynucleosides;

(ii) a 5' wing segment consisting of six linked nucleosides;

(iii) a 3' wing segment consisting of six linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:

(i) a gap segment consisting of eight linked deoxynucleosides;

(ii) a 5' wing segment consisting of five linked nucleosides;

(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32 or a salt thereof and a pharmaceutically acceptable carrier or diluent.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs:

12, 22, 28, 30, 32, and 33 or a salt thereof and a pharmaceutically acceptable carrier or diluent.

Certain embodiments provide methods of treating, preventing, or ameliorating Huntington's disease.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs:12, 22, 28, 30, 32, and 33.

In certain embodiments, the animal is a human.

In certain embodiments, the administering prevents, treats, ameliorates, or slows progression Huntington's disease as described herein.

In certain embodiments, the compound is co-administered with a second agent.

In certain embodiments, the compound and the second agent are administered concomitantly.

In certain embodiments, the administering is parenteral administration. In certain embodiments, the parenteral administration is intracranial administration. In certain embodiments, the intracranial administration is intrathecal or intracerebroventricular administration.

Certain embodiments further provide a method to reduce huntingtin mRNA or protein expression in an animal comprising administering to the animal a compound or composition as described herein to reduce huntingtin mRNA or protein expression in the animal. In certain embodiments, the animal is a human. In certain embodiments, reducing huntingtin mRNA or protein expression prevents, treats, ameliorates, or slows progression of Huntington's disease.

Certain embodiments provide a method for treating a human with Huntington's disease comprising identifying the human with the disease and administering to the human a therapeutically effective amount of a compound or composition as described herein. In certain embodiments, the treatment reduces a symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy.

Further provided is a method for reducing or preventing Huntington's disease comprising administering to a human a therapeutically effective amount compound or composition as described herein, thereby reducing or preventing Huntington's disease.

Further provided is a method for ameliorating a symptom of Huntington's disease, comprising administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby ameliorating a symptom of Huntington's disease in the human.

Further provided is a method for reducing the rate of progression of a symptom associated with Huntington's Disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of Huntington's disease in the human.

Further provided is a method for reversing degeneration indicated by a symptom associated with Huntington's disease, administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby reversing degeneration indicated by a symptom of Huntington's disease in the human.

In certain embodiments, the symptom is a physical, cognitive, psychiatric, or peripheral symptom. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

Also provided are methods and compounds for the preparation of a medicament for the treatment, prevention, or amelioration of Huntington's disease.

Certain embodiments provide the use of a compound as described herein in the manufacture of a medicament for treating, ameliorating, or preventing Huntington's disease.

Certain embodiments provide a compound as described herein for use in treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein in a patient who is subsequently administered an additional agent or therapy as described herein.

Certain embodiments provide a kit for treating, preventing, or ameliorating Huntington's disease as described herein wherein the kit comprises:

(i) a compound as described herein; and alternatively (ii) an additional agent or therapy as described herein.

A kit as described herein may further include instructions for using the kit to treat, prevent, or ameliorate Huntington's disease as described herein by combination therapy as described herein.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in treating an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12-30 linked nucleosides, wherein the linked nucleosides at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound so that expression of huntingtin is inhibited.

Certain embodiments provide compounds comprising a modified oligonucleotide consisting of 12-30 linked nucleosides, wherein the linked nucleosides comprise at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound to prevent, treat, ameliorate, or slow progression of Huntington's disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a huntingtin nucleic acid is 12 to 30 nucleotides in length. In other words, antisense compounds are from 12 to 30 linked nucleobases. In other embodiments, the antisense compound comprises a modified oligonucleotide consisting of 8 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a huntingtin nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as “X-Y-Z”, where “X” represents the length of the 5' wing region, “Y” represents the length of the gap region, and “Z” represents the length of the 3' wing region. As used herein, a gapmer described as “X-Y-Z” has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6 or 5-8-5.

In certain embodiments, the antisense compound as a “wingmer” motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a huntingtin nucleic acid possess a 5-10-5 gapmer motif.

In certain embodiments, antisense compounds targeted to a huntingtin nucleic acid possess a 6-8-6 gapmer motif.

In certain embodiments, antisense compounds targeted to a huntingtin nucleic acid possess a 5-8-5 gapmer motif.

In certain embodiments, an antisense compound targeted to a huntingtin nucleic acid has a gap-widened motif.

In certain embodiments, a gap-widened antisense oligonucleotide targeted to a huntingtin nucleic acid has a gap segment of ten 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of six chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode huntingtin include, without limitation, the following: GENBANK Accession No. NM_002111.6, first deposited with GENBANK® on May 31, 2006 incorporated herein as SEQ ID NO: 1; GENBANK Accession No. NT_006081.17 truncated from nucleotides 462000 to 634000, first deposited with GENBANK® on Aug. 19, 2004, and incorporated herein as SEQ ID NO: 2; GENBANK Accession No. NM_010414.1, first deposited with GENBANK® on Mar. 23, 2004, incorporated herein as SEQ ID NO: 3; the complement of GENBANK Accession No. NW_001109716.1 truncated at nucleotides 698000 to 866000, first deposited with GENBANK® on Jun. 14, 2006, incorporated herein as SEQ ID NO: 4, and GENBANK Accession No. NM_024357.2, first deposited with GENBANK® on Jun. 5, 2008, incorporated herein as SEQ ID NO: 5.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in huntingtin mRNA levels are indicative of inhibition of huntingtin expression. Reductions in levels of a huntingtin protein are also indicative of inhibition of target mRNA expression. Further, phenotypic changes are indicative of inhibition of huntingtin expression. For example, increase in brain size to normal, improvement in motor coordination, decrease in continual muscular spasms (dystonia), decrease in irritability and/or anxiety, improvement of memory, or an increase in energy, among other phenotypic changes that may be assayed. Other phenotypic indications, e.g., symptoms associated with Huntington's disease, may also be assessed as described below.

Hybridization

In some embodiments, hybridization occurs between an antisense compound disclosed herein and a huntingtin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a huntingtin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a huntingtin nucleic acid).

An antisense compound may hybridize over one or more segments of a huntingtin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a huntingtin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a huntingtin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a huntingtin nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a huntingtin nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a huntingtin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2)2OCH3 substituent groups. The substituent at the 2' position can also be selected from allyl, amino, azido, thio, O-allyl, O-C1-C10 alkyl, OCF3, O(CH2)2SCH3, O(CH2)2-O—N(Rm)(Rn), and O-CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2; 4'-(CH2)-O-2' (LNA); 4'-(CH2)2-O-2' (ENA); 4'-C(CH3)2-O-2' (see PCT/US2008/068922); 4'-CH(CH3)¬-O-2' and 4'-C¬H(CH2OCH3)¬O-2' (see U.S. Pat. No. 7,399,845, issued on Jul. 15, 2008); 4'-CH2-N(OCH3)-2' (see PCT/US2008/064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C¬(=CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

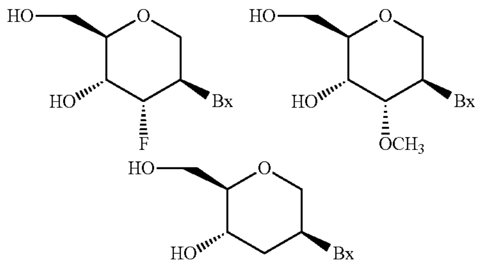

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a huntingtin nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a huntingtin nucleic acid comprise one or more modified nucleobases. In certain embodiments, gap-widened antisense oligonucleotides targeted to a huntingtin nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a huntingtin nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a huntingtin nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of huntingtin nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a huntingtin nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a huntingtin nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of huntingtin nucleic acids can be assessed by measuring huntingtin protein levels. Protein levels of huntingtin can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat huntingtin are commercially available.

In Vivo Testing of Antisense Compounds

Antisense compounds, for example, antisense oligonucleotides, are tested in animals to assess their ability to inhibit expression of huntingtin and produce phenotypic changes. Testing may be performed in normal animals, or in experimental disease models. For administration to animals, antisense oligonucleotides are formulated in a pharmaceutically acceptable diluent, such as phosphate-buffered saline.

Administration includes parenteral routes of administration. Following a period of treatment with antisense oligonucleotides, RNA is isolated from tissue and changes in huntingtin nucleic acid expression are measured. Changes in huntingtin protein levels are also measured.

Certain Compounds

About seventeen hundred newly designed antisense compounds of various lengths, motifs and backbone composition were tested for their effect on human huntingtin mRNA in vitro in several cell types. The new compounds were compared with about two hundred and fifty previously designed compounds including ISIS 387916 which had previously been determined to be one of the most potent antisense compounds in vitro (see e.g., U.S. Patent Publication Nos. 2008/0039418 and 2007/0299027. Of the about seventeen hundred newly designed antisense compounds, about sixty compounds were selected for further study based on in vitro potency compared to ISIS 387916. The selected compounds were tested for systemic tolerability (see Example 3) and activity and tolerability in the brain of BACHD mice (see Example 4) compared to previously designed ISIS 388241 and ISIS 387916. From these studies, compounds having a nucleobase sequence of a sequence recited in SEQ ID NO: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 or 32 were selected as having high tolerability and high in vivo potency. By virtue of their complementary sequence, the compounds are complementary to the regions 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 or 4928-4947 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419628, ISIS 419637, ISIS 419640, ISIS 419641, ISIS 451541, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663.

Compounds described above as having high in vivo potency and tolerability were then tested by CNS bolus injection in rat to further assess neurotoxicity (see Example 5) along with several additional compounds having a nucleobase sequence of a sequence recited in SEQ ID NO: 7, 8, 11, 16, 17. Of these, ten compounds having a nucleobase sequence of a sequence recited in SEQ ID NO: 24, 25, 26, 6, 12, 28, 21, 22, 32 or 13 were selected as having high tolerability. By virtue of their complementary sequence, the compounds are complementary to the regions 4384-4403, 4609-4628, 4610-4629, 4860-4877, 4862-4881, 4925-4944, 4928-4947, 4931-4950, 4955-4974, or 5809-5829 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419640, ISIS 419641, ISIS 419642, ISIS 436665, ISIS 436671, ISIS 436689, ISIS 437507, ISIS 443139, ISIS 444591, and ISIS 444661. Selected compounds were compared with previously designed compound ISIS 388241 by ICV administration in BACHD mice.

Additional studies were then run on compounds described above as having high in vivo potency and tolerability. The additional studies were designed to further assess neurotoxicity. Studies included ICV administration in wild-type mouse (see Example 16) and bolus administration in rat (see Example 17). SEQ ID NOs: 12, 22, 28, 30, 32, and 33 were selected as having high neurotolerability. By virtue of their complementary sequence, the compounds are complementary to the regions 4862-4881, 4609-4628, 5809-5828, 5809-5826, 5801-5820, and 4955-4974 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by ISIS 388241, ISIS 443139, ISIS 436671, ISIS 444591, ISIS 437527, ISIS 444584, ISIS 444652, and ISIS 436689.

Accordingly, provided herein are antisense compounds with improved characteristics. In certain embodiments, provided herein are compounds comprising a modified oligonucleotide as further described herein targeted to or specifically hybridizable with the region of nucleotides of SEQ ID NO: 1.

In certain embodiments, the compounds as described herein are efficacious by virtue of having at least one of an in vitro IC50 of less than 7 uM, less than 6 uM, less than 5, uM, less than 4 uM, less than 3 uM, less than 2 uM, less than 1 uM when delivered to a human fibroblast cell line as described herein or an ED50 of less than 10 μg, less than 9 μg, less than 8 μg, less than 7.5 μg, less than 7.4 μg, less than 7.0 μg, less than 6 μg, less than 5 μg, less than 4 μg, less than 3 μg, or less than 2 μg by bolus injection. As described herein, ICV infusion can result in 3 to 4 fold higher ED50 values for the compounds described herein. In certain embodiments, the compounds as described herein are highly tolerable as demonstrated by having at least one of an increase an ALT or AST value of no more than 4 fold, 3 fold, or 2 fold over saline treated animals; an increase in liver, spleen or kidney weight of no more than 30%, 20%, 15%, 12%, 10%, 5% or 2%; or an increase AIF1 levels by no more than 350%, 300%, 275%, 250% 200%, 150% or 100% over control.

Certain Indications

In certain embodiments, provided herein are methods of treating an individual comprising administering one or more pharmaceutical compositions as described herein. In certain embodiments, the individual has Huntington's disease.

As shown in the examples below, compounds targeted to huntingtin as described herein have been shown to reduce the severity of physiological symptoms of Huntington's disease. In certain of the experiments, the compounds reduced rate of degeneration, e.g., the animals continued to experience symptoms, but the symptoms were less severe compared to untreated animals. In other of the experiments, however, the compounds appear to result in regeneration of function over time; e.g., animals treated for a longer period of time experienced less severe symptoms than those administered the compounds for a shorter period of time. As discussed above, Huntington's disease is a degenerative disease with a progression typified by increased severity of symptoms over time. The ability of the compounds exemplified below to restore function therefore demonstrates that symptoms of the disease may be reversed by treatment with a compound as described herein.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

In certain embodiments, the methods described herein include administering a compound comprising a modified oligonucleotide having a contiguous nucleobases portion as described herein of a sequence recited in SEQ ID NO: 6, 9, 10, 11, 12, 13, 14, 15, 18, 19, 20, 21, 22, 23, 24, 25, 26, 27, 28, 29, 30, 32, 33, 35, 36, 10, 11, 12, 13, 18, 22 or 32. In certain embodiments, the methods described herein include administering a compound comprising a modified oligonucleotide having a contiguous nucleobases portion as described herein of a sequence recited in SEQ ID NOs: 12, 22, 28, 30, 32, and 33.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

The median effective concentration ($EC_{50}$) of an antisense compounds for inhibiting huntingtin mRNA expression was calculated after either ICV infusion or bolus injection (see Examples 9 and 10). The $EC_{50}$ for the compound after intrastriatal injection was determined to be 0.45 μg/g. The $EC_{50}$ after ICV administration was determined to be 26.4 μg/g.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

The half-life of MOE gapmer oligonucleotides in brain tissue is about 20 days (see Examples 9-11). The duration of action as measured by inhibition of huntingtin mRNA is prolonged in the brain (see Examples 9 and 10). Intracerebroventricular infusion of antisense oligonucleotides for 2 weeks results in inhibition of huntingtin mRNA by at least 50% in striatal tissue of BACHD mice for at least 91 days after termination of dosing. Administration by bolus injection resulted in a similar duration of action.

In certain embodiments, delivery of a compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days. In certain embodiments, delivery to the CNS is by intraparenchymal administration, intrathecal administration, or intracerebroventricular administration.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Oligonucleotides Targeted to Human Huntingtin Gene Sequences

About seventeen hundred newly designed antisense compounds of various lengths, motifs and backbone composition targeting the human huntingtin gene sequence were tested for their effect on human huntingtin mRNA in vitro in several cell types. These gapmers were further designed with internucleoside linkages that are either only phosphorothioate linkages (described in Table 1) or that are phosphorothioate and phosphodiester linkages (described in Table 5). A number of the newly designed oligos and two benchmark oligonucleotides (previously designed and disclosed) are provided in Tables 1 and 5.

Gapmers with Fully Phosphorothioate Internucleoside Linkages

Certain of the compounds presented in Table 1 have a motif of 5-10-5 MOE, 6-8-6 MOE, or 5-8-5 MOE. The 5-10-5 gapmers have twenty linked nucleosides, wherein the central gap segment has ten 2'-deoxynucleosides and is flanked on both sides (in the 5' and 3' directions) by wings having five nucleosides each. The 6-8-6 gapmer has twenty linked nucleosides, wherein the central gap segment has eight 2'-deoxynucleosides and is flanked on both sides (in the 5' and 3' directions) by wings having six nucleosides each. The 5-8-5 gapmers have eighteen linked nucleosides, wherein the central gap segment has eight 2'-deoxynucleosides and is flanked on both sides (in the 5' and 3' directions) by wings having five nucleosides each. For all gapmers listed in Table 1, each nucleoside in the 5' wing segment and each nucleoside in the 3' wing segment has a 2'-MOE modification. The internucleoside linkages throughout each gapmer are phosphorothioate (P═S) internucleoside linkages. All cytosines throughout each gapmer are 5-methylcytosines. Each gapmer in Table 1 is targeted to SEQ ID NO: 1 (GENBANK Accession No. NM_002111.6) or SEQ ID NO: 2 (GENBANK Accession No. NT_006081.17 truncated from nucleotides 462000 to 634000). 'Start site' indicates the 5'-most nucleotide to which the gapmer is targeted in the human gene sequence. 'Stop site' indicates the 3'-most nucleotide to which the gapmer is targeted in the human gene sequence.

TABLE 1

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4384 | 4403 | 1 | 436665 | TAGCATTCTTATCTGCACGG | 5-10-5 | 6 |
| 4511 | 4530 | 1 | 436668 | ACCCGTAACTGAACCAGCTG | 5-10-5 | 7 |
| 4599 | 4618 | 1 | 419627 | TTCCCTGAACTGGCCCACTT | 5-10-5 | 8 |
| 4605 | 4624 | 1 | 419628 | CTCTGATTCCCTGAACTGGC | 5-10-5 | 9 |
| 4607 | 4626 | 1 | 444607 | GCCTCTGATTCCCTGAACTG | 5-10-5 | 10 |
| 4608 | 4627 | 1 | 419629 | TGCCTCTGATTCCCTGAACT | 5-10-5 | 11 |
| 4608 | 4627 | 1 | 444578 | TGCCTCTGATTCCCTGAACT | 6-8-6 | 11 |
| 4609 | 4628 | 1 | 436671 | TTGCCTCTGATTCCCTGAAC | 5-10-5 | 12 |
| 4610 | 4629 | 1 | 444608 | ATTGCCTCTGATTCCCTGAA | 5-10-5 | 13 |
| 4617 | 4636 | 1 | 444615 | TGGAATGATTGCCTCTGATT | 5-10-5 | 14 |
| 4622 | 4639 | 1 | 437168 | GTTTGGAATGATTGCCTC | 5-8-5 | 15 |
| 4679 | 4698 | 1 | 419630 | CCAATGATCTGTTTTGAATG | 5-10-5 | 16 |
| 4733 | 4752 | 1 | 419636 | GCCTTCCTTCCACTGGCCAT | 5-10-5 | 17 |
| 4813 | 4832 | 1 | 444618 | CTGCATCAGCTTTATTTGTT | 5-10-5 | 18 |
| 4814 | 4833 | 1 | 419637 | CCTGCATCAGCTTTATTTGT | 5-10-5 | 19 |
| 4823 | 4842 | 1 | 444627 | AGCTCTTTTCCTGCATCAGC | 5-10-5 | 20 |
| 4860 | 4877 | 1 | 437507 | GTAACATTGACACCACCA | 5-8-5 | 21 |
| 4862 | 4881 | 1 | 388241 | CTCAGTAACATTGACACCAC | 5-10-5 | 22 |

TABLE 1-continued

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4868 | 4887 | 1 | 436684 | ATGAGTCTCAGTAACATTGA | 5-10-5 | 23 |
| 4925 | 4944 | 1 | 419640 | TCCTTGTGGCACTGCTGCAG | 5-10-5 | 24 |
| 4928 | 4947 | 1 | 419641 | TTCTCCTTGTGGCACTGCTG | 5-10-5 | 25 |
| 4931 | 4950 | 1 | 419642 | TCATTCTCCTTGTGGCACTG | 5-10-5 | 26 |
| 4931 | 4948 | 1 | 437442 | ATTCTCCTTGTGGCACTG | 5-8-5 | 27 |
| 4955 | 4974 | 1 | 436689 | CGAGACAGTCGCTTCCACTT | 5-8-5 | 28 |
| 4960 | 4977 | 1 | 437175 | TGTCGAGACAGTCGCTTC | 5-8-5 | 29 |
| 5801 | 5820 | 1 | 444584 | TTGCACATTCCAAGTTTGGC | 5-10-5 | 30 |
| 5807 | 5826 | 1 | 387916 | TCTCTATTGCACATTCCAAG | 5-10-5 | 31 |
| 5809 | 5828 | 1 | 444591 | TTTCTCTATTGCACATTCCA | 5-10-5 | 32 |
| 5809 | 5826 | 1 | 437527 | TCTCTATTGCACATTCCA | 5-8-5 | 33 |
| 1446 | 1465 | 2 | 388817 | GCAGGGTTACCGCCATCCCC | 5-10-5 | 34 |
| 101088 | 101105 | 2 | 437441 | ACCTTATCTGCACGGTTC | 5-8-5 | 35 |
| 115066 | 115085 | 2 | 436754 | CTCTCTGTGTATCACCTTCC | 5-10-5 | 36 |

The complementarity of the gapmers in Table 1 with mouse, rhesus monkey and rat huntingtin gene sequences is further described in Tables 2, 3, and 4.

The gapmers of Table 2 are complementary with mouse huntingtin mRNA (GENBANK Accession No. NM_010414.1, designated herein as SEQ ID NO: 3). ‘Mouse target start site’ indicates the 5'-most nucleotide to which the gapmer is targeted in the mouse mRNA. ‘Mouse target stop site’ indicates the 3'-most nucleotide to which the gapmer is targeted in the mouse mRNA. ‘Human Target Start Site’ indicates the 5'-most nucleotide to which the gapmer is targeted in the human gene sequence. ‘Human Target Stop Site’ indicates the 3'-most nucleotide to which the gapmer is targeted in the human gene sequence. ‘Number of mismatches’ indicates the number of mismatches between the human oligonucleotide and the mouse mRNA sequence.

TABLE 2

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4384 | 4403 | 1 | 436665 | 4343 | 4362 | 0 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |

TABLE 2-continued

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 0 | 24 |
| 4928 | 4947 | 1 | 419641 | 4887 | 4906 | 0 | 25 |
| 4931 | 4950 | 1 | 419642 | 4890 | 4909 | 0 | 26 |
| 4931 | 4948 | 1 | 437442 | 4890 | 4907 | 0 | 27 |
| 4955 | 4974 | 1 | 436689 | 4914 | 4933 | 3 | 28 |
| 5807 | 5826 | 1 | 387916 | 5763 | 5782 | 1 | 31 |
| 5809 | 5826 | 1 | 437527 | 5765 | 5782 | 1 | 33 |
| 5809 | 5828 | 1 | 444591 | 5765 | 5784 | 1 | 32 |
| 101088 | 101105 | 2 | 437441 | 4340 | 4357 | 2 | 35 |

The gapmers of Table 3 are complementary with the rhesus monkey huntingtin genomic sequence (the complement of GENBANK Accession No. NW_001109716.1 truncated at nucleotides 698000 to 866000, designated herein as SEQ ID NO: 4). ‘Rhesus monkey target start site’ indicates the 5'-most nucleotide to which the gapmer is targeted in the rhesus monkey gene sequence. ‘Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rhesus monkey gene sequence.

TABLE 3

Complementarity of antisense oligonucleotides having phosphorothioate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mis-matches | SEQ ID NO. |
|---|---|---|---|---|---|---|---|
| 4511 | 4530 | 1 | 436665 | 98182 | 98201 | 0 | 6 |
| 4599 | 4618 | 1 | 419627 | 101353 | 101372 | 1 | 8 |
| 4609 | 4628 | 1 | 436671 | 102256 | 102275 | 3 | 12 |
| 4610 | 4629 | 1 | 444608 | 102257 | 102276 | 2 | 13 |
| 4617 | 4636 | 1 | 444615 | 102264 | 102283 | 0 | 14 |
| 4622 | 4639 | 1 | 437168 | 102269 | 102286 | 0 | 15 |
| 4679 | 4698 | 1 | 419630 | 102326 | 102345 | 0 | 16 |
| 4733 | 4752 | 1 | 419636 | 102380 | 102399 | 0 | 17 |
| 4813 | 4832 | 1 | 444618 | 105030 | 105049 | 0 | 18 |
| 4814 | 4833 | 1 | 419637 | 105031 | 105050 | 0 | 19 |
| 4823 | 4842 | 1 | 444627 | 105040 | 105059 | 0 | 20 |
| 4860 | 4877 | 1 | 437507 | 105077 | 105094 | 1 | 21 |
| 4862 | 4881 | 1 | 388241 | 105079 | 105098 | 1 | 22 |
| 4868 | 4887 | 1 | 436684 | 105085 | 105104 | 0 | 23 |
| 4925 | 4944 | 1 | 419640 | 106844 | 106863 | 0 | 24 |
| 4928 | 4947 | 1 | 419641 | 106847 | 106866 | 0 | 25 |
| 4931 | 4950 | 1 | 419642 | 106850 | 106869 | 0 | 26 |
| 4931 | 4948 | 1 | 437442 | 106850 | 106867 | 0 | 27 |
| 4955 | 4974 | 1 | 436689 | 106874 | 106893 | 0 | 28 |
| 4960 | 4977 | 1 | 437175 | 106879 | 106896 | 0 | 29 |
| 5801 | 5820 | 1 | 444584 | 125331 | 125350 | 0 | 30 |
| 5807 | 5826 | 1 | 387916 | 125337 | 125356 | 0 | 31 |
| 5809 | 5826 | 1 | 437527 | 125339 | 125356 | 0 | 33 |
| 5809 | 5828 | 1 | 444591 | 125339 | 125358 | 0 | 32 |
| 101088 | 101105 | 2 | 437441 | 97904 | 97921 | 0 | 35 |
| 115066 | 115085 | 2 | 436754 | 110518 | 110537 | 0 | 36 |

The gapmers of Table 4 are complementary with rat huntingtin mRNA (GENBANK Accession No. NM_024357.2, designated herein as SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rat mRNA sequence.

TABLE 4

Complementarity of antisense oligonucleotides having phosphorothioate linkages with rat mRNA (SEQ ID NO: 5)

| Human Start Site | Human Stop Site | Human Target SEQ ID NO. | ISIS No. | Rat Start Site | Rat Stop Site | No. of mis-matches | SEQ ID NO. |
|---|---|---|---|---|---|---|---|
| 4384 | 4403 | 1 | 436665 | 4343 | 4362 | 1 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 1 | 24 |
| 4928 | 4947 | 1 | 419641 | 4887 | 4906 | 1 | 25 |
| 4931 | 4950 | 1 | 419642 | 4890 | 4909 | 1 | 26 |
| 4931 | 4948 | 1 | 437442 | 4890 | 4907 | 1 | 27 |
| 4955 | 4974 | 1 | 436689 | 4914 | 4933 | 3 | 28 |
| 5801 | 5820 | 1 | 444584 | 5757 | 5776 | 3 | 30 |
| 5807 | 5826 | 1 | 387916 | 5763 | 5782 | 0 | 31 |
| 5809 | 5826 | 1 | 437527 | 5765 | 5782 | 0 | 33 |
| 5809 | 5828 | 1 | 444591 | 5765 | 5784 | 0 | 32 |
| 101088 | 101105 | 2 | 437441 | 4340 | 4357 | 2 | 35 |

Gapmers with Mixed Phosphorothioate and Phosphodiester Internucleoside Linkages

The chimeric antisense oligonucleotides in Table 5 were designed as 5-10-5 MOE gapmers. The 5-10-5 gapmers have twenty linked nucleosides, wherein the central gap segment has ten 2'-deoxynucleotides and is flanked on both sides (in the 5' and 3' directions) by wings having five nucleosides each. Each nucleoside in the 5' wing segment and each nucleoside in the 3' wing segment has a 2'-MOE modification. The internucleoside linkages within the central gap segment, the linkages connecting the gap segment to the 5' or 3' wing segment, and the linkages for the 5'-most and 3'-most nucleosides of each wing segments are all phosphorothioate (P=S) linkages; the internucleoside linkages connecting the rest of the nucleosides of both the 5' and 3' wing segments are phosphodiester linkages; i.e. the gapmer has a mixed backbone. All cytosines throughout each gapmer are 5-methylcytosines. Each gapmer in Table 5 is targeted to the human mRNA sequence (GENBANK Accession No. NM_002111.6, designated herein as SEQ ID NO: 1). 'Start site' indicates the 5'-most nucleotide to which the gapmer is targeted in the human mRNA. 'Stop site' indicates the 3'-most nucleotide to which the gapmer is targeted in the human mRNA.

TABLE 5

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4607 | 4626 | 1 | 444658 | GCCTCTGATTCCCTGAACTG | 5-10-5 | 10 |
| 4608 | 4627 | 1 | 444659 | TGCCTCTGATTCCCTGAACT | 5-10-5 | 11 |
| 4609 | 4628 | 1 | 444660 | TTGCCTCTGATTCCCTGAAC | 5-10-5 | 12 |
| 4610 | 4629 | 1 | 444661 | ATTGCCTCTGATTCCCTGAA | 5-10-5 | 13 |
| 4813 | 4832 | 1 | 444663 | CTGCATCAGCTTTATTTGTT | 5-10-5 | 18 |
| 4862 | 4881 | 1 | 443139 | CTCAGTAACATTGACACCAC | 5-10-5 | 22 |
| 5809 | 5828 | 1 | 444652 | TTTCTCTATTGCACATTCCA | 5-10-5 | 32 |
| 4928 | 4947 | 1 | 451541 | TTCTCCTTGTGGCACTGCTG | 5-10-5 | 25 |

The complementarity of the gapmers in Table 5 with mouse, rhesus monkey and rat huntingtin gene sequences are further described in Tables 6, 7, and 8.

The gapmers of Table 6 are complementary with mouse huntingtin mRNA (GENBANK Accession No. NM_010414.1; SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the mouse mRNA sequence.

TABLE 6

Complementarity of antisense oligonucleotides having mixed phosphorothioate and phosphate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 1 | 32 |

The gapmers of Table 7 are complementary with the rhesus monkey huntingtin genomic sequence (the complement of GENBANK Accession No. NW_001109716.1 truncated at nucleotides 698000 to 866000; SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rhesus monkey gene sequence.

TABLE 7

Complementarity of antisense oligonucleotides having mixed phosphorothioate and phosphate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mis-matches | SEQ ID NO. |
|---|---|---|---|---|---|---|---|
| 4609 | 4628 | 1 | 444660 | 102256 | 102275 | 3 | 12 |
| 4610 | 4629 | 1 | 444661 | 102257 | 102276 | 2 | 13 |
| 4813 | 4832 | 1 | 444663 | 105030 | 105049 | 0 | 18 |
| 4862 | 4881 | 1 | 443139 | 105079 | 105098 | 1 | 22 |
| 5809 | 5828 | 1 | 444652 | 125339 | 125358 | 0 | 32 |

The gapmers of Table 8 are complementary with rat huntingtin mRNA (GENBANK Accession No. NM_024357.2; SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rat mRNA sequence.

TABLE 8

Complementarity of antisense oligonucleotides having mixed phosphorothioate and phosphate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 0 | 32 |

Example 2

Dose-dependent Antisense Inhibition of Human Huntingtin mRNA in Vitro

About seventeen hundred newly designed antisense compounds of various lengths, motifs and backbone composition were tested for their effect on human huntingtin mRNA in vitro in several cell types. These compounds were compared to about two hundred and fifty previously designed compounds including the compound ISIS 387916 which was previously determined to be a compound of considerable potency in vivo. As shown in this example, ISIS 419640, ISIS 419641, ISIS 419642, ISIS 436665, ISIS 436671, ISIS 436689, ISIS 437507, ISIS 443139, ISIS 444591, ISIS 444661, ISIS 437527, ISIS 444584, and ISIS 444652 and previously designed ISIS 388241 were found to have similar or better potency than the benchmark compound ISIS 387916 in vitro.

A. GM04281 Fibroblasts

Cultured GM04281 fibroblasts at a density of 25,000 cells per well were transfected using electroporation with 500 nM, 1000 nM, 2000 nM, 4000 nM, or 8000 nM of antisense oligonucleotide. After a treatment period of approximately 16 hours, RNA was isolated from the cells and huntingtin mRNA levels were measured by quantitative real-time PCR. Human primer probe set RTS2617 (forward sequence CTCCGTCCGGTAGACATGCT, designated herein as SEQ ID NO: 37; reverse sequence GGAAATCAGAACCCTCAAAATGG, designated herein as SEQ ID NO: 38; probe sequence TGAGCACTGTTCAACTGTGGATATCGGGAX, designated herein as SEQ ID NO: 39) was used to measure mRNA levels. Huntingtin mRNA levels were adjusted according to total RNA content, as measured by RIBOGREEN®. Results are presented in Table 9 as percent inhibition of huntingtin mRNA, relative to untreated control cells and demonstrate antisense oligonucleotide-mediated dose-dependent reduction of huntingtin mRNA levels.

The half maximal inhibitory concentration ($IC_{50}$) of each oligonucleotide is also presented in Table 9 and was calculated by plotting the concentrations of oligonucleotides used versus the percent inhibition of huntingtin mRNA expression achieved at each concentration, and noting the concentration of oligonucleotide at which 50% inhibition of huntingtin mRNA expression was achieved compared to the control. The $IC_{50}$ is expressed in µM.

TABLE 9

Dose dependent reduction of huntingtin mRNA in GM04281 fibroblasts

| ISIS No. | 500 nM | 1000 nM | 2000 nM | 4000 nM | 8000 nM | $IC_{50}$ (µM) |
|---|---|---|---|---|---|---|
| 387916 | 33 | 73 | 90 | 96 | 97 | 1.00 |
| 388241 | 44 | 70 | 82 | 95 | 97 | 0.61 |
| 419641 | 26 | 32 | 71 | 90 | 93 | 1.06 |
| 436665 | 56 | 67 | 87 | 95 | 96 | 0.32 |
| 436671 | 12 | 35 | 68 | 82 | 91 | 1.55 |
| 436689 | 10 | 34 | 61 | 80 | 91 | 1.89 |

ISIS 387916, ISIS 388241, and ISIS 437507 were further tested for their effect on human huntingtin mRNA in vitro. Cultured GM04281 fibroblasts were tested in a similar procedure, as described above. The results are presented in Table 10 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 10 expressed in µM.

TABLE 10

Dose dependent reduction of huntingtin mRNA in GM04281 fibroblasts

| ISIS No. | 500 nM | 1000 nM | 2000 nM | 4000 nM | 8000 nM | $IC_{50}$ (µM) |
|---|---|---|---|---|---|---|
| 387916 | 56 | 84 | 94 | 98 | 99 | 0.34 |
| 388241 | 58 | 75 | 94 | 98 | 99 | 0.23 |
| 437507 | 61 | 74 | 85 | 93 | 93 | 0.22 |

ISIS 387916, ISIS 388241, and ISIS 437507 were further tested for their effect on human huntingtin mRNA in vitro. Cultured GM04281 fibroblasts were tested in a similar procedure as described above. The results are presented in Table 11 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 11 expressed in µM.

TABLE 11

Dose dependent reduction of huntingtin mRNA in GM04281 fibroblasts

| ISIS No. | 500 nM | 1000 nM | 2000 nM | 4000 nM | 8000 nM | $IC_{50}$ (µM) |
|---|---|---|---|---|---|---|
| 387916 | 40 | 61 | 85 | 94 | 97 | 0.70 |
| 388241 | 51 | 72 | 86 | 94 | 98 | 0.41 |
| 437507 | 30 | 55 | 71 | 79 | 82 | 1.07 |

ISIS 387916, ISIS 388241, ISIS 419641, and ISIS 436754 were further tested for their effect on human huntingtin mRNA in vitro. Cultured GM04281 fibroblasts were tested in a similar procedure as described above. The results are presented in Table 12 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 12 expressed in µM.

TABLE 12

| Dose dependent reduction of huntingtin mRNA in GM04281 fibroblasts | | | | | | |
|---|---|---|---|---|---|---|
| ISIS No. | 500 nM | 1000 nM | 2000 nM | 4000 nM | 8000 nM | $IC_{50}$ (μM) |
| 387916 | 58 | 75 | 93 | 98 | 98 | 0.22 |
| 388241 | 40 | 68 | 85 | 95 | 98 | 0.73 |
| 419641 | 37 | 58 | 86 | 92 | 95 | 0.80 |
| 436754 | 44 | 62 | 63 | 84 | 93 | 0.59 |

ISIS 387916, ISIS 388241, and ISIS 437507 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 13 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 13 expressed in μM.

TABLE 13

| Dose dependent reduction of huntingtin mRNA in GM04281 fibroblasts | | | | | | | |
|---|---|---|---|---|---|---|---|
| ISIS No. | 250 nM | 500 nM | 1000 Nm | 2000 nM | 4000 nM | 8000 nM | $IC_{50}$ (μM) |
| 387916 | 10 | 9 | 61 | 85 | 97 | 99 | 0.79 |
| 388241 | 0 | 18 | 42 | 90 | 98 | 99 | 1.08 |
| 437507 | 1 | 0 | 32 | 71 | 92 | 98 | 1.30 |

ISIS 387916, ISIS 388241, ISIS 419628, ISIS 419629, ISIS 419637, ISIS 436684, ISIS 443139, ISIS 444584, ISIS 444615, ISIS 444627, ISIS 444652, ISIS 444658, ISIS 444659, ISIS 444660, and ISIS 444661 were further tested for their effect on human huntingtin mRNA in vitro. Cultured GM04281 fibroblasts at a density of 25,000 cells per well were transfected using electroporation with 156.25 nM, 312.5 nM, 625 nM, 1250 nM, or 2500 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 14 as percent inhibition of huntingtin mRNA, relative to untreated control cells, and demonstrate antisense oligonucleotide-mediated dose-dependent reduction of huntingtin mRNA levels. The data presented is the average of two experiments. The $IC_{50}$ of each antisense oligonucleotide is also presented in Table 14 expressed in μM.

TABLE 14

| Dose dependent reduction of huntingtin mRNA in GM04281 fibroblasts | | | | | | |
|---|---|---|---|---|---|---|
| ISIS No | 156.25 nM | 312.5 Nm | 625 nM | 1250 nM | 2500 nM | $IC_{50}$ (μM) |
| 387916 | 19 | 22 | 44 | 62 | 85 | 0.73 |
| 388241 | 3 | 13 | 24 | 42 | 71 | 1.42 |
| 419628 | 56 | 45 | 59 | 71 | 83 | 0.20 |
| 419629 | 42 | 38 | 67 | 70 | 89 | 0.33 |
| 419637 | 24 | 17 | 32 | 61 | 77 | 0.91 |
| 436684 | 15 | 28 | 55 | 73 | 85 | 0.59 |
| 443139 | 13 | 45 | 50 | 64 | 81 | 0.61 |
| 444584 | 0 | 0 | 25 | 50 | 74 | 1.28 |
| 444615 | 36 | 35 | 37 | 38 | 70 | 0.12 |
| 444627 | 40 | 38 | 48 | 73 | 87 | 0.43 |
| 444652 | 15 | 28 | 55 | 73 | 85 | 0.59 |
| 444658 | 50 | 54 | 75 | 84 | 96 | 0.18 |
| 444659 | 47 | 61 | 69 | 79 | 93 | 0.18 |
| 444660 | 41 | 61 | 65 | 84 | 95 | 0.22 |
| 444661 | 47 | 59 | 72 | 84 | 96 | 0.19 |

ISIS 387916, ISIS 436671, ISIS 444661, ISIS 419641, and ISIS 436665 were further tested for their effect on human huntingtin mRNA in vitro. Cultured GM04281 fibroblasts at a density of 25,000 cells per well were transfected using electroporation with 13.6719 nM, 27.3438 nM, 54.6875 nM, 109.375 nM, 218.75 nM, 437.5 nM, 875 nM, 1750 nM, 3500 nM, or 7000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15 expressed in μM.

TABLE 15

| Dose dependent reduction of huntingtin mRNA in GM04281 fibroblasts | | | | | | | | | | |
|---|---|---|---|---|---|---|---|---|---|---|
| ISIS No. | 13.6719 nM | 27.3438 nM | 54.6875 nM | 109.375 nM | 218.75 nM | 437.5 nM | 875 nM | 1750 nM | 3500 nM | 7000 nM | $IC_{50}$ (μM) |
| 387916 | 0 | 31 | 14 | 43 | 44 | 68 | 86 | 89 | 97 | 97 | 0.31 |
| 436671 | 0 | 0 | 21 | 31 | 54 | 73 | 77 | 83 | 88 | 97 | 0.31 |
| 444661 | 0 | 10 | 25 | 53 | 66 | 73 | 87 | 96 | 99 | 99 | 0.16 |
| 419641 | 5 | 23 | 33 | 48 | 44 | 75 | 79 | 90 | 94 | 98 | 0.17 |
| 436665 | 26 | 37 | 47 | 44 | 65 | 83 | 89 | 94 | 98 | 98 | 0.07 |

ISIS 387916, ISIS 388241, ISIS 437168, and ISIS 437175 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM, and 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15.1 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.1 expressed in μM.

TABLE 15.1

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 22 | 63 | 70 | 83 | 95 | 96 | 0.62 |
| 388241 | 17 | 45 | 65 | 87 | 96 | 97 | 0.56 |
| 437175 | 47 | 31 | 56 | 60 | 79 | 91 | 1.19 |
| 437168 | 32 | 46 | 64 | 81 | 89 | 95 | 0.59 |

ISIS 387916, ISIS 388241, ISIS 437441, and ISIS 437442 were further tested for their effect on human huntingtin mRNA in vitro. Cultured GM04281 fibroblasts were tested in a similar procedure as described above. The results are presented in Table 15.2 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.2 expressed in μM.

TABLE 15.2

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 26 | 47 | 58 | 79 | 91 | 95 | 0.65 |
| 388241 | 30 | 52 | 60 | 81 | 94 | 97 | 0.55 |
| 437441 | 25 | 37 | 56 | 69 | 86 | 47 | 0.81 |
| 437442 | 39 | 43 | 47 | 70 | 85 | 50 | 0.59 |

ISIS 387916, ISIS 388241, ISIS 437175, and ISIS 437527 were further tested for their effect on human huntingtin mRNA in vitro. Cultured GM04281 fibroblasts were tested in a similar procedure as described above. The results are presented in Table 15.3 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15.3 expressed in μM.

TABLE 15.3

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | $IC_{50}$ |
|---|---|---|---|---|---|---|---|
| 387916 | 40 | 45 | 47 | 76 | 92 | 96 | 0.50 |
| 388241 | 40 | 37 | 50 | 90 | 96 | 97 | 0.80 |
| 437175 | 48 | 55 | 55 | 63 | 80 | 93 | 0.37 |
| 437527 | 33 | 52 | 61 | 80 | 86 | 95 | 0.52 |

B. A549 Cells

Some of the antisense oligonucleotides described in Example 1 were tested for their effect on human huntingtin mRNA in vitro. Cultured A549 cells at a density of 4,000 cells per well were transfected using lipofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 16 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 16 expressed in nM.

TABLE 16

Dose dependent reduction of huntingtin mRNA in A549 cells

| ISIS No. | 7.4074 nM | 22.222 nM | 66.667 nM | 200.00 nM | $IC_{50}$ (nM) |
|---|---|---|---|---|---|
| 387916 | 12 | 37 | 76 | 92 | 33 |
| 419640 | 21 | 45 | 73 | 93 | 27 |
| 419641 | 34 | 60 | 83 | 96 | 15 |
| 419642 | 30 | 58 | 85 | 95 | 16 |

ISIS 387916, ISIS 388241, and ISIS 437507 were further tested for their effect on human huntingtin mRNA in vitro. Cultured A549 cells at a density of 20,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 17 expressed as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 17 expressed in μM.

TABLE 17

| Dose dependent reduction of huntingtin mRNA in A549 cells | | | | | | | |
|---|---|---|---|---|---|---|---|
| ISIS No. | 250 nM | 500 nM | 1000 nM | 2000 nM | 4000 nM | 8000 nM | $IC_{50}$ (μM) |
| 387916 | 15 | 17 | 25 | 36 | 52 | 75 | 3.09 |
| 388241 | 12 | 22 | 38 | 58 | 77 | 91 | 1.43 |
| 437507 | 25 | 28 | 38 | 57 | 58 | 76 | 1.84 |

C. LLC-MK2 Cells

Some of the antisense oligonucleotides described in Example 1 and targeted to a human huntingtin nucleic acid were tested for their effect on rhesus monkey huntingtin mRNA in vitro. Cultured LLC-MK2 cells at a density of 25,000 cells per well were transfected using electroporation with 625 nM, 1250 nM, 2500 nM, 5000 nM, 10,000 nM, or 20,000 nM of antisense oligonucleotide. After a treatment period of approximately 16 hours, RNA was isolated from the cells and huntingtin mRNA levels were measured by quantitative real-time PCR. Human primer probe set RTS2686 (forward sequence GTCTGAGCCTCTCTCGGT-CAA, designated herein as SEQ ID NO: 40; reverse sequence AAGGGATGCTGGGCTCTGT, designated herein as SEQ ID NO: 41; probe sequence AGCAAAGCT-TGGTGTCTTGGCACTGTTAGTX, designated herein as SEQ ID NO: 42) was used to measure mRNA levels. Huntingtin mRNA levels were adjusted according to total RNA content, as measured by RIBOGREEN®. Results are presented in Table 18 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 18 expressed in μM.

TABLE 18

| Dose dependent reduction of huntingtin mRNA in LLC-MK2 cells | | | | | | | |
|---|---|---|---|---|---|---|---|
| ISIS No. | 625 nM | 1250 nM | 2500 nM | 5000 nM | 10000 nM | 20000 nM | $IC_{50}$ (μM) |
| 388241 | 21 | 12 | 35 | 46 | 46 | 94 | 4.1 |
| 444591 | 37 | 46 | 51 | 52 | 82 | 96 | 1.9 |
| 419641 | 32 | 52 | 69 | 87 | 94 | 97 | 1.2 |
| 444661 | 45 | 59 | 66 | 85 | 91 | 95 | 0.8 |
| 419642 | 6 | 3 | 56 | 81 | 91 | 98 | 2.9 |
| 436665 | 40 | 43 | 70 | 73 | 84 | 89 | 1.2 |
| 436671 | 31 | 51 | 68 | 82 | 90 | 97 | 1.2 |
| 436689 | 24 | 37 | 59 | 74 | 89 | 98 | 1.9 |
| 437507 | 21 | 15 | 11 | 33 | 55 | 92 | 6.4 |
| 443139 | 31 | 36 | 37 | 56 | 76 | 97 | 2.6 |

ISIS 387916, ISIS 388241, ISIS 436684, ISIS 437168, ISIS 437175, ISIS 437441, ISIS 437507, ISIS 437527, ISIS 444578, ISIS 444584, ISIS 444591, and ISIS 444607 were further tested for their effect on rhesus monkey huntingtin mRNA in vitro. Cultured LLC-MK2 cells were tested in a similar procedure as described above. The results are presented in Table 19 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 19 expressed in μM.

TABLE 19

| Dose dependent reduction of huntingtin mRNA in LLC-MK2 cells | | | | | | | |
|---|---|---|---|---|---|---|---|
| ISIS No. | 625.0 nM | 1250.0 nM | 2500.0 nM | 5000.0 nM | 10000.0 nM | 20000.0 nM | $IC_{50}$ |
| 387916 | 23 | 42 | 57 | 81 | 88 | 96 | 1.95 |
| 388241 | 6 | 12 | 37 | 43 | 62 | 84 | 5.32 |
| 437168 | 72 | 47 | 60 | 78 | 83 | 92 | 1.43 |
| 437175 | 27 | 48 | 36 | 56 | 68 | 78 | 3.58 |
| 437441 | 29 | 34 | 50 | 67 | 56 | 85 | 2.43 |
| 437507 | 18 | 29 | 18 | 33 | 45 | 66 | 6.12 |
| 437527 | 36 | 36 | 48 | 57 | 81 | 90 | 2.71 |
| 436684 | 0 | 12 | 24 | 29 | 36 | 49 | n.d. |
| 444578 | 34 | 40 | 65 | 74 | 82 | 87 | 1.70 |
| 444584 | 28 | 38 | 68 | 75 | 90 | 94 | 1.69 |
| 444591 | 25 | 45 | 55 | 74 | 85 | 94 | 1.84 |
| 444607 | 41 | 54 | 76 | 87 | 92 | 94 | 0.96 |

n.d. = $IC_{50}$ could not be measured for that compound

ISIS 387916, ISIS 388241, ISIS 444608, ISIS 444615, ISIS 444618, ISIS 444627, ISIS 444652, ISIS 444658, ISIS 444659, ISIS 444660, and ISIS 444661 were further tested for their effect on rhesus monkey huntingtin mRNA in vitro. Cultured LLC-MK2 cells were tested in a similar procedure as described above. The results are presented in Table 20 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 20 expressed in μM.

TABLE 20

| Dose dependent reduction of huntingtin mRNA in LLC-MK2 cells | | | | | | | |
|---|---|---|---|---|---|---|---|
| ISIS No | 625.0 nM | 1250.0 nM | 2500.0 nM | 5000.0 nM | 10000.0 nM | 20000.0 nM | IC50 |
| 387916 | 35 | 44 | 68 | 74 | 90 | 96 | 1.35 |
| 388241 | 23 | 37 | 54 | 56 | 68 | 89 | 2.64 |
| 444608 | 43 | 50 | 64 | 83 | 90 | 95 | 1.07 |
| 444615 | 29 | 45 | 55 | 76 | 90 | 97 | 1.67 |
| 444618 | 30 | 34 | 57 | 73 | 89 | 95 | 1.66 |
| 444627 | 35 | 56 | 76 | 90 | 97 | 98 | 1.00 |
| 444652 | 32 | 55 | 66 | 55 | 92 | 98 | 1.23 |
| 444658 | 50 | 62 | 80 | 90 | 95 | 97 | 0.55 |
| 444659 | 31 | 56 | 68 | 86 | 95 | 97 | 1.17 |
| 444660 | 38 | 49 | 62 | 86 | 89 | 96 | 1.26 |
| 444661 | 41 | 50 | 75 | 68 | 95 | 97 | 0.95 |

ISIS 387916, ISIS 419627, ISIS 419628, ISIS 419629, ISIS 419630, ISIS 419636, ISIS 419637, ISIS 419640, ISIS 419641, and ISIS 419642 were further tested for their effect on rhesus monkey huntingtin mRNA in vitro. Cultured LLC-MK2 cells at a density of 3,000 cells per well were transfected using lipofectin transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 21 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 21 expressed in nM.

TABLE 21

| Dose dependent reduction of huntingtin mRNA in LLC-MK2 cells | | | | | | | |
|---|---|---|---|---|---|---|---|
| ISIS No. | 6.25 nM | 12.5 nM | 25.0 nM | 50.0 nM | 100.0 nM | 200.0 nM | $IC_{50}$ |
| 387916 | 1 | 37 | 37 | 53 | 84 | 90 | 35 |
| 419627 | 0 | 9 | 18 | 45 | 58 | 72 | 75 |
| 419628 | 9 | 30 | 49 | 63 | 73 | 77 | 31 |
| 419629 | 9 | 16 | 40 | 56 | 80 | 85 | 36 |
| 419630 | 17 | 8 | 43 | 58 | 71 | 81 | 40 |
| 419636 | 23 | 25 | 38 | 55 | 72 | 78 | 37 |
| 419637 | 10 | 35 | 31 | 62 | 78 | 76 | 33 |
| 419640 | 3 | 28 | 39 | 59 | 74 | 87 | 36 |
| 419641 | 11 | 34 | 51 | 65 | 85 | 87 | 26 |
| 419642 | 25 | 30 | 49 | 65 | 85 | 88 | 24 |

ISIS 387916, ISIS 419641, and ISIS 436689 were further tested for their effect on rhesus monkey huntingtin mRNA in vitro. Cultured LLC-MK2 cells at a density of 3,000 cells per well were transfected using LipofectAMINE2000 transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 22 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 22 expressed in nM.

TABLE 22

| Dose dependent reduction of huntingtin mRNA in LLC-MK2 cells | | | | | | | |
|---|---|---|---|---|---|---|---|
| ISIS No | 6.25 nM | 12.5 nM | 25 nM | 50 nM | 100 nM | 200 nM | $IC_{50}$ (nM) |
| 387916 | 0 | 50 | 31 | 68 | 83 | 90 | 47 |
| 419641 | 28 | 23 | 28 | 51 | 65 | 81 | 74 |
| 436689 | 16 | 30 | 29 | 48 | 67 | 83 | 69 |

ISIS 387916, ISIS 388241, ISIS 436665, ISIS 436671, and ISIS 436689 were further tested for their effect on rhesus monkey huntingtin mRNA in vitro. Cultured LLC-MK2 cells at a density of 3,000 cells per well were transfected using lipofectin transfection reagent with 4.6875 nM, 9.375 nM, 18.75 nM, 37.5 nM, 75 nM, or 150 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 23 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 23 expressed in nM.

TABLE 23

| Dose dependent reduction of huntingtin mRNA in LLC-MK2 cells | | | | | | | |
|---|---|---|---|---|---|---|---|
| ISIS No. | 4.6875 nM | 9.375 nM | 18.75 nM | 37.5 nM | 75.0 nM | 150.0 nM | $IC_{50}$ (nM) |
| 387916 | 7 | 6 | 38 | 59 | 82 | 91 | 32 |
| 388241 | 0 | 0 | 5 | 35 | 62 | 81 | 60 |
| 436665 | 7 | 0 | 36 | 59 | 64 | 69 | 37 |
| 436671 | 21 | 7 | 35 | 59 | 80 | 86 | 31 |
| 436689 | 38 | 45 | 45 | 59 | 76 | 86 | 15 |

D. BACHD Transgenic Mouse Hepatocyes

Some of the antisense oligonucleotides described in Example 1 and targeted to a human huntingtin nucleic acid were tested for their effect on human huntingtin mRNA in vitro. Cultured BACHD mouse hepatocytes at a density of 10,000 cells per well were transfected using cytofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 24 as percent inhibition of huntingtin mRNA, relative to untreated control cells, and demonstrate antisense oligonucleotide-mediated dose-dependent reduction of huntingtin mRNA levels. The data presented is the average of two experiments. The $IC_{50}$ of each antisense oligonucleotide is also presented in Table 24 expressed in nM.

TABLE 24

| Dose dependent reduction of huntingtin mRNA in BACHD transgenic murine hepatocytes | | | | | |
|---|---|---|---|---|---|
| ISIS No. | 7.4074 nM | 22.222 nM | 66.667 nM | 200.00 nM | $IC_{50}$ (nM) |
| 387916 | 8 | 19 | 58 | 89 | 40 |
| 419640 | 15 | 30 | 64 | 93 | 33 |
| 419641 | 20 | 35 | 73 | 97 | 31 |
| 419642 | 3 | 29 | 70 | 96 | 43 |

ISIS 387916, ISIS 388241, and ISIS 419641 were further tested for their effect on human huntingtin mRNA in vitro. Cultured BACHD mouse hepatocytes at a density of 10,000 cells per well were transfected using cytofectin transfection reagent with 12.5 nM, 25 nM, 50 nM, 100 nM or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 25 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 25 expressed in nM.

TABLE 25

| Dose dependent reduction of huntingtin mRNA in BACHD transgenic murine hepatocytes | | | | | | |
|---|---|---|---|---|---|---|
| ISIS No. | 12.5 nM | 25 nM | 50 Nm | 100 nM | 200 nM | $IC_{50}$ (nM) |
| 387916 | 0 | 37 | 51 | 78 | 91 | 51 |
| 388241 | 0 | 10 | 45 | 70 | 92 | 68 |
| 419641 | 17 | 38 | 70 | 88 | 96 | 34 |

ISIS 387916, ISIS 388241, ISIS 419641, ISIS 436665, ISIS 436671, and ISIS 436689 were further tested for their effect on human huntingtin mRNA in vitro. Cultured BACHD mouse hepatocytes were tested in an identical manner as described above. The results are presented in Table 26 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 26 expressed in nM.

TABLE 26

| Dose dependent reduction of huntingtin mRNA in BACHD transgenic murine hepatocytes | | | | | | |
|---|---|---|---|---|---|---|
| ISIS No. | 12.5 nM | 25 nM | 50 nM | 100 nM | 200 nM | $IC_{50}$ (nM) |
| 387916 | 19 | 48 | 64 | 86 | 93 | 32 |
| 388241 | 20 | 34 | 54 | 81 | 93 | 38 |
| 419641 | 38 | 54 | 70 | 85 | 95 | 21 |
| 436665 | 32 | 40 | 67 | 84 | 93 | 29 |
| 436671 | 32 | 42 | 58 | 78 | 91 | 32 |
| 436689 | 35 | 44 | 70 | 88 | 96 | 25 |

ISIS 387916, ISIS 419640, ISIS 419641, and ISIS 419642 were further tested for their effect on mouse huntingtin mRNA in vitro. Cultured BACHD mouse hepatocytes at a density of 20,000 cells per well were transfected using cytofectin transfection reagent with 6.667 nM, 20 nM, 60 nM, or 180 nM of antisense oligonucleotide. After a treatment period of approximately 16 hours, RNA was isolated from the cells and huntingtin mRNA levels were measured by quantitative real-time PCR. Murine primer probe set RTS2633 (forward sequence CAGAGCTGGTCAACCG-TATCC, designated herein as SEQ ID NO: 43; reverse sequence GGCTTAAACAGGGAGCCAAAA, designated herein as SEQ ID NO: 44; probe sequence ACTTCATGAT-GAGCTCGGAGTTCAACX, designated herein as SEQ ID NO: 45) was used to measure mRNA levels. Huntingtin mRNA levels were adjusted according to total RNA content, as measured by RIBOGREEN®. Results are presented in Table 27 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 27 expressed in nM.

TABLE 27

| Dose dependent reduction of huntingtin mRNA in BACHD transgenic murine hepatocytes | | | | | |
|---|---|---|---|---|---|
| ISIS No. | 6.667 nM | 20 nM | 60 nM | 180 nM | $IC_{50}$ (nM) |
| 387916 | 15 | 15 | 68 | 94 | 37 |
| 419640 | 4 | 39 | 73 | 94 | 32 |
| 419641 | 16 | 45 | 81 | 96 | 24 |
| 419642 | 23 | 39 | 75 | 93 | 25 |

Example 3

Systemic Administration of Antisense Oligonucleotides Against Huntingtin mRNA in BACHD Mice Of the about seventeen hundred newly designed antisense compounds, sixty six compounds were selected based on in vitro potency compared to ISIS 387916 for testing in systemic tolerability screens.

BACHD mice were treated with ISIS oligonucleotides and evaluated for changes in the levels of various metabolic markers as well as inhibition of huntingtin mRNA in the liver. Antisense oligonucleotides which caused adverse changes in body weight, organ weight or in the levels of metabolic markers were deemed unsuitable for utilization in further studies.

Study 1.

Treatment

Nineteen groups of four BACHD mice each were injected intraperitoneally with 12.5 mg/kg of ISIS 387916, ISIS 388241, ISIS 419629, ISIS 419637, ISIS 436684, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 28 and 29 and were calculated as percent inhibition of human and murine huntingtin expression levels respectively, relative to the PBS control. All the antisense oligonucleotides effect significant inhibition of human huntingtin mRNA levels. ISIS 388241 has more than three mismatches with the murine huntingtin mRNA (SEQ ID NO: 3) and therefore did not show significant inhibition of murine mRNA levels compared to the control.

TABLE 28

| Percent inhibition of human huntingtin mRNA in BACHD mice | |
|---|---|
| ISIS No. | % inhibition |
| 387916 | 82 |
| 388241 | 52 |
| 419629 | 80 |
| 419637 | 83 |

TABLE 28-continued

Percent inhibition of human huntingtin mRNA in BACHD mice

| ISIS No. | % inhibition |
|---|---|
| 436684 | 55 |
| 444578 | 70 |
| 444584 | 62 |
| 444591 | 54 |
| 444607 | 76 |
| 444608 | 61 |
| 444615 | 89 |
| 444618 | 91 |
| 444627 | 92 |
| 444652 | 79 |
| 444658 | 62 |
| 444659 | 74 |
| 444660 | 66 |
| 444661 | 72 |
| 444663 | 77 |

TABLE 29

Percent inhibition of murine huntingtin mRNA in BACHD mice

| ISIS No. | % inhibition |
|---|---|
| 387916 | 77 |
| 419629 | 75 |
| 419637 | 87 |
| 436684 | 32 |
| 444578 | 64 |
| 444584 | 20 |
| 444591 | 32 |
| 444607 | 76 |
| 444608 | 66 |
| 444615 | 60 |
| 444618 | 88 |
| 444627 | 58 |
| 444652 | 66 |
| 444658 | 53 |
| 444659 | 62 |
| 444660 | 47 |
| 444661 | 67 |
| 444663 | 60 |

Organ Weight Measurements

Liver, spleen and kidney weights were measured at the end of the study, and are presented in Table 30 as a percent of the saline control normalized to body weight.

TABLE 30

Percent change in organ weight of BACHD mice after antisense oligonucleotide treatment

| ISIS No. | Liver | Spleen | Kidney |
|---|---|---|---|
| 387916 | −5 | −13 | +6 |
| 388241 | −1 | +14 | −5 |
| 419629 | +5 | +13 | −12 |
| 419637 | −6 | −17 | −25 |
| 436684 | −2 | −3 | +6 |
| 444578 | +11 | +18 | +1 |
| 444584 | +8 | +54 | +1 |
| 444591 | +4 | −4 | −3 |
| 444607 | +3 | +22 | −8 |
| 444608 | +6 | +18 | −3 |
| 444615 | +6 | +1 | +3 |
| 444618 | +11 | +0 | −2 |
| 444627 | +3 | −14 | +14 |
| 444652 | −11 | −4 | −18 |
| 444658 | −1 | 0 | −16 |

TABLE 30-continued

Percent change in organ weight of BACHD mice after antisense oligonucleotide treatment

| ISIS No. | Liver | Spleen | Kidney |
|---|---|---|---|
| 444659 | +1 | +15 | −2 |
| 444660 | −5 | +4 | −6 |
| 444661 | −1 | +7 | −1 |
| 444663 | +7 | +10 | +8 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 31.

TABLE 31

Effect of antisense oligonucleotide treatment on markers of liver function

| | ALT | AST |
|---|---|---|
| PBS | 40 | 69 |
| 387916 | 69 | 84 |
| 388241 | 42 | 76 |
| 419629 | 51 | 71 |
| 419637 | 59 | 86 |
| 436684 | 60 | 87 |
| 444578 | 62 | 93 |
| 444584 | 48 | 76 |
| 444591 | 39 | 53 |
| 444607 | 51 | 111 |
| 444608 | 48 | 75 |
| 444615 | 74 | 95 |
| 444618 | 687 | 908 |
| 444627 | 105 | 127 |
| 444652 | 54 | 64 |
| 444658 | 46 | 59 |
| 444659 | 90 | 138 |
| 444660 | 34 | 64 |
| 444661 | 49 | 99 |
| 444663 | 90 | 164 |

Study 2

Treatment

Fourteen groups of four BACHD mice each were injected intraperitoneally with 12.5 mg/kg or 50 mg/kg of ISIS 419581, ISIS 419602, ISIS 419628, ISIS 419629, ISIS 419640, ISIS 419641, or ISIS 419642 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 32 and 33 and were calculated as percent inhibition of human and murine huntingtin expression levels respectively, relative to the PBS control.

TABLE 32

| Percent inhibition of human huntingtin mRNA in BACHD mice | | |
|---|---|---|
| ISIS No. | Dose (mg/kg) | % inhibition |
| 387916 | 12.5 | 71 |
| 419581 | 12.5 | 54 |
| | 50 | 68 |
| 419602 | 12.5 | 72 |
| | 50 | 77 |
| 419628 | 12.5 | 65 |
| | 50 | 76 |
| 419629 | 12.5 | 87 |
| | 50 | 93 |
| 419640 | 12.5 | 69 |
| | 50 | 79 |
| 419641 | 12.5 | 61 |
| | 50 | 80 |
| 419642 | 12.5 | 76 |
| | 50 | 83 |

TABLE 33

| Percent inhibition of murine huntingtin mRNA in BACHD mice | | |
|---|---|---|
| ISIS No. | Dose (mg/kg) | % inhibition |
| 387916 | 12.5 | 70 |
| 419581 | 12.5 | 42 |
| | 50 | 86 |
| 419602 | 12.5 | 77 |
| | 50 | 85 |
| 419628 | 12.5 | 67 |
| | 50 | 86 |
| 419629 | 12.5 | 90 |
| | 50 | 93 |
| 419640 | 12.5 | 63 |
| | 50 | 84 |
| 419641 | 12.5 | 52 |
| | 50 | 81 |
| 419642 | 12.5 | 56 |
| | 50 | 83 |

Organ Weight Measurements

Liver, spleen and kidney weights were measured at the end of the study, and are presented in Table 34 as a percent of the saline control normalized to body weight.

TABLE 34

| Percent change in organ weight of BACHD mice after antisense oligonucleotide treatment | | | | |
|---|---|---|---|---|
| ISIS No. | Dose (mg/kg) | Liver | Spleen | Kidney |
| 387916 | 12.5 | −9 | 3 | −4 |
| 419581 | 12.5 | −2 | −6 | −1 |
| | 50 | 14 | −1 | −11 |
| 419602 | 12.5 | 10 | 1 | −2 |
| | 50 | 28 | 9 | −3 |
| 419628 | 12.5 | −2 | −7 | −2 |
| | 50 | −3 | 7 | −9 |
| 419629 | 12.5 | −7 | −5 | −10 |
| | 50 | 16 | 0 | −8 |
| 419640 | 12.5 | −5 | −2 | −8 |
| | 50 | 1 | −20 | −4 |
| 419641 | 12.5 | −7 | −10 | −11 |
| | 50 | −2 | −13 | −9 |
| 419642 | 12.5 | −11 | −21 | −19 |
| | 50 | −1 | −8 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/Land the results are presented in Table 35.

TABLE 35

| Effect of antisense oligonucleotide treatment on markers of liver function | | | |
|---|---|---|---|
| | Dose (mg/kg) | ALT | AST |
| PBS | | 44 | 80 |
| 387916 | 12.5 | 44 | 75 |
| 419581 | 12.5 | 56 | 101 |
| | 50 | 390 | 281 |
| 419602 | 12.5 | 86 | 108 |
| | 50 | 240 | 229 |
| 419628 | 12.5 | 52 | 110 |
| | 50 | 51 | 73 |
| 419629 | 12.5 | 104 | 118 |
| | 50 | 1262 | 1150 |
| 419640 | 12.5 | 36 | 65 |
| | 50 | 38 | 55 |
| 419641 | 12.5 | 56 | 103 |
| | 50 | 57 | 172 |
| 419642 | 12.5 | 40 | 64 |
| | 50 | 47 | 101 |

Study 3

Treatment

Eighteen groups of four BACHD mice each were injected intraperitoneally with 12.5 mg/kg or 50 mg/kg of ISIS 388250, ISIS 388251, ISIS 388263, ISIS 388264, ISIS 419641, ISIS 436645, ISIS 436649, ISIS 436668, or ISIS 436689 twice a week for 2 weeks. A group of four BACHD mice was injected intraperitoneally with 12.5 mg/kg of ISIS 388241 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 36 and 37 and were calculated as percent inhibition of human and murine huntingtin expression levels respectively, relative to the PBS control. All the antisense oligonucleotides effect significant inhibition of human huntingtin mRNA levels. ISIS 388241, ISIS 388250, ISIS 388251, ISIS 388263, ISIS 388264, and ISIS 436645 have more than three mismatches with the murine huntingtin mRNA (SEQ ID NO: 3) and therefore did not show significant inhibition of murine mRNA levels compared to the control. ISIS 436649 and ISIS 436689 have three mismatches with the murine huntingtin mRNA (SEQ ID NO: 3) and therefore did not show significant inhibition of murine mRNA levels compared to the control.

TABLE 36

| Percent inhibition of human huntingtin mRNA in BACHD mice | | |
|---|---|---|
| ISIS No. | Dose (mg/kg) | % inhibition |
| 388241 | 12.5 | 32 |
| 388250 | 12.5 | 21 |
| | 50 | 45 |

TABLE 36-continued

| Percent inhibition of human huntingtin mRNA in BACHD mice | | |
|---|---|---|
| ISIS No. | Dose (mg/kg) | % inhibition |
| 388251 | 12.5 | 30 |
| | 50 | 34 |
| 388263 | 12.5 | 29 |
| | 50 | 35 |
| 388264 | 12.5 | 35 |
| | 50 | 42 |
| 419641 | 12.5 | 71 |
| | 50 | 73 |
| 436645 | 12.5 | 43 |
| | 50 | 48 |
| 436649 | 12.5 | 40 |
| | 50 | 38 |
| 436668 | 12.5 | 45 |
| | 50 | 69 |
| 436689 | 12.5 | 62 |
| | 50 | 78 |

TABLE 37

| Percent inhibition of murine huntingtin mRNA in BACHD mice | | |
|---|---|---|
| ISIS No. | Dose (mg/kg) | % inhibition |
| 419641 | 12.5 | 68 |
| | 50 | 77 |
| 436668 | 12.5 | 41 |
| | 50 | 62 |

Organ Weight Measurements

Liver, spleen and kidney weights were measured at the end of the study, and are presented in Table 38 as a percent of the saline control normalized to body weight. Mice treated with ISIS 388263 and ISIS 436645 suffered increases in liver weight at the 50 mg/kg dose compared to the PBS control.

TABLE 38

| Percent change in organ weight of BACHD mice after antisense oligonucleotide treatment | | | | |
|---|---|---|---|---|
| ISIS No. | Dose (mg/kg) | Liver | Spleen | Kidney |
| 388241 | 12.5 | 1 | 6 | 9 |
| 388250 | 12.5 | 2 | 1 | −2 |
| | 50 | 1 | 30 | 3 |
| 388251 | 12.5 | 4 | −8 | 1 |
| | 50 | 19 | 19 | 2 |
| 388263 | 12.5 | 4 | 8 | 9 |
| | 50 | 23 | 52 | 1 |
| 388264 | 12.5 | 2 | −2 | 3 |
| | 50 | 12 | 9 | 6 |
| 419641 | 12.5 | −1 | −9 | 3 |
| | 50 | 2 | −4 | 3 |
| 436645 | 12.5 | 8 | 6 | 5 |
| | 50 | 26 | 25 | 9 |
| 436649 | 12.5 | 1 | 0 | 6 |
| | 50 | 0 | 1 | 3 |
| 436668 | 12.5 | 1 | 5 | 10 |
| | 50 | −2 | 3 | 11 |
| 436689 | 12.5 | −3 | −5 | 4 |
| | 50 | 6 | 11 | 5 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 39.

TABLE 39

| Effect of antisense oligonucleotide treatment on markers of liver function | | | |
|---|---|---|---|
| | Dose (mg/kg) | ALT | AST |
| PBS | | 43 | 76 |
| 388241 | 12.5 | 43 | 88 |
| 388250 | 12.5 | 37 | 55 |
| | 50 | 44 | 89 |
| 388251 | 12.5 | 42 | 98 |
| | 50 | 67 | 91 |
| 388263 | 12.5 | 51 | 90 |
| | 50 | 55 | 93 |
| 388264 | 12.5 | 31 | 59 |
| | 50 | 65 | 90 |
| 419641 | 12.5 | 39 | 70 |
| | 50 | 42 | 83 |
| 436645 | 12.5 | 43 | 82 |
| | 50 | 179 | 143 |
| 436649 | 12.5 | 35 | 47 |
| | 50 | 38 | 76 |
| 436668 | 12.5 | 36 | 73 |
| | 50 | 28 | 57 |
| 436689 | 12.5 | 31 | 52 |
| | 50 | 49 | 164 |

Study 4

Treatment

Eighteen groups of four BACHD mice each were injected intraperitoneally with 12.5 mg/kg or 50 mg/kg of ISIS 388241, ISIS 437123, ISIS 437132, ISIS 437140, ISIS 437442, ISIS 437446, ISIS 437477, ISIS 437478, or ISIS 437490 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 40 and 41 and were calculated as percent inhibition of human and murine huntingtin expression levels respectively, relative to the PBS control. ISIS 388241 and ISIS 437490 have more than three mismatches with the murine huntingtin mRNA (SEQ ID NO: 3) and therefore did not show significant inhibition of murine mRNA levels compared to the control. ISIS 437132 has three mismatches with the murine huntingtin mRNA (SEQ ID NO: 3) and therefore did not show significant inhibition of murine mRNA levels compared to the control. ISIS 437123 and ISIS 437140 have two mismatches with the murine huntingtin mRNA (SEQ ID NO: 3) and do not show significant inhibition of murine mRNA levels compared to the control.

TABLE 40

| Percent inhibition of human huntingtin mRNA in BACHD mice | | |
|---|---|---|
| ISIS No. | Dose (mg/kg) | % inhibition |
| 387916 | 12.5 | 51 |
| 388241 | 12.5 | 47 |
| | 50 | 67 |
| 437123 | 12.5 | 0 |
| | 50 | 21 |
| 437132 | 12.5 | 31 |
| | 50 | 33 |
| 437140 | 12.5 | 7 |
| | 50 | 32 |
| 437442 | 12.5 | 42 |
| | 50 | 85 |
| 437446 | 12.5 | 39 |
| | 50 | 70 |
| 437477 | 12.5 | 52 |
| | 50 | 75 |
| 437478 | 12.5 | 54 |
| | 50 | 78 |
| 437490 | 12.5 | 42 |
| | 50 | 44 |

TABLE 41

| Percent inhibition of murine huntingtin mRNA in BACHD mice | | |
|---|---|---|
| ISIS No. | Dose (mg/kg) | % inhibition |
| 387916 | 12.5 | 48 |
| 437442 | 12.5 | 27 |
| | 50 | 76 |
| 437446 | 12.5 | 38 |
| | 50 | 71 |
| 437477 | 12.5 | 63 |
| | 50 | 87 |
| 437478 | 12.5 | 60 |
| | 50 | 89 |

Organ Weight Measurements

Liver, spleen and kidney weights were measured at the end of the study, and are presented in Table 42 as a percent of the saline control normalized to body weight.

TABLE 42

| Percent change in organ weight of BACHD mice after antisense oligonucleotide treatment | | | | |
|---|---|---|---|---|
| ISIS No. | Dose (mg/kg) | Liver | Spleen | Kidney |
| 387916 | 12.5 | 1 | 6 | 12 |
| 388241 | 12.5 | −3 | 16 | −2 |
| | 50 | −6 | 10 | 0 |
| 437123 | 12.5 | −4 | 0 | 4 |
| | 50 | 4 | 0 | −4 |
| 437132 | 12.5 | −2 | −3 | −5 |
| | 50 | 2 | −6 | −2 |
| 437140 | 12.5 | −4 | 11 | −3 |
| | 50 | 4 | 5 | −5 |
| 437442 | 12.5 | −10 | 9 | 3 |
| | 50 | −3 | −20 | −10 |
| 437446 | 12.5 | −6 | 7 | 2 |
| | 50 | −4 | 1 | −1 |
| 437477 | 12.5 | 1 | −2 | 0 |
| | 50 | 25 | −9 | −6 |
| 437478 | 12.5 | −7 | −4 | −9 |
| | 50 | 22 | 4 | 3 |
| 437490 | 12.5 | −5 | 0 | −5 |
| | 50 | −7 | 3 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 43.

TABLE 43

| Effect of antisense oligonucleotide treatment on markers of liver function | | | |
|---|---|---|---|
| | Dose (mg/kg) | ALT | AST |
| PBS | | 32 | 58 |
| 387916 | 12.5 | 40 | 122 |
| 388241 | 12.5 | 39 | 93 |
| | 50 | 28 | 62 |
| 437123 | 12.5 | 38 | 88 |
| | 50 | 34 | 66 |
| 437132 | 12.5 | 34 | 52 |
| | 50 | 30 | 52 |
| 437140 | 12.5 | 30 | 62 |
| | 50 | 40 | 63 |
| 437442 | 12.5 | 40 | 106 |
| | 50 | 63 | 119 |
| 437446 | 12.5 | 35 | 119 |
| | 50 | 35 | 89 |
| 437477 | 12.5 | 39 | 68 |
| | 50 | 52 | 162 |
| 437478 | 12.5 | 37 | 53 |
| | 50 | 55 | 71 |
| 437490 | 12.5 | 48 | 71 |
| | 50 | 34 | 59 |

Study 5

Treatment

Eleven groups of four BACHD mice each were injected intraperitoneally with 12.5 mg/kg of ISIS 388241, ISIS 419640, ISIS 419641, ISIS 419642, ISIS 436665, ISIS 436671, ISIS 436689, ISIS 437507, ISIS 443139, ISIS 444591, or ISIS 444661 twice a week for 2 weeks. A control group of four mice was injected intraperitoneally with phosphate buffered saline (PBS) twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 44 and 45 and were calculated as percent inhibition of human and murine huntingtin expression levels respectively, relative to the PBS control. All the antisense oligonucleotides effect significant inhibition of human huntingtin mRNA levels. ISIS 388241, ISIS 437507, and ISIS 443139 have more than three mismatches with the murine huntingtin mRNA (SEQ ID NO: 3) and therefore do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 44

| Percent inhibition of human huntingtin mRNA in BACHD mice | |
|---|---|
| ISIS No. | % inhibition |
| 388241 | 53 |
| 419640 | 34 |
| 419641 | 63 |
| 419642 | 55 |
| 436665 | 63 |
| 436671 | 66 |
| 436689 | 57 |
| 437507 | 54 |
| 443139 | 39 |
| 444591 | 48 |
| 444661 | 50 |

TABLE 45

| Percent inhibition of murine huntingtin mRNA in BACHD mice | |
|---|---|
| ISIS No. | % inhibition |
| 419640 | 24 |
| 419641 | 51 |
| 419642 | 34 |
| 436665 | 49 |
| 436671 | 63 |
| 444591 | 41 |
| 444661 | 46 |

Body Weight and Organ Weight Measurements

The body weights of the mice were measured at the onset of the study and subsequently twice a week. The body weights of the mice are presented in Table 46 and are expressed as a percent change over the weights taken at the start of the study. The results indicate that treatment with these oligonucleotides did not cause any adverse change in body weight of the mice throughout the study.

TABLE 46

| Percent change in body weight of BACHD mice after antisense oligonucleotide treatment | | | | |
|---|---|---|---|---|
| | day 4 | day 7 | day 10 | day 12 |
| PBS | −3 | 0 | +2 | +1 |
| ISIS 388241 | −2 | −1 | −1 | +1 |
| ISIS 419640 | +1 | 0 | +3 | +4 |
| ISIS 419641 | +1 | +1 | +2 | 0 |
| ISIS 419642 | −3 | −2 | +1 | −5 |
| ISIS 436665 | +1 | +4 | +5 | +1 |
| ISIS 436671 | +1 | +2 | +5 | +4 |
| ISIS 436689 | +1 | +3 | 0 | −1 |
| ISIS 437507 | −1 | −2 | +2 | −2 |
| ISIS 443139 | −2 | +6 | +4 | +1 |
| ISIS 444591 | −1 | +1 | +2 | 0 |
| ISIS 444661 | +1 | +3 | +2 | 0 |

Liver, spleen and kidney weights were measured at the end of the study, and are presented in Table 47 as a percent of the saline control normalized to body weight.

TABLE 47

| Percent change in organ weight of BACHD mice after antisense oligonucleotide treatment | | | |
|---|---|---|---|
| ISIS No. | Liver | Spleen | Kidney |
| 388241 | +2 | +13 | −7 |
| 419640 | −2 | +12 | −12 |

TABLE 47-continued

| Percent change in organ weight of BACHD mice after antisense oligonucleotide treatment | | | |
|---|---|---|---|
| ISIS No. | Liver | Spleen | Kidney |
| 419641 | +4 | +3 | −13 |
| 419642 | +5 | +19 | −8 |
| 436665 | −3 | +3 | −13 |
| 436671 | 0 | +1 | −18 |
| 436689 | −6 | −10 | −12 |
| 437507 | −5 | −5 | −14 |
| 443139 | −2 | −9 | −13 |
| 444591 | −2 | −10 | −12 |
| 444661 | 0 | −16 | −12 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L. Plasma levels of bilirubin and albumin were also measured using the same clinical chemistry analyzer and expressed in g/dL. The results are presented in Table 48.

TABLE 48

| Effect of antisense oligonucleotide treatment on markers of liver function | | | | |
|---|---|---|---|---|
| | ALT | AST | Bilirubin | Albumin |
| PBS | 42.5 | 86.5 | 0.2 | 3.1 |
| ISIS 388241 | 39.3 | 54.5 | 0.3 | 3.0 |
| ISIS 419640 | 36.8 | 85.8 | 0.2 | 2.9 |
| ISIS 419641 | 50.0 | 71.8 | 0.2 | 3.0 |
| ISIS 419642 | 42.8 | 77.0 | 0.1 | 3.0 |
| ISIS 436665 | 51.5 | 123.0 | 0.2 | 3.0 |
| ISIS 436671 | 52.0 | 71.0 | 0.1 | 3.0 |
| ISIS 436689 | 38.3 | 75.3 | 0.2 | 3.1 |
| ISIS 437507 | 37.0 | 77.5 | 0.1 | 3.0 |
| ISIS 443139 | 41.3 | 124.8 | 0.2 | 3.0 |
| ISIS 444591 | 46.5 | 61.3 | 0.2 | 3.0 |
| ISIS 444661 | 67.5 | 109.8 | 0.2 | 3.1 |

Measurement of Kidney Function

To evaluate the impact of ISIS oligonucleotides on the kidney function of mice described above, plasma concentrations of blood urea nitrogen (BUN) and creatinine were measured using an automated clinical chemistry analyzer (Hitachi Olympus AU400e, Melville, N.Y.). Results are presented in Table 49 expressed in mg/dL.

TABLE 49

| Effect of antisense oligonucleotide treatment on markers of kidney function | | |
|---|---|---|
| | BUN | Creatinine |
| PBS | 24.0 | 0.17 |
| ISIS 388241 | 22.6 | 0.17 |
| ISIS 419640 | 21.4 | 0.16 |
| ISIS 419641 | 19.9 | 0.16 |
| ISIS 419642 | 23.6 | 0.18 |
| ISIS 436665 | 20.2 | 0.17 |
| ISIS 436671 | 22.6 | 0.17 |
| ISIS 436689 | 19.2 | 0.18 |

TABLE 49-continued

| Effect of antisense oligonucleotide treatment on markers of kidney function | | |
|---|---|---|
| | BUN | Creatinine |
| ISIS 437507 | 19.9 | 0.16 |
| ISIS 443139 | 23.3 | 0.16 |
| ISIS 444591 | 23.5 | 0.18 |
| ISIS 444661 | 25.4 | 0.18 |

Measurement of Other Metabolic Parameters

To evaluate the impact of ISIS oligonucleotides on other metabolic functions in mice described above, plasma concentrations of glucose, cholesterol and triglycerides were measured using an automated clinical chemistry analyzer (Hitachi Olympus AU400e, Melville, N.Y.). Results are presented in Table 50 expressed in mg/dL and demonstrate that treatment with these oligonucleotides did not cause any adverse changes in the levels of these metabolic markers between the control and treatment groups.

TABLE 50

| Effect of antisense oligonucleotide treatment on metabolic markers | | | |
|---|---|---|---|
| | Glucose | Cholesterol | Triglycerides |
| PBS | 198 | 142 | 225 |
| ISIS 388241 | 197 | 133 | 185 |
| ISIS 419640 | 198 | 132 | 189 |
| ISIS 419641 | 188 | 140 | 219 |
| ISIS 419642 | 184 | 128 | 192 |
| ISIS 436665 | 199 | 134 | 152 |
| ISIS 436671 | 196 | 148 | 174 |
| ISIS 436689 | 194 | 132 | 174 |
| ISIS 437507 | 198 | 139 | 155 |
| ISIS 443139 | 178 | 122 | 239 |
| ISIS 444591 | 202 | 145 | 263 |
| ISIS 444661 | 180 | 140 | 247 |

Example 4

Bolus Administration of Antisense Oligonucleotides Against Huntingtin mRNA to the Striatum of BACHD Mice BACHD mice were treated with ISIS oligonucleotides via bolus administration to a defined mouse brain area, the striatum, for the purpose of screening the activity of the oligonucleotides in brain tissue against human and mouse huntingtin mRNA expression.

Treatment and Surgery

Groups of four BACHD mice each were administered with ISIS 388241, ISIS 419628, ISIS 419637, ISIS 419640, ISIS 419641, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661 or ISIS 444663 delivered as a single bolus injection at 3 μg, 10 μg or 25 μg concentrations into the striatum.

A control group of 4 BACHD mice were similarly treated with PBS. ISIS 388241 was administered in seven groups of 4 mice each and the results presented are the average of the data derived from the 28 mice. ISIS 419628 was administered in 2 groups of 4 BACHD mice each and the results presented are the average of the data derived from the 8 mice. Seven days after the bolus administration, the mice were euthanized using isoflurane and the organs were removed. The animals were decapitated and the brain was removed for dissection of the striatal tissue.

RNA Analysis

RNA was extracted from striatal tissue for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. The results for human huntingtin mRNA levels are presented in Table 51 and are expressed as percent inhibition compared to the PBS control group. All the antisense oligonucleotides effect dose-dependent inhibition of human huntingtin mRNA levels. The results for murine huntingtin mRNA levels are presented in Table 52 and are expressed as percent inhibition compared to the PBS control group.

The effective doses ($ED_{50}$) of each oligonucleotide for human huntingtin mRNA and mouse huntingtin mRNA were calculated by plotting the concentrations of oligonucleotides used versus the percent inhibition of huntingtin mRNA expression levels of either species and noting the concentrations at which 50% inhibition of huntingtin mRNA expression was achieved for each species compared to the corresponding controls. The $ED_{50}$ (μg) for each antisense oligonucleotide is also presented in Tables 51 and 52 for human and murine huntingtin mRNA respectively.

ISIS 388241, ISIS 436684, ISIS 436754, ISIS 437175, ISIS 437507, ISIS 443139, and ISIS 444584 are each mismatched by 8 base pairs or more with murine huntingtin mRNA (SEQ ID NO: 3) and therefore do not show significant inhibition of murine mRNA levels compared to the control. ISIS 437168 and ISIS 437441 have 2 mismatches each with the murine huntingtin mRNA (SEQ ID NO: 3) and do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 51

| Percent inhibition of human huntingtin mRNA levels in vivo and $ED_{50}$ of the antisense oligonucleotides | | | | |
|---|---|---|---|---|
| ISIS No. | 3 mg | 10 mg | 25 mg | $ED_{50}$ |
| 388241 | 33 | 55 | 68 | 7.4 |
| 419628 | 49 | 58 | 83 | 5.1 |
| 419637 | 40 | 62 | 79 | 6.1 |
| 419640 | 52 | 64 | 77 | 4.8 |
| 419641 | 71 | 77 | 89 | 2.2 |
| 419642 | 67 | 70 | 83 | 3.0 |
| 436665 | 52 | 71 | 60 | 5.8 |
| 436671 | 68 | 80 | 84 | 2.4 |
| 436684 | 2 | 18 | 37 | 36.9 |
| 436689 | 27 | 63 | 81 | 7.0 |
| 436754 | 31 | 54 | 61 | 10.5 |
| 437168 | 2 | 49 | 60 | 15.2 |
| 437175 | 0 | 53 | 64 | 12.9 |
| 437441 | 3 | 32 | 38 | 35.3 |
| 437442 | 38 | 50 | 56 | 11.9 |
| 437507 | 38 | 59 | 79 | 6.6 |
| 437527 | 37 | 47 | 59 | 11.9 |
| 443139 | 39 | 61 | 70 | 6.7 |
| 444578 | 51 | 66 | 75 | 4.6 |
| 444584 | 30 | 63 | 71 | 7.8 |
| 444591 | 60 | 54 | 70 | 5.6 |
| 444607 | 57 | 69 | 75 | 3.2 |
| 444608 | 67 | 68 | 82 | 3.1 |
| 444615 | 47 | 55 | 91 | 5.2 |

TABLE 51-continued

Percent inhibition of human huntingtin mRNA levels in vivo and $ED_{50}$ of the antisense oligonucleotides

| ISIS No. | 3 mg | 10 mg | 25 mg | $ED_{50}$ |
|---|---|---|---|---|
| 444618 | 57 | 64 | 83 | 4.0 |
| 444627 | 47 | 70 | 61 | 5.0 |
| 444652 | 36 | 62 | 66 | 7.8 |
| 444658 | 60 | 66 | 79 | 3.6 |
| 444659 | 61 | 67 | 84 | 3.4 |
| 444660 | 55 | 62 | 66 | 4.2 |
| 444661 | 48 | 57 | 70 | 6.4 |
| 444663 | 42 | 60 | 80 | 5.5 |

TABLE 52

Percent inhibition of murine huntingtin mRNA levels in vivo and $ED_{50}$ of the antisense oligonucleotides

| ISIS No. | 3 mg | 10 mg | 25 mg | $ED_{50}$ |
|---|---|---|---|---|
| 419628 | 50 | 55 | 83 | 5.1 |
| 419637 | 63 | 79 | 86 | 2.6 |
| 419640 | 51 | 60 | 86 | 4.9 |
| 419641 | 65 | 80 | 87 | 2.7 |
| 419642 | 69 | 73 | 88 | 2.5 |
| 436665 | 68 | 82 | 66 | 2.7 |
| 436671 | 75 | 87 | 90 | 2 |
| 437442 | 30 | 53 | 82 | 9 |
| 437527 | 67 | 73 | 90 | 2.7 |
| 444578 | 50 | 65 | 74 | 4.9 |
| 444591 | 69 | 69 | 81 | 2.8 |
| 444607 | 57 | 70 | 75 | 3.8 |
| 444608 | 70 | 72 | 90 | 2.5 |
| 444615 | 30 | 37 | 88 | 9.5 |
| 444618 | 66 | 71 | 90 | 2.8 |
| 444627 | 41 | 60 | 57 | 8.8 |
| 444652 | 47 | 62 | 66 | 4.7 |
| 444658 | 60 | 62 | 85 | 3.9 |
| 444659 | 54 | 62 | 85 | 4.2 |
| 444660 | 42 | 48 | 64 | 9.5 |
| 444661 | 49 | 57 | 74 | 5.9 |
| 444663 | 42 | 65 | 84 | 5.1 |

The ten compounds marked with an asterisk had an improved ED50 over ISIS 388241.

Example 5

Assay for Neurotoxic Effects of Bolus Administration of Antisense Oligonucleotides in the Striatal Tissue of Rats About 30 compounds were selected as having high tolerability and high potency. Compounds were then tested by CNS bolus injection in rat to further assess neurotoxicity.

Sprague-Dawley rats each were treated with ISIS oligonucleotides via bolus administration to a defined brain area, the striatum, for the purpose of screening for the induction of the microglial marker AIF1 as a measure of CNS toxicity.

Treatment and Surgery

Groups of four Sprague-Dawley rats were administered with ISIS 387916, ISIS 388241, ISIS 419627, ISIS 419628, ISIS 419629, ISIS 419630, ISIS 419636, ISIS 419637, ISIS 419640, ISIS 419641, ISIS 419642, ISIS 436665, ISIS 436668, ISIS 4196671, ISIS 436684, ISIS 436689, ISIS 436754, ISIS 443168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 delivered as a single bolus injection at 50 μg concentration into the striatum.

A control group of 4 rats were similarly treated with PBS. A group of 4 rats were similarly treated with ISIS 104838, an antisense oligonucleotide against TNF-α, as a negative control group. ISIS 387916 was administered in four groups of 4 rats each and the results presented are an average of the data derived from the 16 rats. ISIS 419628 was administered in two groups of 4 rats each and the results presented are the average of the data from the 8 rats. ISIS 419629, ISIS 444584 and ISIS 444618, which had toxic indicators in the systemic administration study (Example 3) were also tested in this study. Seven days after bolus administration, the rats were euthanized using isoflurane and the organs were removed. The animals were decapitated and the brain was removed for dissection of the striatal tissue.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219 (forward sequence AGGAGAAAAACAAAGAACACCAGAA, designated herein as SEQ ID NO: 46; reverse sequence CAATTAGGGCAACTCAGAAATAGCT, designated herein as SEQ ID NO: 47; probe sequence CCAACTGGTCCCCCAGCCAAGAX, designated herein as SEQ ID NO: 48). Results were calculated as the percentage of AIF1 expression over that of the PBS control and are presented in Table 53. ISIS 419629, ISIS 444584, and ISIS 444618, which had toxic indicators in the systemic administration study (in Example 3), also had toxic indicators in this study (greater than 300% above saline control). Later studies showed that ISIS 444584 is neurotolerable and exhibits negligible toxic indicators (see Example 16 and 17).

TABLE 53

Percent expression of AIF1 mRNA levels in vivo as a measure of neurotoxicity

| ISIS No. | % expression |
|---|---|
| 104838 | 111 |
| 387916 | 870 |
| 388241 | 236 |
| 419627 | 168 |
| 419628 | 497 |
| 419629 | 247 |
| 419630 | 227 |
| 419636 | 464 |
| 419637 | 275 |
| 419640 | 305 |
| 419641 | 206 |
| 419642 | 173 |
| 436665 | 217 |
| 436668 | 447 |
| 436671 | 239 |
| 436684 | 700 |
| 436689 | 149 |
| 436754 | 125 |
| 437168 | 130 |
| 437175 | 131 |
| 437441 | 158 |
| 437442 | 157 |
| 437507 | 133 |
| 437527 | 184 |
| 443139 | 143 |
| 444578 | 352 |
| 444584 | 317 |
| 444591 | 194 |
| 444607 | 362 |
| 444608 | 476 |
| 444615 | 645 |
| 444618 | 547 |

TABLE 53-continued

| Percent expression of AIF1 mRNA levels in vivo as a measure of neurotoxicity | |
|---|---|
| ISIS No. | % expression |
| 444627 | 377 |
| 444652 | 336 |
| 444658 | 364 |
| 444659 | 319 |
| 444660 | 411 |
| 444661 | 249 |
| 444663 | 448 |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343 (forward sequence CAGAGCTGGTGAACCGTATCC, designated herein as SEQ ID NO: 49; reverse sequence GGCTTAAGCAGGGAGCCAAAA, designated herein as SEQ ID NO: 50; probe sequence ACTTCATGATGAGCTCGGAGTTCAACX, designated herein as SEQ ID NO: 51). Results were calculated as the percentage reduction of huntingtin expression over that of the PBS control and are presented in Table 54. ISIS 388241, ISIS 436684, ISIS 436754, ISIS 437175, ISIS 437507, and ISIS 443139 are each mismatched by 6 base pairs or more with the rat gene sequence (SEQ ID NO: 5) and therefore do not show significant inhibition of rat mRNA levels compared to the control. ISIS 419640, ISIS 419641, ISIS 419642, ISIS 436665, ISIS 436668, ISIS 437442, ISIS 444615, and ISIS 444627 have 1 mismatch each with the rat gene sequence (SEQ ID NO: 5) and do not show significant inhibition of rat mRNA levels compared to the control. ISIS 437168 and ISIS 437441 have 2 mismatches each with the rat gene sequence (SEQ ID NO: 5) and do not show significant inhibition of rat mRNA levels compared to the control. ISIS 436689 and ISIS 444584 have 3 mismatches each with the rat gene sequence (SEQ ID NO: 5) and do not show significant inhibition of rat mRNA levels compared to the control.

TABLE 54

| Percent reduction of rat huntingtin mRNA levels in rats | |
|---|---|
| ISIS No. | % reduction |
| 387916 | 70 |
| 419627 | 67 |
| 419628 | 57 |
| 419629 | 85 |
| 419630 | 11 |
| 419636 | 53 |
| 419637 | 84 |
| 436671 | 77 |
| 437527 | 86 |
| 444578 | 72 |
| 444591 | 35 |
| 444607 | 57 |
| 444608 | 68 |
| 444618 | 56 |
| 444652 | 75 |
| 444658 | 61 |
| 444659 | 55 |
| 444660 | 63 |
| 444661 | 52 |
| 444663 | 59 |

Example 6

Intracerebroventricular Administration of Antisense Oligonucleotides Against Huntingtin mRNA-tolerability Study in BACHD Mice Selected compounds were compared with previously designed compound ISIS 388241 by ICV administration in BACHD mice.

Selected compounds plus the benchmark 388241 were selected based on in vitro and systemic potency and systemic tolerability as well as CNS potency and tolerability.

BACHD mice were treated with ISIS oligonucleotides via intracerebroventricular (ICV) administration to a defined mouse brain area, the right lateral ventricle, for the purpose of evaluating the tolerability of ICV dosing in mice.

Treatment and Surgery

Groups of five BACHD mice each were administered ISIS 388241, ISIS 437507, ISIS 443139, ISIS 419640, ISIS 419641, ISIS 419642, ISIS 444591, ISIS 436665, ISIS 436671, ISIS 444661, or ISIS 436689 at 150 μg/day delivered ICV with Alzet 2002 pumps at the rate of 12 μL/day for 2 weeks. A control group of 4 BACHD mice were similarly treated with PBS. The mice were surgically implanted with the pumps in the following manner: Mice were individually anaesthetized with 3% isoflurane for pump implantation. After two weeks, the mice were anesthetized again and the pump was surgically removed. The animals were then allowed to recover for two more weeks before being euthanized.

The body weights of the mice were taken weekly during the treatment and recovery periods. After 4 weeks, the mice were euthanized using isoflurane and decapitated. The brain was removed for tissue acquisition from the anterior and posterior sections.

RNA Analysis

RNA was extracted from the right hemisphere of the anterior cortex and the posterior cerebellar section of the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Results were calculated as percent inhibition of human and murine huntingtin mRNA expression compared to the control and are presented in Tables 56 and 57 respectively. All the antisense oligonucleotides effect significant inhibition of human huntingtin mRNA levels. ISIS 388241, ISIS 437507, and ISIS 443139 are each mismatched by 8 base pairs or more with the murine huntingtin mRNA (SEQ ID NO: 3) and therefore do not show significant inhibition of murine mRNA levels compared to the control. ISIS 444591 has 1 mismatch with the murine huntingtin mRNA (SEQ ID NO: 3) and does not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 56

| Percent reduction of human huntingtin mRNA levels in BACHD mice via ICV administration of antisense oligonucleotides | | | |
|---|---|---|---|
| ISIS No. | Number of mice | Anterior cortex | Posterior cortex |
| 388241 | 3 | 82 | 70 |
| 419640 | 1 | 60 | 46 |
| 419641 | 2 | 75 | 66 |

TABLE 56-continued

| Percent reduction of human huntingtin mRNA levels in BACHD mice via ICV administration of antisense oligonucleotides | | | |
|---|---|---|---|
| ISIS No. | Number of mice | Anterior cortex | Posterior cortex |
| 419642 | 3 | 29 | 42 |
| 436665 | 5 | 62 | 38 |
| 436671 | 3 | 69 | 77 |
| 436689 | 3 | 49 | 40 |
| 437507 | 3 | 77 | 66 |
| 443139 | 5 | 93 | 90 |
| 444591 | 5 | 79 | 78 |

TABLE 57

| Percent reduction of murine huntingtin mRNA levels in BACHD mice via ICV administration of antisense oligonucleotides | | | |
|---|---|---|---|
| ISIS No. | Number of mice | Anterior cortex | Posterior cortex |
| 419640 | 1 | 22 | 34 |
| 419641 | 2 | 40 | 26 |
| 419642 | 3 | 63 | 71 |
| 436665 | 5 | 72 | 56 |
| 436671 | 3 | 80 | 71 |

Body Weight Measurement

The body weights of the mice were measured at the onset of the study and subsequently once a week. The body weights of the mice are presented in Table 58 and are expressed as a percent change over the weights taken at the start of the study. The body weights were considered a measure of the tolerability of the mice to the ICV administration of antisense oligonucleotide. 'n.d.' means that there was no data available for that time period.

TABLE 58

| Percent change in body weight of BACHD mice during antisense oligonucleotide treatment | | | | |
|---|---|---|---|---|
| | week 1 | week 2 | week 3 | week 4 |
| PBS | −1 | +2 | +6 | +6 |
| ISIS 388241 | +3 | +11 | +15 | +7 |
| ISIS 437507 | +21 | +10 | +13 | −4 |
| ISIS 443139 | +10 | +10 | +16 | +12 |
| ISIS 419640 | +21 | +11 | −10 | +9 |
| ISIS 419641 | +24 | +3 | −5 | −12 |
| ISIS 419642 | +45 | +39 | +12 | +1 |
| ISIS 444591 | +18 | +38 | +27 | +17 |
| ISIS 436665 | +34 | +43 | +23 | +9 |
| ISIS 436671 | +19 | +17 | +11 | 0 |
| ISIS 444661 | +19 | −10 | −21 | n.d. |
| ISIS 436689 | +49 | +40 | +2 | −17 |

Survival of the Mice

The survival of the mice was assessed throughout the entire study period. Table 59 below shows the survival pattern in the groups of mice treated with ISIS oligonucleotides as well as the control.

TABLE 59

| Number of survivals during antisense oligonucleotide treatment | | | | |
|---|---|---|---|---|
| | week 1 | week 2 | week 3 | week 4 |
| PBS | 5 | 5 | 5 | 5 |
| ISIS 388241 | 4 | 3 | 3 | 3 |
| ISIS 437507 | 5 | 5 | 4 | 4 |

TABLE 59-continued

| Number of survivals during antisense oligonucleotide treatment | | | | |
|---|---|---|---|---|
| | week 1 | week 2 | week 3 | week 4 |
| ISIS 443139 | 5 | 5 | 5 | 5 |
| ISIS 419640 | 5 | 5 | 4 | 1 |
| ISIS 419641 | 5 | 5 | 4 | 2 |
| ISIS 419642 | 5 | 5 | 4 | 2 |
| ISIS 444591 | 5 | 5 | 5 | 5 |
| ISIS 436665 | 5 | 5 | 5 | 5 |
| ISIS 436671 | 4 | 4 | 3 | 3 |
| ISIS 444661 | 5 | 5 | 1 | 0 |
| ISIS 436689 | 4 | 4 | 4 | 3 |

Example 7

Intracerebroventricular Administration of Antisense Oligonucleotides Against Huntingtin in C57/BL6 Mice Wild-type C57/BL6 mice were treated with ISIS oligonucleotides via intracerebroventricular (ICV) administration to a defined mouse brain area, the right lateral ventricle, for the purpose of evaluating the potency of the oligonucleotides against mouse huntingtin in these mice.

Treatment and Surgery

Groups of ten C57/BL6 mice each were administered ISIS 408737 (5' TCCTAGTGTTACATTACCGC 3' (SEQ ID NO: 52), start site 5263 of SEQ ID NO: 3) at 50 μg/day delivered ICV with Alzet 2002 pumps at the rate of 0.5 μL/day for 7 days or 14 days. A control group of six C57/BL6 mice were similarly treated with PBS. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 7 or 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Mouse huntingtin mRNA levels were measured using the murine primer probe set ABI # Mm01213820_m1 (Applied Biosystems) and normalized to peptidylprolyl isomerase A mRNA levels. Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and monoclonal MAB2166 antibody (Millipore) that reacts specifically with murine huntingtin protein. Immunoblots were quantified using Odyssey V3.0 software.

The results are presented in Table 60 as percent reduction compared to the PBS control and demonstrate significant inhibition of huntingtin mRNA and protein levels by the antisense oligonucleotide both at day 7 and day 14.

TABLE 60

Percent inhibition of murine huntingtin mRNA in C57/BL6 mice

| | day 7 | day 14 |
|---|---|---|
| mRNA | 66 | 68 |
| protein | 21 | 49 |

Example 8

Intracerebroventricular Administration of Antisense Oligonucleotides Against Huntingtin mRNA in Cynomologous Monkeys Cynomologous monkeys were treated with ISIS oligonucleotides via intracerebroventricular (ICV) administration to a defined brain area, the lateral ventricles, for the purpose of screening the activity of the oligonucleotides in brain tissue against huntingtin mRNA expression.

Treatment and Surgery

Two groups of 3 cynomologous monkeys each were administered either 0.635 mg/ml (1.5 mg/day) or 1.67 mg/ml (4 mg/day) of ISIS 436689 delivered ICV with individual ambulatory pumps (Pegasus Vario) at the rate of 0.05 ml/hr for 4 weeks. A control group of 2 cynomologous monkeys were administered with PBS in a similar manner. The groups were administered ISIS 436689 bilaterally. One animal was administered ISIS 436689 at the 4 mg/day dose unilaterally to the right ventricle.

Animals were allowed 10 days to recover from surgery prior to infusion being performed. During the post surgery recovery period, the animals were maintained on PBS ICV infusion at a flow rate of 0.05 mL/h using one ambulatory infusion pump per ventricle. At the end of the recovery period, each cannula was connected to an individual ambulatory pump (Pegasus Vario) placed within a primate jacket (Lomir, PJ-02NB). The pumps remained connected until completion of the infusion period. After 4 weeks administration, the animals were euthanized and the brain, liver and kidney were harvested.

RNA Analysis of Htt mRNA

RNA was extracted from the anterior caudate, posterior caudate, temporal cortex, parietal cortex, hypothalamus, mid-brain, hippocampus, and spinal cords, as well as the liver and kidney for real-time PCR analysis of huntingtin mRNA levels. Huntingtin mRNA levels were measured using the human primer probe set RTS2617 and normalized to monkey cyclophilin A levels. Results were calculated as percent inhibition of huntingtin mRNA expression compared to the PBS control and are presented in Table 61. ISIS 436689 effected significant inhibition of human huntingtin mRNA levels in the CNS.

TABLE 61

Percent reduction of huntingtin mRNA levels in cynomologous monkeys via ICV administration of antisense oligonucleotides

| | Dose (mg/day) | | | |
|---|---|---|---|---|
| Tissue | 1.5 (bilateral) | 4 (bilateral) | 4 (right unilateral) | 4 (left unilateral) |
| Anterior caudate | 59 | 49 | 85 | 12 |
| Posterior caudate | 52 | 81 | 63 | 0 |
| Temporal cortex | 10 | 34 | 41 | 31 |
| Parietal cortex | 22 | 38 | 46 | 24 |
| Hypothalamus | 59 | 71 | 35 | 100 |
| Mid-brain | 32 | 38 | 2 | 0 |
| Hippocampus | 18 | 18 | 28 | 10 |
| Cervical cord | 58 | 65 | n.d. | n.d. |
| Thoracic cord | 50 | 67 | n.d. | n.d. |
| Lumbar cord | 49 | 62 | n.d. | n.d. |
| Liver | 0 | 13 | n.d. | n.d. |
| Kidney | 0 | 13 | n.d. | n.d. |

n.d. = no data

Example 9

Measurement of Half-life of ISIS 387898 in the Striatum of C57/BL6 Mice Via Single Bolus Administration C57/BL6 mice were administered ISIS 387898 as a single bolus to the striatum for the purpose of measuring half-life and duration of action of the antisense oligonucleotide against huntingtin mRNA expression in that tissue.

Treatment

Forty C57/BL6 mice were treated with ISIS 387898 (5' CTCGACTAAAGCAGGATTTC 3' (SEQ ID NO: 53); start position 4042 of SEQ ID NO: 1 and start position 4001 of SEQ ID NO: 3) delivered as a single bolus of 50 μg in a procedure similar to that described in Example 5. Eight control C57/BL6 mice were treated with PBS in a similar procedure. Groups of 4 mice each were euthanized at various time points and striatal tissue extracted in a procedure similar to that described in Example 5.

RNA Analysis

RNA was extracted from striatal tissue for real-time PCR analysis of huntingtin mRNA levels. Mouse normal huntingtin mRNA levels were measured using the murine primer probe set RTS2633. The results are presented in Table 62 and are expressed as percent inhibition compared to the PBS control group at day 7. The inhibitory effect of ISIS 387898 was observed to be prolonged for at least 91 days.

TABLE 62

Effect of ISIS 387898 as a single bolus administration on murine huntingtin mRNA expression at various time points in C57/BL6 striatum

| Treatment | Days after dosing | % inhibition |
|---|---|---|
| ISIS 387898 | 1 | 66 |
| | 7 | 74 |
| | 14 | 68 |
| | 21 | 77 |
| | 28 | 75 |
| | 50 | 63 |
| | 73 | 55 |
| | 91 | 48 |
| PBS | 50 | 5 |

Analysis of Antisense Oligonucleotide Concentration in the Brain:

Brain tissues were minced, weighed, homogenized, and extracted using a phenol/chloroform liquid-liquid extraction method. This was followed by solid phase extraction of the supernatant on a phenyl-bonded column before capillary gel electrophoresis electrokinetic injection. A P/ACE MDQ capillary electrophoresis instrument (Beckman Coulter, Fullerton, Calif.) was used for gel-filled capillary electrophoretic analysis. Oligonucleotide peaks were detected by UV absorbance at 260 nm.

Figure 1:
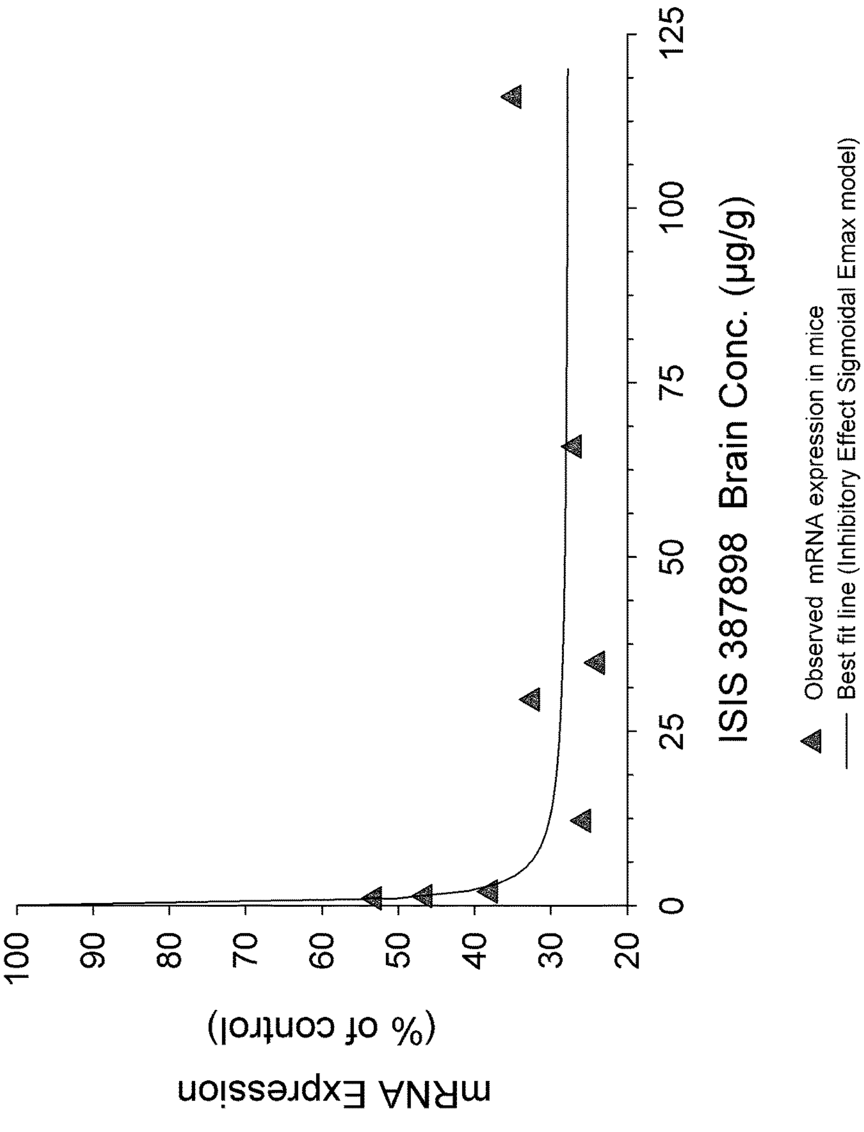
FIG. 1: The PK/PD relationship of huntingtin mRNA expression in intrastriatal tissue with ISIS 387898 concentration in mouse brain. C57/BL6 mice were administered a single bolus of 50 μg of ISIS 387898 and huntingtin mRNA expression as well as the concentration of the antisense oligonucleotide in the tissue were measured. The $EC_{50}$ of ISIS 387898 was also calculated.
Figure 2:
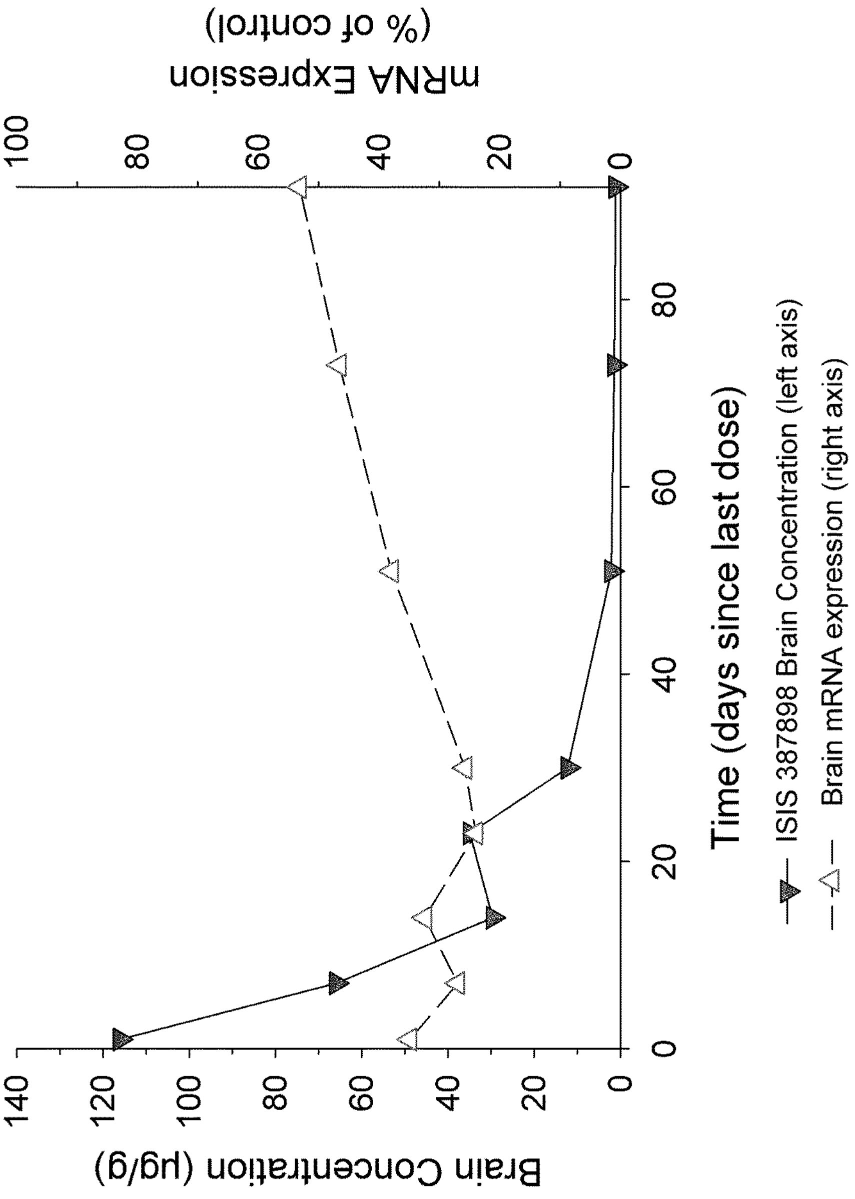
FIG. 2: Comparison of huntingtin mRNA expression in intrastriatal tissue and ISIS 387898 concentrations at various time points. C57/BL6 mice were administered a single bolus of 50 μg of ISIS 387898 and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

The concentration of ISIS 387898 in the brain (μg/g) was plotted against the expression of human huntingtin as a percentage of the PBS control (Table 63 and FIG. 1). The concentration of ISIS 387898 which achieves 50% inhibition of huntingtin mRNA expression ($EC_{50}$) was calculated. The $EC_{50}$ was determined to be 0.45 μg/g. The time-dependent concentration of ISIS 387898 in the brain tissue and corresponding percentage huntingtin mRNA expression was also plotted (Table 64 and FIG. 2) and the half-life of the oligonucleotide was calculated as 21 days.

TABLE 63

Concentration of ISIS 387898 in brain tissue and its effect on htt mRNA expression as a percentage of the control

| concentration (μg/g) | % mRNA expression |
|---|---|
| 0 | 105.0 |
| 25 | 28.8 |
| 50 | 28.2 |
| 75 | 27.9 |
| 100 | 27.8 |
| 125 | 27.8 |

TABLE 64

Time-dependent concentration of ISIS 387898 in brain tissue and its effect on htt mRNA expression as a percentage of the control

| Time (day) | Conc (μg/g) | mRNA % expression |
|---|---|---|
| 1 | 116 | 35 |
| 7 | 65.7 | 27 |
| 14 | 30 | 32 |
| 23 | 34.9 | 24 |
| 30 | 12.2 | 26 |
| 51 | 2.1 | 38 |
| 73 | 1.4 | 47 |
| 92 | 1.1 | 53 |

Example 10

Measurement of Half-life of ISIS 387898 in the Lateral Ventricles of BACHD Mice Via ICV Administration BACHD mice were administered ISIS 387898 by ICV to the lateral ventricles of the brain for the purpose of measuring half-life and duration of action of the antisense oligonucleotide against huntingtin mRNA expression in that tissue.

Treatment

Twenty eight BACHD mice were treated with ISIS 387898 delivered by ICV administration at 75 μg/day for 2 weeks in a procedure similar to that described in Example 9. Twenty eight control BACHD mice were treated with PBS in a procedure similar to that described in Example 9. Groups of 4 mice each from both the treatment and control groups were euthanized at biweekly time points and anterior cortical tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Human mutant huntingtin mRNA expression levels are presented in Table 65 and are expressed as percent inhibition compared to the average of that measured in the PBS control groups. Murine normal huntingtin mRNA expression levels are presented in Table 66 and are expressed as percent inhibition compared to the average of that measured in the PBS control groups. The inhibitory effect of ISIS 387898 was observed to be prolonged for 91 days.

TABLE 65

Effect of ISIS 387898 administered ICV on human huntingtin mRNA expression at various time points

| Treatment | Days after dosage | anterior | posterior |
|---|---|---|---|
| ISIS 387898 | 14 | 74 | 65 |
| | 28 | 67 | 61 |
| | 42 | 70 | 61 |
| | 56 | 57 | 52 |
| | 70 | 57 | 43 |
| | 91 | 41 | 61 |
| | 127 | 28 | 16 |
| PBS | 14 | 0 | 0 |
| | 28 | 0 | 0 |
| | 42 | 1 | 0 |
| | 56 | 9 | 10 |
| | 70 | 13 | 10 |
| | 91 | 13 | 25 |
| | 127 | 11 | 0 |

TABLE 66

Effect of ISIS 387898 administered ICV on murine huntingtin mRNA expression at various time points

| Treatment | Days after dosage | anterior | posterior |
|---|---|---|---|
| ISIS 387898 | 14 | 85 | 81 |
| | 28 | 81 | 69 |
| | 42 | 86 | 79 |
| | 56 | 74 | 69 |
| | 70 | 73 | 58 |
| | 91 | 39 | 63 |
| | 127 | 39 | 0 |
| PBS | 14 | 0 | 0 |
| | 28 | 0 | 0 |
| | 42 | 0 | 0 |
| | 56 | 17 | 14 |
| | 70 | 5 | 24 |
| | 91 | 9 | 17 |
| | 127 | 32 | 0 |

Figure 3:
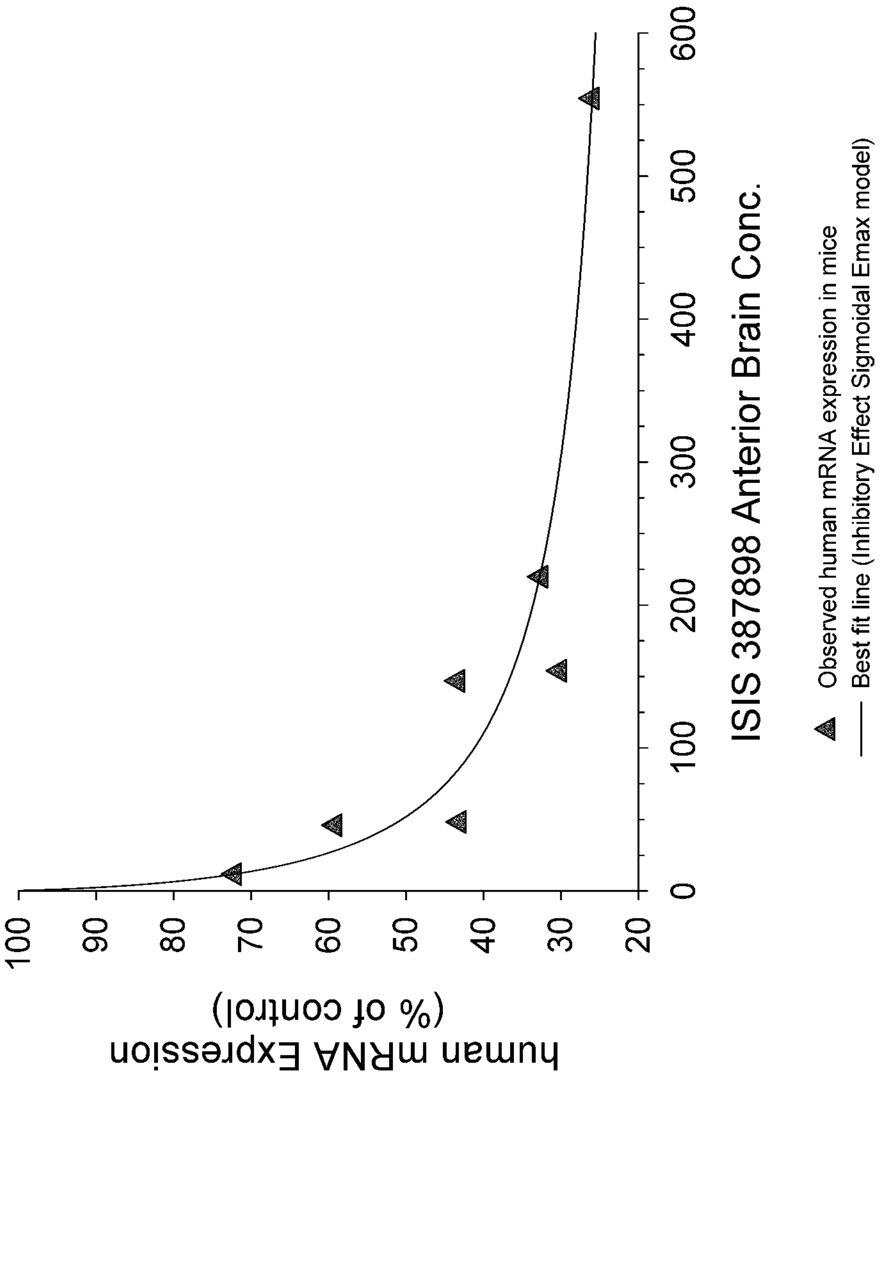
FIG. 3: The PK/PD relationship of huntingtin mRNA expression in the anterior cortex tissue with ISIS 387898 concentration in mouse brain. BACHD mice were administered an intracerebroventricular infusion of 75 μg of ISIS 387898 for 2 weeks and huntingtin mRNA expression as well as the concentration of the antisense oligonucleotide in the tissue were measured. The $EC_{50}$ of ISIS 387898 was also calculated.
Figure 4:
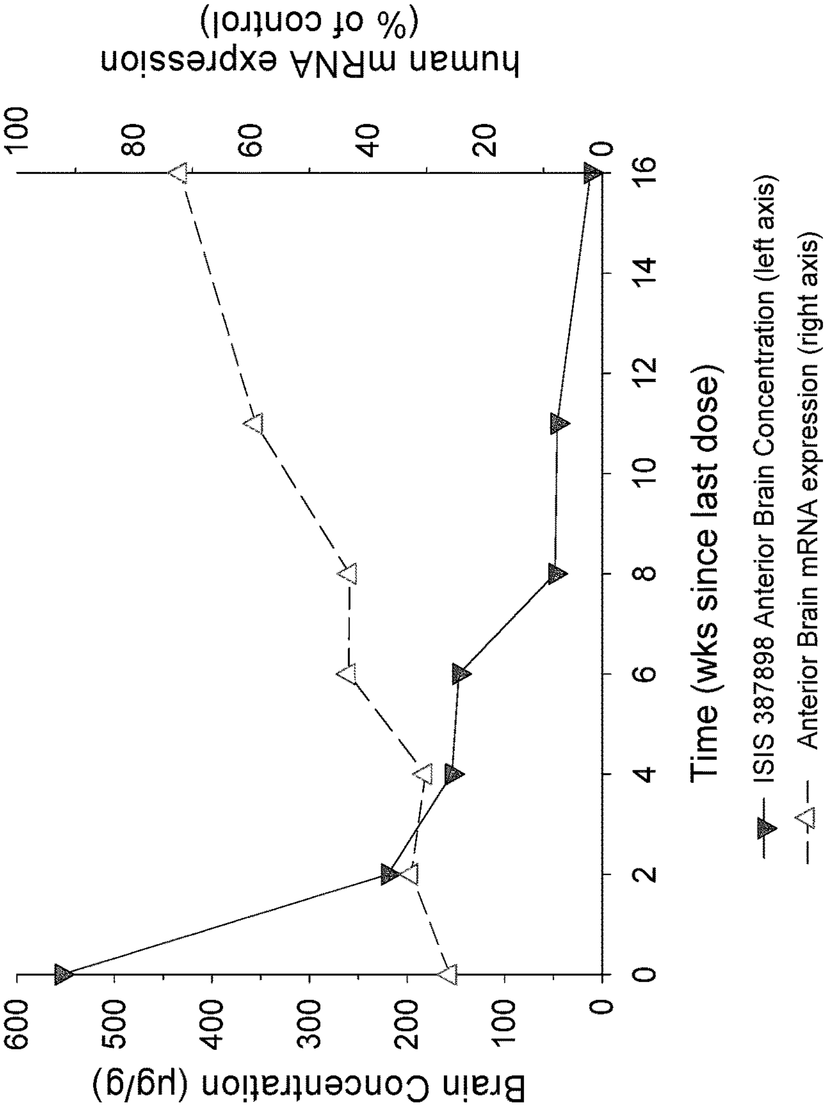
FIG. 4: Comparison of huntingtin mRNA expression in anterior cortex tissue and ISIS 387898 concentrations at various time points. BACHD mice were administered intracerebroventricular infusion of 75 μg of ISIS 387898 for 2 weeks, and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

Analysis of Antisense Oligonucleotide Concentration in the Brain:

Brain tissue was processed in a procedure similar to that described in Example 9. The concentration of ISIS 387898 in the anterior cortex of the brain (μg/g) was plotted against the inhibition of human huntingtin as a percentage of the PBS control (Table 67 and FIG. 3), and the $EC_{50}$ was calculated to be 26.4 μg/g. The time-dependent concentration of ISIS 387898 in the brain tissue was also plotted (Table 68 and FIG. 4) and the half-life of the oligonucleotide was calculated as 21 days.

TABLE 67

Concentration of ISIS 387898 in brain tissue and its effect on htt mRNA expression as a percentage of the control

| Concentration (μg/g) | % mRNA expression |
|---|---|
| 0 | 105 |
| 10 | 90.7 |
| 100 | 19.3 |
| 200 | 14.3 |
| 300 | 13.2 |
| 400 | 12.7 |
| 500 | 12.5 |
| 600 | 12.4 |

TABLE 68

Time-dependent concentration of ISIS 387898 in brain tissue and its effect on htt mRNA expression as a percentage of the control

| Days after last dose | Conc (mg/g) | % mRNA expression |
|---|---|---|
| 14 | 554.3 | 12 |
| 28 | 219.8 | 15 |
| 42 | 154 | 13 |
| 56 | 146.9 | 32 |
| 70 | 48.3 | 28 |
| 91 | 46.1 | 66 |
| 127 | 11.8 | 90 |

Example 11

Measurement of Half-life of ISIS 388241 and ISIS 443139 in the Lateral Ventricles of BACHD Mice Via ICV Administration BACHD mice were administered ISIS 388241 or ISIS 443139 by ICV to the lateral ventricles of the brain for the purpose of measuring half-life and duration of action of the antisense oligonucleotide against huntingtin mRNA expression in that tissue.

Treatment

Twenty BACHD mice were treated with ISIS 38241 delivered by ICV administration at 50 μg/day for 2 weeks in a procedure similar to that described in Example 9. Twenty BACHD mice were treated with ISIS 443139 delivered by ICV administration at 50 μg/day for 2 weeks in a procedure similar to that described in Example 9. Twenty control BACHD mice were treated with PBS in a procedure similar to that described in Example 9. Groups of 4 mice each from both the treatment groups and control group were euthanized at biweekly time points and tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. The results are presented in Table 69 and are expressed as percent inhibition compared to the average of that measured in the PBS control groups. The inhibitory effects of both ISIS 388241 and ISIS 443139 were observed to be prolonged for at least 16 weeks.

Both ISIS 388241 and its mixed backbone equivalent, ISIS 443139, have more than 3 mismatches with murine huntingtin mRNA (SEQ ID NO: 5) and therefore did not show significant inhibition of murine mRNA levels compared to the control.

TABLE 69

Effect of ISIS 388241 and ISIS 443139 administered ICV on human huntingtin mRNA expression at various time points

| Treatment | Weeks after dosage | anterior | posterior |
|---|---|---|---|
| ISIS 388241 | 0 | 63 | 64 |
| | 4 | 79 | 56 |
| | 8 | 67 | 51 |
| | 12 | 76 | 68 |
| | 16 | 35 | 34 |
| ISIS 443139 | 0 | 35 | 55 |
| | 4 | 20 | 62 |
| | 8 | 61 | 59 |
| | 12 | 67 | 53 |
| | 16 | 46 | 37 |
| PBS | 0 | 15 | 10 |
| | 4 | 0 | 2 |
| | 8 | 5 | 0 |
| | 12 | 32 | 4 |
| | 16 | 6 | 2 |

Figure 5:
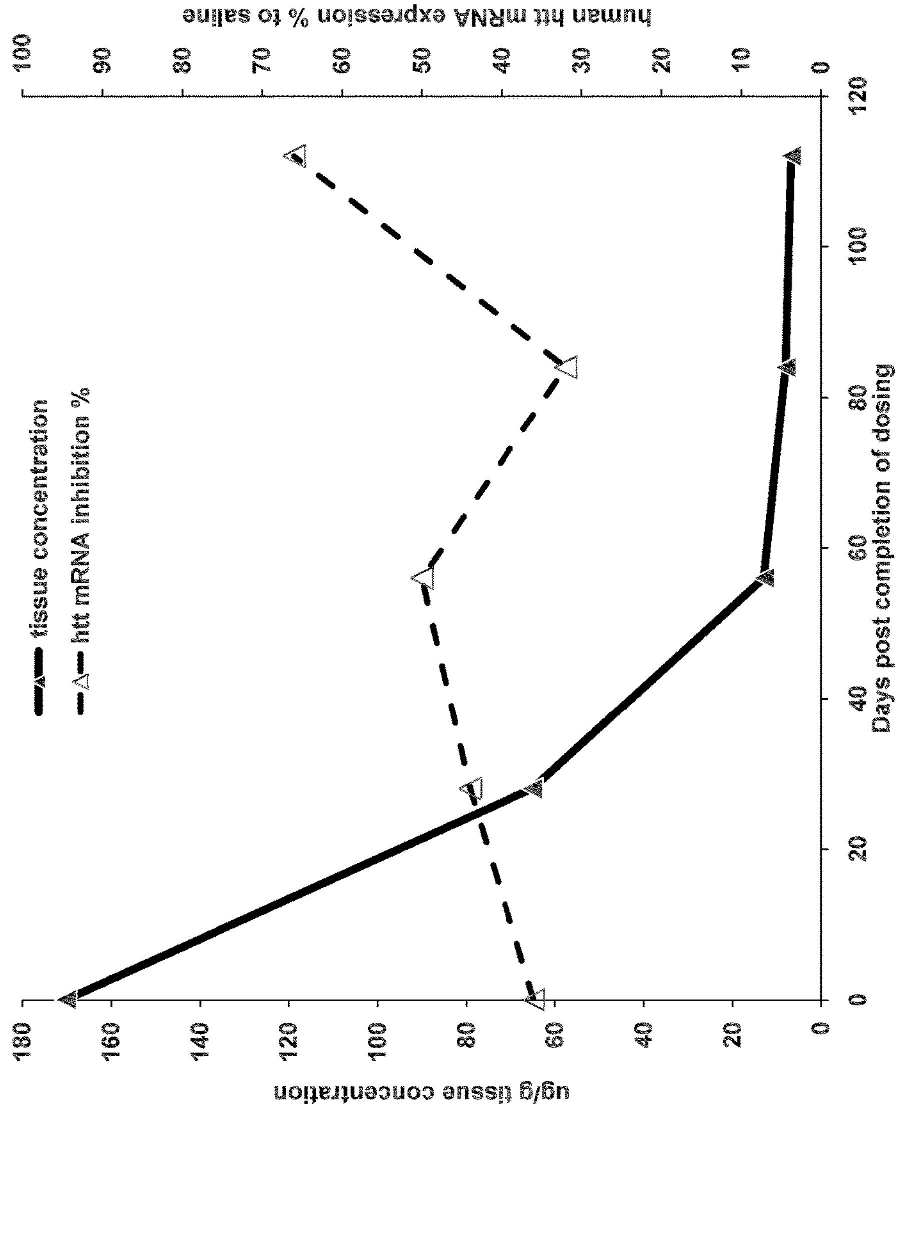
FIG. 5: Comparison of huntingtin mRNA expression in posterior cortex tissue and ISIS 388241 concentrations at various time points. BACHD mice were administered intracerebroventricular infusion of 50 μg of ISIS 388241 for 2 weeks, and huntingtin mRNA expression as well as the concentration of the antisense oligonucleotide in the tissue were measured. The duration of action (as measured by htt mRNA expression) of ISIS 388241 (dashed line) was observed to be longer even after the concentration of the oligonucleotide (solid line) in the tissue.

Analysis of Antisense Oligonucleotide Concentration in the Brain:

Brain tissue was processed in a procedure similar to that described in Example 9. The time-dependent concentration of ISIS 388241 in the posterior brain tissue was plotted (Table 70 and FIG. 5) and the half-life of the oligonucleotide was calculated as 20 days. The time-dependent concentration of ISIS 443139 in the posterior brain tissue was plotted (Table 71 and FIG. 6) and the half-life of the oligonucleotide was calculated as 20 days.

TABLE 70

Concentration of ISIS 384241 in brain tissue and its effect on htt mRNA expression as a percentage of the control

| Days after last dose | Conc (ug/g) | % mRNA expression |
|---|---|---|
| 0 | 170.3 | 36 |
| 28 | 65.2 | 43 |
| 56 | 13 | 49 |
| 84 | 8.2 | 32 |
| 112 | 6.9 | 66 |

TABLE 71

| Concentration of ISIS 443139 in brain tissue and its effect on htt mRNA expression as a percentage of the control | | |
|---|---|---|
| Days after last dose | Conc (ug/g) | % mRNA expression |
| 0 | 71.3 | 45 |
| 28 | 47.4 | 38 |
| 56 | 11.3 | 41 |
| 84 | 11.1 | 46 |
| 112 | 5.6 | 63 |

Example 12

Effect of Antisense Inhibition of Mutant Human Huntingtin on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Six month old BACHD mice and their non-transgenic littermates were trained to run on the rotarod for one week prior to treatment. This consisted of three consecutive trials of 5 minutes each, with a 20 minute rest period between trials. A group of 15 BACHD mice were then treated with ISIS 388241 at 50 μg/day delivered ICV with Alzet 2002 pumps at the rate of 12 μL/day for 2 weeks. The mice were surgically implanted with the pumps in a similar procedure as that described in Example 6. A control group of 14 BACHD mice were treated with PBS in a similar manner. A control group of 9 non-transgenic littermates were treated with PBS in a similar manner.

Rotarod Performance Assay

At the end of the treatment period, the pumps were removed and two weeks later, the first post-treatment rotarod assay was conducted. Rotarod behavior was analyzed monthly till the mice were 11 months of age. Each month, the animals were placed on the rotarod for three trial runs a day for 2 days. The results are presented in FIG. 7, as well as in Table 72 expressed as duration to fall in seconds. Baseline values at 6 months age were taken before the treatment and the time points given are the age of the mice at which the assay was conducted. The data indicates that treatment of BACHD mice with ISIS 388241 increased the duration to fall compared to that observed in untreated BACHD mice.

TABLE 72

| Effect of antisense inhibition of mutant huntingtin mRNA on duration to fall (sec) | | | | | | |
|---|---|---|---|---|---|---|
| | 6 months | 7 month | 8 months | 9 months | 10 months | 11 months |
| ISIS 388241 | 97 | 108 | 154 | 148 | 144 | 159 |
| PBS control | 94 | 117 | 115 | 104 | 99 | 92 |
| Non-transgenic control | 197 | 198 | 215 | 207 | 198 | 199 |

Example 13

Effect of Antisense Inhibition of Mutant Human Huntingtin and Wild Type Murine Huntingtin mRNA on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Two month old BACHD mice and their non-transgenic littermates were trained to run on the rotarod for one week prior to treatment. This consisted of three consecutive trials of 5 minutes each, with a 20 minute rest period between trials. Groups of 17-21 BACHD mice each were then treated with ISIS 388241 at 50 μg/day, ISIS 408737 at 75 μg/day, or ISIS 387898 at 75 μg/day, delivered ICV with Alzet 2002 pumps at the rate of 0.5 μL/hour for 2 weeks. The mice were surgically implanted with the pumps in a similar procedure as that described in Example 6. A control group of 20 BACHD mice were treated with PBS in a similar manner. Groups of non-transgenic control mice were also similarly treated with ISIS oligonucleotides or PBS in a similar manner.

Rotarod Performance Assay

At the end of the treatment period, the pumps were removed and two weeks later, the first post-treatment rotarod assay was conducted. Rotarod behavior was analyzed monthly till the mice were 10 months of age. Each month, the animals were placed on the rotarod for 3-5 trial runs a day for 3 consecutive days. The results are presented in Table 73 expressed as duration to fall in seconds. Baseline values at 2 months age were taken before the treatment and the time points given are the age of the mice at which the assay was conducted. ISIS 387898 (designated in the table as Human-mouse ASO) is cross-reactive for both mouse and human huntingtin mRNA and therefore would inhibit both human mutant huntingtin mRNA and wild-type murine huntingtin mRNA in the mice. ISIS 388241 (designated in the table as Human ASO) specifically targets human huntingtin mRNA and is mismatched by 8 base pairs with murine huntingtin mRNA. Therefore, ISIS 388241 would specifically inhibit only human mutant huntingtin mRNA and not wild-type murine huntingtin mRNA in the mice. ISIS 408737 (designated in the table as Mouse ASO) specifically targets murine huntingtin mRNA and is mismatched by 7 base pairs with human huntingtin mRNA. Therefore, ISIS 408737 would specifically inhibit only wild-type murine huntingtin mRNA and not human mutant huntingtin mRNA in the mice. 'Tg' indicates the BACHD mice and 'Non-Tg' indicates the non-transgenic control mice.

The results of the study indicate that inhibition of human mutant huntingtin mRNA by ISIS 388241 (Tg-Human ASO) significantly improved the performance of the mice in the rotarod assay compared to the control (Tg-PBS). The results also indicate that treatment of mice with ISIS 387898 (Tg-Human-mouse ASO), which targets both mutant and wild-type huntingtin mRNA in the mice, did not cause any deleterious effects on the motor performance of the mice and, in fact, also significantly improved rotarod performance compared to the control (Tg-PBS). The mice treated with ISIS 408737 (Tg-Mouse ASO) did not show improved rotarod performance compared to the PBS control, as expected, since the oligonucleotide does not target the mutant huntingtin mRNA. The non-transgenic controls were utilized as positive controls in this assay.

ISIS 388817 delivered in a similar manner. A control group of five R6/2 mice was administered 50 μg/day of ISIS 141923 delivered in a similar manner. A control group of nine R6/2 mice was administered PBS delivered in a similar manner. A group of eight non-transgenic littermates was administered PBS delivered in a similar manner. A group of four untreated eight-week old pre-symptomatic R6/2 were also included in the study.

Brain Weight Measurement

Animals were anaesthetized with isofluorane and then subjected to transcardial perfusion with ice-cold Sorenson's phosphate buffer (SPB), and fixed with 4% paraformaldyhyde in SPB. Brains were removed, and trimmed with coronal cuts immediately rostral to the forebrain (removing the olfactory bulbs) and immediately caudal to the cerebellum (removing the spinal cord). The remaining brain was weighed in mg. The results are presented in FIG. 8 and Table 74 and demonstrate the increase in brain weight in R6/2 mice treated with ISIS 388817 compared to the PBS control

TABLE 73

Effect of antisense inhibition of huntingtin mRNA on duration to fall (sec)

| | 2 months | 3 months | 4 months | 5 months | 6 months | 7 months | 8 months | 9 months | 10 months |
|---|---|---|---|---|---|---|---|---|---|
| Tg-Human ASO | 146 | 167 | 190 | 192 | 190 | 188 | 181 | 191 | 191 |
| Tg-mouse ASO | 151 | 142 | 152 | 143 | 139 | 144 | 139 | 123 | 130 |
| Tg-Human-mouse ASO | 149 | 187 | 203 | 199 | 196 | 194 | 189 | 194 | 171 |
| Tg-PBS | 152 | 164 | 169 | 160 | 159 | 155 | 148 | 135 | 136 |
| Non-Tg-Human ASO | 212 | 223 | 234 | 236 | 247 | 248 | 245 | 247 | 235 |
| Non-Tg-Mouse ASO | 201 | 212 | 215 | 213 | 231 | 243 | 244 | 250 | 247 |
| Non-Tg-Human-mouse ASO | 220 | 240 | 239 | 224 | 243 | 244 | 246 | 229 | 235 |
| Non-Tg-PBS | 193 | 220 | 228 | 227 | 228 | 216 | 220 | 208 | 208 |

Example 14

Effect of Antisense Inhibition of Huntingtin mRNA on the Brain Mass of R6/2 Mice R6/2 mice were treated with ISIS oligonucleotides via intracerebroventricular (ICV) administration for the purpose of evaluating the effect of the oligonucleotides against huntingtin mRNA expression on brain weight and volume.

Treatment

R6/2 mice were housed in groups of up to 5 per cage (mixed genotypes, single sex), All mice were housed in shoe-box cages with sterile wood bedding covering the ground that were changed as frequently as needed to provide the animals with dry bedding. This basic environment was enriched with the addition of play tunnels, shredded nestlet, and plastic bones for all mice; i.e. an environmentally-enriched cage containing a Mouse Tunnel, (amber color, certified, transparent, BioServ Product# K3323), a Petite Green Gumabone (BioServ Product # K3214) and a nestlet (Hockley et al., Ann Neurol. 2002, 51: 235-242). Food and water were available ad libitum to the mice in their home cages.

A group of ten six month old R6/2 mice was administered 50 μg/day of ISIS 388817 delivered ICV with Alzet 1004 pumps at the rate of 0.12 μl/hr for 4 weeks. A group of two non-transgenic littermates was administered 50 μg/day of

TABLE 74

Effect of antisense inhibition of mutant huntingtin mRNA on brain weight (mg)

| Mouse model | Treatment | Brain weight |
|---|---|---|
| R6/2 | PBS | 367 |
| | ISIS 141923 | 375 |
| | ISIS 388817 | 394 |
| R6/2 (8 weeks old) | None | 402 |
| Non-transgenic | ISIS 141923 | 452 |
| | ISIS 388817 | 436 |

Example 15

Effect of Antisense Inhibition of Huntingtin mRNA on Anxiety Performance of YAC128 Mice YAC128 mice were treated with ISIS oligonucleotides via intracerebroventricular (ICV) administration for the purpose of evaluating the effect of the oligonucleotides against huntingtin mRNA expression on anxiety in these mice as measured by their performance in the open field and elevated plus maze assays.

Treatment

A group of seven five-month old YAC128 mice was administered 50 μg/day of ISIS 388241 delivered ICV with Alzet 1004 pumps at the rate of 0.5 μl/hr for 14 days. A control group of four YAC128 mice were similarly treated with PBS. A control group of eight non-transgenic FVB/NJ littermates were included in the study and did not receive any treatment. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 14 days, after which the pumps were removed. The animals were allowed to recover for 2 weeks after which behavioral analysis was done and the mice were finally euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

Open Field Assay

Mice were placed in an open field arena (Med Associates) that uses photobeam breaks to measure horizontal and vertical movement over a 30 min test session. Data was analyzed using Activity Monitor software to examine total ambulatory movement within the arena and movement within the center of the arena as a measure of anxiety. YAC128 control mice were expected to spend less time at the centre of the arena compared to their non-transgenic, less anxiety-prone FVB/NJ littermates. The results are presented in FIG. 9 and Table 75 and indicate that treatment of YAC128 mice with antisense oligonucleotide decreased anxiety in these mice, according to the parameters of the open field assay.

TABLE 75

Effect of antisense inhibition of mutant htt mRNA on open field performance of YAC128 mice

| Mice model | Time in center (sec) |
|---|---|
| FVB control | 1326 |
| YAC128 control | 964 |
| ISIS 388241 treated YAC128 | 1433 |

Elevated Plus Maze Assay

The apparatus consisted of two open arms and two closed arms each measuring 65×6.25 cm and elevated 50 cm above the ground. Mice were placed in the center of the apparatus and their location was recorded over a 5 minute test session. YAC128 control mice were expected to spend less time at the open arms of the apparatus compared to their non-transgenic, less anxiety-prone FVB/NJ littermates. The results are presented in FIG. 10 and Table 76 and indicate that treatment of YAC128 mice with antisense oligonucleotide decreased anxiety in these mice, according to the parameters of the elevated plus maze assay.

TABLE 76

Effect of antisense inhibition of mutant htt mRNA on elevated plus maze performance of YAC128 mice

| Mice model | % time in open arms |
|---|---|
| FVB control | 32 |
| YAC128 control | 18 |
| ISIS 388241 treated YAC128 | 27 |

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Human huntingtin mRNA levels were measured using the human primer probe set RTS2686 and normalized to peptidylprolyl isomerase A mRNA levels.

Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and mouse monoclonal EM48 antibody that reacts specifically with human huntingtin protein (Millipore). Immunoblots were quantified using Odyssey V3.0 software.

The results are presented in Table 77 as percent reduction compared to the PBS control and demonstrate significant inhibition of huntingtin mRNA and protein levels by the antisense oligonucleotide.

TABLE 77

Percent inhibition of huntingtin mRNA in YAC128 mice

| | % inhibition |
|---|---|
| mRNA | 85 |
| protein | 86 |

Example 16

Intracerebroventricular Administration of Antisense Oligonucleotides Against Huntingtin in C57/BL6 Mice C57/BL6 mice were treated with ISIS oligonucleotides via intracerebroventricular (ICV) administration to the right lateral ventricle, for the purpose of evaluating the tolerability of the oligonucleotides in these mice.

Treatment and Surgery

Groups of five C57/BL6 mice each were administered ISIS 387916, ISIS 437527, ISIS 444578, ISIS 444584, ISIS 444607, ISIS 444608, ISIS 444627, ISIS 444652, ISIS 444659, ISIS 444660, or ISIS 444661 at 150 μg/day delivered ICV with Alzet 2002 pumps at the rate of 0.5 μL/day for 2 weeks. A control group of six C57/BL6 mice were similarly treated with PBS. The procedure for implanting the pumps and oligonucleotide administration is described in Example 6.

The animals were allowed to recover for two weeks before being euthanized using isoflurane. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being the most rostral and S5 the most caudal.

RNA Analysis

Total RNA was extracted from anterior and posterior cortices of the brain for real-time PCR analysis of huntingtin mRNA levels using an RNeasy Mini prep kit (Qiagen). RT-PCR reactions were conducted on an ABI Prism 7700 Sequence Detector (Applied Biosystems). Mouse huntingtin mRNA levels were measured using a murine primer probe set RTS2633 and normalized to cyclophilin mRNA levels. The results are presented in Table 78 as percent reduction compared to the PBS control. ISIS 387916, ISIS 437527, ISIS 444627, and ISIS 444652 all have one mismatch with the murine huntingtin mRNA (SEQ ID NO: 3) and therefore did not show significant inhibition of murine mRNA levels compared to the control.

The microglial marker, AIF1 was also measured by RT-PCR analysis using murine primer probe set mAIF1_LTS00328 (forward sequence TGGTCCCCCAGCCAAGA, designated herein as SEQ ID NO: 54; reverse sequence CCCACCGTGTGACATCCA, designated herein as SEQ ID NO: 55; probe sequence AGCTATCTCCGAGCTGCCCTGATTGG, designated herein as SEQ ID NO: 56). The results are presented in Table 79 and indicate that the tested ISIS oligonucleotides did not induce an inflammatory response.

TABLE 78

Percent inhibition of murine huntingtin mRNA compared to the control in C57/BL6 mice

| ISIS No | anterior | posterior |
|---|---|---|
| 387916 | 72 | 74 |
| 437527 | 59 | 62 |
| 444578 | 69 | 69 |
| 444584 | 0 | 9 |
| 444607 | 59 | 79 |
| 444608 | 41 | 66 |
| 444627 | 41 | 45 |
| 444652 | 61 | 64 |
| 444660 | 35 | 33 |
| 444661 | 72 | 69 |

TABLE 79

Percent increase in AIF1 mRNA expression compared to the control in C57/BL6 mice

| ISIS No | anterior | posterior |
|---|---|---|
| 387916 | 159 | 67 |
| 437527 | 102 | 77 |
| 444578 | 22 | 7 |
| 444584 | 33 | 37 |
| 444607 | 34 | 58 |
| 444608 | 29 | 1 |
| 444627 | 46 | 22 |
| 444652 | 59 | 50 |
| 444660 | −3 | 11 |
| 444661 | 67 | 62 |

Body Weight Measurements

Body weights were measured at regular intervals throughout the study period, and are presented in Table 80. These weights were utilized as an indicator of tolerability. Mice treated with ISIS 437527, ISIS 444584, and ISIS 444652 had consistent body weight throughout the study period and were deemed the most tolerable of all the ISIS oligonucleotides included in the study. 'n/a' indicates no data for that group of mice.

TABLE 80

Body weights of C57/BL6 mice after antisense oligonucleotide treatment

| | Day 0 | Day 4 | Day 8 | Day 12 | Day 16 | Day 19 | Day 23 | Day 26 | Day 28 |
|---|---|---|---|---|---|---|---|---|---|
| PBS | 105 | 108 | 111 | 114 | 111 | 111 | 113 | 114 | 112 |
| ISIS 387916 | 107 | 108 | 106 | 111 | 106 | 104 | 101 | 101 | 97 |
| ISIS 437527 | 105 | 116 | 116 | 120 | 111 | 112 | 112 | 108 | 108 |
| ISIS 444578 | 105 | 116 | 112 | 115 | 103 | 98 | 83 | 81 | 87 |
| ISIS 444584 | 105 | 117 | 115 | 111 | 105 | 105 | 103 | 104 | 102 |
| ISIS 444607 | 105 | 115 | 112 | 110 | 101 | 98 | 106 | 109 | 106 |
| ISIS 444608 | 102 | 111 | 112 | 112 | 97 | 91 | 78 | 75 | 87 |
| ISIS 444627 | 105 | 116 | 124 | 126 | 105 | 104 | 93 | 94 | 91 |
| ISIS 444652 | 106 | 122 | 124 | 126 | 119 | 113 | 111 | 111 | 108 |
| ISIS 444659 | 105 | 118 | 123 | 116 | 92 | 89 | 68 | n/a | n/a |
| ISIS 444660 | 104 | 115 | 120 | 118 | 103 | 93 | 89 | 84 | 90 |
| ISIS 444661 | 107 | 125 | 120 | 106 | 76 | 86 | 89 | 86 | 91 |

Example 17

Assay for Neurotoxic Effects of Bolus Administration of Antisense Oligonucleotides in the Striatal Tissue of Rats Sprague-Dawley rats were treated with ISIS oligonucleotides via bolus administration to the striatum, for the purpose of screening for the induction of the microglial marker AIF1 as a measure of CNS toxicity.

Treatment and Surgery

Groups of four Sprague-Dawley rats were administered ISIS 388241, ISIS 443139, ISIS 436671, ISIS 437527, ISIS 444584, ISIS 444591, or ISIS 444652 delivered as a single bolus at a concentration of 25 µg, 50 µg, 75 µg, or 100 µg.

A group of 4 rats were similarly treated with ISIS 387916, delivered as a single bolus at 10 µg, 25 µg, 50 µg, or 75 µg concentrations. A control group of 4 rats were similarly treated with PBS. Seven days after bolus administration, the rats were euthanized using isoflurane and the organs were removed. The animals were decapitated and the brain was removed for dissection of the striatal tissue. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 81. The results indicate that ISIS 388241, ISIS 443139, ISIS 436671, ISIS 444591, ISIS 437527, ISIS 444584, and ISIS 444652 were well tolerated in rat brain.

TABLE 81

Percent expression of AIF1 mRNA levels in vivo as a measure of neurotoxicity

| ISIS No | Dose (μg) | % increase |
|---|---|---|
| 387916 | 10 | 145 |
| | 25 | 157 |
| | 50 | 247 |
| | 75 | 316 |
| 388241 | 25 | 29 |
| | 50 | 12 |
| | 75 | 30 |
| | 100 | 41 |
| 436671 | 25 | 37 |
| | 50 | 2 |
| | 75 | 13 |
| | 100 | 50 |
| 443139 | 25 | 0 |
| | 50 | 7 |
| | 75 | 167 |
| | 100 | 26 |
| 444591 | 25 | 18 |
| | 50 | 80 |
| | 75 | 50 |
| | 100 | 207 |
| 437527 | 25 | 98 |
| | 50 | 45 |
| | 75 | 23 |
| | 100 | 126 |
| 444584 | 25 | −1 |
| | 50 | 10 |
| | 75 | 35 |
| | 100 | 31 |
| 444652 | 25 | 17 |
| | 50 | 46 |
| | 75 | 39 |
| | 100 | 48 |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343. Results were calculated as the percentage reduction of huntingtin expression over that of the PBS control and are presented in Table 82. ISIS 388241 and ISIS 443139 are each mismatched by 6 base pairs or more with the rat gene sequence (SEQ ID NO: 5) and therefore do not show significant inhibition of rat mRNA levels compared to the control. ISIS 444584 has 3 mismatches with the rat gene sequence (SEQ ID NO: 5) and therefore does not show significant inhibition of rat mRNA levels compared to the control.

TABLE 82

Percent reduction of rat huntingtin mRNA levels in rats

| ISIS No | Dose (μg) | % inhibition |
|---|---|---|
| 387916 | 10 | 6 |
| | 25 | 39 |
| | 50 | 55 |
| | 75 | 60 |
| 388241 | 25 | 8 |
| | 50 | 23 |
| | 75 | 27 |
| | 100 | 19 |
| 436671 | 25 | 52 |
| | 50 | 57 |
| | 75 | 57 |
| | 100 | 70 |
| 443139 | 25 | 35 |
| | 50 | 29 |
| | 75 | 28 |
| | 100 | 27 |
| 444591 | 25 | 26 |
| | 50 | 57 |
| | 75 | 68 |
| | 100 | 69 |
| 437527 | 25 | 40 |
| | 50 | 55 |
| | 75 | 60 |
| | 100 | 74 |
| 444584 | 25 | 43 |
| | 50 | 38 |
| | 75 | 38 |
| | 100 | 41 |
| 444652 | 25 | 49 |
| | 50 | 70 |
| | 75 | 55 |
| | 100 | 59 |

Example 18

Dose-Dependent Antisense Inhibition of Huntingtin mRNA in Cynomolgous Primary Hepatocytes ISIS 437527, ISIS 444584, and ISIS 444652 were tested in cynomolgous primary hepatocytes at various doses. The benchmark oligonucleotides, ISIS 387916 and ISIS 388241 were also included for comparison. Cells were plated at a density of 35,000 cells per well and transfected using electroporation with 39.0625 nM, 78.125 nM, 156.25 nM, 312.5 nM, 625 nM, 1,250 nM, 2,500 nM, 5,000 nM, 10,000 nM, and 20,000 nM concentrations of each antisense oligonucleotide. After approximately 16 hours, RNA was isolated from the cells and huntingtin mRNA transcript levels were measured by quantitative real-time PCR using primer probe set RTS2686. Huntingtin mRNA transcript levels were normalized to total RNA content, as measured by RIBOGREEN®. Results are presented in Table 83 as percent inhibition of huntingtin, relative to untreated control cells. Control oligonucleotide, ISIS 141923 was included in this assay and did not demonstrate inhibition of huntingtin mRNA, as expected.

ISIS 437527, ISIS 444584, and ISIS 444652 had lower $IC_{50}$ values than the benchmark oligonucleotide, ISIS 388241. ISIS 437527 and ISIS 444652 had as low or lower $IC_{50}$ values than the benchmark oligonucleotide, ISIS 387916.

TABLE 83

Dose-dependent antisense inhibition of huntingtin mRNA in cynomolgous primary hepatocytes

| | ISIS 387916 | ISIS 388241 | ISIS 437527 | ISIS 444584 | ISIS 444652 | ISIS 141923 |
|---|---|---|---|---|---|---|
| 39.0625 nM | 0 | 6 | 0 | 0 | 0 | 0 |
| 78.125 nM | 17 | 4 | 19 | 0 | 16 | 0 |
| 156.25 nM | 6 | 0 | 27 | 11 | 12 | 3 |
| 312.5 nM | 19 | 0 | 23 | 16 | 35 | 0 |
| 625.0 nM | 31 | 0 | 37 | 30 | 50 | 0 |
| 1250.0 nM | 45 | 0 | 28 | 23 | 52 | 0 |
| 2500.0 nM | 62 | 4 | 33 | 47 | 74 | 0 |
| 5000.0 nM | 78 | 54 | 55 | 42 | 86 | 0 |
| 10000.0 nM | 82 | 80 | 68 | 77 | 91 | 0 |
| 20000.0 nM | 84 | 75 | 70 | 69 | 92 | 0 |
| $IC_{50}$ (μM) | 1.4 | 5.4 | 2.0 | 4.0 | 0.8 | >20 |

Example 19

Measurement of Half-life of ISIS Oligonucleotides in BACHD Mice Via Single Intrastriatal Bolus Administration BACHD mice were administered ISIS oligonucleotides as a single bolus to the striatum for the purpose of measuring the duration of action of the antisense oligonucleotides against huntingtin mRNA expression, or its half-life, in that tissue.

Treatment and Surgery

Groups of 25 BACD mice each were treated with ISIS 388241, ISIS 436689, ISIS 436671, or ISIS 444591, delivered as a single bolus of 40 μg in a procedure similar to that described in Example 4. A control group of 25 BACHD mice were treated with PBS in a similar procedure. At various time points, 5 mice from each group were euthanized and striatal tissue was extracted. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis

RNA was extracted from anterior and posterior sections of the striatal tissue for real-time PCR analysis of huntingtin mRNA levels. Human mutant huntingtin mRNA levels were measured using RTS2617. Mouse normal huntingtin mRNA levels were measured using the murine primer probe set RTS2633. The results are presented in Tables 84 and 85 and are expressed as percent inhibition compared to the average of the PBS control group at week 1, week 10, and week 20. The half-life of the ISIS oligonucleotides in the anterior section of the brain was calculated from the inhibition data and is presented in Table 86.

TABLE 84

Percent inhibition of human huntingtin mRNA expression at various time points

| ISIS No | Time (weeks) | Posterior | Anterior |
|---|---|---|---|
| 388241 | 1 | 72 | 91 |
| | 5 | 65 | 86 |
| | 10 | 52 | 73 |
| | 15 | 26 | 56 |
| | 20 | 14 | 53 |
| 436671 | 1 | 82 | 92 |
| | 5 | 78 | 89 |
| | 10 | 68 | 82 |
| | 15 | 61 | 77 |
| | 20 | 30 | 77 |
| 444591 | 1 | 60 | 85 |
| | 5 | 58 | 76 |
| | 10 | 48 | 60 |
| | 15 | 27 | 43 |
| | 20 | 27 | 36 |
| 436689 | 1 | 72 | 83 |
| | 5 | 72 | 87 |
| | 10 | 60 | 74 |
| | 15 | 50 | 74 |
| | 20 | 44 | 59 |

TABLE 85

Percent inhibition of mouse huntingtin mRNA expression at various time points

| ISIS No | Time (weeks) | Posterior | Anterior |
|---|---|---|---|
| 388241 | 1 | 1 | 12 |
| | 5 | 22 | 36 |
| | 10 | 17 | 14 |
| | 15 | 7 | 18 |
| | 20 | 9 | 38 |
| 436671 | 1 | 84 | 96 |
| | 5 | 77 | 80 |
| | 10 | 64 | 86 |
| | 15 | 51 | 78 |
| | 20 | 19 | 75 |
| 444591 | 1 | 74 | 95 |
| | 5 | 70 | 90 |
| | 10 | 57 | 67 |
| | 15 | 34 | 47 |
| | 20 | 33 | 38 |
| 436689 | 1 | 40 | 32 |
| | 5 | 47 | 40 |
| | 10 | 35 | 18 |
| | 15 | 34 | 22 |
| | 20 | 36 | 5 |

TABLE 86

Half-life of ISIS oligonucleotides in the anterior section of the brain in BACHD mice after intrastriatal bolus injection

| ISIS No | Half-life (days) |
|---|---|
| 436671 | 46.6 |
| 436689 | 39.4 |

TABLE 86-continued

Half-life of ISIS oligonucleotides in the anterior section of the brain in BACHD mice after intrastriatal bolus injection

| ISIS No | Half-life (days) |
|---|---|
| 444591 | 24.3 |
| 388241 | 25.8 |

Body Weight Measurements

Body weights were measured at regular intervals, and are presented in Table 87 as a percent of the weight of the mice at the start of the study. These weights were utilized as an indicator of tolerability. There were no adverse changes in body weight in any of the mice treated with ISIS oligonucleotides.

TABLE 87

Percent change in body weight of BACHD mice after antisense oligonucleotide treatment

| | Week 5 | Week 10 | Week 15 | Week 20 |
|---|---|---|---|---|
| PBS | 8 | 19 | 26 | 28 |
| ISIS 388241 | 9 | 22 | 29 | 26 |
| ISIS 436671 | 5 | 19 | 35 | 38 |
| ISIS 444591 | 7 | 21 | 30 | 43 |
| ISIS 436689 | 3 | 18 | 31 | 38 |

Example 20

Effect of Intrathecal Administration of ISIS 437527 in Sprague Dawley Rats

Sprague Dawley rats were dosed with ISIS 437527 by intrathecal (IT) administration either as a single dose, repeated doses, or continuous infusion.

Treatment and Surgery

Rats were anesthetized with isoflurane and a 28-gauge polyurethane catheter was placed into the IT lumbar space of each rat. The proximal end of the catheter was attached to a dosing pedestal that was extended through the skin for animals in groups receiving bolus injections. The catheter for animals in the group receiving continuous infusion was attached to an ALZET pump (Model 2ML1) which was placed in a subcutaneous pocket on the dorsal aspect of each animal. Post-surgically the animals received a single intramuscular dose of ceftiofur sodium (5 mg/kg) and butorphanol tartrate (0.05 mg/kg). The rats receiving continuous infusion began receiving the oligonucleotide dose immediately. The animals that would receive bolus injections were allowed a surgical recovery period of at least five days after which the patency of the catheter was evaluated.

A group of 5 Sprague Dawley rats was administered a single bolus injection of 350 μg of ISIS 437527 delivered intrathecally. Another group of 5 Sprague Dawley rats was administered bolus injections of 120 μg of ISIS 437527 delivered intrathecally three times over the course of 1 week. Another group of 5 Sprague Dawley rats was administered bolus injections of 350 μg of ISIS 437527 delivered intrathecally three times over the course of 1 week. Another group of 5 Sprague Dawley rats was administered 50 μg/day of ISIS 437527 delivered by continuous infusion at a rate of 0.01 mL/hr for 7 days. A control group of 5 Sprague Dawley rats was administered bolus injections of PBS delivered intrathecally three times over the course of 1 week. Each group was given a recovery period of 7 days, after which the rats were euthanized. The brain and spinal cord from all groups were harvested and analyzed.

RNA Analysis of Huntingtin Expression Levels

RNA was extracted from the frontal cortex, temporal cortex, and the cervical cord for real-time PCR analysis of huntingtin mRNA levels. Rat huntingtin mRNA levels were measured using the primer probe set rHtt_LTS00343 normalized to Cyclophilin levels. The results are presented in Table 88 and are expressed as percent inhibition compared to the average of the PBS control groups.

TABLE 88

Percent inhibition of huntingtin mRNA expression in Sprague Dawley rats

| Tissue | Dose schedule | Dose | % inhibition |
|---|---|---|---|
| Frontal Cortex | IT Infusion | 50 μg/day | 11 |
| | Single IT Bolus | 350 μg | 28 |
| | Repeated IT Bolus | 120 μg × 3 | 21 |
| | Repeated IT Bolus | 350 μg × 3 | 0 |
| Temporal Cortex | IT Infusion | 50 μg/day | 0 |
| | Single IT Bolus | 350 μg | 34 |
| | Repeated IT Bolus | 120 μg × 3 | 44 |
| | Repeated IT Bolus | 350 μg × 3 | 48 |
| Cervical Cord | IT Infusion | 50 μg/day | 22 |
| | Single IT Bolus | 350 μg | 45 |
| | Repeated IT Bolus | 120 μg × 3 | 58 |
| | Repeated IT Bolus | 350 μg × 3 | 46 |

RNA Analysis of AIF1 Expression Levels

RNA was extracted from frontal cortex, temporal cortex, and the cervical cord for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 89. The results indicate that repeated IT bolus administrations lead to inflammation at the cervical cord tissues. Continuous IT administration and single IT bolus administrations were well tolerated in the rats.

TABLE 89

Percent expression of AIF1 mRNA levels in Sprague Dawley rats as a measure of neurotoxicity

| Tissue | Dose schedule | Dose | % inhibition |
|---|---|---|---|
| Frontal Cortex | IT Infusion | 50 μg/day | −36 |
| | Single IT Bolus | 350 μg | −4 |
| | Repeated IT Bolus | 120 μg × 3 | 41 |
| | Repeated IT Bolus | 350 μg × 3 | −7 |
| Temporal Cortex | IT Infusion | 50 μg/day | 15 |
| | Single IT Bolus | 350 μg | 22 |
| | Repeated IT Bolus | 120 μg × 3 | 25 |
| | Repeated IT Bolus | 350 μg × 3 | 76 |

TABLE 89-continued

| Percent expression of AIF1 mRNA levels in Sprague Dawley rats as a measure of neurotoxicity | | | |
|---|---|---|---|
| Tissue | Dose schedule | Dose | % inhibition |
| Cervical Cord | IT Infusion | 50 μg/day | 108 |
| | Single IT Bolus | 350 μg | 72 |
| | Repeated IT Bolus | 120 μg × 3 | 473 |
| | Repeated IT Bolus | 350 μg × 3 | 268 |

Example 21

Measurement of Half-life of ISIS 436689 in the CNS Tissues of Cynomolgous Monkeys Via Intrathecal Administration Cynomolgous monkeys were administered ISIS 436689 intrathecally (IT) for the purpose of measuring the half-life and duration of action of the antisense oligonucleotide against huntingtin mRNA expression in various CNS tissues.

Treatment

The study was conducted at Northern Biomedical Research, MI. Prior to the start of the treatment, the monkeys were kept in quarantine for a 4-week time period, during which standard panels of serum chemistry and hematology, examination of fecal samples for ova and parasites, and a tuberculosis test, were conducted to screen out abnormal or ailing monkeys. The monkeys were implanted with intrathecal lumbar catheters using polyurethane catheters connected to a subcutaneous titanium access port (P.A.S. PORT® Elite Plastic/Titanium portal with Ultra lock connector). For continuous infusion using an external pump, the animals were anesthetized to attach the dosing apparatus to the port. The animals were pretreated with atropine sulfate by subcutaneous injection at a dose of 0.04 mg/kg. Approximately 15 minutes later, an intramuscular dose of 8 mg/kg of ketamine HCl was administered to induce sedation. The animals were masked to a surgical plane of anesthesia, intubated and maintained on approximately 1 L/min of oxygen and 2% halothane or isoflurane. The animals received a single intramuscular dose of 5 mg/kg ceftiofur sodium antibiotic. An incision was made near the port for placement of the modified needle support. The modified needle was placed in the port and secured with sutures. Upon recovery from surgery, a jacket was placed on the animal.

Fifteen male cynomolgus monkeys were administered 4 mg/day of ISIS 436689 at a concentration of 1.67 mg/mL and at a flow rate of 2.4 mL/day for 21 days. A control group of 3 cynomolgus monkeys was administered with PBS in a similar manner for the same time period. Groups of 3 monkeys each were allowed recovery periods of 1 day, 2 weeks, 4 weeks, or 8 weeks, after which they were euthanized. During the study period, the monkeys were observed daily for signs of illness or distress.

All animals were sedated with an intramuscular injection of 8.0 mg/kg of ketamine HCl, maintained on a halothane or isoflurane/oxygen mixture, and provided with an intravenous bolus of heparin Na at 200 IU/kg. The animals were perfused via the left cardiac ventricle with 0.001% sodium nitrite in saline.

At the time of sacrifice, the brain was cut in a brain matrix at 3 mm coronal slice thickness. Several brain structures were sampled using a 4 mm biopsy punch. One 4 mm diameter sample from each structure was placed in 2 mL screw capped tubes containing 1.0 mL of RNAlater RNA stabilization solution (Qiagen, Calif.), incubated for 1 hour at ambient temperature and then frozen. Adjacent 6 mm diameter samples were placed in 2 mL screw capped tubes and frozen for pharmacokinetic analysis.

The spinal cord was sectioned into cervical, thoracic and lumbar sections, and approximately 3 mm thick sections of each area of the spinal cord were taken for RNA and pharmacokinetic analysis. These samples were processed in a manner similar to those of the brain samples.

Samples of the liver were harvested for RNA and pharmacokinetic analyses. These samples were processed in a manner similar to those of the brain and spinal cord described above.

RNA Analysis

RNA was extracted from the lumbar spinal cord, thoracic spinal cord, cervical spinal cord, frontal cortex, occipital cortex, cerebellar cortex, caudate tissue, hippocampus, middle brain, and pons for real-time PCR analysis of huntingtin mRNA levels with primer probe set RTS2617. The results measured in the various sections of the spinal cord are presented in Table 90 and are expressed as percent inhibition compared to that measured in the PBS control group at 8 weeks. The results measured in the various sections of the brain are presented in Table 91 and are expressed as percent inhibition compared to that measured in the PBS control group at 8 weeks.

TABLE 90

| Effect of ISIS 436689 administered IT on huntingtin mRNA expression in the spinal cord at various time points | | | |
|---|---|---|---|
| Recovery period | Lumbar spinal cord | Thoracic spinal cord | Cervical spinal cord |
| 1 Day | 36 | 66 | 65 |
| 2 Weeks | 56 | 55 | 54 |
| 4 Weeks | 0 | 63 | 65 |
| 8 Weeks | 48 | 48 | 44 |

TABLE 91

| Effect of ISIS 436689 administered IT on huntingtin mRNA expression in various brain tissues at various time points | | | | | | | |
|---|---|---|---|---|---|---|---|
| Recovery period | Frontal cortex | Occipital cortex | Cerebellar cortex | Caudate | Hippo-campus | Middle brain | Pons |
| 1 Day | 53 | 37 | 8 | 21 | 19 | 24 | 22 |
| 2 Weeks | 42 | 28 | 16 | 3 | 28 | 0 | 32 |
| 4 Weeks | 47 | 32 | 25 | 7 | 22 | 2 | 43 |
| 8 Weeks | 33 | 34 | 11 | 17 | 27 | 5 | 22 |

Oligonucleotide Concentration Measurement by ELISA

Tissues (20 mg) were minced, weighed, and homogenized prior to liquid/liquid extraction using phenol/chloroform. The supernatant was removed, lyophilized, and reconstituted in human EDTA plasma (1 mL) before being analyzed using a hybridization ELISA procedure.

ISIS 436689 was detected in the tissues by hybridization to a labeled complementary cutting probe (digoxigenin at the 5' end and a C18 spacer and BioTEG at the 3' end). The complex was then captured on a neutravidin-coated plate and S1 nuclease was added to digest the unhybridized cutting probes. Since ISIS 436689 protected the cutting probe from digestion, the undigested cutting probe was used as a measure of the oligonucleotide concentration. The undigested cutting probe was detected using an anti-digoxigenin antibody conjugated to alkaline phosphatase followed by fluorogenic substrate readout. Oligonucleotide concentrations were measured in the cervical, thoracic, and lumbar sections of the spinal cord and in the liver on days 7, 20, 34, and 62 of the recovery period, and are presented in Table 92. The half-life of ISIS 436689 in these tissues was calculated from this data, and is presented in Table 93. The data indicates that the oligonucleotide was mainly concentrated in the CNS with negligible concentrations in the systemic tissues.

TABLE 92

Concentrations (μg/g tissue) of ISIS 436689 administered IT on huntingtin mRNA expression in various tissues at various time points

| Organ | Day 7 | Day 20 | Day 34 | Day 62 |
|---|---|---|---|---|
| Cervical cord | 118.9 | 78.7 | 79.8 | 42.8 |
| Thoracic cord | 503.5 | 215.8 | 101.6 | 61.4 |
| Lumbar cord | 557.1 | 409.5 | 143.3 | 49.5 |
| Liver | 33.6 | 10.3 | 2.0 | 0.2 |

TABLE 93

Half-life of ISIS 436689 administered IT on huntingtin mRNA expression in various tissues

| Organ | Half-life |
|---|---|
| Cervical cord | 4.0 |
| Thoracic cord | 15.1 |
| Lumbar cord | 18.7 |
| Liver | 7.6 |

What is claimed is:

1. A single-stranded modified oligonucleotide consisting of 18 linked nucleosides and having:

a gap segment consisting of eight linked deoxynucleosides;

a 5' wing segment consisting of five linked nucleosides; and a 3' wing segment consisting of five linked nucleosides;

wherein the gap segment is positioned between the 5' wing segment and the 3' wing segment;

wherein each nucleoside of each wing segment comprises a 2' O-methoxyethyl sugar; and wherein the nucleobase sequence of the oligonucleotide consists of the sequence recited in SEQ ID NO: 33, or a pharmaceutically acceptable salt thereof.

2. The single-stranded modified oligonucleotide of claim 1, wherein at least one nucleoside comprises a modified nucleobase.

3. The single-stranded modified oligonucleotide of claim 2, wherein the modified nucleobase is a 5-methylcytosine.

4. The single-stranded modified oligonucleotide of claim 1, wherein each cytosine is a 5-methylcytosine.

5. The single-stranded modified oligonucleotide of claim 1, wherein at least one internucleoside linkage is a modified internucleoside linkage.

6. The compound of claim 1, wherein each internucleoside linkage is a phosphorothioate internucleoside linkage.

7. The single-stranded modified oligonucleotide of claim 4, wherein at least one internucleoside linkage is a modified internucleoside linkage.

8. The compound of claim 4, wherein each internucleoside linkage is a phosphorothioate internucleoside linkage.

9. A composition comprising the single-stranded modified oligonucleotide or pharmaceutically acceptable salt thereof of claim 1 and at least one pharmaceutically acceptable carrier or diluent.

10. A composition comprising the single-stranded modified oligonucleotide or pharmaceutically acceptable salt thereof of claim 4 and at least one pharmaceutically acceptable carrier or diluent.

11. A composition comprising the single-stranded modified oligonucleotide or pharmaceutically acceptable salt thereof of claim 6 and at least one pharmaceutically acceptable carrier or diluent.

12. A composition comprising the single-stranded modified oligonucleotide or pharmaceutically acceptable salt thereof of claim 8 and at least one pharmaceutically acceptable carrier or diluent.

13. The single-stranded modified oligonucleotide of claim 1, which is capable of inhibiting huntingtin expression.

14. The single-stranded modified oligonucleotide of claim 4, which is capable of inhibiting huntingtin expression.

15. The single-stranded modified oligonucleotide of claim 6, which is capable of inhibiting huntingtin expression.

16. The single-stranded modified oligonucleotide of claim 8, which is capable of inhibiting huntingtin expression.

* * * * *